United States Patent
Wu et al.

(10) Patent No.: US 11,766,478 B2
(45) Date of Patent: Sep. 26, 2023

(54) METHODS FOR ENHANCING ANTIGEN-SPECIFIC IMMUNE RESPONSES

(71) Applicant: The Johns Hopkins University, Baltimore, MD (US)

(72) Inventors: Tzyy-Choou Wu, Stevenson, MD (US); Chien-Fu Hung, Timonium, MD (US)

(73) Assignee: The Johns Hopkins University, Baltimore, MD (US)

( * ) Notice: Subject to any disclaimer, the term of this patent is extended or adjusted under 35 U.S.C. 154(b) by 97 days.

(21) Appl. No.: 17/006,224

(22) Filed: Aug. 28, 2020

(65) Prior Publication Data

US 2020/0390885 A1 Dec. 17, 2020

Related U.S. Application Data

(62) Division of application No. 15/543,806, filed as application No. PCT/US2016/013545 on Jan. 15, 2016, now Pat. No. 10,799,579.

(60) Provisional application No. 62/104,464, filed on Jan. 16, 2015.

(51) Int. Cl.
| | |
|---|---|
| *A61K 39/39* | (2006.01) |
| *A61K 39/00* | (2006.01) |
| *C07K 14/47* | (2006.01) |
| *A61K 38/17* | (2006.01) |
| *A61K 47/64* | (2017.01) |
| *A61K 33/243* | (2019.01) |
| *A61K 9/00* | (2006.01) |

(52) U.S. Cl.
CPC ............ *A61K 39/39* (2013.01); *A61K 9/0019* (2013.01); *A61K 33/243* (2019.01); *A61K 38/1709* (2013.01); *A61K 39/0011* (2013.01); *A61K 47/643* (2017.08); *A61K 47/646* (2017.08); *C07K 14/4721* (2013.01); *A61K 2039/54* (2013.01); *A61K 2039/545* (2013.01); *A61K 2039/55516* (2013.01); *C07K 2319/40* (2013.01); *C07K 2319/50* (2013.01)

(58) Field of Classification Search
CPC .... A61K 39/39; A61K 9/0019; A61K 33/243; A61K 38/1709; A61K 39/0011; A61K 47/646; A61K 2039/54; A61K 2039/545; A61K 2039/55516; C07K 2319/40; C07K 2319/50; A61P 35/00
USPC ..................................................... 424/130.1
See application file for complete search history.

(56) References Cited

U.S. PATENT DOCUMENTS

| | | | |
|---|---|---|---|
| 10,799,579 B2 | 10/2020 | Wu et al. | |
| 2006/0258584 A1 | 11/2006 | Lind et al. | |
| 2013/0331546 A1 | 12/2013 | Ohlfest et al. | |
| 2014/0370122 A1* | 12/2014 | Story | A61P 35/00 |
| | | | 435/375 |
| 2020/0390885 A1 | 12/2020 | Wu et al. | |

FOREIGN PATENT DOCUMENTS

| | | |
|---|---|---|
| KR | 10-0835879 B1 | 6/2008 |
| KR | 10-2013-0012936 A | 2/2013 |
| WO | WO-2014189335 A1 | 11/2014 |

OTHER PUBLICATIONS

Cheng et al., "CD8+ T cells, NK cells and IFN-gama are important for control of tumor with downegulated MHC class I expression by DNA vaccination," Gene Ther, 10:1311-1320 (2003).
Clay et al., "Assays for monitoring cellular immune responses to active immunotherapy of cancer," Clin Cancer Res, 7:1127-1135 (2001).
Currier et al. "A panel of MHC class I restricted viral peptides for use as a quality control for vaccine trial Eli Spot assays," J Immunol Methods, 260:157-172 (2002).
D'Amico et al., "Apoptosis and a re-investigation of the biologic basis for cancer therapy," Radiother Oncol, 33:3-10 (1994).
Dewey et al., "Radiation-induced apoptosis: relevance to radiotherapy," Int J Radiat Oncol Biol Phys, 33:781-796 (1995).
Dive et al., "Induction of apoptosis—new targets for cancer chemotherapy," Sem Cancer Biol, 3:417-427 (1992).
Ernst et al., "Preparation and characterization of an endogenously fluorescent anexin for detection of apoptotic cells," Analyt Biochem, 260:18-23 (1998).
Fischer-Colbrie et al., "EGFR and steroid receptors in ovarian carcinoma: comparison with prognostic parameters and outcome of patients," Anticancer Res, 17:613-619 (1997).
Hassan et al., "Mesothelin: a new target for immunotherapy," Clin Cancer Res, 10:3937-3942 (2004).
Hung et al., "A DNA vaccine encoding a single-chain trimer of HLA-A2 linked to human mesothelin peptide generates anti-tumor effects against human mesothelin-expressing tumors," Vaccine, 25:127-135 (2007).

(Continued)

*Primary Examiner* — Yan Xiao
(74) *Attorney, Agent, or Firm* — Foley Hoag LLP

(57) ABSTRACT

Described herein are methods comprising administering to a mammalian subject an effective amount of an annexin chimeric fusion protein, wherein the annexin chimeric fusion protein comprises at least one immunogenic antigen, thereby enhancing the antigen specific immune response relative to administration of the immunogenic antigen alone. Methods and kits for treating or preventing recurrence of hyper proliferating diseases, e.g., cancer, are described. A method may comprise priming a mammal by administering to the mammal an effective amount of a chemotherapeutic agent and boosting the mammal by administering to the mammal an effective amount of an annexin chimeric fusion.

9 Claims, 8 Drawing Sheets

Specification includes a Sequence Listing.

(56) References Cited

OTHER PUBLICATIONS

Inada et al., "Evaluation of malignancy and the prognosis of esophageal cancer based on an immunohistochemical study (p53, E-cadherin, epidermal growth factor receptor)," Surg Today, 29:493-503 (1999).

International Search Report and Written Opinion for International Application No. PCT/US2016/013545 dated Apr. 26, 2016.

Kang et al., "Targeted coating with antigenic peptide renders tumor cells susceptible to CD8+ T cell-mediated killing," Mol Ther, 21:542-553 (2013).

Kersemaekers et al., "Oncogene alterations in carcinomas of the uterine cervix: overexpression of the epidermal growth factor receptor is associated with poor prognosis," Clin Cancer Res, 5:577-586 (1999).

Lin et al., "Treatment of established tumors with a novel vaccine that enhances major histocompatibility class II presentation of tumor antigen," Cancer Res, 56:21-26 (1996).

Lu et al., "Multiepitope Trojan antigen peptide vaccines for the induction of antituor CTL and Th immune responses," J Immunol, 172:4575-4582 (2004).

Maurizi et al., "Prognostic significance of epidermal growth factor receptor in laryngeal squamous cell carcinoma," Br J Cancer, 74:1253-1257 (1996).

Mellon et al., "Long-term outcome related to epidermal growth factor receptor status in bladder cancer," J Urol, 153:919-925 (1995).

Nicholson et al., "EGFR and cancer prognosis," Eur J Cancer, 37 Suppl 4:S9-15 (2001).

Normano et al., "Epidermal growth factor receptor (EGFR) signaling in cancer," Gene, 366:2-16 (2006).

Peng et al., "Effcient delivery of DNA vaccines using human papilomavirus pseudovirions," Gene Ther, 17:1453-1464 (2010).

Schmitt et al., "Apoptosis and therapy," J Pathol, 187:127-137 (1999).

Scholler et al., "Soluble member(s) of the mesothelin/megakarocyte potentiating factor family are detectable in sera from patients with ovarian carcinoma," Proc Natl Acad Sci USA, 96:11531-11536 (1999).

Sen et al., "Apoptosis biochemical events and relevance to cancer chemotherapy," FEBS Lett, 307:122-127 (1992).

Sznol et al., "Antigen-specific agents in development.," Semin Oncol, 24(2):173-186 (1997).

Tannous et al., "Codonoptimized Gaussia luciferase cDNA for mamalian gene expression in culture and in vivo," Mol Ther, 11:435-443 (2005).

Wang et al., "Intramuscular administration of E7-transfected dendritic cells generates the most potent E7-specific antitumor immunity," Gene Ther, 7:726-733 (2000).

* cited by examiner

A

B

SEQUENCE LISTING

<160> NUMBER OF SEQ ID NOS: 154

<210> SEQ ID NO 1
<211> LENGTH: 297
<212> TYPE: DNA
<213> ORGANISM: Human papillomavirus
<220> FEATURE:
<221> NAME/KEY: CDS
<222> LOCATION: (1)..(297)

<400> SEQUENCE: 1

```
atg cat gga gat aca cct aca ttg cat gaa tat atg tta gat ttg caa      48
Met His Gly Asp Thr Pro Thr Leu His Glu Tyr Met Leu Asp Leu Gln
1               5                   10                  15 cca gag aca act gat ctc tac tgt tat gag caa tta aat gac agc tca      96
Pro Glu Thr Thr Asp Leu Tyr Cys Tyr Glu Gln Leu Asn Asp Ser Ser
                20                  25                  30 gag gag gag gat gaa ata gat ggt cca gct gga caa gca gaa ccg gac     144
Glu Glu Glu Asp Glu Ile Asp Gly Pro Ala Gly Gln Ala Glu Pro Asp
            35                  40                  45 aga gcc cat tac aat att gta acc ttt tgt tgc aag tgt gac tct acg     192
Arg Ala His Tyr Asn Ile Val Thr Phe Cys Cys Lys Cys Asp Ser Thr
        50                  55                  60 ctt cgg ttg tgc gta caa agc aca cac gta gac att cgt act ttg gaa     240
Leu Arg Leu Cys Val Gln Ser Thr His Val Asp Ile Arg Thr Leu Glu
65                  70                  75                  80 gac ctg tta atg ggc aca cta gga att gtg tgc ccc atc tgt tct cag     288
Asp Leu Leu Met Gly Thr Leu Gly Ile Val Cys Pro Ile Cys Ser Gln
                85                  90                  95
```

```
gat aag ctt                                                              297
Asp Lys Leu <210> SEQ ID NO 2
<211> LENGTH: 99
<212> TYPE: PRT
<213> ORGANISM: Human papillomavirus

<400> SEQUENCE: 2

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Asp Lys Leu

<210> SEQ ID NO 3
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met His Gly Asp Thr Pro Thr Leu His Glu Tyr Met Leu Asp Leu Gln
1               5                   10                  15

Pro Glu Thr Thr Asp Leu Tyr Gly Tyr Glu Gly Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 4
<211> LENGTH: 477
<212> TYPE: DNA
<213> ORGANISM: Human papillomavirus
<220> FEATURE:
<221> NAME/KEY: CDS
<222> LOCATION: (1)..(474)

<400> SEQUENCE: 4 atg cac caa aag aga act gca atg ttt cag gac cca cag gag cga ccc    48
Met His Gln Lys Arg Thr Ala Met Phe Gln Asp Pro Gln Glu Arg Pro
1               5                   10                  15 aga aag tta cca cag tta tgc aca gag ctg caa aca act ata cat gat    96
```

```
Arg Lys Leu Pro Gln Leu Cys Thr Glu Leu Gln Thr Thr Ile His Asp
            20                  25                  30 ata ata tta gaa tgt gtg tac tgc aag caa cag tta ctg cga cgt gag      144
Ile Ile Leu Glu Cys Val Tyr Cys Lys Gln Gln Leu Leu Arg Arg Glu
            35                  40                  45 gta tat gac ttt gct ttt cgg gat tta tgc ata gta tat aga gat ggg      192
Val Tyr Asp Phe Ala Phe Arg Asp Leu Cys Ile Val Tyr Arg Asp Gly
 50                  55                  60 aat cca tat gct gta tgt gat aaa tgt tta aag ttt tat tct aaa att      240
Asn Pro Tyr Ala Val Cys Asp Lys Cys Leu Lys Phe Tyr Ser Lys Ile
 65                  70                  75                  80 agt gag tat aga cat tat tgt tat agt ttg tat gga aca aca tta gaa      288
Ser Glu Tyr Arg His Tyr Cys Tyr Ser Leu Tyr Gly Thr Thr Leu Glu
                 85                  90                  95 cag caa tac aac aaa ccg ttg tgt gat ttg tta att agg tgt att aac      336
Gln Gln Tyr Asn Lys Pro Leu Cys Asp Leu Leu Ile Arg Cys Ile Asn
            100                 105                 110 tgt caa aag cca ctg tgt cct gaa gaa aag caa aga cat ctg gac aaa      384
Cys Gln Lys Pro Leu Cys Pro Glu Glu Lys Gln Arg His Leu Asp Lys
            115                 120                 125 aag caa aga ttc cat aat ata agg ggt cgg tgg acc ggt cga tgt atg      432
Lys Gln Arg Phe His Asn Ile Arg Gly Arg Trp Thr Gly Arg Cys Met
130                 135                 140 tct tgt tgc aga tca tca aga aca cgt aga gaa acc cag ctg taa          477
Ser Cys Cys Arg Ser Ser Arg Thr Arg Arg Glu Thr Gln Leu
145                 150                 155

<210> SEQ ID NO 5
<211> LENGTH: 158
<212> TYPE: PRT
<213> ORGANISM: Human papillomavirus

<400> SEQUENCE: 5

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
            35                  40                  45

Val Tyr Asp Phe Ala Phe Arg Asp Leu Cys Ile Val Tyr Arg Asp Gly
 50                  55                  60

Asn Pro Tyr Ala Val Cys Asp Lys Cys Leu Lys Phe Tyr Ser Lys Ile
 65                  70                  75                  80

Ser Glu Tyr Arg His Tyr Cys Tyr Ser Leu Tyr Gly Thr Thr Leu Glu
                 85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
            115                 120                 125

Lys Gln Arg Phe His Asn Ile Arg Gly Arg Trp Thr Gly Arg Cys Met
130                 135                 140

Ser Cys Cys Arg Ser Ser Arg Thr Arg Arg Glu Thr Gln Leu
145                 150                 155

<210> SEQ ID NO 6
<211> LENGTH: 151
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 6

```
Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150
```

<210> SEQ ID NO 7
<211> LENGTH: 1698
<212> TYPE: DNA
<213> ORGANISM: Influenza virus

<400> SEQUENCE: 7

| | |
|---|---|
| atgaaggcaa acctactggt cctgttaagt gcacttgcag ctgcagatgc agacacaata | 60 |
| tgtataggct accatgcgaa caattcaacc gacactgttg acacagtact cgagaagaat | 120 |
| gtgacagtga cacactctgt taacctgctc gaagacagcc acaacggaaa actatgtaga | 180 |
| ttaaaaggaa tagccccact acaattgggg aaatgtaaca tcgccggatg gctcttggga | 240 |
| aacccagaat gcgacccact gcttccagtg agatcatggt cctacattgt agaaacacca | 300 |
| aactctgaga tggaatatg ttatccagga gatttcatcg actatgagga gctgagggag | 360 |
| caattgagct cagtgtcatc attcgaaaga ttcgaaatat ttcccaaaga aagctcatgg | 420 |
| cccaaccaca cacaaacgg agtaacggca gcatgctccc atgaggggaa aagcagtttt | 480 |
| tacagaaatt tgctatggct gacggagaag gagggctcat acccaaagct gaaaaattct | 540 |
| tatgtgaaca aaaagggaa agaagtcctt gtactgtggg gtattcatca cccgcctaac | 600 |
| agtaaggaac aacagaatat ctatcagaat gaaaatgctt atgtctctgt agtgacttca | 660 |
| aattataaca ggagatttac cccggaaata gcagaaagac ccaaagtaag agatcaagct | 720 |
| gggaggatga actattactg gaccttgcta aaacccggag acacaataat atttgaggca | 780 |
| aatggaaatc taatagcacc aatgtatgct ttcgcactga gtagaggctt tgggtccggc | 840 |
| atcatcacct caaacgcatc aatgcatgag tgtaacacga gtgtcaaac cccctggga | 900 |
| gctataaaca gcagtctccc ttaccagaat atacacccag tcacaatagg agagtgccca | 960 |
| aaatacgtca ggagtgccaa attgaggatg gttacaggac taaggaacac tccgtccatt | 1020 |
| caatccagag gtctatttgg agccattgcc ggttttattg aaggggatg gactggaatg | 1080 |

```
atagatggat ggtatggtta tcatcatcag aatgaacagg gatcaggcta tgcagcggat    1140
caaaaaagca cacaaaatgc cattaacggg attacaaaca aggtgaacac tgttatcgag    1200
aaaatgaaca ttcaattcac agctgtgggt aaagaattca acaaattaga aaaaggatg    1260 gaaaatttaa ataaaaaagt tgatgatgga tttctggaca tttggacata taatgcagaa    1320
ttgttagttc tactggaaaa tgaaaggact ctggatttcc atgactcaaa tgtgaagaat    1380
ctgtatgaga agtaaaaag ccaattaaag aataatgcca agaaatcgg aaatggatgt    1440 tttgagttct accacaagtg tgacaatgaa tgcatggaaa gtgtaagaaa tgggacttat    1500
gattatccca atattcaga agagtcaaag ttgaacaggg aaaaggtaga tggagtgaaa    1560
ttggaatcaa tggggatcta tcagattctg gcgatctact caactgtcgc cagttcactg    1620
gtgcttttgg tctccctggg ggcaatcagt ttctggatgt gttctaatgg atctttgcag    1680
tgcagaatat gcatctga                                                  1698
```

<210> SEQ ID NO 8
<211> LENGTH: 565
<212> TYPE: PRT
<213> ORGANISM: Influenza virus

<400> SEQUENCE: 8

```
Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
        50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
```

```
                260                 265                 270
Leu Ser Arg Gly Phe Gly Ser Gly Ile Ile Thr Ser Asn Ala Ser Met
    275                 280                 285

His Glu Cys Asn Thr Lys Cys Gln Thr Pro Leu Gly Ala Ile Asn Ser
290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 9
<211> LENGTH: 386
<212> TYPE: PRT
<213> ORGANISM: Gallus gallus

<400> SEQUENCE: 9

Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
            20                  25                  30

Ile Ala Ile Met Ser Ala Leu Ala Met Val Tyr Leu Gly Ala Lys Asp
        35                  40                  45

Ser Thr Arg Thr Gln Ile Asn Lys Val Val Arg Phe Asp Lys Leu Pro
    50                  55                  60
```

```
Gly Phe Gly Asp Ser Ile Glu Ala Gln Cys Gly Thr Ser Val Asn Val
 65                  70                  75                  80

His Ser Ser Leu Arg Asp Ile Leu Asn Gln Ile Thr Lys Pro Asn Asp
                 85                  90                  95

Val Tyr Ser Phe Ser Leu Ala Ser Arg Leu Tyr Ala Glu Arg Tyr
            100                 105                 110

Pro Ile Leu Pro Glu Tyr Leu Gln Cys Val Lys Glu Leu Tyr Arg Gly
            115                 120                 125

Gly Leu Glu Pro Ile Asn Phe Gln Thr Ala Ala Asp Gln Ala Arg Glu
            130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
            165                 170                 175

Asn Ala Ile Val Phe Lys Gly Leu Trp Glu Lys Thr Phe Lys Asp Glu
            180                 185                 190

Asp Thr Gln Ala Met Pro Phe Arg Val Thr Glu Gln Glu Ser Lys Pro
            195                 200                 205

Val Gln Met Met Tyr Gln Ile Gly Leu Phe Arg Val Ala Ser Met Ala
            210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
                260                 265                 270

Val Met Glu Glu Arg Lys Ile Lys Val Tyr Leu Pro Arg Met Lys Met
            275                 280                 285

Glu Glu Lys Tyr Asn Leu Thr Ser Val Leu Met Ala Met Gly Ile Thr
            290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
            355                 360                 365

Ile Lys His Ile Ala Thr Asn Ala Val Leu Phe Phe Gly Arg Cys Val
            370                 375                 380

Ser Pro
385

<210> SEQ ID NO 10
<211> LENGTH: 501
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atggcggccc ccggcgcccg gcggccgctg ctcctgctgc tgctggcagg ccttgcacat     60
ggcgcctcag cactctttga ggatctaatc atgcatggag atacacctac attgcatgaa    120
tatatgttag atttgcaacc agagacaact gatctctact gttatgagca attaaatgac    180
```

```
agctcagagg aggaggatga aatagatggt ccagctggac aagcagaacc ggacagagcc    240
cattacaata ttgttacctt ttgttgcaag tgtgactcta cgcttcggtt gtgcgtacaa    300
agcacacacg tagacattcg tactttggaa gacctgttaa tgggcacact aggaattgtg    360
tgccccatct gttctcagga tcttaacaac atgttgatcc ccattgctgt gggcggtgcc    420
ctggcagggc tggtcctcat cgtcctcatt gcctacctca ttggcaggaa gaggagtcac    480
gccggctatc agaccatcta g                                              501
```

<210> SEQ ID NO 11
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Ala Ala Pro Gly Ala Arg Arg Pro Leu Leu Leu Leu Leu Leu Ala
1               5                   10                  15

Gly Leu Ala His Gly Ala Ser Ala Leu Phe Glu Asp Leu Ile Met His
            20                  25                  30

Gly Asp Thr Pro Thr Leu His Glu Tyr Met Leu Asp Leu Gln Pro Glu
        35                  40                  45

Thr Thr Asp Leu Tyr Cys Tyr Glu Gln Leu Asn Asp Ser Ser Glu Glu
    50                  55                  60

Glu Asp Glu Ile Asp Gly Pro Ala Gly Gln Ala Glu Pro Asp Arg Ala
65                  70                  75                  80

His Tyr Asn Ile Val Thr Phe Cys Cys Lys Cys Asp Ser Thr Leu Arg
                85                  90                  95

Leu Cys Val Gln Ser Thr His Val Asp Ile Arg Thr Leu Glu Asp Leu
            100                 105                 110

Leu Met Gly Thr Leu Gly Ile Val Cys Pro Ile Cys Ser Gln Asp Leu
        115                 120                 125

Asn Asn Met Leu Ile Pro Ile Ala Val Gly Gly Ala Leu Ala Gly Leu
    130                 135                 140

Val Leu Ile Val Leu Ile Ala Tyr Leu Ile Gly Arg Lys Arg Ser His
145                 150                 155                 160

Ala Gly Tyr Gln Thr Ile
                165

<210> SEQ ID NO 12
<211> LENGTH: 5915
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
gacggatcgg gagatctccc gatcccctat ggtcgactct cagtacaatc tgctctgatg    60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
```

```
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagaattca    960
tggcggcccc cggcgcccgg cggccgctgc tcctgctgct gctggcaggc cttgcacatg   1020
gcgcctcagc actctttgag gatctaatca tgcatggaga tacacctaca ttgcatgaat   1080
atatgttaga tttgcaacca gagacaactg atctctactg ttatgagcaa ttaaatgaca   1140
gctcagagga ggaggatgaa atagatggtc cagctggaca agcagaaccg gacagagccc   1200
attacaatat tgttaccttt tgttgcaagt gtgactctac gcttcggttg tgcgtacaaa   1260
gcacacacgt agacattcgt actttggaag acctgttaat gggcacacta ggaattgtgt   1320
gccccatctg ttctcaggat cttaacaaca tgttgatccc cattgctgtg gcggtgccc   1380
tggcagggct ggtcctcatc gtcctcattg cctacctcat tggcaggaag aggagtcacg   1440
ccggctatca gaccatctag ggatccgagc tcggtaccaa gcttaagttt aaaccgctga   1500
tcagcctcga ctgtgccttc tagttgccag ccatctgttg tttgcccctc cccgtgcct   1560
tccttgaccc tggaaggtgc cactcccact gtcctttcct aataaaatga ggaaattgca   1620
tcgcattgtc tgagtaggtg tcattctatt ctggggggtg gggtggggca ggacagcaag   1680
ggggaggatt gggaagacaa tagcaggcat gctgggatg cggtgggctc tatggcttct   1740
gaggcggaaa gaaccagctg gggctctagg gggtatcccc acgcgccctg tagcggcgca   1800
ttaagcgcgg cgggtgtggt ggttacgcgc agcgtgaccg ctacacttgc cagcgcccta   1860
gcgcccgctc ctttcgcttt cttcccttcc tttctcgcca cgttcgccgg ctttccccgt   1920
caagctctaa atcggggcat ccctttaggg ttccgattta gtgctttacg cacctcgac   1980
cccaaaaaac ttgattaggg tgatggttca cgtagtgggc catcgccctg atagacggtt   2040
tttcgccctt tgacgttgga gtccacgttc tttaatagtg gactcttgtt ccaaactgga   2100
acaacactca accctatctc ggtctattct tttgatttat aagggatttt ggggatttcg   2160
gcctattggt taaaaatga gctgatttaa caaaaattta acgcgaatta attctgtgga   2220
atgtgtgtca gttagggtgt ggaaagtccc caggctcccc aggcaggcag aagtatgcaa   2280
agcatgcatc tcaattagtc agcaaccagg tgtggaaagt ccccaggctc ccagcaggc   2340
agaagtatgc aaagcatgca tctcaattag tcagcaacca tagtcccgcc cctaactccg   2400
cccatcccgc ccctaactcc gcccagttcc gcccattctc cgccccatgg ctgactaatt   2460
ttttttattt atgcagaggc cgaggccgcc tctgcctctg agctattcca gaagtagtga   2520
ggaggctttt ttggaggcct aggcttttgc aaaaagctcc cggagcttg tatatccatt    2580
ttcggatctg atcaagagac aggatgagga tcgtttcgca tgattgaaca agatggattg   2640
cacgcaggtt ctccggccgc ttgggtggag aggctattcg gctatgactg ggcacaacag   2700
```

```
acaatcggct gctctgatgc cgccgtgttc cggctgtcag cgcaggggcg cccggttctt    2760
tttgtcaaga ccgacctgtc cggtgccctg aatgaactgc aggacgaggc agcgcggcta    2820
tcgtggctgg ccacgacggg cgttccttgc gcagctgtgc tcgacgttgt cactgaagcg    2880
ggaagggact ggctgctatt gggcgaagtg ccggggcagg atctcctgtc atctcacctt    2940
gctcctgccg agaaagtatc catcatggct gatgcaatgc ggcggctgca tacgcttgat    3000
ccggctacct gcccattcga ccaccaagcg aaacatcgca tcgagcgagc acgtactcgg    3060
atggaagccg tcttgtcga tcaggatgat ctggacgaag agcatcaggg gctcgcgcca    3120
gccgaactgt tcgccaggct caaggcgcgc atgcccgacg cgaggatctc gtcgtgacc     3180
catggcgatg cctgcttgcc gaatatcatg gtggaaaatg gccgcttttc tggattcatc    3240
gactgtggcc ggctgggtgt ggcggaccgc tatcaggaca tagcgttggc tacccgtgat    3300
attgctgaag agcttggcgg cgaatgggct gaccgcttcc tcgtgcttta cggtatcgcc    3360
gctcccgatt cgcagcgcat cgccttctat cgccttcttg acgagttctt ctgagcggga    3420
ctctggggtt cgaaatgacc gaccaagcga cgcccaacct gccatcacga gatttcgatt    3480
ccaccgccgc cttctatgaa aggttgggct tcggaatcgt tttccgggac gccggctgga    3540
tgatcctcca gcgcggggat ctcatgctgg agttcttcgc ccaccccaac ttgtttattg    3600
cagcttataa tggttacaaa taaagcaata gcatcacaaa tttcacaaat aaagcatttt    3660
tttcactgca ttctagttgt ggtttgtcca aactcatcaa tgtatcttat catgtctgta    3720
taccgtcgac ctctagctag agcttggcgt aatcatggtc atagctgttt cctgtgtgaa    3780
attgttatcc gctcacaatt ccacacaaca tacgagccgg aagcataaag tgtaaagcct    3840
ggggtgccta atgagtgagc taactcacat taattgcgtt gcgctcactg cccgctttcc    3900
agtcgggaaa cctgtcgtgc cagctgcatt aatgaatcgg ccaacgcgcg gggagaggcg    3960
gtttgcgtat tgggcgctct tccgcttcct cgctcactga ctcgctgcgc tcggtcgttc    4020
ggctgcggcg agcggtatca gctcactcaa aggcggtaat acggttatcc acagaatcag    4080
gggataacgc aggaaagaac atgtgagcaa aaggccagca aaaggccagg aaccgtaaaa    4140
aggccgcgtt gctggcgttt ttccataggc tccgcccccc tgacgagcat cacaaaaatc    4200
gacgctcaag tcagaggtgg cgaaacccga caggactata agataccag gcgtttcccc    4260
ctggaagctc cctcgtgcgc tctcctgttc cgaccctgcc gcttaccgga tacctgtccg    4320
cctttctccc ttcgggaagc gtggcgcttt ctcaatgctc acgctgtagg tatctcagtt    4380
cggtgtaggt cgttcgctcc aagctgggct gtgtgcacga accccccgtt cagcccgacc    4440
gctgcgcctt atccggtaac tatcgtcttg agtccaaccc ggtaagacac gacttatcgc    4500
cactggcagc agccactggt aacaggatta gcagagcgag gtatgtaggc ggtgctacag    4560
agttcttgaa gtggtggcct aactacggct acactagaag gacagtattt ggtatctgcg    4620
ctctgctgaa gccagttacc ttcggaaaaa gagttggtag ctcttgatcc ggcaaacaaa    4680
ccaccgctgg tagcggtggt ttttttgttt gcaagcagca gattacgcgc agaaaaaaag    4740
gatctcaaga agatcctttg atcttttcta cggggtctga cgctcagtgg aacgaaaact    4800
cacgttaagg gattttggtc atgagattat caaaaaggat cttcacctag atccttttaa    4860
attaaaaatg aagttttaaa tcaatctaaa gtatatatga gtaaacttgg tctgacagtt    4920
accaatgctt aatcagtgag gcacctatct cagcgatctg tctatttcgt tcatccatag    4980
ttgcctgact ccccgtcgtg tagataacta cgatacggga gggcttacca tctggcccca    5040
gtgctgcaat gataccgcga gacccacgct caccggctcc agatttatca gcaataaacc    5100
```

```
agccagccgg aagggccgag cgcagaagtg gtcctgcaac tttatccgcc tccatccagt    5160
ctattaattg ttgccgggaa gctagagtaa gtagttcgcc agttaatagt ttgcgcaacg    5220
ttgttgccat tgctacaggc atcgtggtgt cacgctcgtc gtttggtatg gcttcattca    5280
gctccggttc ccaacgatca aggcgagtta catgatcccc catgttgtgc aaaaaagcgg    5340
ttagctcctt cggtcctccg atcgttgtca gaagtaagtt ggccgcagtg ttatcactca    5400
tggttatggc agcactgcat aattctctta ctgtcatgcc atccgtaaga tgcttttctg    5460
tgactggtga gtactcaacc aagtcattct gagaatagtg tatgcggcga ccgagttgct    5520
cttgcccggc gtcaatacgg gataataccg cgccacatag cagaacttta aaagtgctca    5580
tcattggaaa acgttcttcg gggcgaaaac tctcaaggat cttaccgctg ttgagatcca    5640
gttcgatgta acccactcgt gcacccaact gatcttcagc atcttttact ttcaccagcg    5700
tttctgggtg agcaaaaaca ggaaggcaaa atgccgcaaa aaagggaata agggcgacac    5760
ggaaatgttg aatactcata ctcttccttt tcaatatta ttgaagcatt tatcagggtt    5820
attgtctcat gagcggatac atatttgaat gtatttagaa aaataaacaa atagggg ttc    5880 cgcgcacatt tccccgaaaa gtgccacctg acgtc                               5915

<210> SEQ ID NO 13
<211> LENGTH: 1878
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atggctcgtg cggtcgggat cgacctcggg accaccaact ccgtcgtctc ggttctggaa      60
ggtggcgacc cggtcgtcgt cgccaactcc gagggctcca ggaccacccc gtcaattgtc     120
gcgttcgccc gcaacggtga ggtgctggtc ggccagcccg ccaagaacca ggcagtgacc     180
aacgtcgatc gcaccgtgcg ctcggtcaag cgacacatgg gcagcgactg gtccatagag     240
attgacggca agaaatacac cgcgccggag atcagcgccc gcattctgat gaagctgaag     300
cgcgacgccg aggcctacct cggtgaggac attaccgacg cggttatcac gacgcccgcc     360
tacttcaatg acgcccagcg tcaggccacc aaggacgccg ccagatcgc cggcctcaac      420 gtgctgcgga tcgtcaacga gccgaccgcg gccgcgctgg cctacggcct cgacaagggc     480
gagaaggagc agcgaatcct ggtcttcgac ttgggtggtg gcactttcga cgtttccctg     540
ctggagatcg gcgagggtgt ggttgaggtc cgtgccactt cgggtgacaa ccacctcggc     600
ggcgacgact gggaccagcg ggtcgtcgat tggctggtgg acaagttcaa gggcaccagc     660
ggcatcgatc tgaccaagga caagatggcg atgcagcggc tgcgggaagc cgccgagaag     720
gcaaagatcg agctgagttc gagtcagtcc acctcgatca acctgcccta catcaccgtc     780
gacgccgaca gaacccgtt gttcttagac gagcagctga cccgcgcgga gttccaacgg     840
atcactcagg acctgctgga ccgcactcgc aagccgttcc agtcggtgat cgctgacacc     900
ggcatttcgg tgtcggagat cgatcacgtt gtgctcgtgg gtggttcgac ccggatgccc     960
gcggtgaccg atctggtcaa ggaactcacc ggcggcaagg aacccaacaa gggcgtcaac    1020
cccgatgagg ttgtcgcggt gggagccgct ctgcaggccg gcgtcctcaa gggcgaggtg    1080
aaagacgttc tgctgcttga tgttacccgc ctgagcctgg gtatcgagac caagggcggg    1140
gtgatgacca ggctcatcga gcgcaacacc acgatcccca ccaagcggtc ggagactttc    1200
```

```
accaccgccg acgacaacca accgtcggtg cagatccagg tctatcaggg ggagcgtgag    1260
atcgccgcgc acaacaagtt gctcgggtcc ttcgagctga ccggcatccc gccggcgccg    1320
cgggggattc cgcagatcga ggtcactttc gacatcgacg ccaacggcat tgtgcacgtc    1380
accgccaagg acaagggcac cggcaaggag aacacgatcc gaatccagga aggctcgggc    1440
ctgtccaagg aagacattga ccgcatgatc aaggacgccg aagcgcacgc cgaggaggat    1500
cgcaagcgtc gcgaggaggc cgatgttcgt aatcaagccg agacattggt ctaccagacg    1560
gagaagttcg tcaaagaaca gcgtgaggcc gagggtggtt cgaaggtacc tgaagacacg    1620
ctgaacaagg ttgatgccgc ggtggcgaaa gcgaaggcgg cacttggcgg atcggatatt    1680
tcggccatca agtcggcgat ggagaagctg gccaggagt cgcaggctct ggggcaagcg    1740
atctacgaag cagctcaggc tgcgtcacag gccactggcg ctgcccaccc cggcggcgag    1800
ccgggcggtg cccaccccgg ctcggctgat gacgttgtgg acgcggaggt ggtcgacgac    1860
ggccgggagg ccaagtga                                                  1878
```

<210> SEQ ID NO 14
<211> LENGTH: 625
<212> TYPE: PRT
<213> ORGANISM: Mycobacterium tuberculosis

<400> SEQUENCE: 14

```
Met Ala Arg Ala Val Gly Ile Asp Leu Gly Thr Thr Asn Ser Val Val
1               5                   10                  15

Ser Val Leu Glu Gly Gly Asp Pro Val Val Ala Asn Ser Glu Gly
            20                  25                  30

Ser Arg Thr Thr Pro Ser Ile Val Ala Phe Ala Arg Asn Gly Glu Val
        35                  40                  45

Leu Val Gly Gln Pro Ala Lys Asn Gln Ala Val Thr Asn Val Asp Arg
    50                  55                  60

Thr Val Arg Ser Val Lys Arg His Met Gly Ser Asp Trp Ser Ile Glu
65                  70                  75                  80

Ile Asp Gly Lys Lys Tyr Thr Ala Pro Glu Ile Ser Ala Arg Ile Leu
                85                  90                  95

Met Lys Leu Lys Arg Asp Ala Glu Ala Tyr Leu Gly Glu Asp Ile Thr
            100                 105                 110

Asp Ala Val Ile Thr Thr Pro Ala Tyr Phe Asn Asp Ala Gln Arg Gln
        115                 120                 125

Ala Thr Lys Asp Ala Gly Gln Ile Ala Gly Leu Asn Val Leu Arg Ile
    130                 135                 140

Val Asn Glu Pro Thr Ala Ala Ala Leu Ala Tyr Gly Leu Asp Lys Gly
145                 150                 155                 160

Glu Lys Glu Gln Arg Ile Leu Val Phe Asp Leu Gly Gly Gly Thr Phe
                165                 170                 175

Asp Val Ser Leu Leu Glu Ile Gly Glu Gly Val Val Glu Val Arg Ala
            180                 185                 190

Thr Ser Gly Asp Asn His Leu Gly Gly Asp Asp Trp Asp Gln Arg Val
        195                 200                 205

Val Asp Trp Leu Val Asp Lys Phe Lys Gly Thr Ser Gly Ile Asp Leu
    210                 215                 220

Thr Lys Asp Lys Met Ala Met Gln Arg Leu Arg Glu Ala Ala Glu Lys
225                 230                 235                 240

Ala Lys Ile Glu Leu Ser Ser Ser Gln Ser Thr Ser Ile Asn Leu Pro
```

```
                    245                 250                 255
        Tyr Ile Thr Val Asp Ala Asp Lys Asn Pro Leu Phe Leu Asp Glu Gln
                        260                 265                 270

Leu Thr Arg Ala Glu Phe Gln Arg Ile Thr Gln Asp Leu Leu Asp Arg
                        275                 280                 285

Thr Arg Lys Pro Phe Gln Ser Val Ile Ala Asp Thr Gly Ile Ser Val
                        290                 295                 300

Ser Glu Ile Asp His Val Val Leu Val Gly Gly Ser Thr Arg Met Pro
        305                 310                 315                 320

Ala Val Thr Asp Leu Val Lys Glu Leu Thr Gly Gly Lys Glu Pro Asn
                        325                 330                 335

Lys Gly Val Asn Pro Asp Glu Val Val Ala Val Gly Ala Ala Leu Gln
                        340                 345                 350

Ala Gly Val Leu Lys Gly Glu Val Lys Asp Val Leu Leu Leu Asp Val
                        355                 360                 365

Thr Pro Leu Ser Leu Gly Ile Glu Thr Lys Gly Gly Val Met Thr Arg
                        370                 375                 380

Leu Ile Glu Arg Asn Thr Thr Ile Pro Thr Lys Arg Ser Glu Thr Phe
        385                 390                 395                 400

Thr Thr Ala Asp Asp Asn Gln Pro Ser Val Gln Ile Gln Val Tyr Gln
                        405                 410                 415

Gly Glu Arg Glu Ile Ala Ala His Asn Lys Leu Leu Gly Ser Phe Glu
                        420                 425                 430

Leu Thr Gly Ile Pro Pro Ala Pro Arg Gly Ile Pro Gln Ile Glu Val
                        435                 440                 445

Thr Phe Asp Ile Asp Ala Asn Gly Ile Val His Val Thr Ala Lys Asp
                        450                 455                 460

Lys Gly Thr Gly Lys Glu Asn Thr Ile Arg Ile Gln Glu Gly Ser Gly
        465                 470                 475                 480

Leu Ser Lys Glu Asp Ile Asp Arg Met Ile Lys Asp Ala Glu Ala His
                        485                 490                 495

Ala Glu Glu Asp Arg Lys Arg Arg Glu Glu Ala Asp Val Arg Asn Gln
                        500                 505                 510

Ala Glu Thr Leu Val Tyr Gln Thr Glu Lys Phe Val Lys Glu Gln Arg
                        515                 520                 525

Glu Ala Glu Gly Gly Ser Lys Val Pro Glu Asp Thr Leu Asn Lys Val
                        530                 535                 540

Asp Ala Ala Val Ala Glu Ala Lys Ala Ala Leu Gly Gly Ser Asp Ile
        545                 550                 555                 560

Ser Ala Ile Lys Ser Ala Met Glu Lys Leu Gly Gln Glu Ser Gln Ala
                        565                 570                 575

Leu Gly Gln Ala Ile Tyr Glu Ala Ala Gln Ala Ala Ser Gln Ala Thr
                        580                 585                 590

Gly Ala Ala His Pro Gly Gly Glu Pro Gly Gly Ala His Pro Gly Ser
                        595                 600                 605

Ala Asp Asp Val Val Asp Ala Glu Val Val Asp Gly Arg Glu Ala
                        610                 615                 620

Lys
        625

<210> SEQ ID NO 15
<211> LENGTH: 2104
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 15

| | | | | | |
|---|---|---|---|---|---|
| atgcatggag | atacacctac | attgcatgaa | tatatgttag | atttgcaacc | agagacaact | 60 |
| gatctctact | gttatgagca | attaaatgac | agctcagagg | aggaggatga | aatagatggt | 120 |
| ccagctggac | aagcagaacc | ggacagagcc | cattacaata | ttgtaacctt | ttgttgcaag | 180 |
| tgtgactcta | cgcttcggtt | gtgcgtacaa | agcacacacg | tagacattcg | tactttggaa | 240 |
| gacctgttaa | tgggcacact | aggaattgtg | tgccccatct | gttctcaagg | atccatggct | 300 |
| cgtgcggtcg | ggatcgacct | cgggaccacc | aactccgtcg | tctcggttct | ggaaggtggc | 360 |
| gacccggtcg | tcgtcgccaa | ctccgagggc | tccaggacca | ccccgtcaat | tgtcgcgttc | 420 |
| gcccgcaacg | gtgaggtgct | ggtcggccag | cccgccaaga | accaggcagt | gaccaacgtc | 480 |
| gatcgcaccg | tgcgctcggt | caagcgacac | atgggcagcg | actggtccat | agagattgac | 540 |
| ggcaagaaat | acaccgcgcc | ggagatcagc | gcccgcattc | tgatgaagct | gaagcgcgac | 600 |
| gccgaggcct | acctcggtga | ggacattacc | gacgcggtta | tcacgacgcc | cgcctacttc | 660 |
| aatgacgccc | agcgtcaggc | caccaaggac | gccggccaga | tcgccggcct | caacgtgctg | 720 |
| cggatcgtca | cgagccgac | cgcggccgcg | ctggcctacg | gcctcgacaa | gggcgagaag | 780 |
| gagcagcgaa | tcctggtctt | cgacttgggt | ggtggcactt | tcgacgtttc | cctgctggag | 840 |
| atcggcgagg | gtgtggttga | ggtccgtgcc | acttcgggtg | acaaccacct | cggcggcgac | 900 |
| gactgggacc | agcgggtcgt | cgattggctg | gtggacaagt | tcaagggcac | cagcggcatc | 960 |
| gatctgacca | aggacaagat | ggcgatgcag | cggctgcggg | aagccgccga | gaaggcaaag | 1020 |
| atcgagctga | gttcgagtca | gtccaccttcg | atcaacctgc | cctacatcac | cgtcgacgcc | 1080 |
| gacaagaacc | cgttgttctt | agacgagcag | ctgacccgcg | cggagttcca | acggatcact | 1140 |
| caggacctgt | ggaccgcac | tcgcaagccg | ttccagtcgg | tgatcgctga | caccggcatt | 1200 |
| tcggtgtcgg | agatcgatca | cgttgtgctc | gtgggtggtt | cgacccggat | gccgcgggtg | 1260 |
| accgatctgg | tcaaggaact | caccggcggc | aaggaaccca | acaagggcgt | caaccccgat | 1320 |
| gaggttgtcg | cggtgggagc | cgctctgcag | gccggcgtcc | tcaagggcga | ggtgaaagac | 1380 |
| gttctgctgc | ttgatgttac | cccgctgagc | ctgggtatcg | agaccaaggg | cggggtgatg | 1440 |
| accaggctca | tcgagcgcaa | caccacgatc | cccaccaagc | ggtcggagac | tttcaccacc | 1500 |
| gccgacgaca | accaaccgtc | ggtgcagatc | caggtctatc | aggggagcg | tgagatcgcc | 1560 |
| gcgcacaaca | agttgctcgg | gtccttcgag | ctgaccggca | tcccgccggc | gccgcggggg | 1620 |
| attccgcaga | tcgaggtcac | tttcgacatc | gacgccaacg | gcattgtgca | cgtcaccgcc | 1680 |
| aaggacaagg | gcaccggcaa | ggagaacacg | atccgaatcc | aggaaggctc | gggcctgtcc | 1740 |
| aaggaagaca | ttgaccgcat | gatcaaggac | gccgaagcgc | acgccgagga | ggatcgcaag | 1800 |
| cgtcgcgagg | aggccgatgt | tcgtaatcaa | gccgagacat | tggtctacca | gacggagaag | 1860 |
| ttcgtcaaag | aacagcgtga | ggccgagggt | ggttcgaagg | tacctgaaga | cacgctgaac | 1920 |
| aaggttgatg | ccgcggtggc | ggaagcgaag | gcggcacttg | gcggatcgga | tatttcggcc | 1980 |
| atcaagtcgg | cgatggagaa | gctgggccag | gagtcgcagg | ctctggggca | agcgatctac | 2040 |
| gaagcagctc | aggctgcgtc | acaggccact | ggcgctgccc | accccggctc | ggctgatgaa | 2100 |
| agca | | | | | | 2104 |

```
<210> SEQ ID NO 16
<211> LENGTH: 701
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16
```

| | | | | | | | | | | | | | | |
|---|---|---|---|---|---|---|---|---|---|---|---|---|---|---|
| Met | His | Gly | Asp | Thr | Pro | Thr | Leu | His | Glu | Tyr | Met | Leu | Asp | Leu | Gln |
| 1 | | | | 5 | | | | | 10 | | | | | 15 | |
| Pro | Glu | Thr | Thr | Asp | Leu | Tyr | Cys | Tyr | Glu | Gln | Leu | Asn | Asp | Ser | Ser |
| | | | 20 | | | | | 25 | | | | | 30 | | |
| Glu | Glu | Glu | Asp | Glu | Ile | Asp | Gly | Pro | Ala | Gly | Gln | Ala | Glu | Pro | Asp |
| | | 35 | | | | | 40 | | | | | 45 | | | |
| Arg | Ala | His | Tyr | Asn | Ile | Val | Thr | Phe | Cys | Cys | Lys | Cys | Asp | Ser | Thr |
| | 50 | | | | | 55 | | | | | 60 | | | | |
| Leu | Arg | Leu | Cys | Val | Gln | Ser | Thr | His | Val | Asp | Ile | Arg | Thr | Leu | Glu |
| 65 | | | | | 70 | | | | | 75 | | | | | 80 |
| Asp | Leu | Leu | Met | Gly | Thr | Leu | Gly | Ile | Val | Cys | Pro | Ile | Cys | Ser | Gln |
| | | | | 85 | | | | | 90 | | | | | 95 | |
| Gly | Ser | Met | Ala | Arg | Ala | Val | Gly | Ile | Asp | Leu | Gly | Thr | Thr | Asn | Ser |
| | | | 100 | | | | | 105 | | | | | 110 | | |
| Val | Val | Ser | Val | Leu | Glu | Gly | Gly | Asp | Pro | Val | Val | Ala | Asn | Ser | |
| | | 115 | | | | | 120 | | | | | 125 | | | |
| Glu | Gly | Ser | Arg | Thr | Thr | Pro | Ser | Ile | Val | Ala | Phe | Ala | Arg | Asn | Gly |
| | 130 | | | | | 135 | | | | | 140 | | | | |
| Glu | Val | Leu | Val | Gly | Gln | Pro | Ala | Lys | Asn | Gln | Ala | Val | Thr | Asn | Val |
| 145 | | | | | 150 | | | | | 155 | | | | | 160 |
| Asp | Arg | Thr | Val | Arg | Ser | Val | Lys | Arg | His | Met | Gly | Ser | Asp | Trp | Ser |
| | | | | 165 | | | | | 170 | | | | | 175 | |
| Ile | Glu | Ile | Asp | Gly | Lys | Lys | Tyr | Thr | Ala | Pro | Glu | Ile | Ser | Ala | Arg |
| | | | 180 | | | | | 185 | | | | | 190 | | |
| Ile | Leu | Met | Lys | Leu | Lys | Arg | Asp | Ala | Glu | Ala | Tyr | Leu | Gly | Glu | Asp |
| | | 195 | | | | | 200 | | | | | 205 | | | |
| Ile | Thr | Asp | Ala | Val | Ile | Thr | Thr | Pro | Ala | Tyr | Phe | Asn | Asp | Ala | Gln |
| | 210 | | | | | 215 | | | | | 220 | | | | |
| Arg | Gln | Ala | Thr | Lys | Asp | Ala | Gly | Gln | Ile | Ala | Gly | Leu | Asn | Val | Leu |
| 225 | | | | | 230 | | | | | 235 | | | | | 240 |
| Arg | Ile | Val | Asn | Glu | Pro | Thr | Ala | Ala | Ala | Leu | Ala | Tyr | Gly | Leu | Asp |
| | | | | 245 | | | | | 250 | | | | | 255 | |
| Lys | Gly | Glu | Lys | Glu | Gln | Arg | Ile | Leu | Val | Phe | Asp | Leu | Gly | Gly | Gly |
| | | | 260 | | | | | 265 | | | | | 270 | | |
| Thr | Phe | Asp | Val | Ser | Leu | Leu | Glu | Ile | Gly | Glu | Gly | Val | Val | Glu | Val |
| | | 275 | | | | | 280 | | | | | 285 | | | |
| Arg | Ala | Thr | Ser | Gly | Asp | Asn | His | Leu | Gly | Gly | Asp | Trp | Asp | Gln | |
| | 290 | | | | | 295 | | | | | 300 | | | | |
| Arg | Val | Val | Asp | Trp | Leu | Val | Asp | Lys | Phe | Lys | Gly | Thr | Ser | Gly | Ile |
| 305 | | | | | 310 | | | | | 315 | | | | | 320 |
| Asp | Leu | Thr | Lys | Asp | Lys | Met | Ala | Met | Gln | Arg | Leu | Arg | Glu | Ala | Ala |
| | | | | 325 | | | | | 330 | | | | | 335 | |
| Glu | Lys | Ala | Lys | Ile | Glu | Leu | Ser | Ser | Gln | Ser | Thr | Ser | Ile | Asn | |
| | | | 340 | | | | | 345 | | | | | 350 | | |
| Leu | Pro | Tyr | Ile | Thr | Val | Asp | Ala | Asp | Lys | Asn | Pro | Leu | Phe | Leu | Asp |
| | | 355 | | | | | 360 | | | | | 365 | | | |

```
Glu Gln Leu Thr Arg Ala Glu Phe Gln Arg Ile Thr Gln Asp Leu Leu
    370             375             380
Asp Arg Thr Arg Lys Pro Phe Gln Ser Val Ile Ala Asp Thr Gly Ile
385             390             395             400
Ser Val Ser Glu Ile Asp His Val Val Leu Val Gly Gly Ser Thr Arg
                405             410             415
Met Pro Ala Val Thr Asp Leu Val Lys Glu Leu Thr Gly Gly Lys Glu
            420             425             430
Pro Asn Lys Gly Val Asn Pro Asp Glu Val Val Ala Val Gly Ala Ala
        435             440             445
Leu Gln Ala Gly Val Leu Lys Gly Glu Val Lys Asp Val Leu Leu Leu
    450             455             460
Asp Val Thr Pro Leu Ser Leu Gly Ile Glu Thr Lys Gly Gly Val Met
465             470             475             480
Thr Arg Leu Ile Glu Arg Asn Thr Thr Ile Pro Thr Lys Arg Ser Glu
                485             490             495
Thr Phe Thr Thr Ala Asp Asp Asn Gln Pro Ser Val Gln Ile Gln Val
            500             505             510
Tyr Gln Gly Glu Arg Glu Ile Ala Ala His Asn Lys Leu Leu Gly Ser
        515             520             525
Phe Glu Leu Thr Gly Ile Pro Pro Ala Pro Arg Gly Ile Pro Gln Ile
    530             535             540
Glu Val Thr Phe Asp Ile Asp Ala Asn Gly Ile Val His Val Thr Ala
545             550             555             560
Lys Asp Lys Gly Thr Gly Lys Glu Asn Thr Ile Arg Ile Gln Glu Gly
                565             570             575
Ser Gly Leu Ser Lys Glu Asp Ile Asp Arg Met Ile Lys Asp Ala Glu
            580             585             590
Ala His Ala Glu Glu Asp Arg Lys Arg Arg Glu Ala Asp Val Arg
        595             600             605
Asn Gln Ala Glu Thr Leu Val Tyr Gln Thr Glu Lys Phe Val Lys Glu
    610             615             620
Gln Arg Glu Ala Glu Gly Gly Ser Lys Val Pro Glu Asp Thr Leu Asn
625             630             635             640
Lys Val Asp Ala Ala Val Ala Glu Ala Lys Ala Leu Gly Gly Ser
                645             650             655
Asp Ile Ser Ala Ile Lys Ser Ala Met Glu Lys Leu Gly Gln Glu Ser
            660             665             670
Gln Ala Leu Gly Gln Ala Ile Tyr Glu Ala Ala Gln Ala Ala Ser Gln
        675             680             685
Ala Thr Gly Ala Ala His Pro Gly Ser Ala Asp Glu Ser
    690             695             700

<210> SEQ ID NO 17
<211> LENGTH: 2760
<212> TYPE: DNA
<213> ORGANISM: Pseudomonas aeruginosa

<400> SEQUENCE: 17
ctgcagctgg tcaggccgtt ccgcaacgc ttgaagtcct ggccgatata ccggcagggc    60
cagccatcgt tcgacgaata aagccacctc agccatgatg cccttttccat ccccagcgga  120 accccgacat ggacgccaaa gccctgctcc tcggcagcct ctgccggcc gccccattcg    180 ccgacgcggc gacgctcgac aatgctctct ccgcctgcct cgccgcccgg ctcggtgcac  240
```

```
cgcacacggc ggagggccag ttgcacctgc cactcaccct tgaggcccgg cgctccaccg      300
gcgaatgcgg ctgtacctcg gcgctggtgc gatatcggct gctggccagg ggcgccagcg      360
ccgacagcct cgtgcttcaa gagggctgct cgatagtcgc caggacacgc cgcgcacgct      420
gaccctggcg gcggacgccg gcttggcgag cggccgcgaa ctggtcgtca ccctgggttg      480
tcaggcgcct gactgacagg ccgggctgcc accaccaggc cgagatggac gccctgcatg      540
tatcctccga tcggcaagcc tcccgttcgc acattcacca ctctgcaatc cagttcataa      600
atcccataaa agccctcttc cgctccccgc cagcctcccc gcatcccgca ccctagacgc      660
cccgccgctc tccgccggct cgcccgacaa gaaaaaccaa ccgctcgatc agcctcatcc      720
ttcacccatc acaggagcca tcgcgatgca cctgataccc cattggatcc ccctggtcgc      780
cagcctcggc ctgctcgccg gcggctcgtc cgcgtccgcc gccgaggaag ccttcgacct      840
ctggaacgaa tgcgccaaag cctgcgtgct cgacctcaag gacggcgtgc gttccagccg      900
catgagcgtc gacccggcca tcgccgacac caacggccag ggcgtgctgc actactccat      960
ggtcctggag ggcggcaacg acgcgctcaa gctggccatc gacaacgccc tcagcatcac     1020
cagcgacggc ctgaccatcc gcctcgaagg cggcgtcgag ccgaacaagc cggtgcgcta     1080
cagctacacg cgccaggcgc gcggcagttg gtcgctgaac tggctggtac cgatcggcca     1140
cgagaagccc tcgaacatca aggtgttcat ccacgaactg aacgccggca accagctcag     1200
ccacatgtcg ccgatctaca ccatcgagat gggcgacgag ttgctggcga agctggcgcg     1260
cgatgccacc ttcttcgtca gggcgcacga gagcaacgag atgcagccga cgctcgccat     1320
cagccatgcc ggggtcagcg tggtcatggc ccagacccag ccgcgccggg aaaagcgctg     1380
gagcgaatgg ccagcggca aggtgttgtg cctgctcgac ccgctggacg gggtctacaa     1440
ctacctcgcc cagcaacgct gcaacctcga cgatacctgg gaaggcaaga tctaccgggt     1500
gctcgccggc aacccggcga agcatgacct ggacatcaaa cccacggtca tcagtcatcg     1560
cctgcacttt cccgagggcg gcagcctggc cgcgctgacc gcgcaccagg cttgccacct     1620
gccgctggag actttcaccc gtcatcgcca gccgcgcggc tgggaacaac tggagcagtg     1680
cggctatccg gtgcagcggc tggtcgccct ctacctggcg gcgcggctgt cgtggaacca     1740
ggtcgaccag gtgatccgca acgccctggc cagccccggc agcggcggcg acctgggcga     1800
agcgatccgc gagcagccgg agcaggcccg tctggccctg accctggccg ccgccgagag     1860
cgagcgcttc gtccggcagg gcaccggcaa cgacgaggcc ggcgcggcca acgccgacgt     1920
ggtgagcctg acctgcccgg tcgccgccgg tgaatgcgcg ggcccggcgg acagcggcga     1980
cgccctgctg gagcgcaact atcccactgg cgcggagttc ctcggcgacg gcggcgacgt     2040
cagcttcagc acccgcggca cgcagaactg gacggtggag cggctgctcc aggcgcaccg     2100
ccaactggag gagcgcggct atgtgttcgt cggctaccac ggcaccttcc tcgaagcggc     2160
gcaaagcatc gtcttcggcg gggtgcgcgc gcgcagccag gacctcgacg cgatctggcg     2220
cggtttctat atcgccggcg atccggcgct ggcctacggc tacgcccagg accaggaacc     2280
cgacgcacgc ggccggatcc gcaacggtgc cctgctgcgg gtctatgtgc cgcgctcgag     2340
cctgccgggc ttctaccgca ccagcctgac cctggccgcg ccggaggcgg cgggcgaggt     2400
cgaacggctg atcggccatc cgctgccgct gcgcctggac gccatcaccg ccccgaggag     2460
ggaaggcggg cgcctggaga ccattctcgg ctggccgctg gccgagcgca ccgtggtgat     2520
tccctcggcg atccccaccg acccgcgcaa cgtcggcggc gacctcgacc cgtccagcat     2580
ccccgacaag gaacaggcga tcagcgccct gccggactac gccagccagc ccggcaaacc     2640
```

```
gccgcgcgag gacctgaagt aactgccgcg accggccggc tcccttcgca ggagccggcc   2700
ttctcggggc ctggccatac atcaggtttt cctgatgcca gcccaatcga atatgaattc   2760
```

<210> SEQ ID NO 18
<211> LENGTH: 638
<212> TYPE: PRT
<213> ORGANISM: Pseudomonas aeruginosa

<400> SEQUENCE: 18

```
Met His Leu Ile Pro His Trp Ile Pro Leu Val Ala Ser Leu Gly Leu
1               5                   10                  15

Leu Ala Gly Gly Ser Ser Ala Ser Ala Ala Glu Glu Ala Phe Asp Leu
            20                  25                  30

Trp Asn Glu Cys Ala Lys Ala Cys Val Leu Asp Leu Lys Asp Gly Val
        35                  40                  45

Arg Ser Ser Arg Met Ser Val Asp Pro Ala Ile Ala Asp Thr Asn Gly
    50                  55                  60

Gln Gly Val Leu His Tyr Ser Met Val Leu Glu Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
        115                 120                 125

Pro Ile Gly His Glu Lys Pro Ser Asn Ile Lys Val Phe Ile His Glu
    130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Val Met Ala Gln Thr Gln Pro Arg Arg
        195                 200                 205

Glu Lys Arg Trp Ser Glu Trp Ala Ser Gly Lys Val Leu Cys Leu Leu
    210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
            260                 265                 270

Leu His Phe Pro Glu Gly Gly Ser Leu Ala Ala Leu Thr Ala His Gln
        275                 280                 285

Ala Cys His Leu Pro Leu Glu Thr Phe Thr Arg His Arg Gln Pro Arg
    290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Asp Leu Gly Glu
            340                 345                 350
```

Ala Ile Arg Glu Gln Pro Glu Gln Ala Arg Leu Ala Leu Thr Leu Ala
            355                 360                 365

Ala Ala Glu Ser Glu Arg Phe Val Arg Gln Gly Thr Gly Asn Asp Glu
    370                 375                 380

Ala Gly Ala Ala Asn Ala Asp Val Val Ser Leu Thr Cys Pro Val Ala
385                 390                 395                 400

Ala Gly Glu Cys Ala Gly Pro Ala Asp Ser Gly Asp Ala Leu Leu Glu
                405                 410                 415

Arg Asn Tyr Pro Thr Gly Ala Glu Phe Leu Gly Asp Gly Asp Val
            420                 425                 430

Ser Phe Ser Thr Arg Gly Thr Gln Asn Trp Thr Val Glu Arg Leu Leu
    435                 440                 445

Gln Ala His Arg Gln Leu Glu Glu Arg Gly Tyr Val Phe Val Gly Tyr
450                 455                 460

His Gly Thr Phe Leu Glu Ala Ala Gln Ser Ile Val Phe Gly Gly Val
465                 470                 475                 480

Arg Ala Arg Ser Gln Asp Leu Asp Ala Ile Trp Arg Gly Phe Tyr Ile
                485                 490                 495

Ala Gly Asp Pro Ala Leu Ala Tyr Gly Tyr Ala Gln Asp Gln Glu Pro
            500                 505                 510

Asp Ala Arg Gly Arg Ile Arg Asn Gly Ala Leu Leu Arg Val Tyr Val
        515                 520                 525

Pro Arg Ser Ser Leu Pro Gly Phe Tyr Arg Thr Ser Leu Thr Leu Ala
    530                 535                 540

Ala Pro Glu Ala Ala Gly Glu Val Glu Arg Leu Ile Gly His Pro Leu
545                 550                 555                 560

Pro Leu Arg Leu Asp Ala Ile Thr Gly Pro Glu Glu Glu Gly Gly Arg
                565                 570                 575

Leu Glu Thr Ile Leu Gly Trp Pro Leu Ala Glu Arg Thr Val Val Ile
            580                 585                 590

Pro Ser Ala Ile Pro Thr Asp Pro Arg Asn Val Gly Gly Asp Leu Asp
        595                 600                 605

Pro Ser Ser Ile Pro Asp Lys Glu Gln Ala Ile Ser Ala Leu Pro Asp
    610                 615                 620

Tyr Ala Ser Gln Pro Gly Lys Pro Pro Arg Glu Asp Leu Lys
625                 630                 635

<210> SEQ ID NO 19
<211> LENGTH: 171
<212> TYPE: PRT
<213> ORGANISM: Pseudomonas aeruginosa

<400> SEQUENCE: 19

Arg Leu His Phe Pro Glu Gly Gly Ser Leu Ala Ala Leu Thr Ala His
1               5                   10                  15

Gln Ala Cys His Leu Pro Leu Glu Thr Phe Thr Arg His Arg Gln Pro
                20                  25                  30

Arg Gly Trp Glu Gln Leu Glu Gln Cys Gly Tyr Pro Val Gln Arg Leu
            35                  40                  45

Val Ala Leu Tyr Leu Ala Ala Arg Leu Ser Trp Asn Gln Val Asp Gln
        50                  55                  60

Val Ile Arg Asn Ala Leu Ala Ser Pro Gly Ser Gly Gly Asp Leu Gly
65                  70                  75                  80

Glu Ala Ile Arg Glu Gln Pro Glu Gln Ala Arg Leu Ala Leu Thr Leu
                85                  90                  95

```
Ala Ala Ala Glu Ser Glu Arg Phe Val Arg Gln Gly Thr Gly Asn Asp
            100                 105                 110

Glu Ala Gly Ala Ala Asn Ala Asp Val Val Ser Leu Thr Cys Pro Val
        115                 120                 125

Ala Ala Gly Glu Cys Ala Gly Pro Ala Asp Ser Gly Asp Ala Leu Leu
130                 135                 140

Glu Arg Asn Tyr Pro Thr Gly Ala Glu Phe Leu Gly Asp Gly Gly Asp
145                 150                 155                 160

Val Ser Phe Ser Thr Arg Gly Thr Gln Asn Trp
                165                 170

<210> SEQ ID NO 20
<211> LENGTH: 870
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atgcgcctgc actttcccga gggcggcagc ctggccgcgc tgaccgcgca ccaggcttgc     60
cacctgccgc tggagacttt cacccgtcat cgccagccgc gcggctggga caactggag    120 cagtgcggct atccggtgca gcggctggtc gccctctacc tggcggcgcg gctgtcgtgg    180
aaccaggtcg accaggtgat ccgcaacgcc ctggccagcc ccggcagcgg cggcgacctg    240
ggcgaagcga tccgcgagca gccggagcag gcccgtctgg ccctgaccct ggccgccgcc    300
gagagcgagc gcttcgtccg cagggcacc ggcaacgacg aggccggcgc ggccaacgcc    360
gacgtggtga gctgacctg cccggtcgcc gccggtgaat gcgcgggccc ggcggacagc    420
ggcgacgccc tgctggagcg caactatccc actggcgcgg agttcctcgg cgacggcggc    480
gacgtcagct tcagcacccg cggcacgcag aacgaattca tgcatggaga tacacctaca    540
ttgcatgaat atatgttaga tttgcaacca gagacaactg atctctactg ttatgagcaa    600
ttaaatgaca gctcagagga ggaggatgaa atagatggtc cagctggaca agcagaaccg    660
gacagagccc attacaatat tgtaaccttt tgttgcaagt gtgactctac gcttcggttg    720
tgcgtacaaa gcacacacgt agacattcgt actttggaag acctgttaat gggcacacta    780
ggaattgtgt gccccatctg ttctcaagga tccgagctcg gtaccaagct taagtttaaa    840
ccgctgatca gcctcgactg tgccttctag                                     870

<210> SEQ ID NO 21
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Arg Leu His Phe Pro Glu Gly Gly Ser Leu Ala Ala Leu Thr Ala
1               5                   10                  15

His Gln Ala Cys His Leu Pro Leu Glu Thr Phe Thr Arg His Arg Gln
            20                  25                  30

Pro Arg Gly Trp Glu Gln Leu Glu Gln Cys Gly Tyr Pro Val Gln Arg
        35                  40                  45

Leu Val Ala Leu Tyr Leu Ala Ala Arg Leu Ser Trp Asn Gln Val Asp
    50                  55                  60
```

```
Gln Val Ile Arg Asn Ala Leu Ala Ser Pro Gly Ser Gly Gly Asp Leu
 65                  70                  75                  80

Gly Glu Ala Ile Arg Glu Gln Pro Glu Gln Ala Arg Leu Ala Leu Thr
                 85                  90                  95

Leu Ala Ala Ala Glu Ser Glu Arg Phe Val Arg Gln Gly Thr Gly Asn
            100                 105                 110

Asp Glu Ala Gly Ala Ala Asn Ala Asp Val Val Ser Leu Thr Cys Pro
        115                 120                 125

Val Ala Ala Gly Glu Cys Ala Gly Pro Ala Asp Ser Gly Asp Ala Leu
130                 135                 140

Leu Glu Arg Asn Tyr Pro Thr Gly Ala Glu Phe Leu Gly Asp Gly Gly
145                 150                 155                 160

Asp Val Ser Phe Ser Thr Arg Gly Thr Gln Asn Glu Phe Met His Gly
                165                 170                 175

Asp Thr Pro Thr Leu His Glu Tyr Met Leu Asp Leu Gln Pro Glu Thr
            180                 185                 190

Thr Asp Leu Tyr Cys Tyr Glu Gln Leu Asn Asp Ser Ser Glu Glu Glu
        195                 200                 205

Asp Glu Ile Asp Gly Pro Ala Gly Gln Ala Glu Pro Asp Arg Ala His
    210                 215                 220

Tyr Asn Ile Val Thr Phe Cys Cys Lys Cys Asp Ser Thr Leu Arg Leu
225                 230                 235                 240

Cys Val Gln Ser Thr His Val Asp Ile Arg Thr Leu Glu Asp Leu Leu
                245                 250                 255

Met Gly Thr Leu Gly Ile Val Cys Pro Ile Cys Ser Gln Gly Ser Glu
            260                 265                 270

Leu Gly Thr Lys Leu Lys Phe Lys Pro Leu Ile Ser Leu Asp Cys Ala
        275                 280                 285

Phe
```

<210> SEQ ID NO 22
<211> LENGTH: 1257
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(1254)

<400> SEQUENCE: 22

```
atg acc tct cgc cgc tcc gtg aag tcg ggt ccg cgg gag gtt ccg cgc     48
Met Thr Ser Arg Arg Ser Val Lys Ser Gly Pro Arg Glu Val Pro Arg
 1               5                  10                  15 gat gag tac gag gat ctg tac tac acc ccg tct tca ggt atg gcg agt     96
Asp Glu Tyr Glu Asp Leu Tyr Tyr Thr Pro Ser Ser Gly Met Ala Ser
             20                  25                  30 ccc gat agt ccg cct gac acc tcc cgc cgt ggc gcc cta cag aca cgc    144
Pro Asp Ser Pro Pro Asp Thr Ser Arg Arg Gly Ala Leu Gln Thr Arg
         35                  40                  45 tcg cgc cag agg ggc gag gtc cgt ttc gtc cag tac gac gag tcg gat    192
Ser Arg Gln Arg Gly Glu Val Arg Phe Val Gln Tyr Asp Glu Ser Asp
     50                  55                  60 tat gcc ctc tac ggg ggc tcg tct tcc gaa gac gac gaa cac ccg gag    240
Tyr Ala Leu Tyr Gly Gly Ser Ser Ser Glu Asp Asp Glu His Pro Glu
 65                  70                  75                  80
```

| | | |
|---|---|---|
| gtc ccc cgg acg cgg cgt ccc gtt tcc ggg gcg gtt ttg tcc ggc ccg<br>Val Pro Arg Thr Arg Arg Pro Val Ser Gly Ala Val Leu Ser Gly Pro<br>                85                      90                      95 | | 288 |
| ggg cct gcg cgg gcg cct ccg cca ccc gct ggg tcc gga ggg gcc gga<br>Gly Pro Ala Arg Ala Pro Pro Pro Ala Gly Ser Gly Gly Ala Gly<br>              100                        105                        110 | | 336 |
| cgc aca ccc acc acc gcc ccc cgg gcc ccc cga acc cag cgg gtg gcg<br>Arg Thr Pro Thr Thr Ala Pro Arg Ala Pro Arg Thr Gln Arg Val Ala<br>                115                        120                        125 | | 384 |
| tct aag gcc ccc gcg gcc ccg gcg gcg gag acc acc cgc ggc agg aaa<br>Ser Lys Ala Pro Ala Ala Pro Ala Ala Glu Thr Thr Arg Gly Arg Lys<br>130                      135                        140 | | 432 |
| tcg gcc cag cca gaa tcc gcc gca ctc cca gac gcc ccc gcg tcg acg<br>Ser Ala Gln Pro Glu Ser Ala Ala Leu Pro Asp Ala Pro Ala Ser Thr<br>145                      150                        155                        160 | | 480 |
| gcg cca acc cga tcc aag aca ccc gcg cag ggg ctg gcc aga aag ctg<br>Ala Pro Thr Arg Ser Lys Thr Pro Ala Gln Gly Leu Ala Arg Lys Leu<br>                        165                        170                        175 | | 528 |
| cac ttt agc acc gcc ccc cca aac ccc gac gcg cca tgg acc ccc cgg<br>His Phe Ser Thr Ala Pro Pro Asn Pro Asp Ala Pro Trp Thr Pro Arg<br>              180                        185                        190 | | 576 |
| gtg gcc ggc ttt aac aag cgc gtc ttc tgc gcc gcg gtc ggg cgc ctg<br>Val Ala Gly Phe Asn Lys Arg Val Phe Cys Ala Ala Val Gly Arg Leu<br>                195                        200                        205 | | 624 |
| gcg gcc atg cat gcc cgg atg gcg gct gtc cag ctc tgg gac atg tcg<br>Ala Ala Met His Ala Arg Met Ala Ala Val Gln Leu Trp Asp Met Ser<br>              210                        215                        220 | | 672 |
| cgt ccg cgc aca gac gaa gac ctc aac gaa ctc ctt ggc atc acc acc<br>Arg Pro Arg Thr Asp Glu Asp Leu Asn Glu Leu Leu Gly Ile Thr Thr<br>225                      230                        235                        240 | | 720 |
| atc cgc gtg acg gtc tgc gag ggc aaa aac ctg ctt cag cgc gcc aac<br>Ile Arg Val Thr Val Cys Glu Gly Lys Asn Leu Leu Gln Arg Ala Asn<br>                        245                        250                        255 | | 768 |
| gag ttg gtg aat cca gac gtg gtg cag gac gtc gac gcg gcc acg gcg<br>Glu Leu Val Asn Pro Asp Val Val Gln Asp Val Asp Ala Ala Thr Ala<br>              260                        265                        270 | | 816 |
| act cga ggg cgt tct gcg gcg tcg cgc ccc acc gag cga cct cga gcc<br>Thr Arg Gly Arg Ser Ala Ala Ser Arg Pro Thr Glu Arg Pro Arg Ala<br>              275                        280                        285 | | 864 |
| cca gcc cgc tcc gct tct cgc ccc aga cgg ccc gtc gag ggt acc gag<br>Pro Ala Arg Ser Ala Ser Arg Pro Arg Arg Pro Val Glu Gly Thr Glu<br>              290                        295                        300 | | 912 |
| ctc gga tcc atg cat gga gat aca cct aca ttg cat gaa tat atg tta<br>Leu Gly Ser Met His Gly Asp Thr Pro Thr Leu His Glu Tyr Met Leu<br>305                      310                        315                        320 | | 960 |
| gat ttg caa cca gag aca act gat ctc tac tgt tat gag caa tta aat<br>Asp Leu Gln Pro Glu Thr Thr Asp Leu Tyr Cys Tyr Glu Gln Leu Asn<br>                      325                        330                        335 | | 1008 |
| gac agc tca gag gag gag gat gaa ata gat ggt cca gct gga caa gca<br>Asp Ser Ser Glu Glu Glu Asp Glu Ile Asp Gly Pro Ala Gly Gln Ala<br>                        340                        345                        350 | | 1056 |
| gaa ccg gac aga gcc cat tac aat att gta acc ttt tgt tgc aag tgt<br>Glu Pro Asp Arg Ala His Tyr Asn Ile Val Thr Phe Cys Cys Lys Cys<br>                355                        360                        365 | | 1104 |
| gac tct acg ctt cgg ttg tgc gta caa agc aca cac gta gac att cgt<br>Asp Ser Thr Leu Arg Leu Cys Val Gln Ser Thr His Val Asp Ile Arg<br>              370                        375                        380 | | 1152 |
| act ttg gaa gac ctg tta atg ggc aca cta gga att gtg tgc ccc atc<br>Thr Leu Glu Asp Leu Leu Met Gly Thr Leu Gly Ile Val Cys Pro Ile<br>385                      390                        395                        400 | | 1200 |

```
tgt tct cag gat aag ctt aag ttt aaa ccg ctg atc agc ctc gac tgt    1248
Cys Ser Gln Asp Lys Leu Lys Phe Lys Pro Leu Ile Ser Leu Asp Cys
            405                 410                 415 gcc ttc tag                                                         1257
Ala Phe
```

<210> SEQ ID NO 23
<211> LENGTH: 1254
<212> TYPE: DNA
<213> ORGANISM: Homo sapiens

<400> SEQUENCE: 23

```
atgctgctat ccgtgccgct gctgctcggc ctcctcggcc tggccgtcgc cgagcccgcc    60
gtctacttca aggagcagtt tctggacgga cgggtgga cttcccgctg atcgaatcc     120
aaacacaagt cagattttgg caaattcgtt ctcagttccg gcaagttcta cggtgacgag   180
gagaaagata aggtttgca gacaagccag gatgcacgct tttatgctct gtcggccagt   240
ttcgagcctt tcagcaacaa aggccagacg ctggtggtgc agttcacggt gaaacatgag   300
cagaacatcg actgtggggg cggctatgtg aagctgtttc taatagttt ggaccagaca   360
gacatgcacg gagactcaga atacaacatc atgtttggtc ccgacatctg tggccctggc   420
accaagaagg ttcatgtcat cttcaactac aagggcaaga acgtgctgat caacaaggac   480
atccgttgca aggatgatga gtttacacac ctgtacacac tgattgtgcg ccagacaac   540
acctatgagg tgaagattga acagccag gtggagtccg gctccttgga agacgattgg   600
gacttcctgc cacccaagaa gataaaggat cctgatgctt caaaaccgga agactgggat   660
gagcgggcca agatcgatga tcccacagac tccaagcctg aggactggga caagcccgag   720
catatccctg accctgatgc taagaagccc aggactgggg atgaagagat ggacggagag   780
tgggaacccc cagtgattca gaaccctgag tacaagggtg agtggaagcc ccggcagatc   840
gacaacccag attacaaggg cacttggatc caccccagaaa ttgacaaccc cgagtattct   900
cccgatccca gtatctatgc ctatgataac tttggcgtgc tgggcctgga cctctggcag   960
gtcaagtctg gcaccatctt tgacaacttc ctcatcacca cgatgaggc atacgctgag   1020
gagtttggca cgagacgtg gggcgtaaca aaggcagcag agaaacaaat gaaggacaaa   1080
caggacgagg agcagaggct taaggaggag gaagaagaca agaaacgcaa agaggaggag   1140
gaggcagagg acaaggagga tgatgaggac aaagatgagg atgaggagga tgaggaggac   1200
aaggaggaag atgaggagga agatgtcccc ggccaggcca aggacgagct gtag        1254
```

<210> SEQ ID NO 24
<211> LENGTH: 417
<212> TYPE: PRT
<213> ORGANISM: Homo sapiens

<400> SEQUENCE: 24

```
Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp Gly
                20                  25                  30

Trp Thr Ser Arg Trp Ile Glu Ser Lys His Lys Ser Asp Phe Gly Lys
        35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
```

```
                65                  70                  75                  80

Phe Glu Pro Phe Ser Asn Lys Gly Gln Thr Leu Val Val Gln Phe Thr
                     85                  90                  95

Val Lys His Glu Gln Asn Ile Asp Cys Gly Gly Tyr Val Lys Leu
                    100                 105                 110

Phe Pro Asn Ser Leu Asp Gln Thr Asp Met His Gly Asp Ser Glu Tyr
                    115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
    145                 150                 155                 160

Ile Arg Cys Lys Asp Asp Glu Phe Thr His Leu Tyr Thr Leu Ile Val
                    165                 170                 175

Arg Pro Asp Asn Thr Tyr Glu Val Lys Ile Asp Asn Ser Gln Val Glu
                    180                 185                 190

Ser Gly Ser Leu Glu Asp Asp Trp Asp Phe Leu Pro Pro Lys Lys Ile
                    195                 200                 205

Lys Asp Pro Asp Ala Ser Lys Pro Glu Asp Trp Asp Glu Arg Ala Lys
    210                 215                 220

Ile Asp Asp Pro Thr Asp Ser Lys Pro Glu Asp Trp Asp Lys Pro Glu
    225                 230                 235                 240

His Ile Pro Asp Pro Asp Ala Lys Lys Pro Glu Asp Trp Asp Glu Glu
                    245                 250                 255

Met Asp Gly Glu Trp Glu Pro Pro Val Ile Gln Asn Pro Glu Tyr Lys
                    260                 265                 270

Gly Glu Trp Lys Pro Arg Gln Ile Asp Asn Pro Asp Tyr Lys Gly Thr
                    275                 280                 285

Trp Ile His Pro Glu Ile Asp Asn Pro Glu Tyr Ser Pro Asp Pro Ser
                    290                 295                 300

Ile Tyr Ala Tyr Asp Asn Phe Gly Val Leu Gly Leu Asp Leu Trp Gln
    305                 310                 315                 320

Val Lys Ser Gly Thr Ile Phe Asp Asn Phe Leu Ile Thr Asn Asp Glu
                    325                 330                 335

Ala Tyr Ala Glu Glu Phe Gly Asn Glu Thr Trp Gly Val Thr Lys Ala
                    340                 345                 350

Ala Glu Lys Gln Met Lys Asp Lys Gln Asp Glu Glu Gln Arg Leu Lys
                    355                 360                 365

Glu Glu Glu Glu Asp Lys Lys Arg Lys Glu Glu Glu Ala Glu Asp
                    370                 375                 380

Lys Glu Asp Asp Glu Asp Lys Asp Glu Asp Glu Asp Glu Glu Asp
    385                 390                 395                 400

Lys Glu Glu Asp Glu Glu Asp Val Pro Gly Gln Ala Lys Asp Glu
                    405                 410                 415

Leu

<210> SEQ ID NO 25
<211> LENGTH: 170
<212> TYPE: PRT
<213> ORGANISM: Homo sapiens

<400> SEQUENCE: 25

Met Leu Leu Ser Val Pro Leu Leu Gly Leu Leu Gly Leu Ala Val
    1                   5                   10                  15

Ala Glu Pro Ala Val Tyr Phe Lys Glu Gln Phe Leu Asp Gly Asp Gly
```

```
                20                  25                  30
Trp Thr Ser Arg Trp Ile Glu Ser Lys His Lys Ser Asp Phe Gly Lys
            35                  40                  45
Phe Val Leu Ser Ser Gly Lys Phe Tyr Gly Asp Glu Lys Asp Lys
        50                  55                  60
Gly Leu Gln Thr Ser Gln Asp Ala Arg Phe Tyr Ala Leu Ser Ala Ser
65                  70                  75                  80
Phe Glu Pro Phe Ser Asn Lys Gly Gln Thr Leu Val Val Gln Phe Thr
                85                  90                  95
Val Lys His Glu Gln Asn Ile Asp Cys Gly Gly Gly Tyr Val Lys Leu
            100                 105                 110
Phe Pro Asn Ser Leu Asp Gln Thr Asp Met His Gly Asp Ser Glu Tyr
        115                 120                 125
Asn Ile Met Phe Gly Pro Asp Ile Cys Gly Pro Gly Thr Lys Lys Val
        130                 135                 140
His Val Ile Phe Asn Tyr Lys Gly Lys Asn Val Leu Ile Asn Lys Asp
145                 150                 155                 160
Ile Arg Cys Lys Asp Asp Glu Phe Thr His
                165                 170

<210> SEQ ID NO 26
<211> LENGTH: 109
<212> TYPE: PRT
<213> ORGANISM: Homo sapiens

<400> SEQUENCE: 26

Leu Tyr Thr Leu Ile Val Arg Pro Asp Asn Thr Tyr Glu Val Lys Ile
1               5                   10                  15
Asp Asn Ser Gln Val Glu Ser Gly Ser Leu Glu Asp Asp Trp Asp Phe
                20                  25                  30
Leu Pro Pro Lys Lys Ile Lys Asp Pro Asp Ala Ser Lys Pro Glu Asp
            35                  40                  45
Trp Asp Glu Arg Ala Lys Ile Asp Pro Thr Asp Ser Lys Pro Glu
        50                  55                  60
Asp Trp Asp Lys Pro Glu His Ile Pro Asp Pro Asp Ala Lys Lys Pro
65                  70                  75                  80
Glu Asp Trp Asp Glu Glu Met Asp Gly Glu Trp Glu Pro Pro Val Ile
                85                  90                  95
Gln Asn Pro Glu Tyr Lys Gly Glu Trp Lys Pro Arg Gln
            100                 105

<210> SEQ ID NO 27
<211> LENGTH: 138
<212> TYPE: PRT
<213> ORGANISM: Homo sapiens

<400> SEQUENCE: 27

Ile Asp Asn Pro Asp Tyr Lys Gly Thr Trp Ile His Pro Glu Ile Asp
1               5                   10                  15
Asn Pro Glu Tyr Ser Pro Asp Pro Ser Ile Tyr Ala Tyr Asp Asn Phe
                20                  25                  30
Gly Val Leu Gly Leu Asp Leu Trp Gln Val Lys Ser Gly Thr Ile Phe
            35                  40                  45
Asp Asn Phe Leu Ile Thr Asn Asp Glu Ala Tyr Ala Glu Glu Phe Gly
        50                  55                  60
Asn Glu Thr Trp Gly Val Thr Lys Ala Ala Glu Lys Gln Met Lys Asp
```

```
                     65                  70                  75                  80
Lys Gln Asp Glu Glu Gln Arg Leu Lys Glu Glu Glu Asp Lys Lys
                         85                  90                  95

Arg Lys Glu Glu Glu Ala Glu Asp Lys Glu Asp Asp Glu Asp Lys
                100                 105                 110

Asp Glu Asp Glu Glu Asp Glu Asp Lys Glu Glu Asp Glu Glu Glu
            115                 120                 125

Asp Val Pro Gly Gln Ala Lys Asp Glu Leu
            130                 135

<210> SEQ ID NO 28
<211> LENGTH: 1254
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
atgctgctat ccgtgccgct gctgctcggc ctcctcggcc tggccgtcgc cgagcccgcc      60
gtctacttca aggagcagtt tctggacgga gacgggtgga cttcccgctg gatcgaatcc     120
aaacacaagt cagattttgg caaattcgtt ctcagttccg gcaagttcta cggtgacgag     180
gagaaagata aggtttgca gacaagccag atgcacgct tttatgctct gtcggccagt      240
ttcgagcctt tcagcaacaa aggccagacg ctggtggtgc agttcacggt gaaacatgag     300
cagaacatcg actgtggggg cggctatgtg aagctgtttc ctaatagttt ggaccagaca     360
gacatgcacg gagactcaga atacaacatc atgtttggtc ccgacatctg tggccctggc     420
accaagaagg ttcatgtcat cttcaactac aagggcaaga acgtgctgat caacaaggac     480
atccgttgca aggatgatga gtttacacac ctgtacacac tgattgtgcg gccagacaac     540
acctatgagg tgaagattga acagccag gtggagtccg gctccttgga agacgattgg       600
gacttcctgc cacccaagaa gataaaggat cctgatgctt caaaaccgga agactgggat     660
gagcgggcca agatcgatga tcccacagac tccaagcctg aggactggga caagcccgag     720
catatccctg accctgatgc taagaagccc gaggactggg atgaagagat ggacggagag     780 tgggaaccc cagtgattca gaaccctgag tacaagggtg agtggaagcc ccggcagatc      840
gacaacccag attacaaggg cacttggatc cacccagaaa ttgacaaccc cgagtattct     900
cccgatccca gtatctatgc ctatgataac tttggcgtgc tgggcctgga cctctggcag     960
gtcaagtctg gcaccatctt tgacaacttc ctcatcacca cgatgaggc atacgctgag     1020 gagtttggca cgagacgtg gggcgtaaca aaggcagcag agaaacaaat gaaggacaaa     1080
caggacgagg agcagaggct taaggaggag gaagaagaca agaaacgcaa agaggaggag     1140
gaggcagagg acaaggagga tgatgaggac aaagatgagg atgaggagga tgaggaggac     1200
aaggaggaag atgaggagga agatgtcccc ggccaggcca aggacgagct gtag          1254

<210> SEQ ID NO 29
<211> LENGTH: 540
<212> TYPE: DNA
<213> ORGANISM: Homo sapiens

<400> SEQUENCE: 29
atgctgctat ccgtgccgct gctgctcggc ctcctcggcc tggccgtcgc cgagcccgcc      60
gtctacttca aggagcagtt tctggacgga gacgggtgga cttcccgctg gatcgaatcc     120
```

| | |
|---|---|
| aaacacaagt cagattttgg caaattcgtt ctcagttccg gcaagttcta cggtgacgag | 180 |
| gagaaagata aaggtttgca gacaagccag gatgcacgct tttatgctct gtcggccagt | 240 |
| ttcgagcctt tcagcaacaa aggccagacg ctggtggtgc agttcacggt gaaacatgag | 300 |
| cagaacatcg actgtggggg cggctatgtg aagctgtttc ctaatagttt ggaccagaca | 360 |
| gacatgcacg gagactcaga atacaacatc atgtttggtc ccgacatctg tggccctggc | 420 |
| accaagaagg ttcatgtcat cttcaactac aagggcaaga acgtgctgat caacaaggac | 480 |
| atccgttgca aggatgatga gtttacacac ctgtacacac tgattgtgcg gccagacaac | 540 |

<210> SEQ ID NO 30
<211> LENGTH: 267
<212> TYPE: DNA
<213> ORGANISM: Homo sapiens

<400> SEQUENCE: 30

| | |
|---|---|
| acctatgagg tgaagattga caacagccag gtggagtccg gctccttgga agacgattgg | 60 |
| gacttcctgc cacccaagaa gataaaggat cctgatgctt caaaaccgga agactgggat | 120 |
| gagcgggcca agatcgatga tcccacagac tccaagcctg aggactggga caagcccgag | 180 |
| catatccctg accctgatgc taagaagccc gaggactggg atgaagagat ggacggagag | 240 |
| tgggaaccc cagtgattca gaaccct | 267 |

<210> SEQ ID NO 31
<211> LENGTH: 444
<212> TYPE: DNA
<213> ORGANISM: Homo sapiens

<400> SEQUENCE: 31

| | |
|---|---|
| gagtacaagg gtgagtggaa gccccggcag atcgacaacc cagattacaa gggcacttgg | 60 |
| atccacccag aaattgacaa ccccgagtat tctcccgatc cagtatctga tgcctatgat | 120 |
| aactttggcg tgctgggcct ggacctctgg caggtcaagt ctggcaccat ctttgacaac | 180 |
| ttcctcatca ccaacgatga ggcatacgct gaggagtttg gcaacgagac gtggggcgta | 240 |
| acaaaggcag cagagaaaca aatgaaggac aaacaggacg aggagcagag gcttaaggag | 300 |
| gaggaagaag acaagaaacg caaagaggag gaggaggcag aggacaagga ggatgatgag | 360 |
| gacaaagatg aggatgagga ggatgaggag gacaaggagg aagatgagga ggaagatgtc | 420 |
| cccggccagg ccaaggacga gctg | 444 |

<210> SEQ ID NO 32
<211> LENGTH: 5970
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

| | |
|---|---|
| gctccgcccc cctgacgagc atcacaaaaa tcgacgctca agtcagaggt ggcgaaaccc | 60 |
| gacaggacta taaagatacc aggcgtttcc ccctggaagc tccctcgtgc gctctcctgt | 120 |
| tccgaccctg ccgcttaccg gatacctgtc cgcctttctc ccttcgggaa gcgtggcgct | 180 |
| ttctcatagc tcacgctgta ggtatctcag ttcggtgtag gtcgttcgct ccaagctggg | 240 |
| ctgtgtgcac gaaccccccg ttcagcccga ccgctgcgcc ttatccggta actatcgtct | 300 |
| tgagtccaac ccggtaagac acgacttatc gccactggca gcagccactg gtaacaggat | 360 |

```
tagcagagcg aggtatgtag gcggtgctac agagttcttg aagtggtggc ctaactacgg     420
ctacactaga agaacagtat ttggtatctg cgctctgctg aagccagtta ccttcggaaa     480
aagagttggt agctcttgat ccggcaaaca aaccaccgct ggtagcggtg gttttttttgt    540
ttgcaagcag cagattacgc gcagaaaaaa aggatctcaa gaagatcctt tgatcttttc     600
tacgggtct gacgctcagt ggaacgaaaa ctcacgttaa gggattttgg tcatgagatt      660
atcaaaaagg atcttcacct agatcctttt aaattaaaaa tgaagtttta atcaatcta      720
aagtatatat gagtaaactt ggtctgacag ttaccaatgc ttaatcagtg aggcacctat     780
ctcagcgatc tgtctatttc gttcatccat agttgcctga ctcggggggg ggggcgctg     840
aggtctgcct cgtgaagaag gtgttgctga ctcataccag ggcaacgttg ttgccattgc     900
tacaggcatc gtggtgtcac gctcgtcgtt tggtatggct tcattcagct ccggttccca    960
acgatcaagg cgagttacat gatccccat gttgtgcaaa aaagcggtta gctccttcgg     1020
tcctccgatc gttgtcagaa gtaagttggc cgcagtgtta tcactcatgg ttatggcagc    1080
actgcataat tctcttactg tcatgccatc cgtaagatgc ttttctgtga ctggtgagta    1140
ctcaaccaag tcattctgag aatagtgtat gcggcgaccg agttgctctt gcccggcgtc    1200
aatacgggat aataccgcgc cacatagcag aactttaaaa gtgctcatca ttggaaaacg    1260
ttcttcgggg cgaaaactct caaggatctt accgctgttg agatccagtt cgatgtaacc    1320
cactcgtgca cctgaatcgc cccatcatcc agccagaaag tgagggagcc acggttgatg    1380
agagctttgt tgtaggtgga ccagttggtg attttgaact tttgctttgc cacggaacgg    1440
tctgcgttgt cgggaagatg cgtgatctga tccttcaact cagcaaaagt tcgatttatt    1500
caacaaagcc gccgtcccgt caagtcagcg taatgctctg ccagtgttac aaccaattaa    1560
ccaattctga ttagaaaaac tcatcgagca tcaaatgaaa ctgcaattta ttcatatcag    1620
gattatcaat accatatttt tgaaaaagcc gtttctgtaa tgaaggagaa aactcaccga    1680
ggcagttcca taggatggca agatcctggt atcggtctgc gattccgact cgtccaacat    1740
caatacaacc tattaatttc ccctcgtcaa aaataaggtt atcaagtgag aaatcaccat    1800
gagtgacgac tgaatccggt gagaatggca aaagcttatg catttctttc cagacttgtt    1860
caacaggcca gccattacgc tcgtcatcaa aatcactcgc atcaaccaaa ccgttattca    1920
ttcgtgattg cgcctgagcg agacgaaata cgcgatcgct gttaaaagga caattacaaa    1980
caggaatcga atgcaaccgg cgcaggaaca ctgccagcgc atcaacaata ttttcacctg    2040
aatcaggata ttcttctaat acctggaatg ctgttttccc ggggatcgca gtggtgagta    2100
accatgcatc atcaggagta cggataaaat gcttgatggt cggaagaggc ataaattccg    2160
tcagccagtt tagtctgacc atctcatctg taacatcatt ggcaacgcta cctttgccat    2220
gtttcagaaa caactctggc gcatcgggct tcccatacaa tcgatagatt gtcgcacctg    2280
attgcccgac attatcgcga gcccatttat acccatataa atcagcatcc atgttggaat    2340
ttaatcgcgg cctcgagcaa gacgtttccc gttgaatatg gctcataaca ccccttgtat    2400
tactgtttat gtaagcagac agttttattg ttcatgatga tatattttta tcttgtgcaa    2460
tgtaacatca gagattttga gacacaacgt ggctttcccc cccccccat tattgaagca     2520
tttatcaggg ttattgtctc atgagcggat acatatttga atgtatttag aaaaataaac    2580
aaatagggt tccgcgcaca tttccccgaa aagtgccacc tgacgtctaa gaaaccatta     2640
ttatcatgac attaacctat aaaaataggc gtatcacgag gccctttcgt ctcgcgcgtt    2700
tcggtgatga cggtgaaaac ctctgacaca tgcagctccc ggagacggtc acagcttgtc    2760
```

```
tgtaagcgga tgccgggagc agacaagccc gtcagggcgc gtcagcgggt gttggcgggt    2820
gtcgggcctg gcttaactat gcggcatcag agcagattgt actgagagtg caccatatgc    2880
ggtgtgaaat accgcacaga tgcgtaagga gaaaataccg catcagattg gctattggcc    2940
attgcatacg ttgtatccat atcataatat gtacatttat attggctcat gtccaacatt    3000
accgccatgt tgacattgat tattgactag ttattaatag taatcaatta cgggtcatt     3060
agttcatagc ccatatatgg agttccgcgt tacataactt acggtaaatg gcccgcctgg    3120
ctgaccgccc aacgaccccc gcccattgac gtcaataatg acgtatgttc ccatagtaac    3180
gccaataggg actttccatt gacgtcaatg ggtggagtat ttacggtaaa ctgcccactt    3240
ggcagtacat caagtgtatc atatgccaag tacgccccct attgacgtca atgacggtaa    3300
atggcccgcc tggcattatg cccagtacat gaccttatgg gactttccta cttggcagta    3360
catctacgta ttagtcatcg ctattaccat ggtgatgcgg ttttggcagt acatcaatgg    3420
gcgtggatag cggtttgact cacggggatt tccaagtctc cacccccattg acgtcaatgg   3480
gagtttgttt tggcaccaaa atcaacggga ctttccaaaa tgtcgtaaca actccgcccc    3540
attgacgcaa atgggcggta ggcgtgtacg gtgggaggtc tatataagca gagctcgttt    3600
agtgaaccgt cagatcgcct ggagacgcca tccacgctgt tttgacctcc atagaagaca    3660
ccgggaccga tccagcctcc gcggccggga acggtgcatt ggaacgcgga ttccccgtgc    3720
caagagtgac gtaagtaccg cctatagact ctataggcac cccctttgg ctcttatgca     3780
tgctatactg tttttggctt ggggcctata caccccgct tccttatgct ataggtgatg      3840
gtatagctta gcctataggt gtgggttatt gaccattatt gaccactcca acggtggagg    3900
gcagtgtagt ctgagcagta ctcgttgctg ccgcgcgcgc caccagacat aatagctgac    3960
agactaacag actgttcctt tccatgggtc ttttctgcag tcaccgtcgt cgacatgctg    4020
ctatccgtgc cgctgctgct cggcctcctc ggcctggccg tcgccgagcc tgccgtctac    4080
ttcaaggagc agtttctgga cggggacggg tggacttccc gctggatcga atccaaacac    4140
aagtcagatt ttggcaaatt cgttctcagt tccggcaagt tctacggtga cgaggagaaa    4200
gataaaggtt tgcagacaag ccaggatgca cgcttttatg ctctgtcggc cagtttcgag    4260
cctttcagca acaaaggcca gacgctggtg gtgcagttca cggtgaaaca tgagcagaac    4320
atcgactgtg gggcggcta tgtgaagctg tttcctaata gtttgaccac gacagacatg      4380
cacggagact cagaatacaa catcatgttt ggtcccgaca tctgtggccc tggcaccaag    4440
aaggttcatg tcatcttcaa ctacaagggc aagaacgtgc tgatcaacaa ggacatccgt    4500
tgcaaggatg atgagtttac acacctgtac acactgattg tgcggccaga caacacctat    4560
gaggtgaaga ttgacaacag ccaggtgagg tccggctcct ggaagacga ttgggacttc       4620
ctgccaccca agaagataaa ggatcctgat gcttcaaaac cggaagactg gatgagcggg     4680
gccaagatcg atgatcccac agactccaag cctgaggact gggacaagcc cgagcatatc    4740
cctgaccctg atgctaagaa gcccgaggac tgggatgaag agatggacgg agagtgggaa    4800
cccccagtga ttcagaaccc tgagtacaag ggtgagtgga gcccccggca gatcgacaac    4860
ccagattaca agggcacttg gatccaccca gaaattgaca ccccgagta ttctcccgat     4920
cccagtatct atgcctatga taactttggc gtgctgggcc tggacctctg gcaggtcaag    4980
tctggcacca tctttgacaa cttcctcatc accaacgatg aggcatacgc tgaggagttt    5040
ggcaacgaga cgtgggcgt aacaaaggca gcagagaaac aaatgaagga caaacaggac    5100
```

```
gaggagcaga ggcttaagga ggaggaagaa gacaagaaac gcaaagagga ggaggaggca    5160
gaggacaagg aggatgatga ggacaaagat gaggatgagg aggatgagga ggacaaggag    5220
gaagatgagg aggaagatgt cccccggccag gccaaggacg agctggaatt catgcatgga   5280
gatacaccta cattgcatga atatatgtta gatttgcaac cagagacaac tgatctctac    5340
ggttatgggc aattaaatga cagctcagag gaggaggatg aaatagatgg tccagctgga    5400
caagcagaac cggacagagc ccattacaat attgtaacct tttgttgcaa gtgtgactct    5460
acgcttcggt tgtgcgtaca agcacacac gtagacattc gtactttgga agacctgtta     5520
atgggcacac taggaattgt gtgccccatc tgttctcaga accataagg atccagatct      5580 tttcctct gccaaaaatt atgggacat catgaagccc cttgagcatc tgacttctgg       5640
ctaataaagg aaatttattt tcattgcaat agtgtgttgg aatttttgt gtctctcact     5700 cggaaggaca tatgggaggg caaatcattt aaaacatcag aatgagtatt tggtttagag     5760
tttggcaaca tatgcccatt cttccgcttc ctcgctcact gactcgctgc gctcggtcgt    5820
tcggctgcgg cgagcggtat cagctcactc aaaggcggta atacgttgtat ccacagaatc    5880 agggagataac gcaggaaaga acatgtgagc aaaaggccag caaaaggcca ggaaccgtaa   5940
aaaggccgcg ttgctggcgt ttttccatag                                     5970
```

<210> SEQ ID NO 33
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(903)

<400> SEQUENCE: 33

```
atg acc tct cgc cgc tcc gtg aag tcg ggt ccg cgg gag gtt ccg cgc    48
Met Thr Ser Arg Arg Ser Val Lys Ser Gly Pro Arg Glu Val Pro Arg
1               5                   10                  15 gat gag tac gag gat ctg tac tac acc ccg tct tca ggt atg gcg agt    96
Asp Glu Tyr Glu Asp Leu Tyr Tyr Thr Pro Ser Ser Gly Met Ala Ser
            20                  25                  30 ccc gat agt ccg cct gac acc tcc cgc cgt ggc gcc cta cag aca cgc   144
Pro Asp Ser Pro Pro Asp Thr Ser Arg Arg Gly Ala Leu Gln Thr Arg
        35                  40                  45 tcg cgc cag agg ggc gag gtc cgt ttc gtc cag tac gac gag tcg gat   192
Ser Arg Gln Arg Gly Glu Val Arg Phe Val Gln Tyr Asp Glu Ser Asp
    50                  55                  60 tat gcc ctc tac ggg ggc tcg tct tcc gaa gac gac gaa cac ccg gag   240
Tyr Ala Leu Tyr Gly Gly Ser Ser Ser Glu Asp Asp Glu His Pro Glu
65                  70                  75                  80 gtc ccc cgg acg cgg cgt ccc gtt tcc ggg gcg gtt ttg tcc ggc ccg   288
Val Pro Arg Thr Arg Arg Pro Val Ser Gly Ala Val Leu Ser Gly Pro
                85                  90                  95 ggg cct gcg cgg gcg cct ccg cca ccc gct ggg tcc gga ggg gcc gga   336
Gly Pro Ala Arg Ala Pro Pro Pro Pro Ala Gly Ser Gly Gly Ala Gly
            100                 105                 110 cgc aca ccc acc acc gcc ccc cgg gcc ccc cga acc cag cgg gtg gcg   384
Arg Thr Pro Thr Thr Ala Pro Arg Ala Pro Arg Thr Gln Arg Val Ala
        115                 120                 125 tct aag gcc ccc gcg gcc ccg gcg gcg gag acc acc cgc ggc agg aaa   432
Ser Lys Ala Pro Ala Ala Pro Ala Ala Glu Thr Thr Arg Gly Arg Lys
    130                 135                 140
```

```
tcg gcc cag cca gaa tcc gcc gca ctc cca gac gcc ccc gcg tcg acg      480
Ser Ala Gln Pro Glu Ser Ala Ala Leu Pro Asp Ala Pro Ala Ser Thr
145                 150                 155                 160 gcg cca acc cga tcc aag aca ccc gcg cag ggg ctg gcc aga aag ctg      528
Ala Pro Thr Arg Ser Lys Thr Pro Ala Gln Gly Leu Ala Arg Lys Leu
                165                 170                 175 cac ttt agc acc gcc ccc cca aac ccc gac gcg cca tgg acc ccc cgg      576
His Phe Ser Thr Ala Pro Pro Asn Pro Asp Ala Pro Trp Thr Pro Arg
            180                 185                 190 gtg gcc ggc ttt aac aag cgc gtc ttc tgc gcc gcg gtc ggg cgc ctg      624
Val Ala Gly Phe Asn Lys Arg Val Phe Cys Ala Ala Val Gly Arg Leu
            195                 200                 205 gcg gcc atg cat gcc cgg atg gcg gct gtc cag ctc tgg gac atg tcg      672
Ala Ala Met His Ala Arg Met Ala Ala Val Gln Leu Trp Asp Met Ser
210                 215                 220 cgt ccg cgc aca gac gaa gac ctc aac gaa ctc ctt ggc atc acc acc      720
Arg Pro Arg Thr Asp Glu Asp Leu Asn Glu Leu Leu Gly Ile Thr Thr
225                 230                 235                 240 atc cgc gtg acg gtc tgc gag ggc aaa aac ctg ctt cag cgc gcc aac      768
Ile Arg Val Thr Val Cys Glu Gly Lys Asn Leu Leu Gln Arg Ala Asn
                245                 250                 255 gag ttg gtg aat cca gac gtg gtg cag gac gtc gac gcg gcc acg gcg      816
Glu Leu Val Asn Pro Asp Val Val Gln Asp Val Asp Ala Ala Thr Ala
            260                 265                 270 act cga ggg cgt tct gcg gcg tcg cgc ccc acc gag cga cct cga gcc      864
Thr Arg Gly Arg Ser Ala Ala Ser Arg Pro Thr Glu Arg Pro Arg Ala
            275                 280                 285 cca gcc cgc tcc gct tct cgc ccc aga cgg ccc gtc gag                  903
Pro Ala Arg Ser Ala Ser Arg Pro Arg Arg Pro Val Glu
290                 295                 300

<210> SEQ ID NO 34
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1254)

<400> SEQUENCE: 34 atg acc tct cgc cgc tcc gtg aag tcg ggt ccg cgg gag gtt ccg cgc       48
Met Thr Ser Arg Arg Ser Val Lys Ser Gly Pro Arg Glu Val Pro Arg
1               5                   10                  15 gat gag tac gag gat ctg tac tac acc ccg tct tca ggt atg gcg agt       96
Asp Glu Tyr Glu Asp Leu Tyr Tyr Thr Pro Ser Ser Gly Met Ala Ser
                20                  25                  30 ccc gat agt ccg cct gac acc tcc cgc cgt ggc gcc cta cag aca cgc      144
Pro Asp Ser Pro Pro Asp Thr Ser Arg Arg Gly Ala Leu Gln Thr Arg
            35                  40                  45 tcg cgc cag agg ggc gag gtc cgt ttc gtc cag tac gac gag tcg gat      192
Ser Arg Gln Arg Gly Glu Val Arg Phe Val Gln Tyr Asp Glu Ser Asp
        50                  55                  60 tat gcc ctc tac ggg ggc tcg tct tcc gaa gac gac gaa cac ccg gag      240
Tyr Ala Leu Tyr Gly Gly Ser Ser Ser Glu Asp Asp Glu His Pro Glu
65                  70                  75                  80 gtc ccc cgg acg cgg cgt ccc gtt tcc ggg gcg gtt ttg tcc ggc ccg      288
Val Pro Arg Thr Arg Arg Pro Val Ser Gly Ala Val Leu Ser Gly Pro
                85                  90                  95
```

-continued

| | | |
|---|---|---|
| ggg cct gcg cgg gcg cct ccg cca ccc gct ggg tcc gga ggg gcc gga<br>Gly Pro Ala Arg Ala Pro Pro Pro Ala Gly Ser Gly Gly Ala Gly<br>                100                             105                          110 | | 336 |
| cgc aca ccc acc acc gcc ccc cgg gcc ccc cga acc cag cgg gtg gcg<br>Arg Thr Pro Thr Thr Ala Pro Arg Ala Pro Arg Thr Gln Arg Val Ala<br>              115                            120                        125 | | 384 |
| tct aag gcc ccc gcg gcc ccg gcg gcg gag acc acc cgc ggc agg aaa<br>Ser Lys Ala Pro Ala Ala Pro Ala Ala Glu Thr Thr Arg Gly Arg Lys<br>130                          135                            140 | | 432 |
| tcg gcc cag cca gaa tcc gcc gca ctc cca gac gcc ccc gcg tcg acg<br>Ser Ala Gln Pro Glu Ser Ala Ala Leu Pro Asp Ala Pro Ala Ser Thr<br>145                          150                            155                        160 | | 480 |
| gcg cca acc cga tcc aag aca ccc gcg cag ggg ctg gcc aga aag ctg<br>Ala Pro Thr Arg Ser Lys Thr Pro Ala Gln Gly Leu Ala Arg Lys Leu<br>                          165                            170                        175 | | 528 |
| cac ttt agc acc gcc ccc cca aac ccc gac gcg cca tgg acc ccc cgg<br>His Phe Ser Thr Ala Pro Pro Asn Pro Asp Ala Pro Trp Thr Pro Arg<br>                             180                            185                          190 | | 576 |
| gtg gcc ggc ttt aac aag cgc gtc ttc tgc gcc gcg gtc ggg cgc ctg<br>Val Ala Gly Phe Asn Lys Arg Val Phe Cys Ala Ala Val Gly Arg Leu<br>                    195                             200                        205 | | 624 |
| gcg gcc atg cat gcc cgg atg gcg gct gtc cag ctc tgg gac atg tcg<br>Ala Ala Met His Ala Arg Met Ala Ala Val Gln Leu Trp Asp Met Ser<br>          210                            215                            220 | | 672 |
| cgt ccg cgc aca gac gaa gac ctc aac gaa ctc ctt ggc atc acc acc<br>Arg Pro Arg Thr Asp Glu Asp Leu Asn Glu Leu Leu Gly Ile Thr Thr<br>225                          230                            235                        240 | | 720 |
| atc cgc gtg acg gtc tgc gag ggc aaa aac ctg ctt cag cgc gcc aac<br>Ile Arg Val Thr Val Cys Glu Gly Lys Asn Leu Leu Gln Arg Ala Asn<br>                             245                            250                        255 | | 768 |
| gag ttg gtg aat cca gac gtg gtg cag gac gtc gac gcg gcc acg gcg<br>Glu Leu Val Asn Pro Asp Val Val Gln Asp Val Asp Ala Ala Thr Ala<br>                        260                            265                        270 | | 816 |
| act cga ggg cgt tct gcg gcg tcg cgc ccc acc gag cga cct cga gcc<br>Thr Arg Gly Arg Ser Ala Ala Ser Arg Pro Thr Glu Arg Pro Arg Ala<br>                275                            280                        285 | | 864 |
| cca gcc cgc tcc gct tct cgc ccc aga cgg ccc gtc gag ggt acc gag<br>Pro Ala Arg Ser Ala Ser Arg Pro Arg Arg Pro Val Glu Gly Thr Glu<br>          290                            295                            300 | | 912 |
| ctc gga tcc atg cat gga gat aca cct aca ttg cat gaa tat atg tta<br>Leu Gly Ser Met His Gly Asp Thr Pro Thr Leu His Glu Tyr Met Leu<br>305                          310                            315                        320 | | 960 |
| gat ttg caa cca gag aca act gat ctc tac tgt tat gag caa tta aat<br>Asp Leu Gln Pro Glu Thr Thr Asp Leu Tyr Cys Tyr Glu Gln Leu Asn<br>                             325                            330                        335 | | 1008 |
| gac agc tca gag gag gag gat gaa ata gat ggt cca gct gga caa gca<br>Asp Ser Ser Glu Glu Glu Asp Glu Ile Asp Gly Pro Ala Gly Gln Ala<br>                        340                            345                        350 | | 1056 |
| gaa ccg gac aga gcc cat tac aat att gta acc ttt tgt tgc aag tgt<br>Glu Pro Asp Arg Ala His Tyr Asn Ile Val Thr Phe Cys Cys Lys Cys<br>                             355                            360                        365 | | 1104 |
| gac tct acg ctt cgg ttg tgc gta caa agc aca cac gta gac att cgt<br>Asp Ser Thr Leu Arg Leu Cys Val Gln Ser Thr His Val Asp Ile Arg<br>          370                            375                            380 | | 1152 |
| act ttg gaa gac ctg tta atg ggc aca cta gga att gtg tgc ccc atc<br>Thr Leu Glu Asp Leu Leu Met Gly Thr Leu Gly Ile Val Cys Pro Ile<br>385                          390                            395                        400 | | 1200 |
| tgt tct cag gat aag ctt aag ttt aaa ccg ctg atc agc ctc gac tgt<br>Cys Ser Gln Asp Lys Leu Lys Phe Lys Pro Leu Ile Ser Leu Asp Cys<br>                             405                            410                        415 | | 1248 |

```
gcc ttc tag                                                          1257
Ala Phe
```

<210> SEQ ID NO 35
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
atgggggatt ctgaaaggcg gaaatcggaa cggcgtcgtt cccttggata tccctctgca    60
tatgatgacg tctcgattcc tgctcgcaga ccatcaacac gtactcagcg aaatttaaac   120
caggatgatt tgtcaaaaca tggaccattt accgaccatc aaacacaaaa acataaatcg   180
gcgaaagccg tatcggaaga cgtttcgtct accacccggg gtggctttac aaacaaaccc   240
cgtaccaagc ccgggtcag agctgtacaa agtaataaat tcgctttcag tacggctcct    300
tcatcagcat ctagcacttg gagatcaaat acagtggcat ttaatcagcg tatgttttgc   360
ggagcggttg caactgtggc tcaatatcac gcataccaag gcgcgctcgc cctttggcgt   420
caagatcctc cgcgaacaaa tgaagaatta gatgcatttc tttccagagc tgtcattaaa   480
attaccattc aagagggtcc aaatttgatg ggggaagccg aaacctgtgc ccgcaaacta   540
ttggaagagt ctggattatc ccaggggaac gagaacgtaa agtccaaatc tgaacgtaca   600
accaaatctg aacgtacaag acgcggcggt gaaattgaaa tcaaatcgcc agatccggga   660
tctcatcgta cacataaccc tcgcactccc gcaacttcgc gtcgccatca ttcatccgcc   720
cgcggatatc gtagcagtga tagcgaataa                                    750
```

<210> SEQ ID NO 36
<211> LENGTH: 301
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Met Thr Ser Arg Arg Ser Val Lys Ser Gly Pro Arg Glu Val Pro Arg
1               5                   10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
    50                  55                  60

Tyr Ala Leu Tyr Gly Gly Ser Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Ala Gly Ser Gly Gly Ala Gly
            100                 105                 110

Arg Thr Pro Thr Thr Ala Pro Arg Ala Pro Arg Thr Gln Arg Val Ala
        115                 120                 125

Ser Lys Ala Pro Ala Ala Pro Ala Ala Glu Thr Thr Arg Gly Arg Lys
    130                 135                 140
```

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
            165                 170                 175

His Phe Ser Thr Ala Pro Pro Asn Pro Asp Ala Pro Trp Thr Pro Arg
            180                 185                 190

Val Ala Gly Phe Asn Lys Arg Val Phe Cys Ala Ala Val Gly Arg Leu
            195                 200                 205

Ala Ala Met His Ala Arg Met Ala Ala Val Gln Leu Trp Asp Met Ser
            210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
            245                 250                 255

Glu Leu Val Asn Pro Asp Val Val Gln Asp Val Asp Ala Ala Thr Ala
            260                 265                 270

Thr Arg Gly Arg Ser Ala Ala Ser Arg Pro Thr Glu Arg Pro Arg Ala
            275                 280                 285

Pro Ala Arg Ser Ala Ser Arg Pro Arg Arg Pro Val Glu
290                 295                 300

<210> SEQ ID NO 37
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Thr Ser Arg Arg Ser Val Lys Ser Gly Pro Arg Glu Val Pro Arg
1               5                   10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
50                  55                  60

Tyr Ala Leu Tyr Gly Gly Ser Ser Glu Asp Asp Glu His Pro Glu
65                  70                  75                  80

Val Pro Arg Thr Arg Arg Pro Val Ser Gly Ala Val Leu Ser Gly Pro
            85                  90                  95

Gly Pro Ala Arg Ala Pro Pro Pro Ala Gly Ser Gly Gly Ala Gly
            100                 105                 110

Arg Thr Pro Thr Thr Ala Pro Arg Ala Pro Arg Thr Gln Arg Val Ala
            115                 120                 125

Ser Lys Ala Pro Ala Ala Pro Ala Ala Glu Thr Thr Arg Gly Arg Lys
130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
            165                 170                 175

His Phe Ser Thr Ala Pro Pro Asn Pro Asp Ala Pro Trp Thr Pro Arg
            180                 185                 190

Val Ala Gly Phe Asn Lys Arg Val Phe Cys Ala Ala Val Gly Arg Leu
            195                 200                 205

Ala Ala Met His Ala Arg Met Ala Val Gln Leu Trp Asp Met Ser
        210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Val Val Gln Asp Val Asp Ala Ala Thr Ala
            260                 265                 270

Thr Arg Gly Arg Ser Ala Ala Ser Arg Pro Thr Glu Arg Pro Arg Ala
        275                 280                 285

Pro Ala Arg Ser Ala Ser Arg Pro Arg Pro Val Glu Gly Thr Glu
    290                 295                 300

Leu Gly Ser Met His Gly Asp Thr Pro Thr Leu His Glu Tyr Met Leu
305                 310                 315                 320

Asp Leu Gln Pro Glu Thr Thr Asp Leu Tyr Cys Tyr Glu Gln Leu Asn
                325                 330                 335

Asp Ser Ser Glu Glu Asp Glu Ile Asp Gly Pro Ala Gly Gln Ala
            340                 345                 350

Glu Pro Asp Arg Ala His Tyr Asn Ile Val Thr Phe Cys Cys Lys Cys
        355                 360                 365

Asp Ser Thr Leu Arg Leu Cys Val Gln Ser Thr His Val Asp Ile Arg
370                 375                 380

Thr Leu Glu Asp Leu Leu Met Gly Thr Leu Gly Ile Val Cys Pro Ile
385                 390                 395                 400

Cys Ser Gln Asp Lys Leu Lys Phe Lys Pro Leu Ile Ser Leu Asp Cys
                405                 410                 415

Ala Phe

<210> SEQ ID NO 38
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Gly Asp Ser Glu Arg Arg Lys Ser Glu Arg Arg Ser Leu Gly
1               5                   10                  15

Tyr Pro Ser Ala Tyr Asp Asp Val Ser Ile Pro Ala Arg Arg Pro Ser
            20                  25                  30

Thr Arg Thr Gln Arg Asn Leu Asn Gln Asp Asp Leu Ser Lys His Gly
        35                  40                  45

Pro Phe Thr Asp His Pro Thr Gln Lys His Lys Ser Ala Lys Ala Val
    50                  55                  60

Ser Glu Asp Val Ser Ser Thr Thr Arg Gly Gly Phe Thr Asn Lys Pro
65                  70                  75                  80

Arg Thr Lys Pro Gly Val Arg Ala Val Gln Ser Asn Lys Phe Ala Phe
                85                  90                  95

Ser Thr Ala Pro Ser Ser Ala Ser Ser Thr Trp Arg Ser Asn Thr Val
            100                 105                 110

Ala Phe Asn Gln Arg Met Phe Cys Gly Ala Val Ala Thr Val Ala Gln
        115                 120                 125

Tyr His Ala Tyr Gln Gly Ala Leu Ala Leu Trp Arg Gln Asp Pro Pro
    130                 135                 140

```
Arg Thr Asn Glu Glu Leu Asp Ala Phe Leu Ser Arg Ala Val Ile Lys
145                 150                 155                 160

Ile Thr Ile Gln Glu Gly Pro Asn Leu Met Gly Ala Glu Thr Cys
        165                 170                 175

Ala Arg Lys Leu Leu Glu Glu Ser Gly Leu Ser Gln Gly Asn Glu Asn
            180                 185                 190

Val Lys Ser Lys Ser Glu Arg Thr Thr Lys Ser Glu Arg Thr Arg Arg
        195                 200                 205

Gly Gly Glu Ile Glu Ile Lys Ser Pro Asp Pro Gly Ser His Arg Thr
            210                 215                 220

His Asn Pro Arg Thr Pro Ala Thr Ser Arg Arg His His Ser Ser Ala
225                 230                 235                 240

Arg Gly Tyr Arg Ser Ser Asp Ser Glu
                245

<210> SEQ ID NO 39
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

<210> SEQ ID NO 40
<211> LENGTH: 5431
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
```

```
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagaattcc    960
accacactgg actagtggat ccgagctcgg taccaagctt aagtttaaac cgctgatcag   1020
cctcgactgt gccttctagt tgccagccat ctgttgtttg cccctccccc gtgccttcct   1080
tgaccctgga aggtgccact cccactgtcc tttcctaata aaatgaggaa attgcatcgc   1140
attgtctgag taggtgtcat tctattctgg gggtggggt ggggcaggac agcaaggggg    1200
aggattggga agacaatagc aggcatgctg ggatgcggt gggctctatg cttctgagg     1260
cggaaagaac cagctggggc tctaggggt atccccacgc gccctgtagc ggcgcattaa    1320
gcgcggcggt tgtggtggtt acgcgcagcg tgaccgctac acttgccagc gccctagcgc   1380
ccgctccttt cgctttcttc ccttcctttc tcgccacgtt cgccggcttt cccgtcaag    1440
ctctaaatcg gggcatccct ttagggttcc gatttagtgc tttacggcac ctcgaccca    1500
aaaaacttga ttagggtgat ggttcacgta gtgggccatc gccctgatag acggtttttc   1560
gccctttgac gttggagtcc acgttcttta atagtggact cttgttccaa actggaacaa   1620
cactcaaccc tatctcggtc tattcttttg atttataagg gattttgggg atttcggcct   1680
attggttaaa aaatgagctg atttaacaaa aatttaacgc gaattaattc tgtggaatgt   1740
gtgtcagtta gggtgtggaa agtccccagg ctccccaggc aggcagaagt atgcaaagca   1800
tgcatctcaa ttagtcagca accaggtgtg gaaagtcccc aggctcccca gcaggcagaa   1860
gtatgcaaag catgcatctc aattagtcag caaccatagt cccgccccta actccgccca   1920
tcccgcccct aactccgccc agttccgccc attctccgcc ccatggctga ctaatttttt   1980
ttatttatgc agaggccgag gccgcctctg cctctgagct attccagaag tagtgaggag   2040
gcttttttgg aggcctaggc ttttgcaaaa agctcccggg agcttgtata tccattttcg   2100
gatctgatca agagacagga tgaggatcgt ttcgcatgat tgaacaagat ggattgcacg   2160
caggttctcc ggccgcttgg gtggagaggc tattcggcta tgactgggca acagacaa    2220
tcggctgctc tgatgccgcc gtgttccggc tgtcagcgca gggcgcccg gttctttttg    2280
tcaagaccga cctgtccggt gccctgaatg aactgcagga cgaggcagcg cggctatcgt   2340
ggctggccac gacgggcgtt ccttgcgcag ctgtgctcga cgttgtcact gaagcgggaa   2400
gggactggct gctattgggc gaagtgccgg ggcaggatct cctgtcatct caccttgctc   2460
ctgccgagaa agtatccatc atggctgatg caatgcggcg gctgcatacg cttgatccgg   2520
ctacctgccc attcgaccac caagcgaaac atcgcatcga gcgagcacgt actcggatgg   2580
aagccggtct tgtcgatcag gatgatctgg acgaagagca tcaggggctc gcgccagccg   2640
aactgttcgc caggctcaag gcgcgcatgc ccgacgcga ggatctcgtc gtgacccatg    2700
gcgatgcctg cttgccgaat atcatggtgg aaaatggccg cttttctgga ttcatcgact   2760
gtggccggct gggtgtggcg gaccgctatc aggacatagc gttggctacc cgtgatattg   2820
ctgaagagct tggcggcgaa tgggctgacc gcttcctcgt gctttacggt atcgccgctc   2880
```

```
ccgattcgca gcgcatcgcc ttctatcgcc ttcttgacga gttcttctga gcgggactct    2940
ggggttcgaa atgaccgacc aagcgacgcc caacctgcca tcacgagatt tcgattccac    3000
cgccgccttc tatgaaaggt tgggcttcgg aatcgttttc cgggacgccg gctggatgat    3060
cctccagcgc ggggatctca tgctggagtt cttcgcccac cccaacttgt ttattgcagc    3120
ttataatggt tacaaataaa gcaatagcat cacaaatttc acaaataaag cattttttc     3180
actgcattct agttgtggtt tgtccaaact catcaatgta tcttatcatg tctgtatacc    3240
gtcgacctct agctagagct tggcgtaatc atggtcatag ctgtttcctg tgtgaaattg    3300
ttatccgctc acaattccac acaacatacg agccggaagc ataaagtgta agcctggggg   3360
tgcctaatga gtgagctaac tcacattaat tgcgttgcgc tcactgcccg ctttccagtc    3420
gggaaacctg tcgtgccagc tgcattaatg aatcggccaa cgcgcgggga gaggcggttt    3480
gcgtattggg cgctcttccg cttcctcgct cactgactcg ctgcgctcgg tcgttcggct    3540
gcggcgagcg gtatcagctc actcaaaggc ggtaatacgg ttatccacag aatcaggggga   3600
taacgcagga aagaacatgt gagcaaaagg ccagcaaaag gccaggaacc gtaaaaaggc    3660
cgcgttgctg gcgttttcc ataggctccg cccccctgac gagcatcaca aaaatcgacg     3720
ctcaagtcag aggtggcgaa acccgacagg actataaaga taccaggcgt ttccccctgg    3780
aagctccctc gtgcgctctc ctgttccgac cctgccgctt accggatacc tgtccgcctt    3840
tctcccttcg ggaagcgtgg cgctttctca atgctcacgc tgtaggtatc tcagttcggt    3900
gtaggtcgtt cgctccaagc tgggctgtgt gcacgaaccc cccgttcagc ccgaccgctg    3960
cgccttatcc ggtaactatc gtcttgagtc aacccggta agacacgact tatcgccact     4020
ggcagcagcc actggtaaca ggattagcag agcgaggtat gtaggcggtg ctacagagtt    4080
cttgaagtgg tggcctaact acggctacac tagaaggaca gtatttggta tctgcgctct    4140
gctgaagcca gttaccttcg gaaaaagagt tggtagctct tgatccggca acaaaccac     4200
cgctggtagc ggtggttttt tgtttgcaa gcagcagatt acgcgcagaa aaaaaggatc     4260
tcaagaagat cctttgatct tttctacggg gtctgacgct cagtggaacg aaaactcacg    4320
ttaagggatt ttggtcatga gattatcaaa aaggatcttc acctagatcc ttttaaatta    4380
aaaatgaagt tttaaatcaa tctaaagtat atatgagtaa acttggtctg acagttacca    4440
atgcttaatc agtgaggcac ctatctcagc gatctgtcta tttcgttcat ccatagttgc    4500
ctgactcccc gtcgtgtaga taactacgat acgggagggc ttaccatctg gccccagtgc    4560
tgcaatgata ccgcgagacc cacgctcacc ggctccagat ttatcagcaa taaaccagcc    4620
agccggaagg gccgagcgca gaagtggtcc tgcaacttta tccgcctcca tccagtctat    4680
taattgttgc cgggaagcta gagtaagtag ttcgccagtt aatagtttgc gcaacgttgt    4740
tgccattgct acaggcatcg tggtgtcacg ctcgtcgttt ggtatggctt cattcagctc    4800
cggttcccaa cgatcaaggc gagttacatg atccccatg ttgtgcaaaa aagcggttag     4860
ctccttcggt cctccgatcg ttgtcagaag taagttggcc gcagtgttat cactcatggt    4920
tatggcagca ctgcataatt ctcttactgt catgccatcc gtaagatgct tttctgtgac    4980
tggtgagtac tcaaccaagt cattctgaga atagtgtatg cggcgaccga gttgctcttg    5040
cccggcgtca atacgggata ataccgcgcc acatagcaga actttaaaag tgctcatcat    5100
tggaaaacgt tcttcgggc gaaaactctc aaggatctta ccgctgttga tccagttc      5160
gatgtaaccc actcgtgcac ccaactgatc ttcagcatct tttactttca ccagcgtttc    5220
tgggtgagca aaaacaggaa ggcaaaatgc cgcaaaaaag ggaataaggg cgacacggaa    5280
```

```
atgttgaata ctcatactct tccttttca atattattga agcatttatc agggttattg    5340
tctcatgagc ggatacatat ttgaatgtat ttagaaaaat aaacaaatag gggttccgcg    5400
cacatttccc cgaaaagtgc cacctgacgt c                                   5431

<210> SEQ ID NO 41
<211> LENGTH: 4479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
tggccattgc atacgttgta tccatatcat aatatgtaca tttatattgg ctcatgtcca      60
acattaccgc catgttgaca ttgattattg actagttatt aatagtaatc aattacgggg     120
tcattagttc atagcccata tatggagttc cgcgttacat aacttacggt aaatggcccg     180
cctggctgac cgcccaacga cccccgccca ttgacgtcaa taatgacgta tgttcccata     240
gtaacgccaa tagggacttt ccattgacgt caatgggtgg agtatttacg gtaaactgcc     300
cacttggcag tacatcaagt gtatcatatg ccaagtacgc cccctattga cgtcaatgac     360
ggtaaatggc ccgcctggca ttatgcccag tacatgacct tatgggactt tcctacttgg     420
cagtacatct acgtattagt catcgctatt accatggtga tgcggttttg gcagtacatc     480
aatgggcgtg gatagcggtt tgactcacgg ggatttccaa gtctccaccc cattgacgtc     540
aatgggagtt tgttttggca ccaaaatcaa cgggactttc caaaatgtcg taacaactcc     600
gccccattga cgcaaatggg cggtaggcgt gtacggtggg aggtctatat aagcagagct     660
cgtttagtga accgtcagat cgcctggaga cgccatccac gctgttttga cctccataga     720
agacaccggg accgatccag cctccgcggc cgggaacggt gcattggaac gcggattccc     780
cgtgccaaga gtgacgtaag taccgcctat agagtctata ggcccacccc cttggcttct     840
tatgcatgct atactgtttt tggcttgggg tctatacacc cccgcttcct catgttatag     900
gtgatggtat agcttagcct ataggtgtgg gttattgacc attattgacc actccaacgg     960
tggagggcag tgtagtctga gcagtactcg ttgctgccgc gcgcgccacc agacataata    1020
gctgacagac taacgactg ttcctttcca tgggtctttt ctgcagtcac cgtcgtcgac    1080
ggtatcgata agcttgatat cgaattcacg tgggcccggt accgtatact ctagagcggc    1140
cgcggatcca gatctttttc cctcgccaaa aattatgggg acatcatgaa gccccttgag    1200
catctgactt ctggctaata aaggaaattt atttcattgc aatagtgtgt tggaattttt    1260
tgtgtctctc actcggaagg acatatggga gggcaaatca tttaaaacat cagaatcagt    1320
atttggttta gagtttggca acatatgcca ttcttccgct tcctcgctca ctgactcgct    1380
gcgctcggtc gttcggctgc ggcgagcggt atcagctcac tcaaaggcgg taatacggtt    1440
atccacagaa tcaggggata acgcaggaaa gaacatgtga gcaaaaggcc agcaaaaggc    1500
caggaaccgt aaaaaggccg cgttgctggc gtttttccat aggctccgcc cccctgacga    1560
gcatcacaaa aatcgacgct caagtcagag gtggcgaaac ccgacaggac tataaagata    1620
ccaggcgttt ccccctggaa gctccctcgt gcgctctcct gttccgaccc tgccgcttac    1680
cggatacctg tccgcctttc tcccttcggg aagcgtggcg ctttctcaat gctcacgctg    1740
taggtatctc agttcggtgt aggtcgttcg ctccaagctg ggctgtgtgc acgaaccccc    1800
cgttcagccc gaccgctgcg ccttatccgg taactatcgt cttgagtcca acccggtaag    1860
```

```
acacgactta tcgccactgg cagcagccac tggtaacagg attagcagag cgaggtatgt    1920
aggcggtgct acagagttct tgaagtggtg gcctaactac ggctacacta gaaggacagt    1980
atttggtatc tgcgctctgc tgaagccagt taccttcgga aaaagagttg gtagctcttg    2040
atccggcaaa caaaccaccg ctggtagcgg tggttttttt gtttgcaagc agcagattac    2100
gcgcagaaaa aaaggatctc aagaagatcc tttgatcttt tctacggggt ctgacgctca    2160
gtggaacgaa aactcacgtt aagggatttt ggtcatgaga ttatcaaaaa ggatcttcac    2220
ctagatcctt ttaaattaaa aatgaagttt taaatcaatc taaagtatat atgagtaaac    2280
ttggtctgac agttaccaat gcttaatcag tgaggcacct atctcagcga tctgtctatt    2340
tcgttcatcc atagttgcct gactccgggg ggggggggcg ctgaggtctg cctcgtgaag    2400
aaggtgttgc tgactcatac cagggcaacg ttgttgccat tgctacaggc atcgtggtgt    2460
cacgctcgtc gtttggtatg gcttcattca gctccggttc ccaacgatca aggcgagtta    2520
catgatcccc catgttgtgc aaaaaagcgg ttagctcctt cggtcctccg atcgttgtca    2580
gaagtaagtt ggccgcagtg ttatcactca tggttatggc agcactgcat aattctctta    2640
ctgtcatgcc atccgtaaga tgcttttctg tgactggtga gtactcaacc aagtcattct    2700
gagaatagtg tatgcggcga ccgagttgct cttgcccggc gtcaatacgg gataataccg    2760
cgccacatag cagaacttta aaagtgctca tcattggaaa acgttcttcg gggcgaaaac    2820
tctcaaggat cttaccgctg ttgagatcca gttcgatgta acccactcgt gcacctgaat    2880
cgccccatca tccagccaga aagtgaggga gccacggttg atgagagctt tgttgtaggt    2940
ggaccagttg gtgattttga acttttgctt tgccacggaa cggtctgcgt tgtcgggaag    3000
atgcgtgatc tgatccttca actcagcaaa agttcgattt attcaacaaa gccgccgtcc    3060
cgtcaagtca gcgtaatgct ctgccagtgt acaaccaat taaccaattc tgattagaaa    3120
aactcatcga gcatcaaatg aaactgcaat ttattcatat caggattatc aataccatat    3180
ttttgaaaaa gccgtttctg taatgaagga gaaaactcac cgaggcagtt ccataggatg    3240
gcaagatcct ggtatcggtc tgcgattccg actcgtccaa catcaataca acctattaat    3300
ttcccctcgt caaaaataag gttatcaagt gagaaatcac catgagtgac gactgaatcc    3360
ggtgagaatg gcaaaagctt atgcatttct ttccagactt gttcaacagg ccagccatta    3420
cgctcgtcat caaaatcact cgcatcaacc aaaccgttat tcattcgtga ttgcgcctga    3480
gcgagacgaa atacgcgatc gctgttaaaa ggacaattac aaacaggaat cgaatgcaac    3540
cggcgcagga acactgccag cgcatcaaca atattttcac ctgaatcagg atattcttct    3600
aatacctgga atgctgtttt cccggggatc gcagtggtga gtaaccatgc atcatcagga    3660
gtacggataa aatgcttgat ggtcggaaga ggcataaatt ccgtcagcca gtttagtctg    3720
accatctcat ctgtaacatc attggcaacg ctacctttgc catgtttcag aaacaactct    3780
ggcgcatcgg gcttcccata caatcgatag attgtcgcac ctgattgccc gacattatcg    3840
cgagcccatt tatacccata taaatcagca tccatgttgg aatttaatcg cggcctcgag    3900
caagacgttt cccgttgaat atggctcata cacccccttg tattactgtt tatgtaagca    3960
gacagtttta ttgttcatga tgatatattt ttatcttgtg caatgtaaca tcagagattt    4020
tgagacacaa cgtggctttc ccccccccccc cattattgaa gcatttatca gggttattgt    4080
ctcatgagcg gatacatatt tgaatgtatt tagaaaaata acaaataggg gttccgcgc    4140 acatttcccc gaaaagtgcc acctgacgtc taagaaacca ttattatcat gacattaacc    4200
```

```
tataaaaata ggcgtatcac gaggcccttt cgtcctcgcg cgtttcggtg atgacggtga      4260
aaacctctga cacatgcagc tcccggagac ggtcacagct tgtctgtaag cggatgccgg      4320
gagcagacaa gcccgtcagg gcgcgtcagc gggtgttggc gggtgtcggg gctggcttaa      4380
ctatgcggca tcagagcaga ttgtactgag agtgcaccat atgcggtgtg aaataccgca      4440
cagatgcgta aggagaaaat accgcatcag attggctat                            4479
```

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 42

```
ugccuacgaa cucuucaccu t                                               21
```

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 43

```
ggugaagagu ucguaggcat t                                               21
```

<210> SEQ ID NO 44
<211> LENGTH: 627
<212> TYPE: DNA
<213> ORGANISM: Mus musculus

<400> SEQUENCE: 44

```
atggcatctg gacaaggacc aggtcccccg aaggtgggct gcgatgagtc cccgtcccct      60
tctgaacagc aggttgccca ggacacagag gaggtctttc gaagctacgt ttttttacctc     120 caccagcagg aacaggagac ccaggggcgg ccgcctgcca accccgagat ggacaacttg      180
cccctggaac ccaacagcat cttgggtcag gtgggtcggc agcttgctct catcggagat      240
gatattaacc ggcgctacga cacagagttc cagaatttac tagaacagct tcagcccaca      300
gccgggaatg cctacgaact cttcaccaag atcgcctcca gcctatttaa gagtggcatc      360
agctggggcc gcgtggtggc tctcctgggc tttggctacc gtctggccct gtacgtctac      420
cagcgtggtt tgaccggctt cctgggccag gtgacctgct ttttggctga tatcatactg      480
catcattaca tcgccagatg gatcgcacag agaggcggtt gggtggcagc cctgaatttg      540
cgtagagacc ccatcctgac cgtaatggtg attttttggtg tggttctgtt gggccaattc      600
gtggtacaca gattcttcag atcatga                                         627
```

<210> SEQ ID NO 45
<211> LENGTH: 19
<212> TYPE: DNA
<213> ORGANISM: Mus musculus

<400> SEQUENCE: 45
tgcctacgaa ctcttcacc                                                19

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
uauggagcug cagaggaugt t                                             21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
cauccucugc agcuccauau t                                             21

<210> SEQ ID NO 48
<211> LENGTH: 579
<212> TYPE: DNA
<213> ORGANISM: Mus musculus

<400> SEQUENCE: 48
atggacgggt ccggggagca gcttgggagc ggcgggccca ccagctctga acagatcatg      60
aagacagggg ccttttttgct acagggtttc atccaggatc gagcagggag gatggctggg    120
gagacacctg agctgacctt ggagcagccg ccccaggatg cgtccaccaa gaagctgagc    180
gagtgtctcc ggcgaattgg agatgaactg gatagcaata tggagctgca gaggatgatt    240
gctgacgtgg acacggactc cccccgagag gtcttcttcc gggtggcagc tgacatgttt    300
gctgatggca acttcaactg gggccgcgtg gttgccctct tctactttgc tagcaaactg    360
gtgctcaagg ccctgtgcac taaagtgccc gagctgatca gaaccatcat gggctggaca    420
ctggacttcc tccgtgagcg gctgcttgtc tggatccaag accagggtgg ctgggaaggc    480
ctcctctcct acttcgggac ccccacatgg cagacagtga ccatctttgt ggctggagtc    540
ctcaccgcct cgctcaccat ctggaagaag atgggctga                            579

<210> SEQ ID NO 49
<211> LENGTH: 19
<212> TYPE: DNA
<213> ORGANISM: Mus musculus

<400> SEQUENCE: 49
tatggagctg cagaggatg                                                19

<210> SEQ ID NO 50
<211> LENGTH: 1491
<212> TYPE: DNA

<213> ORGANISM: Homo sapiens

<400> SEQUENCE: 50

```
atggacttca gcagaaatct ttatgatatt ggggaacaac tggacagtga agatctggcc      60
tccctcaagt tcctgagcct ggactacatt ccgcaaagga agcaagaacc catcaaggat     120
gccttgatgt tattccagag actccaggaa agagaatgt tggaggaaag caatctgtcc      180
ttcctgaagg agctgctctt ccgaattaat agactggatt tgctgattac ctacctaaac     240
actagaaagg aggagatgga aagggaactt cagacaccag gcagggctca aatttctgcc     300
tacaggttcc acttctgccg catgagctgg gctgaagcaa acagccagtg ccagacacag     360
tctgtacctt tctggcggag ggtcgatcat ctattaataa gggtcatgct ctatcagatt     420
tcagaagaag tgagcagatc agaattgagg tcttttaagt ttcttttgca agaggaaatc     480
tccaaatgca aactggatga tgacatgaac ctgctggata ttttcataga gatggagaag     540
agggtcatcc tgggagaagg aaagttggac atcctgaaaa gagtctgtgc ccaaatcaac     600
aagagcctgc tgaagataat caacgactat gaagaattca gcaaagggga ggagttgtgt     660
ggggtaatga caatctcgga ctctccaaga gaacaggata gtgaatcaca gactttggac     720
aaagtttacc aaatgaaaag caaacctcgg ggatactgtc tgatcatcaa caatcacaat     780
tttgcaaaag cacgggagaa agtgcccaaa cttcacagca ttagggacag gaatggaaca     840
cacttggatg caggggcttt gaccacgacc tttgaagagc ttcattttga gatcaagccc     900
cacgatgact gcacagtaga gcaaatctat gagattttga aaatctacca actcatggac     960
cacagtaaca tggactgctt catctgctgt atcctctccc atggagacaa gggcatcatc    1020
tatggcactg atggacagga ggcccccatc tatgagctga catctcagtt cactggtttg    1080
aagtgccctt cccttgctgg aaaacccaaa gtgttttta ttcaggcttg tcagggggat     1140
aactaccaga aaggtatacc tgttgagact gattcagagg agcaacccta tttagaaatg    1200
gatttatcat cacctcaaac gagatatatc ccggatgagg ctgactttct gctggggatg    1260
gccactgtga ataactgtgt tcctaccgga acccctgcag agggaacctg gtacatccag    1320
tcactttgcc agagcctgag agagcgatgt cctcgaggcg atgatattct caccatcctg    1380
actgaagtga actatgaagt aagcaacaag gatgacaaga aaaacatggg gaaacagatg    1440
cctcagccta ctttcacact aagaaaaaaa cttgtcttcc cttctgattg a              1491
```

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51

```
aaccucgggg auacugucug att                                               23
```

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
Synthetic oligonucleotide

<400> SEQUENCE: 52
ucagacagua uccccgaggu utt                                          23

<210> SEQ ID NO 53
<211> LENGTH: 1251
<212> TYPE: DNA
<213> ORGANISM: Homo sapiens

<400> SEQUENCE: 53
atggacgaag cggatcggcg gctcctgcgg cggtgccggc tgcggctggt ggaagagctg     60
caggtggacc agctctggga cgccctgctg agccgcgagc tgttcaggcc ccatatgatc    120
gaggacatcc agcgggcagg ctctggatct cggcgggatc aggccaggca gctgatcata    180
gatctggaga ctcgagggag tcaggctctt cctttgttca tctcctgctt agaggacaca    240
ggccaggaca tgctggcttc gtttctgcga actaacaggc aagcagcaaa gttgtcgaag    300
ccaaccctag aaaaccttac cccagtggtg ctcagaccag agattcgcaa accagaggtt    360
ctcagaccgg aaacacccag accagtgac attggttctg gaggatttgg tgatgtcggt    420
gctcttgaga gtttgagggg aaatgcagat ttggcttaca tcctgagcat ggagccctgt    480
ggccactgcc tcattatcaa caatgtgaac ttctgccgtg agtccgggct ccgcacccgc    540
actggctcca acatcgactg tgagaagttg cggcgtcgct tctcctcgct gcatttcatg    600
gtggaggtga agggcgacct gactgccaag aaaatggtgc tggctttgct ggagctggcg    660
cagcaggacc acggtgctct ggactgctgc gtggtggtca ttctctctca cggctgtcag    720
gccagccacc tgcagttccc aggggctgtc tacggcacag atggatgccc tgtgtcggtc    780
gagaagattg tgaacatctt caatgggacc agctgcccca gcctgggagg gaagcccaag    840
ctctttttca tccaggcctg tggtggggag cagaaagacc atgggtttga ggtggcctcc    900
acttcccctg aagacgagtc ccctggcagt aaccccgagc cagatgccac cccgttccag    960
gaaggtttga ggaccttcga ccagctggac gccatatcta gtttgcccac acccagtgac   1020
atctttgtgt cctactctac tttcccaggt tttgttcct ggagggaccc caagagtggc   1080
tcctggtacg ttgagaccct ggacgacatc tttgagcagt gggctcactc tgaagacctg   1140
cagtccctcc tgcttagggt cgctaatgct gtttcggtga aagggattta taacagatg   1200 cctggttgct ttaatttcct ccggaaaaaa cttttcttta aacatcata a               1251

<210> SEQ ID NO 54
<211> LENGTH: 834
<212> TYPE: DNA
<213> ORGANISM: Homo sapiens

<400> SEQUENCE: 54
atggagaaca ctgaaaactc agtggattca aaatccatta aaaatttgga accaaagatc     60
atacatggaa gcgaatcaat ggactctgga atatccctgg acaacagtta taaaatggat    120
tatcctgaga tgggttttatg tataataatt aataataaga attttcataa aagcactgga    180
atgacatctc ggtctggtac agatgtcgat gcagcaaacc tcagggaaac attcagaaac    240
ttgaaatatg aagtcaggaa taaaaatgat cttacacgtg aagaaattgt ggaattgatg    300
cgtgatgttt ctaaagaaga tcacagcaaa aggagcagtt ttgttgtgt gcttctgagc    360 catggtgaag aaggaataat ttttggaaca aatggacctg ttgacctgaa aaaaataaca    420

```
aactttttca gagggatcg ttgtagaagt ctaactggaa aacccaaact tttcattatt    480
caggcctgcc gtggtacaga actggactgt ggcattgaga cagacagtgg tgttgatgat    540
gacatggcgt gtcataaaat accagtggag gccgacttct tgtatgcata ctccacagca    600
cctggttatt attcttggcg aaattcaaag gatggctcct ggttcatcca gtcgctttgt    660
gccatgctga acagtatgc cgacaagctt gaatttatgc acattcttac ccgggttaac    720
cgaaaggtgg caacagaatt tgagtccttt tcctttgacg ctactttca tgcaaagaaa    780 cagattccat gtattgtttc catgctcaca aaagaactct attttatca ctaa          834
```

<210> SEQ ID NO 55
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
atggcgtacc catacgatgt tccagattac gctagcttga gatctaccat gtctcagagc     60
aaccgggagc tggtggttga cttctctctcc tacaagcttt cccagaaagg atacagctgg   120
agtcagttta gtgatgtgga agagaacagg actgaggccc agaagggac tgaatcggag    180 atggagaccc ccagtgccat caatggcaac ccatcctggc acctggcaga cagccccgcg    240
gtgaatggag ccactgcgca cagcagcagt ttggatgccc gggaggtgat ccccatggca    300
gcagtaaagc aagcgctgag ggaggcaggc gacgagtttg aactgcggta ccggcgggca    360
ttcagtgacc tgacatccca gctccacatc accccaggga cagcatatca gagctttgaa    420
caggtagtga atgaactctt ccgggatggg gtaaactggg gtcgcattgt ggccttttc    480 tccttcggcg gggcactgtg cgtggaaagc gtagacaagg agatgcaggt attggtgagt    540
cggatcgcag cttggatggc cacttacctg aatgaccacc tagagccttg gatccaggag    600
aacggcggct gggatacttt tgtggaactc tatgggaaca atgcagcagc cgagagccga    660
aagggccagg aacgcttcaa ccgctggttc ctgacgggca tgactgtggc cggcgtggtt    720
ctgctgggct cactcttcag tcggaaatga                                      750
```

<210> SEQ ID NO 56
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Met Ala Tyr Pro Tyr Asp Val Pro Asp Tyr Ala Ser Leu Arg Ser Thr
1               5                   10                  15

Met Ser Gln Ser Asn Arg Glu Leu Val Val Asp Phe Leu Ser Tyr Lys
            20                  25                  30

Leu Ser Gln Lys Gly Tyr Ser Trp Ser Gln Phe Ser Asp Val Glu Glu
        35                  40                  45

Asn Arg Thr Glu Ala Pro Glu Gly Thr Glu Ser Glu Met Glu Thr Pro
    50                  55                  60

Ser Ala Ile Asn Gly Asn Pro Ser Trp His Leu Ala Asp Ser Pro Ala
65                  70                  75                  80

Val Asn Gly Ala Thr Ala His Ser Ser Ser Leu Asp Ala Arg Glu Val
                85                  90                  95
```

```
Ile Pro Met Ala Ala Val Lys Gln Ala Leu Arg Glu Ala Gly Asp Glu
            100                 105                 110
Phe Glu Leu Arg Tyr Arg Arg Ala Phe Ser Asp Leu Thr Ser Gln Leu
        115                 120                 125
His Ile Thr Pro Gly Thr Ala Tyr Gln Ser Phe Glu Gln Val Val Asn
    130                 135                 140
Glu Leu Phe Arg Asp Gly Val Asn Trp Gly Arg Ile Val Ala Phe Phe
145                 150                 155                 160
Ser Phe Gly Gly Ala Leu Cys Val Glu Ser Val Asp Lys Glu Met Gln
                165                 170                 175
Val Leu Val Ser Arg Ile Ala Ala Trp Met Ala Thr Tyr Leu Asn Asp
            180                 185                 190
His Leu Glu Pro Trp Ile Gln Glu Asn Gly Gly Trp Asp Thr Phe Val
        195                 200                 205
Glu Leu Tyr Gly Asn Asn Ala Ala Ala Glu Ser Arg Lys Gly Gln Glu
    210                 215                 220
Arg Phe Asn Arg Trp Phe Leu Thr Gly Met Thr Val Ala Gly Val Val
225                 230                 235                 240
Leu Leu Gly Ser Leu Phe Ser Arg Lys
                245

<210> SEQ ID NO 57
<211> LENGTH: 6187
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gacggatcgg gagatctccc gatccctat ggtcgactct cagtacaatc tgctctgatg     60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
gtttaaacgg gccctctaga ctcgagcggc cgccactgtg ctggatatct gcagaattcc   960
accacactgg actagtggat ctatggcgta cccatacgat gttccagatt acgctagctt  1020
gagatctacc atgtctcaga gcaaccggga gctggtggtt gactttctct cctacaagct  1080
ttcccagaaa ggatacagct ggagtcagtt tagtgatgtg gaagagaaca ggactgaggc  1140
```

```
cccagaaggg actgaatcgg agatggagac ccccagtgcc atcaatggca acccatcctg   1200
gcacctggca gacagccccg cggtgaatgg agccactgcg cacagcagca gtttggatgc   1260
ccggaggtg  atccccatgg cagcagtaaa gcaagcgctg agggaggcag gcgacgagtt   1320
tgaactgcgg taccggcggg cattcagtga cctgacatcc cagctccaca tcaccccagg   1380
gacagcatat cagagctttg aacaggtagt gaatgaactc ttccgggatg gggtaaactg   1440
gggtcgcatt gtggccttt  tctccttcgg cggggcactg tgcgtggaaa gcgtagacaa   1500
ggagatgcag gtattggtga gtcggatcgc agcttggatg gccacttacc tgaatgacca   1560
cctagagcct tggatccagg agaacggcgg ctgggatact tttgtggaac tctatgggaa   1620
caatgcagca gccgagagcc gaaagggcca ggaacgcttc aaccgctggt tcctgacggg   1680
catgactgtg gccggcgtgg ttctgctggg ctcactcttc agtcggaaat gaagatccga   1740
gctcggtacc aagcttaagt ttaaaccgct gatcagcctc gactgtgcct tctagttgcc   1800
agccatctgt tgtttgcccc tccccgtgc  cttccttgac cctggaaggt gccactccca   1860
ctgtcctttc ctaataaaat gaggaaaatg catcgcattg tctgagtagg tgtcattcta   1920
ttctgggggg tggggtgggg caggacagca agggggagga ttgggaagac aatagcaggc   1980
atgctgggga tgcggtgggc tctatggctt ctgaggcgga agaaccagc  tggggctcta   2040
gggggtatcc ccacgcgccc tgtagcggcg cattaagcgc ggcgggtgtg gtggttacgc   2100
gcagcgtgac cgctacactt gccagcgccc tagcgcccgc tcctttcgct ttcttccctt   2160
cctttctcgc cacgttcgcc ggctttcccc gtcaagctct aaatcggggc atccctttag   2220
ggttccgatt tagtgcttta cggcacctcg accccaaaaa acttgattag ggtgatggtt   2280
cacgtagtgg gccatcgccc tgatagacgg ttttcgccc  tttgacgttg gagtccacgt   2340
tctttaatag tggactcttg ttccaaactg gaacaacact caaccctatc tcggtctatt   2400
cttttgattt ataagggatt ttggggattt cggcctattg gttaaaaaat gagctgattt   2460
aacaaaaatt taacgcgaat taattctgtg gaatgtgtgt cagttagggt gtggaaagtc   2520
cccaggctcc ccaggcaggc agaagtatgc aaagcatgca tctcaattag tcagcaacca   2580
ggtgtggaaa gtccccaggc tccccagcag gcagaagtat gcaaagcatg catctcaatt   2640
agtcagcaac catagtcccg cccctaactc cgcccatccc gcccctaact ccgcccagtt   2700
ccgcccattc tccgccccat ggctgactaa ttttttttat ttatgcagag gccgaggccg   2760
cctctgcctc tgagctattc cagaagtagt gaggaggctt ttttggaggc ctaggctttt   2820
gcaaaaagct cccgggagct gtatatccca ttttcggatc tgatcaagag acaggatgag   2880
gatcgtttcg catgattgaa caagatggat tgcacgcagg ttctccggcc gcttgggtgg   2940
agaggctatt cggctatgac tgggcacaac agacaatcgg ctgctctgat gccgccgtgt   3000
tccggctgtc agcgcagggg cgcccggttc ttttgtcaa  gaccgacctg tccggtgccc   3060
tgaatgaact gcaggacgag gcagcgcggc tatcgtggct ggccacgacg gcgttcctt   3120
gcgcagctgt gctcgacgtt gtcactgaag cgggaaggga ctggctgcta ttgggcgaag   3180
tgccggggca ggatctcctg tcatctcacc ttgctcctgc cgagaaagta tccatcatgg   3240
ctgatgcaat gcggcggctg catacgcttg atccggctac ctgcccattc gaccaccaag   3300
cgaaacatcg catcgagcga gcacgtactc ggatggaagc cggtcttgtc gatcaggatg   3360
atctggacga agagcatcag gggctcgcgc cagccgaact gttcgccagg ctcaaggcgc   3420
gcatgcccga cggcgaggat ctcgtcgtga cccatggcga tgcctgcttg ccgaatatca   3480
```

```
tggtggaaaa tggccgcttt tctggattca tcgactgtgg ccggctgggt gtggcggacc    3540
gctatcagga catagcgttg gctacccgtg atattgctga agagcttggc ggcgaatggg    3600
ctgaccgctt cctcgtgctt tacggtatcg ccgctcccga ttcgcagcgc atcgccttct    3660
atcgccttct tgacgagttc ttctgagcgg gactctgggg ttcgaaatga ccgaccaagc    3720
gacgcccaac ctgccatcac gagatttcga ttccaccgcc gccttctatg aaaggttggg    3780
cttcggaatc gttttccggg acgccggctg gatgatcctc cagcgcgggg atctcatgct    3840
ggagttcttc gcccacccca acttgtttat tgcagcttat aatggttaca aataaagcaa    3900
tagcatcaca aatttcacaa ataaagcatt ttttcactg cattctagtt gtggtttgtc    3960
caaactcatc aatgtatctt atcatgtctg tataccgtcg acctctagct agagcttggc    4020
gtaatcatgg tcatagctgt ttcctgtgtg aaattgttat ccgctcacaa ttccacacaa    4080
catacgagcc ggaagcataa agtgtaaagc ctggggtgcc taatgagtga gctaactcac    4140
attaattgcg ttgcgctcac tgcccgcttt ccagtcggga acctgtcgt gccagctgca    4200 ttaatgaatc ggccaacgcg cggggagagg cggtttgcgt attgggcgct cttccgcttc    4260
ctcgctcact gactcgctgc gctcggtcgt tcggctgcgg cgagcggtat cagctcactc    4320
aaaggcggta atacggttat ccacagaatc aggggataac gcaggaaaga acatgtgagc    4380
aaaaggccag caaaaggcca ggaaccgtaa aaaggccgcg ttgctggcgt ttttccatag    4440
gctccgcccc cctgacgagc atcacaaaaa tcgacgctca gtcagaggt ggcgaaaccc    4500 gacaggacta taaagatacc aggcgtttcc ccctggaagc tccctcgtgc gctctcctgt    4560
tccgaccctg ccgcttaccg gatacctgtc cgcctttctc ccttcgggaa gcgtggcgct    4620
ttctcaatgc tcacgctgta ggtatctcag ttcggtgtag tcgttcgct ccaagctggg    4680 ctgtgtgcac gaaccccccg ttcagcccga ccgctgcgcc ttatccggta actatcgtct    4740
tgagtccaac ccggtaagac acgacttatc gccactggca gcagccactg gtaacaggat    4800
tagcagagcg aggtatgtag gcggtgctac agagttcttg aagtggtggc ctaactacgg    4860
ctacactaga aggacagtat ttggtatctg cgctctgctg aagccagtta ccttcggaaa    4920
aagagttggt agctcttgat ccggcaaaca aaccaccgct ggtagcggtg ttttttttgt    4980
ttgcaagcag cagattacgc gcagaaaaaa aggatctcaa gaagatcctt tgatcttttc    5040
tacggggtct gacgctcagt ggaacgaaaa ctcacgttaa gggattttgg tcatgagatt    5100
atcaaaaagg atcttcacct agatcctttt aaattaaaaa tgaagtttta aatcaatcta    5160
aagtatatat gagtaaactt ggtctgacag ttaccaatgc ttaatcagtg aggcaccta    5220 ctcagcgatc tgtctatttc gttcatccat agttgcctga ctccccgtcg tgtagataac    5280
tacgatacgg gagggcttac catctggccc cagtgctgca atgataccgc gagacccacg    5340
ctcaccggct ccagatttat cagcaataaa ccagccagcc ggaagggccg agcgcagaag    5400
tggtcctgca actttatccg cctccatcca gtctattaat tgttgccggg aagctagagt    5460
aagtagttcg ccagttaata gtttgcgcaa cgttgttgcc attgctacag gcatcgtggt    5520
gtcacgctcg tcgtttggta tggcttcatt cagctccggt tcccaacgat caaggcgagt    5580
tacatgatcc cccatgttgt gcaaaaaagc ggttagctcc ttcggtcctc cgatcgttgt    5640
cagaagtaag ttggccgcag tgttatcact catggttatg gcagcactgc ataattctct    5700
tactgtcatg ccatccgtaa gatgcttttc tgtgactggt gagtactcaa ccaagtcatt    5760
ctgagaatag tgtatgcggc gaccgagttg ctcttgcccg gcgtcaatac gggataatac    5820
cgcgccacat agcagaactt taaaagtgct catcattgga aaacgttctt cggggcgaaa    5880
```

```
actctcaagg atcttaccgc tgttgagatc cagttcgatg taacccactc gtgcacccaa    5940
ctgatcttca gcatctttta ctttcaccag cgtttctggg tgagcaaaaa caggaaggca    6000
aaatgccgca aaaagggaa taagggcgac acggaaatgt tgaatactca tactcttcct     6060
ttttcaatat tattgaagca tttatcaggg ttattgtctc atgagcggat acatatttga    6120
atgtatttag aaaataaac aatagggt tccgcgcaca tttccccgaa aagtgccacc       6180
tgacgtc                                                               6187

<210> SEQ ID NO 58
<211> LENGTH: 6452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg     780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagaattca    960
tgcatggaga tacacctaca ttgcatgaat atatgttaga tttgcaacca gagacaactg    1020
atctctactg ttatgagcaa ttaaatgaca gctcagagga ggaggatgaa atagatggtc    1080
cagctggaca agcagaaccg gacagagccc attacaatat tgtaacccttt tgttgcaagt   1140 gtgactctac gcttcggttg tgcgtacaaa gcacacacgt agacattcgt actttggaag    1200
acctgttaat gggcacacta ggaattgtgt gccccatctg ttctcagaaa ccaggatcta    1260
tggcgtaccc atacgatgtt ccagattacg ctagcttgag atctaccatg tctcagagca    1320
accgggagct ggtggttgac tttctctcct acaagctttc ccagaaagga tacagctgga    1380
gtcagtttag tgatgtggaa gagaacagga ctgaggcccc agaagggact gaatcggaga    1440
tggagacccc cagtgccatc aatggcaacc catcctggca cctggcagac agccccgcgg    1500
tgaatggagc cactgcgcac agcagcagtt tggatgcccg ggaggtgatc cccatggcag    1560
cagtaaagca agcgctgagg gaggcaggcg acgagtttga actgcggtac cggcgggcat    1620
tcagtgacct gacatcccag ctccacatca ccccagggac agcatatcag agctttgaac    1680
```

```
aggtagtgaa tgaactcttc cgggatgggg taaactgggg tcgcattgtg gccttttctt    1740
ccttcggcgg ggcactgtgc gtggaaagcg tagacaagga gatgcaggta ttggtgagtc    1800
ggatcgcagc ttggatggcc acttacctga atgaccacct agagccttgg atccaggaga    1860
acggcggctg ggatactttt gtggaactct atgggaacaa tgcagcagcc gagagccgaa    1920
agggccagga acgcttcaac cgctggttcc tgacgggcat gactgtggcc ggcgtggttc    1980
tactgggctc actcttcagt cggaaatgaa gatccaagct taagtttaaa ccgctgatca    2040
gcctcgactg tgccttctag ttgccagcca tctgttgttt gcccctcccc cgtgccttcc    2100
ttgaccctgg aaggtgccac tcccactgtc ctttcctaat aaaatgagga aattgcatcg    2160
cattgtctga gtaggtgtca ttctattctg ggggtgggg tggggcagga cagcaagggg    2220
gaggattggg aagacaatag caggcatgct ggggatgcgg tgggctctat ggcttctgag    2280
gcggaaagaa ccagctgggg ctctaggggg tatccccacg cgccctgtag cggcgcatta    2340
agcgcggcgg gtgtggtggt tacgcgcagc gtgaccgcta cacttgccag cgccctagcg    2400
cccgctcctt tcgctttctt cccttccttt ctcgccacgt tcgccggctt tccccgtcaa    2460
gctctaaatc gggcatccc tttagggttc cgatttagtg ctttacggca cctcgacccc    2520
aaaaaacttg attagggtga tggttcacgt agtgggccat cgccctgata acggttttt    2580 cgcccttga cgttggagtc cacgttcttt aatagtggac tcttgttcca aactggaaca    2640
acactcaacc ctatctcggt ctattctttt gatttataag ggattttggg gatttcggcc    2700
tattggttaa aaaatgagct gatttaacaa aaatttaacg cgaattaatt ctgtggaatg    2760
tgtgtcagtt agggtgtgga aagtccccag gctccccagg caggcagaag tatgcaaagc    2820
atgcatctca attagtcagc aaccaggtgt ggaaagtccc caggctcccc agcaggcaga    2880
agtatgcaaa gcatgcatct caattagtca gcaaccatag tcccgcccct aactccgccc    2940
atcccgcccc taactccgcc cagttccgcc cattctccgc cccatggctg actaattttt    3000
tttatttatg cagaggccga ggccgcctct gcctctgagc tattccagaa gtagtgagga    3060 ggctttttg gaggcctagg cttttgcaaa aagctcccgg gagcttgtat atccattttc    3120
ggatctgatc aagagacagg atgaggatcg tttcgcatga ttgaacaaga tggattgcac    3180
gcaggttctc cggccgcttg ggtggagagg ctattcggct atgactgggc acaacagaca    3240
atcggctgct ctgatgccgc cgtgttccgg ctgtcagcgc agggg cgccc ggttcttttt    3300 gtcaagaccg acctgtccgg tgccctgaat gaactgcagg acgaggcagc gcggctatcg    3360
tggctggcca cgacgggcgt tccttgcgca gctgtgctcg acgttgtcac tgaagcggga    3420
agggactggc tgctattggg cgaagtgccg gggcaggatc tcctgtcatc tcaccttgct    3480
cctgccgaga aagtatccat catggctgat gcaatgcggc ggctgcatac gcttgatccg    3540
gctacctgcc cattcgacca ccaagcgaaa catcgcatcg agcgagcacg tactcggatg    3600
gaagccggtc ttgtcgatca ggatgatctg gacgaagagc atcaggggct cgcgccagcc    3660
gaactgttcg ccaggctcaa ggcgcgcatg cccgacggcg aggatctcgt cgtgacccat    3720
ggcgatgcct gcttgccgaa tatcatggtg gaaaatggcc gcttttctgg attcatcgac    3780
tgtggccggc tgggtgtggc ggaccgctat caggacatag cgttggctac ccgtgatatt    3840
gctgaagagc ttggcggcga atgggctgac cgcttcctcg tgctttacgg tatcgccgct    3900
cccgattcgc agcgcatcgc cttctatcgc cttcttgacg agttcttctg agcgggactc    3960
tggggttcga aatgaccgac caagcgacgc ccaacctgcc atcacgagat ttcgattcca    4020
```

| | |
|---|---|
| ccgccgcctt ctatgaaagg ttgggcttcg gaatcgtttt ccgggacgcc ggctggatga | 4080 |
| tcctccagcg cggggatctc atgctggagt tcttcgccca ccccaacttg tttattgcag | 4140 |
| cttataatgg ttacaaataa agcaatagca tcacaaattt cacaaataaa gcattttttt | 4200 |
| cactgcattc tagttgtggt ttgtccaaac tcatcaatgt atcttatcat gtctgtatac | 4260 |
| cgtcgacctc tagctagagc ttggcgtaat catggtcata gctgtttcct gtgtgaaatt | 4320 |
| gttatccgct cacaattcca cacaacatac gagccggaag cataaagtgt aaagcctggg | 4380 |
| gtgcctaatg agtgagctaa ctcacattaa ttgcgttgcg ctcactgccc gctttccagt | 4440 |
| cgggaaacct gtcgtgccag ctgcattaat gaatcggcca acgcgcgggg agaggcggtt | 4500 |
| tgcgtattgg gcgctcttcc gcttcctcgc tcactgactc gctgcgctcg tcgttcggc | 4560 |
| tgcggcgagc ggtatcagct cactcaaagg cggtaatacg ttatccaca gaatcagggg | 4620 |
| ataacgcagg aaagaacatg tgagcaaaag gccagcaaaa ggccaggaac cgtaaaaagg | 4680 |
| ccgcgttgct ggcgtttttc cataggctcc gcccccctga cgagcatcac aaaaatcgac | 4740 |
| gctcaagtca gaggtggcga aacccgacag gactataaag ataccaggcg tttccccctg | 4800 |
| gaagctccct cgtgcgctct cctgttccga ccctgccgct taccggatac ctgtccgcct | 4860 |
| ttctcccttc gggaagcgtg gcgctttctc aatgctcacg ctgtaggtat ctcagttcgg | 4920 |
| tgtaggtcgt tcgctccaag ctgggctgtg tgcacgaacc ccccgttcag cccgaccgct | 4980 |
| gcgccttatc cggtaactat cgtcttgagt ccaacccggt aagacacgac ttatcgccac | 5040 |
| tggcagcagc cactggtaac aggattagca gagcgaggta tgtaggcggt gctacagagt | 5100 |
| tcttgaagtg gtggcctaac tacggctaca ctagaaggac agtatttggt atctgcgctc | 5160 |
| tgctgaagcc agttaccttc ggaaaaagag ttggtagctc ttgatccggc aaacaaacca | 5220 |
| ccgctggtag cggtggtttt tttgtttgca agcagcagat tacgcgcaga aaaaaggat | 5280 |
| ctcaagaaga tcctttgatc ttttctacgg ggtctgacgc tcagtggaac gaaaactcac | 5340 |
| gttaagggat tttggtcatg agattatcaa aaaggatctt cacctagatc cttttaaatt | 5400 |
| aaaaatgaag ttttaaatca atctaaagta tatatgagta aacttggtct gacagttacc | 5460 |
| aatgcttaat cagtgaggca cctatctcag cgatctgtct atttcgttca tccatagttg | 5520 |
| cctgactccc cgtcgtgtag ataactacga tacgggaggg cttaccatct ggccccagtg | 5580 |
| ctgcaatgat accgcgagac ccacgctcac cggctccaga tttatcagca ataaaccagc | 5640 |
| cagccggaag ggccgagcgc agaagtggtc ctgcaacttt atccgcctcc atccagtcta | 5700 |
| ttaattgttg ccgggaagct agagtaagta gttcgccagt taatagtttg cgcaacgttg | 5760 |
| ttgccattgc tacaggcatc gtggtgtcac gctcgtcgtt tggtatggct tcattcagct | 5820 |
| ccggttccca acgatcaagg cgagttacat gatcccccat gttgtgcaaa aaagcggtta | 5880 |
| gctccttcgg tcctccgatc gttgtcagaa gtaagttggc cgcagtgtta tcactcatgg | 5940 |
| ttatggcagc actgcataat tctcttactg tcatgccatc cgtaagatgc ttttctgtga | 6000 |
| ctggtgagta ctcaaccaag tcattctgag aatagtgtat gcggcgaccg agttgctctt | 6060 |
| gcccggcgtc aatacgggat aataccgcgc cacatagcag aactttaaaa gtgctcatca | 6120 |
| ttggaaaacg ttcttcgggg cgaaaactct caaggatctt accgctgttg agatccagtt | 6180 |
| cgatgtaacc cactcgtgca cccaactgat cttcagcatc ttttactttc accagcgttt | 6240 |
| ctgggtgagc aaaaacagga aggcaaaatg ccgcaaaaaa gggaataagg cgacacgga | 6300 |
| aatgttgaat actcatactc ttccttttc aatattattg aagcatttat cagggttatt | 6360 |
| gtctcatgag cggatacata tttgaatgta tttagaaaaa taaacaaata ggggttccgc | 6420 | gcacatttcc ccgaaaagtg ccacctgacg tc                                    6452

<210> SEQ ID NO 59
<211> LENGTH: 349
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Gly Ser Met Ala Tyr Pro Tyr Asp Val Pro Tyr Ala Ser
            100                 105                 110

Leu Arg Ser Thr Met Ser Gln Ser Asn Arg Glu Leu Val Val Asp Phe
        115                 120                 125

Leu Ser Tyr Lys Leu Ser Gln Lys Gly Tyr Ser Trp Ser Gln Phe Ser
130                 135                 140

Asp Val Glu Glu Asn Arg Thr Glu Ala Pro Glu Gly Thr Glu Ser Glu
145                 150                 155                 160

Met Glu Thr Pro Ser Ala Ile Asn Gly Asn Pro Ser Trp His Leu Ala
                165                 170                 175

Asp Ser Pro Ala Val Asn Gly Ala Thr Ala His Ser Ser Ser Leu Asp
            180                 185                 190

Ala Arg Glu Val Ile Pro Met Ala Ala Val Lys Gln Ala Leu Arg Glu
        195                 200                 205

Ala Gly Asp Glu Phe Glu Leu Arg Tyr Arg Arg Ala Phe Ser Asp Leu
    210                 215                 220

Thr Ser Gln Leu His Ile Thr Pro Gly Thr Ala Tyr Gln Ser Phe Glu
225                 230                 235                 240

Gln Val Val Asn Glu Leu Phe Arg Asp Gly Val Asn Trp Gly Arg Ile
                245                 250                 255

Val Ala Phe Phe Ser Phe Gly Gly Ala Leu Cys Val Glu Ser Val Asp
            260                 265                 270

Lys Glu Met Gln Val Leu Val Ser Arg Ile Ala Ala Trp Met Ala Thr
        275                 280                 285

Tyr Leu Asn Asp His Leu Glu Pro Trp Ile Gln Glu Asn Gly Gly Trp
    290                 295                 300

Asp Thr Phe Val Glu Leu Tyr Gly Asn Asn Ala Ala Ala Glu Ser Arg
305                 310                 315                 320

Lys Gly Gln Glu Arg Phe Asn Arg Trp Phe Leu Thr Gly Met Thr Val
                325                 330                 335

Ala Gly Val Val Leu Leu Gly Ser Leu Phe Ser Arg Lys
            340                 345

<210> SEQ ID NO 60
<211> LENGTH: 750
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60

```
atggcgtacc catacgatgt tccagattac gctagcttga gatctaccat gtctcagagc    60
aaccgggagc tggtggttga ctttctctcc tacaagcttt cccagaaagg atacagctgg   120
agtcagttta gtgatgtgga agagaacagg actgaggccc cagaagggac tgaatcggag   180
atggagaccc ccagtgccat caatggcaac catcctggc acctggcaga cagccccgcg   240
gtgaatggag ccactgcgca cagcagcagt ttggatgccc gggaggtgat ccccatggca   300
gcagtaaagc aagcgctgag ggaggcaggc gacgagtttg aactgcggta ccggcgggca   360
ttcagtgacc tgacatccca gctccacatc accccaggga cagcatatca gagctttgaa   420
caggtagtga atgaactctt ccgggatggg gtagccattc ttcgcattgt ggccttttttc   480
tccttcggcg gggcactgtg cgtggaaagc gtagacaagg agatgcaggt attggtgagt   540
cggatcgcag cttggatggc acttacctg aatgaccacc tagagccttg atccaggag   600
aacggcggct gggatacttt tgtggaactc tatgggaaca atgcagcagc cgagagccga   660
aagggccagg aacgcttcaa ccgctggttc ctgacgggca tgactgtggc cggcgtggtt   720
ctgctgggct cactcttcag tcggaaatga                                    750
```

<210> SEQ ID NO 61
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

```
Met Ala Tyr Pro Tyr Asp Val Pro Asp Tyr Ala Ser Leu Arg Ser Thr
  1               5                  10                  15

Met Ser Gln Ser Asn Arg Glu Leu Val Val Asp Phe Leu Ser Tyr Lys
             20                  25                  30

Leu Ser Gln Lys Gly Tyr Ser Trp Ser Gln Phe Ser Asp Val Glu Glu
         35                  40                  45

Asn Arg Thr Glu Ala Pro Glu Gly Thr Glu Ser Glu Met Glu Thr Pro
     50                  55                  60

Ser Ala Ile Asn Gly Asn Pro Ser Trp His Leu Ala Asp Ser Pro Ala
 65                  70                  75                  80

Val Asn Gly Ala Thr Ala His Ser Ser Ser Leu Asp Ala Arg Glu Val
                 85                  90                  95

Ile Pro Met Ala Ala Val Lys Gln Ala Leu Arg Glu Ala Gly Asp Glu
            100                 105                 110

Phe Glu Leu Arg Tyr Arg Arg Ala Phe Ser Asp Leu Thr Ser Gln Leu
        115                 120                 125

His Ile Thr Pro Gly Thr Ala Tyr Gln Ser Phe Glu Gln Val Val Asn
    130                 135                 140

Glu Leu Phe Arg Asp Gly Val Ala Ile Leu Arg Ile Val Ala Phe Phe
145                 150                 155                 160
```

```
Ser Phe Gly Gly Ala Leu Cys Val Glu Ser Val Asp Lys Glu Met Gln
            165                 170                 175

Val Leu Val Ser Arg Ile Ala Ala Trp Met Ala Thr Tyr Leu Asn Asp
        180                 185                 190

His Leu Glu Pro Trp Ile Gln Glu Asn Gly Gly Trp Asp Thr Phe Val
            195                 200                 205

Glu Leu Tyr Gly Asn Asn Ala Ala Glu Ser Arg Lys Gly Gln Glu
        210                 215                 220

Arg Phe Asn Arg Trp Phe Leu Thr Gly Met Thr Val Ala Gly Val Val
225                 230                 235                 240

Leu Leu Gly Ser Leu Phe Ser Arg Lys
            245

<210> SEQ ID NO 62
<211> LENGTH: 349
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
            85                  90                  95

Lys Pro Gly Ser Met Ala Tyr Pro Tyr Asp Val Pro Asp Tyr Ala Ser
            100                 105                 110

Leu Arg Ser Thr Met Ser Gln Ser Asn Arg Glu Leu Val Val Asp Phe
        115                 120                 125

Leu Ser Tyr Lys Leu Ser Gln Lys Gly Tyr Ser Trp Ser Gln Phe Ser
    130                 135                 140

Asp Val Glu Glu Asn Arg Thr Glu Ala Pro Glu Gly Thr Glu Ser Glu
145                 150                 155                 160

Met Glu Thr Pro Ser Ala Ile Asn Gly Asn Pro Ser Trp His Leu Ala
            165                 170                 175

Asp Ser Pro Ala Val Asn Gly Ala Thr Ala His Ser Ser Ser Leu Asp
        180                 185                 190

Ala Arg Glu Val Ile Pro Met Ala Ala Val Lys Gln Ala Leu Arg Glu
    195                 200                 205

Ala Gly Asp Glu Phe Glu Leu Arg Tyr Arg Arg Ala Phe Ser Asp Leu
210                 215                 220

Thr Ser Gln Leu His Ile Thr Pro Gly Thr Ala Tyr Gln Ser Phe Glu
225                 230                 235                 240

Gln Val Val Asn Glu Leu Phe Arg Asp Gly Val Ala Ile Leu Arg Ile
            245                 250                 255

Val Ala Phe Phe Ser Phe Gly Gly Ala Leu Cys Val Glu Ser Val Asp
            260                 265                 270
```

```
Lys Glu Met Gln Val Leu Val Ser Arg Ile Ala Ala Trp Met Ala Thr
            275                 280                 285
Tyr Leu Asn Asp His Leu Glu Pro Trp Ile Gln Glu Asn Gly Gly Trp
        290                 295                 300
Asp Thr Phe Val Glu Leu Tyr Gly Asn Asn Ala Ala Ala Glu Ser Arg
305                 310                 315                 320
Lys Gly Gln Glu Arg Phe Asn Arg Trp Phe Leu Thr Gly Met Thr Val
                325                 330                 335
Ala Gly Val Val Leu Leu Gly Ser Leu Phe Ser Arg Lys
            340                 345

<210> SEQ ID NO 63
<211> LENGTH: 6187
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
```

| | | | | | |
|---|---|---|---|---|---|
| gacggatcgg | gagatctccc | gatcccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggac | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaacgg | gccctctaga | ctcgagcggc | cgccactgtg | ctggatatct | gcagaattcc | 960 |
| accacactgg | actagtggat | ctatggcgta | cccatacgat | gttccagatt | acgctagctt | 1020 |
| gagatctacc | atgtctcaga | gcaaccggga | gctggtggtt | gactttctct | cctacaagct | 1080 |
| ttcccagaaa | ggatacagct | ggagtcagtt | tagtgatgtg | gaagagaaca | ggactgaggc | 1140 |
| cccagaaggg | actgaatcgg | agatggagac | ccccagtgcc | atcaatggca | acccatcctg | 1200 |
| gcacctggca | gacagccccg | cggtgaatgg | agccactgcg | cacagcagca | gtttggatgc | 1260 |
| ccggaggtg | atccccatgg | cagcagtaaa | gcaagcgctg | agggaggcag | gcgacgagtt | 1320 |
| tgaactgcgg | taccggcggg | cattcagtga | cctgacatcc | cagctccaca | tcaccccagg | 1380 |
| gacagcatat | cagagctttg | aacaggtagt | gaatgaactc | ttccgggatg | gggtagccat | 1440 |
| tcttcgcatt | gtggccttt | tctccttcgg | cggggcactg | tgcgtggaaa | gcgtagacaa | 1500 |
| ggagatgcag | gtattggtga | gtcggatcgc | agcttggatg | ccacttacc | tgaatgacca | 1560 |

```
cctagagcct tggatccagg agaacggcgg ctgggatact tttgtggaac tctatgggaa    1620
caatgcagca gccgagagcc gaaagggcca ggaacgcttc aaccgctggt tcctgacggg    1680
catgactgtg gccggcgtgg ttctgctggg ctcactcttc agtcggaaat gaagatccga    1740
gctcggtacc aagcttaagt ttaaaccgct gatcagcctc gactgtgcct tctagttgcc    1800
agccatctgt tgtttgcccc tcccccgtgc cttccttgac cctggaaggt gccactccca    1860
ctgtcctttc ctaataaaat gaggaaaatg catcgcattg tctgagtagg tgtcattcta    1920
ttctgggggg tggggtgggg caggacagca agggggagga ttgggaagac aatagcaggc    1980
atgctgggga tgcggtgggc tctatggctt ctgaggcgga agaaccagc tgggctcta     2040 gggggtatcc ccacgcgccc tgtagcggcg cattaagcgc ggcgggtgtg gtggttacgc    2100
gcagcgtgac cgctacactt gccagcgccc tagcgcccgc tcctttcgct ttcttccctt    2160
cctttctcgc cacgttcgcc ggctttcccc gtcaagctct aaatcggggc atccctttag    2220
ggttccgatt tagtgcttta cggcacctcg accccaaaaa acttgattag ggtgatggtt    2280
cacgtagtgg gccatcgccc tgatagacgg ttttcgccc tttgacgttg gagtccacgt     2340
tctttaatag tggactcttg ttccaaactg gaacaacact caaccctatc tcggtctatt    2400
cttttgattt ataagggatt tgggggattt cggcctattg gttaaaaaat gagctgattt    2460
aacaaaaatt taacgcgaat taattctgtg gaatgtgtgt cagttagggt gtggaaagtc    2520
cccaggctcc ccaggcaggc agaagtatgc aaagcatgca tctcaattag tcagcaacca    2580
ggtgtggaaa gtccccaggc tccccagcag gcagaagtat gcaaagcatg catctcaatt    2640
agtcagcaac catagtcccg cccctaactc cgcccatccc gcccctaact ccgcccagtt    2700
ccgcccattc tccgccccat ggctgactaa ttttttttat ttatgcagag gccgaggccg    2760
cctctgcctc tgagctattc cagaagtagt gaggaggctt ttttggaggc ctaggctttt    2820
gcaaaaagct cccgggagct tgtatatcca ttttcggatc tgatcaagag acaggatgag    2880
gatcgtttcg catgattgaa caagatggat tgcacgcagg ttctccggcc gcttgggtgg    2940
agaggctatt cggctatgac tgggcacaac agacaatcgg ctgctctgat gccgccgtgt    3000
tccggctgtc agcgcagggg cgcccggttc tttttgtcaa gaccgacctg tccggtgccc    3060
tgaatgaact gcaggacgag gcagcgcggc tatcgtggct ggccacgacg ggcgttcctt    3120
gcgcagctgt gctcgacgtt gtcactgaag cgggaaggga ctggctgcta ttgggcgaag    3180
tgccggggca ggatctcctg tcatctcacc ttgctcctgc cgagaaagta tccatcatgg    3240
ctgatgcaat gcggcggctg catacgcttg atccggctac ctgcccattc gaccaccaag    3300
cgaaacatcg catcgagcga gcacgtactc ggatggaagc cggtcttgtc gatcaggatg    3360
atctggacga agagcatcag gggctcgcgc cagccgaact gttcgccagg ctcaaggcgc    3420
gcatgcccga cggcgaggat ctcgtcgtga cccatggcga tgcctgcttg ccgaatatca    3480
tggtggaaaa tggccgcttt tctggattca tcgactgtgg ccggctgggt gtggcggacc    3540
gctatcagga catagcgttg gctacccgtg atattgctga agagcttggc ggcgaatggg    3600
ctgaccgctt cctcgtgctt tacggtatcg ccgctcccga ttcgcagcgc atcgccttct    3660
atcgccttct tgacgagttc ttctgagcgg gactctgggg ttcgaaatga ccgaccaagc    3720
gacgcccaac ctgccatcac gagatttcga ttccaccgcc gccttctatg aaaggttggg    3780
cttcggaatc gttttccggg acgccggctg atgatcctc cagcgcgggg atctcatgct     3840
ggagttcttc gcccacccca acttgtttat tgcagcttat aatggttaca ataaagcaa     3900 tagcatcaca aatttcacaa ataaagcatt ttttttcactg cattctagtt gtggtttgtc    3960
```

```
caaactcatc aatgtatctt atcatgtctg tataccgtcg acctctagct agagcttggc    4020
gtaatcatgg tcatagctgt ttcctgtgtg aaattgttat ccgctcacaa ttccacacaa    4080
catacgagcc ggaagcataa agtgtaaagc ctggggtgcc taatgagtga gctaactcac    4140
attaattgcg ttgcgctcac tgcccgcttt ccagtcggga aacctgtcgt gccagctgca    4200
ttaatgaatc ggccaacgcg cggggagagg cggtttgcgt attgggcgct cttccgcttc    4260
ctcgctcact gactcgctgc gctcggtcgt tcggctgcgg cgagcggtat cagctcactc    4320
aaaggcggta atacggttat ccacagaatc aggggataac gcaggaaaga acatgtgagc    4380
aaaaggccag caaaaggcca ggaaccgtaa aaaggccgcg ttgctggcgt ttttccatag    4440
gctccgcccc cctgacgagc atcacaaaaa tcgacgctca agtcagaggt ggcgaaaccc    4500
gacaggacta taaagatacc aggcgtttcc ccctggaagc tccctcgtgc gctcctgt     4560 tccgaccctg ccgcttaccg gatacctgtc cgcctttctc ccttcgggaa gcgtggcgct    4620
ttctcaatgc tcacgctgta ggtatctcag ttcggtgtag tcgttcgct ccaagctggg     4680 ctgtgtgcac gaaccccccg ttcagcccga ccgctgcgcc ttatccggta actatcgtct    4740
tgagtccaac ccggtaagac acgacttatc gccactggca gcagccactg gtaacaggat    4800
tagcagagcg aggtatgtag gcggtgctac agagttcttg aagtggtggc ctaactacgg    4860
ctacactaga aggacagtat ttggtatctg cgctctgctg aagccagtta ccttcggaaa    4920
aagagttggt agctcttgat ccggcaaaca aaccaccgct ggtagcggtg ttttttgt    4980 ttgcaagcag cagattacgc gcagaaaaaa aggatctcaa gaagatcctt tgatcttttc    5040 tacgggtct gacgctcagt ggaacgaaaa ctcacgttaa gggattttgg tcatgagatt      5100
atcaaaaagg atcttcacct agatcctttt aaattaaaaa tgaagtttta aatcaatcta    5160 agtatatat gagtaaactt ggtctgacag ttaccaatgc ttaatcagtg aggcacctat      5220
ctcagcgatc tgtctatttc gttcatccat agttgcctga ctccccgtcg tgtagataac    5280
tacgatacgg gagggcttac catctggccc cagtgctgca atgataccgc gagacccacg    5340
ctcaccggct ccagatttat cagcaataaa ccagccagcc ggaagggccg agcgcagaag    5400
tggtcctgca actttatccg cctccatcca gtctattaat tgttgccggg aagctagagt    5460
aagtagttcg ccagttaata gtttgcgcaa cgttgttgcc attgctacag gcatcgtggt    5520
gtcacgctcg tcgtttggta tggcttcatt cagctccggt tcccaacgat caaggcgagt    5580
tacatgatcc cccatgttgt gcaaaaaagc ggttagctcc ttcggtcctc cgatcgttgt    5640
cagaagtaag ttggccgcag tgttatcact catggttatg gcagcactgc ataattctct    5700
tactgtcatg ccatccgtaa gatgcttttc tgtgactggt gagtactcaa ccaagtcatt    5760
ctgagaatag tgtatgcggc gaccgagttg ctcttgcccg gcgtcaatac gggataatac    5820
cgcgccacat agcagaactt taaaagtgct catcattgga aaacgttctt cggggcgaaa    5880
actctcaagg atcttaccgc tgttgagatc cagttcgatg taacccactc gtgcacccaa    5940
ctgatcttca gcatctttta ctttcaccag cgtttctggg tgagcaaaaa caggaaggca    6000
aaatgccgca aaaagggaa taagggcgac acggaaatgt tgaatactca tactcttcct    6060
ttttcaatat tattgaagca tttatcaggg ttattgtctc atgagcggat acatatttga    6120
atgtatttag aaaaataaac aaataggggt tccgcgcaca tttccccgaa aagtgccacc    6180
tgacgtc                                                              6187
```

<210> SEQ ID NO 64

<211> LENGTH: 6451
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

| | | | | | |
|---|---|---|---|---|---|
| acggatcggg | agatctcccg | atcccctatg | gtcgactctc | agtacaatct | gctctgatgc | 60 |
| cgcatagtta | agccagtatc | tgctccctgc | ttgtgtgttg | gaggtcgctg | agtagtgcgc | 120 |
| gagcaaaatt | taagctacaa | caaggcaagg | cttgaccgac | aattgcatga | agaatctgct | 180 |
| tagggttagg | cgttttgcgc | tgcttcgcga | tgtacgggcc | agatatacgc | gttgacattg | 240 |
| attattgact | agttattaat | agtaatcaat | tacgggtca | ttagttcata | gcccatatat | 300 |
| ggagttccgc | gttacataac | ttacggtaaa | tggcccgcct | ggctgaccgc | ccaacgaccc | 360 |
| ccgcccattg | acgtcaataa | tgacgtatgt | tcccatagta | acgccaatag | ggactttcca | 420 |
| ttgacgtcaa | tgggtggact | atttacggta | aactgcccac | ttggcagtac | atcaagtgta | 480 |
| tcatatgcca | agtacgcccc | ctattgacgt | caatgacggt | aaatggcccg | cctggcatta | 540 |
| tgcccagtac | atgaccttat | gggactttcc | tacttggcag | tacatctacg | tattagtcat | 600 |
| cgctattacc | atggtgatgc | ggttttggca | gtacatcaat | gggcgtggat | agcggtttga | 660 |
| ctcacgggga | tttccaagtc | tccaccccat | tgacgtcaat | gggagtttgt | tttggcacca | 720 |
| aaatcaacgg | gactttccaa | aatgtcgtaa | caactccgcc | ccattgacgc | aaatgggcgg | 780 |
| taggcgtgta | cggtgggagg | tctatataag | cagagctctc | tggctaacta | gagaacccac | 840 |
| tgcttactgg | cttatcgaaa | ttaatacgac | tcactatagg | gagacccaag | ctggctagcg | 900 |
| tttaaacggg | ccctctagac | tcgagcggcc | gccactgtgc | tggatatctg | cagaattcat | 960 |
| gcatggagat | acacctacat | tgcatgaata | tatgttagat | ttgcaaccag | agacaactga | 1020 |
| tctctactgt | tatgagcaat | taaatgacag | ctcagaggag | gaggatgaaa | tagatggtcc | 1080 |
| agctggacaa | gcagaaccgg | acagagccca | ttacaatatt | gtaacctttt | gttgcaagtg | 1140 |
| tgactctacg | cttcggttgt | gcgtacaaag | cacacacgta | gacattcgta | ctttggaaga | 1200 |
| cctgttaatg | ggcacactag | gaattgtgtg | ccccatctgt | tctcagaaac | caggatctat | 1260 |
| ggcgtaccca | tacgatgttc | cagattacgc | tagcttgaga | tctaccatgt | ctcagagcaa | 1320 |
| ccgggagctg | gtggttgact | ttctctccta | caagcttttcc | cagaaaggat | acagctggag | 1380 |
| tcagtttagt | gatgtggaag | agaacaggac | tgaggcccca | gaagggactg | aatcggagat | 1440 |
| ggagaccccc | agtgccatca | atggcaaccc | atcctggcac | ctggcagaca | gccccgcggt | 1500 |
| gaatggagcc | actgcgcaca | gcagcagttt | ggatgcccgg | gaggtgatcc | ccatggcagc | 1560 |
| agtaaagcaa | gcgctgaggg | aggcaggcga | cgagtttgaa | ctgcgtgtacc | ggcgggcatt | 1620 |
| cagtgacctg | acatcccagc | tccacatcac | cccagggaca | gcatatcaga | gctttgaaca | 1680 |
| ggtagtgaat | gaactcttcc | gggatggggt | agccattctt | cgcattgtgg | cctttttctc | 1740 |
| cttcggcggg | gcactgtgcg | tggaaagcgt | agacaaggag | atgcaggtat | tggtgagtcg | 1800 |
| gatcgcagct | tggatggcca | cttacctgaa | tgaccactta | gagccttgga | tccaggagaa | 1860 |
| cggcggctgg | gatactttg | tggaactcta | tgggaacaat | gcagcagccg | agagccgaaa | 1920 |
| gggccaggaa | cgcttcaacc | gctggttcct | gacgggcatg | actgtggccg | gcgtggttct | 1980 |
| gctgggctca | ctcttcagtc | ggaaatgaag | atccaagctt | aagtttaaac | cgctgatcag | 2040 |
| cctcgactgt | gccttctagt | tgccagccat | ctgttgtttg | cccctccccc | gtgccttcct | 2100 |

-continued

```
tgaccctgga aggtgccact cccactgtcc tttcctaata aaatgaggaa attgcatcgc    2160
attgtctgag taggtgtcat tctattctgg ggggtggggt ggggcaggac agcaaggggg    2220
aggattggga agacaatagc aggcatgctg gggatgcggt gggctctatg gcttctgagg    2280
cggaaagaac cagctggggc tctagggggt atccccacgc gccctgtagc ggcgcattaa    2340
gcgcggcggg tgtggtggtt acgcgcagcg tgaccgctac acttgccagc gccctagcgc    2400
ccgctccttt cgctttcttc ccttcctttc tcgccacgtt cgccggcttt ccccgtcaag    2460
ctctaaatcg gggcatccct ttagggttcc gatttagtgc tttacggcac ctcgacccca    2520
aaaaacttga ttagggtgat ggttcacgta gtgggccatc gccctgatag acggtttttc    2580
gccctttgac gttggagtcc acgttcttta atagtggact cttgttccaa actggaacaa    2640
cactcaaccc tatctcggtc tattcttttg atttataagg gattttgggg atttcggcct    2700
attggttaaa aaatgagctg atttaacaaa aatttaacgc gaattaattc tgtggaatgt    2760
gtgtcagtta gggtgtggaa agtccccagg ctccccaggc aggcagaagt atgcaaagca    2820
tgcatctcaa ttagtcagca accaggtgtg gaaagtcccc aggctcccca gcaggcagaa    2880
gtatgcaaag catgcatctc aattagtcag caaccatagt cccgccccta actccgccca    2940
tcccgcccct aactccgccc agttccgccc attctccgcc ccatggctga ctaattttttt    3000
ttatttatgc agaggccgag gccgcctctg cctctgagct attccagaag tagtgaggag    3060
gcttttttgg aggcctaggc ttttgcaaaa agctcccggg agcttgtata tccattttcg    3120
gatctgatca agagacagga tgaggatcgt ttcgcatgat tgaacaagat ggattgcacg    3180
caggttctcc ggccgcttgg gtggagaggc tattcggcta tgactgggca caacagacaa    3240
tcggctgctc tgatgccgcc gtgttccggc tgtcagcgca ggggcgcccg gttcttttttg    3300
tcaagaccga cctgtccggt gccctgaatg aactgcagga cgaggcagcg cggctatcgt    3360
ggctggccac gacgggcgtt ccttgcgcag ctgtgctcga cgttgtcact gaagcgggaa    3420
gggactggct gctattgggc gaagtgccgg ggcaggatct cctgtcatct caccttgctc    3480
ctgccgagaa agtatccatc atggctgatg caatgcggcg gctgcatacg cttgatccgg    3540
ctacctgccc attcgaccac caagcgaaac atcgcatcga gcgagcacgt actcggatgg    3600
aagccggtct tgtcgatcag gatgatctgg acgaagagca tcaggggctc gcgccagccg    3660
aactgttcgc caggctcaag gcgcgcatgc ccgacggcga ggatctcgtc gtgacccatg    3720
gcgatgcctg cttgccgaat atcatggtgg aaaatggccg cttttctgga ttcatcgact    3780
gtggccggct gggtgtggcg gaccgctatc aggacatagc gttggctacc cgtgatattg    3840
ctgaagagct tggcggcgaa tgggctgacc gcttcctcgt gctttacggt atcgccgctc    3900
ccgattcgca gcgcatcgcc ttctatcgcc ttcttgacga gttcttctga gcgggactct    3960
ggggttcgaa atgaccgacc aagcgacgcc caacctgcca tcacgagatt tcgattccac    4020
cgccgccttc tatgaaaggt tgggcttcgg aatcgttttc cgggacgccg gctggatgat    4080
cctccagcgc ggggatctca tgctggagtt cttcgcccac cccaacttgt ttattgcagc    4140
ttataatggt tacaaataaa gcaatagcat cacaaatttc acaaataaag catttttttc    4200
actgcattct agttgtggtt tgtccaaact catcaatgta tcttatcatg tctgtatacc    4260
gtcgacctct agctagagct tggcgtaatc atggtcatag ctgtttcctg tgtgaaattg    4320
ttatccgctc acaattccac acaacatacg agccggaagc ataaagtgta aagcctgggg    4380
tgcctaatga gtgagctaac tcacattaat tgcgttgcgc tcactgcccg ctttccagtc    4440
gggaaacctg tcgtgccagc tgcattaatg aatcggccaa cgcgcgggga gaggcggttt    4500
```

```
gcgtattggg cgctcttccg cttcctcgct cactgactcg ctgcgctcgg tcgttcggct    4560
gcggcgagcg gtatcagctc actcaaaggc ggtaatacgg ttatccacag aatcaggggga   4620 taacgcagga agaacatgt gagcaaaagg ccagcaaaag gccaggaacc gtaaaaaggc     4680
cgcgttgctg gcgttttttcc ataggctccg ccccctgac gagcatcaca aaaatcgacg    4740
ctcaagtcag aggtggcgaa acccgacagg actataaaga taccaggcgt ttccccctgg    4800
aagctccctc gtgcgctctc ctgttccgac cctgccgctt accggatacc tgtccgcctt    4860
tctcccttcg ggaagcgtgg cgctttctca atgctcacgc tgtaggtatc tcagttcggt    4920
gtaggtcgtt cgctccaagc tgggctgtgt gcacgaaccc cccgttcagc ccgaccgctg    4980
cgccttatcc ggtaactatc gtcttgagtc caacccggta agacacgact tatcgccact    5040
ggcagcagcc actggtaaca ggattagcag agcgaggtat gtaggcggtg ctacagagtt    5100
cttgaagtgg tggcctaact acggctacac tagaaggaca gtatttggta tctgcgctct    5160
gctgaagcca gttaccttcg gaaaaagagt tggtagctct tgatccggca acaaaccac     5220 cgctggtagc ggtggttttt tgtttgcaa gcagcagatt acgcgcagaa aaaaggatc      5280 tcaagaagat ccttttgatct tttctacggg gtctgacgct cagtggaacg aaaactcacg   5340
ttaagggatt ttggtcatga gattatcaaa aaggatcttc acctagatcc ttttaaatta    5400
aaaatgaagt tttaaatcaa tctaaagtat atatgagtaa acttggtctg acagttacca    5460
atgcttaatc agtgaggcac ctatctcagc gatctgtcta tttcgttcat ccatagttgc    5520
ctgactcccc gtcgtgtaga taactacgat acgggagggc ttaccatctg gccccagtgc    5580
tgcaatgata ccgcgagacc cacgctcacc ggctccagat ttatcagcaa taaaccagcc    5640
agccggaagg gccgagcgca gaagtggtcc tgcaacttta tccgcctcca tccagtctat    5700
taattgttgc cgggaagcta gagtaagtag ttcgccagtt aatagtttgc gcaacgttgt    5760
tgccattgct acaggcatcg tggtgtcacg ctcgtcgttt ggtatggctt cattcagctc    5820
cggttcccaa cgatcaaggc gagttacatg atcccccatg ttgtgcaaaa aagcggttag    5880
ctccttcggt cctccgatcg ttgtcagaag taagttggcc gcagtgttat cactcatggt    5940
tatggcagca ctgcataatt ctcttactgt catgccatcc gtaagatgct tttctgtgac    6000
tggtgagtac tcaaccaagt cattctgaga atagtgtatg cggcgaccga gttgctcttg    6060
cccggcgtca tacgggata ataccgcgcc acatagcaga actttaaaag tgctcatcat     6120
tggaaaacgt tcttcggggc gaaaactctc aaggatctta ccgctgttga tccagttc      6180 gatgtaaccc actcgtgcac ccaactgatc ttcagcatct tttactttca ccagcgtttc    6240
tgggtgagca aaaacaggaa ggcaaaatgc cgcaaaaaag ggaataaggg cgacacggaa    6300
atgttgaata ctcatactct tcctttttca atattattga agcatttatc agggttattg    6360
tctcatgagc ggatacatat ttgaatgtat ttagaaaaat aaacaaatag gggttccgcg    6420
cacatttccc cgaaaagtgc cacctgacgt c                                    6451
```

<210> SEQ ID NO 65
<211> LENGTH: 12347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
atggcggatg tgtgacatac acgacgccaa aagatttgt tccagctcct gccacctccg      60
```

-continued

```
ctacgcgaga gattaaccac ccacgatggc cgccaaagtg catgttgata ttgaggctga    120
cagcccattc atcaagtctt tgcagaaggc atttccgtcg ttcgaggtgg agtcattgca    180
ggtcacacca aatgaccatg caaatgccag agcattttcg cacctggcta ccaaattgat    240
cgagcaggag actgacaaag acacactcat cttggatatc ggcagtgcgc cttccaggag    300
aatgatgtct acgcacaaat accactgcgt atgccctatg cgcagcgcag aagaccccga    360
aaggctcgat agctacgcaa agaaactggc agcggcctcc gggaaggtgc tggatagaga    420
gatcgcagga aaaatcaccg acctgcagac cgtcatggct acgccagacg ctgaatctcc    480 tacctttgc ctgcatacag acgtcacgtg tcgtacggca gccgaagtgg ccgtatacca     540
ggacgtgtat gctgtacatg caccaacatc gctgtaccat caggcgatga aggtgtcag    600 aacgcgtat tggattgggt ttgacaccac cccgtttatg tttgacgcgc tagcaggcgc     660
gtatccaacc tacgccacaa actgggccga cgagcaggtg ttacaggcca ggaacatagg    720
actgtgtgca gcatccttga ctgagggaag actcggcaaa ctgtccattc tccgcaagaa    780
gcaattgaaa ccttgcgaca cagtcatgtt ctcggtagga tctacattgt acactgagag    840
cagaaagcta ctgaggagct ggcacttacc ctccgtattc cacctgaaag gtaaacaatc    900
ctttacctgt aggtgcgata ccatcgtatc atgtgaaggg tacgtagtta agaaaatcac    960
tatgtgcccc ggcctgtacg gtaaaacggt agggtacgcc gtgacgtatc acgcggaggg   1020
attcctagtg tgcaagacca cagacactgt caaaggagaa agagtctcat tccctgtatg   1080
cacctacgtc ccctcaacca tctgtgatca aatgactggc atactagcga ccgacgtcac   1140
accggaggac gcacagaagt tgttagtggg attgaatcag aggatagttg tgaacggaag   1200
aacacagcga aacactaaca cgatgaagaa ctatctgctt ccgattgtgg ccgtcgcatt   1260
tagcaagtgg gcgagggaat acaaggcaga ccttgatgat gaaaaacctc tgggtgtccg   1320
agagaggtca cttacttgct gctgcttgtg ggcatttaaa acgaggaaga tgcacaccat   1380
gtacaagaaa ccagacaccc agacaatagt gaaggtgcct tcagagttta actcgttcgt   1440
catcccgagc ctatggtcta caggcctcgc aatcccagtc agatcacgca ttaagatgct   1500
tttggccaag aagaccaagc gagagttaat acctgttctc gacgcgtcgt cagccaggga   1560
tgctgaacaa gaggagaagg agaggttgga ggccgagctg actagagaag ccttaccacc   1620
cctcgtcccc atcgcgccgg cggagacggg agtcgtcgac gtcgacgttg aagaactaga   1680
gtatcacgca ggtgcagggg tcgtggaaac acctcgcagc gcgttgaaag tcaccgcaca   1740
gccgaacgac gtactactag gaaattacgt agttctgtcc ccgcagaccg tgctcaagag   1800
ctccaagttg gccccgtgc accctctagc agagcaggtg aaaataataa cacataacgg    1860
gagggccggc ggttaccagg tcgacggata tgacggcagg gtcctactac catgtggatc   1920
ggccattccg gtccctgagt ttcaagcttt gagcgagagc gccactatgg tgtacaacga   1980
aagggagttc gtcaacagga aactatacca tattgccgtt cacggaccgt cgctgaacac   2040
cgacgaggag aactacgaga agtcagagc tgaaagaact gacgccgagt acgtgttcga    2100
cgtagataaa aaatgctgcg tcaagagaga ggaagcgtcg ggtttggtgt tggtgggaga   2160
gctaaccaac cccccgttcc atgaattcgc ctacgaaggg ctgaagatca ggccgtcggc   2220
accatataag actacagtag taggagtctt tggggttccg ggatcaggca agtctgctat   2280
tattaagagc ctcgtgacca aacacgatct ggtcaccagc ggcaagaagg agaactgcca   2340
ggaaatagtt aacgacgtga agaagcaccg cgggaagggg acaagtaggg aaaacagtga   2400
```

```
ctccatcctg ctaaacgggt gtcgtcgtgc cgtggacatc ctatatgtgg acgaggcttt    2460
cgctagccat tccggtactc tgctggccct aattgctctt gttaaacctc ggagcaaagt    2520
ggtgttatgc ggagacccca agcaatgcgg attcttcaat atgatgcagc ttaaggtgaa    2580
cttcaaccac aacatctgca ctgaagtatg tcataaaagt atatccagac gttgcacgcg    2640
tccagtcacg gccatcgtgt ctacgttgca ctacggaggc aagatgcgca cgaccaaccc    2700
gtgcaacaaa cccataatca tagacaccac aggacagacc aagcccaagc caggagacat    2760
cgtgttaaca tgcttccgag gctgggcaaa gcagctgcag ttggactacc gtggacacga    2820
agtcatgaca gcagcagcat ctcagggcct cacccgcaaa ggggtatacg ccgtaaggca    2880
gaaggtgaat gaaaatccct tgtatgcccc tgcgtcggag cacgtgaatg tactgctgac    2940
gcgcactgag gataggctgg tgtggaaaac gctggccggc gatccctgga ttaaggtcct    3000
atcaaacatt ccacagggta actttacggc cacattggaa gaatggcaag aagaacacga    3060
caaaataatg aaggtgattg aaggaccggc tgcgcctgtg gacgcgttcc agaacaaagc    3120
gaacgtgtgt tgggcgaaaa gcctggtgcc tgtcctggac actgccggaa tcagattgac    3180
agcagaggag tggagcacca taattacagc atttaaggag gacagagctt actctccagt    3240
ggtggccttg aatgaaattt gcaccaagta ctatggagtt gacctggaca gtggcctgtt    3300
ttctgccccg aaggtgtccc tgtattacga gaacaaccac tgggataaca gacctggtgg    3360
aaggatgtat ggattcaatg ccgcaacagc tgccaggctg gaagctagac ataccttcct    3420
gaaggggcag tggcatacgg gcaagcaggc agttatcgca gaaagaaaaa tccaaccgct    3480
ttctgtgctg gacaatgtaa ttcctatcaa ccgcaggctg ccgcacgccc tggtggctga    3540
gtacaagacg gttaaaggca gtagggttga gtggctggtc aataaagtaa gagggtacca    3600
cgtcctgctg gtgagtgagt acaacctggc tttgcctcga cgcagggtca cttggttgtc    3660
accgctgaat gtcacaggcg ccgataggtg ctacgaccta agtttaggac tgccggctga    3720
cgccggcagg ttcgacttgg tctttgtgaa cattcacacg gaattcagaa tccaccacta    3780
ccagcagtgt gtcgaccacg ccatgaagct gcagatgctt gggggagatg cgctacgact    3840
gctaaaaccc ggcggcatct tgatgagagc ttacggatac gccgataaaa tcagcgaagc    3900
cgttgtttcc tccttaagca gaaagttctc gtctgcaaga gtgttgcgcc cggattgtgt    3960
caccagcaat acagaagtgt tcttgctgtt ctccaacttt gacaacggaa agagaccctc    4020
tacgctacac cagatgaata ccaagctgag tgccgtgtat gccggagaag ccatgcacac    4080
ggccgggtgt gcaccatcct acagagttaa gagagcagac atagccacgt gcacagaagc    4140
ggctgtggtt aacgcagcta acgcccgtgg aactgtaggg gatggcgtat gcagggccgt    4200
ggcgaagaaa tggccgtcag cctttaaggg agcagcaaca ccagtgggca caattaaaac    4260
agtcatgtgc ggctcgtacc ccgtcatcca cgctgtagcg cctaatttct ctgccacgac    4320
tgaagcggaa ggggaccgcg aattggccgc tgtctaccgg gcagtggccg ccgaagtaaa    4380
cagactgtca ctgagcagcg tagccatccc gctgctgtcc acaggagtgt tcagcggcgg    4440
aagagatagg ctgcagcaat ccctcaacca tctattcaca gcaatggacg ccacggacgc    4500
tgacgtgacc atctactgca gagacaaaag ttgggagaag aaaatccagg aagccattga    4560
catgaggacg gctgtggagt tgctcaatga tgacgtggag ctgaccacag acttggtgag    4620
agtgcacccg gacagcagcc tggtgggtcg taagggctac agtaccactg acggtcgct    4680 gtactcgtac tttgaaggta cgaaattcaa ccaggctgct attgatatgg cagagatact    4740
gacgttgtgg cccagactgc aagaggcaaa cgaacagata tgcctatacg cgctgggcga    4800
```

-continued

```
aacaatggac aacatcagat ccaaatgtcc ggtgaacgat tccgattcat caacacctcc  4860
caggacagtg ccctgcctgt gccgctacgc aatgacagca gaacggatcg cccgccttag  4920
gtcacaccaa gttaaaagca tggtggtttg ctcatctttt ccctcccga ataccatgt   4980 agatggggtg cagaaggtaa agtgcgagaa ggttctcctg ttcgacccga cggtaccttc  5040
agtggttagt ccgcggaagt atgccgcatc tacgacggac cactcagatc ggtcgttacg  5100
agggtttgac ttggactgga ccaccgactc gtcttccact gccagcgata ccatgtcgct  5160
acccagtttg cagtcgtgtg acatcgactc gatctacgag ccaatggctc ccatagtagt  5220
gacggctgac gtacaccctg aacccgcagg catcgcggac ctggcggcag atgtgcaccc  5280
tgaacccgca gaccatgtgg acctcgagaa cccgattcct ccaccgcgcc cgaagagagc  5340
tgcataccct gcctcccgcg cggcggagcg accggtgccg gcgccgagaa agccgacgcc  5400
tgccccaagg actgcgttta ggaacaagct gcctttgacg ttcggcgact ttgacgagca  5460
cgaggtcgat gcgttggcct ccggattac tttcggagac ttcgacgacg tcctgcgact   5520
aggccgcgcg ggtgcatata ttttctcctc ggacactggc agcggacatt tacaacaaaa  5580
atccgttagg cagcacaatc tccagtgcgc acaactggat gcggtccagg aggagaaaat  5640
gtacccgcca aaattggata ctgagaggga gaagctgttg ctgctgaaaa tgcagatgca  5700
cccatcggag gctaataaga gtcgatacca gtctcgcaaa gtggagaaca tgaaagccac  5760
ggtggtggac aggctcacat cggggggcag attgtacacg ggagcggacg taggccgcat  5820
accaacatac gcggttcggt accccgccc cgtgtactcc cctaccgtga tcgaaagatt  5880
ctcaagcccc gatgtagcaa tcgcagcgtg caacgaatac ctatccagaa attacccaac  5940
agtggcgtcg taccagataa cagatgaata cgacgcatac ttggacatgg ttgacgggtc  6000
ggatagttgc ttgacagag cgacattctg cccggcgaag ctccggtgct acccgaaaca   6060
tcatgcgtac caccagccga ctgtacgcag tgccgtcccg tcacccttc agaacacact   6120 acagaacgtg ctagcggccg ccaccaagag aaactgcaac gtcacgcaaa tgcgagaact  6180
acccaccatg gactcggcag tgttcaacgt ggagtgcttc aagcgctatg cctgctccgg  6240
agaatattgg gaagaatatg ctaaacaacc tatccggata accactgaga acatcactac  6300
ctatgtgacc aaattgaaag ccccgaaagc tgctgccttg ttcgctaaga cccacaactt  6360
ggttccgctg caggaggttc ccatggacag attcacggtc gacatgaaac gagatgtcaa  6420
agtcactcca gggacgaaac acacagagga agacccaaa gtccaggtaa ttcaagcagc   6480
ggagccattg gcgaccgctt acctgtgcgg catccacagg gaattagtaa ggagactaaa  6540
tgctgtgtta cgccctaacg tgcacacatt gtttgatatg tcggccgaag actttgacgc  6600
gatcatcgcc tctcacttcc acccaggaga cccggttcta gagacggaca ttgcatcatt  6660
cgacaaaagc caggacgact ccttggctct tacaggttta atgatcctcg aagatctagg  6720
ggtggatcag tacctgctgg acttgatcga ggcagccttt gggaaatat ccagctgtca    6780 cctaccaact ggcacgcgct tcaagttcgg agctatgatg aaatcgggca tgtttctgac  6840
tttgtttatt aacactgttt tgaacatcac catagcaagc agggtactgg agcagagact  6900
cactgactcc gcctgtgcgg ccttcatcgg cgacgacaac atcgttcacg gagtgatctc  6960
cgacaagctg atggcggaga ggtgcgcgtc gtgggtcaac atggaggtga agatcattga  7020
cgctgtcatg ggcgaaaaac ccccatattt ttgtgggggga ttcatagttt ttgacagcgt  7080
cacacagacc gcctgccgtg tttcagaccc acttaagcgc ctgttcaagt tgggtaagcc  7140
```

-continued

```
gctaacagct gaagacaagc aggacgaaga caggcgacga gcactgagtg acgaggttag    7200
caagtggttc cggacaggct tgggggccga actggaggtg gcactaacat ctaggtatga    7260
ggtagagggc tgcaaaagta tcctcatagc catggccacc ttggcgaggg acattaaggc    7320
gtttaagaaa ttgagaggac ctgttataca cctctacggc ggtcctagat tggtgcgtta    7380
atacacagaa ttctgattgg atcccaaacg ggccctctag actcgagcgg ccgccactgt    7440
gctggatatc tgcagaattc caccacactg gactagtgga tctatggcgt acccatacga    7500
tgttccagat tacgctagct tgagatctac catgtctcag agcaaccggg agctggtggt    7560
tgactttctc tcctacaagc tttcccagaa aggatacagc tggagtcagt ttagtgatgt    7620
ggaagagaac aggactgagg ccccagaagg gactgaatcg gagatggaga cccccagtgc    7680
catcaatggc aacccatcct ggacctggca gacagcccc gcggtgaatg gagccactgc     7740
gcacagcagc agtttggatg cccgggaggt gatccccatg gcagcagtaa agcaagcgct    7800
gagggaggca ggcgacgagt ttgaactgcg gtaccggcgg gcattcagtg acctgacatc    7860
ccagctccac atcaccccag ggacagcata tcagagcttt gaacaggtag tgaatgaact    7920
cttccgggat ggggtaaact ggggtcgcat tgtggccttt ttctccttcg gcggggcact    7980
gtgcgtggaa agcgtagaca aggagatgca ggtattggtg agtcggatcg cagcttggat    8040
ggccacttac ctgaatgacc acctagagcc ttggatccag gagaacggcg gctgggatac    8100
ttttgtggaa ctctatggga caatgcagc agccgagagc cgaaagggcc aggaacgctt    8160
caaccgctgg ttcctgacgg gcatgactgt ggccggcatg gttctactgg gctcactctt    8220
cagtcggaaa tgaagatccg agctcggtac caagcttaag tttgggtaat taattgaatt    8280
acatccctac gcaaacgttt tacggccgcc ggtggcgccc gcgccggcg gccgtccttt    8340
ggccgttgca ggccactccg gtggctcccg tcgtccccga cttccaggcc cagcagatgc    8400
agcaactcat cagcgccgta aatgcgctga caatgagaca gaacgcaatt gctcctgcta    8460
ggcctcccaa accaagaag aagaagacaa ccaaaccaaa gccgaaaacg cagcccaaga    8520
agatcaacgg aaaaacgcag cagcaaaaga agaaagacaa gcaagccgac aagaagaaga    8580
agaaacccgg aaaagagaa agaatgtgca tgaagattga aaatgactgt atcttcgtat    8640
gcggctagcc acagtaacgt agtgtttcca gacatgtcgg gcaccgcact atcatgggtg    8700
cagaaaatct cggtggtct ggggggccttc gcaatcggcg ctatcctggt gctggttgtg    8760
gtcacttgca ttgggctccg cagataagtt agggtaggca atggcattga tatagcaaga    8820
aaattgaaaa cagaaaaagt tagggtaagc aatggcatat aaccataact gtataacttg    8880
taacaaagcg caacaagacc tgcgcaattg gccccgtggt ccgcctcacg gaaactcggg    8940
gcaactcata ttgacacatt aattggcaat aattggaagc ttacataagc ttaattcgac    9000
gaataattgg atttttattt tattttgcaa ttggttttta atatttccaa aaaaaaaaa    9060
aaaaaaaaa aaaaaaaaa aaaaaaaaa aaaaaaaaa aaaaaaaaa aaaaaaact    9120
agtgatcata atcagccata ccacatttgt agaggtttta cttgctttaa aaacctccc    9180
acacctcccc ctgaacctga acataaaat gaatgcaatt gttgttgtta acttgtttat    9240
tgcagcttat aatggttaca aataaagcaa tagcatcaca aatttcacaa ataaagcatt    9300
tttttcactg cattctagtt gtggtttgtc caaactcatc aatgtatctt atcatgtctg    9360
gatctagtct gcattaatga atcggccaac gcgcggggag aggcggtttg cgtattgggc    9420
gctcttccgc ttcctcgctc actgactcgc tgcgctcggt cgttcggctg cggcgagcgg    9480
tatcagctca ctcaaaggcg gtaatacggt tatccacaga atcaggggat aacgcaggaa    9540
```

```
agaacatgtg agcaaaaggc cagcaaaagg ccaggaaccg taaaaaggcc gcgttgctgg   9600
cgttttccca taggctccgc cccctgacg  agcatcacaa aaatcgacgc tcaagtcaga   9660
ggtggcgaaa cccgacagga ctataaagat accaggcgtt tccccctgga agctccctcg   9720
tgcgctctcc tgttccgacc ctgccgctta ccggatacct gtccgccttt ctcccttcgg   9780
gaagcgtggc gctttctcaa tgctcgcgct gtaggtatct cagttcggtg taggtcgttc   9840
gctccaagct gggctgtgtg cacgaacccc ccgttcagcc cgaccgctgc gccttatccg   9900
gtaactatcg tcttgagtcc aacccggtaa gacacgactt atcgccactg gcagcagcca   9960
ctggtaacag gattagcaga gcgaggtatg taggcggtgc tacagagttc ttgaagtggt  10020
ggcctaacta cggctacact agaaggacag tatttggtat ctgcgctctg ctgaagccag  10080
ttaccttcgg aaaaagagtt ggtagctctt gatccggcaa acaaaccacc gctggtagcg  10140
gtggtttttt tgtttgcaag cagcagatta cgcgcagaaa aaaggatctc aagaagatc   10200
ctttgatctt ttctacgggg cattctgacg ctcagtggaa cgaaaactca cgttaaggga  10260
ttttggtcat gagattatca aaaggatctt cacctagat  ccttttaaat taaaaatgaa  10320
gttttaaatc aatctaaagt atatatgagt aaacttggtc tgacagttac caatgcttaa  10380
tcagtgaggc acctatctca gcgatctgtc tatttcgttc atccatagtt gcctgactcc  10440
ccgtcgtgta gataactacg atacgggagg gcttaccatc tggccccagt gctgcaatga  10500
taccgcgaga cccacgctca ccggctccag atttatcagc aataaaccag ccagccggaa  10560
gggccgagcg cagaagtggt cctgcaactt tatccgcctc catccagtct attaattgtt  10620
gccgggaagc tagagtaagt agttcgccag ttaatagttt gcgcaacgtt gttgccattg  10680
ctacaggcat cgtggtgtca cgctcgtcgt ttggtatggc ttcattcagc tccggttccc  10740
aacgatcaag gcgagttaca tgatccccca tgttgtgcaa aaaagcggtt agctccttcg  10800
gtcctccgat cgttgtcaga agtaagttgg ccgcagtgtt atcactcatg gttatggcag  10860
cactgcataa ttctcttact gtcatgccat ccgtaagatg cttttctgtg actggtgagt  10920
actcaaccaa gtcattctga gaatagtgta tgcggcgacc gagttgctct tgcccggcgt  10980
caatacggga taataccgcg ccacatagca gaactttaaa agtgctcatc attggaaaac  11040
gttcttcggg gcgaaaactc tcaaggatct taccgctgtt gagatccagt tcgatgtaac  11100
ccactcgtgc acccaactga tcttcagcat cttttacttt caccagcgtt tctgggtgag  11160
caaaaacagg aaggcaaaat gccgcaaaaa agggaataag ggcgacacgg aaatgttgaa  11220
tactcatact cttccttttt caatattatt gaagcattta tcagggttat tgtctcatga  11280
gcggatacat atttgaatgt atttagaaaa ataaacaaat aggggttccg cgcacatttc  11340
cccgaaaagt gccacctgac gtctaagaaa ccattattat catgacatta acctataaaa  11400
ataggcgtat cacgaggccc tttcgtctcg cgcgtttcgg tgatgacggt gaaaacctct  11460
gacacatgca gctcccggag acggtcacag cttctgtcta gcggatgcc  gggagcagac  11520
aagcccgtca gggcgcgtca gcgggtgttg gcgggtgtcg ggctggctt  aactatgcgg  11580
catcagagca gattgtactg agagtgcacc atatcgacgc tctcccttat gcgactcctg  11640
cattaggaag cagcccagta ctaggttgag gccgttgagc accgccgccg caaggaatgg  11700
tgcatgcgta atcaattacg gggtcattag ttcatagccc atatatggag ttccgcgtta  11760
cataacttac ggtaaatggc ccgcctggct gaccgcccaa cgacccccgc ccattgacgt  11820
caataatgac gtatgttccc atagtaacgc caatagggac tttccattga cgtcaatggg  11880
```

```
tggagtattt acggtaaact gcccacttgg cagtacatca agtgtatcat atgccaagta    11940 cgcccccctat tgacgtcaat gacggtaaat ggcccgcctg gcattatgcc cagtacatga    12000
ccttatggga ctttcctact tggcagtaca tctacgtatt agtcatcgct attaccatgg    12060
tgatgcggtt ttggcagtac atcaatgggc gtggatagcg gtttgactca cggggatttc    12120
caagtctcca ccccattgac gtcaatggga gtttgttttg gcaccaaaat caacgggact    12180
ttccaaaatg tcgtaacaac tccgccccat tgacgcaaat gggcggtagg cgtgtacggt    12240
gggaggtcta tataagcaga gctctctggc taactagaga acccactgct taactggctt    12300
atcgaaatta atacgactca ctatagggag accggaagct tgaattc                  12347

<210> SEQ ID NO 66
<211> LENGTH: 12612
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
atggcggatg tgtgacatac acgacgccaa aagattttgt tccagctcct gccacctccg      60
ctacgcgaga gattaaccac ccacgatggc cgccaaagtg catgttgata ttgaggctga     120
cagcccattc atcaagtctt tgcagaaggc atttccgtcg ttcgaggtgg agtcattgca     180
ggtcacacca aatgaccatg caaatgccag agcattttcg cacctggcta ccaaattgat     240
cgagcaggag actgacaaag acacactcat cttggatatc ggcagtgcgc cttccaggag     300
aatgatgtct acgcacaaat accactgcgt atgccctatg cgcagcgcag aagaccccga     360
aaggctcgat agctacgcaa agaaactggc agcggcctcc gggaaggtgc tggatagaga     420
gatcgcagga aaaatcaccg acctgcagac cgtcatggct acgccagacg ctgaatctcc     480 tacctttgc ctgcatacag acgtcacgtg tcgtacggca gccgaagtgg ccgtatacca      540
ggacgtgtat gctgtacatg caccaacatc gctgtaccat caggcgatga aggtgtcag     600 aacggcgtat tggattgggt ttgacaccac cccgtttatg tttgacgcgc tagcaggcgc     660
gtatccaacc tacgccacaa actgggccga cgagcaggtg ttacaggcca ggaacatagg     720
actgtgtgca gcatccttga ctgagggaag actcggcaaa ctgtccattc tccgcaagaa     780
gcaattgaaa ccttgcgaca cagtcatgtt ctcggtagga tctacattgt acactgagag     840
cagaaagcta ctgaggagct ggcacttacc ctccgtattc cacctgaaag gtaaacaatc     900
ctttacctgt aggtgcgata ccatcgtatc atgtgaaggg tacgtagtta agaaaatcac     960
tatgtgcccc ggcctgtacg gtaaaacggt agggtacgcc gtgacgtatc acgcggaggg    1020
attcctagtg tgcaagacca cagacactgt caaaggagaa agagtctcat tccctgtatg    1080
cacctacgtc ccctcaacca tctgtgatca aatgactggc atactagcga ccgacgtcac    1140 accgaggac gcacagaagt tgttagtggg attgaatcag aggatagttg taacggaag     1200 aacacagcga aacactaaca cgatgaagaa ctatctgctt ccgattgtgg ccgtcgcatt    1260
tagcaagtgg gcgagggaat acaaggcaga ccttgatgat gaaaaacctc tgggtgtccg    1320
agagaggtca cttacttgct gctgcttgtg ggcatttaaa acgaggaaga tgcacaccat    1380
gtacaagaaa ccagacaccc agacaatagt gaaggtgcct tcagagttta actcgttcgt    1440
catcccgagc ctatggtcta caggcctcgc aatcccagtc agatcacgca ttaagatgct    1500
tttggccaag aagaccaagc gagagttaat acctgttctc gacgcgtcgt cagccaggga    1560
```

```
tgctgaacaa gaggagaagg agaggttgga ggccgagctg actagagaag ccttaccacc   1620
cctcgtcccc atcgcgccgg cggagacggg agtcgtcgac gtcgacgttg aagaactaga   1680
gtatcacgca ggtgcagggg tcgtggaaac acctcgcagc gcgttgaaag tcaccgcaca   1740
gccgaacgac gtactactag gaaattacgt agttctgtcc ccgcagaccg tgctcaagag   1800
ctccaagttg gccccgtgc accctctagc agagcaggtg aaaataataa cacataacgg    1860
gagggccggc ggttaccagg tcgacggata tgacggcagg gtcctactac catgtggatc   1920
ggccattccg gtccctgagt ttcaagcttt gagcgagagc gccactatgg tgtacaacga   1980
aagggagttc gtcaacagga aactatacca tattgccgtt cacgaccgt cgctgaacac    2040
cgacgaggag aactacgaga agtcagagc tgaaagaact gacgccgagt acgtgttcga    2100
cgtagataaa aaatgctgcg tcaagagaga ggaagcgtcg ggtttggtgt tggtgggaga   2160
gctaaccaac cccccgttcc atgaattcgc ctacgaaggg ctgaagatca ggccgtcggc   2220
accatataag actacagtag taggagtctt tggggttccg ggatcaggca agtctgctat   2280
tattaagagc ctcgtgacca acacgatct ggtcaccagc ggcaagaagg agaactgcca    2340
ggaaatagtt aacgacgtga agaagcaccg cgggaagggg acaagtaggg aaaacagtga   2400
ctccatcctg ctaaacgggt gtcgtcgtgc cgtggacatc ctatatgtgg acgaggcttt   2460
cgctagccat tccggtactc tgctggccct aattgctctt gttaaacctc ggagcaaagt   2520
ggtgttatgc ggagacccca agcaatgcgg attcttcaat atgatgcagc ttaaggtgaa   2580
cttcaaccac aacatctgca ctgaagtatg tcataaaagt atatccagac gttgcacgcg   2640
tccagtcacg gccatcgtgt ctacgttgca ctacggaggc aagatgcgca cgaccaaccc   2700
gtgcaacaaa cccataatca tagacaccac aggacagacc aagcccaagc caggagacat   2760
cgtgttaaca tgcttccgag ctgggcaaa gcagctgcag ttggactacc gtggacacga    2820
agtcatgaca gcagcagcat ctcagggcct cacccgcaaa ggggtatacg ccgtaaggca   2880
gaaggtgaat gaaaatccct tgtatgcccc tgcgtcggag cacgtgaatg tactgctgac   2940
gcgcactgag gataggctgg tgtggaaaac gctggccggc gatccctgga ttaaggtcct   3000
atcaaacatt ccacagggta actttacggc cacattggaa gaatggcaag aagaacacga   3060
caaaataatg aaggtgattg aaggaccggc tgcgcctgtg gacgcgttcc agaacaaagc   3120
gaacgtgtgt tgggcgaaaa gcctggtgcc tgtcctggac actgccggaa tcagattgac   3180
agcagaggag tggagcacca taattacagc atttaaggag gacagagctt actctccagt   3240
ggtggccttg aatgaaattt gcaccaagta ctatggagtt gacctggaca gtggcctgtt   3300
ttctgccccg aaggtgtccc tgtattacga gaacaaccac tgggataaca gacctggtgg   3360
aaggatgtat ggattcaatg ccgcaacagc tgccaggctg gaagctagac ataccttcct   3420
gaaggggcag tggcatacgg gcaagcaggc agttatcgca gaaagaaaaa tccaaccgct   3480
ttctgtgctg acaatgtaa ttcctatcaa ccgcaggctg ccgcacgccc tggtggctga    3540
gtacaagacg gttaaaggca gtagggttga gtggctggtc aataaagtaa gagggtacca   3600
cgtcctgctg gtgagtgagt acaacctggc tttgcctcga cgcagggtca cttggttgtc   3660
accgctgaat gtcacaggcg ccgataggtg ctacgaccta agtttaggac tgccggctga   3720
cgccggcagg ttcgacttgg tctttgtgaa cattcacacg gaattcagaa tccaccacta   3780
ccagcagtgt gtcgaccacg ccatgaagct gcagatgctt ggggagatg cgctacgact    3840
gctaaaaccc ggcggcatct tgatgagagc ttacggatac gccgataaaa tcagcgaagc   3900
cgttgtttcc tccttaagca gaaagttctc gtctgcaaga gtgttgcgcc cggattgtgt   3960
```

-continued

```
caccagcaat acagaagtgt tcttgctgtt ctccaacttt gacaacgaa agagaccctc    4020 tacgctacac cagatgaata ccaagctgag tgccgtgtat gccggagaag ccatgcacac    4080
ggccgggtgt gcaccatcct acagagttaa gagagcagac atagccacgt gcacagaagc    4140
ggctgtggtt aacgcagcta acgcccgtgg aactgtaggg gatggcgtat gcagggccgt    4200
ggcgaagaaa tggccgtcag cctttaaggg agcagcaaca ccagtgggca caattaaaac    4260
agtcatgtgc ggctcgtacc ccgtcatcca cgctgtagcg cctaatttct ctgccacgac    4320
tgaagcggaa ggggaccgcg aattggccgc tgtctaccgg gcagtggccg ccgaagtaaa    4380
cagactgtca ctgagcagcg tagccatccc gctgctgtcc acaggagtgt tcagcggcgg    4440
aagagatagg ctgcagcaat ccctcaacca tctattcaca gcaatggacg ccacggacgc    4500
tgacgtgacc atctactgca gagacaaaag ttgggagaag aaaatccagg aagccattga    4560
catgaggacg gctgtggagt tgctcaatga tgacgtggag ctgaccacag acttggtgag    4620
agtgcacccg gacagcagcc tggtgggtcg taagggctac agtaccactg acgggtcgct    4680
gtactcgtac tttgaaggta cgaaattcaa ccaggctgct attgatatgg cagagatact    4740
gacgttgtgg cccagactgc aagaggcaaa cgaacagata tgcctatacg cgctgggcga    4800
aacaatggac aacatcagat ccaaatgtcc ggtgaacgat tccgattcat caacacctcc    4860
caggacagtg ccctgcctgt gccgctacgc aatgacagca gaacggatcg cccgccttag    4920
gtcacaccaa gttaaaagca tggtggtttg ctcatctttt cccctcccga ataccatgt     4980 agatggggtg cagaaggtaa agtgcgagaa ggttctcctg ttcgacccga cggtaccttc    5040
agtggttagt ccgcggaagt atgccgcatc tacgacggac cactcagatc ggtcgttacg    5100
agggtttgac ttggactgga ccaccgactc gtcttccact gccagcgata ccatgtcgct    5160
acccagtttg cagtcgtgtg acatcgactc gatctacgag ccaatggctc ccatagtagt    5220
gacggctgac gtacaccctg aacccgcagg catcgcggac ctggcggcag atgtgcaccc    5280
tgaacccgca gaccatgtgg acctcgagaa cccgattcct ccaccgcgcc cgaagagagc    5340
tgcatacctt gcctcccgcg cggcggagcc accggtgccg gcgccgagaa agccgacgcc    5400
tgccccaagg actgcgttta ggaacaagct gcctttgacg ttcggcgact ttgacgagca    5460
cgaggtcgat gcgttggcct ccggattac tttcggagac ttcgacgacg tcctgcgact    5520
aggccgcgcg ggtgcatata ttttctcctc ggacactggc agcggacatt tacaacaaaa    5580
atccgttagg cagcacaatc tccagtgcgc acaactggat gcggtccagg aggagaaaat    5640
gtacccgcca aaattggata ctgagaggga gaagctgttg ctgctgaaaa tgcagatgca    5700
cccatcggag gctaataaga gtcgatacca gtctcgcaaa gtggagaaca tgaaagccac    5760
ggtggtggac aggctcacat cgggggccag attgtacacg ggagcggacg taggccgcat    5820
accaacatac gcggttcggt accccgccc cgtgtactcc cctaccgtga tcgaaagatt    5880
ctcaagcccc gatgtagcaa tcgcagcgtg caacgaatac ctatccagaa attacccaac    5940
agtggcgtcg taccagataa cagatgaata cgacgcatac ttggacatgg ttgacgggtc    6000
ggatagttgc ttggacagag cgacattctg cccggcgaag ctccggtgct acccgaaaca    6060
tcatgcgtac caccagccga ctgtacgcag tgccgtcccg tcacccttc agaacacact    6120 acagaacgtg ctagcggccg ccaccaagag aaactgcaac gtcacgcaaa tgcgagaact    6180
acccaccatg gactcggcag tgttcaacgt ggagtgcttc aagcgctatg cctgctccgg    6240
agaatattgg gaagaatatg ctaaacaacc tatccggata accactgaga acatcactac    6300
```

```
ctatgtgacc aaattgaaag gcccgaaagc tgctgccttg ttcgctaaga cccacaactt   6360
ggttccgctg caggaggttc ccatggacag attcacggtc gacatgaaac gagatgtcaa   6420
agtcactcca gggacgaaac acacagagga aagacccaaa gtccaggtaa ttcaagcagc   6480
ggagccattg cgaccgcttc acctgtgcgg catccacagg gaattagtaa ggagactaaa   6540
tgctgtgtta cgccctaacg tgcacacatt gtttgatatg tcggccgaag actttgacgc   6600
gatcatcgcc tctcacttcc acccaggaga cccggttcta gagacggaca ttgcatcatt   6660
cgacaaaagc caggacgact ccttggctct tacaggttta atgatcctcg aagatctagg   6720
ggtggatcag tacctgctgg acttgatcga ggcagccttt ggggaaatat ccagctgtca   6780
cctaccaact ggcacgcgct tcaagttcgg agctatgatg aaatcgggca tgtttctgac   6840
tttgttattt aacactgttt tgaacatcac catagcaagc agggtactgg agcagagact   6900
cactgactcc gcctgtgcgg ccttcatcgg cgacgacaac atcgttcacg gagtgatctc   6960
cgacaagctg atggcggaga ggtgcgcgtc gtgggtcaac atggaggtga agatcattga   7020
cgctgtcatg ggcgaaaaac ccccatattt ttgtggggga ttcatagttt ttgacagcgt   7080
cacacagacc gcctgccgtg tttcagaccc acttaagcgc ctgttcaagt tgggtaagcc   7140
gctaacagct gaagacaagc aggacgaaga caggcgacga gcactgagtg acgaggttag   7200
caagtggttc cggacaggct tgggggccga actggaggtg gcactaacat ctaggtatga   7260
ggtagagggc tgcaaaagta tcctcatagc catggccacc ttggcgaggg acattaaggc   7320
gtttaagaaa ttgagaggac ctgttataca cctctacggc ggtcctagat tggtgcgtta   7380
atacacagaa ttctgattgg atcccaaacg ggccctctag actcgagcgg ccgccactgt   7440
gctggatatc tgcagaattc atgcatggag atacacctac attgcatgaa tatatgttag   7500
atttgcaacc agagacaact gatctctact gttatgagca attaaatgac agctcagagg   7560
aggaggatga aatagatggt ccagctggac aagcagaacc ggacagagcc cattacaata   7620
ttgtaacctt ttgttgcaag tgtgactcta cgcttcggtt gtgcgtacaa agcacacacg   7680
tagacattcg tactttggaa gacctgttaa tgggcacact aggaattgtg tgccccatct   7740
gttctcagaa accaggatct atggcgtacc catacgatgt tccagattac gctagcttga   7800
gatctaccat gtctcagagc aaccgggagc tggtggttga cttcctctcc tacaagcttt   7860
cccagaaagg atacagctgg agtcagttta gtgatgtgga agagaacagg actgaggccc   7920
cagaagggac tgaatcggag atggagaccc ccagtgccat caatggcaac ccatcctggc   7980
acctggcaga cagccccgcg gtgaatgagc ccactgcgca cagcagcagt ttggatgccc   8040
gggaggtgat ccccatggca gcagtaaagc aagcgctgag ggaggcaggc gacgagtttg   8100
aactgcggta ccggcgggca ttcagtgacc tgacatccca gctccacatc accccaggga   8160
cagcatatca gagctttgaa caggtagtga atgaactctt ccgggatggg gtaaactggg   8220
gtcgcattgt ggccttttc tccttcggcg gggcactgtg cgtggaaagc gtagacaagg   8280
agatgcaggt attggtgagt cggatcgcag cttggatggc acttacctg aatgaccacc   8340 tagagccttg gatccaggag aacggcggct gggatacttt tgtggaactc tatgggaaca   8400
atgcagcagc cgagagccga aagggccagg aacgcttcaa ccgctggttc ctgacgggca   8460
tgactgtggc cggcgtggtt ctgctgggct cactcttcag tcggaaatga agatccaagc   8520
ttaagtttgg gtaattaatt gaattacatc cctacgcaaa cgttttacgg ccgccggtgg   8580
cgcccgcgcc cggcggcccg tccttggccg ttgcaggcca ctccggtggc tcccgtcgtc   8640
cccgacttcc aggcccagca gatgcagcaa ctcatcagcg ccgtaaatgc gctgacaatg   8700
```

```
agacagaacg caattgctcc tgctaggcct cccaaaccaa agaagaagaa gacaaccaaa    8760
ccaaagccga aaacgcagcc caagaagatc aacggaaaaa cgcagcagca aaagaagaaa    8820
gacaagcaag ccgacaagaa gaagaagaaa cccggaaaaa gagaaagaat gtgcatgaag    8880
attgaaaatg actgtatctt cgtatgcggc tagccacagt aacgtagtgt ttccagacat    8940
gtcgggcacc gcactatcat gggtgcagaa aatctcgggt ggtctggggg ccttcgcaat    9000
cggcgctatc ctggtgctgg ttgtggtcac ttgcattggg ctccgcagat aagttagggt    9060
aggcaatggc attgatatag caagaaaatt gaaaacagaa aaagttaggg taagcaatgg    9120
catataacca taactgtata acttgtaaca aagcgcaaca agacctgcgc aattggcccc    9180
gtggtccgcc tcacggaaac tcgggcaac tcatattgac acattaattg gcaataattg     9240
gaagcttaca taagcttaat tcgacgaata attggatttt tattttattt tgcaattggt    9300
ttttaatatt tccaaaaaaa aaaaaaaaaa aaaaaaaaaa aaaaaaaaaa aaaaaaaaa     9360 aaaaaaaaaa aaaaaaaaaa aaactagtga tcataatcag ccataccaca tttgtagagg    9420
ttttacttgc tttaaaaaac ctcccacacc tcccccctgaa cctgaaacat aaaatgaatg    9480
caattgttgt tgttaacttg tttattgcag cttataatgg ttacaaataa agcaatagca    9540
tcacaaattt cacaaataaa gcattttttt cactgcattc tagttgtggt ttgtccaaac    9600
tcatcaatgt atcttatcat gtctggatct agtctgcatt aatgaatcgg ccaacgcgcg    9660
gggagaggcg gtttgcgtat tgggcgctct tccgcttcct cgctcactga ctcgctgcgc    9720
tcggtcgttc ggctgcggcg agcggtatca gctcactcaa aggcggtaat acggttatcc    9780
acagaatcag gggataacgc aggaaagaac atgtgagcaa aaggccagca aaaggccagg    9840
aaccgtaaaa aggccgcgtt gctggcgttt ttccataggc tccgcccccc tgacgagcat    9900
cacaaaaatc gacgctcaag tcagaggtgg cgaaacccga caggactata agataccag    9960 gcgtttcccc ctggaagctc cctcgtgcgc tctcctgttc cgaccctgcc gcttaccgga   10020
tacctgtccg cctttctccc ttcgggaagc gtggcgcttt ctcaatgctc gcgctgtagg   10080
tatctcagtt cggtgtaggt cgttcgctcc aagctgggct gtgtgcacga acccccgtt    10140 cagcccgacc gctgcgcctt atccggtaac tatcgtcttg agtccaaccc ggtaagacac   10200
gacttatcgc cactggcagc agccactggt aacaggatta gcagagcgag gtatgtaggc   10260
ggtgctacag agttcttgaa gtggtggcct aactacggct acactagaag gacagtattt   10320
ggtatctgcg ctctgctgaa gccagttacc ttcggaaaaa gagttggtag ctcttgatcc   10380
ggcaaacaaa ccaccgctgg tagcggtggt ttttttgttt gcaagcagca gattacgcgc   10440
agaaaaaaag gatctcaaga agatcctttg atcttttcta cggggcattc tgacgctcag   10500
tggaacgaaa actcacgtta agggattttg gtcatgagat tatcaaaaag gatcttcacc   10560
tagatccttt taaattaaaa atgaagtttt aaatcaatct aaagtatata tgagtaaact   10620
tggtctgaca gttaccaatg cttaatcagt gaggcaccta tctcagcgat ctgtctattt   10680
cgttcatcca tagttgcctg actccccgtc gtgtagataa ctacgatacg ggagggctta   10740
ccatctggcc ccagtgctgc aatgataccg cgagacccac gctcaccggc tccagattta   10800
tcagcaataa accagccagc cggaagggcc gagcgcagaa gtggtcctgc aactttatcc   10860
gcctccatcc agtctattaa ttgttgccgg gaagctagag taagtagttc gccagttaat   10920
agtttgcgca acgttgttgc cattgctaca ggcatcgtgg tgtcacgctc gtcgtttggt   10980
atggcttcat tcagctccgg ttcccaacga tcaaggcgag ttacatgatc ccccatgttg   11040
```

```
tgcaaaaaag cggttagctc cttcggtcct ccgatcgttg tcagaagtaa gttggccgca    11100
gtgttatcac tcatggttat ggcagcactg cataattctc ttactgtcat gccatccgta    11160
agatgctttt ctgtgactgg tgagtactca accaagtcat tctgagaata gtgtatgcgg    11220
cgaccgagtt gctcttgccc ggcgtcaata cgggataata ccgcgccaca tagcagaact    11280
ttaaaagtgc tcatcattgg aaaacgttct cgggcgaa aactctcaag gatcttaccg     11340
ctgttgagat ccagttcgat gtaacccact cgtgcaccca actgatcttc agcatctttt    11400
actttcacca gcgtttctgg gtgagcaaaa acaggaaggc aaaatgccgc aaaaaaggga    11460
ataagggcga cacggaaatg ttgaatactc atactcttcc ttttttcaata ttattgaagc    11520 atttatcagg gttattgtct catgagcgga tacatatttg aatgtattta gaaaaataaa    11580
caaatagggg ttccgcgcac atttccccga aaagtgccac ctgacgtcta agaaaccatt    11640
attatcatga cattaaccta taaaaatagg cgtatcacga ggccctttcg tctcgcgcgt    11700
ttcggtgatg acggtgaaaa cctctgacac atgcagctcc cggagacggt cacagcttct    11760
gtctaagcgg atgccgggag cagacaagcc cgtcagggcg cgtcagcggg tgttggcggg    11820
tgtcggggct ggcttaacta tgcggcatca gagcagattg tactgagagt gcaccatatc    11880
gacgctctcc cttatgcgac tcctgcatta ggaagcagcc cagtactagg ttgaggccgt    11940
tgagcaccgc cgccgcaagg aatggtgcat gcgtaatcaa ttacgggtc attagttcat    12000 agcccatata tggagttccg cgttacataa cttacggtaa atggcccgcc tggctgaccg    12060
cccaacgacc cccgcccatt gacgtcaata atgacgtatg ttcccatagt aacgccaata    12120
gggactttcc attgacgtca atgggtggag tatttacggt aaactgccca cttggcagta    12180
catcaagtgt atcatatgcc aagtacgccc cctattgacg tcaatgacgg taaatggccc    12240
gcctggcatt atgcccagta catgacctta tgggactttc ctacttggca gtacatctac    12300
gtattagtca tcgctattac catggtgatg cggttttggc agtacatcaa tgggcgtgga    12360
tagcggtttg actcacgggg atttccaagt ctccaccca ttgacgtcaa tgggagtttg    12420
ttttggcacc aaaatcaacg ggactttcca aaatgtcgta caactccgc cccattgacg    12480 caaatgggcg gtaggcgtgt acggtgggag gtctatataa gcagagctct ctggctaact    12540
agagaaccca ctgcttaact ggcttatcga aattaatacg actcactata gggagaccgg    12600
aagcttgaat tc                                                       12612
```

<210> SEQ ID NO 67
<211> LENGTH: 12347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
atggcggatg tgtgacatac acgacgccaa aagattttgt tccagctcct gccacctccg      60
ctacgcgaga gattaaccac ccacgatggc cgccaaagtg catgttgata ttgaggctga     120
cagcccattc atcaagtctt tgcagaaggc atttccgtcg ttcgaggtgg agtcattgca     180
ggtcacacca aatgaccatg caaatgccag agcattttcg cacctggcta ccaaattgat     240
cgagcaggag actgacaaag acacactcat cttggatatc ggcagtgcgc cttccaggag     300
aatgatgtct acgcacaaat accactgcgt atgccctatg cgcagcgcag aagaccccga     360
aaggctcgat agctacgcaa agaaactggc agcggcctcc gggaaggtgc tggatagaga     420
```

| | |
|---|---|
| gatcgcagga aaaatcaccg acctgcagac cgtcatggct acgccagacg ctgaatctcc | 480 |
| taccttttgc ctgcatacag acgtcacgtg tcgtacggca gccgaagtgg ccgtatacca | 540 |
| ggacgtgtat gctgtacatg caccaacatc gctgtaccat caggcgatga aggtgtcag | 600 |
| aacggcgtat tggattgggt ttgacaccac cccgtttatg tttgacgcgc tagcaggcgc | 660 |
| gtatccaacc tacgccacaa actgggccga cgagcaggtg ttacaggcca ggaacatagg | 720 |
| actgtgtgca gcatccttga ctgagggaag actcggcaaa ctgtccattc tccgcaagaa | 780 |
| gcaattgaaa ccttgcgaca cagtcatgtt ctcggtagga tctacattgt acactgagag | 840 |
| cagaaagcta ctgaggagct ggcacttacc ctccgtattc cacctgaaag gtaaacaatc | 900 |
| ctttacctgt aggtgcgata ccatcgtatc atgtgaaggg tacgtagtta agaaaatcac | 960 |
| tatgtgcccc ggcctgtacg gtaaaacggt agggtacgcc gtgacgtatc acgcggaggg | 1020 |
| attcctagtg tgcaagacca cagacactgt caaaggagaa agagtctcat tccctgtatg | 1080 |
| cacctacgtc ccctcaacca tctgtgatca aatgactggc atactagcga ccgacgtcac | 1140 |
| accggaggac gcacagaagt tgttagtggg attgaatcag aggatagttg tgaacggaag | 1200 |
| aacacagcga aacactaaca cgatgaagaa ctatctgctt ccgattgtgg ccgtcgcatt | 1260 |
| tagcaagtgg gcgagggaat acaaggcaga ccttgatgat gaaaaacctc tgggtgtccg | 1320 |
| agagaggtca cttacttgct gctgcttgtg gcatttaaa acgaggaaga tgcacaccat | 1380 |
| gtacaagaaa ccagacaccc agacaatagt gaaggtgcct tcagagttta actcgttcgt | 1440 |
| catcccgagc ctatggtcta caggcctcgc aatcccagtc agatcacgca ttaagatgct | 1500 |
| tttggccaag aagaccaagc gagagttaat acctgttctc gacgcgtcgt cagccaggga | 1560 |
| tgctgaacaa gaggagaagg agaggttgga ggccgagctg actagagaag ccttaccacc | 1620 |
| cctcgtcccc atcgcgccgg cggagacggg agtcgtcgac gtcgacgttg aagaactaga | 1680 |
| gtatcacgca ggtgcagggg tcgtggaaac acctcgcagc gcgttgaaag tcaccgcaca | 1740 |
| gccgaacgac gtactactag gaaattacgt agttctgtcc ccgcagaccg tgctcaagag | 1800 |
| ctccaagttg gcccccgtgc accctctagc agagcaggtg aaaataataa cacataacgg | 1860 |
| gagggccggc ggttaccagg tcgacggata tgacggcagg gtcctactac catgtggatc | 1920 |
| ggccattccg gtccctgagt ttcaagcttt gagcgagagc gccactatgg tgtacaacga | 1980 |
| aagggagttc gtcaacagga aactatacca tattgccgtt cacggaccgt cgctgaacac | 2040 |
| cgacgaggag aactacgaga agtcagagc tgaaagaact gacgccgagt acgtgttcga | 2100 |
| cgtagataaa aaatgctgcg tcaagagaga ggaagcgtcg ggtttggtgt tggtgggaga | 2160 |
| gctaaccaac ccccgttcc atgaattcgc ctacgaaggg ctgaagatca ggccgtcggc | 2220 |
| accatataag actacagtag taggagtctt tggggttccg ggatcaggca agtctgctat | 2280 |
| tattaagagc ctcgtgacca acacgatct ggtcaccagc ggcaagaagg agaactgcca | 2340 |
| ggaaatagtt aacgacgtga agaagcaccg cgggaagggg acaagtaggg aaaacagtga | 2400 |
| ctccatcctg ctaaacgggt gtcgtcgtgc cgtggacatc ctatatgtgg acgaggcttt | 2460 |
| cgctagccat tccggtactc tgctggccct aattgctctt gttaaacctc ggagcaaagt | 2520 |
| ggtgttatgc ggagaccca agcaatgcgg attcttcaat atgatgcagc ttaaggtgaa | 2580 |
| cttcaaccac aacatctgca ctgaagtatg tcataaaagt atatccagac gttgcacgcg | 2640 |
| tccagtcacg gccatcgtgt ctacgttgca ctacggaggc aagatgcgca cgaccaaccc | 2700 |
| gtgcaacaaa cccataatca tagacaccac aggacgacc aagcccaagc caggagacat | 2760 |
| cgtgttaaca tgcttccgag gctgggcaaa gcagctgcag ttggactacc gtggacacga | 2820 |

```
agtcatgaca gcagcagcat ctcagggcct cacccgcaaa ggggtatacg ccgtaaggca    2880
gaaggtgaat gaaaatccct tgtatgcccc tgcgtcggag cacgtgaatg tactgctgac    2940
gcgcactgag gataggctgg tgtggaaaac gctggccggc gatccctgga ttaaggtcct    3000
atcaaacatt ccacagggta actttacggc cacattggaa gaatggcaag aagaacacga    3060
caaaataatg aaggtgattg aaggaccggc tgcgcctgtg gacgcgttcc agaacaaagc    3120
gaacgtgtgt tgggcgaaaa gcctggtgcc tgtcctggac actgccggaa tcagattgac    3180
agcagaggag tggagcacca taattacagc atttaaggag gacagagctt actctccagt    3240
ggtggccttg aatgaaattt gcaccaagta ctatggagtt gacctggaca gtggcctgtt    3300
ttctgccccg aaggtgtccc tgtattacga gaacaaccac tgggataaca gacctggtgg    3360
aaggatgtat ggattcaatg ccgcaacagc tgccaggctg gaagctagac ataccttcct    3420 gaagggggcag tggcatacgg gcaagcaggc agttatcgca gaaagaaaaa tccaaccgct    3480
ttctgtgctg gacaatgtaa ttcctatcaa ccgcaggctg ccgcacgccc tggtggctga    3540
gtacaagacg gttaaaggca gtagggttga gtggctggtc aataaagtaa gagggtacca    3600
cgtcctgctg gtgagtgagt acaacctggc tttgcctcga cgcagggtca cttggttgtc    3660
accgctgaat gtcacaggcg ccgataggtg ctacgaccta agtttaggac tgccggctga    3720
cgccggcagg ttcgacttgg tctttgtgaa cattcacacg gaattcagaa tccaccacta    3780
ccagcagtgt gtcgaccacg ccatgaagct gcagatgctt gggggagatg cgctacgact    3840
gctaaaaccc ggcggcatct tgatgagagc ttacggatac gccgataaaa tcagcgaagc    3900
cgttgtttcc tccttaagca gaaagttctc gtctgcaaga gtgttgcgcc cggattgtgt    3960
caccagcaat acagaagtgt tcttgctgtt ctccaacttt gacaacggaa agagaccctc    4020
tacgctacac cagatgaata ccaagctgag tgccgtgtat gccggagaag ccatgcacac    4080
ggccgggtgt gcaccatcct acagagttaa gagagcagac atagccacgt gcacagaagc    4140
ggctgtggtt aacgcagcta acgcccgtgg aactgtaggg gatggcgtat gcagggccgt    4200
ggcgaagaaa tggccgtcag cctttaaggg agcagcaaca ccagtgggca caattaaaac    4260
agtcatgtgc ggctcgtacc ccgtcatcca cgctgtagcg cctaatttct ctgccacgac    4320
tgaagcggaa ggggaccgcg aattggccgc tgtctaccgg gcagtggccg ccgaagtaaa    4380
cagactgtca ctgagcagcg tagccatccc gctgctgtcc acaggagtgt tcagcggcgg    4440
aagagatagg ctgcagcaat ccctcaacca tctattcaca gcaatggacg ccacggacgc    4500
tgacgtgacc atctactgca gagacaaaag ttgggagaag aaaatccagg aagccattga    4560
catgaggacg gctgtggagt tgctcaatga tgacgtggag ctgaccacag acttggtgag    4620
agtgcacccg gacagcagcc tggtgggtcg taagggctac agtaccactg acgggtcgct    4680
gtactcgtac tttgaaggta cgaaattcaa ccaggctgct attgatatgg cagagatact    4740
gacgttgtgg cccagactgc aagaggcaaa cgaacagata tgcctatacg cgctgggcga    4800
aacaatggac aacatcagat ccaaatgtcc ggtgaacgat tccgattcat caacacctcc    4860
caggacagtg ccctgcctgt gccgctacgc aatgacagca gaacggatcg cccgccttag    4920
gtcacaccaa gttaaaagca tggtggtttg ctcatctttt cccctcccga ataccatgt     4980 agatggggtg cagaaggtaa agtgcgagaa ggttctcctg ttcgacccga cggtaccttc    5040
agtggttagt ccgcggaagt atgccgcatc tacgacggac cactcagatc ggtcgttacg    5100
agggtttgac ttggactgga ccaccgactc gtcttccact gccagcgata ccatgtcgct    5160
```

-continued

```
acccagtttg cagtcgtgtg acatcgactc gatctacgag ccaatggctc ccatagtagt    5220
gacggctgac gtacaccctg aacccgcagg catcgcggac ctggcggcag atgtgcaccc    5280
tgaacccgca gaccatgtgg acctcgagaa cccgattcct ccaccgcgcc cgaagagagc    5340
tgcataccct gcctcccgcg cggcggacg accggtgccg cgccgagaa agccgacgcc     5400 tgccccaagg actgcgttta ggaacaagct gcctttgacg ttcggcgact ttgacgagca    5460
cgaggtcgat gcgttggcct ccgggattac tttcggagac ttcgacgacg tcctgcgact    5520
aggccgcgcg ggtgcatata ttttctcctc ggacactggc agcggacatt tacaacaaaa    5580
atccgttagg cagcacaatc tccagtgcgc acaactggat gcggtccagg aggagaaaat    5640
gtacccgcca aaattggata ctgagaggga gaagctgttg ctgctgaaaa tgcagatgca    5700
cccatcggag gctaataaga gtcgatacca gtctcgcaaa gtggagaaca tgaaagccac    5760
ggtggtggac aggctcacat cgggggccag attgtacacg ggagcggacg taggccgcat    5820
accaacatac gcggttcggt accccgcccc cgtgtactcc cctaccgtga tcgaaagatt    5880
ctcaagcccc gatgtagcaa tcgcagcgtg caacgaatac ctatccagaa attacccaac    5940
agtggcgtcg taccagataa cagatgaata cgacgcatac ttggacatgg ttgacgggtc    6000
ggatagttgc ttggacagag cgacattctg cccggcgaag ctccggtgct acccgaaaca    6060
tcatgcgtac caccagccga ctgtacgcag tgccgtcccg tcacccttc agaacacact     6120 acagaacgtg ctagcggccg ccaccaagag aaactgcaac gtcacgcaaa tgcgagaact    6180
acccaccatg gactcggcag tgttcaacgt ggagtgcttc aagcgctatg cctgctccgg    6240
agaatattgg gaagaatatg ctaaacaacc tatccggata accactgaga acatcactac    6300
ctatgtgacc aaattgaaag gcccgaaagc tgctgccttg ttcgctaaga cccacaactt    6360
ggttccgctg caggaggttc ccatggacag attcacggtc gacatgaaac gagatgtcaa    6420
agtcactcca gggacgaaac acacagagga aagacccaaa gtccaggtaa ttcaagcagc    6480
ggagccattg gcgaccgctt acctgtgcgg catccacagg gaattagtaa ggagactaaa    6540
tgctgtgtta cgccctaacg tgcacacatt gtttgatatg tcggccgaag actttgacgc    6600
gatcatcgcc tctcacttcc acccaggaga cccggttcta gagacggaca ttgcatcatt    6660
cgacaaaagc caggacgact ccttggctct tacaggttta atgatcctcg aagatctagg    6720
ggtggatcag tacctgctgg acttgatcga ggcagccttt gggaaatat ccagctgtca     6780 cctaccaact ggcacgcgct tcaagttcgg agctatgatg aaatcgggca tgtttctgac    6840
tttgtttatt aacactgttt tgaacatcac catagcaagc agggtactgg agcagagact    6900
cactgactcc gcctgtgcgg ccttcatcgg cgacgacaac atcgttcacg gagtgatctc    6960
cgacaagctg atggcggaga ggtgcgcgtc gtgggtcaac atggaggtga agatcattga    7020
cgctgtcatg ggcgaaaaac ccccatattt tgtgggggga ttcatagttt ttgacagcgt    7080
cacacagacc gcctgccgtg tttcagaccc acttaagcgc ctgttcaagt tgggtaagcc    7140
gctaacagct gaagacaagc aggacgaaga caggcgacga gcactgagtg acgaggttag    7200
caagtggttc cggacaggct ggggggccga actggaggtg gcactaacat ctaggtatga    7260
ggtagagggc tgcaaaagta tcctcatagc catggccacc ttggcgaggg acattaaggc    7320
gtttaagaaa ttgagaggac ctgttataca cctctacggc ggtcctagat tggtgcgtta    7380
atacacagaa ttctgattgg atcccaaacg ggccctctag actcgagcgg ccgccactgt    7440
gctggatatc tgcagaattc caccacactg gactagtgga tctatggcgt acccatacga    7500
tgttccagat tacgctagct tgagatctac catgtctcag agcaaccggg agctggtggt    7560
```

```
tgactttctc tcctacaagc tttcccagaa aggatacagc tggagtcagt ttagtgatgt     7620
ggaagagaac aggactgagg ccccagaagg gactgaatcg gagatggaga cccccagtgc     7680
catcaatggc aacccatcct ggcacctggc agacagcccc gcggtgaatg gagccactgc     7740
gcacagcagc agtttggatg cccgggaggt gatccccatg gcagcagtaa agcaagcgct     7800
gagggaggca ggcgacgagt ttgaactgcg gtaccggcgg gcattcagtg acctgacatc     7860
ccagctccac atcaccccag ggacagcata tcagagcttt gaacaggtag tgaatgaact     7920
cttccgggat ggggtagcca ttcttcgcat tgtggccttt ttctccttcg gcggggcact     7980
gtgcgtggaa agcgtagaca aggagatgca ggtattggtg agtcggatcg cagcttggat     8040
ggccacttac ctgaatgacc acctagagcc ttggatccag gagaacggcg gctgggatac     8100
ttttgtggaa ctctatggga acaatgcagc agccgagagc cgaaagggcc aggaacgctt     8160
caaccgctgg ttcctgacgg gcatgactgt ggccggcgtg gttctgctgg gctcactctt     8220
cagtcggaaa tgaagatccg agctcggtac caagcttaag tttgggtaat taattgaatt     8280
acatccctac gcaaacgttt tacggccgcc ggtggcgccc gcgcccggcg cccgtccttt     8340
ggccgttgca ggccactccg gtggctcccg tcgtccccga cttccaggcc agcagatgc     8400 agcaactcat cagcgccgta atgcgctga caatgagaca gaacgcaatt gctcctgcta     8460
ggcctcccaa accaaagaag aagaagacaa ccaaaccaaa gccgaaaacg cagcccaaga     8520
agatcaacgg aaaaacgcag cagcaaaaga agaaagacaa gcaagccgac aagaagaaga     8580
agaaacccgg aaaaagagaa agaatgtgca tgaagattga aaatgactgt atcttcgtat     8640
gcggctagcc acagtaacgt agtgtttcca gacatgtcgg gcaccgcact atcatgggtg     8700
cagaaaatct cgggtggtct gggggccttc gcaatcggcg ctatcctggt gctggttgtg     8760
gtcacttgca ttgggctccg cagataagtt agggtaggca atggcattga tatagcaaga     8820
aaattgaaaa cagaaaaagt tagggtaagc aatggcatat aaccataact gtataacttg     8880
taacaaagcg caacaagacc tgcgcaattg gccccgtggt ccgcctcacg gaaactcggg     8940
gcaactcata ttgacacatt aattggcaat aattggaagc ttacataagc ttaattcgac     9000
gaataattgg attttatttt tattttgcaa ttggtttttta atatttccaa aaaaaaaaaa     9060
aaaaaaaaaa aaaaaaaaaa aaaaaaaaaa aaaaaaaaaa aaaaaaaaaa aaaaaaaact     9120
agtgatcata atcagccata ccacatttgt agaggtttta cttgctttaa aaaacctccc     9180
acacctcccc ctgaacctga aacataaaat gaatgcaatt gttgttgtta acttgtttat     9240
tgcagcttat aatggttaca aataaagcaa tagcatcaca aatttcacaa ataaagcatt     9300
tttttcactg cattctagtt gtggtttgtc caaactcatc aatgtatctt atcatgtctg     9360
gatctagtct gcattaatga atcggccaac gcgcggggag aggcggtttg cgtattgggc     9420
gctcttccgc ttcctcgctc actgactcgc tgcgctcggt cgttcggctg cggcgagcgg     9480
tatcagctca ctcaaaggcg gtaatacggt tatccacaga atcaggggat aacgcaggaa     9540
agaacatgtg agcaaaaggc cagcaaaagg ccaggaaccg taaaaaggcc gcgttgctgg     9600 cgttttttcca taggctccgc ccccctgacg agcatcacaa aaatcgacgc tcaagtcaga     9660
ggtggcgaaa cccgacagga ctataaagat accaggcgtt tccccctgga agctccctcg     9720
tgcgctctcc tgttccgacc ctgccgctta ccggatacct gtccgccttt ctcccttcgg     9780
gaagcgtggc gctttctcaa tgctcgcgct gtaggtatct cagttcggtg taggtcgttc     9840
gctccaagct gggctgtgtg cacgaacccc ccgttcagcc cgaccgctgc gccttatccg     9900
```

```
gtaactatcg tcttgagtcc aacccggtaa gacacgactt atcgccactg gcagcagcca    9960
ctggtaacag gattagcaga gcgaggtatg taggcggtgc tacagagttc ttgaagtggt   10020
ggcctaacta cggctacact agaaggacag tatttggtat ctgcgctctg ctgaagccag   10080
ttaccttcgg aaaaagagtt ggtagctctt gatccggcaa acaaaccacc gctggtagcg   10140
gtggtttttt tgtttgcaag cagcagatta cgcgcagaaa aaaggatctc aagaagatc    10200
ctttgatctt ttctacgggg cattctgacg ctcagtggaa cgaaaactca cgttaaggga   10260
ttttggtcat gagattatca aaaaggatct tcacctagat ccttttaaat taaaaatgaa   10320
gttttaaatc aatctaaagt atatatgagt aaacttggtc tgacagttac caatgcttaa   10380
tcagtgaggc acctatctca gcgatctgtc tatttcgttc atccatagtt gcctgactcc   10440
ccgtcgtgta gataactacg atacgggagg gcttaccatc tggccccagt gctgcaatga   10500
taccgcgaga cccacgctca ccggctccag atttatcagc aataaaccag ccagccggaa   10560
gggccgagcg cagaagtggt cctgcaactt tatccgcctc catccagtct attaattgtt   10620
gccgggaagc tagagtaagt agttcgccag ttaatagttt cgcaacgtt gttgccattg    10680
ctacaggcat cgtggtgtca cgctcgtcgt ttggtatggc ttcattcagc tccggttccc   10740
aacgatcaag gcgagttaca tgatccccca tgttgtgcaa aaaagcggtt agctccttcg   10800
gtcctccgat cgttgtcaga agtaagttgg ccgcagtgtt atcactcatg gttatggcag   10860
cactgcataa ttctcttact gtcatgccat ccgtaagatg cttttctgtg actggtgagt   10920
actcaaccaa gtcattctga gaatagtgta tgcggcgacc gagttgctct tgcccggcgt   10980
caatacggga taataccgcg ccacatagca gaactttaaa agtgctcatc attggaaaac   11040
gttcttcggg gcgaaaactc tcaaggatct taccgctgtt gagatccagt tcgatgtaac   11100
ccactcgtgc acccaactga tcttcagcat cttttacttt caccagcgtt tctgggtgag   11160
caaaaacagg aaggcaaaat gccgcaaaaa agggaataag ggcgacacgg aaatgttgaa   11220
tactcatact cttcctttt caatattatt gaagcattta tcagggttat tgtctcatga    11280
gcggatacat atttgaatgt atttagaaaa ataaacaaat aggggttccg cgcacatttc   11340
cccgaaaagt gccacctgac gtctaagaaa ccattattat catgacatta acctataaaa   11400
ataggcgtat cacgaggccc tttcgtctcg cgcgtttcgg tgatgacggt gaaaacctct   11460
gacacatgca gctcccggag acggtcacag cttctgtcta gcggatgcc gggagcagac    11520
aagcccgtca gggcgcgtca gcgggtgttg gcgggtgtcg gggctggctt aactatgcgg   11580
catcagagca gattgtactg agagtgcacc atatcgacgc tctcccttat gcgactcctg   11640
cattaggaag cagcccagta ctaggttgag gccgttgagc accgccgccg caaggaatgg   11700
tgcatgcgta atcaattacg gggtcattag ttcatagccc atatatggag ttccgcgtta   11760
cataacttac ggtaaatggc ccgcctggct gaccgcccaa cgacccccgc ccattgacgt   11820
caataatgac gtatgttccc atagtaacgc caatagggac tttccattga cgtcaatggg   11880
tggagtattt acggtaaact gcccacttgg cagtacatca agtgtatcat atgccaagta   11940
cgccccctat tgacgtcaat gacggtaaat ggcccgcctg gcattatgcc cagtacatga   12000
ccttatggga ctttcctact tggcagtaca tctacgtatt agtcatcgct attaccatgg   12060
tgatgcggtt ttggcagtac atcaatgggc gtggatagcg gtttgactca cggggatttc   12120
caagtctcca ccccattgac gtcaatggga gtttgttttg gcaccaaaat caacgggact   12180
ttccaaaatg tcgtaacaac tccgccccat tgacgcaaat gggcggtagg cgtgtacggt   12240
gggaggtcta tataagcaga gctctctggc taactagaga acccactgct taactggctt   12300
```

```
atcgaaatta atacgactca ctatagggag accggaagct tgaattc              12347
```

<210> SEQ ID NO 68
<211> LENGTH: 12612
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

```
atggcggatg tgtgacatac acgacgccaa aagattttgt tccagctcct gccacctccg    60
ctacgcgaga gattaaccac ccacgatggc cgccaaagtg catgttgata ttgaggctga   120
cagcccattc atcaagtctt tgcagaaggc atttccgtcg ttcgaggtgg agtcattgca   180
ggtcacacca aatgaccatg caaatgccag agcatttttcg cacctggcta ccaaattgat   240
cgagcaggag actgacaaag acacactcat cttggatatc ggcagtgcgc cttccaggag   300
aatgatgtct acgcacaaat accactgcgt atgccctatg cgcagcgcag aagacccga   360
aaggctcgat agctacgcaa agaaactggc agcggcctcc gggaaggtgc tggatagaga   420
gatcgcagga aaaatcaccg acctgcagac cgtcatggct acgccagacg ctgaatctcc   480
tacctttgc ctgcatacag acgtcacgtg tcgtacggca gccgaagtgg ccgtatacca   540
ggacgtgtat gctgtacatg caccaacatc gctgtaccat caggcgatga aggtgtcag   600
aacggcgtat tggattgggt ttgacaccac cccgtttatg tttgacgcgc tagcaggcgc   660
gtatccaacc tacgccacaa actgggccga cgagcaggtg ttacaggcca ggaacatagg   720
actgtgtgca gcatccttga ctgagggaag actcggcaaa ctgtccattc tccgcaagaa   780
gcaattgaaa ccttgcgaca cagtcatgtt ctcggtagga tctacattgt acactgagag   840
cagaaagcta ctgaggagct ggcacttacc ctccgtattc cacctgaaag gtaaacaatc   900
ctttacctgt aggtgcgata ccatcgtatc atgtgaaggg tacgtagtta agaaaatcac   960
tatgtgcccc ggcctgtacg gtaaaacggt agggtacgcc gtgacgtatc acgcggaggg  1020
attcctagtg tgcaagacca cagacactgt caaaggagaa agagtctcat tccctgtatg  1080
cacctacgtc ccctcaacca tctgtgatca aatgactggc atactagcga ccgacgtcac  1140
accggaggac gcacagaagt tgttagtggg attgaatcag aggatagttg tgaacggaag  1200
aacacagcga aacactaaca cgatgaagaa ctatctgctt ccgattgtgg ccgtcgcatt  1260
tagcaagtgg gcgagggaat acaaggcaga ccttgatgat gaaaaacctc tgggtgtccg  1320
agagaggtca cttacttgct gctgcttgtg ggcatttaaa acgaggaaga tgcacaccat  1380
gtacaagaaa ccagacaccc agacaatagt gaaggtgcct tcagagttta actcgttcgt  1440
catcccgagc ctatggtcta caggcctcgc aatcccagtc agatcacgca ttaagatgct  1500
tttggccaag aagaccaagc gagagttaat acctgttctc gacgcgtcgt cagccaggga  1560
tgctgaacaa gaggagaagg agaggttgga ggccgagctg actagagaag ccttaccacc  1620
cctcgtcccc atcgcgccgg cggagacggg agtcgtcgac gtcgacgttg aagaactaga  1680
gtatcacgca ggtgcagggg tcgtggaaac acctcgcagc gcgttgaaag tcaccgcaca  1740
gccgaacgac gtactactag aaattacgt agttctgtcc ccgcagaccg tgctcaagag  1800
ctccaagttg gcccccgtgc accctctagc agagcaggtg aaaataataa cacataacgg  1860
gagggccggc ggttaccagg tcgacggata tgacggcagg gtcctactac catgtggatc  1920
ggccattccg gtccctgagt ttcaagcttt gagcgagagc gccactatgg tgtacaacga  1980
```

```
aagggagttc gtcaacagga aactatacca tattgccgtt cacggaccgt cgctgaacac    2040
cgacgaggag aactacgaga aagtcagagc tgaaagaact gacgccgagt acgtgttcga    2100
cgtagataaa aaatgctgcg tcaagagaga ggaagcgtcg ggtttggtgt tggtgggaga    2160
gctaaccaac cccccgttcc atgaattcgc ctacgaaggg ctgaagatca ggccgtcggc    2220
accatataag actacagtag taggagtctt tgggggttccg ggatcaggca agtctgctat    2280
tattaagagc ctcgtgacca aacacgatct ggtcaccagc ggcaagaagg agaactgcca    2340
ggaaatagtt aacgacgtga agaagcaccg cgggaagggg acaagtaggg aaaacagtga    2400
ctccatcctg ctaaacgggt gtcgtcgtgc cgtggacatc ctatatgtgg acgaggcttt    2460
cgctagccat tccggtactc tgctggccct aattgctctt gttaaacctc ggagcaaagt    2520
ggtgttatgc ggagaccccca agcaatgcgg attcttcaat atgatgcagc ttaaggtgaa    2580
cttcaaccac aacatctgca ctgaagtatg tcataaaagt atatccagac gttgcacgcg    2640
tccagtcacg gccatcgtgt ctacgttgca ctacggaggc aagatgcgca cgaccaaccc    2700
gtgcaacaaa cccataatca tagacaccac aggacagacc aagcccaagc caggagacat    2760
cgtgttaaca tgcttccgag gctgggcaaa gcagctgcag ttggactacc gtggacacga    2820
agtcatgaca gcagcagcat ctcagggcct cacccgcaaa ggggtatacg ccgtaaggca    2880
gaaggtgaat gaaaatccct tgtatgcccc tgcgtcggag cacgtgaatg tactgctgac    2940
gcgcactgag gataggctgg tgtggaaaac gctggccggc gatccctgga ttaaggtcct    3000
atcaaacatt ccacagggta actttacggc cacattggaa gaatggcaag aagaacacga    3060
caaaataatg aaggtgattg aaggaccggc tgcgcctgtg gacgcgttcc agaacaaagc    3120
gaacgtgtgt tgggcgaaaa gcctggtgcc tgtcctggac actgccggaa tcagattgac    3180
agcagaggag tggagcacca taattacagc atttaaggag gacagagctt actctccagt    3240
ggtggccttg aatgaaattt gcaccaagta ctatggagtt gacctggaca gtggcctgtt    3300
ttctgccccg aaggtgtccc tgtattacga gaacaaccac tgggataaca gacctggtgg    3360
aaggatgtat ggattcaatg ccgcaacagc tgccaggctg gaagctagac ataccttcct    3420
gaaggggcag tggcatacgg gcaagcaggc agttatcgca gaaagaaaaa tccaaccgct    3480
ttctgtgctg gacaatgtaa ttcctatcaa ccgcaggctg ccgcacgccc tggtggctga    3540
gtacaagacg gttaaaggca gtagggttga gtggctggtc aataaagtaa gagggtacca    3600
cgtcctgctg gtgagtgagt acaacctggc tttgcctcga cgcagggtca cttggttgtc    3660
accgctgaat gtcacaggcg ccgataggtg ctacgaccta agtttaggac tgccggctga    3720
cgccggcagg ttcgacttgg tctttgtgaa cattcacacg gaattcagaa tccaccacta    3780
ccagcagtgt gtcgaccacg ccatgaagct gcagatgctt ggggagatg cgctacgact    3840 gctaaaaccc ggcggcatct tgatgagagc ttacggatac gccgataaaa tcagcgaagc    3900
cgttgtttcc tccttaagca gaaagttctc gtctgcaaga gtgttgcgcc cggattgtgt    3960
caccagcaat acagaagtgt tcttgctgtt ctccaacttt gacaacggaa agagaccctc    4020
tacgctacac cagatgaata ccaagctgag tgccgtgtat gccggagaag ccatgcacac    4080
ggccgggtgt gcaccatcct acagagttaa gagagcagac atagccacgt gcacagaagc    4140
ggctgtggtt aacgcagcta acgcccgtgg aactgtaggg gatggcgtat gcagggccgt    4200
ggcgaagaaa tggccgtcag cctttaaggg agcagcaaca ccagtgggca caattaaaac    4260
agtcatgtgc ggctcgtacc ccgtcatcca cgctgtagcg cctaatttct ctgccacgac    4320
```

```
tgaagcggaa ggggaccgcg aattggccgc tgtctaccgg gcagtggccg ccgaagtaaa   4380
cagactgtca ctgagcagcg tagccatccc gctgctgtcc acaggagtgt tcagcggcgg   4440
aagagatagg ctgcagcaat ccctcaacca tctattcaca gcaatggacg ccacggacgc   4500
tgacgtgacc atctactgca gagacaaaag ttgggagaag aaaatccagg aagccattga   4560
catgaggacg gctgtggagt tgctcaatga tgacgtggag ctgaccacag acttggtgag   4620
agtgcacccg gacagcagcc tggtgggtcg taagggctac agtaccactg acgggtcgct   4680
gtactcgtac tttgaaggta cgaaattcaa ccaggctgct attgatatgg cagagatact   4740
gacgttgtgg cccagactgc aagaggcaaa cgaacagata tgcctatacg cgctgggcga   4800
aacaatggac aacatcagat ccaaatgtcc ggtgaacgat tccgattcat caacacctcc   4860
caggacagtg ccctgcctgt gccgctacgc aatgacagca gaacggatcg cccgccttag   4920
gtcacaccaa gttaaaagca tggtggtttg ctcatctttt cccctcccga ataccatgt    4980 agatggggtg cagaaggtaa agtgcgagaa ggttctcctg ttcgacccga cggtaccttc   5040
agtggttagt ccgcggaagt atgccgcatc tacgacggac cactcagatc ggtcgttacg   5100
agggtttgac ttggactgga ccaccgactc gtcttccact gccagcgata ccatgtcgct   5160
acccagtttg cagtcgtgtg acatcgactc gatctacgag ccaatggctc ccatagtagt   5220
gacggctgac gtacaccctg aacccgcagg catcgcggac ctggcggcag atgtgcaccc   5280
tgaacccgca gaccatgtgg acctcgagaa cccgattcct ccaccgcgcc cgaagagagc   5340
tgcatacctt gcctcccgcg cggcggagcg accggtgccg gcgccgagaa agccgacgcc   5400
tgccccaagg actgcgttta ggaacaagct gcctttgacg ttcggcgact ttgacgagca   5460
cgaggtcgat gcgttggcct ccgggattac tttcggagac ttcgacgacg tcctgcgact   5520
aggccgcgcg ggtgcatata ttttctcctc ggacactggc agcggacatt tacaacaaaa   5580
atccgttagg cagcacaatc tccagtgcgc acaactggat gcggtccagg aggagaaaat   5640
gtacccgcca aaattggata ctgagaggga gaagctgttg ctgctgaaaa tgcagatgca   5700
cccatcggag gctaataaga gtcgatacca gtctcgcaaa gtggagaaca tgaaagccac   5760 ggtggttggac aggctcacat cgggggccag attgtacacg ggagcggacg taggccgcat   5820
accaacatac gcggttcggt accccgcccc cgtgtactcc cctaccgtga tcgaaagatt   5880
ctcaagcccc gatgtagcaa tcgcagcgtg caacgaatac ctatccagaa attacccaac   5940
agtggcgtcg taccagataa cagatgaata cgacgcatac ttggacatgg ttgacgggtc   6000
ggatagttgc ttggacagag cgacattctg cccggcgaag ctccggtgct acccgaaaca   6060
tcatgcgtac caccagccga ctgtacgcag tgccgtcccg tcacccttc agaacacact    6120 acagaacgtg ctagcggccg ccaccaagag aaactgcaac gtcacgcaaa tgcgagaact   6180
acccaccatg gactcggcag tgttcaacgt ggagtgcttc aagcgctatg cctgctccgg   6240
agaatattgg gaagaatatg ctaaacaacc tatccggata accactgaga acatcactac   6300
ctatgtgacc aaattgaaag gcccgaaagc tgctgccttg ttcgctaaga cccacaactt   6360
ggttccgctg caggaggttc ccatggacag attcacggtc gacatgaaac gagatgtcaa   6420
agtcactcca gggacgaaac acacagagga aagacccaaa gtccaggtaa ttcaagcagc   6480
ggagccattg gcgaccgctt acctgtgcgg catccacagg gaattagtaa ggagactaaa   6540
tgctgtgtta cgccctaacg tgcacacatt gtttgatatg tcggccgaag actttgacgc   6600
gatcatcgcc tctcacttcc acccaggaga cccggttcta gagacggaca ttgcatcatt   6660
cgacaaaagc caggacgact ccttggctct tacaggttta atgatcctcg aagatctagg   6720
```

```
ggtggatcag tacctgctgg acttgatcga ggcagccttt ggggaaatat ccagctgtca   6780
cctaccaact ggcacgcgct tcaagttcgg agctatgatg aaatcgggca tgtttctgac   6840
tttgtttatt aacactgttt tgaacatcac catagcaagc agggtactgg agcagagact   6900
cactgactcc gcctgtgcgg ccttcatcgg cgacgacaac atcgttcacg gagtgatctc   6960
cgacaagctg atggcggaga ggtgcgcgtc gtgggtcaac atggaggtga agatcattga   7020
cgctgtcatg ggcgaaaaac ccccatattt ttgtgggggga ttcatagttt ttgacagcgt   7080
cacacagacc gcctgccgtg tttcagaccc acttaagcgc ctgttcaagt gggtaagcc    7140 gctaacagct gaagacaagc aggacgaaga caggcgacga gcactgagtg acgaggttag   7200
caagtggttc cggacaggct tggggccga actggaggtg gcactaacat ctaggtatga    7260
ggtagagggc tgcaaaagta tcctcatagc catggccacc ttggcgaggg acattaaggc   7320
gtttaagaaa ttgagaggac ctgttataca cctctacggc ggtcctagat tggtgcgtta   7380
atacacagaa ttctgattgg atcccaaacg ggccctctag actcgagcgg ccgccactgt   7440
gctggatatc tgcagaattc atgcatggag atacacctac attgcatgaa tatatgttag   7500
atttgcaacc agagacaact gatctctact gttatgagca attaaatgac agctcagagg   7560
aggaggatga aatagatggt ccagctggac aagcagaacc ggacagagcc cattacaata   7620
ttgtaacctt ttgttgcaag tgtgactcta cgcttcggtt gtgcgtacaa agcacacacg   7680
tagacattcg tactttggaa gacctgttaa tgggcacact aggaattgtg tgccccatct   7740
gttctcagaa accaggatct atggcgtacc catacgatgt tccagattac gctagcttga   7800
gatctaccat gtctcagagc aaccgggagc tggtggttga cttcctctcc tacaagcttt   7860
cccagaaagg atacagctgg agtcagttta gtgatgtgga agagaacagg actgaggccc   7920
cagaagggac tgaatcggag atggagaccc ccagtgccat caatggcaac ccatcctggc   7980
acctggcaga cagccccgcg gtgaatgagg ccactgcgca cagcagcagt ttggatgccc   8040
gggaggtgat ccccatggca gcagtaaagc aagcgctgag ggaggcaggc gacgagtttg   8100
aactgcggta ccggcgggca ttcagtgacc tgacatccca gctccacatc accccaggga   8160
cagcatatca gagctttgaa caggtagtga atgaactctt ccgggatggg gtagccattc   8220
ttcgcattgt ggcctttttc tccttcggcg gggcactgtg cgtggaaagc gtagacaagg   8280
agatgcaggt attggtgagt cggatcgcag cttggatggc cacttacctg aatgaccacc   8340
tagagccttg gatccaggag aacggcggct gggatacttt tgtggaactc tatgggaaca   8400
atgcagcagc cgagagccga aagggccagg aacgcttcaa ccgctggttc ctgacgggca   8460
tgactgtggc cggcgtggtt ctgctgggct cactcttcag tcggaaatga agatccaagc   8520
ttaagtttgg gtaattaatt gaattacatc cctacgcaaa cgttttacgg ccgccggtgg   8580
cgcccgcgcc cggcggcccg tccttggccg ttgcaggcca ctccggtggc tcccgtcgtc   8640
cccgacttcc aggcccagca gatgcagcaa ctcatcagcg ccgtaaatgc gctgacaatg   8700
agacagaacg caattgctcc tgctaggcct cccaaaccaa agaagaagaa gacaaccaaa   8760
ccaaagccga aaacgcagcc caagaagatc aacggaaaaa cgcagcagca aaagaagaaa   8820
gacaagcaag ccgacaagaa gaagaagaaa cccgaaaaaa gagaaagaat gtgcatgaag   8880
attgaaaatg actgtatctt cgtatgcggc tagccacagt aacgtagtgt ttccagacat   8940
gtcgggcacc gcactatcat gggtgcagaa aatctcgggt ggtctggggg ccttcgcaat   9000
cggcgctatc ctggtgctgg ttgtggtcac ttgcattggg ctccgcagat aagttagggt   9060
```

```
aggcaatggc attgatatag caagaaaatt gaaaacagaa aaagttaggg taagcaatgg    9120
catataacca taactgtata acttgtaaca aagcgcaaca agacctgcgc aattggcccc    9180
gtggtccgcc tcacggaaac tcggggcaac tcatattgac acattaattg gcaataattg    9240
gaagcttaca taagcttaat tcgacgaata attggatttt tattttattt tgcaattggt    9300
ttttaatatt tccaaaaaaa aaaaaaaaaa aaaaaaaaaa aaaaaaaaaa aaaaaaaaaa    9360
aaaaaaaaaa aaaaaaaaaa aaactagtga tcataatcag ccataccaca tttgtagagg    9420
ttttacttgc tttaaaaaac ctcccacacc tcccccctgaa cctgaaacat aaaatgaatg    9480
caattgttgt tgttaacttg tttattgcag cttataatgg ttacaaataa agcaatagca    9540
tcacaaattt cacaaataaa gcattttttt cactgcattc tagttgtggt ttgtccaaac    9600
tcatcaatgt atcttatcat gtctggatct agtctgcatt aatgaatcgg ccaacgcgcg    9660
gggagaggcg gtttgcgtat tgggcgctct tccgcttcct cgctcactga ctcgctgcgc    9720
tcggtcgttc ggctgcggcg agcggtatca gctcactcaa aggcggtaat acggttatcc    9780
acagaatcag gggataacgc aggaaagaac atgtgagcaa aaggccagca aaaggccagg    9840
aaccgtaaaa aggccgcgtt gctggcgttt ttccataggc tccgcccccc tgacgagcat    9900
cacaaaaatc gacgctcaag tcagaggtgg cgaaacccga caggactata agataccag    9960 gcgtttcccc ctggaagctc cctcgtgcgc tctcctgttc cgaccctgcc gcttaccgga    10020
tacctgtccg cctttctccc ttcgggaagc gtggcgcttt ctcaatgctc gcgctgtagg    10080
tatctcagtt cggtgtaggt cgttcgctcc aagctgggct gtgtgcacga accccccgtt    10140
cagcccgacc gctgcgcctt atccggtaac tatcgtcttg agtccaaccc ggtaagacac    10200
gacttatcgc cactggcagc agccactggt aacaggatta gcagagcgag gtatgtaggc    10260
ggtgctacag agttcttgaa gtggtggcct aactacggct acactagaag gacagtattt    10320
ggtatctgcg ctctgctgaa gccagttacc ttcggaaaaa gagttggtag ctcttgatcc    10380
ggcaaacaaa ccaccgctgg tagcggtggt ttttttgttt gcaagcagca gattacgcgc    10440
agaaaaaaag gatctcaaga agatcctttg atcttttcta cggggcattc tgacgctcag    10500
tggaacgaaa actcacgtta agggattttg gtcatgagat tatcaaaaag gatcttcacc    10560
tagatccttt taaattaaaa atgaagtttt aaatcaatct aaagtatata tgagtaaact    10620
tggtctgaca gttaccaatg cttaatcagt gaggcaccta tctcagcgat ctgtctattt    10680
cgttcatcca tagttgcctg actccccgtc gtgtagataa ctacgatacg ggagggctta    10740
ccatctggcc ccagtgctgc aatgataccg cgagacccac gctcaccggc tccagattta    10800
tcagcaataa accagccagc cggaagggcc gagcgcagaa gtggtcctgc aactttatcc    10860
gcctccatcc agtctattaa ttgttgccgg gaagctagag taagtagttc gccagttaat    10920
agtttgcgca acgttgttgc cattgctaca ggcatcgtgg tgtcacgctc gtcgtttggt    10980
atggcttcat tcagctccgg ttcccaacga tcaaggcgag ttacatgatc ccccatgttg    11040
tgcaaaaaag cggttagctc cttcggtcct ccgatcgttg tcagaagtaa gttggccgca    11100
gtgttatcac tcatggttat ggcagcactg cataattctc ttactgtcat gccatccgta    11160
agatgctttt ctgtgactgg tgagtactca accaagtcat tctgagaata gtgtatgcgg    11220
cgaccgagtt gctcttgccc ggcgtcaata cgggataata ccgcgccaca tagcagaact    11280
ttaaaagtgc tcatcattgg aaaacgttct tcggggcgaa aactctcaag gatcttaccg    11340
ctgttgagat ccagttcgat gtaacccact cgtgcaccca actgatcttc agcatctttt    11400
actttcacca gcgtttctgg gtgagcaaaa acaggaaggc aaaatgccgc aaaaaaggga    11460
```

```
ataagggcga cacggaaatg ttgaatactc atactcttcc tttttcaata ttattgaagc    11520
atttatcagg gttattgtct catgagcgga tacatatttg aatgtattta gaaaaataaa    11580
caaatagggg ttccgcgcac atttccccga aaagtgccac ctgacgtcta agaaaccatt    11640
attatcatga cattaaccta taaaatagg cgtatcacga ggccctttcg tctcgcgcgt     11700
ttcggtgatg acggtgaaaa cctctgacac atgcagctcc cggagacggt cacagcttct    11760
gtctaagcgg atgccgggag cagacaagcc cgtcagggcg cgtcagcggg tgttggcggg    11820
tgtcggggct ggcttaacta tgcggcatca gagcagattg tactgagagt gcaccatatc    11880
gacgctctcc cttatgcgac tcctgcatta ggaagcagcc cagtactagg ttgaggccgt    11940
tgagcaccgc cgccgcaagg aatggtgcat gcgtaatcaa ttacgggggtc attagttcat    12000
agcccatata tggagttccg cgttacataa cttacggtaa atggcccgcc tggctgaccg    12060
cccaacgacc cccgcccatt gacgtcaata atgacgtatg ttcccatagt aacgccaata    12120
gggactttcc attgacgtca atgggtggag tatttacggt aaactgccca cttggcagta    12180
catcaagtgt atcatatgcc aagtacgccc cctattgacg tcaatgacgg taaatggccc    12240
gcctggcatt atgcccagta catgacctta tgggactttc ctacttggca gtacatctac    12300
gtattagtca tcgctattac catggtgatg cggttttggc agtacatcaa tgggcgtgga    12360
tagcggtttg actcacgggg atttccaagt ctccacccca ttgacgtcaa tgggagtttg    12420
ttttggcacc aaaatcaacg ggactttcca aaatgtcgta caactccgc cccattgacg     12480
caaatgggcg gtaggcgtgt acggtgggag gtctatataa gcagagctct ctggctaact    12540
agagaaccca ctgcttaact ggcttatcga aattaatacg actcactata gggagaccgg    12600
aagcttgaat tc                                                         12612
```

<210> SEQ ID NO 69
<211> LENGTH: 4832
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
gtcgacttct gaggcggaaa gaaccagctg tggaatgtgt gtcagttagg gtgtggaaag      60
tcccccaggct ccccagcagg cagaagtatg caaagcatgc atctcaatta gtcagcaacc    120
aggtgtggaa agtccccagg ctccccagca ggcagaagta tgcaaagcat gcatctcaat    180
tagtcagcaa ccatagtccc gcccctaact ccgcccatcc cgcccctaac tccgcccagt    240
tccgcccatt ctccgcccca tggctgacta atttttttta tttatgcaga ggccgaggcc    300
gcctcggcct ctgagctatt ccagaagtag tgaggaggct ttttggagg cctaggcttt      360
tgcaaaaagc tggatcgatc ctgagaactt caggtgagt ttggggaccc ttgattgttc      420
tttctttttc gctattgtaa aattcatgtt atatggaggg gcaaagtttt caggggtgtt    480
gtttagaatg ggaagatgtc ccttgtatca ccatggaccc tcatgataat ttgtttctt      540
tcactttcta ctctgttgac aaccattgtc tcctcttatt ttcttttcat tttctgtaac    600
tttttcgtta aactttagct tgcatttgta acgaattttt aaattcactt tgtttatttt    660
gtcagattgt aagtactttc tctaatcact tttttttcaa ggcaatcagg gtatattata    720
ttgtacttca gcacagttttt agagaacaat tgttataatt aaatgataag gtagaatatt    780
tctgcatata aattctggct ggcgtggaaa tattcttatt ggtagaaaca actacatcct    840
```

-continued

```
ggtcatcatc ctgcctttct ctttatggtt acaatgatat acactgtttg agatgaggat      900
aaaatactct gagtccaaac cgggcccctc tgctaaccat gttcatgcct tcttcttttt      960
cctacagctc ctgggcaacg tgctggttat tgtgctgtct catcattttg gcaaagaatt     1020
gtaatacgac tcactatagg gcgaattcgg atccagatct atggcgtacc catacgatgt     1080
tccagattac gctagcttga gatctaccat gtctcagagc aaccgggagc tggtggttga     1140
cttctctcc tacaagcttt cccagaaagg atacagctgg agtcagttta gtgatgtgga      1200
agagaacagg actgaggccc cagaagggac tgaatcggag atggagaccc ccagtgccat     1260
caatggcaac ccatcctggc acctggcaga cagccccgcg gtgaatggag ccactgcgca     1320
cagcagcagt ttggatgccc gggaggtgat ccccatggca gcagtaaagc aagcgctgag     1380
ggaggcaggc gacgagtttg aactgcggta ccggcgggca ttcagtgacc tgacatccca     1440
gctccacatc accccaggga cagcatatca gagctttgaa caggtagtga atgaactctt     1500
ccgggatggg gtaaactggg gtcgcattgt ggccttttc tccttcggcg ggcactgtg       1560
cgtggaaagc gtagacaagg agatgcaggt attggtgagt cggatcgcag cttggatggc     1620
cacttacctg aatgaccacc tagagccttg gatccaggag aacggcggct gggatacttt     1680
tgtggaactc tatgggaaca atgcagcagc cgagagccga aagggccagg aacgcttcaa     1740
ccgctggttc ctgacgggca tgactgtggc cggcgtggtt ctgctgggct cactcttcag     1800
tcggaaatga agatcttatt aaagcagaac ttgtttattg cagcttataa tggttacaaa     1860
taaagcaata gcatcacaaa tttcacaaat aaagcatttt tttcactgca ttctagttgt     1920
ggtttgtcca aactcatcaa tgtatcttat catgtctggt cgactctaga ctcttccgct     1980
tcctcgctca ctgactcgct gcgctcggtc gttcggctgc ggcgagcggt atcagctcac     2040
tcaaaggcgg taatacggtt atccacagaa tcaggggata cgcaggaaa gaacatgtga     2100
gcaaaggcca gcaaaaggcc aggaaccgta aaaaggccgc gttgctggcg ttttttccat     2160
aggctccgcc cccctgacga gcatcacaaa aatcgacgct caagtcagag gtggcgaaac     2220
ccgacaggac tataaagata ccaggcgttt cccctggaa gctccctcgt gcgctctcct      2280
gttccgaccc tgccgcttac cggatacctg tccgcctttc tcccttcggg aagcgtggcg     2340
ctttctcaat gctcacgctg taggtatctc agttcggtgt aggtcgttcg ctccaagctg     2400
ggctgtgtgc acgaaccccc cgttcagccc gaccgctgcg ccttatccgg taactatcgt     2460
cttgagtcca acccggtaag acacgactta tcgccactgg cagcagccac tggtaacagg     2520
attagcagag cgaggtatgt aggcggtgct acagagttct tgaagtggtg gcctaactac     2580
ggctacacta aggacagt atttggtatc tgcgctctgc tgaagccagt taccttcgga       2640
aaaagagttg gtagctcttg atccggcaaa caaaccaccg ctggtagcgg tggtttttt      2700
gtttgcaagc agcagattac gcgcagaaaa aaggatctc aagaagatcc tttgatcttt      2760
tctacggggt ctgacgctca gtggaacgaa aactcacgtt aagggatttt ggtcatgaga     2820
ttatcaaaaa ggatcttcac ctagatcctt ttaaattaaa aatgaagttt taaatcaatc     2880
taaagtatat atgagtaaac ttggtctgac agttaccaat gcttaatcag tgaggcacct     2940
atctcagcga tctgtctatt tcgttcatcc atagttgcct gactccccgt cgtgtagata     3000
actacgatac gggagggctt accatctggc cccagtgctg caatgatacc gcgagaccca     3060
cgctcaccgg ctccagattt atcagcaata aaccagccag ccggaagggc cgagcgcaga     3120
agtggtcctg caactttatc cgcctccatc cagtctatta attgttgccg ggaagctaga     3180
```

| | | | | |
|---|---|---|---|---|
| gtaagtagtt | cgccagttaa | tagtttgcgc | aacgttgttg | ccattgctac aggcatcgtg | 3240 |
| gtgtcacgct | cgtcgtttgg | tatggcttca | ttcagctccg | gttcccaacg atcaaggcga | 3300 |
| gttacatgat | cccccatgtt | gtgcaaaaaa | gcggttagct | ccttcggtcc tccgatcgtt | 3360 |
| gtcagaagta | agttggccgc | agtgttatca | ctcatggtta | tggcagcact gcataattct | 3420 |
| cttactgtca | tgccatccgt | aagatgcttt | tctgtgactg | gtgagtactc aaccaagtca | 3480 |
| ttctgagaat | agtgtatgcg | gcgaccgagt | tgctcttgcc | cggcgtcaat acgggataat | 3540 |
| accgcgccac | atagcagaac | tttaaaagtg | ctcatcattg | gaaaacgttc ttcggggcga | 3600 |
| aaactctcaa | ggatcttacc | gctgttgaga | tccagttcga | tgtaacccac tcgtgcaccc | 3660 |
| aactgatctt | cagcatcttt | tactttcacc | agcgtttctg | ggtgagcaaa acaggaagg | 3720 |
| caaaatgccg | caaaaaaggg | aataagggcg | acacggaaat | gttgaatact catactcttc | 3780 |
| tttttcaat | attattgaag | catttatcag | ggttattgtc | tcatgagcgg atacatattt | 3840 |
| gaatgtattt | agaaaaataa | acaaataggg | gttccgcgca | catttccccg aaaagtgcca | 3900 |
| cctgacgtct | aagaaaccat | tattatcatg | acattaacct | ataaaaatag gcgtatcacg | 3960 |
| aggccccttt | cgtctcgcgc | gtttcggtga | tgacggtgaa | aacctctgac acatgcagct | 4020 |
| cccggagacg | gtcacagctt | gtctgtaagc | ggatgccggg | agcagacaag cccgtcaggg | 4080 |
| cgcgtcagcg | ggtgttggcg | ggtgtcgggg | ctggcttaac | tatgcggcat cagagcagat | 4140 |
| tgtactgaga | gtgcaccata | tgcggtgtga | ataccgcac | agatgcgtaa ggagaaaata | 4200 |
| ccgcatcagg | aaattgtaaa | cgttaatatt | ttgttaaaat | tcgcgttaaa tttttgttaa | 4260 |
| atcagctcat | tttttaacca | ataggccgaa | atcggcaaaa | tcccttataa atcaaaagaa | 4320 |
| tagaccgaga | tagggttgag | tgttgttcca | gtttggaaca | agagtccact attaaagaac | 4380 |
| gtggactcca | acgtcaaagg | gcgaaaaacc | gtctatcagg | gcgatggccc actacgtgaa | 4440 |
| ccatcaccct | aatcaagttt | tttggggtcg | aggtgccgta | aagcactaaa tcggaaccct | 4500 |
| aaagggagcc | cccgatttag | agcttgacgg | ggaaagccgg | cgaacgtggc gagaaaggaa | 4560 |
| gggaagaaag | cgaaaggagc | gggcgctagg | gcgctggcaa | gtgtagcggt cacgctgcgc | 4620 |
| gtaaccacca | cacccgccgc | gcttaatgcg | ccgctacagg | gcgcgtcgcg ccattcgcca | 4680 |
| ttcaggctac | gcaactgttg | ggaagggcga | tcggtgcggg | cctcttcgct attacgccag | 4740 |
| ctggcgaagg | ggggatgtgc | tgcaaggcga | ttaagttggg | taacgccagg gttttcccag | 4800 |
| tcacgacgtt | gtaaaacgac | ggccagtgaa | tt | | 4832 |

<210> SEQ ID NO 70
<211> LENGTH: 4832
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

| | | | | |
|---|---|---|---|---|
| gtcgacttct | gaggcggaaa | gaaccagctg | tggaatgtgt | gtcagttagg gtgtggaaag | 60 |
| tccccaggct | ccccagcagg | cagaagtatg | caaagcatgc | atctcaatta gtcagcaacc | 120 |
| aggtgtggaa | agtccccagg | ctccccagca | ggcagaagta | tgcaaagcat gcatctcaat | 180 |
| tagtcagcaa | ccatagtccc | gcccctaact | ccgcccatcc | cgcccctaac tccgcccagt | 240 |
| tccgcccatt | ctccgcccca | tggctgacta | attttttta | tttatgcaga ggccgaggcc | 300 |
| gcctcggcct | ctgagctatt | ccagaagtag | tgaggaggct | ttttggagg cctaggcttt | 360 |

```
tgcaaaaagc tggatcgatc ctgagaactt cagggtgagt ttggggaccc ttgattgttc      420 tttcttttc gctattgtaa aattcatgtt atatggaggg ggcaaagttt tcagggtgtt       480
gtttagaatg ggaagatgtc ccttgtatca ccatggaccc tcatgataat tttgtttctt       540
tcactttcta ctctgttgac aaccattgtc tcctcttatt ttcttttcat tttctgtaac       600
tttttcgtta aactttagct tgcatttgta acgaattttt aaattcactt ttgtttattt       660
gtcagattgt aagtactttc tctaatcact ttttttcaa ggcaatcagg gtatattata        720
ttgtacttca gcacagtttt agagaacaat tgttataatt aaatgataag gtagaatatt       780
tctgcatata aattctggct ggcgtggaaa tattcttatt ggtagaaaca actacatcct       840
ggtcatcatc ctgcctttct ctttatggtt acaatgatat acactgtttg agatgaggat       900
aaaatactct gagtccaaac cgggcccctc tgctaaccat gttcatgcct tcttctttt        960 cctacagctc ctgggcaacg tgctggttat tgtgctgtct catcattttg gcaaagaatt      1020
gtaatacgac tcactatagg gcgaattcgg atccagatct atggcgtacc catacgatgt      1080
tccagattac gctagcttga gatctaccat gtctcagagc aaccgggagc tggtggttga      1140
ctttctctcc tacaagcttt cccagaaagg atacagctgg agtcagttta gtgatgtgga      1200
agagaacagg actgaggccc cagaagggac tgaatcggag atggagaccc ccagtgccat      1260
caatggcaac catcctggc acctggcaga cagccccgcg gtgaatggag ccactgcgca       1320
cagcagcagt ttgatgcccc gggaggtgat ccccatggca gcagtaaagc aagcgctgag      1380
ggaggcaggc gacgagtttg aactgcggta ccggcgggca ttcagtgacc tgacatccca      1440
gctccacatc accccaggga cagcatatca gagctttgaa caggtagtga atgaactctt      1500
ccgggatggg gtagccattc ttcgcattgt ggcctttttc tccttcggcg gggcactgtg      1560
cgtggaaagc gtagacaagg agatgcaggt attggtgagt cggatcgcag cttggatggc      1620
cacttacctg aatgaccacc tagagccttg gatccaggag aacggcggct gggatacttt      1680
tgtgaaactc tatgggaaca atgcagcagc cgagagccga aagggccagg aacgcttcaa      1740
ccgctggttc ctgacgggca tgactgtggc cggcgtggtt ctgctgggct cactcttcag      1800
tcggaaatga agatcttatt aaagcagaac ttgtttattg cagcttataa tggttacaaa      1860
taaagcaata gcatcacaaa tttcacaaat aaagcatttt tttcactgca ttctagttgt      1920
ggtttgtcca aactcatcaa tgtatcttat catgtctggt cgactctaga ctcttccgct      1980
tcctcgctca ctgactcgct gcgctcggtc gttcggctgc ggcgagcggt atcagctcac      2040
tcaaaggcgg taatacggtt atccacagaa tcaggggata acgcaggaaa gaacatgtga      2100
gcaaaggcca gcaaaaggcc aggaaccgta aaaaggccgc gttgctggcg ttttttccat      2160
aggctccgcc cccctgacga gcatcacaaa aatcgacgct caagtcagag gtggcgaaac      2220
ccgacaggac tataaagata ccaggcgttt ccccctggaa gctccctcgt gcgctctcct      2280
gttccgaccc tgccgcttac cggatacctg tccgcctttc tcccttcggg aagcgtggcg      2340
ctttctcaat gctcacgctg taggtatctc agttcggtgt aggtcgttcg ctccaagctg      2400
ggctgtgtgc acgaacccc cgttcagccc gaccgctgcg ccttatccgg taactatcgt       2460
cttgagtcca acccggtaag acacgactta tcgccactgg cagcagccac tggtaacagg      2520
attagcagag cgaggtatgt aggcggtgct acagagttct tgaagtggtg gcctaactac      2580
ggctacacta aaggacagt attggtatc tgcgctctgc tgaagccagt taccttcgga        2640
aaaagagttg gtagctcttg atccggcaaa caaaccaccg ctggtagcgg tggttttttt      2700
gtttgcaagc agcagattac gcgcagaaaa aaaggatctc aagaagatcc tttgatcttt      2760
```

```
tctacggggt ctgacgctca gtggaacgaa aactcacgtt aagggatttt ggtcatgaga    2820
ttatcaaaaa ggatcttcac ctagatcctt ttaaattaaa aatgaagttt taaatcaatc    2880
taaagtatat atgagtaaac ttggtctgac agttaccaat gcttaatcag tgaggcacct    2940
atctcagcga tctgtctatt tcgttcatcc atagttgcct gactcccgt cgtgtagata    3000 actacgatac gggagggctt accatctggc cccagtgctg caatgatacc gcgagaccca    3060
cgctcaccgg ctccagattt atcagcaata accagccag ccggaagggc cgagcgcaga    3120
agtggtcctg caactttatc cgcctccatc cagtctatta attgttgccg gaagctaga    3180 gtaagtagtt cgccagttaa tagtttgcgc aacgttgttg ccattgctac aggcatcgtg    3240
gtgtcacgct cgtcgtttgg tatggcttca ttcagctccg gttcccaacg atcaaggcga    3300
gttacatgat cccccatgtt gtgcaaaaaa gcggttagct ccttcggtcc tcgatcgtt    3360 gtcagaagta agttggccgc agtgttatca ctcatggtta tggcagcact gcataattct    3420
cttactgtca tgccatccgt aagatgcttt tctgtgactg gtgagtactc aaccaagtca    3480
ttctgagaat agtgtatgcg cgaccgagt tgctcttgcc cggcgtcaat acgggataat    3540
accgcgccac atagcagaac tttaaaagtg ctcatcattg gaaaacgttc ttcggggcga    3600
aaactctcaa ggatcttacc gctgttgaga tccagttcga tgtaacccac tcgtgcaccc    3660
aactgatctt cagcatcttt tactttcacc agcgtttctg ggtgagcaaa acaggaagg    3720 caaaatgccg caaaaagggg aataagggcg acacggaaat gttgaatact catactcttc    3780
ttttttcaat attattgaag catttatcag ggttattgtc tcatgagcgg atacatattt    3840
gaatgtattt agaaaaataa acaaataggg gttccgcgca catttccccg aaaagtgcca    3900
cctgacgtct aagaaaccat tattatcatg acattaacct ataaaaatag gcgtatcacg    3960 aggcccttt cgtctcgcgc gtttcggtga tgacggtgaa aacctctgac acatgcagct    4020
cccggagacg gtcacagctt gtctgtaagc ggatgccggg agcagacaag cccgtcaggg    4080
cgcgtcagcg ggtgttggcg ggtgtcgggg ctggcttaac tatgcggcat cagagcagat    4140
tgtactgaga gtgcaccata tgcggtgtga aataccgcac agatgcgtaa ggagaaaata    4200
ccgcatcagg aaattgtaaa cgttaatatt ttgttaaaat tcgcgttaaa ttttgttaa     4260 atcagctcat ttttaacca ataggccgaa atcggcaaaa tcccttataa atcaaaagaa    4320
tagaccgaga tagggttgag tgttgttcca gtttggaaca agagtccact attaagaac    4380 gtggactcca acgtcaaagg gcgaaaaacc gtctatcagg gcgatggccc actacgtgaa    4440
ccatcaccct aatcaagttt tttggggtcg aggtgccgta agcactaaa tcggaaccct    4500 aaagggagcc cccgatttag agcttgacgg ggaaagccgg cgaacgtggc gagaaaggaa    4560
gggaagaaag cgaaaggagc gggcgctagg gcgctggcaa gtgtagcggt cacgctgcgc    4620
gtaaccacca caccccgccgc gcttaatgcg ccgctacagg gcgcgtcgcg ccattcgcca    4680
ttcaggctac gcaactgttg gaagggcga tcggtgcggg cctcttcgct attacgccag    4740
ctggcgaagg ggggatgtgc tgcaaggcga ttaagttggg taacgccagg gttttcccag    4800
tcacgacgtt gtaaaacgac ggccagtgaa tt                                  4832
```

<210> SEQ ID NO 71
<211> LENGTH: 1499
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

```
atgactttta acagttttga aggatctaaa acttgtgtac ctgcagacat caataaggaa      60
gaagaatttg tagaagagtt taatagatta aaaacttttg ctaattttcc aagtggtagt     120
cctgtttcag catcaacact ggcacgagca gggtttcttt atactggtga aggagatacc     180
gtgcggtgct ttagttgtca tgcagctgta gatagatggc aatatggaga ctcagcagtt     240
ggaagacaca ggaaagtatc cccaaattgc agatttatca acggctttta tcttgaaaat     300
agtgccacgc agtctacaaa ttctggtatc cagaatggtc agtacaaagt tgaaaactat     360
ctgggaagca gagatcattt tgccttagac aggccatctg agacacatgc agactatctt     420
ttgagaactg gcaggttgt agatatatca gacaccatat acccgaggaa ccctgccatg      480
tattgtgaag aagctagatt aaagtccttt cagaactggc cagactatgc tcacctaacc     540
ccaagagagt tagcaagtgc tggactctac tacacaggta ttggtgacca agtgcagtgc     600
ttttgttgtg gtggaaaact gaaaaattgg gaaccttgtg atcgtgcctg gtcagaacac     660
aggcgacact ttcctaattg cttctttgtt ttgggccgga atcttaatat tcgaagtgaa     720
tctgatgctg tgagttctga taggaatttc ccaaattcaa caaatcttcc aagaaatcca     780
tccatggcag attatgaagc acggatcttt acttttggga catggatata ctcagttaac     840
aaggagcagc ttgcaagagc tggattttat gctttaggtg aaggtgataa agtaaagtgc     900
tttcactgtg gaggagggct aactgattgg aagcccagtg aagacccttg ggaacaacat     960
gctaaatggt atccagggtg caaatatctg ttagaacaga agggacaaga atatataaac    1020
aatattcatt taactcattc acttgaggag tgtctggtaa gaactactga gaaaacacca    1080
tcactaacta gaagaattga tgataccatc ttccaaaatc ctatggtaca agaagctata    1140
cgaatggggt tcagtttcaa ggacattaag aaaataatgg aggaaaaaat tcagatatct    1200
gggagcaact ataaatcact tgaggttctg gttgcagatc tagtgaatgc tcagaaagac    1260
agtatgcaag atgagtcaag tcagacttca ttacagaaag agattagtac tgaagagcag    1320
ctaaggcgcc tgcaagagga gaagctttgc aaaatctgta tggatagaaa tattgctatc    1380
gttttttgttc cttgtggaca tctagtcact tgtaaacaat gtgctgaagc agttgacaag    1440
tgtcccatgt gctacacagt cattactttc aagcaaaaaa ttttttatgtc ttaatctaa    1499
```

<210> SEQ ID NO 72
<211> LENGTH: 497
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

```
Met Thr Phe Asn Ser Phe Glu Gly Ser Lys Thr Cys Val Pro Ala Asp
1               5                   10                  15

Ile Asn Lys Glu Glu Glu Phe Val Glu Glu Phe Asn Arg Leu Lys Thr
            20                  25                  30

Phe Ala Asn Phe Pro Ser Gly Ser Pro Val Ser Ala Ser Thr Leu Ala
        35                  40                  45

Arg Ala Gly Phe Leu Tyr Thr Gly Glu Gly Asp Thr Val Arg Cys Phe
    50                  55                  60

Ser Cys His Ala Ala Val Asp Arg Trp Gln Tyr Gly Asp Ser Ala Val
65                  70                  75                  80
```

```
Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
            100                 105                 110

Gly Gln Tyr Lys Val Glu Asn Tyr Leu Gly Ser Arg Asp His Phe Ala
        115                 120                 125

Leu Asp Arg Pro Ser Glu Thr His Ala Asp Tyr Leu Leu Arg Thr Gly
    130                 135                 140

Gln Val Val Asp Ile Ser Asp Thr Ile Tyr Pro Arg Asn Pro Ala Met
145                 150                 155                 160

Tyr Cys Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
            180                 185                 190

Gly Ile Gly Asp Gln Val Gln Cys Phe Cys Cys Gly Gly Lys Leu Lys
        195                 200                 205

Asn Trp Glu Pro Cys Asp Arg Ala Trp Ser Glu His Arg Arg His Phe
    210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
            260                 265                 270

Gly Thr Trp Ile Tyr Ser Val Asn Lys Glu Gln Leu Ala Arg Ala Gly
        275                 280                 285

Phe Tyr Ala Leu Gly Glu Gly Asp Lys Val Lys Cys Phe His Cys Gly
    290                 295                 300

Gly Gly Leu Thr Asp Trp Lys Pro Ser Glu Asp Pro Trp Glu Gln His
305                 310                 315                 320

Ala Lys Trp Tyr Pro Gly Cys Lys Tyr Leu Leu Glu Gln Lys Gly Gln
                325                 330                 335

Glu Tyr Ile Asn Asn Ile His Leu Thr His Ser Leu Glu Glu Cys Leu
            340                 345                 350

Val Arg Thr Thr Glu Lys Thr Pro Ser Leu Thr Arg Arg Ile Asp Asp
        355                 360                 365

Thr Ile Phe Gln Asn Pro Met Val Gln Glu Ala Ile Arg Met Gly Phe
    370                 375                 380

Ser Phe Lys Asp Ile Lys Lys Ile Met Glu Glu Lys Ile Gln Ile Ser
385                 390                 395                 400

Gly Ser Asn Tyr Lys Ser Leu Glu Val Leu Val Ala Asp Leu Val Asn
                405                 410                 415

Ala Gln Lys Asp Ser Met Gln Asp Glu Ser Ser Gln Thr Ser Leu Gln
            420                 425                 430

Lys Glu Ile Ser Thr Glu Glu Gln Leu Arg Arg Leu Gln Glu Glu Lys
        435                 440                 445

Leu Cys Lys Ile Cys Met Asp Arg Asn Ile Ala Ile Val Phe Val Pro
    450                 455                 460

Cys Gly His Leu Val Thr Cys Lys Gln Cys Ala Glu Ala Val Asp Lys
465                 470                 475                 480

Cys Pro Met Cys Tyr Thr Val Ile Thr Phe Lys Gln Lys Ile Phe Met
                485                 490                 495

Ser
```

<210> SEQ ID NO 73
<211> LENGTH: 5575
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

```
gtcgacttct gaggcggaaa gaaccagctg tggaatgtgt gtcagttagg gtgtggaaag      60
tccccaggct ccccagcagg cagaagtatg caaagcatgc atctcaatta gtcagcaacc     120
aggtgtggaa agtccccagg ctccccagca ggcagaagta tgcaaagcat gcatctcaat     180
tagtcagcaa ccatagtccc gcccctaact ccgcccatcc cgcccctaac tccgcccagt     240
tccgcccatt ctccgcccca tggctgacta atttttttta tttatgcaga ggccgaggcc     300
gcctcggcct ctgagctatt ccagaagtag tgaggaggct tttttggagg cctaggcttt     360
tgcaaaaagc tggatcgatc ctgagaactt cagggtgagt ttggggaccc ttgattgttc     420
tttcttttc gctattgtaa aattcatgtt atatggaggg gcaaagtttc agggtgtt      480
gtttagaatg ggaagatgtc ccttgtatca ccatggaccc tcatgataat tttgtttctt     540
tcactttcta ctctgttgac aaccattgtc tcctcttatt ttcttttcat tttctgtaac     600
tttttcgtta aactttagct tgcatttgta acgaattttt aaattcactt tgtttattt     660
gtcagattgt aagtactttc tctaatcact ttttttcaa ggcaatcagg gtatattata     720
ttgtacttca gcacagtttt agagaacaat tgttataatt aaatgataag gtagaatatt     780
tctgcatata aattctggct ggcgtggaaa taatcttatt ggtagaaaca actacatcct     840
ggtcatcatc ctgcctttct ctttatggtt acaatgatat acactgtttg agatgaggat     900
aaaatactct gagtccaaac cgggcccctc tgctaaccat gttcatgcct tcttctttt     960
cctacagctc ctgggcaacg tgctggttat tgtgctgtct catcattttg caaagaatt    1020
gtaatacgac tcactatagg gcgaattcgg atccatgact tttaacagtt tgaaggatc    1080
taaaacttgt gtacctgcag acatcaataa ggaagaagaa tttgtagaag agtttaatag    1140
attaaaaact tttgctaatt ttccaagtgg tagtcctgtt tcagcatcaa cactggcacg    1200
agcagggttt ctttatactg gtgaaggaga taccgtgcgg tgctttagtt gtcatgcagc    1260
tgtagataga tggcaatatg gagactcagc agttggaaga cacaggaaag tatccccaaa    1320
ttgcagattt atcaacggct tttatcttga aaatagtgcc acgcagtcta caaattctgg    1380
tatccagaat ggtcagtaca agttgaaaa ctatctggga agcagagatc attttgcctt    1440
agacaggcca tctgagacac atgcagacta tcttttgaga actgggcagg ttgtagatat    1500
atcagacacc atatacccga ggaaccctgc catgtattgt gaagaagcta gattaaagtc    1560
ctttcagaac tggccagact atgctcacct aaccccaaga gagttagcaa gtgctggact    1620
ctactacaca ggtattggtg accaagtgca gtgcttttgt gtggtggaa aactgaaaaa    1680
ttgggaacct tgtgatcgtg cctggtcaga acacaggcga cactttccta attgcttctt    1740
tgttttgggc cggaatctta atattcgaag tgaatctgat gctgtgagtt ctgataggaa    1800
tttcccaaat tcaacaaatc ttccaagaaa tccatccatg gcagattatg aagcacggat    1860
ctttacttt gggacatgga tatactcagt taacaaggag cagcttgcaa gagctggatt    1920
ttatgcttta ggtgaaggtg ataaagtaaa gtgctttcac tgtggaggag gctaactga    1980
ttggaagccc agtgaagacc cttgggaaca acatgctaaa tggtatccag ggtgcaaata    2040
```

```
tctgttagaa cagaagggac aagaatatat aaacaatatt catttaactc attcacttga   2100
ggagtgtctg gtaagaacta ctgagaaaac accatcacta actagaagaa ttgatgatac   2160
catcttccaa aatcctatgg tacaagaagc tatacgaatg gggttcagtt tcaaggacat   2220
taagaaaata atggaggaaa aaattcagat atctgggagc aactataaat cacttgaggt   2280
tctggttgca gatctagtga atgctcagaa agacagtatg caagatgagt caagtcagac   2340
ttcattacag aaagagatta gtactgaaga gcagctaagg cgcctgcaag aggagaagct   2400
ttgcaaaatc tgtatggata gaaatattgc tatcgttttt gttccttgtg gacatctagt   2460
cacttgtaaa caatgtgctg aagcagttga caagtgtccc atgtgctaca cagtcattac   2520
tttcaagcaa aaaatttttt tgtcttaatc taaagatctt attaaagcag aacttgttta   2580
ttgcagctta taatggttac aaataaagca atagcatcac aaatttcaca aataaagcat   2640 tttttttcact gcattctagt tgtggtttgt ccaaactcat caatgtatct tatcatgtct   2700
ggtcgactct agactcttcc gcttcctcgc tcactgactc gctgcgctcg gtcgttcggc   2760
tgcggcgagc ggtatcagct cactcaaagg cggtaatacg gttatccaca gaatcagggg   2820
ataacgcagg aaagaacatg tgagcaaaag gccagcaaaa ggccaggaac cgtaaaaagg   2880
ccgcgttgct ggcgtttttc cataggctcc gcccccctga cgagcatcac aaaaatcgac   2940
gctcaagtca gaggtggcga aacccgacag gactataaag ataccaggcg tttccccctg   3000
gaagctccct cgtgcgctct cctgttccga cctgccgct taccggatac ctgtccgcct   3060
ttctcccttc gggaagcgtg gcgctttctc aatgctcacg ctgtaggtat ctcagttcgg   3120
tgtaggtcgt tcgctccaag ctgggctgtg tgcacgaacc ccccgttcag cccgaccgct   3180
gcgccttatc cggtaactat cgtcttgagt ccaacccggt aagacacgac ttatcgccac   3240
tggcagcagc cactggtaac aggattagca gagcgaggta tgtaggcggt gctacagagt   3300
tcttgaagtg gtggcctaac tacggctaca ctagaaggac agtatttggt atctgcgctc   3360
tgctgaagcc agttaccttc ggaaaaagag ttggtagctc ttgatccggc aaacaaacca   3420
ccgctggtag cggtggtttt tttgtttgca agcagcagat tacgcgcaga aaaaaaggat   3480
ctcaagaaga tcctttgatc ttttctacgg ggtctgacgc tcagtggaac gaaaactcac   3540
gttaagggat tttggtcatg agattatcaa aaaggatctt cacctagatc cttttaaatt   3600
aaaaatgaag ttttaaatca atctaaagta tatatgagta aacttggtct gacagttacc   3660
aatgcttaat cagtgaggca cctatctcag cgatctgtct atttcgttca tccatagttg   3720
cctgactccc cgtcgtgtag ataactacga tacgggaggg cttaccatct ggccccagtg   3780
ctgcaatgat accgcgagac ccacgctcac cggctccaga tttatcagca ataaaccagc   3840
cagccggaag ggccgagcgc agaagtggtc ctgcaacttt atccgcctcc atccagtcta   3900
ttaattgttg ccgggaagct agagtaagta gttcgccagt taatagtttg cgcaacgttg   3960
ttgccattgc tacaggcatc gtggtgtcac gctcgtcgtt tggtatggct tcattcagct   4020
ccggttccca acgatcaagg cgagttacat gatcccccat gttgtgcaaa aaagcggtta   4080
gctccttcgg tcctccgatc gttgtcagaa gtaagttggc cgcagtgtta tcactcatgg   4140
ttatggcagc actgcataat tctcttactg tcatgccatc cgtaagatgc ttttctgtga   4200
ctggtgagta ctcaaccaag tcattctgag aatagtgtat gcggcgaccg agttgctctt   4260
gcccggcgtc aatacgggat aataccgcgc cacatagcag aactttaaaa gtgctcatca   4320
ttggaaaacg ttcttcgggg cgaaaactct caaggatctt accgctgttg agatccagtt   4380
```

```
cgatgtaacc cactcgtgca cccaactgat cttcagcatc ttttactttc accagcgttt   4440
ctgggtgagc aaaaacagga aggcaaaatg ccgcaaaaaa gggaataagg gcgacacgga   4500
aatgttgaat actcatactc ttcttttttc aatattattg aagcatttat cagggttatt   4560
gtctcatgag cggatacata tttgaatgta tttagaaaaa taaacaaata ggggttccgc   4620
gcacatttcc ccgaaaagtg ccacctgacg tctaagaaac cattattatc atgacattaa   4680
cctataaaaa taggcgtatc acgaggcccc tttcgtctcg cgcgtttcgg tgatgacggt   4740
gaaaacctct gacacatgca gctcccggag acggtcacag cttgtctgta agcggatgcc   4800
gggagcagac aagcccgtca gggcgcgtca gcgggtgttg gcgggtgtcg gggctggctt   4860
aactatgcgg catcagagca gattgtactg agagtgcacc atatgcggtg tgaaataccg   4920
cacagatgcg taaggagaaa ataccgcatc aggaaattgt aaacgttaat attttgttaa   4980
aattcgcgtt aaattttgt taaatcagct cattttttaa ccataggcc gaaatcggca    5040 aaatccctta taaatcaaaa gaatagaccg atagggtt gagtgttgtt ccagtttgga     5100
acaagagtcc actattaaag aacgtggact ccaacgtcaa agggcgaaaa accgtctatc   5160
agggcgatgg cccactacgt gaaccatcac cctaatcaag ttttttgggg tcgaggtgcc   5220
gtaaagcact aaatcggaac cctaaaggga gcccccgatt tagagcttga cggggaaagc   5280
cggcgaacgt ggcgagaaag gaagggaaga aagcgaaagg agcgggcgct agggcgctgg   5340
caagtgtagc ggtcacgctg cgcgtaacca ccacacccgc cgcgcttaat gcgccgctac   5400
agggcgcgtc gcgccattcg ccattcaggc tacgcaactg ttgggaaggg cgatcggtgc   5460
gggcctcttc gctattacgc cagctggcga aggggggatg tgctgcaagg cgattaagtt   5520
gggtaacgcc agggttttcc cagtcacgac gttgtaaaac gacggccagt gaatt         5575
```

<210> SEQ ID NO 74
<211> LENGTH: 1395
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 74

```
atggacttca gcagaaatct ttatgatatt ggggaacaac tggacagtga agatctggcc      60
tccctcaagt tcctgagcct ggactacatt ccgcaaagga agcaagaacc catcaaggat    120
gccttgatgt tattccagag actccaggaa aagagaatgt tggaggaaag caatctgtcc    180
ttcctgaagg agctgctctt ccgaattaat agactggatt tgctgattac ctacctaaac    240
actagaaagg aggagatgga aagggaactt cagacaccag gcagggctca aatttctgcc    300
tacagggtca tgctctatca gatttcagaa gaagtgagca gatcagaatt gaggtctttt    360 aagtttctt tgcaagagga aatctccaaa tgcaaactgg atgatgacat gaacctgctg    420 gatatttca tagagatgga agagggtc atcctgggag aaggaaagtt ggacatcctg    480
aaaagagtct gtgcccaaat caacaagagc ctgctgaaga taatcaacga ctatgaagaa    540
ttcagcaaag gggaggagtt gtgtgggta atgacaatct cggactctcc aagagaacag    600
gatagtgaat cacagacttt ggacaaagtt taccaaatga aaagcaaacc tcggggatac    660
tgtctgatca tcaacaatca caatttgca aaagcacggg agaaagtgcc caaacttcac    720
agcattaggg acaggaatgg aacacacttg gatcaggggg ctttgaccac gacctttgaa    780
gagcttcatt ttgagatcaa gccccacgat gactgcacag tagagcaaat ctatgagatt    840
```

-continued

```
ttgaaaatct accaactcat ggaccacagt aacatggact gcttcatctg ctgtatcctc    900
tcccatggag acaagggcat catctatggc actgatggac aggaggcccc catctatgag    960
ctgacatctc agttcactgg tttgaagtgc ccttcccttg ctggaaaacc caaagtgttt   1020
tttattcagg cttgtcaggg ggataactac cagaaaggta tacctgttga gactgattca   1080
gaggagcaac cctatttaga aatggattta tcatcacctc aaacgagata tatcccggat   1140
gaggctgact ttctgctggg gatggccact gtgaataact gtgtttccta ccgaaaccct   1200
gcagagggaa cctggtacat ccagtcactt tgccagagcc tgagagagcg atgtcctcga   1260
ggcgatgata ttctcaccat cctgactgaa gtgaactatg aagtaagcaa caaggatgac   1320
aagaaaaaca tggggaaaca gatgcctcag cctactttca cactaagaaa aaaacttgtc   1380
ttcccttctg attga                                                   1395
```

<210> SEQ ID NO 75
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Gly Glu Glu Leu Cys Gly Val Met Thr
            180                 185                 190

Ile Ser Asp Ser Pro Arg Glu Gln Asp Ser Glu Ser Gln Thr Leu Asp
        195                 200                 205

Lys Val Tyr Gln Met Lys Ser Lys Pro Arg Gly Tyr Cys Leu Ile Ile
    210                 215                 220

Asn Asn His Asn Phe Ala Lys Ala Arg Glu Lys Val Pro Lys Leu His
225                 230                 235                 240

Ser Ile Arg Asp Arg Asn Gly Thr His Leu Asp Ala Gly Ala Leu Thr
                245                 250                 255
```

Thr Thr Phe Glu Glu Leu His Phe Glu Ile Lys Pro His Asp Asp Cys
            260                 265                 270

Thr Val Glu Gln Ile Tyr Glu Ile Leu Lys Ile Tyr Gln Leu Met Asp
        275                 280                 285

His Ser Asn Met Asp Cys Phe Ile Cys Cys Ile Leu Ser His Gly Asp
    290                 295                 300

Lys Gly Ile Ile Tyr Gly Thr Asp Gly Gln Glu Ala Pro Ile Tyr Glu
305                 310                 315                 320

Leu Thr Ser Gln Phe Thr Gly Leu Lys Cys Pro Ser Leu Ala Gly Lys
                325                 330                 335

Pro Lys Val Phe Phe Ile Gln Ala Cys Gln Gly Asp Asn Tyr Gln Lys
            340                 345                 350

Gly Ile Pro Val Glu Thr Asp Ser Glu Glu Gln Pro Tyr Leu Glu Met
        355                 360                 365

Asp Leu Ser Ser Pro Gln Thr Arg Tyr Ile Pro Asp Glu Ala Asp Phe
    370                 375                 380

Leu Leu Gly Met Ala Thr Val Asn Asn Cys Val Ser Tyr Arg Asn Pro
385                 390                 395                 400

Ala Glu Gly Thr Trp Tyr Ile Gln Ser Leu Cys Gln Ser Leu Arg Glu
                405                 410                 415

Arg Cys Pro Arg Gly Asp Asp Ile Leu Thr Ile Leu Thr Glu Val Asn
            420                 425                 430

Tyr Glu Val Ser Asn Lys Asp Asp Lys Lys Asn Met Gly Lys Gln Met
        435                 440                 445

Pro Gln Pro Thr Phe Thr Leu Arg Lys Lys Leu Val Phe Pro Ser Asp
    450                 455                 460

<210> SEQ ID NO 76
<211> LENGTH: 5471
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
gtcgacttct gaggcggaaa gaaccagctg tggaatgtgt gtcagttagg gtgtggaaag      60
tccccaggct ccccagcagg cagaagtatg caaagcatgc atctcaatta gtcagcaacc     120
aggtgtggaa agtccccagg ctccccagca ggcagaagta tgcaaagcat gcatctcaat     180
tagtcagcaa ccatagtccc gcccctaact ccgcccatcc cgcccctaac tccgcccagt     240
tccgcccatt ctccgcccca tggctgacta atttttttta tttatgcaga ggccgaggcc     300
gcctcggcct ctgagctatt ccagaagtag tgaggaggct tttttggagg cctaggcttt     360
tgcaaaaagc tggatcgatc ctgagaactt cagggtgagt ttggggaccc ttgattgttc     420 tttcttttc gctattgtaa aattcatgtt atatggaggg gcaaagtttt caggctgtt      480 gtttagaatg ggaagatgtc ccttgtatca ccatggaccc tcatgataat tttgtttctt     540
tcactttcta ctctgttgac aaccattgtc tcctcttatt ttcttttcat tttctgtaac     600
ttttccgtta aacttttagct tgcatttgta acgaattttt aaattcactt ttgtttattt     660
gtcagattgt aagtactttc tctaatcact ttttttttcaa ggcaatcagg gtatattata     720
ttgtacttca gcacagtttt agagaacaat tgttataatt aaatgataag gtagaatatt     780
tctgcatata aattctggct ggcgtggaaa tattcttatt ggtagaaaca actacatcct     840
ggtcatcatc ctgcctttct ctttatggtt acaatgatat acactgtttg agatgaggat     900

```
aaaatactct gagtccaaac cgggcccctc tgctaaccat gttcatgcct tcttctttt      960 cctacagctc ctgggcaacg tgctggttat tgtgctgtct catcattttg gcaaagaatt     1020
gtaatacgac tcactatagg gcgaattcat ggacttcagc agaaatcttt atgatattgg     1080
ggaacaactg gacagtgaag atctggcctc cctcaagttc ctgagcctgg actacattcc     1140
gcaaaggaag caagaaccca tcaaggatgc cttgatgtta ttccagagac tccaggaaaa     1200
gagaatgttg gaggaaagca atctgtcctt cctgaaggag ctgctcttcc gaattaatag     1260
actggatttg ctgattacct acctaaacac tagaaaggag gagatggaaa gggaacttca     1320
gacaccaggc agggctcaaa tttctgccta cagggtcatg ctctatcaga tttcagaaga     1380
agtgagcaga tcagaattga ggtcttttaa gtttcttttg caagaggaaa tctccaaatg     1440
caaactggat gatgacatga acctgctgga tattttcata gagatggaga agagggtcat     1500
cctgggagaa ggaaagttgg acatcctgaa aagagtctgt gcccaaatca acaagagcct     1560
gctgaagata atcaacgact atgaagaatt cagcaaaggg gaggagttgt gtggggtaat     1620
gacaatctcg gactctccaa gagaacagga tagtgaatca cagactttgg acaaagttta     1680
ccaaatgaaa agcaaacctc gggatactgt ctgatcatca acaatcacaa ttttgcaaaa     1740
gcacgggaga aagtgcccca aacttcacag cattagggac aggaatggaa cacacttgga     1800 tgcagggget tgaccacga cctttgaaga gcttcatttt gagatcaagc cccacgatga     1860
ctgcacagta gagcaaatct atgagatttt gaaaatctac caactcatgg accacagtaa     1920
catggactgc ttcatctgct gtatcctctc ccatggagac aagggcatca tctatggcac     1980
tgatggacag gaggccccca tctatgagct gacatctcag ttcactggtt tgaagtgccc     2040
ttcccttgct ggaaaaccca agtgtttttt tattcaggct tgtcaggggg ataactacca     2100
gaaaggtata cctgttgaga ctgattcaga ggagcaaccc tatttagaaa tggatttatc     2160
atcacctcaa acgagatata tcccggatga ggctgacttt ctgctgggga tggccactgt     2220
gaataactgt gtttcctacc gaaaccctgc agagggaacc tggtacatcc agtcactttg     2280
ccagagcctg agagagcgat gtcctcgagg cgatgatatt ctcaccatcc tgactgaagt     2340
gaactatgaa gtaagcaaca aggatgacaa gaaaaacatg gggaaacaga tgcctcagcc     2400
tactttcaca ctaagaaaaa aacttgtctt cccttctgat tgaggatcca gatcttatta     2460
aagcagaact tgtttattgc agcttataat ggttacaaat aaagcaatag catcacaaat     2520
ttcacaaata aagcattttt ttcactgcat tctagttgtg gtttgtccaa actcatcaat     2580
gtatcttatc atgtctggtc gactctagac tcttccgctt cctcgctcac tgactcgctg     2640
cgctcggtcg ttcggctgcg gcgagcggta tcagctcact caaaggcggt aatacggtta     2700
tccacagaat caggggataa cgcaggaaag aacatgtgag caaaaggcca gcaaaaggcc     2760
aggaaccgta aaaaggccgc gttgctggcg tttttccata ggctccgccc cctgacgag     2820 catcacaaaa atcgacgctc aagtcagagg tggcgaaacc cgacaggact ataaagatac     2880
caggcgtttc cccctggaag ctccctcgtg cgctctcctg ttccgaccct gccgcttacc     2940
ggatacctgt ccgcctttct cccttcggga agcgtggcgc tttctcaatg ctcacgctgt     3000
aggtatctca gttcggtgta ggtcgttcgc tccaagctgg gctgtgtgca cgaaccccc      3060 gttcagcccg accgctgcgc cttatccggt aactatcgtc ttgagtccaa cccggtaaga     3120
cacgacttat cgccactggc agcagccact ggtaacagga ttagcagagc gaggtatgta     3180
ggcggtgcta cagagttctt gaagtggtgg cctaactacg gctacactag aaggacagta     3240
```

```
tttggtatct gcgctctgct gaagccagtt accttcggaa aaagagttgg tagctcttga    3300
tccggcaaac aaaccaccgc tggtagcggt ggttttttttg tttgcaagca gcagattacg    3360
cgcagaaaaa aaggatctca agaagatcct ttgatctttt ctacggggtc tgacgctcag    3420
tggaacgaaa actcacgtta agggattttg gtcatgagat tatcaaaaag gatcttcacc    3480
tagatccttt taaattaaaa atgaagtttt aaatcaatct aaagtatata tgagtaaact    3540
tggtctgaca gttaccaatg cttaatcagt gaggcaccta tctcagcgat ctgtctattt    3600
cgttcatcca tagttgcctg actccccgtc gtgtagataa ctacgatacg ggagggctta    3660
ccatctggcc ccagtgctgc aatgataccg cgagacccac gctcaccggc tccagattta    3720
tcagcaataa accagccagc cggaagggcc gagcgcagaa gtggtcctgc aactttatcc    3780
gcctccatcc agtctattaa ttgttgccgg gaagctagag taagtagttc gccagttaat    3840
agtttgcgca acgttgttgc cattgctaca ggcatcgtgg tgtcacgctc gtcgtttggt    3900
atggcttcat tcagctccgg ttcccaacga tcaaggcgag ttacatgatc ccccatgttg    3960
tgcaaaaaag cggttagctc cttcggtcct ccgatcgttg tcagaagtaa gttggccgca    4020
gtgttatcac tcatggttat ggcagcactg cataattctc ttactgtcat gccatccgta    4080
agatgctttt ctgtgactgg tgagtactca accaagtcat tctgagaata gtgtatgcgg    4140
cgaccgagtt gctcttgccc ggcgtcaata cgggataata ccgcgccaca tagcagaact    4200
ttaaaagtgc tcatcattgg aaaacgttct cggggcgaaa actctcaaga tcttaccg    4260
ctgttgagat ccagttcgat gtaacccact cgtgcaccca actgatcttc agcatctttt    4320
actttcacca gcgtttctgg gtgagcaaaa acaggaaggc aaaatgccgc aaaaaaggga    4380
ataagggcga cacggaaatg ttgaatactc atactcttcc tttttcaata ttattgaagc    4440
atttatcagg gttattgtct catgagcgga tacatatttg aatgtattta gaaaaataaa    4500
caaatagggg ttccgcgcac atttccccga aaagtgccac ctgacgtcta agaaaccatt    4560
attatcatga cattaaccta taaaaatagg cgtatcacga ggcccctttc gtctcgcgcg    4620
tttcggtgat gacggtgaaa acctctgaca catgcagctc ccggagacgg tcacagcttg    4680
tctgtaagcg gatgccggga gcagacaagc ccgtcagggc gcgtcagcgg gtgttggcgg    4740
gtgtcgggc tggcttaact atgcggcatc agagcagatt gtactgagag tgcaccatat    4800
gcggtgtgaa ataccgcaca gatgcgtaag gagaaaatac cgcatcagga aattgtaaac    4860
gttaatattt tgttaaaatt cgcgttaaat ttttgttaaa tcagctcatt ttttaaccaa    4920
taggccgaaa tcggcaaaat cccttataaa tcaaaagaat agaccgagat agggttgagt    4980
gttgttccag tttggaacaa gagtccacta ttaaagaacg tggactccaa cgtcaaaggg    5040
cgaaaaaccg tctatcaggg cgatggccca ctacgtgaac catcacccta atcaagtttt    5100
ttggggtcga ggtgccgtaa agcactaaat cggaacccta aagggagccc ccgatttaga    5160
gcttgacggg gaaagccggc gaacgtggcg agaaaggaag ggaagaaagc gaaaggagcg    5220
ggcgctaggg cgctggcaag tgtagcggtc acgctgcgcg taaccaccac acccgccgcg    5280
cttaatgcgc cgctacaggg cgcgtcgcgc cattcgccat tcaggctacg caactgttgg    5340
gaagggcgat cggtgcgggc ctcttcgcta ttacgccagc tggcgaaggg gggatgtgct    5400
gcaaggcgat taagttgggt aacgccaggg ttttcccagt cacgacgttg taaaacgacg    5460
gccagtgaat t                                                        5471
```

<210> SEQ ID NO 77
<211> LENGTH: 618

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
atggcgcacg ctgggagaac agggtacgat aaccgggaga tagtgatgaa gtacatccat    60
tataagctgt cgcagagggg ctacgagtgg gatgcgggag atgtgggcgc cgcgcccccg   120
ggggccgccc ccgcaccggg catcttctcc tcccagcccg gcacacgcc ccatccagcc    180 gcatcccggg accggtcgc caggacctcg ccgctgcaga ccccggctgc cccggcgcc    240 gccgcgggc ctgcgctcag cccggtgcca cctgtggtcc acctgaccct ccgccaggcc    300
ggcgacgact tctcccgccg ctaccgccgc gacttcgccg agatgtccag ccagctgcac    360
ctgacgccct tcaccgcgcg gggacgcttt gccacggtgg tggaggagct cttcagggac    420
ggggtgaact gggggaggat tgtggccttc tttgagttcg gtggggtcat gtgtgtggag    480
agcgtcaacc gggagatgtc gcccctggtg acaacatcg ccctgtggat gactgagtac    540
ctgaaccggc acctgcacac ctggatccag ataacggag gctgggtagg tgcacttggt    600
gatgtgagtc tgggctga                                                  618

<210> SEQ ID NO 78
<211> LENGTH: 205
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Val Gly Ala Leu Gly Asp Val Ser Leu Gly
        195                 200                 205
```

<210> SEQ ID NO 79
<211> LENGTH: 4699
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

| | | | | | | |
|---|---|---|---|---|---|---|
| gtcgacttct | gaggcggaaa | gaaccagctg | tggaatgtgt | gtcagttagg | gtgtggaaag | 60 |
| tccccaggct | ccccagcagg | cagaagtatg | caaagcatgc | atctcaatta | gtcagcaacc | 120 |
| aggtgtggaa | agtccccagg | ctccccagca | ggcagaagta | tgcaaagcat | gcatctcaat | 180 |
| tagtcagcaa | ccatagtccc | gcccctaact | ccgcccatcc | cgcccctaac | tccgcccagt | 240 |
| tccgcccatt | ctccgcccca | tggctgacta | attttttta | tttatgcaga | ggccgaggcc | 300 |
| gcctcggcct | ctgagctatt | ccagaagtag | tgaggaggct | tttttggagg | cctaggcttt | 360 |
| tgcaaaaagc | tggatcgatc | ctgagaactt | cagggtgagt | ttggggaccc | ttgattgttc | 420 |
| tttcttttc | gctattgtaa | aattcatgtt | atatggaggg | ggcaaagttt | tcagggtgtt | 480 |
| gtttagaatg | ggaagatgtc | ccttgtatca | ccatggaccc | tcatgataat | tttgtttctt | 540 |
| tcactttcta | ctctgttgac | aaccattgtc | tcctcttatt | ttcttttcat | tttctgtaac | 600 |
| tttttcgtta | aactttagct | tgcatttgta | acgaattttt | aaattcactt | ttgtttattt | 660 |
| gtcagattgt | aagtactttc | tctaatcact | ttttttcaa | ggcaatcagg | gtatattata | 720 |
| ttgtacttca | gcacagtttt | agagaacaat | tgttataatt | aaatgataag | gtagaatatt | 780 |
| tctgcatata | aattctggct | ggcgtggaaa | tattcttatt | ggtagaaaca | actacatcct | 840 |
| ggtcatcatc | ctgcctttct | ctttatggtt | acaatgatat | acactgtttg | agatgaggat | 900 |
| aaaatactct | gagtccaaac | cgggcccctc | tgctaaccat | gttcatgcct | tcttcttttt | 960 |
| cctacagctc | ctgggcaacg | tgctggttat | tgtgctgtct | catcattttg | gcaaagaatt | 1020 |
| gtaatacgac | tcactatagg | gcgaattcgg | atccagatct | atggcgcacg | ctgggagaac | 1080 |
| agggtacgat | aaccgggaga | tagtgatgaa | gtacatccat | tataagctgt | cgcagagggg | 1140 |
| ctacgagtgg | gatgcgggag | atgtgggcgc | cgcgcccccg | ggggccgccc | ccgcaccggg | 1200 |
| catcttctcc | tcccagcccg | ggcacacgcc | ccatccagcc | gcatcccggg | acccggtcgc | 1260 |
| caggacctcg | ccgctgcaga | ccccggctgc | ccccggcgcc | gccgcggggc | ctgcgctcag | 1320 |
| cccggtgcca | cctgtggtcc | acctgaccct | ccgccaggcc | ggcgacgact | ctctcccgcc | 1380 |
| ctaccgccgc | gacttcgccg | agatgtccag | ccagctgcac | ctgacgccct | tcaccgcgcg | 1440 |
| gggacgcttt | gccacggtgg | tggaggagct | cttcagggac | ggggtgaact | ggggggagga | 1500 |
| tgtggccttc | tttgagttcg | gtgggtcat | gtgtgtggag | agcgtcaacc | gggagatgtc | 1560 |
| gccccctggtg | gacaacatcg | ccctgtggat | gactgagtac | ctgaaccggc | acctgcacac | 1620 |
| ctggatccag | gataacggag | gctgggtagg | tgcacttggt | gatgtgagtc | tgggctgaag | 1680 |
| atcttattaa | agcagaactt | gtttattgca | gcttataatg | gttacaaata | aagcaatagc | 1740 |
| atcacaaatt | tcacaaataa | agcatttttt | tcactgcatt | ctagttgtgg | tttgtccaaa | 1800 |
| ctcatcaatg | tatcttatca | tgtctggtcg | actctagact | cttccgcttc | ctcgctcact | 1860 |
| gactcgctgc | gctcggtcgt | tcggctgcgg | cgagcggtat | cagctcactc | aaaggcggta | 1920 |
| atacggttat | ccacagaatc | aggggataac | gcaggaaaga | acatgtgagc | aaaaggccag | 1980 |
| caaaaggcca | ggaaccgtaaa | aaggccgcgt | tgctggcgtt | tttccatagg | ctccgccccc | 2040 |

```
ctgacgagca tcacaaaaat cgacgctcaa gtcagaggtg gcgaaacccg acaggactat    2100
aaagatacca ggcgtttccc cctggaagct ccctcgtgcg ctctcctgtt ccgaccctgc    2160
cgcttaccgg atacctgtcc gcctttctcc cttcgggaag cgtggcgctt tctcaatgct    2220
cacgctgtag gtatctcagt tcggtgtagg tcgttcgctc caagctgggc tgtgtgcacg    2280 aacccccgt tcagcccgac cgctgcgcct tatccggtaa ctatcgtctt gagtccaacc    2340
cggtaagaca cgacttatcg ccactggcag cagccactgg taacaggatt agcagagcga    2400
ggtatgtagg cggtgctaca gagttcttga agtggtggcc taactacggc tacactagaa    2460
ggacagtatt tggtatctgc gctctgctga agccagttac cttcggaaaa agagttggta    2520
gctcttgatc cggcaaacaa accaccgctg gtagcggtgg ttttttttgtt tgcaagcagc    2580 agattacgcg cagaaaaaaa ggatctcaag aagatccttt gatcttttct acggggtctg    2640
acgctcagtg gaacgaaaac tcacgttaag ggattttggt catgagatta tcaaaaagga    2700
tcttcaccta gatcctttta aattaaaaat gaagttttaa atcaatctaa agtatatatg    2760
agtaaacttg gtctgacagt taccaatgct taatcagtga ggcacctatc tcagcgatct    2820
gtctatttcg ttcatccata gttgcctgac tccccgtcgt gtagataact acgatacggg    2880
agggcttacc atctggcccc agtgctgcaa tgataccgcg agacccacgc tcaccggctc    2940
cagatttatc agcaataaac cagccagccg aagggccga gcgcagaagt ggtcctgcaa    3000
ctttatccgc ctccatccag tctattaatt gttgccggga agctagagta agtagttcgc    3060
cagttaatag tttgcgcaac gttgttgcca ttgctacagg catcgtggtg tcacgctcgt    3120
cgtttggtat ggcttcattc agctccggtt cccaacgatc aaggcgagtt acatgatccc    3180
ccatgttgtg caaaaaagcg gttagctcct tcggtcctcc gatcgttgtc agaagtaagt    3240
tggccgcagt gttatcactc atggttatgg cagcactgca taattctctt actgtcatgc    3300
catccgtaag atgcttttct gtgactggtg agtactcaac caagtcattc tgagaatagt    3360
gtatgcggcg accgagttgc tcttgcccgg cgtcaatacg ggataatacc gcgccacata    3420
gcagaacttt aaaagtgctc atcattggaa aacgttcttc ggggcgaaaa ctctcaagga    3480
tcttaccgct gttgagatcc agttcgatgt aacccactcg tgcacccaac tgatcttcag    3540
catcttttac tttcaccagc gtttctgggt gagcaaaaac aggaaggcaa aatgccgcaa    3600
aaaagggaat aagggcgaca cggaaatgtt gaatactcat actcttcttt ttcaatatt    3660 attgaagcat ttatcagggt tattgtctca tgagcggata catatttgaa tgtatttaga    3720
aaaataaaca aataggggtt ccgcgcacat ttccccgaaa agtgccacct gacgtctaag    3780
aaaccattat tatcatgaca ttaacctata aaaataggcg tatcacgagg ccccttcgt    3840 ctcgcgcgtt tcggtgatga cggtgaaaac ctctgacaca tgcagctccc ggagacggtc    3900
acagcttgtc tgtaagcgga tgccgggagc agacaagccc gtcagggcgc gtcagcgggt    3960
gttggcgggt gtcggggctg gcttaactat gcggcatcag agcagattgt actgagagtg    4020
caccatatgc ggtgtgaaat accgcacaga tgcgtaagga gaaaataccg catcaggaaa    4080
ttgtaaacgt taatattttg ttaaaattcg cgttaaattt ttgttaaatc agctcatttt    4140
ttaaccaata ggccgaaatc ggcaaaatcc cttataaatc aaaagaatag accgagatag    4200
ggttgagtgt tgttccagtt tggaacaaga gtccactatt aaagaacgtg gactccaacg    4260 tcaaagggcga aaaaccgtc tatcagggcg atggcccact acgtgaacca tcaccctaat    4320
caagtttttt ggggtcgagg tgccgtaaag cactaaatcg aaccctaaa gggagccccc    4380
```

```
gatttagagc ttgacgggga aagccggcga acgtggcgag aaaggaaggg aagaaagcga      4440
aaggagcggg cgctagggcg ctggcaagtg tagcggtcac gctgcgcgta accaccacac      4500
ccgccgcgct taatgcgccg ctacagggcg cgtcgcgcca ttcgccattc aggctacgca      4560
actgttggga agggcgatcg gtgcgggcct cttcgctatt acgccagctg gcgaaggggg      4620
gatgtgctgc aaggcgatta agttgggtaa cgccagggtt ttcccagtca cgacgttgta      4680
aaacgacggc cagtgaatt                                                   4699

<210> SEQ ID NO 80
<211> LENGTH: 5471
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
gtcgacttct gaggcggaaa gaaccagctg tggaatgtgt gtcagttagg gtgtggaaag        60
tccccaggct ccccagcagg cagaagtatg caaagcatgc atctcaatta gtcagcaacc       120
aggtgtggaa agtccccagg ctccccagca ggcagaagta tgcaaagcat gcatctcaat       180
tagtcagcaa ccatagtccc gcccctaact ccgcccatcc cgcccctaac tccgcccagt       240
tccgcccatt ctccgcccca tggctgacta attttttttta tttatgcaga ggccgaggcc      300
gcctcggcct ctgagctatt ccagaagtag tgaggaggct ttttggagg cctaggcttt        360 tgcaaaaagc tggatcgatc ctgagaactt cagggtgagt ttggggaccc ttgattgttc       420 tttcttttc gctattgtaa aattcatgtt atatggaggg ggcaaagttt tcagggtgtt        480
gtttagaatg ggaagatgtc ccttgtatca ccatggaccc tcatgataat tttgtttctt       540
tcactttcta ctctgttgac aaccattgtc tcctcttatt ttcttttcat tttctgtaac      600 ttttttcgtta aactttagct tgcatttgta acgaattttt aaattcactt tgtttatt      660 gtcagattgt aagtactttc tctaatcact ttttttttcaa ggcaatcagg gtatattata     720
ttgtacttca gcacagtttt agagaacaat tgttataatt aaatgataag gtagaatatt      780
tctgcatata aattctggct ggcgtggaaa tattcttatt ggtagaaaca actacatcct      840
ggtcatcatc ctgcctttct ctttatggtt acaatgatat acactgtttg agatgaggat      900
aaaatactct gagtccaaac cgggcccctc tgctaaccat gttcatgcct tcttctttt       960 cctacagctc ctgggcaacg tgctggttat tgtgctgtct catcattttg gcaaagaatt     1020
gtaatacgac tcactatagg gcgaattcgg atccatggac ttcagcagaa atctttatga     1080
tattggggaa caactggaca gtgaagatct ggcctccctc aagttcctga gcctggacta     1140
cattccgcaa aggaagcaag aacccatcaa ggatgccttg atgttattcc agagactcca     1200
ggaaaagaga atgttggagg aaagcaatct gtccttcctg aaggagctgc tcttccgaat     1260
taatagactg gatttgctga ttacctacct aaacactaga aaggaggaga tggaaaggga     1320
acttcagaca ccaggcaggg ctcaaatttc tgcctacagg gtcatgctct atcagatttc     1380
agaagaagtg agcagatcag aattgaggtc ttttaagttt ctttttgcaag aggaaatctc     1440 caaatgcaaa ctggatgatg acatgaacct gctggatatt ttcatagaga tggagaagag     1500
ggtcatcctg ggagaaggaa agttggacat cctgaaaaga gtctgtgccc aaatcaacaa     1560
gagcctgctg aagataatca acgactatga agaattcagc aaaggggagg agttgtgtgg     1620
ggtaatgaca atctcggact ctccaagaga acaggatagt gaatcacaga ctttggacaa     1680
```

-continued

```
agtttaccaa atgaaaagca aacctcgggg atactgtctg atcatcaaca atcacaattt   1740
tgcaaaagca cgggagaaag tgcccaaact tcacagcatt agggacagga atggaacaca   1800
cttggatgca ggggctttga ccacgacctt tgaagagctt cattttgaga tcaagcccca   1860
cgatgactgc acagtagagc aaatctatga gattttgaaa atctaccaac tcatggacca   1920
cagtaacatg gactgcttca tctgctgtat cctctcccat ggagacaagg gcatcatcta   1980
tggcactgat ggacaggagg cccccatcta tgagctgaca tctcagttca ctggtttgaa   2040
gtgcccttcc cttgctggaa aacccaaagt gttttttatt caggcttctc aggggataa    2100 ctaccagaaa ggtatacctg ttgagactga ttcagaggag caaccctatt tagaaatgga   2160
tttatcatca cctcaaacga gatatatccc ggatgaggct gactttctgc tggggatggc   2220
cactgtgaat aactgtgttt cctaccgaaa ccctgcagag ggaacctggt acatccagtc   2280
actttgccag agcctgagag agcgatgtcc tcgaggcgat gatattctca ccatcctgac   2340
tgaagtgaac tatgaagtaa gcaacaagga tgacaagaaa acatggggga acagatgcc    2400 tcagcctact ttcacactaa gaaaaaaact tgtcttccct tctgattgaa gatcttatta   2460
aagcagaact tgtttattgc agcttataat ggttacaaat aaagcaatag catcacaaat   2520
ttcacaaata aagcattttt ttcactgcat tctagttgtg gtttgtccaa actcatcaat   2580
gtatcttatc atgtctggtc gactctagac tcttccgctt cctcgctcac tgactcgctg   2640
cgctcggtcg ttcggctgcg gcgagcggta tcagctcact caaaggcggt aatacggtta   2700
tccacagaat caggggataa cgcaggaaag aacatgtgag caaaaggcca gcaaaggcc    2760 aggaaccgta aaaaggccgc gttgctggcg ttttcccata ggctccgccc ccctgacgag   2820
catcacaaaa atcgacgctc aagtcagagg tggcgaaacc cgacaggact ataaagatac   2880
caggcgtttc cccctggaag ctccctcgtg cgctctcctg ttccgaccct gccgcttacc   2940
ggatacctgt ccgcctttct cccttcggga agcgtggcgc tttctcaatg ctcacgctgt   3000
aggtatctca gttcggtgta ggtcgttcgc tccaagctgg gctgtgtgca cgaacccccc   3060
gttcagcccg accgctgcgc cttatccggt aactatcgtc ttgagtccaa cccggtaaga   3120
cacgacttat cgccactggc agcagccact ggtaacagga ttagcagagc gaggtatgta   3180
ggcggtgcta cagagttctt gaagtggtgg cctaactacg gctacactag aaggacagta   3240
tttggtatct gcgctctgct gaagccagtt accttcggaa aaagagttgg tagctcttga   3300
tccggcaaac aaaccaccgc tggtagcggt ggtttttttg tttgcaagca gcagattacg   3360
cgcagaaaaa aaggatctca agaagatcct ttgatctttt ctacggggtc tgacgctcag   3420
tggaacgaaa actcacgtta agggattttg gtcatgagat tatcaaaaag gatcttcacc   3480
tagatccttt taaattaaaa atgaagtttt aaatcaatct aaagtatata tgagtaaact   3540
tggtctgaca gttaccaatg cttaatcagt gaggcaccta tctcagcgat ctgtctattt   3600
cgttcatcca tagttgcctg actccccgtc gtgtagataa ctacgatacg ggagggctta   3660
ccatctggcc ccagtgctgc aatgataccg cgagacccac gctcaccggc tccagattta   3720
tcagcaataa accagccagc cggaagggcc gagcgcagaa gtggtcctgc aactttatcc   3780
gcctccatcc agtctattaa ttgttgccgg gaagctagag taagtagttc gccagttaat   3840
agtttgcgca acgttgttgc cattgctaca ggcatcgtgg tgtcacgctc gtcgtttggt   3900
atggcttcat tcagctccgg ttcccaacga tcaaggcgag ttacatgatc ccccatgttg   3960
tgcaaaaaag cggttagctc cttcggtcct ccgatcgttg tcagaagtaa gttggccgca   4020
gtgttatcac tcatggttat ggcagcactg cataattctc ttactgtcat gccatccgta   4080
```

```
agatgctttt ctgtgactgg tgagtactca accaagtcat tctgagaata gtgtatgcgg    4140
cgaccgagtt gctcttgccc ggcgtcaata cgggataata ccgcgccaca tagcagaact    4200
ttaaaagtgc tcatcattgg aaaacgttct tcggggcgaa aactctcaag gatcttaccg    4260
ctgttgagat ccagttcgat gtaacccact cgtgcaccca actgatcttc agcatctttt    4320
actttcacca gcgtttctgg gtgagcaaaa acaggaaggc aaaatgccgc aaaaaaggga    4380
ataagggcga cacggaaatg ttgaatactc atactcttct ttttcaata ttattgaagc     4440 atttatcagg gttattgtct catgagcgga tacatatttg aatgtattta gaaaaataaa    4500
caaatagggg ttccgcgcac atttccccga aaagtgccac ctgacgtcta agaaaccatt    4560
attatcatga cattaaccta taaaaatagg cgtatcacga ggccccttc gtctcgcgcg     4620 tttcggtgat gacggtgaaa acctctgaca catgcagctc ccggagacgg tcacagcttg    4680
tctgtaagcg gatgccggga gcagacaagc ccgtcagggc gcgtcagcgg tgttggcgg    4740 gtgtcgggc tggcttaact atgcggcatc agagcagatt gtactgagag tgcaccatat    4800
gcggtgtgaa ataccgcaca gatgcgtaag gagaaaatac cgcatcagga aattgtaaac    4860
gttaatattt tgttaaaatt cgcgttaaat ttttgttaaa tcagctcatt ttttaaccaa    4920
taggccgaaa tcggcaaaat cccttataaa tcaaaagaat agaccgagat agggttgagt    4980
gttgttccag tttggaacaa gagtccacta ttaaagaacg tggactccaa cgtcaaaggg    5040
cgaaaaaccg tctatcaggg cgatggccca ctacgtgaac catcaccta atcaagtttt    5100 ttggggtcga ggtgccgtaa agcactaaat cggaacccta agggagccc ccgatttaga    5160 gcttgacggg gaaagccggc gaacgtggcg agaaaggaag ggaagaaagc gaaaggagcg    5220
ggcgctaggg cgctggcaag tgtagcggtc acgctgcgcg taaccaccac acccgccgcg    5280
cttaatgcgc cgctacaggg cgcgtcgcgc cattcgccat tcaggctacg caactgttgg    5340
gaagggcgat cggtgcgggc ctcttcgcta ttacgccagc tggcgaaggg gggatgtgct    5400
gcaaggcgat taagttgggt aacgccaggg ttttcccagt cacgacgttg taaaacgacg    5460
gccagtgaat t                                                         5471
```

<210> SEQ ID NO 81
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 81

```
Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
```

```
                100             105             110
Ser Arg Ser Glu Leu Arg Ser Phe Lys Phe Leu Leu Gln Glu Glu Ile
            115                 120                 125

Ser Lys Cys Lys Leu Asp Asp Met Asn Leu Leu Asp Ile Phe Ile
130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Gly Glu Glu Leu Cys Gly Val Met Thr
                180                 185                 190

Ile Ser Asp Ser Pro Arg Glu Gln Asp Ser Glu Ser Gln Thr Leu Asp
                195                 200                 205

Lys Val Tyr Gln Met Lys Ser Lys Pro Arg Gly Tyr Cys Leu Ile Ile
210                 215                 220

Asn Asn His Asn Phe Ala Lys Ala Arg Glu Lys Val Pro Lys Leu His
225                 230                 235                 240

Ser Ile Arg Asp Arg Asn Gly Thr His Leu Asp Ala Gly Ala Leu Thr
                245                 250                 255

Thr Thr Phe Glu Glu Leu His Phe Glu Ile Lys Pro His Asp Asp Cys
                260                 265                 270

Thr Val Glu Gln Ile Tyr Glu Ile Leu Lys Ile Tyr Gln Leu Met Asp
                275                 280                 285

His Ser Asn Met Asp Cys Phe Ile Cys Cys Ile Leu Ser His Gly Asp
            290                 295                 300

Lys Gly Ile Ile Tyr Gly Thr Asp Gly Gln Glu Ala Pro Ile Tyr Glu
305                 310                 315                 320

Leu Thr Ser Gln Phe Thr Gly Leu Lys Cys Pro Ser Leu Ala Gly Lys
                325                 330                 335

Pro Lys Val Phe Phe Ile Gln Ala Ser Gln Gly Asp Asn Tyr Gln Lys
                340                 345                 350

Gly Ile Pro Val Glu Thr Asp Ser Glu Glu Gln Pro Tyr Leu Glu Met
            355                 360                 365

Asp Leu Ser Ser Pro Gln Thr Arg Tyr Ile Pro Asp Glu Ala Asp Phe
            370                 375                 380

Leu Leu Gly Met Ala Thr Val Asn Asn Cys Val Ser Tyr Arg Asn Pro
385                 390                 395                 400

Ala Glu Gly Thr Trp Tyr Ile Gln Ser Leu Cys Gln Ser Leu Arg Glu
                405                 410                 415

Arg Cys Pro Arg Gly Asp Asp Ile Leu Thr Ile Leu Thr Glu Val Asn
                420                 425                 430

Tyr Glu Val Ser Asn Lys Asp Asp Lys Lys Asn Met Gly Lys Gln Met
            435                 440                 445

Pro Gln Pro Thr Phe Thr Leu Arg Lys Lys Leu Val Phe Pro Ser Asp
450                 455                 460

<210> SEQ ID NO 82
<211> LENGTH: 5327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
```

```
gtcgacttct gaggcggaaa gaaccagctg tggaatgtgt gtcagttagg gtgtggaaag    60
tccccaggct ccccagcagg cagaagtatg caaagcatgc atctcaatta gtcagcaacc   120
aggtgtggaa agtccccagg ctccccagca ggcagaagta tgcaaagcat gcatctcaat   180
tagtcagcaa ccatagtccc gccccctaact ccgcccatcc cgcccctaac tccgcccagt  240
tccgcccatt ctccgcccca tggctgacta attttttttta tttatgcaga ggccgaggcc  300
gcctcggcct ctgagctatt ccagaagtag tgaggaggct tttttggagg cctaggcttt   360
tgcaaaaagc tggatcgatc ctgagaactt cagggtgagt ttggggaccc ttgattgttc   420
tttcttttc gctattgtaa aattcatgtt atatggaggg ggcaaagttt tcagggtgtt   480
gtttagaatg ggaagatgtc ccttgtatca ccatggaccc tcatgataat tttgtttctt    540
tcactttcta ctctgttgac aaccattgtc tcctcttatt ttcttttcat tttctgtaac   600
ttttcgtta aactttagct tgcatttgta acgaatttt aaattcactt ttgtttattt   660
gtcagattgt aagtactttc tctaatcact ttttttttcaa ggcaatcagg gtatattata   720
ttgtacttca gcacagtttt agagaacaat tgttataatt aaatgataag gtagaatatt   780
tctgcatata aattctggct ggcgtggaaa tattcttatt ggtagaaaca actacatcct   840
ggtcatcatc ctgccttct ctttatggtt acaatgatat acactgtttg agatgaggat    900
aaaatactct gagtccaaac cgggcccctc tgctaaccat gttcatgcct tcttctttt   960
cctacagctc ctgggcaacg tgctggttat tgtgctgtct catcattttg gcaaagaatt  1020
gtaatacgac tcactatagg gcgaattcgg atccatggac gaagcggatc ggcggctcct  1080
gcggcggtgc cggctgcggc tggtggaaga gctgcaggtg gaccagctct gggacgccct  1140
gctgagccgc gagctgttca ggccccatat gatcgaggac atccagcggg caggctctgg  1200
atctcggcgg gatcaggcca ggcagctgat catagatctg gagactcgag ggagtcaggc  1260
tcttcctttg ttcatctcct gcttagagga cacaggccag gacatgctgg cttcgttct   1320
gcgaactaac aggcaagcag caaagttgtc gaagccaacc ctagaaaacc ttaccccagt  1380
ggtgctcaga ccagagattc gcaaaccaga ggttctcaga ccggaaacac ccagaccagt  1440
ggacattggt tctggaggat ttggtgatgt cggtgctctt gagagtttga ggggaaatgc  1500
agatttggct tacatcctga gcatggagcc ctgtggccac tgcctcatta tcaacaatgt  1560
gaacttctgc cgtgagtccg ggctccgcac ccgcactggc tccaacatcg actgtgagaa  1620
gttgcggcgt cgcttctcct cgctgcattt catggtggag gtgaagggcg acctgactgc  1680
caagaaaatg gtgctggctt tgctggagct ggcgcagcag gaccacggtg ctctggactg  1740
ctgcgtggtg gtcattctct ctcacggctg tcaggccagc cacctgcagt cccaggggc   1800
tgtctacgc acagatggat gccctgtgtc ggtcagaag attgtgaaca tcttcaatgg   1860
gaccagctgc cccagcctgg agggaagcc caagctcttt ttcatccagg cctctggtgg  1920
ggagcagaaa gaccatgggt ttgaggtggc ctccacttcc cctgaagacg agtcccctgg  1980
cagtaacccc gagccagatg ccaccccgtt ccaggaaggt ttgaggacct tcgaccagct  2040
ggacgccata tctagtttgc ccacacccag tgacatcttt gtgtcctact ctactttccc  2100
aggttttgtt tcctggaggg accccaagag tggctcctgg tacgttgaga ccctggacga  2160
catctttgag cagtgggctc actctgaaga cctgcagtcc ctcctgctta gggtcgctaa  2220
tgctgtttcg gtgaagggga tttataaaca gatgcctggt tgctttaatt tcctccggaa  2280
aaaactttc tttaaaacat cataaagatc ttattaaagc agaacttgtt tattgcagct  2340
tataatggtt acaaataaag caatagcatc acaaatttca caaataaagc atttttttca  2400
```

```
ctgcattcta gttgtggttt gtccaaactc atcaatgtat cttatcatgt ctggtcgact    2460
ctagactctt ccgcttcctc gctcactgac tcgctgcgct cggtcgttcg gctgcggcga    2520
gcggtatcag ctcactcaaa ggcggtaata cggttatcca cagaatcagg gataacgca     2580 ggaaagaaca tgtgagcaaa aggccagcaa aaggccagga accgtaaaaa ggccgcgttg    2640
ctggcgtttt tccataggct ccgcccccct gacgagcatc acaaaaatcg acgctcaagt    2700
cagaggtggc gaaacccgac aggactataa agataccagg cgtttccccc tggaagctcc    2760
ctcgtgcgct ctcctgttcc gaccctgccg cttaccggat acctgtccgc ctttctccct    2820
tcgggaagcg tggcgctttc tcaatgctca cgctgtaggt atctcagttc ggtgtaggtc    2880
gttcgctcca agctgggctg tgtgcacgaa ccccccgttc agcccgaccg ctgcgcctta    2940
tccggtaact atcgtcttga gtccaacccg gtaagacacg acttatcgcc actggcagca    3000
gccactggta acaggattag cagagcgagg tatgtaggcg gtgctacaga gttcttgaag    3060
tggtggccta actacggcta cactagaagg acagtatttg gtatctgcgc tctgctgaag    3120
ccagttacct tcggaaaaag agttggtagc tcttgatccg gcaaacaaac caccgctggt    3180
agcggtggtt tttttgtttg caagcagcag attacgcgca gaaaaaaagg atctcaagaa    3240
gatcctttga tcttttctac ggggtctgac gctcagtgga acgaaaactc acgttaaggg    3300
attttggtca tgagattatc aaaaaggatc ttcacctaga tccttttaaa ttaaaaatga    3360
agttttaaat caatctaaag tatatatgag taaacttggt ctgacagtta ccaatgctta    3420
atcagtgagg cacctatctc agcgatctgt ctatttcgtt catccatagt tgcctgactc    3480
cccgtcgtgt agataactac gatacgggag ggcttaccat ctggccccag tgctgcaatg    3540
ataccgcgag acccacgctc accggctcca gatttatcag caataaacca gccagccgga    3600
agggccgagc gcagaagtgg tcctgcaact ttatccgcct ccatccagtc tattaattgt    3660
tgccgggaag ctagagtaag tagttcgcca gttaatagtt tgcgcaacgt tgttgccatt    3720
gctacaggca tcgtggtgtc acgctcgtcg tttggtatgg cttcattcag ctccggttcc    3780
caacgatcaa ggcgagttac atgatccccc atgttgtgca aaaaagcggt tagctccttc    3840
ggtcctccga tcgttgtcag aagtaagttg gccgcagtgt tatcactcat ggttatggca    3900
gcactgcata attctcttac tgtcatgcca tccgtaagat gcttttctgt gactggtgag    3960
tactcaacca agtcattctg agaatagtgt atgcggcgac cgagttgctc ttgcccggcg    4020
tcaatacggg ataataccgc gccacatagc agaactttaa aagtgctcat cattggaaaa    4080
cgttcttcgg ggcgaaaact ctcaaggatc ttaccgctgt tgagatccag ttcgatgtaa    4140
cccactcgtg cacccaactg atcttcagca tcttttactt tcaccagcgt ttctgggtga    4200
gcaaaaacag gaaggcaaaa tgccgcaaaa aagggaataa gggcgacacg gaaatgttga    4260
atactcatac tcttcctttt tcaatattat tgaagcattt atcagggtta ttgtctcatg    4320
agcggataca tatttgaatg tatttagaaa aataaacaaa tagggggttcc gcgcacattt    4380 ccccgaaaag tgccacctga cgtctaagaa accattatta tcatgacatt aacctataaa    4440
aataggcgta tcacgaggcc ctttcgtct cgcgcgtttc ggtgatgacg gtgaaaacct    4500
ctgacacatg cagctcccgg agacggtcac agcttgtctg taagcggatg ccgggagcag    4560
acaagcccgt cagggcgcgt cagcgggtgt tggcgggtgt cggggctggc ttaactatgc    4620
ggcatcagag cagattgtac tgagagtgca ccatatgcgg tgtgaaatac cgcacagatg    4680
cgtaaggaga aaataccgca tcaggaaatt gtaaacgtta atattttgtt aaaattcgcg    4740
```

-continued

```
ttaaattttt gttaaatcag ctcattttt  aaccaatagg  ccgaaatcgg  caaaatccct    4800
tataaatcaa aagaatagac cgagataggg  ttgagtgttg  ttccagtttg  gaacaagagt    4860
ccactattaa agaacgtgga ctccaacgtc  aaagggcgaa  aaaccgtcta  tcagggcgat    4920
ggcccactac gtgaaccatc accctaatca  agttttttgg  ggtcgaggtg  ccgtaaagca    4980
ctaaatcgga accctaaagg gagccccga   tttagagctt  gacggggaaa  gccggcgaac    5040
gtggcgagaa aggaagggaa gaaagcgaaa  ggagcgggcg  ctagggcgct  ggcaagtgta    5100
gcggtcacgc tgcgcgtaac caccacaccc  gccgcgctta  atgcgccgct  acagggcgcg    5160
tcgcgccatt cgccattcag gctacgcaac  tgttgggaag  ggcgatcggt  gcgggcctct    5220
tcgctattac gccagctggc gaagggggga  tgtgctgcaa  ggcgattaag  ttgggtaacg    5280
ccagggtttt cccagtcacg acgttgtaaa  acgacggcca  gtgaatt                  5327
```

<210> SEQ ID NO 83
<211> LENGTH: 416
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

```
Met Asp Glu Ala Asp Arg Arg Leu Leu Arg Arg Cys Arg Leu Arg Leu
1               5                   10                  15

Val Glu Glu Leu Gln Val Asp Gln Leu Trp Asp Ala Leu Leu Ser Arg
            20                  25                  30

Glu Leu Phe Arg Pro His Met Ile Glu Asp Ile Gln Ala Gly Ser
        35                  40                  45

Gly Ser Arg Arg Asp Gln Ala Arg Gln Leu Ile Ile Asp Leu Glu Thr
    50                  55                  60

Arg Gly Ser Gln Ala Leu Pro Leu Phe Ile Ser Cys Leu Glu Asp Thr
65                  70                  75                  80

Gly Gln Asp Met Leu Ala Ser Phe Leu Arg Thr Asn Arg Gln Ala Ala
                85                  90                  95

Lys Leu Ser Lys Pro Thr Leu Glu Asn Leu Thr Pro Val Val Leu Arg
            100                 105                 110

Pro Glu Ile Arg Lys Pro Glu Val Leu Arg Pro Glu Thr Pro Arg Pro
        115                 120                 125

Val Asp Ile Gly Ser Gly Gly Phe Gly Asp Val Gly Ala Leu Glu Ser
    130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
            180                 185                 190

Arg Phe Ser Ser Leu His Phe Met Val Glu Val Lys Gly Asp Leu Thr
        195                 200                 205

Ala Lys Lys Met Val Leu Ala Leu Leu Glu Leu Ala Gln Gln Asp His
    210                 215                 220

Gly Ala Leu Asp Cys Cys Val Val Val Ile Leu Ser His Gly Cys Gln
225                 230                 235                 240

Ala Ser His Leu Gln Phe Pro Gly Ala Val Tyr Gly Thr Asp Gly Cys
                245                 250                 255
```

```
Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Ser Gly
        275                 280                 285

Gly Glu Gln Lys Asp His Gly Phe Glu Val Ala Ser Thr Ser Pro Glu
        290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                325                 330                 335

Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
        355                 360                 365

Asp Ile Phe Glu Gln Trp Ala His Ser Glu Asp Leu Gln Ser Leu Leu
        370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
            405                 410                 415

<210> SEQ ID NO 84
<211> LENGTH: 1819
<212> TYPE: DNA
<213> ORGANISM: Mus musculus

<400> SEQUENCE: 84
gaattccggg ctggattgag aagccgcaac tgtgactctg catcatgaat actctgtctg      60
aaggaaatgg caccttttgcc atccatcttt tgaagatgct atgtcaaagc aacccttcca    120
aaaatgtatg ttattctcct gcgagcatct cctctgctct agctatggtt ctcttgggtg    180
caaagggaca gacggcagtc cagatatctc aggcacttgg tttgaataaa gaggaaggca    240
tccatcaggg tttccagttg cttctcagga agctgaacaa gccagacaga aagtactctc    300
ttagagtggc aacaggctc tttgcagaca aaacttgtga agtcctccaa acctttaagg    360
agtcctctct tcacttctat gactcagaga tggagcagct ctcctttgct gaagaagcag    420
aggtgtccag gcaacacata aacacatggg tctccaaaca aactgaaggt aaaattccag    480
agttgttgtc aggtggctcc gtcgattcag aaaccaggct ggttctcatc aatgccttat    540
attttaaagg aaagtggcat caaccattta caaagagta cacaatggac atgcccttta    600
aaataaacaa ggatgagaaa aggccagtgc agatgatgtg tcgtgaagac acatataacc    660
tcgcctatgt gaaggaggtg caggcgcaag tgctggtgat gccatatgaa ggaatggagc    720
tgagcttggt ggttctgctc ccagatgagg gtgtggacct cagcaaggtg gaaaacaatc    780
tcacttttga gaagttaaca gcctggatgg aagcagattt tatgaagagc actgatgttg    840
aggttttcct tccaaaattt aaactccaag aggattatga catggagtct ctgtttcagc    900
gcttgggagt ggtggatgtc ttccaagagg acaaggctga cttatcagga atgtctccag    960
agagaaacct gtgtgtgtcc aagtttgttc cagagtgt agtggagatc aatgaggaag   1020
gcacagaggc tgcagcagcc tctgccatca tagaatttg ctgtgcctct tctgtcccaa   1080
cattctgtgc tgaccacccc ttccttttct tcatcaggca caacaaagca acagcatcc   1140 tgttctgtgg caggttctca tctccataaa gacacatata ctacagggg agagttctct   1200 cttcagtatc cctaccactc ctacagctct gtcaagatgg gcaagtaggg ggaagtcatg   1260
```

```
ttctaagatg aagacacttt ccttctctgt cagcctgatc ttataatgcc tgcattcaac   1320
tctccctgtc ttgaatgcat ctatgccctt taccaggtta tgtctaatga tgccaaatac   1380
cttctgctat gctattgatt gatagcctag ccagtaattt atagccagtt agaactgact   1440
tgactgtgca agaatgctat aatggagcta gagagaaggc acaaacacta ggaaaggttg   1500 ctgttttgc agaggacaca gggacatttc ccaccactca catggctgct acaacctct    1560 ggaaattcca gttctgtcc atgacttgat tcctttcttt ggcttctact ggctccagca    1620
tcctgcacat acatgtatcg tcattcagtt acacacaaac aagtaaaatt ttaaaaataa   1680
ataaaaattt aaagagagag tctaaaattt tagtaatggt tagataatag ctgctattgt   1740 gccttttca ggttttaatg tcattattct tgtgtataaa gtcaataatt tataggaaaa    1800
catcagtgcc ccggaattc                                                1819
```

<210> SEQ ID NO 85
<211> LENGTH: 374
<212> TYPE: PRT
<213> ORGANISM: Mus musculus

<400> SEQUENCE: 85

```
Met Asn Thr Leu Ser Glu Gly Asn Gly Thr Phe Ala Ile His Leu Leu
1               5                   10                  15

Lys Met Leu Cys Gln Ser Asn Pro Ser Lys Asn Val Cys Tyr Ser Pro
            20                  25                  30

Ala Ser Ile Ser Ser Ala Leu Ala Met Val Leu Leu Gly Ala Lys Gly
        35                  40                  45

Gln Thr Ala Val Gln Ile Ser Gln Ala Leu Gly Leu Asn Lys Glu Glu
    50                  55                  60

Gly Ile His Gln Gly Phe Gln Leu Leu Leu Arg Lys Leu Asn Lys Pro
65                  70                  75                  80

Asp Arg Lys Tyr Ser Leu Arg Val Ala Asn Arg Leu Phe Ala Asp Lys
                85                  90                  95

Thr Cys Glu Val Leu Gln Thr Phe Lys Glu Ser Ser Leu His Phe Tyr
            100                 105                 110

Asp Ser Glu Met Glu Gln Leu Ser Phe Ala Glu Glu Ala Glu Val Ser
        115                 120                 125

Arg Gln His Ile Asn Thr Trp Val Ser Lys Gln Thr Glu Gly Lys Ile
    130                 135                 140

Pro Glu Leu Leu Ser Gly Gly Ser Val Asp Ser Glu Thr Arg Leu Val
145                 150                 155                 160

Leu Ile Asn Ala Leu Tyr Phe Lys Gly Lys Trp His Gln Pro Phe Met
                165                 170                 175

Lys Glu Tyr Thr Met Asp Met Pro Phe Lys Ile Asn Lys Asp Glu Lys
            180                 185                 190

Arg Pro Val Gln Met Met Cys Arg Glu Asp Thr Tyr Asn Leu Ala Tyr
        195                 200                 205

Val Lys Glu Val Gln Ala Gln Val Leu Val Met Pro Tyr Glu Gly Met
    210                 215                 220

Glu Leu Ser Leu Val Val Leu Pro Asp Glu Gly Val Asp Leu Ser
225                 230                 235                 240

Lys Val Glu Asn Asn Leu Thr Phe Glu Lys Leu Thr Ala Trp Met Glu
                245                 250                 255

Ala Asp Phe Met Lys Ser Thr Asp Val Glu Val Phe Leu Pro Lys Phe
            260                 265                 270
```

```
Lys Leu Gln Glu Asp Tyr Asp Met Glu Ser Leu Phe Gln Arg Leu Gly
            275                 280                 285

Val Val Asp Val Phe Gln Glu Asp Lys Ala Asp Leu Ser Gly Met Ser
        290                 295                 300

Pro Glu Arg Asn Leu Cys Val Ser Lys Phe Val His Gln Ser Val Val
305                 310                 315                 320

Glu Ile Asn Glu Glu Gly Thr Glu Ala Ala Ala Ser Ala Ile Ile
                325                 330                 335

Glu Phe Cys Cys Ala Ser Ser Val Pro Thr Phe Cys Ala Asp His Pro
                340                 345                 350

Phe Leu Phe Phe Ile Arg His Asn Lys Ala Asn Ser Ile Leu Phe Cys
            355                 360                 365

Gly Arg Phe Ser Ser Pro
        370

<210> SEQ ID NO 86
<211> LENGTH: 1125
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
atgaatactc tgtctgaagg aaatggcacc tttgccatcc atcttttgaa gatgctatgt      60
caaagcaacc cttccaaaaa tgtatgttat tctcctgcga gcatctcctc tgctctagct     120
atggttctct ggggtgcaaa gggacagacg gcagtccaga tatctcaggc acttggtttg     180
aataaagagg aaggcatcca tcagggtttc cagttgcttc tcaggaagct gaacaagcca     240
gacagaaagt actctcttag agtggccaac aggctctttg cagacaaaac ttgtgaagtc     300
ctccaaacct taaggagtc ctctcttcac ttctatgact cagagatgga gcagctctcc     360
tttgctgaag aagcagaggt gtccaggcaa cacataaaca catgggtctc caaacaaact     420
gaaggtaaaa ttccagagtt gttgtcaggt ggctccgtcg attcagaaac caggctggtt     480
ctcatcaatg ccttatattt taaggaaag tggcatcaac catttaacaa agagtacaca     540
atggacatgc cctttaaaat aaacaaggat gagaaaaggc cagtgcagat gatgtgtcgt     600
gaagacacat ataacctcgc ctatgtgaag gaggtgcagg cgcaagtgct ggtgatgcca     660
tatgaaggaa tggagctgag cttggtggtt ctgctcccag atgagggtgt ggacctcagc     720
aaggtggaaa caatctcac ttttgagaag ttaacagcct ggatggaagc agattttatg     780
aagagcactg atgttgaggt tttccttcca aaatttaaac tccaagagga ttatgacatg     840
gagtctctgt ttcagcgctt gggagtggtg gatgtcttcc aagaggacaa ggctgactta     900
tcaggaatgt ctccagagag aaacctgtgt gtgtccaagt tgttcaccaa gagtgtagtg     960
gagatcaatg aggaaggcag agaggctgca gcagcctctg ccatcataga attttgctgt    1020
gcctcttctg tcccaacatt ctgtgctgac cacccctcc ttttcttcat caggcacaac    1080
aaagcaaaca gcatcctgtt ctgtggcagg ttctcatctc cataa                     1125

<210> SEQ ID NO 87
<211> LENGTH: 374
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 87

```
Met Asn Thr Leu Ser Glu Gly Asn Gly Thr Phe Ala Ile His Leu Leu
1               5                   10                  15
Lys Met Leu Cys Gln Ser Asn Pro Ser Lys Asn Val Cys Tyr Ser Pro
            20                  25                  30
Ala Ser Ile Ser Ser Ala Leu Ala Met Val Leu Leu Gly Ala Lys Gly
        35                  40                  45
Gln Thr Ala Val Gln Ile Ser Gln Ala Leu Gly Leu Asn Lys Glu Glu
    50                  55                  60
Gly Ile His Gln Gly Phe Gln Leu Leu Arg Lys Leu Asn Lys Pro
65                  70                  75                  80
Asp Arg Lys Tyr Ser Leu Arg Val Ala Asn Arg Leu Phe Ala Asp Lys
                85                  90                  95
Thr Cys Glu Val Leu Gln Thr Phe Lys Glu Ser Ser Leu His Phe Tyr
            100                 105                 110
Asp Ser Glu Met Glu Gln Leu Ser Phe Ala Glu Ala Glu Val Ser
        115                 120                 125
Arg Gln His Ile Asn Thr Trp Val Ser Lys Gln Thr Glu Gly Lys Ile
    130                 135                 140
Pro Glu Leu Leu Ser Gly Gly Ser Val Asp Ser Glu Thr Arg Leu Val
145                 150                 155                 160
Leu Ile Asn Ala Leu Tyr Phe Lys Gly Lys Trp His Gln Pro Phe Asn
                165                 170                 175
Lys Glu Tyr Thr Met Asp Met Pro Phe Lys Ile Asn Lys Asp Glu Lys
            180                 185                 190
Arg Pro Val Gln Met Met Cys Arg Glu Asp Thr Tyr Asn Leu Ala Tyr
        195                 200                 205
Val Lys Glu Val Gln Ala Gln Val Leu Val Met Pro Tyr Glu Gly Met
    210                 215                 220
Glu Leu Ser Leu Val Val Leu Leu Pro Asp Glu Gly Val Asp Leu Ser
225                 230                 235                 240
Lys Val Glu Asn Asn Leu Thr Phe Glu Lys Leu Thr Ala Trp Met Glu
                245                 250                 255
Ala Asp Phe Met Lys Ser Thr Asp Val Glu Val Phe Leu Pro Lys Phe
            260                 265                 270
Lys Leu Gln Glu Asp Tyr Asp Met Glu Ser Leu Phe Gln Arg Leu Gly
        275                 280                 285
Val Val Asp Val Phe Gln Glu Asp Lys Ala Asp Leu Ser Gly Met Ser
    290                 295                 300
Pro Glu Arg Asn Leu Cys Val Ser Lys Phe Val His Gln Ser Val Val
305                 310                 315                 320
Glu Ile Asn Glu Glu Gly Arg Glu Ala Ala Ala Ser Ala Ile Ile
                325                 330                 335
Glu Phe Cys Cys Ala Ser Ser Val Pro Thr Phe Cys Ala Asp His Pro
            340                 345                 350
Phe Leu Phe Phe Ile Arg His Asn Lys Ala Asn Ser Ile Leu Phe Cys
        355                 360                 365
Gly Arg Phe Ser Ser Pro
    370
```

<210> SEQ ID NO 88
<211> LENGTH: 6539
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 88

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag cttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaacgg gccctctaga ctcgagcggc cgccactgtg ctggatatct gcagaattca     960
tgaatactct gtctgaagga aatggcacct ttgccatcca tcttttgaag atgctatgtc    1020
aaagcaaccc ttccaaaaat gtatgttatt ctcctgcgag catctcctct gctctagcta    1080
tggttctctt gggtgcaaag ggacagacgg cagtccagat atctcaggca cttggtttga    1140
ataaagagga aggcatccat cagggtttcc agttgcttct caggaagctg aacaagccag    1200
acagaaagta ctctcttaga gtggccaaca ggctctttgc agacaaaact tgtgaagtcc    1260
tccaaacctt taaggagtcc tctcttcact tctatgactc agagatggag cagctctcct    1320
ttgctgaaga agcagaggtg tccaggcaac acataaacac atgggtctcc aaacaaactg    1380
aaggtaaaat tccagagttg ttgtcaggtg gctccgtcga ttcagaaacc aggctggttc    1440
tcatcaatgc cttatatttt aaggaaagt ggcatcaacc atttaacaaa gagtacacaa    1500
tggacatgcc ctttaaaata aacaaggatg agaaaaggcc agtgcagatg atgtgtcgtg    1560
aagacacata taacctcgcc tatgtgaagg aggtgcaggc gcaagtgctg gtgatgccat    1620
atgaaggaat ggagctgagc ttggtggttc tgctcccaga tgagggtgtg gacctcagca    1680
aggtggaaaa caatctcact tttgagaagt taacagcctg gatggaagca gattttatga    1740
agagcactga tgttgaggtt ttccttccaa aatttaaact ccaagaggat tatgacatgg    1800
agtctctgtt tcagcgcttg ggagtggtgg atgtcttcca agaggacaag gctgacttat    1860
caggaatgtc tccagagaga aacctgtgtg tgtccaagtt tgttcaccag agtgtagtgg    1920
agatcaatga ggaaggcaca gaggctgcag cagcctctgc catcatagaa ttttgctgtg    1980
cctcttctgt cccaacattc tgtgctgacc accccttcct tttcttcatc aggcacaaca    2040
aagcaaacag catcctgttc tgtggcaggt tctcatctcc ataaggatcc gagctcggta    2100
ccaagcttaa gtttaaaccg ctgatcagcc tcgactgtgc cttctagttg ccagccatct    2160
```

```
gttgtttgcc cctcccccgt gccttccttg accctggaag gtgccactcc cactgtcctt    2220
tcctaataaa atgaggaaat tgcatcgcat tgtctgagta ggtgtcattc tattctgggg    2280
ggtggggtgg ggcaggacag caaggggag gattgggaag acaatagcag gcatgctggg    2340
gatgcggtgg gctctatggc ttctgaggcg gaaagaacca gctggggctc tagggggtat    2400
ccccacgcgc cctgtagcgg cgcattaagc gcggcgggtg tggtggttac gcgcagcgtg    2460
accgctacac ttgccagcgc cctagcgccc gctccttcg ctttcttccc ttcctttctc    2520
gccacgttcg ccggctttcc ccgtcaagct ctaaatcggg gcatcccttt agggttccga    2580
tttagtgctt tacggcacct cgaccccaaa aaacttgatt agggtgatgg ttcacgtagt    2640
gggccatcgc cctgatagac ggttttttcgc cctttgacgt tggagtccac gttctttaat    2700
agtggactct tgttccaaac tggaacaaca ctcaaccta tctcggtcta ttcttttgat    2760
ttataaggga ttttggggat tcggcctat tggttaaaaa atgagctgat ttaacaaaaa    2820
tttaacgcga attaattctg tggaatgtgt gtcagttagg gtgtggaaag tccccaggct    2880
ccccaggcag gcagaagtat gcaaagcatg catctcaatt agtcagcaac caggtgtgga    2940
aagtccccag gctccccagc aggcagaagt atgcaaagca tgcatctcaa ttagtcagca    3000
accatagtcc cgcccctaac tccgcccatc ccgcccctaa ctccgccag ttccgcccat    3060 tctccgcccc atggctgact aattttttt atttatgcag aggccgaggc cgcctctgcc    3120
tctgagctat tccagaagta gtgaggaggc ttttttggag gcctaggctt ttgcaaaaag    3180
ctcccgggag cttgtatatc cattttcgga tctgatcaag agacaggatg aggatcgttt    3240
cgcatgattg aacaagatgg attgcacgca ggttctccgg ccgcttgggt ggagaggcta    3300
ttcggctatg actgggcaca acagacaatc ggctgctctg atgccgccgt gttccggctg    3360
tcagcgcagg ggcgcccggt tctttttgtc aagaccgacc tgtccggtgc cctgaatgaa    3420
ctgcaggacg aggcagcgcg gctatcgtgg ctggccacga cgggcgttcc ttgcgcagct    3480
gtgctcgacg ttgtcactga agcgggaagg gactggctgc tattgggcga agtgccgggg    3540
caggatctcc tgtcatctca ccttgctcct gccgagaaag tatccatcat ggctgatgca    3600
atgcggcggc tgcatacgct tgatccggct acctgcccat tcgaccacca agcgaaacat    3660
cgcatcgagc gagcacgtac tcggatggaa gccggtcttg tcgatcagga tgatctggac    3720
gaagagcatc aggggctcgc gccagccgaa ctgttcgcca ggctcaaggc gcgcatgccc    3780
gacggcgagg atctcgtcgt gacccatggc gatgcctgct tgccgaatat catggtggaa    3840
aatggccgct tttctggatt catcgactgt ggccggctgg gtgtggcgga ccgctatcag    3900
gacatagcgt tggctacccg tgatattgct gaagagcttg gcggcgaatg ggctgaccgc    3960
ttcctcgtgc tttacggtat cgccgctccc gattcgcagc gcatcgcctt ctatcgcctt    4020
cttgacgagt tcttctgagc gggactctgg ggttcgaaat gaccgaccaa gcgacgccca    4080
acctgccatc acgagatttc gattccaccg ccgccttcta tgaaaggttg ggcttcggaa    4140
tcgttttccg ggacgccggc tggatgatcc tccagcgcgg ggatctcatg ctggagttct    4200
tcgcccaccc caacttgttt attgcagctt ataatggtta caaataaagc aatagcatca    4260
caaatttcac aaataaagca ttttttcac tgcattctag ttgtggtttg tccaaactca    4320
tcaatgtatc ttatcatgtc tgtataccgt cgacctctag ctagagcttg gcgtaatcat    4380
ggtcatagct gtttcctgtg tgaaattgtt atccgctcac aattccacac aacatacgag    4440
ccggaagcat aaagtgtaaa gcctggggtg cctaatgagt gagctaactc acattaattg    4500
cgttgcgctc actgcccgct ttccagtcgg gaaacctgtc gtgccagctg cattaatgaa    4560
```

```
tcggccaacg cgcggggaga ggcggtttgc gtattgggcg ctcttccgct tcctcgctca    4620
ctgactcgct gcgctcggtc gttcggctgc ggcgagcggt atcagctcac tcaaaggcgg    4680
taatacggtt atccacagaa tcaggggata cgcaggaaaa gaacatgtga gcaaaaggcc    4740
agcaaaaggc caggaaccgt aaaaaggccg cgttgctggc gtttttccat aggctccgcc    4800 ccccctgacga gcatcacaaa aatcgacgct caagtcagag gtggcgaaac ccgacaggac    4860
tataaagata ccaggcgttt ccccctggaa gctccctcgt gcgctctcct gttccgaccc    4920
tgccgcttac cggatacctg tccgcctttc tcccttcggg aagcgtggcg ctttctcaat    4980
gctcacgctg taggtatctc agttcggtgt aggtcgttcg ctccaagctg ggctgtgtgc    5040
acgaaccccc cgttcagccc gaccgctgcg ccttatccgg taactatcgt cttgagtcca    5100
acccggtaag acacgactta tcgccactgg cagcagccac tggtaacagg attagcagag    5160
cgaggtatgt aggcggtgct acagagttct tgaagtggtg gcctaactac ggctacacta    5220
gaaggacagt atttggtatc tgcgctctgc tgaagccagt taccttcgga aaaagagttg    5280
gtagctcttg atccggcaaa caaaccaccg ctggtagcgg tggttttttt gtttgcaagc    5340
agcagattac gcgcagaaaa aaaggatctc aagaagatcc tttgatcttt tctacggggt    5400
ctgacgctca gtggaacgaa aactcacgtt aagggatttt ggtcatgaga ttatcaaaaa    5460
ggatcttcac ctagatcctt ttaaattaaa aatgaagttt taaatcaatc taagtatat     5520 atgagtaaac ttggtctgac agttaccaat gcttaatcag tgaggcacct atctcagcga    5580
tctgtctatt tcgttcatcc atagttgcct gactccccgt cgtgtagata actacgatac    5640
gggagggctt accatctggc cccagtgctg caatgatacc gcgagaccca cgctcaccgg    5700
ctccagattt atcagcaata aaccagccag ccggaagggc cgagcgcaga agtggtcctg    5760
caactttatc cgcctccatc cagtctatta attgttgccg ggaagctaga gtaagtagtt    5820
cgccagttaa tagtttgcgc aacgttgttg ccattgctac aggcatcgtg gtgtcacgct    5880
cgtcgtttgg tatggcttca ttcagctccg gttcccaacg atcaaggcga gttacatgat    5940
cccccatgtt gtgcaaaaaa gcggttagct ccttcggtcc tccgatcgtt gtcagaagta    6000
agttggccgc agtgttatca ctcatggtta tggcagcact gcataattct cttactgtca    6060
tgccatccgt aagatgcttt tctgtgactg gtgagtactc aaccaagtca ttctgagaat    6120
agtgtatgcg gcgaccgagt tgctcttgcc cggcgtcaat acgggataat accgcgccac    6180
atagcagaac tttaaaagtg ctcatcattg gaaaacgttc ttcggggcga aaactctcaa    6240
ggatcttacc gctgttgaga tccagttcga tgtaacccac tcgtgcaccc aactgatctt    6300
cagcatcttt tactttcacc agcgtttctg ggtgagcaaa aacaggaagg caaaatgccg    6360
caaaaaaggg aataagggcg acacggaaat gttgaatact catactcttc ctttttcaat    6420
attattgaag catttatcag ggttattgtc tcatgagcgg atacatattt gaatgtattt    6480
agaaaaataa acaaataggg gttccgcgca catttccccg aaaagtgcca cctgacgtc     6539
```

<210> SEQ ID NO 89
<211> LENGTH: 6539
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 89

```
gacggatcgg gagatctccc gatcccctat ggtcgactct cagtacaatc tgctctgatg      60
```

-continued

```
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggac tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaacgg gccctctaga ctcgagcggc cgccactgtg ctggatatct gcagaattca      960
tgaatactct gtctgaagga aatggcacct ttgccatcca tcttttgaag atgctatgtc     1020
aaagcaaccc ttccaaaaat gtatgttatt ctcctgcgag catctcctct gctctagcta     1080
tggttctctt gggtgcaaag ggacagacgg cagtccagat atctcaggca cttggtttga     1140
ataaagagga aggcatccat cagggtttcc agttgcttct caggaagctg aacaagccag     1200
acagaaagta ctctcttaga gtggccaaca ggctctttgc agacaaaact tgtgaagtcc     1260
tccaaacctt taaggagtcc tctcttcact tctatgactc agagatggag cagctctcct     1320
ttgctgaaga agcagaggtg tccaggcaac acataaacac atgggtctcc aaacaaactg     1380
aaggtaaaat tccagagttg ttgtcaggtg gctccgtcga ttcagaaacc aggctggttc     1440
tcatcaatgc cttatatttt aaaggaaagt ggcatcaacc atttaacaaa gagtacacaa     1500
tggacatgcc ctttaaaata aacaaggatg agaaaaggcc agtgcagatg atgtgtcgtg     1560
aagacacata taacctcgcc tatgtgaagg aggtgcaggc gcaagtgctg gtgatgccat     1620
atgaaggaat ggagctgagc ttggtggttc tgctcccaga tgagggtgtg acctcagca      1680 aggtggaaaa caatctcact tttgagaagt taacagcctg gatggaagca gattttatga     1740
agagcactga tgttgaggtt ttccttccaa aatttaaact ccaagaggat tatgacatgg     1800
agtctctgtt tcagcgcttg ggagtggtgg atgtcttcca agaggacaag gctgacttat     1860
caggaatgtc tccagagaga aacctgtgtg tgtccaagtt tgttcaccag agtgtagtgg     1920
agatcaatga ggaaggcaga gaggctgcag cagcctctgc catcatagaa ttttgctgtg     1980
cctcttctgt cccaacattc tgtgctgacc accccttcct tttcttcatc aggcacaaca     2040
aagcaaacag catcctgttc tgtggcaggt tctcatctcc ataaggatcc gagctcggta     2100
ccaagcttaa gtttaaaccg ctgatcagcc tcgactgtgc cttctagttg ccagccatct     2160
gttgtttgcc cctcccccgt gccttccttg accctggaag gtgccactcc cactgtcctt     2220
tcctaataaa atgaggaaat tgcatcgcat tgtctgagta ggtgtcattc tattctgggg     2280 ggtgggggtgg ggcaggacag caaggggggag gattgggaag acaatagcag gcatgctggg     2340
gatgcggtgg gctctatggc ttctgaggcg gaaagaacca gctggggctc tagggggtat     2400
```

```
ccccacgcgc cctgtagcgg cgcattaagc gcggcgggtg tggtggttac gcgcagcgtg    2460
accgctacac ttgccagcgc cctagcgccc gctcctttcg ctttcttccc ttcctttctc    2520
gccacgttcg ccggctttcc ccgtcaagct ctaaatcggg gcatcccttt agggttccga    2580
tttagtgctt tacggcacct cgaccccaaa aaacttgatt agggtgatgg ttcacgtagt    2640
gggccatcgc cctgatagac ggttttttcgc cctttgacgt tggagtccac gttctttaat    2700
agtggactct tgttccaaac tggaacaaca ctcaacccta tctcggtcta ttcttttgat    2760
ttataaggga ttttggggat tcggcctat tggttaaaaa atgagctgat ttaacaaaaa    2820
tttaacgcga attaattctg tggaatgtgt gtcagttagg gtgtggaaag tccccaggct    2880
ccccaggcag gcagaagtat gcaaagcatg catctcaatt agtcagcaac caggtgtgga    2940
aagtccccag gctccccagc aggcagaagt atgcaaagca tgcatctcaa ttagtcagca    3000
accatagtcc cgcccctaac tccgcccatc ccgcccctaa ctccgcccag ttccgcccat    3060
tctccgcccc atggctgact aattttttt atttatgcag aggccgaggc cgcctctgcc    3120
tctgagctat tccagaagta gtgaggaggc ttttttggag gcctaggctt ttgcaaaaag    3180
ctcccgggag cttgtatatc cattttcgga tctgatcaag agacaggatg aggatcgttt    3240
cgcatgattg aacaagatgg attgcacgca ggttctccgg ccgcttgggt ggagaggcta    3300
ttcggctatg actgggcaca acagacaatc ggctgctctg atgccgccgt gttccggctg    3360
tcagcgcagg ggcgcccggt tctttttgtc aagaccgacc tgtccggtgc cctgaatgaa    3420
ctgcaggacg aggcagcgcg gctatcgtgg ctggccacga cgggcgttcc ttgcgcagct    3480
gtgctcgacg ttgtcactga agcgggaagg gactggctgc tattgggcga agtgccgggg    3540
caggatctcc tgtcatctca ccttgctcct gccgagaaag tatccatcat ggctgatgca    3600
atgcggcggc tgcatacgct tgatccggct acctgcccat tcgaccacca agcgaaacat    3660
cgcatcgagc gagcacgtac tcggatggaa gccggtcttg tcgatcagga tgatctggac    3720
gaagagcatc aggggctcgc gccagccgaa ctgttcgcca ggctcaaggc gcgcatgccc    3780
gacggcgagg atctcgtcgt gacccatggc gatgcctgct tgccgaatat catggtggaa    3840
aatggccgct tttctggatt catcgactgt ggccggctgg gtgtggcgga ccgctatcag    3900
gacatagcgt tggctacccg tgatattgct gaagagcttg gcggcgaatg gctgaccgc    3960 ttcctcgtgc tttacggtat cgccgctccc gattcgcagc gcatcgcctt ctatcgcctt    4020
cttgacgagt tcttctgagc gggactctgg ggttcgaaat gaccgaccaa gcgacgccca    4080
acctgccatc acgagatttc gattccaccg ccgccttcta tgaaaggttg gcttcggaa    4140 tcgtttttccg ggacgccggc tggatgatcc tccagcgcgg ggatctcatg ctggagttct    4200
tcgcccaccc caacttgttt attgcagctt ataatggtta caaataaagc aatagcatca    4260
caaatttcac aaataaagca tttttttcac tgcattctag ttgtggtttg tccaaactca    4320
tcaatgtatc ttatcatgtc tgtataccgt cgacctctag ctagagcttg gcgtaatcat    4380
ggtcatagct gtttcctgtg tgaaattgtt atccgctcac aattccacac aacatacgag    4440
ccggaagcat aaagtgtaaa gcctggggtg cctaatgagt gagctaactc acattaattg    4500
cgttgcgctc actgcccgct ttccagtcgg gaaacctgtc gtgccagctg cattaatgaa    4560
tcggccaacg cgcggggaga ggcggtttgc gtattgggcg ctcttccgct tcctcgctca    4620
ctgactcgct gcgctcggtc gttcggctgc ggcgagcggt atcagctcac tcaaaggcgg    4680
taatacggtt atccacagaa tcaggggata acgcaggaaa gaacatgtga gcaaaaggcc    4740
agcaaaaggc caggaaccgt aaaaaggccg cgttgctggc gttttccat aggctccgcc    4800
```

| | | | | |
|---|---|---|---|---|
| cccctgacga | gcatcacaaa | aatcgacgct | caagtcagag | gtggcgaaac  ccgacaggac | 4860 |
| tataaagata | ccaggcgttt | cccctggaa | gctccctcgt | gcgctctcct  gttccgaccc | 4920 |
| tgccgcttac | cggatacctg | tccgcctttc | tccttcggg | aagcgtggcg  ctttctcaat | 4980 |
| gctcacgctg | taggtatctc | agttcggtgt | aggtcgttcg | ctccaagctg  gctgtgtgc | 5040 |
| acgaaccccc | cgttcagccc | gaccgctgcg | ccttatccgg | taactatcgt  cttgagtcca | 5100 |
| acccggtaag | acacgactta | tcgccactgg | cagcagccac | tggtaacagg  attagcagag | 5160 |
| cgaggtatgt | aggcggtgct | acagagttct | tgaagtggtg | gcctaactac  ggctacacta | 5220 |
| gaaggacagt | atttggtatc | tgcgctctgc | tgaagccagt | taccttcgga  aaaagagttg | 5280 |
| gtagctcttg | atccggcaaa | caaccaccg | ctggtagcgg | tggtttttt  gtttgcaagc | 5340 |
| agcagattac | gcgcagaaaa | aaaggatctc | aagaagatcc | tttgatcttt  tctacggggt | 5400 |
| ctgacgctca | gtggaacgaa | aactcacgtt | aagggatttt | ggtcatgaga  ttatcaaaaa | 5460 |
| ggatcttcac | ctagatcctt | ttaaattaaa | aatgaagttt | taaatcaatc  taaagtatat | 5520 |
| atgagtaaac | ttggtctgac | agttaccaat | gcttaatcag | tgaggcacct  atctcagcga | 5580 |
| tctgtctatt | tcgttcatcc | atagttgcct | gactccccgt | cgtgtagata  actacgatac | 5640 |
| gggagggctt | accatctggc | cccagtgctg | caatgatacc | gcgagaccca  cgctcaccgg | 5700 |
| ctccagattt | atcagcaata | aaccagccag | ccggaagggc | cgagcgcaga  agtggtcctg | 5760 |
| caactttatc | cgcctccatc | cagtctatta | attgttgccg | ggaagctaga  gtaagtagtt | 5820 |
| cgccagttaa | tagtttgcgc | aacgttgttg | ccattgctac | aggcatcgtg  gtgtcacgct | 5880 |
| cgtcgtttgg | tatggcttca | ttcagctccg | gttcccaacg | atcaaggcga  gttacatgat | 5940 |
| cccccatgtt | gtgcaaaaaa | gcggttagct | ccttcggtcc | tccgatcgtt  gtcagaagta | 6000 |
| agttggccgc | agtgttatca | ctcatggtta | tggcagcact | gcataattct  cttactgtca | 6060 |
| tgccatccgt | aagatgcttt | tctgtgactg | gtgagtactc | aaccaagtca  ttctgagaat | 6120 |
| agtgtatgcg | gcgaccgagt | tgctcttgcc | cggcgtcaat | acgggataat  accgcgccac | 6180 |
| atagcagaac | tttaaaagtg | ctcatcattg | gaaaacgttc | ttcggggcga  aaactctcaa | 6240 |
| ggatcttacc | gctgttgaga | tccagttcga | tgtaacccac | tcgtgcaccc  aactgatctt | 6300 |
| cagcatcttt | tactttcacc | agcgtttctg | ggtgagcaaa | aacaggaagg  caaaatgccg | 6360 |
| caaaaaggg | aataagggcg | acacggaaat | gttgaatact | catactcttc  cttttttcaat | 6420 |
| attattgaag | catttatcag | ggttattgtc | tcatgagcgg | atacatattt  gaatgtattt | 6480 |
| agaaaaataa | acaaataggg | gttccgcgca | catttccccg | aaaagtgcca  cctgacgtc | 6539 |

<210> SEQ ID NO 90
<211> LENGTH: 810
<212> TYPE: DNA
<213> ORGANISM: Homo sapiens

<400> SEQUENCE: 90

| | | | | |
|---|---|---|---|---|
| atggatgacc | agcgcgacct | tatctccaac | aatgagcaac | tgcccatgct  gggccggcgc | 60 |
| cctggggccc | cggagagcaa | gtgcagccgc | ggagccctgt | acacaggctt  ttccatcctg | 120 |
| gtgactctgc | tcctcgctgg | ccaggccacc | accgcctact | tcctgtacca  gcagcagggc | 180 |
| cggctggaca | aactgacagt | cacctcccag | aacctgcagc | tggagaacct  gcgcatgaag | 240 |
| cttgccaagt | tcgtggctgc | ctggaccctg | aaggctgccg | ctgccctgcc  caggggccc | 300 |
| atgcagaatg | ccaccaagta | tggcaacatg | acagaggacc | atgtgatgca  cctgctccag | 360 |

-continued

```
aatgctgacc ccctgaaggt gtacccgcca ctgaagggga gcttccggga gaacctgaga      420
caccttaaga acaccatgga gaccatagac tggaaggtct ttgagagctg gatgcaccat      480
tggctcctgt ttgaaatgag caggcactcc ttggagcaaa agcccactga cgctccaccg      540
aaagtactga ccaagtgcca ggaagaggtc agccacatcc ctgctgtcca cccgggttca      600
ttcaggccca agtgcgacga gaacggcaac tatctgccac tccagtgcta tgggagcatc      660
ggctactgct ggtgtgtctt ccccaacggc acggaggtcc ccaacaccag aagccgcggg      720
caccataact gcagtgagtc actggaactg gaggacccgt cttctgggct gggtgtgacc      780
aagcaggatc tgggcccagt ccccatgtga                                      810
```

```
<210> SEQ ID NO 91
<211> LENGTH: 269
<212> TYPE: PRT
<213> ORGANISM: Homo sapiens

<400> SEQUENCE: 91
```

```
Met Asp Asp Gln Arg Asp Leu Ile Ser Asn Asn Glu Gln Leu Pro Met
1               5                  10                  15

Leu Gly Arg Arg Pro Gly Ala Pro Glu Ser Lys Cys Ser Arg Gly Ala
            20                  25                  30

Leu Tyr Thr Gly Phe Ser Ile Leu Val Thr Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu Ala Lys Phe Val Ala Ala Trp Thr Leu Lys Ala Ala Ala Leu
                85                  90                  95

Pro Gln Gly Pro Met Gln Asn Ala Thr Lys Tyr Gly Asn Met Thr Glu
            100                 105                 110

Asp His Val Met His Leu Leu Gln Asn Ala Asp Pro Leu Lys Val Tyr
        115                 120                 125

Pro Pro Leu Lys Gly Ser Phe Pro Glu Asn Leu Arg His Leu Lys Asn
    130                 135                 140

Thr Met Glu Thr Ile Asp Trp Lys Val Phe Glu Ser Trp Met His His
145                 150                 155                 160

Trp Leu Leu Phe Glu Met Ser Arg His Ser Leu Glu Gln Lys Pro Thr
                165                 170                 175

Asp Ala Pro Pro Lys Val Leu Thr Lys Cys Gln Glu Glu Val Ser His
            180                 185                 190

Ile Pro Ala Val His Pro Gly Ser Phe Arg Pro Lys Cys Asp Glu Asn
        195                 200                 205

Gly Asn Tyr Leu Pro Leu Gln Cys Tyr Gly Ser Ile Gly Tyr Cys Trp
    210                 215                 220

Cys Val Phe Pro Asn Gly Thr Glu Val Pro Asn Thr Arg Ser Arg Gly
225                 230                 235                 240

His His Asn Cys Ser Glu Ser Leu Glu Leu Glu Asp Pro Ser Ser Gly
                245                 250                 255

Leu Gly Val Thr Lys Gln Asp Leu Gly Pro Val Pro Met
            260                 265
```

```
<210> SEQ ID NO 92
<211> LENGTH: 17
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 92

Lys Pro Val Ser Gln Met Arg Met Ala Thr Pro Leu Leu Met Arg Pro
1               5                   10                  15
Met

<210> SEQ ID NO 93
<211> LENGTH: 13
<212> TYPE: PRT
<213> ORGANISM: Homo sapiens

<400> SEQUENCE: 93

Ala Lys Phe Val Ala Ala Trp Thr Leu Lys Ala Ala
1               5                   10

<210> SEQ ID NO 94
<211> LENGTH: 3392
<212> TYPE: DNA
<213> ORGANISM: Homo sapiens

<400> SEQUENCE: 94

| | | | | | |
|---|---|---|---|---|---|
| atgcgttgcc | tggctccacg | ccctgctggg | tcctacctgt | cagagcccca | aggcagctca | 60 |
| cagtgtgcca | ccatggagtt | ggggcccta | aaggtggct | acctggagct | tcttaacagc | 120 |
| gatgctgacc | cctgtgcctc | taccacttct | atgaccagat | ggacctggct | ggagaagaag | 180 |
| agattgagct | ctactcagaa | cccgacacag | acaccatcaa | ctgcgaccag | ttcagcaggc | 240 |
| tgttgtgtga | catggaaggt | gatgaagaga | ccagggaggc | ttatgccaat | atcgcggaac | 300 |
| tggaccagta | tgtcttccag | gactcccagc | tggagggcct | gagcaaggac | attttcaagc | 360 |
| acataggacc | agatgaagtg | atcggtgaga | gtatggagat | gccagcagaa | gttgggcaga | 420 |
| aaagtcagaa | aagacccttc | ccagaggagc | ttccggcaga | cctgaagcac | tggaagccag | 480 |
| ctgagccccc | cactgtggtg | actggcagtc | tcctagtggg | accagtgagc | gactgctcca | 540 |
| ccctgccctg | cctgccactg | cctgcgctgt | tcaaccagga | gccagcctcc | ggccagatgc | 600 |
| gcctggagaa | aaccgaccag | attcccatgc | ctttctccag | ttcctcgttg | agctgcctga | 660 |
| atctccctga | gggacccatc | cagtttgtcc | ccaccatctc | cactctgccc | catgggctct | 720 |
| ggcaaatctc | tgaggctgga | acaggggtct | ccagtatatt | catctaccat | ggtgaggtgc | 780 |
| cccaggccag | ccaagtaccc | cctcccagtg | gattcactgt | ccacggcctc | ccaacatctc | 840 |
| cagaccggcc | aggctccacc | agcccttcg | ctccatcagc | cactgacctg | ccagcatgc | 900 |
| ctgaacctgc | cctgacctcc | cgagcaaaca | tgacagagca | aagacgtcc | cccacccaat | 960 |
| gcccggcagc | tggagaggtc | tccaacaagc | ttccaaaatg | gcctgagccg | gtggagcagt | 1020 |
| tctaccgctc | actgcaggac | acgtatggtg | ccgagcccgc | aggcccggat | ggcatcctag | 1080 |
| tggaggtgga | tctggtgcag | gccaggctgg | agaggagcag | cagcaagagc | ctggagcggg | 1140 |
| aactggccac | cccggactgg | gcagaacggg | agctggccca | aggaggcctg | gctgaggtgc | 1200 |
| tgttggctgc | caaggagcac | cggcggccgc | gtgagacacg | agtgattgct | gtgctgggca | 1260 |
| aagctggtca | gggcaagagc | tattgggctg | ggcagtgag | ccgggcctgg | gcttgtggcc | 1320 |
| ggcttcccca | gtacgacttt | gtcttctctg | tccctgcca | ttgcttgaac | cgtccggggg | 1380 |
| atgcctatgg | cctgcaggat | ctgctcttct | ccctgggccc | acagccactc | gtggcggccg | 1440 |

```
atgaggtttt cagccacatc ttgaagagac ctgaccgcgt tctgctcatc ctagacggct    1500
tcgaggagct ggaagcgcaa gatggcttcc tgcacagcac gtgcggaccg gcaccggcgg    1560
agccctgctc cctccggggg ctgctggccg gccttttcca agaagctg ctccgaggtt      1620 gcacctcct cctcacagcc cggccccggg gccgcctggt ccagagcctg agcaaggccg     1680
acgccctatt tgagctgtcc ggcttctcca tggagcaggc ccaggcatac gtgatgcgct   1740
actttgagag ctcagggatg acagagcacc aagacagagc cctgacgctc ctccgggacc   1800
ggccacttct tctcagtcac agccacagcc ctactttgtg ccgggcagtg tgccagctct   1860
cagaggccct gctggagctt ggggaggacg ccaagctgcc ctccacgctc acggggactct 1920 atgtcggcct gctgggccgt gcagccctcg acagccccc cggggccctg gcagagctgg   1980
ccaagctggc ctgggagctg ggccgcagac atcaaagtac cctacaggag gaccagttcc   2040
catccgcaga cgtgaggacc tgggcgatgg ccaaaggctt agtccaacac ccaccgcggg   2100
ccgcagagtc cgagctggcc ttccccagct cctcctgca atgcttcctg ggggccctgt    2160
ggctggctct gagtggcgaa atcaaggaca aggagctccc gcagtaccta gcattgaccc   2220
caaggaagaa gaggccctat gacaactggc tggagggcgt gccacgcttt ctggctgggc   2280
tgatcttcca gcctccgcc cgctgcctgg agccatact cgggccatcg gcggctgcct    2340
cggtggacag gaagcagaag gtgcttgcga ggtacctgaa gcggctgcag ccggggacac   2400
tgcgggcgcg gcagctgctg gagctgctgc actgcgccca cgaggccgag gaggctggaa   2460
tttggcagca cgtggtacag gagctccccg gccgcctctc ttttctgggc acccgcctca   2520
cgcctcctga tgcacatgta ctgggcaagg ccttggaggc ggcgggccaa gacttctccc   2580
tggacctccg cagcactggc atttgcccct ctggattggg gagcctcgtg ggactcagct   2640
gtgtcacccg tttcagggct gccttgagcg acacggtggc gctgtgggag tccctgcagc   2700
agcatgggga gaccaagcta cttcaggcag cagaggagaa gttcaccatc gagccttca    2760 aagccaagtc cctgaaggat gtggaagacc tgggaaagct tgtgcagact cagaggacga   2820
gaagttcctc ggaagacaca gctggggagc tccctgctgt tcgggaccta agaaactgg    2880 agtttgcgct gggccctgtc tcaggccccc aggctttccc caaactggtg cggatcctca   2940
cggccttttc ctccctgcag catctggacc tggatgcgct gagtgagaac aagatcgggg   3000
acgagggtgt ctcgcagctc tcagccacct tcccccagct gaagtccttg gaaaccctca   3060
atctgtccca gaacaacatc actgacctgg gtgcctacaa actcgccgag gccctgcctt   3120
cgctcgctgc atcccctgctc aggctaagct tgtacaataa ctgcatctgc gacgtgggag  3180
ccgagagctt ggctcgtgtg cttccggaca tggtgtccct ccgggtgatg gacgtccagt   3240
acaacaagtt cacggctgcc ggggcccagc agctcgctgc cagccttcgg aggtgtcctc   3300
atgtggagac gctggcgatg tggacgccca ccatcccatt cagtgtccag gaaacctgc    3360 aacaacagga ttcacggatc agcctgagat ga                                  3392
```

<210> SEQ ID NO 95
<211> LENGTH: 1130
<212> TYPE: PRT
<213> ORGANISM: Homo sapiens

<400> SEQUENCE: 95

Met Arg Cys Leu Ala Pro Arg Pro Ala Gly Ser Tyr Leu Ser Glu Pro
1               5                   10                  15

Gln Gly Ser Ser Gln Cys Ala Thr Met Glu Leu Gly Pro Leu Glu Gly
            20                  25                  30

Gly Tyr Leu Glu Leu Leu Asn Ser Asp Ala Asp Pro Leu Cys Leu Tyr
            35                  40                  45

His Phe Tyr Asp Gln Met Asp Leu Ala Gly Glu Glu Ile Glu Leu
 50                  55                  60

Tyr Ser Glu Pro Asp Thr Asp Thr Ile Asn Cys Asp Gln Phe Ser Arg
 65              70                  75                  80

Leu Leu Cys Asp Met Glu Gly Asp Glu Thr Arg Glu Ala Tyr Ala
                85                  90                  95

Asn Ile Ala Glu Leu Asp Gln Tyr Val Phe Gln Asp Ser Gln Leu Glu
                100                 105                 110

Gly Leu Ser Lys Asp Ile Phe Lys His Ile Gly Pro Asp Glu Val Ile
            115                 120                 125

Gly Glu Ser Met Glu Met Pro Ala Glu Val Gly Gln Lys Ser Gln Lys
            130                 135                 140

Arg Pro Phe Pro Glu Glu Leu Pro Ala Asp Leu Lys His Trp Lys Pro
145                 150                 155                 160

Ala Glu Pro Pro Thr Val Val Thr Gly Ser Leu Leu Val Gly Pro Val
                165                 170                 175

Ser Asp Cys Ser Thr Leu Pro Cys Leu Pro Leu Pro Ala Leu Phe Asn
            180                 185                 190

Gln Glu Pro Ala Ser Gly Gln Met Arg Leu Glu Lys Thr Asp Gln Ile
            195                 200                 205

Pro Met Pro Phe Ser Ser Ser Leu Ser Cys Leu Asn Leu Pro Glu
    210                 215                 220

Gly Pro Ile Gln Phe Val Pro Thr Ile Ser Thr Leu Pro His Gly Leu
225                 230                 235                 240

Trp Gln Ile Ser Glu Ala Gly Thr Gly Val Ser Ser Ile Phe Ile Tyr
                245                 250                 255

His Gly Glu Val Pro Gln Ala Ser Gln Val Pro Pro Pro Ser Gly Phe
            260                 265                 270

Thr Val His Gly Leu Pro Thr Ser Pro Asp Arg Pro Gly Ser Thr Ser
            275                 280                 285

Pro Phe Ala Pro Ser Ala Thr Asp Leu Pro Ser Met Pro Glu Pro Ala
    290                 295                 300

Leu Thr Ser Arg Ala Asn Met Thr Glu His Lys Thr Ser Pro Thr Gln
305                 310                 315                 320

Cys Pro Ala Ala Gly Glu Val Ser Asn Lys Leu Pro Lys Trp Pro Glu
                325                 330                 335

Pro Val Glu Gln Phe Tyr Arg Ser Leu Gln Asp Thr Tyr Gly Ala Glu
                340                 345                 350

Pro Ala Gly Pro Asp Gly Ile Leu Val Glu Val Asp Leu Val Gln Ala
                355                 360                 365

Arg Leu Glu Arg Ser Ser Lys Ser Leu Glu Arg Glu Leu Ala Thr
    370                 375                 380

Pro Asp Trp Ala Glu Arg Gln Leu Ala Gln Gly Leu Ala Glu Val
385                 390                 395                 400

Leu Leu Ala Ala Lys Glu His Arg Arg Pro Arg Glu Thr Arg Val Ile
                405                 410                 415

Ala Val Leu Gly Lys Ala Gly Gln Gly Lys Ser Tyr Trp Ala Gly Ala
            420                 425                 430

Val Ser Arg Ala Trp Ala Cys Gly Arg Leu Pro Gln Tyr Asp Phe Val
            435                 440                 445

```
Phe Ser Val Pro Cys His Cys Leu Asn Arg Pro Gly Asp Ala Tyr Gly
450                 455                 460

Leu Gln Asp Leu Leu Phe Ser Leu Gly Pro Gln Pro Leu Val Ala Ala
465                 470                 475                 480

Asp Glu Val Phe Ser His Ile Leu Lys Arg Pro Asp Arg Val Leu Leu
                485                 490                 495

Ile Leu Asp Gly Phe Glu Leu Glu Ala Gln Asp Gly Phe Leu His
            500                 505                 510

Ser Thr Cys Gly Pro Ala Pro Glu Pro Cys Ser Leu Arg Gly Leu
            515                 520                 525

Leu Ala Gly Leu Phe Gln Lys Lys Leu Leu Arg Gly Cys Thr Leu Leu
530                 535                 540

Leu Thr Ala Arg Pro Arg Gly Arg Leu Val Gln Ser Leu Ser Lys Ala
545                 550                 555                 560

Asp Ala Leu Phe Glu Leu Ser Gly Phe Ser Met Glu Gln Ala Gln Ala
                565                 570                 575

Tyr Val Met Arg Tyr Phe Glu Ser Ser Gly Met Thr Glu His Gln Asp
            580                 585                 590

Arg Ala Leu Thr Leu Leu Arg Asp Arg Pro Leu Leu Leu Ser His Ser
            595                 600                 605

His Ser Pro Thr Leu Cys Arg Ala Val Cys Gln Leu Ser Glu Ala Leu
            610                 615                 620

Leu Glu Leu Gly Glu Asp Ala Lys Leu Pro Ser Thr Leu Thr Gly Leu
625                 630                 635                 640

Tyr Val Gly Leu Leu Gly Arg Ala Ala Leu Asp Ser Pro Pro Gly Ala
                645                 650                 655

Leu Ala Glu Leu Ala Lys Leu Ala Trp Glu Leu Gly Arg Arg His Gln
            660                 665                 670

Ser Thr Leu Gln Glu Asp Gln Phe Pro Ser Ala Asp Val Arg Thr Trp
            675                 680                 685

Ala Met Ala Lys Gly Leu Val Gln His Pro Pro Arg Ala Ala Glu Ser
            690                 695                 700

Glu Leu Ala Phe Pro Ser Phe Leu Leu Gln Cys Phe Leu Gly Ala Leu
705                 710                 715                 720

Trp Leu Ala Leu Ser Gly Glu Ile Lys Asp Lys Glu Leu Pro Gln Tyr
                725                 730                 735

Leu Ala Leu Thr Pro Arg Lys Lys Arg Pro Tyr Asp Asn Trp Leu Glu
            740                 745                 750

Gly Val Pro Arg Phe Leu Ala Gly Leu Ile Phe Gln Pro Pro Ala Arg
            755                 760                 765

Cys Leu Gly Ala Leu Leu Gly Pro Ser Ala Ala Ser Val Asp Arg
770                 775                 780

Lys Gln Lys Val Leu Ala Arg Tyr Leu Lys Arg Leu Gln Pro Gly Thr
785                 790                 795                 800

Leu Arg Ala Arg Gln Leu Leu Glu Leu Leu His Cys Ala His Glu Ala
                805                 810                 815

Glu Glu Ala Gly Ile Trp Gln His Val Val Gln Glu Leu Pro Gly Arg
            820                 825                 830

Leu Ser Phe Leu Gly Thr Arg Leu Thr Pro Pro Asp Ala His Val Leu
            835                 840                 845

Gly Lys Ala Leu Glu Ala Ala Gly Gln Asp Phe Ser Leu Asp Leu Arg
850                 855                 860

Ser Thr Gly Ile Cys Pro Ser Gly Leu Gly Ser Leu Val Gly Leu Ser
```

```
                865                 870                 875                 880
Cys Val Thr Arg Phe Arg Ala Ala Leu Ser Asp Thr Val Ala Leu Trp
                    885                 890                 895
Glu Ser Leu Gln Gln His Gly Glu Thr Lys Leu Leu Gln Ala Ala Glu
                900                 905                 910
Glu Lys Phe Thr Ile Glu Pro Phe Lys Ala Lys Ser Leu Lys Asp Val
                    915                 920                 925
Glu Asp Leu Gly Lys Leu Val Gln Thr Gln Arg Thr Arg Ser Ser Ser
            930                 935                 940
Glu Asp Thr Ala Gly Glu Leu Pro Ala Val Arg Asp Leu Lys Lys Leu
945                 950                 955                 960
Glu Phe Ala Leu Gly Pro Val Ser Gly Pro Gln Ala Phe Pro Lys Leu
                    965                 970                 975
Val Arg Ile Leu Thr Ala Phe Ser Ser Leu Gln His Leu Asp Leu Asp
                980                 985                 990
Ala Leu Ser Glu Asn Lys Ile Gly Asp Glu Gly Val Ser Gln Leu Ser
                995                 1000                1005
Ala Thr Phe Pro Gln Leu Lys Ser Leu Glu Thr Leu Asn Leu Ser
    1010                1015                1020
Gln Asn Asn Ile Thr Asp Leu Gly Ala Tyr Lys Leu Ala Glu Ala
    1025                1030                1035
Leu Pro Ser Leu Ala Ala Ser Leu Leu Arg Leu Ser Leu Tyr Asn
    1040                1045                1050
Asn Cys Ile Cys Asp Val Gly Ala Glu Ser Leu Ala Arg Val Leu
    1055                1060                1065
Pro Asp Met Val Ser Leu Arg Val Met Asp Val Gln Tyr Asn Lys
    1070                1075                1080
Phe Thr Ala Ala Gly Ala Gln Gln Leu Ala Ala Ser Leu Arg Arg
    1085                1090                1095
Cys Pro His Val Glu Thr Leu Ala Met Trp Thr Pro Thr Ile Pro
    1100                1105                1110
Phe Ser Val Gln Glu His Leu Gln Gln Gln Asp Ser Arg Ile Ser
    1115                1120                1125
Leu Arg
    1130

<210> SEQ ID NO 96
<211> LENGTH: 1518
<212> TYPE: DNA
<213> ORGANISM: Human papillomavirus

<400> SEQUENCE: 96
atgagcctgt ggctgcccag cgaggccacc gtgtacctgc ccccgtgcc cgtgagcaag      60 gtggtgagca ccgacgagta cgtggccagg accaacatct actaccacgc cggcaccagc    120
aggctgctgg ccgtgggcca ccctacttc cccatcaaga agcccaacaa caacaagatc     180
ctggtgccca aggtgagcgg cctgcagtac agggtgttca ggatccacct gcccgacccc    240
aacaagttcg gcttccccga caccagcttc tacaaccccg acaccagag gctggtgtgg     300 gcctgcgtgg gcgtggaggt gggcagggc cagcccctgg gcgtgggcat cagcggccac    360
cccctgctga caagctgga cgacaccgag aacgccagcg cctacgccgc caacgccggc    420
gtggacaaca gggagtgcat cagcatggac tacaagcaga cccagctgtg cctgatcggc    480
tgcaagcccc ccatcggcga gcactgggc aagggcagcc cctgcaccaa cgtggccgtg    540
```

-continued

```
aaccccggcg actgccccccc cctggagctg atcaacaccg tgatccagga cggcgacatg      600
gtggacaccg gcttcggcgc catggacttc accaccctgc aggccaacaa gagcgaggtg      660
cccctggaca tctgcaccag catctgcaag taccccgact acatcaagat ggtgagcgag      720
ccctacggcg acagcctgtt cttctacctg aggagggagc agatgttcgt gaggcacctg      780
ttcaacaggg ccggcgccgt gggcgagaac gtgcccgacg acctgtacat caagggcagc      840
ggcagcaccg ccaacctggc cagcagcaac tacttcccca cccccagcgg cagcatggtg      900
accagcgacg cccagatctt caacaagccc tactggctgc agagggccca gggccacaac      960
aacggcatct gctggggcaa ccagctgttc gtgaccgtgg tggacaccac caggagcacc     1020
aacatgagcc tgtgcgccgc catcagcacc agcgagacca cctacaagaa caccaacttc     1080
aaggagtacc tgaggcacgg cgaggagtac gacctgcagt tcatcttcca gctgtgcaag     1140
atcaccctga ccgccgacgt gatgacctac atccacagca tgaacagcac catcctggag     1200
gactggaact tcggcctgca gccccccccc ggcggcaccc tggaggacac ctacaggttc     1260
gtgaccagcc aggccatcgc ctgccagaag cacaccccc ccgcccccaa ggaggacccc      1320
ctgaagaagt acaccttctg ggaggtgaac ctgaaggaga agttcagcgc cgacctggac     1380
cagttccccc tgggcaggaa gttcctgctg caggccggcc tgaaggccaa gcccaagttc     1440
accctgggca gaggaaggc cacccccacc accagcagca ccagcaccac cgccaagagg      1500
aagaagagga agctgtga                                                    1518
```

<210> SEQ ID NO 97
<211> LENGTH: 505
<212> TYPE: PRT
<213> ORGANISM: Human papillomavirus

<400> SEQUENCE: 97

```
Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
```

```
            195                 200                 205
Asp Phe Thr Thr Leu Gln Ala Asn Lys Ser Glu Val Pro Leu Asp Ile
        210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
                260                 265                 270

Asp Asp Leu Tyr Ile Lys Gly Ser Gly Ser Thr Ala Asn Leu Ala Ser
                275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
                340                 345                 350

Thr Thr Tyr Lys Asn Thr Asn Phe Lys Glu Tyr Leu Arg His Gly Glu
                355                 360                 365

Glu Tyr Asp Leu Gln Phe Ile Phe Gln Leu Cys Lys Ile Thr Leu Thr
370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Pro Gly Gly Thr Leu Glu Asp
                405                 410                 415

Thr Tyr Arg Phe Val Thr Ser Gln Ala Ile Ala Cys Gln Lys His Thr
                420                 425                 430

Pro Pro Ala Pro Lys Glu Asp Pro Leu Lys Lys Tyr Thr Phe Trp Glu
            435                 440                 445

Val Asn Leu Lys Glu Lys Phe Ser Ala Asp Leu Asp Gln Phe Pro Leu
450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
            500                 505

<210> SEQ ID NO 98
<211> LENGTH: 1707
<212> TYPE: DNA
<213> ORGANISM: Human papillomavirus

<400> SEQUENCE: 98
atgtgcctgt atacacgggt cctgatatta cattaccatc tactacctct gtatggccca      60
ttgtatcacc cacggcccct gcctctacac agtatattgg tatacatggt acacattatt     120
atttgtggcc attatattat tttattccta agaaacgtaa acgtgttccc tattttttg     180 cagatggctt tgtggcggcc tagtgacaat accgtatatc ttccacctcc ttctgtggca     240
agagttgtaa ataccgatga ttatgtgact cccacaagca tatttatca tgctggcagc     300 tctagattat taactgttgg taatccatat tttagggttc ctgcaggtgg tggcaataag     360
```

```
caggatattc ctaaggtttc tgcataccaa tatagagtat ttagggtgca gttacctgac      420
ccaaataaat ttggtttacc tgatactagt atttataatc ctgaaacaca acgtttagtg      480
tgggcctgtg ctggagtgga aattggccgt ggtcagcctt aggtgttggg ccttagtggg      540
catccatttt ataataaatt agatgacact gaaagttccc atgccgccac gtctaatgtt      600
tctgaggacg ttagggacaa tgtgtctgta gattataagc agacacagtt atgtattttg      660
ggctgtgccc ctgctattgg ggaacactgg gctaaaggca ctgcttgtaa atcgcgtcct      720
ttatcacagg gcgattgccc cccttttagaa cttaaaaaca cagtttttgga agatggtgat      780 atggtagata ctggatatgg tgccatggac tttagtacat tgcaagatac taaatgtgag      840
gtaccattgg atatttgtca gtctatttgt aaatatcctg attatttaca aatgtctgca      900
gatccttatg gggattccat gttttttttgc ttacggcgtg agcagctttt tgctaggcat      960
ttttggaata gagcaggtac tatgggtgac actgtgcctc aatccttata tattaaaggc     1020
acaggtatgc ctgcttcacc tggcagctgt gtgtattctc cctctccaag tggctctatt     1080
gttacctctg actcccagtt gtttaataaa ccatattggt tacataaggc acagggtcat     1140
aacaatggtg tttgctggca taatcaatta tttgttactg tggtagatac cactcccagt     1200
accaatttaa caatatgtgc ttctacacag tctcctgtac ctgggcaata tgatgctacc     1260
aaatttaagc agtatagcag acatgttgag gaatatgatt tgcagtttat ttttcagttg     1320
tgtactatta ctttaactgc agatgttatg tcctatattc atagtatgaa tagcagtatt     1380
ttagaggatt ggaactttgg tgttcccccc cccccaacta ctagtttggt ggatacatat     1440
cgttttgtac aatctgttgc tattacctgt caaaaggatg ctgcaccggc tgaaaataag     1500
gatccctatg ataagttaaa gttttggaat gtggatttaa aggaaaagtt ttctttagac     1560
ttagatcaat atcccctttgg acgtaaattt tggttcagg ctggattgcg tcgcaagccc     1620
accataggcc ctcgcaaacg ttctgctcca tctgccacta cgtcttctaa acctgccaag     1680
cgtgtgcgtg tacgtgccag gaagtaa                                          1707
```

<210> SEQ ID NO 99
<211> LENGTH: 568
<212> TYPE: PRT
<213> ORGANISM: Human papillomavirus

<400> SEQUENCE: 99

Met Cys Leu Tyr Thr Arg Val Leu Ile Leu His Tyr His Leu Leu Pro
1               5                   10                  15

Leu Tyr Gly Pro Leu Tyr His Pro Arg Pro Leu Pro Leu His Ser Ile
            20                  25                  30

Leu Val Tyr Met Val His Ile Ile Ile Cys Gly His Tyr Ile Ile Leu
        35                  40                  45

Phe Leu Arg Asn Val Asn Val Phe Pro Ile Phe Leu Gln Met Ala Leu
    50                  55                  60

Trp Arg Pro Ser Asp Asn Thr Val Tyr Leu Pro Pro Ser Val Ala
65                  70                  75                  80

Arg Val Val Asn Thr Asp Asp Tyr Val Thr Pro Thr Ser Ile Phe Tyr
                85                  90                  95

His Ala Gly Ser Ser Arg Leu Leu Thr Val Gly Asn Pro Tyr Phe Arg
            100                 105                 110

Val Pro Ala Gly Gly Gly Asn Lys Gln Asp Ile Pro Lys Val Ser Ala
        115                 120                 125

Tyr Gln Tyr Arg Val Phe Arg Val Gln Leu Pro Asp Pro Asn Lys Phe

-continued

```
            130                 135                 140
Gly Leu Pro Asp Thr Ser Ile Tyr Asn Pro Glu Thr Gln Arg Leu Val
145                 150                 155                 160

Trp Ala Cys Ala Gly Val Glu Ile Gly Arg Gly Gln Pro Leu Gly Val
                165                 170                 175

Gly Leu Ser Gly His Pro Phe Tyr Asn Lys Leu Asp Asp Thr Glu Ser
                180                 185                 190

Ser His Ala Ala Thr Ser Asn Val Ser Glu Asp Val Arg Asp Asn Val
                195                 200                 205

Ser Val Asp Tyr Lys Gln Thr Gln Leu Cys Ile Leu Gly Cys Ala Pro
                210                 215                 220

Ala Ile Gly Glu His Trp Ala Lys Gly Thr Ala Cys Lys Ser Arg Pro
225                 230                 235                 240

Leu Ser Gln Gly Asp Cys Pro Pro Leu Glu Leu Lys Asn Thr Val Leu
                245                 250                 255

Glu Asp Gly Asp Met Val Asp Thr Gly Tyr Gly Ala Met Asp Phe Ser
                260                 265                 270

Thr Leu Gln Asp Thr Lys Cys Glu Val Pro Leu Asp Ile Cys Gln Ser
                275                 280                 285

Ile Cys Lys Tyr Pro Asp Tyr Leu Gln Met Ser Ala Asp Pro Tyr Gly
                290                 295                 300

Asp Ser Met Phe Phe Cys Leu Arg Arg Glu Gln Leu Phe Ala Arg His
305                 310                 315                 320

Phe Trp Asn Arg Ala Gly Thr Met Gly Asp Thr Val Pro Gln Ser Leu
                325                 330                 335

Tyr Ile Lys Gly Thr Gly Met Pro Ala Ser Pro Gly Ser Cys Val Tyr
                340                 345                 350

Ser Pro Ser Pro Ser Gly Ser Ile Val Thr Ser Asp Ser Gln Leu Phe
                355                 360                 365

Asn Lys Pro Tyr Trp Leu His Lys Ala Gln Gly His Asn Asn Gly Val
                370                 375                 380

Cys Trp His Asn Gln Leu Phe Val Thr Val Val Asp Thr Thr Pro Ser
385                 390                 395                 400

Thr Asn Leu Thr Ile Cys Ala Ser Thr Gln Ser Pro Val Pro Gly Gln
                405                 410                 415

Tyr Asp Ala Thr Lys Phe Lys Gln Tyr Ser Arg His Val Glu Glu Tyr
                420                 425                 430

Asp Leu Gln Phe Ile Phe Gln Leu Cys Thr Ile Thr Leu Thr Ala Asp
                435                 440                 445

Val Met Ser Tyr Ile His Ser Met Asn Ser Ser Ile Leu Glu Asp Trp
                450                 455                 460

Asn Phe Gly Val Pro Pro Pro Pro Thr Thr Ser Leu Val Asp Thr Tyr
465                 470                 475                 480

Arg Phe Val Gln Ser Val Ala Ile Thr Cys Gln Lys Asp Ala Ala Pro
                485                 490                 495

Ala Glu Asn Lys Asp Pro Tyr Asp Lys Leu Lys Phe Trp Asn Val Asp
                500                 505                 510

Leu Lys Glu Lys Phe Ser Leu Asp Leu Asp Gln Tyr Pro Leu Gly Arg
                515                 520                 525

Lys Phe Leu Val Gln Ala Gly Leu Arg Arg Lys Pro Thr Ile Gly Pro
                530                 535                 540

Arg Lys Arg Ser Ala Pro Ser Ala Thr Thr Ser Ser Lys Pro Ala Lys
545                 550                 555                 560
```

Arg Val Arg Val Arg Ala Arg Lys
            565

<210> SEQ ID NO 100
<211> LENGTH: 1533
<212> TYPE: DNA
<213> ORGANISM: Human papillomavirus

<400> SEQUENCE: 100

```
atgtcttgtg gcctaaacga cgtaaacgtg tccactattt ctttgcagat ggctttgtgg      60
cggcctaatg aaagcaaggt atacctacct ccaacacctg tttcaaaggt gatcagtacg     120
gatgtctatg tcacgcggac taatgtgtat taccatggtg gcagttctag gcttctcact     180
gtgggtcatc catattactc tataaagaag agtaataata aggtggctgt gcccaaggta     240
tctgggtacc aatatcgtgt atttcacgtg aagttgccag atccaaataa gtttggcctg     300
cccgatgctg atttgtatga tccagatacc cagagacttc tgtgggcgtg cgtgggagta     360
gaggtgggcc gtgggcagcc tttgggtgtg ggtgtgtctg gtcacccata ttacaataga     420
ctggatgaca ctgaaaatgc acacacacct gatacagctg atgatggcag ggaaaacatt     480
tctatggatt ataaacagac acagctgttc attctgggct gcaaaccccc tattggtgag     540
cactggtcta agggtaccac ctgtaatggg tcttctgctg ctggtgactg cccgcccctc     600
caatttacta cacaactat tgaggacggg atatgggtta aacagggtt cggtgccttg     660
gattttgcca ctctgcagtc aaataagtca gatgttcctt ggatatttg taccaatacc     720
tgtaaatatc ctgattatct gaagatggct gcagagcctt atggtgattc tatgttcttc     780
tcgctgcgta gggaacaaat gttcactcgt cattttttca atctgggtgg taagatgggt     840
gacaccatcc cggatgagtt atacattaaa agtacctcag ttccaactcc aggcagtcat     900
gtttatactt ccactcctag tggctctatg gtgtcctctg aacaacagtt gtttaataag     960
ccttactggc tacggagggc ccaagggcac aacaatggta tgtgctgggg caatagggtc    1020
tttctgactg tggtggacac cacacgtagc actaatgtat ctctgtgtgc cactgaggcg    1080
tctgatacta attataaggc taccaatttt aaggaatatc tcaggcatat ggaggaatat    1140
gatttgcagt tcatcttcca actgtgcaag ataaacctta ctcctgaaat tatggcctat    1200
atacataata tggatcccca gttgttagag gattggaact tcggtgtacc ccctccgccg    1260
tctgccagtt acaggatac ctatagatat ttgcagtccc aggctattac atgtcaaaaa    1320
cctacacctc ctaagacccc taccgatccc tatgcctccc tgacctttg ggatgtggat    1380
ctcagtgaaa gttttccat ggatctggac caatttccct ggggtcgcaa gttttgctg    1440
cagcggggg ctatgcctac cgtgtctcgc aagcgcgccg ctgtttcggg gaccacgccg    1500
cccactagta aacgaaaacg ggtaaggcgt tag                                 1533
```

<210> SEQ ID NO 101
<211> LENGTH: 510
<212> TYPE: PRT
<213> ORGANISM: Human papillomavirus

<400> SEQUENCE: 101

Met Ser Cys Gly Leu Asn Asp Val Asn Val Ser Thr Ile Ser Leu Gln
1               5                  10                  15

Met Ala Leu Trp Arg Pro Asn Glu Ser Lys Val Tyr Leu Pro Pro Thr
            20                  25                  30

Pro Val Ser Lys Val Ile Ser Thr Asp Val Tyr Val Thr Arg Thr Asn

```
                35                  40                  45
Val Tyr Tyr His Gly Gly Ser Ser Arg Leu Leu Thr Val Gly His Pro
 50                  55                  60

Tyr Tyr Ser Ile Lys Lys Ser Asn Asn Lys Val Ala Val Pro Lys Val
65                  70                  75                  80

Ser Gly Tyr Gln Tyr Arg Val Phe His Val Lys Leu Pro Asp Pro Asn
                85                  90                  95

Lys Phe Gly Leu Pro Asp Ala Asp Leu Tyr Asp Pro Asp Thr Gln Arg
            100                 105                 110

Leu Leu Trp Ala Cys Val Gly Val Glu Val Gly Arg Gly Gln Pro Leu
        115                 120                 125

Gly Val Gly Val Ser Gly His Pro Tyr Tyr Asn Arg Leu Asp Asp Thr
130                 135                 140

Glu Asn Ala His Thr Pro Asp Thr Ala Asp Gly Arg Glu Asn Ile
145                 150                 155                 160

Ser Met Asp Tyr Lys Gln Thr Gln Leu Phe Ile Leu Gly Cys Lys Pro
                165                 170                 175

Pro Ile Gly Glu His Trp Ser Lys Gly Thr Thr Cys Asn Gly Ser Ser
            180                 185                 190

Ala Ala Gly Asp Cys Pro Pro Leu Gln Phe Thr Asn Thr Thr Ile Glu
        195                 200                 205

Asp Gly Asp Met Val Glu Thr Gly Phe Gly Ala Leu Asp Phe Ala Thr
210                 215                 220

Leu Gln Ser Asn Lys Ser Asp Val Pro Leu Asp Ile Cys Thr Asn Thr
225                 230                 235                 240

Cys Lys Tyr Pro Asp Tyr Leu Lys Met Ala Ala Glu Pro Tyr Gly Asp
                245                 250                 255

Ser Met Phe Phe Ser Leu Arg Arg Glu Gln Met Phe Thr Arg His Phe
            260                 265                 270

Phe Asn Leu Gly Gly Lys Met Gly Asp Thr Ile Pro Asp Glu Leu Tyr
        275                 280                 285

Ile Lys Ser Thr Ser Val Pro Thr Pro Gly Ser His Val Tyr Thr Ser
290                 295                 300

Thr Pro Ser Gly Ser Met Val Ser Ser Glu Gln Gln Leu Phe Asn Lys
305                 310                 315                 320

Pro Tyr Trp Leu Arg Arg Ala Gln Gly His Asn Asn Gly Met Cys Trp
                325                 330                 335

Gly Asn Arg Val Phe Leu Thr Val Val Asp Thr Thr Arg Ser Thr Asn
            340                 345                 350

Val Ser Leu Cys Ala Thr Glu Ala Ser Asp Thr Asn Tyr Lys Ala Thr
        355                 360                 365

Asn Phe Lys Glu Tyr Leu Arg His Met Glu Glu Tyr Asp Leu Gln Phe
370                 375                 380

Ile Phe Gln Leu Cys Lys Ile Thr Leu Thr Pro Glu Ile Met Ala Tyr
385                 390                 395                 400

Ile His Asn Met Asp Pro Gln Leu Leu Glu Asp Trp Asn Phe Gly Val
                405                 410                 415

Pro Pro Pro Pro Ser Ala Ser Leu Gln Asp Thr Tyr Arg Tyr Leu Gln
            420                 425                 430

Ser Gln Ala Ile Thr Cys Gln Lys Pro Thr Pro Pro Lys Thr Pro Thr
        435                 440                 445

Asp Pro Tyr Ala Ser Leu Thr Phe Trp Asp Val Asp Leu Ser Glu Ser
450                 455                 460
```

Phe Ser Met Asp Leu Asp Gln Phe Pro Leu Gly Arg Lys Phe Leu Leu
465                 470                 475                 480

Gln Arg Gly Ala Met Pro Thr Val Ser Arg Lys Arg Ala Ala Val Ser
            485                 490                 495

Gly Thr Thr Pro Pro Thr Ser Lys Arg Lys Arg Val Arg Arg
            500                 505                 510

<210> SEQ ID NO 102
<211> LENGTH: 1422
<212> TYPE: DNA
<213> ORGANISM: Human papillomavirus

<400> SEQUENCE: 102

| | | | | | |
|---|---|---|---|---|---|
| atgaggcaca | agaggagcgc | caagaggacc | aagagggcca | cgccacccca | gctgtacaag | 60 |
| acctgcaagc | aggccggcac | ctgccccccc | gacatcatcc | ccaaggtgga | gggcaagacc | 120 |
| atcgccgacc | agatcctgca | gtacggcagc | atgggcgtgt | tcttcggcgg | cctgggcatc | 180 |
| ggcaccggca | gcggcaccgg | cggcaggacc | ggctacatcc | cctgggcac | caggcccccc | 240 |
| accgccaccg | acaccctggc | ccccgtgagg | cccccctga | ccgtggaccc | cgtgggcccc | 300 |
| agcgacccca | gcatcgtgag | cctggtggag | gagaccagct | tcatcgacgc | cggcgccccc | 360 |
| accagcgtgc | ccagcatccc | ccccgacgtg | agcggcttca | gcatcaccac | cagcaccgac | 420 |
| accacccccg | ccatcctgga | catcaacaac | accgtgacca | ccgtgaccac | ccacaacaac | 480 |
| cccaccttca | ccgaccccag | cgtgctgcag | ccccccaccc | ccgccgagac | cggcggccac | 540 |
| ttcaccctga | gcagcagcac | catcagcacc | cacaactacg | aggagatccc | catggacacc | 600 |
| ttcatcgtga | gcaccaaccc | caacaccgtg | accagcagca | ccccatccc | cggcagcagg | 660 |
| cccgtggcca | ggctgggcct | gtacagcagg | accacccagc | aggtgaaggt | ggtggacccc | 720 |
| gccttcgtga | ccacccccac | caagctgatc | acctacgaca | accccgccta | cgagggcatc | 780 |
| gacgtggaca | cacccctgta | cttcagcagc | aacgacaaca | gcatcaacat | cgccccccgac | 840 |
| cccgacttcc | tggacatcgt | ggccctgcac | aggcccgccc | tgaccagcag | gaggaccggc | 900 |
| atcaggtaca | gcaggatcgg | caacaagcag | accctgagga | ccaggagcgg | caagagcatc | 960 |
| ggcgccaagg | tgcactacta | ctacgacctg | agcaccatcg | accccgccga | ggagatcgag | 1020 |
| ctgcagacca | tcaccccccag | cacctacacc | accaccagcc | acgccgccag | ccccaccagc | 1080 |
| atcaacaacg | gcctgtacga | catctacgcc | gacgacttca | tcaccgacac | cagcaccacc | 1140 |
| cccgtgccca | gcgtgcccag | caccagcctg | agcggctaca | tccccgccaa | caccaccatc | 1200 |
| cccttcggtg | gcgcctacaa | catccccctg | gtgagcggcc | ccgacatccc | catcaacatc | 1260 |
| accgaccagg | cccccagcct | gatccccatc | gtgcccggca | gccccagta | caccatcatc | 1320 |
| gccgacgccg | gcgacttcta | cctgcacccc | agctactaca | tgctgaggaa | gaggaggaag | 1380 |
| aggctgccct | acttcttcag | cgacgtgagc | ctggccgcct | ga | | 1422 |

<210> SEQ ID NO 103
<211> LENGTH: 473
<212> TYPE: PRT
<213> ORGANISM: Human papillomavirus

<400> SEQUENCE: 103

Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

-continued

```
Ile Pro Lys Val Glu Gly Lys Thr Ile Ala Asp Gln Ile Leu Gln Tyr
         35                  40                  45

Gly Ser Met Gly Val Phe Phe Gly Leu Gly Ile Gly Thr Gly Ser
         50                  55                  60

Gly Thr Gly Gly Arg Thr Gly Tyr Ile Pro Leu Gly Thr Arg Pro Pro
 65                  70                  75                  80

Thr Ala Thr Asp Thr Leu Ala Pro Val Arg Pro Pro Leu Thr Val Asp
                     85                  90                  95

Pro Val Gly Pro Ser Asp Pro Ser Ile Val Ser Leu Val Glu Glu Thr
                100                 105                 110

Ser Phe Ile Asp Ala Gly Ala Pro Thr Ser Val Pro Ser Ile Pro Pro
                115                 120                 125

Asp Val Ser Gly Phe Ser Ile Thr Thr Ser Thr Asp Thr Thr Pro Ala
130                 135                 140

Ile Leu Asp Ile Asn Asn Thr Val Thr Val Thr Thr His Asn Asn
145                 150                 155                 160

Pro Thr Phe Thr Asp Pro Ser Val Leu Gln Pro Pro Thr Pro Ala Glu
                    165                 170                 175

Thr Gly Gly His Phe Thr Leu Ser Ser Ser Thr Ile Ser Thr His Asn
                180                 185                 190

Tyr Glu Glu Ile Pro Met Asp Thr Phe Ile Val Ser Thr Asn Pro Asn
                195                 200                 205

Thr Val Thr Ser Ser Thr Pro Ile Pro Gly Ser Arg Pro Val Ala Arg
210                 215                 220

Leu Gly Leu Tyr Ser Arg Thr Thr Gln Gln Val Lys Val Val Asp Pro
225                 230                 235                 240

Ala Phe Val Thr Thr Pro Thr Lys Leu Ile Thr Tyr Asp Asn Pro Ala
                    245                 250                 255

Tyr Glu Gly Ile Asp Val Asp Asn Thr Leu Tyr Phe Ser Ser Asn Asp
                260                 265                 270

Asn Ser Ile Asn Ile Ala Pro Asp Pro Asp Phe Leu Asp Ile Val Ala
            275                 280                 285

Leu His Arg Pro Ala Leu Thr Ser Arg Arg Thr Gly Ile Arg Tyr Ser
        290                 295                 300

Arg Ile Gly Asn Lys Gln Thr Leu Arg Thr Arg Ser Gly Lys Ser Ile
305                 310                 315                 320

Gly Ala Lys Val His Tyr Tyr Asp Leu Ser Thr Ile Asp Pro Ala
                325                 330                 335

Glu Glu Ile Glu Leu Gln Thr Ile Thr Pro Ser Thr Tyr Thr Thr Thr
                340                 345                 350

Ser His Ala Ala Ser Pro Thr Ser Ile Asn Asn Gly Leu Tyr Asp Ile
            355                 360                 365

Tyr Ala Asp Asp Phe Ile Thr Asp Thr Ser Thr Thr Pro Val Pro Ser
        370                 375                 380

Val Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
                405                 410                 415

Pro Ile Asn Ile Thr Asp Gln Ala Pro Ser Leu Ile Pro Ile Val Pro
            420                 425                 430

Gly Ser Pro Gln Tyr Thr Ile Ile Ala Asp Ala Gly Asp Phe Tyr Leu
        435                 440                 445
```

His Pro Ser Tyr Tyr Met Leu Arg Lys Arg Arg Lys Arg Leu Pro Tyr
        450                 455                 460

Phe Phe Ser Asp Val Ser Leu Ala Ala
465                 470

<210> SEQ ID NO 104
<211> LENGTH: 1389
<212> TYPE: DNA
<213> ORGANISM: Human papillomavirus

<400> SEQUENCE: 104
atggtatccc accgtgccgc acgacgcaaa cgggcttcgg taactgactt atataaaaca      60
tgtaaacaat ctggtacatg tccacctgat gttgttccta aggtggaggg caccacgtta     120
gcagataaaa tattgcaatg gtcaagcctt ggtatatttt gggtggact tggcataggt      180 actggcagtg gtacaggggg tcgtacaggg tacattccat gggtgggcg ttccaataca      240 gtggtggatg ttggtcctac acgtccccca gtggttattg aacctgtggg ccccacagac     300
ccatctattg ttacattaat agaggactcc agtgtggtta catcaggtgc acctaggcct     360
acgtttactg gcacgtctgg gtttgatata acatctgcgg gtacaactac acctgcggtt     420
ttggatatca ccttcgtc tacctctgtg tctatttcca caaccaattt taccaatcct      480
gcattttctg atccgtccat tattgaagtt ccacaaactg gggaggtggc aggtaatgta     540
tttgttggta cccctacatc tggaacacat gggtatgagg aaatacccttt acaaacattt     600 gcttcttctg gtacggggga ggaacccatt agtagtaccc cattgcctac tgtgcggcgt     660
gtagcaggtc cccgcccttta cagtagggcc taccaacaag tgtcagtggc taaccctgag     720
tttcttacac gtccatcctc tttaattaca tatgacaacc cggcctttga gcctgtggac     780
actacattaa catttgatcc tcgtagtgat gttcctgatt cagattttat ggatattatc     840
cgtctacata ggcctgcttt aacatccagg cgtgggactg ttcgctttag tagattaggt     900
caacgggcaa ctatgtttac ccgcagcggt acacaaatag gtgctaggt tcactttttat     960 catgatataa gtcctattgc accttcccca gaatatattg aactgcagcc tttagtatct    1020
gccacggagg acaatgactt gtttgatata tatgcagatg catggaccc tgcagtgcct    1080 gtaccatcgc gttctactac ctccttttgca tttttaaat attcgcccac tatatcttct    1140
gcctcttcct atagtaatgt aacggtccct ttaacctcct cttgggatgt gcctgtatac    1200
acgggtcctg atattacatt accatctact acctctgtat ggcccattgt atcacccacg    1260 gccctgcct ctacacagta tattggtata catggtacac attattattt gtggccatta    1320
tattatttta ttcctaagaa acgtaaacgt gttccctatt ttttgcaga tggctttgtg    1380 gcggcctag                                                            1389

<210> SEQ ID NO 105
<211> LENGTH: 462
<212> TYPE: PRT
<213> ORGANISM: Human papillomavirus

<400> SEQUENCE: 105

Met Val Ser His Arg Ala Ala Arg Arg Lys Arg Ala Ser Val Thr Asp
1               5                   10                  15

Leu Tyr Lys Thr Cys Lys Gln Ser Gly Thr Cys Pro Pro Asp Val Val
            20                  25                  30

Pro Lys Val Glu Gly Thr Thr Leu Ala Asp Lys Ile Leu Gln Trp Ser
        35                  40                  45

-continued

```
Ser Leu Gly Ile Phe Leu Gly Gly Leu Gly Ile Gly Thr Gly Ser Gly
 50                  55                  60

Thr Gly Gly Arg Thr Gly Tyr Ile Pro Leu Gly Gly Arg Ser Asn Thr
 65                  70                  75                  80

Val Val Asp Val Gly Pro Thr Arg Pro Val Val Ile Glu Pro Val
                 85                  90                  95

Gly Pro Thr Asp Pro Ser Ile Val Thr Leu Ile Glu Asp Ser Ser Val
                100                 105                 110

Val Thr Ser Gly Ala Pro Arg Pro Thr Phe Thr Gly Thr Ser Gly Phe
            115                 120                 125

Asp Ile Thr Ser Ala Gly Thr Thr Pro Ala Val Leu Asp Ile Thr
130                 135                 140

Pro Ser Ser Thr Ser Val Ser Ile Ser Thr Thr Asn Phe Thr Asn Pro
145                 150                 155                 160

Ala Phe Ser Asp Pro Ser Ile Ile Glu Val Pro Gln Thr Gly Glu Val
                165                 170                 175

Ala Gly Asn Val Phe Val Gly Thr Pro Thr Ser Gly Thr His Gly Tyr
            180                 185                 190

Glu Glu Ile Pro Leu Gln Thr Phe Ala Ser Ser Gly Thr Gly Glu Glu
            195                 200                 205

Pro Ile Ser Ser Thr Pro Leu Pro Thr Val Arg Arg Val Ala Gly Pro
            210                 215                 220

Arg Leu Tyr Ser Arg Ala Tyr Gln Gln Val Ser Val Ala Asn Pro Glu
225                 230                 235                 240

Phe Leu Thr Arg Pro Ser Ser Leu Ile Thr Tyr Asp Asn Pro Ala Phe
                245                 250                 255

Glu Pro Val Asp Thr Thr Leu Thr Phe Asp Pro Arg Ser Asp Val Pro
            260                 265                 270

Asp Ser Asp Phe Met Asp Ile Ile Arg Leu His Arg Pro Ala Leu Thr
            275                 280                 285

Ser Arg Arg Gly Thr Val Arg Phe Ser Arg Leu Gly Gln Arg Ala Thr
            290                 295                 300

Met Phe Thr Arg Ser Gly Thr Gln Ile Gly Ala Arg Val His Phe Tyr
305                 310                 315                 320

His Asp Ile Ser Pro Ile Ala Pro Ser Pro Glu Tyr Ile Glu Leu Gln
                325                 330                 335

Pro Leu Val Ser Ala Thr Glu Asp Asn Asp Leu Phe Asp Ile Tyr Ala
            340                 345                 350

Asp Asp Met Asp Pro Ala Val Pro Val Pro Ser Arg Ser Thr Thr Ser
            355                 360                 365

Phe Ala Phe Phe Lys Tyr Ser Pro Thr Ile Ser Ser Ala Ser Ser Tyr
            370                 375                 380

Ser Asn Val Thr Val Pro Leu Thr Ser Ser Trp Asp Val Pro Val Tyr
385                 390                 395                 400

Thr Gly Pro Asp Ile Thr Leu Pro Ser Thr Thr Ser Val Trp Pro Ile
                405                 410                 415

Val Ser Pro Thr Ala Pro Ala Ser Thr Gln Tyr Ile Gly Ile His Gly
            420                 425                 430

Thr His Tyr Tyr Leu Trp Pro Leu Tyr Tyr Phe Ile Pro Lys Lys Arg
            435                 440                 445

Lys Arg Val Pro Tyr Phe Phe Ala Asp Gly Phe Val Ala Ala
450                 455                 460
```

<210> SEQ ID NO 106
<211> LENGTH: 1575
<212> TYPE: DNA
<213> ORGANISM: Human papillomavirus

<400> SEQUENCE: 106

```
atgtctgttg gtgattctta tcctaatcgc cttttttattg ttgatgtttt atgtccgttt      60
gttaaaccac acctaacacc cccactttttt tatattgttt tgatacatttt tcattttgat    120
acatttgtgt ttttttttgta tttgctgcgt tttaataaac gtgcaaccat gtctatacgt    180
gccaagcgtc gaaagcgcgc ctcccccaca gacctctatc gtacctgcaa gcaggcaggt    240
acctgcccccc cagacattat cccaagagtg aacagaaca cttttagcaga taaaatcctt    300
aagtggggca gtttaggtgt gttttttggg ggtctaggta taggcaccgg cagcggcaca    360
ggggggcgta ctgggtacat tcctgtaggt tcgcgaccca ccactgtagt tgacattggt    420
ccaacgccca ggccgcctgt tatcattgaa cctgtggggg cctctgaacc ctctattgtc    480
actttggtgg aggactctag catcattaac gcaggagcgt cacatcccac ctttactggt    540
actggtggct tcgaagtgac aacctccacc gttacagacc ccgccgtctt ggatatcacc    600
ccctcaggta ccagtgtgca ggtcagcagc agtagctttc ttaacccact atacactgag    660
ccagctattg tggaggctcc ccaaacaggg gaagtatctg gccatgtact tgttagtaca    720
gccacctcag ggtctcatgg ctatgaggaa ataccaatgc agacgtttgc cacgtcgggg    780
ggcagcggta cagagcctat cagtagcaca ccctccctg gcgtgcggag agttgccgga    840
ccccgcctgt acagtagagc caatcagcaa gtgcaagtca gggatcctgc gtttcttgca    900
aggcctgctg atctagtaac atttgacaat cctgtgtatg cccagagga aactataata    960
tttcagcatc cagacttgca tgagccaccg gatcctgatt ttttggacat agtggcgttg   1020
catcgtcccg ccctcacgtc cagaaggggt actgtccgtt ttagtaggtt gggacgcagg   1080
gctacactcc gcacccgtag tggtaaacaa attgggggcac gggtgcactt ctatcatgat   1140
attagcccta taggtactga ggagttggag atggagccac tgttgccccc agcttctact   1200
gataacacag atatgttata tgatgtttat gctgattcgg atgtccttca gccattgctt   1260
gatgagttac ccgccgccccc tcgcggttca ctctctctgg ctgacactgc tgtgtctgcc   1320
acctccgcat ctacactacg ggggtccact actgtcccctt tatcaagtgg tattgatgtg   1380
cctgtgtaca ccggtcctga cattgaacca cccaatgttc ctggcatggg acctctgatt   1440
cctgtggctc catccttacc atcgtctgtg tacatatttg ggggagatta ttatttgatg   1500
ccaagttatg tcttgtggcc taaacgacgt aaacgtgtcc actatttctt tgcagatggc   1560
tttgtggcgg cctaa                                                     1575
```

<210> SEQ ID NO 107
<211> LENGTH: 524
<212> TYPE: PRT
<213> ORGANISM: Human papillomavirus

<400> SEQUENCE: 107

```
Met Ser Val Gly Asp Ser Tyr Pro Asn Arg Leu Phe Ile Val Asp Val
1               5                   10                  15

Leu Cys Pro Phe Val Lys Pro His Leu Thr Pro Leu Phe Tyr Ile
            20                  25                  30

Val Leu Ile His Phe His Phe Asp Thr Phe Val Phe Leu Tyr Leu
        35                  40                  45

Leu Arg Phe Asn Lys Arg Ala Thr Met Ser Ile Arg Ala Lys Arg Arg
```

```
                50                  55                  60
Lys Arg Ala Ser Pro Thr Asp Leu Tyr Arg Thr Cys Lys Gln Ala Gly
 65                  70                  75                  80

Thr Cys Pro Pro Asp Ile Ile Pro Arg Val Glu Gln Asn Thr Leu Ala
                 85                  90                  95

Asp Lys Ile Leu Lys Trp Gly Ser Leu Gly Val Phe Phe Gly Gly Leu
                100                 105                 110

Gly Ile Gly Thr Gly Ser Gly Thr Gly Gly Arg Thr Gly Tyr Ile Pro
                115                 120                 125

Val Gly Ser Arg Pro Thr Thr Val Val Asp Ile Gly Pro Thr Pro Arg
130                 135                 140

Pro Pro Val Ile Ile Glu Pro Val Gly Ala Ser Glu Pro Ser Ile Val
145                 150                 155                 160

Thr Leu Val Glu Asp Ser Ser Ile Ile Asn Ala Gly Ala Ser His Pro
                165                 170                 175

Thr Phe Thr Gly Thr Gly Gly Phe Glu Val Thr Thr Ser Thr Val Thr
                180                 185                 190

Asp Pro Ala Val Leu Asp Ile Thr Pro Ser Gly Thr Ser Val Gln Val
                195                 200                 205

Ser Ser Ser Ser Phe Leu Asn Pro Leu Tyr Thr Glu Pro Ala Ile Val
210                 215                 220

Glu Ala Pro Gln Thr Gly Glu Val Ser Gly His Val Leu Val Ser Thr
225                 230                 235                 240

Ala Thr Ser Gly Ser His Gly Tyr Glu Glu Ile Pro Met Gln Thr Phe
                245                 250                 255

Ala Thr Ser Gly Gly Ser Gly Thr Glu Pro Ile Ser Ser Thr Pro Leu
                260                 265                 270

Pro Gly Val Arg Arg Val Ala Gly Pro Arg Leu Tyr Ser Arg Ala Asn
                275                 280                 285

Gln Gln Val Gln Val Arg Asp Pro Ala Phe Leu Ala Arg Pro Ala Asp
                290                 295                 300

Leu Val Thr Phe Asp Asn Pro Val Tyr Asp Pro Glu Glu Thr Ile Ile
305                 310                 315                 320

Phe Gln His Pro Asp Leu His Glu Pro Pro Asp Pro Asp Phe Leu Asp
                325                 330                 335

Ile Val Ala Leu His Arg Pro Ala Leu Thr Ser Arg Arg Gly Thr Val
                340                 345                 350

Arg Phe Ser Arg Leu Gly Arg Arg Ala Thr Leu Arg Thr Arg Ser Gly
                355                 360                 365

Lys Gln Ile Gly Ala Arg Val His Phe Tyr His Asp Ile Ser Pro Ile
370                 375                 380

Gly Thr Glu Glu Leu Glu Met Glu Pro Leu Leu Pro Ala Ser Thr
385                 390                 395                 400

Asp Asn Thr Asp Met Leu Tyr Asp Val Tyr Ala Asp Ser Asp Val Leu
                405                 410                 415

Gln Pro Leu Leu Asp Glu Leu Pro Ala Ala Pro Arg Gly Ser Leu Ser
                420                 425                 430

Leu Ala Asp Thr Ala Val Ser Ala Thr Ser Ala Ser Thr Leu Arg Gly
                435                 440                 445

Ser Thr Thr Val Pro Leu Ser Ser Gly Ile Asp Val Pro Val Tyr Thr
                450                 455                 460

Gly Pro Asp Ile Glu Pro Pro Asn Val Pro Gly Met Gly Pro Leu Ile
465                 470                 475                 480
```

```
Pro Val Ala Pro Ser Leu Pro Ser Ser Val Tyr Ile Phe Gly Gly Asp
            485                 490                 495

Tyr Tyr Leu Met Pro Ser Tyr Val Leu Trp Pro Lys Arg Lys Arg
        500                 505                 510

Val His Tyr Phe Phe Ala Asp Gly Phe Val Ala Ala
        515                 520
```

<210> SEQ ID NO 108
<211> LENGTH: 2385
<212> TYPE: DNA
<213> ORGANISM: Homo sapiens

<400> SEQUENCE: 108

| | | | | | |
|---|---|---|---|---|---|
| atggagctga | ggccctggtt | gctatgggtg | gtagcagcaa | caggaacctt | ggtcctgcta | 60 |
| gcagctgatg | ctcagggcca | gaaggtcttc | accaacacgt | gggctgtgcg | catccctgga | 120 |
| ggcccagcgg | tggccaacag | tgtggcacgg | aagcatgggt | tcctcaacct | gggccagatc | 180 |
| ttcgggact | attaccactt | ctggcatcga | ggagtgacga | agcggtccct | gtcgcctcac | 240 |
| cgcccgcggc | acagccggct | gcagagggag | cctcaagtac | agtggctgga | cagcaggtg | 300 |
| gcaaagcgac | ggactaaacg | ggacgtgtac | caggagccca | cagaccccaa | gtttcctcag | 360 |
| cagtggtacc | tgtctggtgt | cactcagcgg | gacctgaatg | tgaaggcggc | ctgggcgcag | 420 |
| ggctacacag | ggcacggcat | tgtggtctcc | attctggacg | atggcatcga | agaaccac | 480 |
| ccggacttgg | caggcaatta | tgatcctggg | gccagttttg | atgtcaatga | ccaggaccct | 540 |
| gaccccagc | ctcggtacac | acagatgaat | gacaacaggc | acggcacacg | tgtgcggggg | 600 |
| gaagtggctg | cggtggccaa | caacggtgtc | tgtggtgtag | gtgtggccta | caacgcccgc | 660 |
| attggagggg | tgcgcatgct | ggatggcgag | gtgacagatg | cagtggaggc | acgctcgctg | 720 |
| ggcctgaacc | ccaaccacat | ccacatctac | agtgccagct | ggggcccga | ggatgacggc | 780 |
| aagacagtgg | atgggccagc | ccgcctcgcc | gaggaggcct | tcttccgtgg | ggttagccag | 840 |
| ggccgagggg | ggctgggctc | catctttgtc | tgggcctcgg | ggaacggggg | ccgggaacat | 900 |
| gacagctgca | actgcgacgg | ctacaccaac | agtatctaca | cgctgtccat | cagcagcgcc | 960 |
| acgcagtttg | gcaacgtgcc | gtggtacagc | gaggcctgct | cgtccacact | ggccacgacc | 1020 |
| tacagcagtg | gcaaccagaa | tgagaagcag | atcgtgacga | ctgacttgcg | gcagaagtgc | 1080 |
| acggagtctc | acacgggcac | ctcagcctct | gccccttag | cagccggcat | cattgctctc | 1140 |
| accctggagg | ccaataagaa | cctcacatgg | cgggacatgc | aacacctggt | ggtacagacc | 1200 |
| tcgaagccag | cccacctcaa | tgccaacgac | tgggccacca | atggtgtggg | ccggaaagtg | 1260 |
| agccactcat | atggctacgg | gcttttggac | gcaggcgcca | tggtggccct | ggcccagaat | 1320 |
| tggaccacag | tggccccca | gcggaagtgc | atcatcgaca | tcctcaccga | gcccaaagac | 1380 |
| atcgggaaac | ggctcgaggt | gcggaagacc | gtgaccgcgt | gcctgggcga | gcccaaccac | 1440 |
| atcactcggc | tggagcacgc | tcaggcgcgg | ctcaccctgt | cctataatcg | ccgtggcgac | 1500 |
| ctggccatcc | acctggtcag | ccccatgggc | acccgctcca | ccctgctggc | agccaggcca | 1560 |
| catgactact | ccgcagatgg | gtttaatgac | tgggccttca | tgacaactca | ttcctgggat | 1620 |
| gaggatccct | ctggcgagtg | ggtcctagag | attgaaaaca | ccagcgaagc | caacaactat | 1680 |
| gggacgctga | ccaagttcac | cctcgtactc | tatggcaccg | ccctgagggg | gctgccgta | 1740 |
| cctccagaaa | gcagtggctg | caagaccctc | acgtccagtc | aggcctgtgt | ggtgtgcgag | 1800 |
| gaaggcttct | ccctgcacca | gaagagctgt | gtccagcact | gccctccagg | gttcgccccc | 1860 |

-continued

```
caagtcctcg atacgcacta tagcaccgag aatgacgtgg agaccatccg ggccagcgtc    1920 tgcgcccct  gccacgcctc atgtgccaca tgccagggc  cggccctgac agactgcctc    1980
agctgcccca gccacgcctc cttggaccct gtggagcaga cttgctcccg gcaaagccag    2040
agcagccgag agtccccgcc acagcagcag ccacctcggc tgcccccgga ggtggaggcg    2100
gggcaacggc tgcgggcagg gctgctgccc tcacacctgc ctgaggtggt ggccggcctc    2160
agctgcgcct tcatcgtgct ggtcttcgtc actgtcttcc tggtcctgca gctgcgctct    2220
ggctttagtt ttcgggggt  gaaggtgtac accatggacc gtggcctcat ctcctacaag    2280
gggctgcccc ctgaagcctg gcaggaggag tgcccgtctg actcagaaga ggacgagggc    2340
cggggcgaga ggaccgcctt tatcaaagac cagagcgccc tctga                    2385
```

<210> SEQ ID NO 109
<211> LENGTH: 794
<212> TYPE: PRT
<213> ORGANISM: Homo sapiens

<400> SEQUENCE: 109

```
Met Glu Leu Arg Pro Trp Leu Leu Trp Val Ala Ala Thr Gly Thr
1               5                   10                  15

Leu Val Leu Leu Ala Ala Asp Ala Gln Gly Gln Lys Val Phe Thr Asn
                20                  25                  30

Thr Trp Ala Val Arg Ile Pro Gly Gly Pro Ala Val Ala Asn Ser Val
            35                  40                  45

Ala Arg Lys His Gly Phe Leu Asn Leu Gly Gln Ile Phe Gly Asp Tyr
        50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
    130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Val Ala Asn Asn
        195                 200                 205

Gly Val Cys Gly Val Gly Val Ala Tyr Asn Ala Arg Ile Gly Gly Val
    210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
            260                 265                 270

Ala Phe Phe Arg Gly Val Ser Gln Gly Arg Gly Gly Leu Gly Ser Ile
```

-continued

```
            275                 280                 285
Phe Val Trp Ala Ser Gly Asn Gly Gly Arg Glu His Asp Ser Cys Asn
290                 295                 300
Cys Asp Gly Tyr Thr Asn Ser Ile Tyr Thr Leu Ser Ile Ser Ser Ala
305                 310                 315                 320
Thr Gln Phe Gly Asn Val Pro Trp Tyr Ser Glu Ala Cys Ser Ser Thr
            325                 330                 335
Leu Ala Thr Thr Tyr Ser Ser Gly Asn Gln Asn Glu Lys Gln Ile Val
            340                 345                 350
Thr Thr Asp Leu Arg Gln Lys Cys Thr Glu Ser His Thr Gly Thr Ser
            355                 360                 365
Ala Ser Ala Pro Leu Ala Ala Gly Ile Ile Ala Leu Thr Leu Glu Ala
            370                 375                 380
Asn Lys Asn Leu Thr Trp Arg Asp Met Gln His Leu Val Val Gln Thr
385                 390                 395                 400
Ser Lys Pro Ala His Leu Asn Ala Asn Asp Trp Ala Thr Asn Gly Val
            405                 410                 415
Gly Arg Lys Val Ser His Ser Tyr Gly Tyr Gly Leu Leu Asp Ala Gly
            420                 425                 430
Ala Met Val Ala Leu Ala Gln Asn Trp Thr Thr Val Ala Pro Gln Arg
            435                 440                 445
Lys Cys Ile Ile Asp Ile Leu Thr Glu Pro Lys Asp Ile Gly Lys Arg
450                 455                 460
Leu Glu Val Arg Lys Thr Val Thr Ala Cys Leu Gly Glu Pro Asn His
465                 470                 475                 480
Ile Thr Arg Leu Glu His Ala Gln Ala Arg Leu Thr Leu Ser Tyr Asn
            485                 490                 495
Arg Arg Gly Asp Leu Ala Ile His Leu Val Ser Pro Met Gly Thr Arg
            500                 505                 510
Ser Thr Leu Leu Ala Ala Arg Pro His Asp Tyr Ser Ala Asp Gly Phe
            515                 520                 525
Asn Asp Trp Ala Phe Met Thr Thr His Ser Trp Asp Glu Asp Pro Ser
530                 535                 540
Gly Glu Trp Val Leu Glu Ile Glu Asn Thr Ser Glu Ala Asn Asn Tyr
545                 550                 555                 560
Gly Thr Leu Thr Lys Phe Thr Leu Val Leu Tyr Gly Thr Ala Pro Glu
            565                 570                 575
Gly Leu Pro Val Pro Pro Glu Ser Ser Gly Cys Lys Thr Leu Thr Ser
            580                 585                 590
Ser Gln Ala Cys Val Val Cys Glu Glu Gly Phe Ser Leu His Gln Lys
            595                 600                 605
Ser Cys Val Gln His Cys Pro Pro Gly Phe Ala Pro Gln Val Leu Asp
            610                 615                 620
Thr His Tyr Ser Thr Glu Asn Asp Val Glu Thr Ile Arg Ala Ser Val
625                 630                 635                 640
Cys Ala Pro Cys His Ala Ser Cys Ala Thr Cys Gln Gly Pro Ala Leu
            645                 650                 655
Thr Asp Cys Leu Ser Cys Pro Ser His Ala Ser Leu Asp Pro Val Glu
            660                 665                 670
Gln Thr Cys Ser Arg Gln Ser Gln Ser Ser Arg Glu Ser Pro Pro Gln
            675                 680                 685
Gln Gln Pro Pro Arg Leu Pro Pro Glu Val Glu Ala Gly Gln Arg Leu
            690                 695                 700
```

```
Arg Ala Gly Leu Leu Pro Ser His Leu Pro Glu Val Val Ala Gly Leu
705                 710                 715                 720

Ser Cys Ala Phe Ile Val Leu Val Phe Val Thr Val Phe Leu Val Leu
                725                 730                 735

Gln Leu Arg Ser Gly Phe Ser Phe Arg Gly Val Lys Val Tyr Thr Met
            740                 745                 750

Asp Arg Gly Leu Ile Ser Tyr Lys Gly Leu Pro Pro Glu Ala Trp Gln
        755                 760                 765

Glu Glu Cys Pro Ser Asp Ser Glu Glu Asp Glu Gly Arg Gly Glu Arg
    770                 775                 780

Thr Ala Phe Ile Lys Asp Gln Ser Ala Leu
785                 790

<210> SEQ ID NO 110
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
aatggaccag ttctaatgt                                                  19

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gtcagcccta aattcttc                                                   18

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
taatacgact cactataggg                                                 20

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
tagaaggcac agtcgagg                                                   18

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 114
atggtgagca agggcgagga g                                             21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
cttgtacagc tcgtccatgc c                                             21

<210> SEQ ID NO 116
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
ccggatcctg ggaagcttgt catcaacgg                                     29

<210> SEQ ID NO 117
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
ggctcgaggc agtgatggca tggactg                                       27

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ser Ile Ile Asn Phe Glu Lys Leu
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Ile Leu Gly Phe Val Phe Thr Leu
1               5

<210> SEQ ID NO 120
<211> LENGTH: 4
<212> TYPE: PRT
<213> ORGANISM: Human papillomavirus

<400> SEQUENCE: 120

```
Gln Asp Lys Leu
1

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Pro Leu Ile Ser Leu Asp Cys Ala Phe
1               5

<210> SEQ ID NO 122
<211> LENGTH: 17
<212> TYPE: PRT
<213> ORGANISM: Epstein-Barr virus

<400> SEQUENCE: 122

Tyr Leu Gln Gln Asn Trp Trp Thr Leu Leu Val Asp Leu Leu Trp Leu
1               5                   10                  15

Leu

<210> SEQ ID NO 123
<211> LENGTH: 16
<212> TYPE: PRT
<213> ORGANISM: Homo sapiens

<400> SEQUENCE: 123

Ile Gly His Val Tyr Ile Phe Ala Thr Cys Leu Gly Leu Ser Tyr Asp
1               5                   10                  15

<210> SEQ ID NO 124
<211> LENGTH: 8
<212> TYPE: PRT
<213> ORGANISM: Mycoplasma penetrans

<400> SEQUENCE: 124

Ile Tyr Ile Phe Ala Ala Cys Leu
1               5

<210> SEQ ID NO 125
<211> LENGTH: 15
<212> TYPE: PRT
<213> ORGANISM: Unknown
<220> FEATURE:
<223> OTHER INFORMATION: Description of Unknown:
      STEAP sequence

<400> SEQUENCE: 125

His Gln Gln Tyr Phe Tyr Lys Ile Pro Ile Leu Val Ile Asn Lys
1               5                   10                  15

<210> SEQ ID NO 126
<211> LENGTH: 15
<212> TYPE: PRT
<213> ORGANISM: Unknown
<220> FEATURE:
<223> OTHER INFORMATION: Description of Unknown:
      STEAP sequence

<400> SEQUENCE: 126

Leu Leu Asn Trp Ala Tyr Gln Gln Val Gln Gln Asn Lys Glu Asp
```

<210> SEQ ID NO 127
<211> LENGTH: 14
<212> TYPE: PRT
<213> ORGANISM: Unknown
<220> FEATURE:
<223> OTHER INFORMATION: Description of Unknown:
    Taxol-resistance-associated gene-3 sequence

<400> SEQUENCE: 127

Glu Phe His Ala Cys Trp Pro Ala Phe Thr Val Leu Gly Glu
1               5                   10

<210> SEQ ID NO 128
<211> LENGTH: 15
<212> TYPE: PRT
<213> ORGANISM: Homo sapiens

<400> SEQUENCE: 128

Trp Gln Pro Phe Leu Lys Asp His Arg Ile Ser Thr Phe Lys Asn
1               5                   10                  15

<210> SEQ ID NO 129
<211> LENGTH: 15
<212> TYPE: PRT
<213> ORGANISM: Human papillomavirus

<400> SEQUENCE: 129

Leu Phe Val Val Tyr Arg Asp Ser Ile Pro His Ala Ala Cys His
1               5                   10                  15

<210> SEQ ID NO 130
<211> LENGTH: 15
<212> TYPE: PRT
<213> ORGANISM: Human papillomavirus

<400> SEQUENCE: 130

Gly Leu Tyr Asn Leu Leu Ile Arg Cys Leu Arg Cys Gln Lys Pro
1               5                   10                  15

<210> SEQ ID NO 131
<211> LENGTH: 13
<212> TYPE: PRT
<213> ORGANISM: Unknown
<220> FEATURE:
<223> OTHER INFORMATION: Description of Unknown:
    Carcinoembryonic antigen sequence

<400> SEQUENCE: 131

Leu Trp Trp Val Asn Asn Gln Ser Leu Pro Val Ser Pro
1               5                   10

<210> SEQ ID NO 132
<211> LENGTH: 25
<212> TYPE: PRT
<213> ORGANISM: Mycobacterium bovis

<400> SEQUENCE: 132

Phe Ser Lys Leu Pro Ala Ser Thr Ile Asp Glu Leu Lys Thr Asn Ser
1               5                   10                  15

Ser Leu Leu Thr Ser Ile Leu Thr Tyr
            20                  25

<210> SEQ ID NO 133

```
<211> LENGTH: 28
<212> TYPE: PRT
<213> ORGANISM: Mycobacterium bovis

<400> SEQUENCE: 133

Gly Asn Ala Asp Val Val Cys Gly Gly Val Ser Thr Ala Asn Ala Thr
1               5                   10                  15

Val Tyr Met Ile Asp Ser Val Leu Met Pro Pro Ala
            20                  25

<210> SEQ ID NO 134
<211> LENGTH: 13
<212> TYPE: PRT
<213> ORGANISM: Homo sapiens

<400> SEQUENCE: 134

Gly Ser Pro Tyr Val Ser Arg Leu Leu Gly Ile Cys Leu
1               5                   10

<210> SEQ ID NO 135
<211> LENGTH: 17
<212> TYPE: PRT
<213> ORGANISM: Homo sapiens

<400> SEQUENCE: 135

Lys Val Pro Ile Lys Trp Met Ala Leu Glu Ser Ile Leu Arg Arg Arg
1               5                   10                  15

Phe

<210> SEQ ID NO 136
<211> LENGTH: 25
<212> TYPE: PRT
<213> ORGANISM: Homo sapiens

<400> SEQUENCE: 136

Pro Gly Val Leu Leu Lys Glu Phe Thr Val Ser Gly Asn Ile Leu Thr
1               5                   10                  15

Ile Arg Leu Thr Ala Ala Asp His Arg
            20                  25

<210> SEQ ID NO 137
<211> LENGTH: 15
<212> TYPE: PRT
<213> ORGANISM: Clostridium tetani

<400> SEQUENCE: 137

Val Ser Ile Asp Lys Phe Arg Ile Phe Cys Lys Ala Asn Pro Lys
1               5                   10                  15

<210> SEQ ID NO 138
<211> LENGTH: 16
<212> TYPE: PRT
<213> ORGANISM: Clostridium tetani

<400> SEQUENCE: 138

Leu Lys Phe Ile Ile Lys Arg Tyr Thr Pro Asn Asn Glu Ile Asp Ser
1               5                   10                  15

<210> SEQ ID NO 139
<211> LENGTH: 15
<212> TYPE: PRT
<213> ORGANISM: Clostridium tetani

<400> SEQUENCE: 139
```

Ile Arg Glu Asp Asn Asn Ile Thr Leu Lys Leu Asp Arg Cys Asn
1               5                   10                  15

<210> SEQ ID NO 140
<211> LENGTH: 21
<212> TYPE: PRT
<213> ORGANISM: Clostridium tetani

<400> SEQUENCE: 140

Phe Asn Asn Phe Thr Val Ser Phe Trp Leu Arg Val Pro Lys Val Ser
1               5                   10                  15

Ala Ser His Leu Glu
            20

<210> SEQ ID NO 141
<211> LENGTH: 14
<212> TYPE: PRT
<213> ORGANISM: Clostridium tetani

<400> SEQUENCE: 141

Gln Tyr Ile Lys Ala Asn Ser Lys Phe Ile Gly Ile Thr Glu
1               5                   10

<210> SEQ ID NO 142
<211> LENGTH: 20
<212> TYPE: PRT
<213> ORGANISM: Hepatitis B virus

<400> SEQUENCE: 142

Pro His His Thr Ala Leu Arg Gln Ala Ile Leu Cys Trp Gly Glu Leu
1               5                   10                  15

Met Thr Leu Ala
            20

<210> SEQ ID NO 143
<211> LENGTH: 13
<212> TYPE: PRT
<213> ORGANISM: Influenza virus

<400> SEQUENCE: 143

Pro Lys Tyr Val Lys Gln Asn Thr Leu Lys Leu Ala Thr
1               5                   10

<210> SEQ ID NO 144
<211> LENGTH: 15
<212> TYPE: PRT
<213> ORGANISM: Hepatitis B virus

<400> SEQUENCE: 144

Phe Phe Leu Leu Thr Arg Ile Leu Thr Ile Pro Gln Ser Leu Asp
1               5                   10                  15

<210> SEQ ID NO 145
<211> LENGTH: 16
<212> TYPE: PRT
<213> ORGANISM: Influenza virus

<400> SEQUENCE: 145

Tyr Ser Gly Pro Leu Lys Ala Glu Ile Ala Gln Arg Leu Glu Asp Val
1               5                   10                  15

<210> SEQ ID NO 146
<211> LENGTH: 18

```
<212> TYPE: PRT
<213> ORGANISM: Plasmodium falciparum

<400> SEQUENCE: 146

Glu Lys Lys Ile Ala Lys Met Glu Lys Ala Ser Ser Val Phe Asn Val
1               5                   10                  15

Val Asn

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Arg Ala His Tyr Asn Ile Val Thr Phe
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Pro Ser Tyr Val Tyr His Gln Phe
1               5

<210> SEQ ID NO 149
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
aaagaattcg atggcacagg ttctcagagg                                    30

<210> SEQ ID NO 150
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
tttagatctg tcatcttctc cacagagca                                     29

<210> SEQ ID NO 151
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 151

His His His His His His
1               5
```

```
<210> SEQ ID NO 152
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Arg Val Lys Arg Ser Ile Ile Asn Phe Glu Lys Leu
1               5                   10

<210> SEQ ID NO 153
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Arg Val Lys Arg Gly Ile Leu Gly Phe Val Phe Thr Leu
1               5                   10

<210> SEQ ID NO 154
<211> LENGTH: 4
<212> TYPE: PRT
<213> ORGANISM: Plasmodium falciparum

<400> SEQUENCE: 154

Asn Ala Asn Pro
1
```

METHODS FOR ENHANCING ANTIGEN-SPECIFIC IMMUNE RESPONSES

RELATED APPLICATIONS

This application is a Divisional of U.S. application Ser. No. 15/543,806, filed on Jul. 14, 2017, which is a 371 National Stage of Application PCT/US16/13545, filed Jan. 15, 2016, which claims the benefit of U.S. Provisional Application Ser. No. 62/104,464, filed on Jan. 16, 2015. The entire contents of these applications are incorporated herein by reference in their entirety.

GOVERNMENTAL SUPPORT

This invention was made with government support under grant CA098252 and CA114425 awarded by the National Institutes of Health. The government has certain rights in this invention.

BACKGROUND

Cancer immunotherapeutics have shown promise for the treatment of a number of tumors and hyper proliferative diseases, but their utility is limited in situations where the tumor is relatively large or rapidly growing. For example, advanced stage cancers are extremely difficult to treat and rarely result in a cure. Efforts to improve early detection and treatment of advanced stage cancers have been relatively unsuccessful. Existing therapies for advanced disease, such as chemotherapy and radiation therapy, have not improved the overall survival of patients with locally advanced or metastatic disease (Early Breast Cancer Trialists' Collaborative Group, Lancet, 339:1-15 (1992); Baum et al., Salmon S E, ed., Adjuvant therapy of cancer V1. Philadelphia: WB. Saunders, 269-74 (1990); Swain, S. M., Surg. Clin. North Am., 70:1061-80 (1990)). Therefore, there is a strong need to develop innovative therapeutic approaches for the control of hyper proliferative diseases, particularly if they have progressed to an advanced stage.

SUMMARY OF THE INVENTION

Provided herein are methods and compositions for increasing or stimulating an immune response, e.g., for treating and/or preventing recurrence of a hyper proliferating disease, e.g., cancer. The methods involve administrating a therapeutic chimeric protein containing a tumor-homing module comprising annexin fused to an immunogenic CTL epitope combined with conventional chemotherapy for the control of advanced stage cancers.

One aspect of the invention relates to a method of inducing or enhancing an antigen-specific immune response in a mammal, comprising administering to the mammal an effective amount of an annexin chimeric fusion protein, wherein the annexin chimeric fusion protein comprises at least one immunogenic antigen, thereby enhancing the antigen specific immune response relative to administration of the immogenic antigen alone.

In certain embodiments, the annexin is Annexin V (annV).

In certain embodiments, the antigen is a tumor-associated antigen (TAA).

In certain embodiments, the antigen is foreign to the mammal.

In certain embodiments, the antigen is selected from the group consisting of ovalbumin (OVA), HPV16 E6, HPV16 E7, modified colon carcinoma antigen AH5, and influenza antigen M1.

In certain embodiments, the annV chimeric fusion protein comprises a furin cleavage site.

In certain embodiments, the annV chimeric fusion protein is administered intradermally, intraperitoneally, or intravenously via injection.

In certain embodiments, the annV chimeric fusion protein is administered intravenously via injection.

In certain embodiments, the administration is repeated at least once.

In certain embodiments, the antigen-specific immune response is mediated at least in part by CD8+ cytotoxic T lymphocytes (CTL).

In certain embodiments, the methods further comprise administering an effective amount of a chemotherapeutic agent.

In certain embodiments, the methods further comprise screening the mammal for the presence of antibodies against the antigen.

In certain embodiments, the mammal is a human.

In certain embodiments, the mammal is afflicted with cancer.

Another aspect of the invention relates to a method of inducing or enhancing an antigen-specific immune response in a mammal, comprising the steps of:
(a) priming the mammal by administering to the mammal an effective amount of a chemotherapeutic agent; and
(b) boosting the mammal by administering to the mammal an effective amount of an annexin chimeric fusion protein,
thereby inducing or enhancing the antigen-specific immune response.

In certain embodiments, the annexin is Annexin V (annV).

In certain embodiments, the antigen is a tumor-associated antigen (TAA).

In certain embodiments, the antigen is foreign to the mammal.

In certain embodiments, the antigen is selected from the group consisting of ovalbumin (OVA), HPV16 E6, HPV16 E7, modified colon carcinoma antigen AH5, and influenza antigen M1.

In certain embodiments, the annV chimeric fusion protein comprises a furin cleavage site.

In certain embodiments, the annV chimeric fusion protein is administered intradermally, intraperitoneally, or intravenously via injection.

In certain embodiments, the annV chimeric fusion protein is administered intravenously via injection.

In certain embodiments, the chemotherapeutic agent is administered intradermally, intraperitoneally, or intravenously via injection.

In certain embodiments, the chemotherapeutic agent is administered intraperitoneally.

In certain embodiments, the antigen-specific immune response is mediated at least in part by CD8+ cytotoxic T lymphocytes (CTL).

In certain embodiments, the chemotherapeutic agent is cisplatin.

In certain embodiments, the methods further comprise screening the mammal for the presence of antibodies against the antigen.

In certain embodiments, the mammal is a human.

In certain embodiments, the mammal is afflicted with cancer.

In certain embodiments, step (a) is performed before step (b), step (a) and step (b) are performed at the same time, or step (a) is performed after step (b).

In certain embodiments, step (a) and/or step (b) is repeated at least once.

In certain embodiments, the dosage used in step (a) is 5 mg/kg.

In certain embodiments, the dosage used in step (b) is 100 ug.

In certain embodiments, the antigen-specific immune response is greater in magnitude than an antigen-specific immune response induced by administration of the annexin chimeric fusion protein alone.

In certain embodiments, the antigen-specific immune response is greater in magnitude than an antigen-specific immune response induced by administration of the chemotherapeutic agent alone.

Another aspect of the invention relates to a method for treating or preventing advanced stage cancer in a mammal comprising (a) priming the mammal by administering to the mammal an effective amount of a chemotherapeutic agent; and (b) boosting the mammal by administering to the mammal an effective amount of an annexin chimeric fusion protein, thereby inducing or enhancing the antigen-specific immune response.

In certain embodiments, the advanced stage cancer is selected from the group consisting of melanoma, thymoma, colon carcinoma, pancreatic carcinoma, and ovarian carcinoma.

In certain embodiments, the annexin is Annexin V (annV).

In certain embodiments, the antigen is selected from the group consisting of ovalbumin (OVA), HPV16 E6, HPV16 E7, modified colon carcinoma antigen AH5, and influenza antigen M1.

In certain embodiments, the chemotherapeutic agent is cisplatin.

Another aspect of the invention relates to a kit comprising a priming composition and a boosting composition, the kit comprising;
(a) a priming composition comprising a chemotherapeutic agent and a pharmaceutically acceptable carrier; and
(b) a boosting composition comprising an annexin chimeric fusion protein and a pharmaceutically acceptable carrier.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 shows the characterization of tumor growth, survival and E7-specific CD8$^+$ T cell immune responses in tumor-bearing mice treated with different regimens. Panel (A) depicts schematic diagram of the treatment regimen. For the in vivo tumor treatment experiment, C57BL/6 mice (ten per group) were injected with $1 \times 10^5$ TC-1 cells/mouse subcutaneously. Three days later, mice were injected with 100 μg/mouse of Annexin V (AnnV) or AnnV-E7 protein or 3.5 μg/mouse of E7 peptide or PBS as a control intravenously three times at 3-day intervals. Panel (B) depicts characterization of tumor growth in treated mice. Line graph depicts TC-1 tumor volume in different treatment groups over time. Panel (C) shows Kaplan-Meier survival analysis of tumor bearing mice in different treatment groups. Panel (D) shows Flow cytometry analysis to demonstrate IFN-γ-secreting E7-specific CD8$^+$ T cells in splenocytes isolated from tumor-bearing mice. $1 \times 10^5$ TC-1 cells/mice were injected into C57BL/6 mice (three per group) subcutaneously. Three days later, mice were treated as outlined in FIG. 1A. One week after the last immunization, splenocytes were isolated from treated tumor-bearing mice and characterized for the presence of E7-specific CD8$^+$ T cells. The isolated splenocytes were stained for CD8 and IFN-γ and analyzed by flow cytometry. Left panel is representative flow cytometry analysis. Right panel is bar graph depicting the number of E7-specific IFN-γ/CD8$^+$ T-cells per $3 \times 10^5$ splenocytes. The data presented are from one representative experiment of two performed. Panel (E) shows In vivo CD8 depletion experiment. Tumor-bearing mice (five per group) were treated with AnnV-E7 protein intraperitoneally three times as described in FIG. 1A. CD8$^+$ T cell depletion of tumor-bearing mice using mAb 2.43 antibody was initiated 1 day before tumor treatment and ended 30 days after tumor challenge. IgG antibody was used as a control. Line graph depicts TC-1 tumor volume over time. Panel (F) shows mice were injected with $1 \times 10^5$ TC-1 cells/mouse subcutaneously (three per group). Three days later, mice were treated with GFP-E7 or AnnV-E7 protein as described in FIG. 1A. One week after the last immunization, PBMCs were isolated and characterized for the presence of E7-specific CD8$^+$ T cells. PBMCs were stained with CD8 antibody and E7 peptide loaded H-2D$^b$ tetramer. Left panel is representative flow cytometry. Right panel is bar graph depicting the percentage of CD8/E7-tetramer positive cells among PBMCs (mean±S.D.).

FIG. 2 shows the combined regimens generate more synergistic CD8$^+$ T cell immune responses and antitumor effects in tumor-bearing mice. Panel (A) depicts representative bioluminescence imaging characterizing the accumulation of protein containing AnnV in tumor loci of tumor-bearing mice after cisplatin treatment. C57BL/6 mice were injected with $1 \times 10^5$ TC-1 cells/mouse subcutaneously. 10 days later, tumor-bearing mice were treated with cisplatin intraperitoneally. After 2 days, mice were injected with PBS, AnnV only or AnnV-Gluc proteins intravenously into the lateral tail vein. Left panel shows bioluminescence imaging one day later. Right panel is bar graph depicting the fluorescence intensity in tumor loci of mice (mean±S.D.). Panel (B) shows mice were subcutaneously injected with $1 \times 10^5$ TC-1 cells each (three mice per group). Five days later, mice were treated with regimens as described in top panel. One week after the last immunization, PBMCs were isolated from treated tumor-bearing mice and characterized for the presence of E7-specific CD8$^+$ T cells. PBMCs were stained with CD8 antibody and E7 tetramer, followed by flow cytometry analysis. Bottom left panel shows representative flow cytometry. Bottom right panel is bar graph depicting the percentage of CD8 and E7-tetramer double positive cells (mean±S.D.). Panel (C) is a line graph depicting tumor volume over time. Panel (D) depicts Kaplan-Meier survival analysis of tumor-bearing mice in different treatment groups.

FIG. 3 depicts the characterization of CT26 tumor growth and antigen-specific CD8$^+$ T cells in tumor-bearing mice treated with cisplatin and AnnV-AH5 protein. Panel (A) shows CT26 tumor-bearing BALB/c mice were treated with regimens as described in top panel. 1 week after the last vaccination, splenocytes were isolated, stained for CD8 and IFN-γ, and analyzed by flow cytometry. Bottom left panel shows representative flow cytometry analysis demonstrating activated IFN-γ-secreting AH1-specific CD8+ T-cells. Bottom right panel is bar graph depicting the number of IFN-γ-secreting AH1-specific CD8+ T cells per $3\times10^5$ splenocytes (mean±SD). Panel (B) shows the characterization of tumor growth in treated mice. Line graph depicts CT26 tumor growth in different treatment groups over time. Panel (C) depicts Kaplan-Meier survival analysis of CT26 tumor-bearing mice in different treatment groups.

FIG. 4 shows generation and characterization of AnnexinV protein conjugated with OVA peptide flanked with or without a furin cleavage site. Panel (A) shows AnnV proteins were purified from *Escherichia coli* BL21 (DE3) strain by Ni+ affinity chromatography. The purity and size of the protein was characterized by SDS-PAGE, followed by staining with Coomassie brilliant blue dye. Panel (B) depicts TC-1 tumor cells ($1\times10^5$ cells/well) were added to 48-well plates and incubated with or without cisplatin. After 18 hours, 0, 1, 5, or 25 μg of AnnV-RO protein was added into the well and 4 hours later, cells were detached. Cells were stained with for OVA257-264 (SIINFEKL) peptide bound to H-2K$^b$ and analyzed using flow cytometry. TC-1 cells treated with 25 μg of AnnV-RO protein and without cisplatin treatment were used as control. Top panel shows the various protein constructs. Bottom panel shows frequency of OVA peptide-loaded MHC class I molecules on TC-1 cells. Panel (C) is representative luminescence imaging to demonstrate in vitro cytotoxicity of OVA-specific CD8+ T cells. Luciferase-expressing TC-1 tumor cells ($1\times10^5$ cells/well) were plated on 24-well plate and incubated with cisplatin. 18 hours later, treated tumor cells were incubated with 5 μg/ml AnnV conjugated with OVA peptide flanked with or without a furin cleavage site. 4 hours later, wells containing TC-1 cells were washed and $2\times10^5$ OVA-specific CD8+ T cells were added. The degree of CTL-mediated killing of the tumor cells was determined by the decrease of luminescence activity using the IVIS luminescence imaging system series 2000. Bioluminescence signals were acquired for 1 min. Left panel shows bioluminescence imaging. Right panel is bar graph depicting viability of tumor cells under the various treatments (mean±SD). Data shown are representative of two experiments performed. Panel (D) shows TC-1 tumor-bearing mice were treated with regimens as described in top panel and splenocytes were collected 1 week after last vaccination. Splenocytes were stained for CD8 and IFN-γ and analyzed by flow cytometry. Bottom left panel is representative flow cytometry. Bottom right panel is bar graph depicting number of IFN-γ-secreting OVA-specific CD8+ T cells per $3\times10^5$ splenocytes (mean±SD). Panel (E) shows tumor infiltrating lymphocytes were isolated from tumor tissues, stained with CD8 antibody and OVA peptide-loaded tetramer, and analyzed by flow cytometry. Left panel is representative flow cytometry. Right panel is bar graph depicting the percentage of infiltrated CD8/OVA-tetramer double positive cells (mean±S.D.). Panel (F) depicts the characterization of tumor growth in treated mice. Line graph depicts TC-1 tumor volume over time. Panel (G) shows Kaplan-Meier survival analysis of TC-1 tumor-bearing mice.

FIG. 5 depicts PancO2 tumor growth in tumor-bearing mice treated with cisplatin in conjunction with AnnexinV-RO protein. Panel (A) shows characterization of tumor growth in treated mice. Line graph depicts PancO2 tumor growth in different treatment groups over time. C57BL/6 mice (5 per group) were injected with $5\times10^6$ PancO2 cells and after 25 days, cisplatin and AnnV-RO or GFP-RO protein treatment was started as indicated in the top panel. Bottom panel is line graph of PancO2 tumor volume over time. Panel (B) depicts Kaplan-Meier survival analysis of PancO2 tumor-bearing mice in different treatment groups.

FIG. 6 depicts characterization of the cytotoxicity of M1-specific CD8+ T cells against OVCAR3 human tumor cells treated with AnnexinV-RM1 protein. Panel (A) is a schematic diagram depicting the various AnnV proteins conjugated with M1 peptide (GILGFVFTL) and flanked with (AnnV-RM1) or without (AnnV-RM1) a furin recognition sequence, as diagrammed. Panel (B) depicts luciferase-expressing OVCAR3 tumor cells ($1\times10^5$ cells/well) were plated on 24-well plate and incubated with cisplatin. 18 hours later, cisplatin-treated cells were incubated with 5 μg/ml of one of the various AnnV-conjugated proteins. 4 hours later, wells containing OVCAR3 cells were washed and $2\times10^5$ M1-specific CD8+ T cells were added. The degree of CTL-mediated killing of the tumor cells was determined by the decrease of luminescence activity using the IVIS luminescence imaging system series 2000. Bioluminescence signals were acquired for 1 min. Representative luminescence image demonstrates in vitro cytotoxicity of M1-specific CD8+ T cells against OVCAR3 tumor cells. Data shown are representative of two experiments performed. Panel (C) shows bar graph depicting viability of tumor cells treated with cisplatin, protein and/or M1-specific cytotoxic T cells (mean±SD).

FIG. 7 depicts characterization of tumor growth in tumor-bearing mice treated with different regimens. Briefly, C57BL/6 mice (five per group) were injected with $1\times10^5$ TC-1 tumor cells/mice subcutaneously. Five days later, tumor-bearing mice were treated with intraperitoneal cisplatin (5 mg/kg body weight) or saline control. Six days later, mice were treated with intraperitoneal AnnexinV-FC or mouse IgG (100 ug/mouse) control. Tumor-bearing mice continue to receive the same protein treatment regimen at a weekly interval. Panel (A) shows the characterization of TC-1 tumor growth in mice treated with either 1) cisplatin+AnnexinV-FC, 2) cisplatin+mouse IgG control, 3) AnnexinV-FC only, and 4) mouse IgG control only. Data shown are mean of each group. Line graph depicts TC-1 tumor growth in different treatment groups over time (mean). Panel (B) is a dot density graph comparing the TC-1 tumor growth in mice treated with cisplatin+AnnexinV-FC and mice treated with cisplatin+mouse IgG control at 42 days after tumor challenge. (mean±SD).

DETAILED DESCRIPTION

Figure 1:
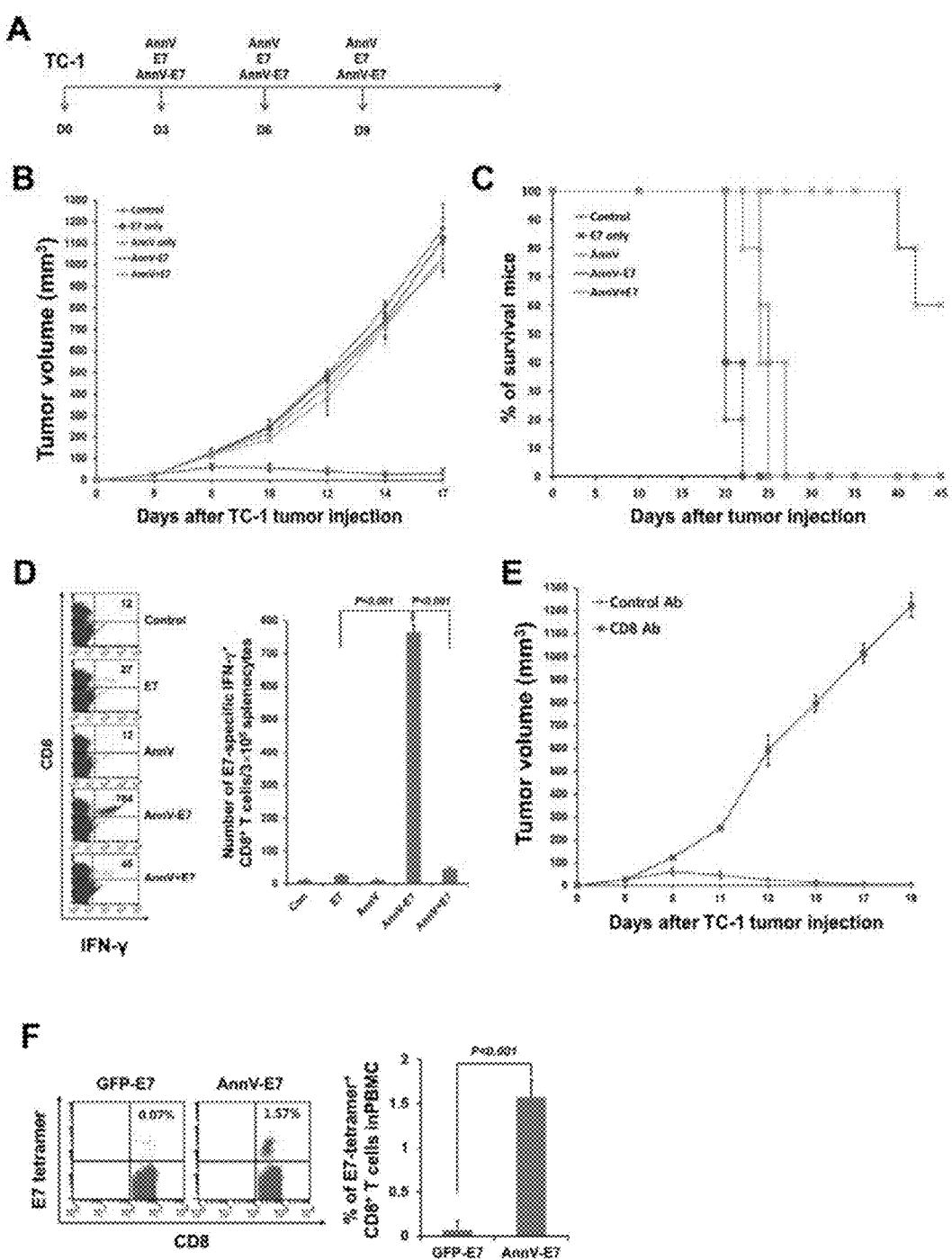
FIG. 1 includes six panels, 1A-1F.

The inventors of the present invention have determined that papillomavirus pseudovirions represents a novel approach for the delivery of naked DNA vaccines to improve transfection efficiency without safety concerns associated with live viral vectors. Accordingly, the present invention is drawn to methods for enhancing an antigen-specific immune response in a mammal using recombinant papillomavirus pseudovirions comprising an antigen.

Partial List of Abbreviations

ANOVA, analysis of variance; APC, antigen presenting cell; CRT, calreticulin; CTL, cytotoxic T lymphocyte; DC, dendritic cell; E6, HPV oncoprotein E6; E7, HPV oncoprotein E7; ELISA, enzyme-linked immunosorbent assay; HPV, human papillomavirus; IFN γ, interferon-γ; i.m., intramuscular(ly); i.t., intratumoral(ly); i.v., intravenous(ly); luc, luciferase; mAB, monoclonal antibody; MOI, multiplicity of infection; OVA, ovalbumin; p-, plasmid-; PBS, phosphate-buffered saline; PCR, polymerase chain reaction; SD, standard deviation; TAA, tumor-associate antigen; WT, wild-type.

Annexins

Annexins represent a highly conserved family of proteins that selectively bind to negatively charged, phosphatidylserine containing phospholipid membranes in the presence of calcium ions ($Ca^{+2}$). The sequences of genes encoding annexins are well known (e.g., Funakoshi et al., *Biochemistry* 26:8087-8092 (1987). Annexin proteins include proteins of the annexin family, such as Annexin II (lipocortin 2, calpactin 1, protein I, p36, chromobindin 8), Annexin III (lipocortin 3, PAP-III), Annexin IV (lipocortin 4, endonexin I, protein II, chromobindin 4), Annexin V ("annV") (Lipocortin 5, Endonexin 2, VAC-alpha, Anchorin CII, PAP-I), Annexin VI (Lipocortin 6, Protein III, Chromobindin 20, p68, p70), Annexin VII (Synexin), Annexin VIII (VAC-beta), Annexin XI (CAP-50), and Annexin XIII (ISA). (Benz and A. Hofmann, *Biol. Chem.* 378:177-183 (1997).)

Annexins are highly abundant and influence various intra- and extra-cellular functions, including membrane trafficking, lymphocyte migration, cell motility, calcium flux, and signal transduction (Gerke, V. et al., "Annexins: From Structure to Function," *Physiol. Rev.*, April 2002. vol. 82, pages 331-371). Dying cells undergoing apoptosis expose these negatively charged lipids on the outer leaflet of the plasma membrane. Therefore, annexins selectively bind to apoptotic cells. (Ernst J D, et al. Preparation and characterization of an endogenously fluorescent annexin for detection of apoptotic cells. *Analytical biochemistry.* 1998; 260:18-23). This diagnostic application of annexins was first demonstrated using fluorescently labeled annexin A5 (V) (Vermes et al. A novel assay for apoptosis. Flow cytometric detection of phosphatidylserine expression on early apoptotic cells using fluorescein labeled Annexin V. (1995) *J. Immunol. Meth.* 184:39-51). The inventors of the present invention have determined that annexins, such as annV, can be used to generate various recombinant proteins which can target an immunogenic CTL epitope to tumor loci.

Accordingly, the methods of the present invention use chimeric proteins containing annV, which binds selectively to apoptotic cells. By fusing the annV to an immunogenic peptide and in combination with conventional chemotherapy, annV can target molecules to tumor loci for cancer therapy following chemotherapy and/or radiation therapy. Immunogenic peptides, include but are not limited to, CTL epitopes or peptides, HPV-16 E7 tumor antigen, HPV-16 E6 tumor antigen, a modified colon carcinoma tumor antigen AH5, ovalbumin (OVA), and influenza antigen M1. Other exemplary antigens are further set forth below. In some embodiments, annV can be conjugated to OVA peptide with or without a furin cleavage site.

Production of the recombinant chimeric protein encoding annexin V and a immunogenic peptide into a suitable vector and expressing the corresponding conformational coding sequences for these proteins in a eukaryotic cell transformed by the vector according to well known methods in the art (especially as those taught in the Examples and references cited therein). The gene(s) is preferably expressed in a bacterial cell system. In other embodiment, eukaryotic expression systems can be used, such as human cells. However, insect and yeast-cell based expression systems are also suitable. Other mammalian cells similarly transfected using appropriate mammalian expression vectors can also be used to produce assembled annV chimeric fusion proteins. Suitable vectors for cloning of expression of the recited DNA sequences are well known in the art and commercially available. Further, suitable regulatory sequences for achieving cloning and expression, e.g., promoters, polyadenylation sequences, enhancers and selectable markers are also well known. The selection of appropriate sequences for obtaining recoverable protein yields is routine to one skilled in the art.

Nucleic Acid (e.g., DNA) Vaccines

Vaccines that may be administered to a mammal include any vaccine, e.g., a nucleic acid vaccine (e.g., a DNA vaccine). In an embodiment of the invention, a nucleic acid vaccine will encode an antigen, e.g., an antigen against which an immune response is desired. Other nucleic acids that may be used are those that increase or enhance an immune reaction, but which do not encode an antigen against which an immune reaction is desired. These vaccines are further described below.

Exemplary antigens include proteins or fragments thereof from a pathogenic organism, e.g., a bacterium or virus or other microorganism, as well as proteins or fragments thereof from a cell, e.g., a cancer cell. In one embodiment, the antigen is from a virus, such as class human papillomavirus (HPV), e.g., E7 or E6. These proteins are also oncogenic proteins, which are important in the induction and maintenance of cellular transformation and co-expressed in most HPV-containing cervical cancers and their precursor lesions. Therefore, cancer vaccines that target E7 or E6 can be used to control of HPV-associated neoplasms (Wu, T-C, *Curr Opin Immunol.* 6:746-54, 1994).

However, as noted, the present invention is not limited to the exemplified antigen(s). Rather, one of skill in the art will appreciate that the same results are expected for any antigen (and epitopes thereof) for which a T cell-mediated response is desired. The response so generated will be effective in providing protective or therapeutic immunity, or both, directed to an organism or disease in which the epitope or antigenic determinant is involved—for example as a cell surface antigen of a pathogenic cell or an envelope or other antigen of a pathogenic virus, or a bacterial antigen, or an antigen expressed as or as part of a pathogenic molecule.

Exemplary antigens and their sequences are set forth below.

E7 Protein from HPV-16

The E7 nucleic acid sequence (SEQ ID NO:1) and amino acid sequence (SEQ ID NO:2) from HPV-16 are shown herein (see GenBank Accession No. NC_001526). The single letter code, the wild type E7 amino acid sequence (SEQ ID NO:2) is shown herein.

In another embodiment (See GenBank Accession No. AF125673, nucleotides 562-858 and the E7 amino acid sequence), the C-terminal four amino acids QDKL (and their codons) above are replaced with the three amino acids QKP (and the codons cag aaa cca), yielding a protein of 98 residues.

When an oncoprotein or an epitope thereof is the immunizing moiety, it is preferable to reduce the tumorigenic risk of the vaccine itself. Because of the potential oncogenicity of the HPV E7 protein, the E7 protein may be used in a "detoxified" form.

To reduce oncogenic potential of E7 in a construct of the present invention, one or more of the following positions of E7 is mutated:

| Original residue | Mutant residue | Preferred codon mutation | nt Position (in SEQ ID NO: 1) | Amino acid (in SEQ ID NO: 2) |
|---|---|---|---|---|
| Cys | Gly (or Ala) | TGT→GGT | 70 | 24 |
| Glu | Gly (or Ala) | GAG→GGG (or GCG) | 77 | 26 |
| Cys | Gly (or Ala) | TGC→GGC | 271 | 91 |

In one embodiment, the E7 (detox) mutant sequence has the following two mutations:
a TGT→GGT mutation resulting in a Cys→Gly substitution at position 24 of SEQ ID NO: 9 and GAG→GGG mutation resulting in a Glu→Gly substitution at position 26 of the wild type E7. This mutated amino acid sequence is shown herein as SEQ ID NO:3.

These substitutions completely eliminate the capacity of the E7 to bind to Rb, and thereby nullify its transforming activity. Any nucleotide sequence that encodes the above E7 or E7(detox) polypeptide, or an antigenic fragment or epitope thereof, can be used in the present compositions and methods, including the E7 and E7(detox) sequences which are shown herein.

E6 Protein from HPV-16

The wild type E6 nucleotide (SEQ ID NO:4) and amino acid sequences (SEQ ID NO:5) are shown herein (see GenBank accession Nos. K02718 and NC_001526). This polypeptide has 158 amino acids and is shown herein in single letter code as SEQ ID NO:5.

E6 proteins from cervical cancer-associated HPV types such as HPV-16 induce proteolysis of the p53 tumor suppressor protein through interaction with E6-AP. Human mammary epithelial cells (MECs) immortalized by E6 display low levels of p53. HPV-16 E6, as well as other cancer-related papillomavirus E6 proteins, also binds the cellular protein E6BP (ERC-55). As with E7, described below a non-oncogenic mutated form of E6 may be used, referred to as "E6(detox)." Several different E6 mutations and publications describing them are discussed below.

The amino acid residues to be mutated are underscored in the E6 amino acid sequence provided herein. Some studies of E6 mutants are based upon a shorter E6 protein of 151 nucleic acids, wherein the N-terminal residue was considered to be the Met at position 8 in the wild type E6. That shorter version of E6 is shown herein as SEQ ID NO:6.

To reduce oncogenic potential of E6 in a construct, one or more of the following positions of E6 is mutated:

| Original residue | Mutant residue | aa position in SEQ ID NO: 5 | aa position in SEQ ID NO: 6 |
|---|---|---|---|
| Cys | Gly (or Ala) | 70 | 63 |
| Cys | Gly (or Ala) | 113 | 106 |
| Ile | Thr | 135 | 128 |

Nguyen et al., *J Virol.* 6:13039-48, 2002, described a mutant of HPV-16 E6 deficient in binding α-helix partners which displays reduced oncogenic potential in vivo. This mutant, which includes a replacement of Ile with Thr as position 128 (of SEQ ID NO: 6), may be used in accordance with the present invention to make an E6 DNA vaccine that has a lower risk of being oncogenic. This E6($I^{128}T$) mutant is defective in its ability to bind at least a subset of α-helix partners, including E6AP, the ubiquitin ligase that mediates E6-dependent degradation of the p53 protein.

Cassetti M C et al., *Vaccine* 22:520-52, 2004, examined the effects of mutations four or five amino acid positions in E6 and E7 to inactivate their oncogenic potential. The following mutations were examined: E6-$C^{63}G$ and E6 $C^{106}G$ (positions based on the wild type E6); E7-$C^{24}G$, E7-$E^{26}G$, and E7 $C^{91}G$ (positions based on the wild type E7). Venezuelan equine encephalitis virus replicon particle (VRP) vaccines encoding mutant or wild type E6 and E7 proteins elicited comparable CTL responses and generated comparable antitumor responses in several HPV16 E6(+)E7 (+) tumor challenge models: protection from either C3 or TC-1 tumor challenge was observed in 100% of vaccinated mice. Eradication of C3 tumors was observed in approximately 90% of the mice. The predicted inactivation of E6 and E7 oncogenic potential was confirmed by demonstrating normal levels of both p53 and Rb proteins in human mammary epithelial cells infected with VRPs expressing mutant E6 and E7 genes.

The HPV16 E6 protein contains two zinc fingers important for structure and function; one cysteine (C) amino acid position in each pair of C—X—X—C (where X is any amino acid) zinc finger motifs may be mutated at E6 positions 63 and 106 (based on the wild type E6). Mutants are created, for example, using the Quick Change Site-Directed Mutagenesis Kit (Stratagene, La Jolla, Calif.). HPV16 E6 containing a single point mutation in the codon for $Cys^{106}$ in the wild type E6 (=Cys 113 in the wild type E6). $Cys^{106}$ neither binds nor facilitates degradation of p53 and is incapable of immortalizing human mammary epithelial cells (MEC), a phenotype dependent upon p53 degradation. A single amino acid substitution at position $Cys^{63}$ of the wild type E6 (=$Cys^{70}$ in the wild type E6) destroys several HPV16 E6 functions: p53 degradation, E6TP-1 degradation, activation of telomerase, and, consequently, immortalization of primary epithelial cells.

Any nucleotide sequence that encodes these E6 polypeptides, one of the mutants thereof, or an antigenic fragment or epitope thereof, can be used in the present invention. Other mutations can be tested and used in accordance with the methods described herein including those described in Cassetti et al., supra. These mutations can be produced from any appropriate starting sequences by mutation of the coding DNA.

The present invention also includes the use of a tandem E6-E7 vaccine, using one or more of the mutations described herein to render the oncoproteins inactive with respect to their oncogenic potential in vivo. VRP vaccines (described in Cassetti et al., supra) comprised fused E6 and E7 genes in one open reading frame which were mutated at four or five amino acid positions. Thus, the present constructs may include one or more epitopes of E6 and E7, which may be arranged in their native order or shuffled in any way that permits the expressed protein to bear the E6 and E7 antigenic epitopes in an immunogenic form. DNA encoding amino acid spacers between E6 and E7 or between individual epitopes of these proteins may be introduced into the vector, provided again, that the spacers permit the expression or presentation of the epitopes in an immunogenic manner after they have been expressed by transduced host cells.

Influenza Hemagglutinin (HA)

A nucleic acid sequence encoding HA is shown herein as SEQ ID NO: 7. The amino acid sequence of HA is shown herein as SEQ ID NO: 8, with the immunodominant epitope underscored.

Ovalbumin (OVA)

An amino acid sequence encoding a representative OVA is shown herein as SEQ ID NO:9.

Other Exemplary Antigens

Exemplary antigens are epitopes of pathogenic microorganisms against which the host is defended by effector T cells responses, including CTL and delayed type hypersensitivity. These typically include viruses, intracellular parasites such as malaria, and bacteria that grow intracellularly such as *Mycobacterium* and *Listeria* species. Thus, the types of antigens included in the vaccine compositions used in the present invention may be any of those associated with such pathogens as well as tumor-specific antigens. It is noteworthy that some viral antigens are also tumor antigens in the case where the virus is a causative factor in the tumor.

In fact, the two most common cancers worldwide, hepatoma and cervical cancer, are associated with viral infection. Hepatitis B virus (HBV) (Beasley, R. P. et al., *Lancet* 2:1129-1133 (1981) has been implicated as etiologic agent of hepatomas. About 80-90% of cervical cancers express the E6 and E7 antigens (discussed above and exemplified herein) from one of four "high risk" human papillomavirus types: HPV-16, HPV-18, HPV-31 and HPV-45 (Gissmann, L. et al., *Ciba Found Symp.* 120:190-207, 1986; Beaudenon, S., et al. *Nature* 321:246-9, 1986, incorporated by reference herein). The HPV E6 and E7 antigens are the most promising targets for virus associated cancers in immunocompetent individuals because of their ubiquitous expression in cervical cancer. In addition to their importance as targets for therapeutic cancer vaccines, virus-associated tumor antigens are also ideal candidates for prophylactic vaccines. Indeed, introduction of prophylactic HBV vaccines in Asia have decreased the incidence of hepatoma (Chang, M H et al. *New Engl. J. Med.* 336, 1855-1859 (1997), representing a great impact on cancer prevention.

Among the most important viruses in chronic human viral infections are HPV, HBV, hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, and influenza virus. Useful antigens include HBV surface antigen or HBV core antigen; ppUL83 or pp89 of CMV; antigens of gp120, gp41 or p24 proteins of HIV-1; ICP27, gD2, gB of HSV; or influenza hemagglutinin or nucleoprotein (Anthony, L S et al., *Vaccine* 1999; 17:373-83). Other antigens associated with pathogens that can be utilized as described herein are antigens of various parasites, including malaria, e.g., malaria peptide based on repeats of NANP.

In certain embodiments, the invention includes methods using foreign antigens in which individuals may have existing T cell immunity (such as influenza, tetanus toxin, herpes etc.). In other embodiments, the skilled artisan would readily be able to determine whether a subject has existing T cell immunity to a specific antigen according to well known methods available in the art and use a foreign antigen to which the subject does not already have an existing T cell immunity.

In alternative embodiments, the antigen is from a pathogen that is a bacterium, such as *Bordetella pertussis; Ehrlichia chaffeensis; Staphylococcus aureus; Toxoplasma gondii; Legionella pneumophila; Brucella suis; Salmonella enterica; Mycobacterium avium; Mycobacterium tuberculosis; Listeria monocytogenes; Chlamydia trachomatis; Chlamydia pneumoniae; Rickettsia rickettsii;* or, a fungus, such as, e.g., *Paracoccidioides brasiliensis;* or other pathogen, e.g., *Plasmodium falciparum.*

As used herein, the term "cancer" includes, but is not limited to, solid tumors and blood borne tumors. The term cancer includes diseases of the skin, tissues, organs, bone, cartilage, blood and vessels. A term used to describe cancer that is far along in its growth, also referred to as "late stage cancer" or "advanced stage cancer," is cancer that is metastatic, e.g., cancer that has spread from its primary origin to another part of the body. In certain embodiments, advanced stage cancer includes stages 3 and 4 cancers. Cancers are ranked into stages depending on the extent of their growth and spread through the body; stages correspond with severity. Determining the stage of a given cancer helps doctors to make treatment recommendations, to form a likely outcome scenario for what will happen to the patient (prognosis), and to communicate effectively with other doctors.

There are multiple staging scales in use. One of the most common ranks cancers into five progressively more severe stages: 0, I, II, III, and IV. Stage 0 cancer is cancer that is just beginning, involving just a few cells. Stages I, II, III, and IV represent progressively more advanced cancers, characterized by larger tumor sizes, more tumors, the aggressiveness with which the cancer grows and spreads, and the extent to which the cancer has spread to infect adjacent tissues and body organs.

Another popular staging system is known as the TNM system, a three dimensional rating of cancer extensiveness. Using the TNM system, doctors rate the cancers they find on each of three scales, where T stands for tumor size, N stands for lymph node involvement, and M stands for metastasis (the degree to which cancer has spread beyond its original locations). Larger scores on each of the three scales indicate more advanced cancer. For example, a large tumor that has not spread to other body parts might be rated T3, N0, M0, while a smaller but more aggressive cancer might be rated T2, N2, M1 suggesting a medium sized tumor that has spread to local lymph nodes and has just gotten started in a new organ location.

Cancers that may be treated by the methods of the present invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In addition to its applicability to human cancer and infectious diseases, the present invention is also intended for use in treating animal diseases in the veterinary medicine context. Thus, the approaches described herein may be readily applied by one skilled in the art for treatment of veterinary herpes virus infections including equine herpes viruses, bovine viruses such as bovine viral diarrhea virus (for example, the E2 antigen), bovine herpes viruses, Marek's disease virus in chickens and other fowl; animal retroviral and lentiviral diseases (e.g., feline leukemia, feline immunodeficiency, simian immunodeficiency viruses, etc.); pseudorabies and rabies; and the like.

As for tumor antigens, any tumor-associated or tumor-specific antigen (or tumor cell derived epitope) (collectively, TAA) that can be recognized by T cells, including CTL, can be used. These include, without limitation, mutant p53, HER2/neu or a peptide thereof, or any of a number of melanoma-associated antigens such as MAGE-1, MAGE-3, MART-1/Melan-A, tyrosinase, gp75, gp100, BAGE, GAGE-1, GAGE-2, GnT-V, and p15 (see, for example, U.S. Pat. No. 6,187,306, incorporated herein by reference).

In one embodiment, it is not necessary to include a full length antigen in a nucleic acid vaccine; it suffices to include a fragment that will be presented by MHC class I and/or II. A nucleic acid may include 1, 2, 3, 4, 5 or more antigens, which may be the same or different ones.

Approaches for Mutagenesis of E6, E7, and Other Antigens

Mutants of the antigens described here may be created, for example, using the Quick Change Site-Directed Mutagenesis Kit (Stratagene, La Jolla, Calif.). Generally, antigens that may be used herein may be proteins or peptides that differ from the naturally-occurring proteins or peptides but yet retain the necessary epitopes for functional activity. In certain embodiments, an antigen may comprise, consist essentially of, or consist of an amino acid sequence that is at least about 50%, 55%, 60%, 65%, 70%, 75%, 80%, 85%, 90%, 95%, 96%, 97%, 98%, or 99% identical to that of the naturally-occurring antigen or a fragment thereof. In certain embodiments, an antigen may also comprise, consist essentially of, or consist of an amino acid sequence that is encoded by a nucleotide sequence that is at least about 50%, 55%, 60%, 65%, 70%, 75%, 80%, 85%, 90%, 95%, 96%, 97%, 98%, or 99% identical to a nucleotide sequence encoding the naturally-occurring antigen or a fragment thereof. In certain embodiments, an antigen may also comprise, consist essentially of, or consist of an amino acid sequence that is encoded by a nucleic acid that hybridizes under high stringency conditions to a nucleic acid encoding the naturally-occurring antigen or a fragment thereof. Hybridization conditions are further described herein.

In one embodiment, an exemplary protein may comprise, consist essentially of, or consist of, an amino acid sequence that is at least about 50%, 55%, 60%, 65%, 70%, 75%, 80%, 85%, 90%, 95%, 96%, 97%, 98%, or 99% identical to that of a viral protein, including for example E6 or E7, such as an E6 or E7 sequence provided herein. Where the E6 or E7 protein is a detox E6 or E7 protein, the amino acid sequence of the protein may comprise, consist essentially of, or consist of an amino acid sequence that is at least about 50%, 55%, 60%, 65%, 70%, 75%, 80%, 85%, 90%, 95%, 96%, 97%, 98%, or 99% identical to that of an E6 or E7 protein, wherein the amino acids that render the protein a "detox" protein are present.

Exemplary Nucleic Acid (e.g., DNA) Vaccines Encoding an Immunogenicity-Potentiating Polypeptide (IPP) and an Antigen In one embodiment, a nucleic acid vaccine encodes a fusion protein comprising an antigen and a second protein, e.g., an IPP. An IPP may act in potentiating an immune response by promoting: processing of the linked antigenic polypeptide via the MHC class I pathway or targeting of a cellular compartment that increases the processing. This basic strategy may be combined with an additional strategy pioneered by the present inventors and colleagues, that involve linking DNA encoding another protein, generically termed a "targeting polypeptide," to the antigen-encoding DNA. Again, for the sake of simplicity, the DNA encoding such a targeting polypeptide will be referred to herein as a "targeting DNA." That strategy has been shown to be effective in enhancing the potency of the vectors carrying only antigen-encoding DNA. See for example, the following PCT publications by Wu et al: WO 01/29233; WO 02/009645; WO 02/061113; WO 02/074920; and WO 02/12281, all of which are incorporated by reference in their entirety. The other strategies include the use of DNA encoding polypeptides that promote or enhance:
  (a) development, accumulation or activity of antigen presenting cells or targeting of antigen to compartments of the antigen presenting cells leading to enhanced antigen presentation;
  (b) intercellular transport and spreading of the antigen;
  (c) sorting of the lysosome-associated membrane protein type 1 (Sig/LAMP-1); or
  (d) any combination of (a)-(c).

The strategy includes use of:
  (a) a viral intercellular spreading protein selected from the group of herpes simplex virus-1 VP22 protein, Marek's disease virus UL49 (see WO 02/09645 and U.S. Pat. No. 7,318,928), protein or a functional homologue or derivative thereof;
  (b) calreticulin (CRT) and other endoplasmic reticulum chaperone polypeptides selected from the group of CRT-like molecules ER60, GRP94, gp96, or a functional homologue or derivative thereof (see WO 02/12281 and U.S. Pat. No. 7,342,002);
  (c) a cytoplasmic translocation polypeptide domains of a pathogen toxin selected from the group of domain II of Pseudomonas exotoxin ETA or a functional homologue or derivative thereof (see published US application 20040086845);
  (d) a polypeptide that targets the centrosome compartment of a cell selected from γ-tubulin or a functional homologue or derivative thereof;
  (e) a polypeptide that stimulates dendritic cell precursors or activates dendritic cell activity selected from the group of GM-CSF, Flt3-ligand extracellular domain, or a functional homologue or derivative thereof;
  (f) a costimulatory signal, such as a B7 family protein, including B7-DC (see U.S. Ser. No. 09/794,210), B7.1, B7.2, soluble CD40, etc.); or
  (g) an anti-apoptotic polypeptide selected from the group consisting of (1) BCL-xL, (2) BCL2, (3) XIAP, (4) FLICEc-s, (5) dominant-negative caspase-8, (6) dominant negative caspase-9, (7) SPI-6, and (8) a functional homologue or derivative of any of (1)-(7). (See WO 2005/047501).

The following publications, all of which are incorporated by reference in their entirety, describe IPPs: Kim T W et al., *J Clin Invest* 112: 109-117, 2003; Cheng W F et al., *J Clin Invest* 108: 669-678, 2001; Hung C F et al., *Cancer Res* 61:3698-3703, 2001; Chen C H et al., 2000, supra; U.S. Pat. No. 6,734,173; published patent applications WO05/081716, WO05/047501, WO03/085085, WO02/12281, WO02/074920, WO02/061113, WO02/09645, and WO01/29233. Comparative studies of these IPPs using HPV E6 as the antigen are described in Peng, S. et al., *J Biomed Sci.* 12:689-700 2005.

An antigen may be linked N-terminally or C-terminally to an IPP. Exemplary IPPs and fusion constructs encoding such are described below.

Lysosomal Associated Membrane Protein 1 (LAMP-1)

The DNA sequence encoding the E7 protein fused to the translocation signal sequence and LAMP-1 domain (Sig-E7-LAMP-1) is shown herein as SEQ ID NO:10. The amino acid sequence of Sig-E7-LAMP-1 is shown herein as SEQ ID NO:11.

The nucleotide sequence of the immunogenic vector pcDNA3-Sig/E7/LAMP-1 is shown herein as SEQ ID NO:13, with the SigE7-LAMP-1 coding sequence in lower case and underscored.

HSP70 from *M. tuberculosis*

The nucleotide sequence encoding HSP70 is shown herein as SEQ ID NO:13) (i.e., nucleotides 10633-12510 of the *M. tuberculosis* genome in GenBank NC_000962). The amino acid sequence of HSP70 is shown herein as SEQ ID NO:14.

The nucleic acid sequences encoding the E7-Hsp70 chimera/fusion polypeptides are shown herein as SEQ ID NO:15 and the corresponding amino acid sequence is shown herein as SEQ ID NO:16. The E7 coding sequence is shown in upper case and underscored.

ETA(dII) from *Pseudomonas aeruginosa*

The complete coding sequence for *Pseudomonas aeruginosa* exotoxin type A (ETA) is shown herein as SEQ ID NO:17 (GenBank Accession No. K01397). The amino acid sequence of ETA is shown herein as SEQ ID NO:18 (GenBank Accession No. K01397).

Residues 1-25 (italicized) represent the signal peptide. The first residue of the mature polypeptide, Ala, is bolded/underscored. The mature polypeptide is residues 26-638 of SEQ ID NO:18.

Domain II (ETA(II)), translocation domain (underscored above) spans residues 247-417 of the mature polypeptide (corresponding to residues 272-442 of SEQ ID NO:18) and is presented below separately herein as SEQ ID NO:19.

The nucleotide construct in which ETA(dII) is fused to HPV-16 E7 is shown herein as SEQ ID NO:20. The corresponding amino acid sequence is shown herein as SEQ ID NO:21. The ETA(dII) sequence appears in plain font, extra codons from plasmid pcDNA3 are italicized. Nucleotides between ETA(dII) and E7 are also bolded (and result in the interposition of two amino acids between ETA(dII) and E7). The E7 amino acid sequence is underscored (ends with Gln at position 269).

Pro Leu Ile Ser Leu Asp Cys Ala Phe AMB

The nucleotide sequence of the pcDNA3 vector encoding E7 and HSP70 (pcDNA3-E7-Hsp70 is shown herein as SEQ ID NO:22.

Calreticulin (CRT)

Calreticulin (CRT), a well-characterized ~46 kDa protein was described briefly above, as were a number of its biological and biochemical activities. As used herein, "calreticulin" or "CRT" refers to polypeptides and nucleic acids molecules having substantial identity to the exemplary human CRT sequences as described herein or homologues thereof, such as rabbit and rat CRT—well-known in the art. A CRT polypeptide is a polypeptide comprising a sequence identical to or substantially identical to the amino acid sequence of CRT. An exemplary nucleotide and amino acid sequence for a CRT used in the present compositions and methods are presented below. The terms "calreticulin" or "CRT" encompass native proteins as well as recombinantly produced modified proteins that, when fused with an antigen (at the DNA or protein level) promote the induction of immune responses and promote angiogenesis, including a CTL response. Thus, the terms "calreticulin" or "CRT" encompass homologues and allelic variants of human CRT, including variants of native proteins constructed by in vitro techniques, and proteins isolated from natural sources. The CRT polypeptides used in the present invention, and sequences encoding them, also include fusion proteins comprising non-CRT sequences, particularly MHC class I-binding peptides; and also further comprising other domains, e.g., epitope tags, enzyme cleavage recognition sequences, signal sequences, secretion signals and the like.

A human CRT coding sequence is shown herein as SEQ ID NO: 23. The amino acid sequence of the human CRT protein encoded by SEQ ID NO:23 is set forth herein as SEQ ID NO:24. This amino acid sequence is highly homologous to GenBank Accession No. NM 004343.

The amino acid sequence of the rabbit and rat CRT proteins are set forth in GenBank Accession Nos. P1553 and NM 022399, respectively. An alignment of human, rabbit and rat CRT shows that these proteins are highly conserved, and most of the amino acid differences between species are conservative in nature. Most of the variation is found in the alignment of the approximately 36 C-terminal residues. Thus, for the present invention, human CRT may be used as well as, DNA encoding any homologue of CRT from any species that has the requisite biological activity (as an IPP) or any active domain or fragment thereof, may be used in place of human CRT or a domain thereof.

Cheng et al., supra, incorporated by reference in its entirety, previously determined that nucleic acid (e.g., DNA) vaccines encoding each of the N, P, and C domains of CRT chimerically linked to HPV-16 E7 elicited potent antigen-specific CD8+ T cell responses and antitumor immunity in mice vaccinated i.d., by gene gun administration. N-CRT/E7, P-CRT/E7 or C-CRT/E7 DNA each exhibited significantly increased numbers of E7-specific CD8$^+$ T cell precursors and impressive antitumor effects against E7-expressing tumors when compared with mice vaccinated with E7 DNA (antigen only). N-CRT DNA administration also resulted in anti-angiogenic antitumor effects. Thus, cancer therapy using DNA encoding N-CRT linked to a tumor antigen may be used for treating tumors through a combination of antigen-specific immunotherapy and inhibition of angiogenesis.

Figure 8:
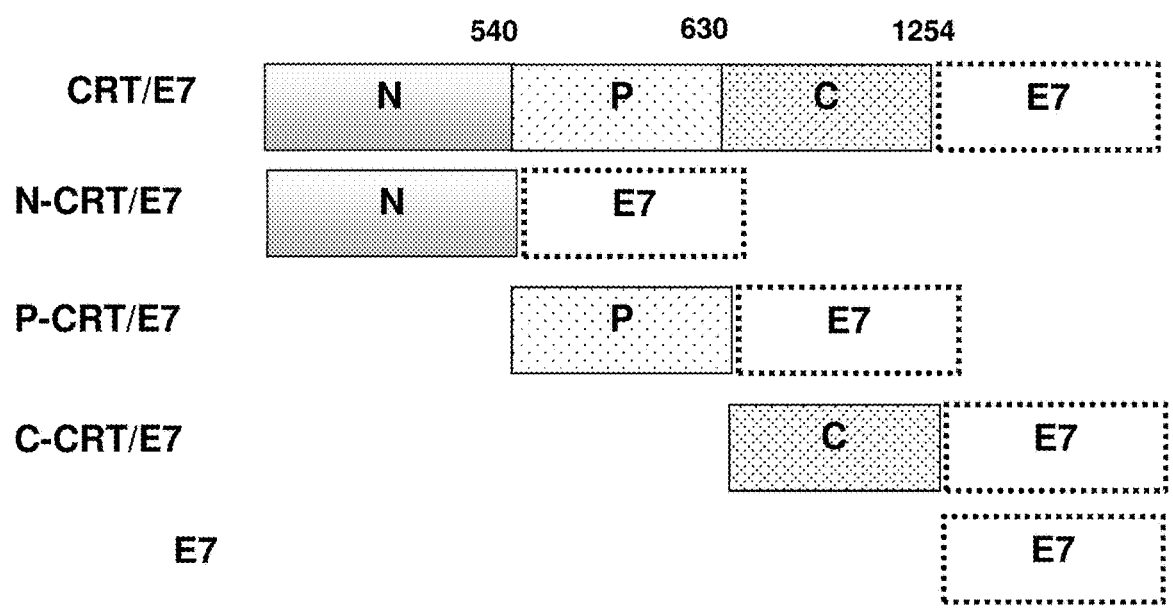
FIG. 8 shows the constructs comprising CRT or one of its domains linked to E7.

The constructs comprising CRT or one of its domains linked to E7 are depicted in FIG. 8.

The amino acid sequences of the 3 human CRT domains are shown herein as annotations of the full length protein, SEQ ID NO:24. The N domain comprises residues 1-170 (normal text); the P domain comprises residues 171-269 (underscored); and the C domain comprises residues 270-417 (bold/italic).

The sequences of the three domains are further shown as separate polypeptides herein as human N-CRT (SEQ ID NO:25), as human P-CRT (SEQ ID NO:26), and as human C-CRT (SEQ ID NO:27).

The present vectors may comprises DNA encoding one or more of these domain sequences, which are shown by annotation of SEQ ID NO:28 herein, wherein the N-domain sequence is upper case, the P-domain sequence is lower case/italic/underscored, and the C domain sequence is lower case. The stop codon is also shown but not counted.

The coding sequence for each separate domain is provided herein as human N-CRT DNA (SEQ ID NO:29), as human P-CRT DNA (SEQ ID NO:30), and as human C-CRT DNA (SEQ ID NO:31). Alternatively, any nucleotide sequences that encodes these domains may be used in the present constructs. Thus, for use in humans, the sequences may be further codon-optimized.

Constructs used in the present invention may employ combinations of one or more CRT domains, in any of a number of orientations. Using the designations $N^{CRT}$, $P^{CRT}$ and $C^{CRT}$ to designate the domains, the following are but a few examples of the combinations that may be used in the nucleic acid (e.g., DNA) vaccine vectors used in the present invention (where it is understood that Ag can be any antigen, including E7(detox) or E6 (detox).

$N^{CRT}$—$P^{CRT}$—Ag; $N^{CRT}$—$P^{CRT}$—Ag; $N^{CRT}$—$C^{CRT}$—Ag; $N^{CRT}$—$N^{CRT}$—Ag; $N^{CRT}$—$N^{CRT}$—$N^{CRT}$—Ag; $P^{CRT}$—$P^{CRT}$—Ag; $P^{CRT}$—$C^{CRT}$—Ag; $P^{CRT}$—$N^{CRT}$—Ag; $C^{CRT}$—$P^{CRT}$—Ag; $N^{CRT}$—$P^{CRT}$—Ag; etc.

The present invention may employ shorter polypeptide fragments of CRT or CRT domains provided such fragments can enhance the immune response to an antigen with which they are paired. Shorter peptides from the CRT or domain sequences shown above that have the ability to promote protein processing via the MHC-1 class I pathway are also included, and may be defined by routine experimentation.

The present invention may also employ shorter nucleic acid fragments that encode CRT or CRT domains provided such fragments are functional, e.g., encode polypeptides that can enhance the immune response to an antigen with which they are paired (e.g., linked). Nucleic acids that encode shorter peptides from the CRT or domain sequences shown above and are functional, e.g., have the ability to promote protein processing via the MHC-1 class I pathway, are also included, and may be defined by routine experimentation.

A polypeptide fragment of CRT may include at least or about 50, 100, 200, 300, or 400 amino acids. A polypeptide fragment of CRT may also include at least or about 25, 50, 75, 100, 25-50, 50-100, or 75-125 amino acids from a CRT domain selected from the group N-CRT, P-CRT, and C-CRT. A polypeptide fragment of CRT may include residues 1-50, 50-75, 75-100, 100-125, 125-150, 150-170 of the N-domain (e.g., of SEQ ID NO:25). A polypeptide fragment of CRT may include residues 1-50, 50-75, 75-100, 100-109 of the P-domain (e.g., of SEQ ID NO:26). A polypeptide fragment of CRT may include residues 1-50, 50-75, 75-100, 100-125, 125-138 of the C-domain (e.g., of SEQ ID NO:27).

A nucleic acid fragment of CRT may encode at least or about 50, 100, 200, 300, or 400 amino acids. A nucleic acid fragment of CRT may also encode at least or about 25, 50, 75, 100, 25-50, 50-100, or 75-125 amino acids from a CRT domain selected from the group N-CRT, P-CRT, and C-CRT. A nucleic acid fragment of CRT may encode residues 1-50, 50-75, 75-100, 100-125, 125-150, 150-170 of the N-domain (e.g., of SEQ ID NO:25). A nucleic acid fragment of CRT may encode residues 1-50, 50-75, 75-100, 100-109 of the P-domain (e.g., of SEQ ID NO:26). A nucleic acid fragment of CRT may encode residues 1-50, 50-75, 75-100, 100-125, 125-138 of the C-domain (e.g., of SEQ ID NO:27).

Polypeptide "fragments" of CRT, as provided herein, do not include full-length CRT. Likewise, nucleic acid "fragments" of CRT, as provided herein, do not include a full-length CRT nucleic acid sequence and do not encode a full-length CRT polypeptide.

In one embodiment, a vector construct of a complete chimeric nucleic acid that can be used in the present invention, is shown herein as SEQ ID NO:32. The sequence is annotated to show plasmid-derived nucleotides (lower case letters), CRT-derived nucleotides (upper case bold letters), and HPV-E7-derived nucleotides (upper case, italicized/underlined letters). Five plasmid nucleotides are found between the CRT and E7 coding sequences and that the stop codon for the E7 sequence is double underscored. This plasmid is also referred to as pNGVL4a-CRT/E7(detox). The Table below describes the structure of the above plasmid.

| Plasmid Position | Genetic Construct | Source of Construct |
|---|---|---|
| 5970-0823 | *E. coli* ORI (ColEl) | pBR/*E. coli*-derived |
| 0837-0881 | portion of transposase (tpnA) | Common plasmid sequence Tn5/Tn903 |
| 0882-1332 | β-Lactamase (Amp$^R$) | pBRpUC derived plasmid |
| 1331-2496 | AphA (Kan$^R$) | Tn903 |

-continued

| Plasmid Position | Genetic Construct | Source of Construct |
|---|---|---|
| 2509-2691 | P3 Promoter DNA binding site | Tn3/pBR322 |
| 2692-2926 | pUC backbone | Common plasmid sequence pBR322-derived |
| 2931-4009 | NF1 binding and promoter | HHV-5(HCMV UL-10 lE1 gene) |
| 4010-4014 | Poly-cloning site | Common plasmid sequence |
| 4015-5265 | Calreticulin (CRT) | Human Calreticulin |
| 5266-5271 | GAATTC plasmid sequence | Remain after cloning |
| 5272-5568 | dE7 gene (detoxified partial) | HPV-16 (E7 gene) incl. stop codon |
| 5569-5580 | Poly-cloning site | Common plasmid sequence |
| 551-5970 | Poly-Adenylation site | Mammalian signal, pHCMV-derived |

In some embodiments, an alternative to CRT is another ER chaperone polypeptide exemplified by ER60, GRP94 or gp96, well-characterized ER chaperone polypeptide that representatives of the HSP90 family of stress-induced proteins (see WO 02/012281, incorporated herein by reference). The term "endoplasmic reticulum chaperone polypeptide" as used herein means any polypeptide having substantially the same ER chaperone function as the exemplary chaperone proteins CRT, tapasin, ER60 or calnexin. Thus, the term includes all functional fragments or variants or mimics thereof. A polypeptide or peptide can be routinely screened for its activity as an ER chaperone using assays known in the art. While the present invention is not limited by any particular mechanism of action, in vivo chaperones promote the correct folding and oligomerization of many glycoproteins in the ER, including the assembly of the MHC class I heterotrimeric molecule (heavy (H) chain, $\beta$2m, and peptide). They also retain incompletely assembled MHC class I heterotrimeric complexes in the ER (Hauri FEBS Lett. 476:32-37, 2000).

Intercellular Spreading Proteins

The potency of naked nucleic acid (e.g., DNA) vaccines may be enhanced by their ability to amplify and spread in vivo. VP22, a herpes simplex virus type 1 (HSV-1) protein and its "homologues" in other herpes viruses, such as the avian Marek's Disease Virus (MDV) have the property of intercellular transport that provide an approach for enhancing vaccine potency. The present inventors have previously created novel fusions of VP22 with a model antigen, human papillomavirus type 16 (HPV-16) E7, in a nucleic acid (e.g., DNA) vaccine which generated enhanced spreading and MHC class I presentation of antigen. These properties led to a dramatic increase in the number of E7-specific CD8+ T cell precursors in vaccinated mice (at least 50-fold) and converted a less effective nucleic acid (e.g., DNA) vaccine into one with significant potency against E7-expressing tumors. In comparison, a non-spreading mutant, VP22(1-267), failed to enhance vaccine potency. Results presented in U.S. Patent Application publication No. 20040028693 (U.S. Pat. No. 7,318,928), hereby incorporated by reference in its entirety, show that the potency of DNA vaccines is dramatically improved through enhanced intercellular spreading and MHC class I presentation of the antigen.

A similar study linking MDV-1 UL49 to E7 also led to a dramatic increase in the number of E7-specific CD8+ T cell precursors and potency response against E7-expressing tumors in vaccinated mice. Mice vaccinated with a MDV-1 UL49 DNA vaccine stimulated E7-specific CD8+ T cell precursor at a level comparable to that induced by HSV-1 VP22/E7. Thus, fusion of MDV-1UL49 DNA to DNA encoding a target antigen gene significantly enhances the DNA vaccine potency.

In one embodiment, the spreading protein may be a viral spreading protein, including a herpes virus VP22 protein. Exemplified herein are fusion constructs that comprise herpes simplex virus-1 (HSV-1) VP22 (abbreviated HVP22) and its homologue from Marek's disease virus (MDV) termed MDV-VP22 or MVP-22. Also included in the invention are the use of homologues of VP22 from other members of the herpesviridae or polypeptides from nonviral sources that are considered to be homologous and share the functional characteristic of promoting intercellular spreading of a polypeptide or peptide that is fused or chemically conjugated thereto.

DNA encoding HVP22 has the sequence SEQ ID NO:33 of the longer sequence SEQ ID NO:34 (which is the full length nucleotide sequence of a vector that comprises HVP22). DNA encoding MDV-VP22 is shown herein as SEQ ID NO:35.

The amino acid sequence of HVP22 polypeptide is SEQ ID NO:36 as amino acid residues 1-301 of SEQ ID NO:37 (i.e., the full length amino acid encoded by the vector).

The amino acid sequence of the MDV-VP22 is shown herein as SEQ ID NO:38.

A DNA clone pcDNA3 VP22/E7, that includes the coding sequence for HVP22 and the HPV-16 protein, E7 (plus some additional vector sequence) is SEQ ID NO:34.

The amino acid sequence of E7 (SEQ ID NO:39) is residues 308-403 of SEQ ID NO:37. This particular clone has only 96 of the 98 residues present in E7. The C-terminal residues of wild-type E7, Lys and Pro, are absent from this construct. This is an example of a deletion variant as the term is described below. Such deletion variants (e.g., terminal truncation of two or a small number of amino acids) of other antigenic polypeptides are examples of the embodiments intended within the scope of the fusion polypeptides that can be used in the present invention.

Homologues of IPPs

Homologues or variants of IPPs described herein, may also be used, provided that they have the requisite biological activity. These include various substitutions, deletions, or additions of the amino acid or nucleic acid sequences. Due to code degeneracy, for example, there may be considerable variation in nucleotide sequences encoding the same amino acid sequence.

A functional derivative of an IPP retains measurable IPP-like activity, including that of promoting immunogenicity of one or more antigenic epitopes fused thereto by promoting presentation by class I pathways. "Functional derivatives" encompass "variants" and "fragments" regardless of whether the terms are used in the conjunctive or the alternative herein.

The term "chimeric" or "fusion" polypeptide or protein refers to a composition comprising at least one polypeptide or peptide sequence or domain that is chemically bound in a linear fashion with a second polypeptide or peptide domain. One embodiment of compositions useful for the present invention is an isolated or recombinant nucleic acid molecule encoding a fusion protein comprising at least two domains, wherein the first domain comprises an IPP and the second domain comprises an antigenic epitope, e.g., an MHC class I-binding peptide epitope. The "fusion" can be an association generated by a peptide bond, a chemical linking, a charge interaction (e.g., electrostatic attractions, such as salt bridges, H-bonding, etc.) or the like. If the polypeptides are recombinant, the "fusion protein" can be translated from a common mRNA. Alternatively, the compositions of the domains can be linked by any chemical or electrostatic means. The chimeric molecules that can be used in the present invention (e.g., targeting polypeptide fusion proteins) can also include additional sequences, e.g., linkers, epitope tags, enzyme cleavage recognition sequences, signal sequences, secretion signals, and the like. Alternatively, a peptide can be linked to a carrier simply to facilitate manipulation or identification/location of the peptide.

Also included is a "functional derivative" of an IPP, which refers to an amino acid substitution variant, a "fragment" of the protein. A functional derivative of an IPP retains measurable activity that may be manifested as promoting immunogenicity of one or more antigenic epitopes fused thereto or co-administered therewith. "Functional derivatives" encompass "variants" and "fragments" regardless of whether the terms are used in the conjunctive or the alternative herein.

A functional homologue must possess the above biochemical and biological activity. In view of this functional characterization, use of homologous proteins including proteins not yet discovered, fall within the scope of the invention if these proteins have sequence similarity and the recited biochemical and biological activity.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the method of alignment includes alignment of Cys residues.

In one embodiment, the length of a sequence being compared is at least 30%, at least 40%, at least 50%, at least 60%, and at least 70%, 80%, 90%, 95%, 96%, 97%, 98%, or 99% of the length of the reference sequence (e.g., an IPP). The amino acid residues (or nucleotides) at corresponding amino acid (or nucleotide) positions are then compared. When a position in the first sequence is occupied by the same amino acid residue (or nucleotide) as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman and Wunsch (*J. Mol. Biol.* 48:444-453 (1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to IPP nucleic acid molecules. BLAST protein searches can be performed with the XBLAST program, score=50, wordlength=3 to obtain amino acid sequences homologous to IPP protein molecules. To obtain gapped alignments for comparison purposes, Gapped BLAST can be utilized as described in Altschul et al. (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

Thus, a homologue of an IPP or of an IPP domain described above is characterized as having (a) functional activity of native IPP or domain thereof and (b) amino acid sequence similarity to a native IPP protein or domain thereof when determined as above, of at least about 50%, 55%, 60%, 65%, 70%, 75%, 80%, 85%, 90%, 95%, 96%, 97%, 98%, or 99%.

It is within the skill in the art to obtain and express such a protein using DNA probes based on the disclosed sequences of an IPP. Then, the fusion protein's biochemical and biological activity can be tested readily using art-recognized methods such as those described herein, for example, a T cell proliferation, cytokine secretion or a cytolytic assay, or an in vivo assay of tumor protection or tumor therapy. A biological assay of the stimulation of antigen-specific T cell reactivity will indicate whether the homologue has the requisite activity to qualify as a "functional" homologue.

A "variant" refers to a molecule substantially identical to either the full protein or to a fragment thereof in which one or more amino acid residues have been replaced (substitution variant) or which has one or several residues deleted (deletion variant) or added (addition variant). A "fragment" of an IPP refers to any subset of the molecule, that is, a shorter polypeptide of the full-length protein.

A number of processes can be used to generate fragments, mutants and variants of the isolated DNA sequence. Small subregions or fragments of the nucleic acid encoding the spreading protein, for example 1-30 bases in length, can be prepared by standard, chemical synthesis. Antisense oligonucleotides and primers for use in the generation of larger synthetic fragment.

A one group of variants are those in which at least one amino acid residue and in certain embodiments only one, has been substituted by different residue. For a detailed description of protein chemistry and structure, see Schulz, G E et al., *Principles of Protein Structure*, Springer-Verlag, New York, 1978, and Creighton, T. E., *Proteins: Structure and Molecular Properties*, W. H. Freeman & Co., San Francisco, 1983, which are hereby incorporated by reference. The types of substitutions that may be made in the protein molecule may be based on analysis of the frequencies of amino acid changes between a homologous protein of different species, such as those presented in Table 1-2 of Schulz et al. (supra) and FIG. 3-9 of Creighton (supra). Based on such an analysis, conservative substitutions are defined herein as exchanges within one of the following five groups:

1. Small aliphatic, nonpolar or slightly polar residues Ala, Ser, Thr (Pro, Gly);
2. Polar, negatively charged residues and their amides Asp, Asn, Glu, Gln;
3. Polar, positively charged residues His, Arg, Lys;
4. Large aliphatic, nonpolar residues Met, Leu, Ile, Val (Cys)
5. Large aromatic residues Phe, Tyr, Trp.

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

More substantial changes in biochemical, functional (or immunological) properties are made by selecting substitutions that are less conservative, such as between, rather than within, the above five groups. Such changes will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (i) substitution of Gly and/or Pro by another amino acid or deletion or insertion of Gly or Pro; (ii) substitution of a hydrophilic residue, e.g., Ser or Thr, for (or by) a hydrophobic residue, e.g., Leu, Ile, Phe, Val or Ala; (iii) substitution of a Cys residue for (or by) any other residue; (iv) substitution of a residue having an electropositive side chain, e.g., Lys, Arg or His, for (or by) a residue having an electronegative charge, e.g., Glu or Asp; or (v) substitution of a residue having a bulky side chain, e.g., Phe, for (or by) a residue not having such a side chain, e.g., Gly.

Most acceptable deletions, insertions and substitutions according to the present invention are those that do not produce radical changes in the characteristics of the wild-type or native protein in terms of its relevant biological activity, e.g., its ability to stimulate antigen specific T cell reactivity to an antigenic epitope or epitopes that are fused to the protein. However, when it is difficult to predict the exact effect of the substitution, deletion or insertion in advance of doing so, one skilled in the art will appreciate that the effect can be evaluated by routine screening assays such as those described here, without requiring undue experimentation.

Exemplary fusion proteins provided herein comprise an IPP protein or homolog thereof and an antigen. For example, a fusion protein may comprise, consist essentially of, or consist of an IPP or an IPP fragment, e.g., N-CRT, P-CRT and/or C-CRT, or an amino acid sequence that is at least about 50%, 55%, 60%, 65%, 70%, 75%, 80%, 85%, 90%, 95%, 96%, 97%, 98%, or 99% identical to the amino acid sequence of the IPP or IPP fragment, wherein the IPP fragment is functionally active as further described herein, linked to an antigen. A fusion protein may also comprise an IPP or an IPP fragment and at least 1, 2, 3, 4, 5, 6, 7, 8, 9, 10 or more amino acids, or about 1-5, 1-10, 1-15, 1-20, 1-25, 1-30, 1-50 amino acids, at the N- and/or C-terminus of the IPP fragment. These additional amino acids may have an amino acid sequence that is unrelated to the amino acid sequence at the corresponding position in the IPP protein.

Homologs of an IPP or an IPP fragments may also comprise, consist essentially of, or consist of an amino acid sequence that differs from that of an IPP or IPP fragment by the addition, deletion, or substitution, e.g., conservative substitution, of at least about 1, 2, 3, 4, 5, 6, 7, 8, 9 or 10 amino acids, or from about 1-5, 1-10, 1-15 or 1-20 amino acids. Homologs of an IPP or IPP fragments may be encoded by nucleotide sequences that are at least about 50%, 55%, 60%, 65%, 70%, 75%, 80%, 85%, 90%, 95%, 96%, 97%, 98%, or 99% identical to the nucleotide sequence encoding an IPP or IPP fragment, such as those described herein.

Yet other homologs of an IPP or IPP fragments are encoded by nucleic acids that hybridize under stringent hybridization conditions to a nucleic acid that encodes an IPP or IPP fragment. For example, homologs may be encoded by nucleic acids that hybridize under high stringency conditions of 0.2 to 1×SSC at 65° C. followed by a wash at 0.2×SSC at 65° C. to a nucleic acid consisting of a sequence described herein. Nucleic acids that hybridize under low stringency conditions of 6×SSC at room temperature followed by a wash at 2×SSC at room temperature to nucleic acid consisting of a sequence described herein or a portion thereof can be used. Other hybridization conditions include 3×SSC at 40 or 50° C., followed by a wash in 1 or 2×SSC at 20, 30, 40, 50, 60, or 65° C. Hybridizations can be conducted in the presence of formaldehyde, e.g., 10%, 20%, 30% 40% or 50%, which further increases the stringency of hybridization. Theory and practice of nucleic acid hybridization is described, e.g., in S. Agrawal (ed.) Methods in Molecular Biology, volume 20; and Tijssen (1993) Laboratory Techniques in biochemistry and molecular biology-hybridization with nucleic acid probes, e.g., part I chapter 2 "Overview of principles of hybridization and the strategy of nucleic acid probe assays," Elsevier, New York provide a basic guide to nucleic acid hybridization.

A fragment of a nucleic acid sequence is defined as a nucleotide sequence having fewer nucleotides than the nucleotide sequence encoding the full length CRT polypeptide, antigenic polypeptide, or the fusion thereof. This invention includes the use of such nucleic acid fragments that encode polypeptides which retain the ability of the fusion polypeptide to induce increases in frequency or reactivity of T cells, including CD8+ T cells, that are specific for the antigen part of the fusion polypeptide.

Nucleic acid sequences that can be used in the present invention may also include linker sequences, natural or modified restriction endonuclease sites and other sequences that are useful for manipulations related to cloning, expression or purification of encoded protein or fragments. For example, a fusion protein may comprise a linker between the antigen and the IPP protein.

Other nucleic acid vaccines that may be used include single chain trimers (SCT), as further described in the Examples and in references cited therein, all of which are specifically incorporated by reference herein.

Backbone of Nucleic Acid Vaccine

A nucleic acid, e.g., DNA vaccine may comprise an "expression vector" or "expression cassette," i.e., a nucleotide sequence which is capable of affecting expression of a protein coding sequence in a host compatible with such sequences. Expression cassettes include at least a promoter operably linked with the polypeptide coding sequence; and, optionally, with other sequences, e.g., transcription termination signals. Additional factors necessary or helpful in effecting expression may also be included, e.g., enhancers.

"Operably linked" means that the coding sequence is linked to a regulatory sequence in a manner that allows expression of the coding sequence. Known regulatory sequences are selected to direct expression of the desired protein in an appropriate host cell. Accordingly, the term "regulatory sequence" includes promoters, enhancers and other expression control elements. Such regulatory sequences are described in, for example, Goeddel, *Gene Expression Technology. Methods in Enzymology*, vol. 185, Academic Press, San Diego, Calif. (1990)).

A promoter region of a DNA or RNA molecule binds RNA polymerase and promotes the transcription of an "operably linked" nucleic acid sequence. As used herein, a "promoter sequence" is the nucleotide sequence of the promoter which is found on that strand of the DNA or RNA which is transcribed by the RNA polymerase. Two sequences of a nucleic acid molecule, such as a promoter and a coding sequence, are "operably linked" when they are linked to each other in a manner which permits both sequences to be transcribed onto the same RNA transcript or permits an RNA transcript begun in one sequence to be extended into the second sequence. Thus, two sequences, such as a promoter sequence and a coding sequence of DNA or RNA are operably linked if transcription commencing in the promoter sequence will produce an RNA transcript of the operably linked coding sequence. In order to be "operably linked" it is not necessary that two sequences be immediately adjacent to one another in the linear sequence.

In one embodiment, certain promoter sequences useful for the present invention must be operable in mammalian cells and may be either eukaryotic or viral promoters. Certain promoters are also described in the Examples, and other useful promoters and regulatory elements are discussed below. Suitable promoters may be inducible, repressible or constitutive. A "constitutive" promoter is one which is active under most conditions encountered in the cell's environmental and throughout development. An "inducible" promoter is one which is under environmental or developmental regulation. A "tissue specific" promoter is active in certain tissue types of an organism. An example of a constitutive promoter is the viral promoter MSV-LTR, which is efficient and active in a variety of cell types, and, in contrast to most other promoters, has the same enhancing activity in arrested and growing cells. Other viral promoters include that present in the CMV-LTR (from cytomegalovirus) (Bashart, M. et al., *Cell* 41:521, 1985) or in the RSV-LTR (from Rous sarcoma virus) (Gorman, C. M., *Proc. Natl. Acad. Sci. USA* 79:6777, 1982). Also useful are the promoter of the mouse metallothionein I gene (Hamer, D, et al., *J. Mol. Appl. Gen.* 1:273-88, 1982; the TK promoter of Herpes virus (McKnight, S, *Cell* 31:355-65, 1982); the SV40 early promoter (Benoist, C., et al., *Nature* 290:304-10, 1981); and the yeast gal4 gene promoter (Johnston, S A et al., *Proc. Natl. Acad. Sci. USA* 79:6971-5, 1982); Silver, P A, et al., *Proc. Natl. Acad. Sci. (USA)* 81:5951-5, 1984)). Other illustrative descriptions of transcriptional factor association with promoter regions and the separate activation and DNA binding of transcription factors include: Keegan et al., *Nature* 231: 699, 1986; Fields et al., *Nature* 340:245, 1989; Jones, *Cell* 61:9, 1990; Lewin, *Cell* 61:1161, 1990; Ptashne et al., *Nature* 346:329, 1990; Adams et al., *Cell* 72:306, 1993.

The promoter region may further include an octamer region which may also function as a tissue specific enhancer, by interacting with certain proteins found in the specific tissue. The enhancer domain of the DNA construct useful for the present invention is one which is specific for the target cells to be transfected, or is highly activated by cellular factors of such target cells. Examples of vectors (plasmid or retrovirus) are disclosed, e.g., in Roy-Burman et al., U.S. Pat. No. 5,112,767, incorporated by reference. For a general discussion of enhancers and their actions in transcription, see, Lewin, B M, *Genes IV*, Oxford University Press pp. 552-576, 1990 (or later edition). Particularly useful are retroviral enhancers (e.g., viral LTR) that is placed upstream from the promoter with which it interacts to stimulate gene expression. For use with retroviral vectors, the endogenous viral LTR may be rendered enhancer-less and substituted with other desired enhancer sequences which confer tissue specificity or other desirable properties such as transcriptional efficiency.

Thus, expression cassettes include plasmids, recombinant viruses, any form of a recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include replicons (e.g., RNA replicons), bacteriophages) to which fragments of DNA may be attached and become replicated. Vectors thus include, but are not limited to RNA, autonomous self-replicating circular or linear DNA or RNA, e.g., plasmids, viruses, and the like (U.S. Pat. No. 5,217,879, incorporated by reference), and includes both the expression and nonexpression plasmids. Where a recombinant cell or culture is described as hosting an "expression vector" this includes both extrachromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

Exemplary virus vectors that may be used include recombinant adenoviruses (Horowitz, M S, In: *Virology*, Fields, B N et al., eds, Raven Press, N Y, 1990, p. 1679; Berkner, K L, *Biotechniques* 6:616-29, 1988; Strauss, S E, In: *The Adenoviruses*, Ginsberg, H S, ed., Plenum Press, NY, 1984, chapter 11) and herpes simplex virus (HSV). Advantages of adenovirus vectors for human gene delivery include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms. Adeno-associated virus is also useful for human therapy (Samulski, R J et al., *EMBO J.* 10:3941, 1991) according to the present invention.

A nucleic acid (e.g., DNA) vaccine may also use a replicon, e.g., an RNA replicon, a self-replicating RNA vector. In one embodiment, a replicon is one based on a Sindbis virus RNA replicon, e.g., SINrep5. The present inventors tested E7 in the context of such a vaccine and showed (see Wu et al, U.S. patent application Ser. No. 10/343,719) that a Sindbis virus RNA vaccine encoding HSV-1 VP22 linked to E7 significantly increased activation of E7-specific CD8 T cells, resulting in potent antitumor immunity against E7-expressing tumors. The Sindbis virus RNA replicon vector used in these studies, SINrep5, has been described (Bredenbeek, P J et al., 1993, J. Virol. 67:6439-6446).

Generally, RNA replicon vaccines may be derived from alphavirus vectors, such as Sindbis virus (Hariharan, M J et al., 1998. J Virol 72:950-8.), Semliki Forest virus (Berglund, P M et al., 1997. AIDS Res Hum Retroviruses 13:1487-95; Ying, H T et al., 1999. Nat Med 5:823-7) or Venezuelan equine encephalitis virus (Pushko, P M et al., 1997. Virology 239:389-401). These self-replicating and self-limiting vaccines may be administered as either (1) RNA or (2) DNA which is then transcribed into RNA replicons in cells transfected in vitro or in vivo (Berglund, P C et al., 1998. Nat Biotechnol 16:562-5; Leitner, W W et al., 2000. Cancer Res 60:51-5). An exemplary Semliki Forest virus is pSCA1 (DiCiommo, D P et al., J Biol Chem 1998; 273:18060-6).

The plasmid vector pcDNA3 or a functional homolog thereof (SEQ ID NO:40) may be used in a nucleic acid (e.g., DNA) vaccine. In other embodiments, pNGVL4a (SEQ ID NO:41) can be used.

pNGVL4a, one plasmid backbone for use in the present invention, was originally derived from the pNGVL3 vector, which has been approved for human vaccine trials. The pNGVL4a vector includes two immunostimulatory sequences (tandem repeats of CpG dinucleotides) in the noncoding region. Whereas any other plasmid DNA that can transform either APCs, including DC's or other cells which, via cross-priming, transfer the antigenic moiety to DCs, is useful in the present invention, pNGFVLA4a may be used because of the fact that it has already been approved for human therapeutic use.

The following references set forth principles and current information in the field of basic, medical and veterinary virology and are incorporated by reference: *Fields Virology*, Fields, B N et al., eds., Lippincott Williams & Wilkins, N Y, 1996; *Principles of Virology: Molecular Biology, Pathogenesis, and Control*, Flint, S. J. et al., eds., Amer Soc Microbiol, Washington D.C., 1999; *Principles and Practice of Clinical Virology*, 4th Edition, Zuckerman. A. J. et al., eds, John Wiley & Sons, N Y, 1999; *The Hepatitis C Viruses*, by Hagedorn, C H et al., eds., Springer Verlag, 1999; *Hepatitis B Virus: Molecular Mechanisms in Disease and Novel Strategies for Therapy*, Koshy, R. et al., eds, World Scientific Pub Co, 1998; *Veterinary Virology*, Murphy, F. A. et al., eds., Academic Press, NY, 1999; *Avian Viruses: Function and Control*. Ritchie, B. W., Iowa State University Press, Ames, 2000; *Virus Taxonomy: Classification and Nomenclature of Viruses: Seventh Report of the International Committee on Taxonomy of Viruses*, by M. H. V. Van Regenmortel, M H V et al., eds., Academic Press; NY, 2000.

Plasmid DNA used for transfection or microinjection may be prepared using methods well-known in the art, for example using the Qiagen procedure (Qiagen), followed by DNA purification using known methods, such as the methods exemplified herein.

Such expression vectors may be used to transfect host cells (in vitro, ex vivo or in vivo) for expression of the DNA and production of the encoded proteins which include fusion proteins or peptides. In one embodiment, a nucleic acid (e.g., DNA) vaccine is administered to or contacted with a cell, e.g., a cell obtained from a subject (e.g., an antigen presenting cell), and administered to a subject, wherein the subject is treated before, after or at the same time as the cells are administered to the subject.

The term "isolated" as used herein, when referring to a molecule or composition, such as a translocation polypeptide or a nucleic acid coding therefor, means that the molecule or composition is separated from at least one other compound (protein, other nucleic acid, etc.) or from other contaminants with which it is natively associated or becomes associated during processing. An isolated composition can also be substantially pure. An isolated composition can be in a homogeneous state and can be dry or in aqueous solution. Purity and homogeneity can be determined, for example, using analytical chemical techniques such as polyacrylamide gel electrophoresis (PAGE) or high performance liquid chromatography (HPLC). Even where a protein has been isolated so as to appear as a homogenous or dominant band in a gel pattern, there are trace contaminants which co-purify with it.

Host cells transformed or transfected to express the fusion polypeptide or a homologue or functional derivative thereof are useful for the present invention. For example, the fusion polypeptide may be expressed in yeast, or mammalian cells such as Chinese hamster ovary cells (CHO) or human cells. In one embodiment, cells for expression according to the present invention are APCs or DCs. Other suitable host cells are known to those skilled in the art.

Other Nucleic Acids for Potentiating Immune Responses

Methods of administrating a chemotherapeutic drug and a vaccine may further comprise administration of one or more other constructs, e.g., to prolong the life of antigen presenting cells. Exemplary constructs are described in the following two sections. Such constructs may be administered simultaneously or at the same time as a nucleic acid (e.g., DNA) vaccine. Alternatively, they may be administered before or after administration of the DNA vaccine or chemotherapeutic drug.

Potentiation of Immune Responses Using siRNA Directed at Apoptotic Pathways

Administration to a subject of a DNA vaccine and a chemotherapeutic drug may be accompanied by administration of one or more other agents, e.g., constructs. In one embodiment, a method comprises further administering to a subject an siRNA directed at an apoptotic pathway, such as described in WO 2006/073970, which is incorporated herein in its entirety.

The present inventors have designed siRNA sequences that hybridize to, and block expression of the activation of Bak and Bax proteins that are central players in the apoptosis signaling pathway. Methods of treating tumors or hyperproliferative diseases involving the administration of siRNA molecules (sequences), vectors containing or encoding the siRNA, expression vectors with a promoter operably linked to the siRNA coding sequence that drives transcription of siRNA sequences that are "specific" for sequences Bak and Bax nucleic acid are also encompassed within the present invention. siRNAs may include single stranded "hairpin" sequences because of their stability and binding to the target mRNA.

Since Bak and Bax are involved, among other death proteins, in apoptosis of APCs, particularly DCs, the present siRNA sequences may be used in conjunction with a broad range of DNA vaccine constructs encoding antigens to enhance and promote the immune response induced by such DNA vaccine constructs, particularly CD8+ T cell mediated immune responses typified by CTL activation and action. This is believed to occur as a result of the effect of the siRNA in prolonging the life of antigen-presenting DCs which may otherwise be killed in the course of a developing immune response by the very same CTLs that the DCs are responsible for inducing.

In addition to Bak and Bax, additional targets for siRNAs designed in an analogous manner include caspase 8, caspase 9 and caspase 3. The present invention includes compositions and methods in which siRNAs targeting any two or more of Bak, Bax, caspase 8, caspase 9 and caspase 3 are used in combination, optionally simultaneously (along with a DNA immunogen that encodes an antigen), to administer to a subject. Such combinations of siRNAs may also be used to transfect DCs (along with antigen loading) to improve the immunogenicity of the DCs as cellular vaccines by rendering them resistant to apoptosis.

siRNAs suppress gene expression through a highly regulated enzyme-mediated process called RNA interference (RNAi) (Sharp, P. A., *Genes Dev.* 15:485-90, 2001; Bernstein, E et al., *Nature* 409:363-66, 2001; Nykanen, A et al., *Cell* 107:309-21, 2001; Elbashir et al., *Genes Dev.* 15:188-200, 2001). RNA interference is the sequence-specific degradation of homologues in an mRNA of a targeting sequence in an siNA. As used herein, the term siNA (small, or short, interfering nucleic acid) is meant to be equivalent to other terms used to describe nucleic acid molecules that are capable of mediating sequence specific RNAi (RNA interference), for example short (or small) interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), translational silencing, and others. RNAi involves multiple RNA-protein interactions characterized by four major steps: assembly of siRNA with the RNA-induced silencing complex (RISC), activation of the RISC, target recognition and target cleavage. These interactions may bias strand selection during siRNA-RISC assembly and activation, and contribute to the overall efficiency of RNAi (Khvorova, A et al., *Cell* 115:209-216 (2003); Schwarz, D S et al. 115:199-208 (2003)))

Considerations to be taken into account when designing an RNAi molecule include, among others, the sequence to be targeted, secondary structure of the RNA target and binding of RNA binding proteins. Methods of optimizing siRNA sequences will be evident to the skilled worker. Typical algorithms and methods are described in Vickers et al. (2003) *J Biol Chem* 278:7108-7118; Yang et al. (2003) *Proc Natl Acad Sci USA* 99:9942-9947; Far et al. (2003) *Nuc. Acids Res.* 31:4417-4424; and Reynolds et al. (2004) *Nature Biotechnology* 22:326-330, all of which are incorporated by reference in their entirety.

The methods described in Far et al., supra, and Reynolds et al., supra, may be used by those of ordinary skill in the art to select targeted sequences and design siRNA sequences that are effective at silencing the transcription of the relevant mRNA. Far et al. suggests options for assessing target accessibility for siRNA and supports the design of active siRNA constructs. This approach can be automated, adapted to high throughput and is open to include additional parameters relevant to the biological activity of siRNA. To identify siRNA-specific features likely to contribute to efficient processing at each of the steps of RNAi noted above. Reynolds et al., supra, present a systematic analysis of 180 siRNAs targeting the mRNA of two genes. Eight characteristics associated with siRNA functionality were identified: low G/C content, a bias towards low internal stability at the sense strand 3'-terminus, lack of inverted repeats, and sense strand base preferences (positions 3, 10, 13 and 19). Application of an algorithm incorporating all eight criteria significantly improves potent siRNA selection. This highlights the utility of rational design for selecting potent siRNAs that facilitate functional gene knockdown.

Candidate siRNA sequences against mouse and human Bax and Bak are selected using a process that involves running a BLAST search against the sequence of Bax or Bak (or any other target) and selecting sequences that "survive" to ensure that these sequences will not be cross matched with any other genes.

siRNA sequences selected according to such a process and algorithm may be cloned into an expression plasmid and tested for their activity in abrogating Bak/Bax function cells of the appropriate animal species. Those sequences that show RNAi activity may be used by direct administration bound to particles, or recloned into a viral vector such as a replication-defective human adenovirus serotype 5 (Ad5).

One advantage of this viral vector is the high titer obtainable (in the range of $10^{10}$) and therefore the high multiplicities-of infection that can be attained. For example, infection with 100 infectious units/cell ensures all cells are infected. Another advantage of this virus is the high susceptibility and infectivity and the host range (with respect to cell types). Even if expression is transient, cells would survive, possibly replicate, and continue to function before Bak/Bax activity would recover and lead to cell death. In one embodiment, constructs include the following:

```
For Bak:
(sense)
                                     (SEQ ID NO: 42)
5'P-UGCCUACGAACUCUUCACCdTdT-3'

(antisense)
                                     (SEQ ID NO: 43)
5'P-GGUGAAGAGUUCGUAGGCAdTdT-3'.
```

The nucleotide sequence encoding the Bak protein (including the stop codon) (GenBank accession No. NM_007523 is shown herein as SEQ ID NO:44 with the targeted sequence in upper case, underscored. The targeted sequence of Bak, TGCCTACGAACTCTTCACC is shown herein as SEQ ID NO:45.

```
For Bax:
(sense)
                                     (SEQ ID NO: 46)
5'P-UAUGGAGCUGCAGAGGAUGdTdT-3'

(antisense)
                                     (SEQ ID NO: 47)
5'P-CAUCCUCUGCAGCUCCAUAdTdT-3'
```

The nucleotide sequence encoding Bax (including the stop codon) (GenBank accession No. L22472 is shown below (SEQ ID NO:48) with the targeted sequence shown in upper case and underscored The targeted sequence of Bax, TATGGAGCTGCAGAGGATG is shown herein as SEQ ID NO:49

In a one embodiment, the inhibitory molecule is a double stranded nucleic acid (i.e., an RNA), used in a method of RNA interference. The following show the "paired" 19 nucleotide structures of the siRNA sequences shown above.

```
Bak:    5'P-UGCCUACGAACUCUUCACCdTdT-3'  (sense)     (SEQ ID NO: 42)
            |||||||||||||||||||
        3'P-dTdtACGGAUGCUUGAGAAGUGG-5'  (antisense) (SEQ ID NO: 43)

Bax:    5'P-UAUGGAGCUGCAGAGGAUGdTdT-3'  (sense)     (SEQ ID NO: 46)
            |||||||||||||||||||
        3'P-dTdTAUACCUCGACGUCUCCUAC-5'  (antisense) (SEQ ID NO: 47)
```

Other Pro-Apoptotic Proteins to be Targeted

1. Caspase 8: The nucleotide sequence of human caspase-8 is shown herein as SEQ ID NO:50 (GenBank Access. #NM_001228). One target sequence for RNAi is underscored. Others may be identified using methods such as those described herein (and in reference cited herein, primarily Far et al., supra and Reynolds et al., supra).

The sequences of sense and antisense siRNA strands for targeting this sequence including dTdT 3' overhangs, are:

```
(sense)
                                    (SEQ ID NO:  51)
5'-AACCUCGGGGAUACUGUCUGAdTdT-3'

(antisense)
                                    (SEQ ID NO:  52)
5'-UCAGACAGUAUCCCCGAGGUUdTdT-3'
```

2. Caspase 9: The nucleotide sequence of human caspase-9 is shown herein as SEQ ID NO:53 (see GenBank Access. #NM_001229). The sequence below is of "variant α" which is longer than a second alternatively spliced variant β, which lacks the underscored part of the sequence shown below (and which is anti-apoptotic). Target sequences for RNAi, expected to fall in the underscored segment, are identified using known methods such as those described herein and in Far et al., supra and Reynolds et al., supra) and siNAs, such as siRNAs, are designed accordingly.

3. Caspase 3: The nucleotide sequence of human caspase-3 is shown herein as SEQ ID NO: 54 (see GenBank Access. #NM_004346). The sequence below is of "variant α" which is the longer of two alternatively spliced variants, all of which encode the full protein. Target sequences for RNAi are identified using known methods such as those described herein and in Far et al., supra and Reynolds et al., supra) and siNAs, such as siRNAs, are designed accordingly.

Long double stranded interfering RNAs, such a miRNAs, appear to tolerate mismatches more readily than do short double stranded RNAs. In addition, as used herein, the term RNAi is meant to be equivalent to other terms used to describe sequence specific RNA interference, such as post transcriptional gene silencing, or an epigenetic phenomenon. For example, siNA molecules useful for the invention can be used to epigenetically silence genes at both the post-transcriptional level or the pre-transcriptional level. In a non-limiting example, epigenetic regulation of gene expression by siNA molecules useful for the present invention can result from siNA mediated modification of chromatin structure and thereby alter gene expression (see, for example, Allshire *Science* 297:1818-19, 2002; Volpe et al., *Science* 297:1833-37, 2002; Jenuwein, *Science* 297:2215-18, 2002; and Hall et al., *Science* 297, 2232-2237, 2002.)

An siNA can be designed to target any region of the coding or non-coding sequence of an mRNA. An siNA is a double-stranded polynucleotide molecule comprising self-complementary sense and antisense regions, wherein the antisense region comprises nucleotide sequence that is complementary to nucleotide sequence in a target nucleic acid molecule or a portion thereof and the sense region has a nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary. The siNA can be assembled from a single oligonucleotide, where the self-complementary sense and antisense regions of the siNA are linked by means of a nucleic acid based or non-nucleic acid-based linker(s). The siNA can be a polynucleotide with a hairpin secondary structure, having self-complementary sense and antisense regions. The siNA can be a circular single-stranded polynucleotide having two or more loop structures and a stem comprising self-complementary sense and antisense regions, wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (or can be an siNA molecule that does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al. (2002) *Cell* 110, 563-574 and Schwarz et al. (2002) *Molecular Cell* 10, 537-568), or 5',3'-diphosphate.

In certain embodiments, the siNA molecule useful for the present invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, Van der Waal's interactions, hydrophobic interactions, and/or stacking interactions.

As used herein, siNA molecules need not be limited to those molecules containing only ribonucleotides but may also further encompass deoxyribonucleotides (as in the siRNAs which each include a dTdT dinucleotide) chemically-modified nucleotides, and non-nucleotides. In certain embodiments, the siNA molecules useful for the present invention lack 2'-hydroxy (2'-OH) containing nucleotides. In certain embodiments, siNAs do not require the presence of nucleotides having a 2'-hydroxy group for mediating RNAi and as such, siNAs useful for the present invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. If modified, the siNAs useful for the present invention can also be referred to as "short interfering modified oligonucleotides" or "siMON." Other chemical modifications, e.g., as described in Int'l Patent Publications WO 03/070918 and WO 03/074654, both of which are incorporated by reference, can be applied to any siNA sequence useful for the present invention.

In one embodiment a molecule mediating RNAi has a 2 nucleotide 3' overhang (dTdT in the sequences disclosed herein). If the RNAi molecule is expressed in a cell from a construct, for example from a hairpin molecule or from an inverted repeat of the desired sequence, then the endogenous cellular machinery will create the overhangs.

Methods of making siRNAs are conventional. In vitro methods include processing the polyribonucleotide sequence in a cell-free system (e.g., digesting long dsRNAs with RNAse III or Dicer), transcribing recombinant double stranded DNA in vitro, and chemical synthesis of nucleotide sequences homologous to Bak or Bax sequences. See, e.g., Tuschl et al., *Genes & Dev.* 13:3191-3197, 1999. In vivo methods include (1) transfecting DNA vectors into a cell such that a substrate is converted into siRNA in vivo. See, for example, Kawasaki et al., *Nucleic Acids Res* 31:700-07, 2003; Miyagishi et al., *Nature Biotechnol* 20:497-500, 2003; Lee et al., *Nature Biotechnol* 20:500-05, 2002; Brummelkamp et al., *Science* 296:550-53, 2002; McManus et al., *RNA* 8:842-50, 2002; Paddison et al., *Genes Dev* 16:948-58, 2002; Paddison et al., *Proc Natl Acad Sci USA* 99:1443-48, 2002; Paul et al., *Nature Biotechnol* 20:505-08, 2002; Sui et al., *Proc Natl Acad Sci USA* 99:5515-20, 2002; Yu et al., *Proc Natl Acad Sci USA* 99:6047-52, 2002)

(2) expressing short hairpin RNAs from plasmid systems using RNA polymerase III (pol III) promoters. See, for example, Kawasaki et al., supra; Miyagishi et al., supra; Lee et al., supra; Brummelkamp et al., supra; McManus et al., supra), Paddison et al., supra (both); Paul et al., supra, Sui et al., supra; and Yu et al., supra; and/or (3) expressing short RNA from tandem promoters. See, for example, Miyagishi et al., supra; Lee et al., supra).

When synthesized in vitro, a typical micromolar scale RNA synthesis provides about 1 mg of siRNA, which is sufficient for about 1000 transfection experiments using a 24-well tissue culture plate format. In general, to inhibit Bak or Bax expression in cells in culture, one or more siRNAs can be added to cells in culture media, typically at about 1 ng/ml to about 10 µg siRNA/ml.

For reviews and more general description of inhibitory RNAs, see Lau et al., *Sci Amer* August 2003: 34-41; McManus et al., *Nature Rev Genetics* 3, 737-47, 2002; and Dykxhoorn et al., *Nature Rev Mol Cell Bio* 4:457-467, 2003. For further guidance regarding methods of designing and preparing siRNAs, testing them for efficacy, and using them in methods of RNA interference (both in vitro and in vivo), see, e.g., Allshire, *Science* 297:1818-19, 2002; Volpe et al., *Science* 297:1833-37, 2002; Jenuwein, *Science* 297:2215-18, 2002; Hall et al., *Science* 297 2232-37, 2002; Hutvagner et al., *Science* 297:2056-60, 2002; McManus et al. *RNA* 8:842-850, 2002; Reinhart et al., *Genes Dev.* 16:1616-26, 2002; Reinhart et al., *Science* 297:1831, 2002; Fire et al. (1998) *Nature* 391:806-11, 2002; Moss, *Curr Biol* 11:R772-5, 2002: Brummelkamp et al., supra; Bass, *Nature* 411 428-9, 2001; Elbashir et al., *Nature* 411:494-8; U.S. Pat. No. 6,506,559; Published US Pat App. 20030206887; and PCT applications WO99/07409, WO99/32619, WO 00/01846, WO 00/44914, WO00/44895, WO01/29058, WO01/36646, WO01/75164, WO01/92513, WO 01/29058, WO01/89304, WO01/90401, WO02/16620, and WO02/29858, all of which are incorporated by reference.

Ribozymes and siNAs can take any of the forms, including modified versions, described for antisense nucleic acid molecules; and they can be introduced into cells as oligonucleotides (single or double stranded), or in the form of an expression vector.

In one embodiment, an antisense nucleic acid, siNA (e.g., siRNA) or ribozyme comprises a single stranded polynucleotide comprising a sequence that is at least about 90% (e.g., at least about 93%, 95%, 97%, 98% or 99%) identical to a target segment (such as those indicted for Bak and Bax above) or a complement thereof. As used herein, a DNA and an RNA encoded by it are said to contain the same "sequence," taking into account that the thymine bases in DNA are replaced by uracil bases in RNA.

Active variants (e.g., length variants, including fragments; and sequence variants) of the nucleic acid-based inhibitors discussed herein are also within the scope of the present invention. An "active" variant is one that retains an activity of the inhibitor from which it is derived (i.e., the ability to inhibit expression). It is to test a variant to determine for its activity using conventional procedures.

As for length variants, an antisense nucleic acid or siRNA may be of any length that is effective for inhibition of a gene of interest. Typically, an antisense nucleic acid is between about 6 and about 50 nucleotides (e.g., at least about 12, 15, 20, 25, 30, 35, 40, 45 or 50 nt), and may be as long as about 100 to about 200 nucleotides or more. Antisense nucleic acids having about the same length as the gene or coding sequence to be inhibited may be used. When referring to length, the terms bases and base pairs (bp) are used interchangeably, and will be understood to correspond to single stranded (ss) and double stranded (ds) nucleic acids. The length of an effective siNA is generally between about 15 bp and about 29 bp in length, between about 19 and about 29 bp (e.g., about 15, 17, 19, 21, 23, 25, 27 or 29 bp), with shorter and longer sequences being acceptable. Generally, siNAs are shorter than about 30 bases to prevent eliciting interferon effects. For example, an active variant of an siRNA having, for one of its strands, the 19 nucleotide sequence of any of SEQ ID NOs:42, 43, 46, and 47 herein can lack base pairs from either, or both, of ends of the dsRNA; or can comprise additional base pairs at either, or both, ends of the ds RNA, provided that the total of length of the siRNA is between about 19 and about 29 bp, inclusive. One embodiment useful for the present invention is an siRNA that "consists essentially of" sequences represented by SEQ ID NOs:42, 43, 46, and 47 or complements of these sequence. An siRNA useful for the present invention may consist essentially of between about 19 and about 29 bp in length.

As for sequence variants, in one embodiment, an inhibitory nucleic acid, whether an antisense molecule, a ribozyme (the recognition sequences), or an siNA, comprises a strand that is complementary (100% identical in sequence) to a sequence of a gene that it is designed to inhibit. However, 100% sequence identity is not required to practice the present invention. Thus, the invention has the advantage of being able to tolerate naturally occurring sequence variations, for example, in human c-met, that might be expected due to genetic mutation, polymorphism, or evolutionary divergence. Alternatively, the variant sequences may be artificially generated. Nucleic acid sequences with small insertions, deletions, or single point mutations relative to the target sequence can be effective inhibitors.

The degree of sequence identity may be optimized by sequence comparison and alignment algorithms well-known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). In one embodiment, at least about 90% sequence identity may be used (e.g., at least about 92%, 95%, 98% or 99%), or even 100% sequence identity, between the inhibitory nucleic acid and the targeted sequence of targeted gene.

Alternatively, an active variant of an inhibitory nucleic acid useful for the present invention is one that hybridizes to the sequence it is intended to inhibit under conditions of high stringency. For example, the duplex region of an siRNA may be defined functionally as a nucleotide sequence that is capable of hybridizing with a portion of the target gene transcript under high stringency conditions (e.g., 400 mM NaCl, 40 mM PIPES pH 6.4, 1 mM EDTA, 50° C. or 70° C., hybridization for 12-16 hours), followed generally by washing.

DC-1 cells or BM-DCs presenting a given antigen X, when not treated with the siRNAs useful for the present invention, respond to sufficient numbers X-specific CD8+ CTL by apoptotic cell death. In contrast, the same cells transfected with the siRNA or infected with a viral vector encoding the present siRNA sequences survive better despite the delivery of killing signals.

Delivery and expression of the siRNA compositions useful for the present invention inhibit the death of DCs in vivo in the process of a developing T cell response, and thereby promote and stimulate the generation of an immune response induced by immunization with an antigen-encoding DNA vaccine vector. These capabilities have been exemplified by showing that:

(1) co-administration of DNA vaccines encoding HPV-16 E7 with siRNA targeted to Bak and Bax prolongs the lives of antigen-presenting DCs in the draining lymph nodes, thereby enhancing antigen-specific CD8$^+$ T cell responses, and eliciting potent antitumor effects against an E7-expressing tumor in vaccinated subjects.

(2) DCs transfected with siRNA targeting Bak and Bax resist killing by T cells in vivo. E7-loaded DCs transfected with Bak/Bax siRNA so that Bak and Bax protein expression is downregulated resist apoptotic death induced by T cells in vivo. When administered to subjects, these DCs generate stronger antigen-specific immune responses and manifest therapeutic effects (compared to DCs transfected with control siRNA).

Thus, siRNA constructs are useful as a part of the nucleic acid vaccination and chemotherapy regimen described in this application.

Potentiation of Immune Responses Using Anti-Apoptotic Proteins

Administration to a subject of a DNA vaccine and a chemotherapeutic drug may also be accompanied by administration of a nucleic acid encoding an anti-apoptotic protein, as described in WO2005/047501 and in U.S. Patent Application Publication No. 20070026076, both of which are incorporated by reference.

The present inventors have designed and disclosed an immunotherapeutic strategy that combines antigen-encoding DNA vaccine compositions with additional DNA vectors comprising anti-apoptotic genes including bcl-2, bc-lxL, XIAP, dominant negative mutants of caspase-8 and caspase-9, the products of which are known to inhibit apoptosis (Wu, et al. U.S. Patent Application Publication No. 20070026076, incorporated herein by reference). Serine protease inhibitor 6 (SPI-6) which inhibits granzyme B, may also be employed in compositions and methods to delay apoptotic cell death of DCs. The present inventors have shown that the harnessing of an additional biological mechanism, that of inhibiting apoptosis, significantly enhances T cell responses to DNA vaccines comprising antigen-coding sequences, as well as linked sequences encoding such IPPs.

Intradermal vaccination by gene gun efficiently delivers a DNA vaccine into DCs of the skin, resulting in the activation and priming of antigen-specific T cells in vivo. DCs, however, have a limited life span, hindering their long-term ability to prime antigen-specific T cells. According to the present invention, a strategy that combines combination therapy with methods to prolong the survival of DNA-transduced DCs enhances priming of antigen-specific T cells and thereby, increase DNA vaccine potency. Co-delivery of DNA encoding inhibitors of apoptosis (BCL-xL, BCL-2, XIAP, dominant negative caspase-9, or dominant negative caspase-8) with DNA encoding an antigen (exemplified as HPV-16 E7 protein) prolongs the survival of transduced DCs. More importantly, vaccinated subjects exhibited significant enhancement in antigen-specific CD8+ T cell immune responses, resulting in a potent antitumor effect against antigen-expressing tumors. Among these anti-apoptotic factors, BCL-XL demonstrated the greatest enhancement of both antigen-specific immune responses and anti-tumor effects. Thus, co-administration of a combination therapy including a DNA vaccine with one or more DNA constructs encoding anti-apoptotic proteins provides a way to enhance DNA vaccine potency.

Serine protease inhibitor 6 (SPI-6), also called Serpinb9, inhibits granzyme B, and may thereby delay apoptotic cell death in DCs. Intradermal co-administration of DNA encoding SPI-6 with DNA constructs encoding E7 linked to various IPPs significantly increased E7-specific CD8+ T cell and CD4+ Th1 cell responses and enhanced anti-tumor effects when compared to vaccination without SPI-6. Thus, in certain embodiments, combined methods are used that enhance MHC class I and II antigen processing with delivery of SPI-6 to potentiate immunity.

A similar approach employs DNA-based alphaviral RNA replicon vectors, also called suicidal DNA vectors. To enhance the immune response to an antigen, e.g., HPV E7, a DNA-based Semliki Forest virus vector, pSCA1, the antigen DNA is fused with DNA encoding an anti-apoptotic polypeptide such BCL-xL, a member of the BCL-2 family. pSCA1 encoding a fusion protein of an antigen polypeptide and/BCL-xL delays cell death in transfected DCs and generates significantly higher antigen-specific CD8+ T-cell-mediated immunity. The antiapoptotic function of BCL-xL is important for the enhancement of antigen-specific CD8+ T-cell responses. Thus, in one embodiment, delaying cell death induced by an otherwise desirable suicidal DNA vaccine enhances its potency.

Thus, the present invention is also directed to combination therapies including administering a chemotherapeutic drug with a nucleic acid composition useful as an immunogen, comprising a combination of: (a) first nucleic acid vector comprising a first sequence encoding an antigenic polypeptide or peptide, which first vector optionally comprises a second sequence linked to the first sequence, which second sequence encodes an immunogenicity-potentiating polypeptide (IPP); b) a second nucleic acid vector encoding an anti-apoptotic polypeptide, wherein, when the second vector is administered with the first vector to a subject, a T cell-mediated immune response to the antigenic polypeptide or peptide is induced that is greater in magnitude and/or duration than an immune response induced by administration of the first vector alone. The first vector above may comprise a promoter operatively linked to the first and/or the second sequence.

In the above compositions the anti-apoptotic polypeptide may be selected from the group consisting of (a) BCL-xL, (b) BCL2, (c) XIAP, (d) FLICEc-s, (e) dominant-negative caspase-8, (0 dominant negative caspase-9, (g) SPI-6, and (h) a functional homologue or a derivative of any of (a)-(g). The anti-apoptotic DNA may be physically linked to the antigen-encoding DNA. Examples of this are provided in U.S. Patent Application publication No. 20070026076, incorporated by reference, primarily in the form of suicidal DNA vaccine vectors. Alternatively, the anti-apoptotic DNA may be administered separately from, but in combination with the antigen-encoding DNA molecule. Even more examples of the co-administration of these two types of vectors are provided in U.S. patent application Ser. No. 10/546,810 (publication number US 2007-0026076).

Exemplary nucleotide and amino acid sequences of anti-apoptotic and other proteins are provided in the sequence listing. Biologically active homologs of these proteins and constructs may also be used. Biologically active homologs is to be understood as described herein in the context of other proteins, e.g., IPPs.

The coding sequence for BCL-xL as present in the pcDNA3 vector useful for the present invention is SEQ ID NO:55; the amino acid sequence of BCL-xL is SEQ ID NO:56; the sequence pcDNA3-BCL-xL is SEQ ID NO:57 (the BCL-xL coding sequence corresponds to nucleotides 983 to 1732); a pcDNA3 vector combining E7 and BCL-xL, designated pcDNA3-E7/BCL-xL is SEQ ID NO:58 (the E7 and BCL-xL sequences correspond to nucleotides 960 to 2009); the amino acid sequence of the E7-BCL-xL chimeric or fusion polypeptide is SEQ ID NO:59; a mutant BCL-xL ("mtBCL-xL") DNA sequence is SEQ ID NO:60; the amino acid sequence of mtBCL-xL is SEQ ID NO:61; the amino acid sequence of the E7-mtBCL-xL chimeric or fusion polypeptide is SEQ ID NO:62; in the pcDNA-mtBCL-xL [SEQ ID NO:63] vector, this mutant sequence is inserted in the same position that BCL-xL is inserted in SEQ ID NO:57 and in the pcDNA-E7/mtBCL-XL [SEQ ID NO:64], this sequence is inserted in the same position as the BCL-xL sequence is in SEQ ID NO:58; the sequence of the suicidal DNA vector pSCA1-BCL-xL is SEQ ID NO:65 (the BCL-xL sequence corresponds to nucleotides 7483 to 8232); the sequence of the "combined" vector, pSCA1-E7/BCL-xL is SEQ ID NO:66 (the sequence of E7 and BCL-xL corresponds to nucleotides 7461 to 8510); the sequence of pSCA1-mtBCL-xL [SEQ ID NO:67] is the same as that for the wild type BCL-xL except that the mtBCL-xL sequence is inserted in the same position as the wild type sequence in the pSCA1-mtBCL-xL vector; the sequence pSCA1-E7/mtBCL-xL [SEQ ID NO:68] is the same as that for the wild type pSCA1-E7/BCL-xL above, except that the mtBCL-xL sequence is inserted in the same position as the wild type sequence; the sequence of the vector pSG5-BCL-xL is SEQ ID NO:69 (the BCL-xL coding sequence corresponds to nucleotides 1061 to 1810); the sequenced of the vector pSG5-mtBCL-xL is SEQ ID NO:70 with the mutant BCL-xL sequence has the mtBCL-xL, shown above, inserted in the same location as for the wild type vector immediately above; the nucleotide sequence of the DNA encoding the XIAP anti-apoptotic protein is SEQ ID NO:71; the amino acid of the vector comprising the XIAP anti-apoptotic protein coding sequence is SEQ ID NO:72; the nucleotide sequence of the vector comprising the XIAP anti-apoptotic protein coding sequence, designated PSG5-XIAP is shown in SEQ ID NO:73 (with the XIAP corresponding to nucleotides 1055 to 2553); the sequence of DNA encoding the anti-apoptotic protein FLICEc-s is SEQ ID NO:74; the amino acid sequence of the anti-apoptotic protein FLICEc-s is SEQ ID NO:75; the PSG5 vector encoding the anti-apoptotic protein FLICEc-s, designated PSG5-FLICEc-s, has the sequence SEQ ID NO:76 (with the FLICEc-s sequence corresponding to nucleotides 1049 to 2443); the sequence of DNA encoding the anti-apoptotic protein Bcl2 is SEQ ID NO:77; the amino acid sequence of Bcl2 is SEQ ID NO:78; the PSG5 vector encoding Bcl2, designated PSG5-BCL2, has the sequence SEQ ID NO:79 (with the Bcl2 sequence corresponding to nucleotides 1061 to 1678); the pSG5-dn-caspase-8 vector is SEQ ID NO:80 (encoding the dominant-negative caspase-8 corresponding to nucleotides 1055 to 2449); the amino acid sequence of dn-caspase-8 is SEQ ID NO:81; the pSG5-dn-caspase-9 vector is SEQ ID NO:82 (encoding the dominant-negative caspase-9 as nucleotides 1055 to 2305); the amino acid sequence of dn-caspase-9 is SEQ ID NO:83; the nucleotide sequence of murine serine protease inhibitor 6 (SPI-6, deposited in GENEBANK as NM_009256) is SEQ ID NO:84; the amino acid sequence of the SPI-6 protein is SEQ ID NO:85; the nucleic acid sequence of the mutant SPI-6 (mtSPI6) is SEQ ID NO:86; the amino acid sequence of the mutant SPI-6 protein (mtSPI-6) is SEQ ID NO:87; the sequence of the pcDNA3-Spi6 vector is SEQ ID NO:88 (the SPI-6 sequence corresponds to nucleotides 960 to 2081); and the sequence of the mutant vector pcDNA3-mtSpi6 vector [SEQ ID NO:89] is the same as that above, except that the mtSPI-6 sequence is inserted in the same location in place of the wild type SPI-6.

Biologically active homologs of these nucleic acids and proteins may be used. Biologically active homologs are to be understood as described in the context of other proteins, e.g., IPPs, herein. For example, a vector may encode an anti-apoptotic protein that is at least about 90%, 95%, 98% or 99% identical to that of a sequence set forth herein.

MHC Class I/II Activators

"MHC class I/II activators" refers to molecules or complexes thereof that increase immune responses by increasing MHC class I or II ("I/II") antigen presentation, such as by increasing MHC class I, class II or class I and class II activity or gene expression. In one embodiment, an MHC class I/II activator is a nucleic acid encoding a protein that enhances MHC class I/II antigen presentation. Exemplary MHC class I/II activators include nucleic acids encoding an MHC class II associated invariant chain (Ii), in which the CLIP region is replaced with a T cell epitope, e.g., a promiscuous T cell epitope, such as the Pan HLA-DR reactive epitope (PADRE), or a variant thereof. Other MHC class I/II activators are nucleic acids encoding the MHC class II transactivator CIITA or a variant thereof.

In one embodiment, an MHC class I/II activator is a nucleic acid, e.g., an isolated nucleic acid, encoding a protein comprising, consisting or consisting essentially of an invariant (Ii) chain, wherein the CLIP region is replaced with a promiscuous CD4+ T cell epitope. A "promiscuous CD4+ T cell epitope" is used interchangeably with "universal CD4+ T cell epitope" and refers to peptides that bind to numerous histocompatibility alleles, e.g., human MHC class II molecules. In one embodiment, the promiscuous CD4+ T cell epitope is a Pan HLA-DR reactive epitope (PADRE), thereby forming an Ii-PADRE protein that is encoded by an Ii-PADRE nucleic acid. In one embodiment, a nucleic acid encodes an Ii chain, wherein amino acids 81-102 (KPVSQMRMATPLLMRPM (SEQ ID NO:92) are replaced with the PADRE sequence AKFVAAWTLKAAA (SEQ ID NO:93). An exemplary human Ii-PADRE amino acid sequence is set forth as SEQ ID NO:91, and is encoded by nucleotide sequence SEQ ID NO:90.

Also provided herein are variants of a protein consisting of SEQ ID NO:91. A protein may comprise, consist essentially of, or consist of an amino acid sequence that is at least about 80%, 85%, 90%, 95%, 96%, 97%, 98% or 99% identical to SEQ ID NO:91. A protein may comprise a PADRE that is identical to the PADRE of SEQ ID NO:91, i.e., consisting of SEQ ID NO:93. A protein may comprise a PADRE sequence that is at least about 80%, 85%, 90%, 95%, 96%, 97%, 98% or 99% identical to SEQ ID NO:93;

and/or an Ii sequence that is at least about 80%, 85%, 90%, 95%, 96%, 97%, 98% or 99% identical to the Ii sequence of SEQ ID NO:91.

An amino acid sequence may differ from that of SEQ ID NO:91 or the Ii or PADRE sequences thereof by the addition, deletion or substitution of at least about 1, 2, 3, 4, 5, 6, 7, 8, 9, 10, 11, 12, 13, 14, 15, 16, 17, 18, 19, 20, 25, 30 or more amino acids. In certain embodiments, a protein lacks one or more, e.g., 2, 3, 4, 5, 6, 7, 8, 9, 10 or more amino acids at the C- and/or N-terminus and/or internal relative to that of SEQ ID NO:91 or the Ii or PADRE region thereof. In certain embodiments, an amino acid sequence differs from that of SEQ ID NO:93 or from that of the Ii sequence by the addition, deletion or substitution of at least about 1, 2, 3, 4, or 5 amino acids.

In addition, comparison (or alignment) of the Ii and PADRE sequences from different species is expected to be helpful in determining which amino acids may be varied and which ones should preferably not be varied.

Other proteins provided herein comprise a PADRE amino acid sequence that replaces a larger portion of Ii, e.g., wherein Ii is lacking about amino acids 81-103, 81-104, 81-105, 81-106, 81-107, 81-108, 81-109, 81-110 or more; is lacking about amino acids 70-102, 71-102, 72-102, 73-102, 74-102, 75-102, 76-102, 77-102, 78-102, 79-102, 80-102 or more.

Other promiscuous CD4+ T cell epitopes that may be used instead of PADRE are listed in Table 1.

TABLE 1

| Exemplary promiscuous CD4+ T cell epitopes | |
|---|---|
| Promiscuous CD4+ T cell epitopes | Reference |
| EBV-latent membrane protein 1 (LMP1$_{159-175}$)<br>YLQQNWWTLLVDLLWLL | (1) |
| MAGE-A6$_{172-187}$; IGHVYIFATCLGLSYD<br>Mycoplasma penetrans HF-2$_{219-226}$; IYIFAACL | (2) |
| six-transmembrane epithelial antigen of prostate (STEAP)<br>STEAP$_{102-116}$ HQQYFYKIPILVINK<br>STEAP$_{192-206}$ LLNWAYQQVQQNKED | (3) |
| Taxol-resistance-associated gene-3 (TRAG3)$_{35-48}$<br>EFHACW PAFTVLGE | (4) |
| Survivin$_{10-24}$ WQPFLKDHRISTFKN | (5) |
| HPV 18-E6$_{52-66}$; LFVVYRDSIPHAACH<br>HPV18-E6$_{97-111}$; GLYNLLIRCLRCQKP | (6) |
| Carcinoembryonic antigen$_{177-189}$; LWWVNNQSLPVSP | (7) |
| mycobacterial antigen MPB70<br>MPB70$_{106-130}$; FSKLPASTIDELKTNSSLLTSILTY<br>MPB70$_{166-193}$; GNADVVCGGVSTANATVYMIDSVLMPPA | (8) |
| HER-2$_{776-788}$ GSPYVSRLLGICL | (9) |
| HER-2$_{833-849}$ KVPIKWMALESILRRRF | (10) |
| NY-ESO-1$_{119-143}$ PGVLLKEFTVSGNILTIRLTAADHR | (11) |
| Tetanus toxin$_{1084-1099}$ VSIDKFRIFCKANPK<br>Tetanus toxin$_{1174-1189}$ LKFIIKRYTPNNEIDS<br>Tetanus toxin$_{1064-1079}$ IREDNNITLKLDRCN<br>Tetanus toxin$_{947-967}$ FNNFTVSFWLRVPKVSASHLE<br>Tetanus toxin$_{830-843}$ QYIKANSKFIGITE<br>HBV nuclear capside$_{50-69}$ PHHTALRQAILCWGELMTLA<br>Influenza haemagglutinin$_{307-319}$ PKYVKQNTLKLAT<br>HBV surface antigen$_{19-33}$ -FFLLTRILTIPQSLD<br>Influenza matrix$_{17-31}$ YSGPLKAEIAQRLEDV<br>P. falciparum CSP$_{380-398}$ EKKIAKMEKASSVFNVVN | (12) |

Variants of SEQ ID NO:91 or the PADRE or Ii regions thereof preferably have a biological activity. Such variants are referred to as "functional homologs" or "functional variants." Functional homologs include variants of SEQ ID NO:91 that increase an immune response, e.g., an antigen specific immune response, in a subject to whom it is administered, or has any of the biological activities set forth in the Examples pertaining to Ii-PADRE. Variants of the PADRE sequence or the Ii sequence may have a biological activity that is associated with that of the wild type PADRE or Ii sequences, respectively. Biological activities can be determined as know in the art or as set forth in the Examples.

1. Kobayashi, H., T. Nagato, M. Takahara, K. Sato, S. Kimura, N. Aoki, M. Azumi, M. Tateno, Y. Harabuchi, and E. Celis. 2008. Induction of EBV-latent membrane protein 1-specific MHC class II-restricted T-cell responses against natural killer lymphoma cells. *Cancer Res* 68:901-908.
2. Vujanovic, L., M. Mandic, W. C. Olson, J. M. Kirkwood, and W. J. Storkus. 2007. A mycoplasma peptide elicits heteroclitic CD4+ T cell responses against tumor antigen MAGE-A6. *Clin Cancer Res* 13:6796-6806.
3. Kobayashi, H., T. Nagato, K. Sato, N. Aoki, S. Kimura, M. Murakami, H. Iizuka, M. Azumi, H. Kakizaki, M.

Tateno, and E. Celis. 2007. Recognition of prostate and melanoma tumor cells by six-transmembrane epithelial antigen of prostate-specific helper T lymphocytes in a human leukocyte antigen class II-restricted manner. *Cancer Res* 67:5498-5504.

4. Janjic, B., P. Andrade, X. F. Wang, J. Fourcade, C. Almunia, P. Kudela, A. Brufsky, S. Jacobs, D. Friedland, R. Stoller, D. Gillet, R. B. Herberman, J. M. Kirkwood, B. Maillere, and H. M. Zarour. 2006. Spontaneous CD4+ T cell responses against TRAG-3 in patients with melanoma and breast cancers. *J Immunol* 177:2717-2727.

5. Piesche, M., Y. Hildebrandt, F. Zettl, B. Chapuy, M. Schmitz, G. Wulf, L. Trumper, and R. Schroers. 2007. Identification of a promiscuous HLA DR-restricted T-cell epitope derived from the inhibitor of apoptosis protein survivin. *Hum Immunol* 68:572-576.

6. Facchinetti, V., S. Seresini, R. Longhi, C. Garavaglia, G. Casorati, and M. P. Protti. 2005. CD4+ T cell immunity against the human papillomavirus-18 E6 transforming protein in healthy donors: identification of promiscuous naturally processed epitopes. *Eur J Immunol* 35:806-815.

7. Campi, G., M. Crosti, G. Consogno, V. Facchinetti, B. M. Conti-Fine, R. Longhi, G. Casorati, P. Dellabona, and M. P. Protti. 2003. CD4(+) T cells from healthy subjects and colon cancer patients recognize a carcinoembryonic antigen-specific immunodominant epitope. *Cancer Res* 63:8481-8486.

8. Al-Attiyah, R., F. A. Shaban, H. G. Wiker, F. Oftung, and A. S. Mustafa. 2003. Synthetic peptides identify promiscuous human Th1 cell epitopes of the secreted mycobacterial antigen MPB70. *Infect Immun* 71:1953-1960.

9. Sotiriadou, R., S. A. Perez, A. D. Gritzapis, P. A. Sotiropoulou, H. Echner, S. Heinzel, A. Mamalaki, G. Pawelec, W. Voelter, C. N. Baxevanis, and M. Papamichail. 2001. Peptide HER2(776-788) represents a naturally processed broad MHC class II-restricted T cell epitope. *Br J Cancer* 85:1527-1534.

10. Kobayashi, H., M. Wood, Y. Song, E. Appella, and E. Celis. 2000. Defining promiscuous MHC class II helper T-cell epitopes for the HER2/neu tumor antigen. *Cancer Res* 60:5228-5236.

11. Zarour, H. M., B. Maillere, V. Brusic, K. Coval, E. Williams, S. Pouvelle-Moratille, F. Castelli, S. Land, J. Bennouna, T. Logan, and J. M. Kirkwood. 2002. NY-ESO-1 119-143 is a promiscuous major histocompatibility complex class II T-helper epitope recognized by Th1- and Th2-type tumor-reactive CD4+ T cells. *Cancer Res* 62:213-218.

12. Falugi, F., R. Petracca, M. Mariani, E. Luzzi, S. Mancianti, V. Carinci, M. L. Melli, O. Finco, A. Wack, A. Di Tommaso, M. T. De Magistris, P. Costantino, G. Del Giudice, S. Abrignani, R. Rappuoli, and G. Grandi. 2001. Rationally designed strings of promiscuous CD4 (+) T cell epitopes provide help to *Haemophilus influenzae* type b oligosaccharide: a model for new conjugate vaccines. *Eur J Immunol* 31:3816-3824.

The CLIP region in an Ii molecule, e.g., having the amino acid sequence of the Ii portion set forth in SEQ ID NO:91, may be replaced with any of the peptides in Table 2 or other promiscuous epitopes set forth in the references of Table 2, or functional variants thereof. Preferred epitopes include those from tetanus toxin and influenza. Any other promiscuous CD4+ T cell epitopes may be used, e.g., those described in the following references:

1. Campi, G., M. Crosti, G. Consogno, V. Facchinetti, B. M. Conti-Fine, R. Longhi, G. Casorati, P. Dellabona, and M. P. Protti. 2003. CD4(+) T cells from healthy subjects and colon cancer patients recognize a carcinoembryonic antigen-specific immunodominant epitope. *Cancer Res* 63:8481-8486.

2. Castelli, F. A., M. Leleu, S. Pouvelle-Moratille, S. Farci, H. M. Zarour, M. Andrieu, C. Auriault, A. Menez, B. Georges, and B. Maillere. 2007. Differential capacity of T cell priming in naive donors of promiscuous CD4+ T cell epitopes of HCV NS3 and Core proteins. *Eur J Immunol* 37:1513-1523.

3. Consogno, G., S. Manici, V. Facchinetti, A. Bachi, J. Hammer, B. M. Conti-Fine, C. Rugarli, C. Traversari, and M. P. Protti. 2003. Identification of immunodominant regions among promiscuous HLA-DR-restricted CD4+ T-cell epitopes on the tumor antigen MAGE-3. *Blood* 101:1038-1044.

4. Depil, S., O. Morales, F. A. Castelli, N. Delhem, V. Francois, B. Georges, F. Dufosse, F. Morschhauser, J. Hammer, B. Maillere, C. Auriault, and V. Pancre. 2007. Determination of a HLA II promiscuous peptide cocktail as potential vaccine against EBV latency II malignancies. *J Immunother* (1997) 30:215-226.

5. Facchinetti, V., S. Seresini, R. Longhi, C. Garavaglia, G. Casorati, and M. P. Protti. 2005. CD4+ T cell immunity against the human papillomavirus-18 E6 transforming protein in healthy donors: identification of promiscuous naturally processed epitopes. *Eur J Immunol* 35:806-815.

6. Kobayashi, H., T. Nagato, K. Sato, N. Aoki, S. Kimura, M. Murakami, H. Iizuka, M. Azumi, H. Kakizaki, M. Tateno, and E. Celis. 2007. Recognition of prostate and melanoma tumor cells by six-transmembrane epithelial antigen of prostate-specific helper T lymphocytes in a human leukocyte antigen class II-restricted manner. *Cancer Res* 67:5498-5504.

7. Kobayashi, H., M. Wood, Y. Song, E. Appella, and E. Celis. 2000. Defining promiscuous MHC class II helper T-cell epitopes for the HER2/neu tumor antigen. *Cancer Res* 60:5228-5236.

8. Mandic, M., C. Almunia, S. Vicel, D. Gillet, B. Janjic, K. Coval, B. Maillere, J. M. Kirkwood, and H. M. Zarour. 2003. The alternative open reading frame of LAGE-1 gives rise to multiple promiscuous HLA-DR-restricted epitopes recognized by T-helper 1-type tumor-reactive CD4+ T cells. *Cancer Res* 63:6506-6515.

9. Neumann, F., C. Wagner, S. Stevanovic, B. Kubuschok, C. Schormann, A. Mischo, K. Ertan, W. Schmidt, and M. Pfreundschuh. 2004. Identification of an HLA-DR-restricted peptide epitope with a promiscuous binding pattern derived from the cancer testis antigen HOM-MEL-40/SSX2. *Int J Cancer* 112:661-668.

10. Ohkuri, T., M. Sato, H. Abe, K. Tsuji, Y. Yamagishi, H. Ikeda, N. Matsubara, H. Kitamura, and T. Nishimura. 2007. Identification of a novel NY-ESO-1 promiscuous helper epitope presented by multiple MHC class II molecules found frequently in the Japanese population. *Cancer Sci* 98:1092-1098.

11. Piesche, M., Y. Hildebrandt, F. Zettl, B. Chapuy, M. Schmitz, G. Wulf, L. Trumper, and R. Schroers. 2007. Identification of a promiscuous HLA DR-restricted T-cell epitope derived from the inhibitor of apoptosis protein survivin. *Hum Immunol* 68:572-576.

12. Sotiriadou, R., S. A. Perez, A. D. Gritzapis, P. A. Sotiropoulou, H. Echner, S. Heinzel, A. Mamalaki, G.

Pawelec, W. Voelter, C. N. Baxevanis, and M. Papamichail. 2001. Peptide HER2(776-788) represents a naturally processed broad MHC class II-restricted T cell epitope. *Br J Cancer* 85:1527-1534.
13. Texier, C., S. Pouvelle-Moratille, C. Buhot, F. A. Castelli, C. Pecquet, A. Menez, F. Leynadier, and B. Maillere. 2002. Emerging principles for the design of promiscuous HLA-DR-restricted peptides: an example from the major bee venom allergen. *Eur J Immunol* 32:3699-3707.
14. Vujanovic, L., M. Mandic, W. C. Olson, J. M. Kirkwood, and W. J. Storkus. 2007. A mycoplasma peptide elicits heteroclitic CD4+ T cell responses against tumor antigen MAGE-A6. *Clin Cancer Res* 13:6796-6806.
15. Zarour, H. M., B. Maillere, V. Brusic, K. Coval, E. Williams, S. Pouvelle-Moratille, F. Castelli, S. Land, J. Bennouna, T. Logan, and J. M. Kirkwood. 2002. NY-ESO-1 119-143 is a promiscuous major histocompatibility complex class II T-helper epitope recognized by Th1- and Th2-type tumor-reactive CD4+ T cells. *Cancer Res* 62:213-218.
16. Gao, M., H. P. Wang, Y. N. Wang, Y. Zhou, and Q. L. Wang. 2006. HCV-NS3 Th1 minigene vaccine based on invariant chain CLIP genetic substitution enhances CD4(+) Th1 cell responses in vivo. *Vaccine* 24:5491-5497.
17. Nagata, T., T. Aoshi, M. Suzuki, M. Uchijima, Y. H. Kim, Z. Yang, and Y. Koide. 2002. Induction of protective immunity to *Listeria monocytogenes* by immunization with plasmid DNA expressing a helper T-cell epitope that replaces the class II-associated invariant chain peptide of the invariant chain. *Infect Immun* 70:2676-2680.
18. Nagata, T., T. Higashi, T. Aoshi, M. Suzuki, M. Uchijima, and Y. Koide. 2001. Immunization with plasmid DNA encoding MHC class II binding peptide/CLIP-replaced invariant chain (Ii) induces specific helper T cells in vivo: the assessment of Ii p31 and p41 isoforms as vehicles for immunization. *Vaccine* 20:105-114.
19. Toda, M., M. Kasai, H. Hosokawa, N. Nakano, Y. Taniguchi, S. Inouye, S. Kaminogawa, T. Takemori, and M. Sakaguchi. 2002. DNA vaccine using invariant chain gene for delivery of CD4+ T cell epitope peptide derived from Japanese cedar pollen allergen inhibits allergen-specific IgE response. *Eur J Immunol* 32:1631-1639.
20. van Bergen, J., M. Camps, R. Offringa, C. J. Melief, F. Ossendorp, and F. Koning. 2000. Superior tumor protection induced by a cellular vaccine carrying a tumor-specific T helper epitope by genetic exchange of the class II-associated invariant chain peptide. *Cancer Res* 60:6427-6433.
21. van Tienhoven, E. A., C. T. ten Brink, J. van Bergen, F. Koning, W. van Eden, and C. P. Broeren. 2001. Induction of antigen specific CD4+ T cell responses by invariant chain based DNA vaccines. *Vaccine* 19:1515-1519.

In certain embodiments, the CLIP region of Ii is replaced with a T cell epitope, e.g., a CD4+ T cell epitope, such as a promiscuous CD4+ T cell epitope, with the proviso that the resulting construct is not one that has been publicly disclosed previously, e.g., one year prior to the filing of the priority application of the instant application. For example, in certain embodiments, the epitope that replaces the CLIP region is not a promiscuous CD4+ T cell epitope from an HCV antigen, Listeria LLO antigen, ovalbumin antigen, Japanese cedar pollen allergen, MuLV env/gp70-derived helper epitope, and Heat Shock Protein 60 (described in references 16-21 above), or epitopes replacing CLIP regions that are described in publications that are referenced to in the Examples.

In certain embodiments, a nucleic acid comprises, consists essentially of, or consists of the nucleotide sequence set forth in SEQ ID NO:90, or comprises a nucleotide sequence sequence encoding the PADRE or Ii portion thereof. A nucleic acid may also comprise a nucleotide sequence that is at least about 80%, 85%, 90%, 95%, 96%, 97%, 98% or 99% identical to SEQ ID NO:90 and/or to the PADRE and/or to the Ii portion thereof. Nucleic acids may differ by the addition, deletion or substitution of one or more, e.g., 1, 3, 5, 10, 15, 20, 25, 30 or more nucleotides, which may be located at the 5' end, 3' end, and/or internally to the sequence.

In certain embodiments, a nucleic acid encodes a protein that is a functional homolog of an Ii-PADRE protein, with the proviso that the Ii sequence and/or PADRE sequence is (or are) not the wild-type or a naturally-occurring sequence, e.g., the wild-type or naturally-occurring human sequence.

In another embodiment, an MHC class I/II activator is a protein that enhances MHC class II expression, e.g., an MHC class II transactivator (CIITA). The nucleotide and amino acid sequences of human CIITA are set forth as GenBank Accession Nos. P33076, NM_000246.3 and NP_000237.2 and set forth as SEQ ID NOs:94 and 95, respectively (GeneID: 4261)).

Variants of the protein may also be used. Exemplary variants comprise, consist essentially of, or consist of an amino acid sequence that is at least about 80%, 85%, 90%, 95%, 96%, 97%, 98% or 99% identical to SEQ ID NO:95. An amino acid sequence may differ from that of SEQ ID NO:95 by the addition, deletion or substitution of at least about 1, 2, 3, 4, 5, 6, 7, 8, 9, 10, 11, 12, 13, 14, 15, 16, 17, 18, 19, 20, 25, 30 or more amino acids. In certain embodiments, a protein lacks one or more, e.g., 2, 3, 4, 5, 6, 7, 8, 9, 10 or more amino acids at the C- and/or N-terminus and/or internally relative to that of SEQ ID NO:95. The locations at which amino acid changes (i.e., deletions, additions or substitutions) may be made may be determined by comparing, i.e., aligning, the amino acid sequences of CIITA homologues, e.g., those from various animal species.

Exemplary amino acids that may be changed include S286, S288 and S293. Indeed, as described in Greer et al., mutation of these amino acids results in a stronger transactivation function relative to the wild-type protein. Changes are preferably not made in the guanine-nucleotide binding motifs within residues 420-561, as these appear to be necessary for CIITA activity (see Chin et al. (1997) PNAS 94:2501). Amino acids 59-94 have also been shown to be necessary for CIITA activity, as further described herein. Additional structure/function data are provided, e.g., in Chin et al., supra.

In certain embodiments, a nucleic acid comprises, consists essentially of, or consists of the nucleotide sequence set forth in SEQ ID NO:94. A nucleic acid may also comprise a nucleotide sequence that is at least about 80%, 85%, 90%, 95%, 96%, 97%, 98% or 99% identical to SEQ ID NO:94. Nucleic acids may differ by the addition, deletion or substitution of one or more, e.g., 1, 3, 5, 10, 15, 20, 25, 30 or more nucleotides, which may be located at the 5' end, 3' end, and/or internally to the sequence.

In certain embodiments, a nucleic acid encodes a protein that is a functional homolog of a CIITA protein, with the proviso that the sequence is not the wild-type or a naturally-occurring sequence, e.g., the wild-type or naturally-occurring human sequence.

Other nucleic acids encoding MHC class I/II activators that may be used include those that hybridize, e.g., under stringent hybridization conditions to a nucleic acid encoding an MHC class I/II activator described herein, e.g., consisting of SEQ ID NO:90 or 94 or portions thereof. Hybridization conditions are further described herein.

Nucleic acids encoding an MHC class I/II activator may be included in plasmids or expression vectors, such as those further described herein in the context of DNA vaccines.

In one embodiment, a nucleic acid encoding an Ii-PADRE protein or functional homolog thereof is administered to a subject who is also receiving a nucleic acid encoding a CIITA protein or functional homolog thereof. The nucleic acids may be administered simultaneously or consecutively. The nucleic acids may also be linked, i.e., forming one nucleic acid molecule. For example, one or more nucleotide sequences encoding an Ii-PADRE protein or a functional variant thereof one or more nucleotide sequences encoding an antigen or a fusion protein comprising an antigen; one or more nucleotide sequences encoding a CIITA protein of a functional variant thereof may be linked to each other, i.e., present on one nucleic acid molecule.

Chemotherapeutic Drugs/Agents

Drugs may also further be administered to a mammal in accordance with the methods and compositions taught herein. Generally, any drug that reduces the growth of cells without significantly affecting the immune system may be used, or at least not suppressing the immune system to the extent of eliminating the positive effects of a DNA vaccine that is administered to the subject. In one embodiment, the drugs are chemotherapeutic drugs.

A wide variety of chemotherapeutic drugs may be used, provided that the drug stimulates the effect of a vaccine, e.g., DNA vaccine. In certain embodiments, a chemotherapeutic drug may be a drug that (a) induces apoptosis of cells, in particular, cancer cells, when contacted therewith; (b) reduces tumor burden; and/or (c) enhances CD8+ T cell-mediated antitumor immunity. In certain embodiments, the drug must also be one that does not inhibit the immune system, or at least not at certain concentrations.

In one embodiment, the chemotherapeutic drug is epigallocatechin-3-gallate (EGCG) or a chemical derivative or pharmaceutically acceptable salt thereof. Epigallocatechin gallate (EGCG) is the major polyphenol component found in green tea. EGCG has demonstrated antitumor effects in various human and animal models, including cancers of the breast, prostate, stomach, esophagus, colon, pancreas, skin, lung, and other sites. EGCG has been shown to act on different pathways to regulate cancer cell growth, survival, angiogenesis and metastasis. For example, some studies suggest that EGCG protects against cancer by causing cell cycle arrest and inducing apoptosis. It is also reported that telomerase inhibition might be one of the major mechanisms underlying the anticancer effects of EGCG. In comparison with commonly-used antitumor agents, including retinoids and doxorubicin, EGCG has a relatively low toxicity and is convenient to administer due to its oral bioavailability. Thus, EGCG has been used in clinical trials and appears to be a potentially ideal antitumor agent.

Exemplary analogs or derivatives of EGCG include (−)-EGCG, (+)-EGCG, (−)-EGCG-amide, (−)-GCG, (+)-GCG, (+)-EGCG-amide, (−)-ECG, (−)-CG, genistein, GTP-1, GTP-2, GTP-3, GTP-4, GTP-5, Bn-(+)-epigallocatechin gallate (US 2004/0186167, incorporated by reference), and dideoxy-epigallocatechin gallate (Furuta, et al., Bioorg. Med. Chem. Letters, 2007, 11: 3095-3098), For additional examples, see US 2004/0186167 (incorporated by reference in its entirety); Waleh, et al., Anticancer Res., 2005, 25: 397-402; Wai, et al., Bioorg. Med. Chem., 2004, 12: 5587-5593; Smith, et al., Proteins: Struc. Func. & Bioinform., 2003, 54: 58-70; U.S. Pat. No. 7,109,236 (incorporated by reference in its entirety); Landis-Piwowar, et al., Int. J. Mol. Med., 2005, 15: 735-742; Landis-Piwowar, et al., J. Cell. Phys., 2007, 213: 252-260; Daniel, et al., Int. J. Mol. Med., 2006, 18: 625-632; Tanaka, et al., Ang. Chemie Int., 2007, 46: 5934-5937.

Another chemotherapeutic drug that may be used is (a) 5,6 di-methylxanthenone-4-acetic acid (DMXAA), or a chemical derivative or analog thereof or a pharmaceutically acceptable salt thereof. Exemplary analogs or derivatives include xanthenone-4-acetic acid, flavone-8-acetic acid, xanthen-9-one-4-acetic acid, methyl (2,2-dimethyl-6-oxo-1,2-dihydro-6H-3,11-dioxacyclopenta[α]anthracen-10-yl)acetate, methyl (2-methyl-6-oxo-1,2-dihydro-6H-3,11-dioxacyclopenta[α]anthracen-10-yl)acetate, methyl (3,3-dimethyl-7-oxo-3H,7H-4,12-dioxabenzo[α]anthracen-10-yl)acetate, methyl-6-alkyloxyxanthen-9-one-4-acetates (Gobbi, et al., 2002, J. Med. Chem., 45: 4931) or a. For additional examples, see WO 2007/023302 A1, WO 2007/023307 A1, US 2006/9505, WO 2004/39363 A1, WO 2003/80044 A1, AU 2003/217035 A1, and AU 2003/282215 A1, each incorporated by reference in their entirety.

A chemotherapeutic drug may also be cisplatin, or a chemical derivative or analog thereof or a pharmaceutically acceptable salt thereof. Exemplary analogs or derivatives include dichloro[4,4'-bis(4,4,4-trifluorobutyl)-2,2'-bipyridine]platinum (Kyler et al., Bioorganic & Medicinal Chemistry, 2006, 14: 8692-8700), cis-[Rh2(—O2CCH3)2 (CH3CN)6]2+(Lutterman et al., J. Am. Chem. Soc., 2006, 128: 738-739), (+)-cis-(1,1-Cyclobutanedicarboxylato) ((2R)-2-methyl-1,4-butanediamine-N,N')platinum (O'Brien et al., Cancer Res., 1992, 52: 4130-4134), cis-bisneodecanoato-trans-R,R-1,2-diaminocyclohexane platinum(II) (Lu et al., J. of Clin. Oncol., 2005, 23: 3495-3501), carboplatin (Woloschuk, Drug Intell. Clin. Pharm., 1988, 22: 843-849), sebriplatin (Kanazawa et al., Head & Neck, 2006, 14: 38-43), satraplatin (Amorino et al., Cancer Chemother. and Pharmacol., 2000, 46: 423-426), azane (dichloroplatinum) (CID: 11961987), azanide (CID: 6712951), platinol (CID: 5702198), lopac-P-4394 (CID: 5460033), MOLI001226 (CID: 450696), trichloroplatinum (CID: 420479), platinate(1-), amminetrichloro-, ammonium (CID: 160995), triammineplatinum (CID: 119232), biocisplatinum (CID: 84691), platiblastin (CID: 2767) and pharmaceutically acceptable salts thereof. For additional examples, see U.S. Pat. Nos. 5,922,689, 4,996,337, 4,937,358, 4,808,730, 6,130,245, 7,232,919, and 7,038,071, each incorporated by reference in their entirety.

Another chemotherapeutic drug that may be used is apigenin, or a chemical derivative or analog thereof or a pharmaceutically acceptable salt thereof. Exemplary analogs or derivatives include acacetin, chrysin, kampherol, luteolin, myricetin, naringenin, quercetin (Wang et al., Nutrition and Cancer, 2004, 48: 106-114), puerarin (US 2006/0276458, incorporated by reference in its entirety) and pharmaceutically acceptable salts thereof. For additional examples, see US 2006/189680 A1, incorporated by reference in its entirety).

Another chemotherapeutic drug that may be used is doxorubicin, or a chemical derivative or analog thereof or a pharmaceutically acceptable salt thereof. Exemplary analogs or derivatives include anthracyclines, 3'-deamino-3'-(3-cyano-4-morpholinyl)doxorubicin, WP744 (Faderl, et al., Cancer Res., 2001, 21: 3777-3784), annamycin (Zou, et al., Cancer Chemother. Pharmacol., 1993, 32:190-196), 5-imino-daunorubicin, 2-pyrrolinodoxorubicin, DA-125 (Lim, et al., Cancer Chemother. Pharmacol., 1997, 40: 23-30), 4-demethoxy-4'-O-methyldoxorubicin, PNU 152243 and pharmaceutically acceptable salts thereof (Yuan, et al., Anti-Cancer Drugs, 2004, 15: 641-646). For additional examples, see EP 1242438 B1, U.S. Pat. No. 6,630,579, AU 2001/29066 B2, U.S. Pat. Nos. 4,826,964, 4,672,057, 4,314,054, AU 2002/358298 A1, and U.S. Pat. No. 4,301,277, each incorporated by reference in their entirety);

Other chemotherapeutic drugs that may be used are anti-death receptor 5 antibodies and binding proteins, and their derivatives, including antibody fragments, single-chain antibodies (scFvs), Avimers, chimeric antibodies, humanized antibodies, human antibodies and peptides binding death receptor 5. For examples, see US 2007/31414 and US 2006/269554, each incorporated by reference in their entirety.

Another chemotherapeutic drug that may be used is bortezomib, or a chemical derivative or analog thereof or a pharmaceutically acceptable salt thereof. Exemplary analogs or derivatives include MLN-273 and pharmaceutically acceptable salts thereof (Witola, et al., Eukaryotic Cell, 2007, doi:10.1128/EC.00229-07). For additional possibilities, see Groll, et al., Structure, 14:451.

Another chemotherapeutic drug that may be used is 5-aza-2-deoxycytidine, or a chemical derivative or analog thereof or a pharmaceutically acceptable salt thereof Exemplary analogs or derivatives include other deoxycytidine derivatives and other nucleotide derivatives, such as deoxyadenine derivatives, deoxyguanine derivatives, deoxythymidine derivatives and pharmaceutically acceptable salts thereof.

Another chemotherapeutic drug that may be used is genistein, or a chemical derivative or analog thereof or a pharmaceutically acceptable salt thereof. Exemplary analogs or derivatives include 7-O-modified genistein derivatives (Zhang, et al., Chem. & Biodiv., 2007, 4: 248-255), 4',5,7-tri[3-(2-hydroxyethylthio)propoxylisoflavone, genistein glycosides (Polkowski, Cancer Letters, 2004, 203: 59-69), other genistein derivatives (Li, et al., Chem & Biodiv., 2006, 4: 463-472; Sarkar, et al., Mini. Rev. Med. Chem., 2006, 6: 401-407) or pharmaceutically acceptable salts thereof. For additional examples, see U.S. Pat. Nos. 6,541,613, 6,958,156, and WO/2002/081491, each incorporated by reference in their entirety.

Another chemotherapeutic drug that may be used is celecoxib, or a chemical derivative or analog thereof or a pharmaceutically acceptable salt thereof. Exemplary analogs or derivatives include N-(2-aminoethyl)-445-(4-tolyl)-3-(trifluoromethyl)-1H-pyrazol-1-yl]benzenesulfonamide, 4-[5-(4-aminophenyl)-3-(trifluoromethyl)-1H-pyrazol-1-yl] benzenesulfonamide, OSU03012 (Johnson, et al., Blood, 2005, 105: 2504-2509), OSU03013 (Tong, et. al, Lung Cancer, 2006, 52: 117-124), dimethyl celecoxib (Backhus, et al., J. Thorac. and Cardiovasc. Surg., 2005, 130: 1406-1412), and other derivatives or pharmaceutically acceptable salts thereof (Ding, et al., Int. J. Cancer, 2005, 113: 803-810; Zhu, et al., Cancer Res., 2004, 64: 4309-4318; Song, et al., J. Natl. Cancer Inst., 2002, 94: 585-591). For additional examples, see U.S. Pat. No. 7,026,346, incorporated by reference in its entirety.

One of skill in the art will readily recognize that other chemotherapeutics can be used with the methods disclosed in the present invention, including proteasome inhibitors (in addition to bortezomib) and inhibitors of DNA methylation. Other drugs that may be used include Paclitaxel; selenium compounds; SN38, etoposide, 5-Fluorouracil; VP-16, cox-2 inhibitors, Vioxx, cyclooxygenase-2 inhibitors, curcumin, MPC-6827, tamoxifen or flutamide, etoposide, PG490, 2-methoxyestradiol, AEE-788, aglycon protopanaxadiol, aplidine, ARQ-501, arsenic trioxide, BMS-387032, canertinib dihydrochloride, canfosfamide hydrochloride, combretastatin A-4 prodrug, idronoxil, indisulam, INGN-201, mapatumumab, motexafin gadolinium, oblimersen sodium, OGX-011, patupilone, PXD-101, rubitecan, tipifarnib, trabectedin PXD-101, methotrexate, Zerumbone, camptothecin, MG-98, VX-680, Ceflatonin, Oblimersen sodium, motexafin gadolinium, 1D09C3, PCK-3145, ME-2 and apoptosis-inducing-ligand (TRAIL/Apo-2 ligand). Others are provided in a report entitled "competitive outlook on apoptosis in oncology, December 2006, published by Bioseeker, and available, e.g., at http://bizwiz.bioseeker.com/bw/Archives/Files/TOC_BSG0612193.pdf.

Generally, any drug that affects an apoptosis target may also be used. Apoptosis targets include the tumour-necrosis factor (TNF)-related apoptosis-inducing ligand (TRAIL) receptors, the BCL2 family of anti-apoptotic proteins (such as Bcl-2), inhibitor of apoptosis (IAP) proteins, MDM2, p53, TRAIL and caspases. Exemplary targets include B-cell CLL/lymphoma 2, Caspase 3, CD4 molecule, Cytosolic ovarian carcinoma antigen 1, Eukaryotic translation elongation factor 2, Farnesyltransferase, CAAX box, alpha; Fc fragment of IgE; Histone deacetylase 1; Histone deacetylase 2; Interleukin 13 receptor, alpha 1; Phosphodiesterase 2A, cGMP-stimulated Phosphodiesterase 5A, cGMP-specific; Protein kinase C, beta 1; Steroid 5-alpha-reductase, alpha polypeptide 1; 8.1.15 Topoisomerase (DNA) I; Topoisomerase (DNA) II alpha; Tubulin, beta polypeptide; and p53 protein.

In certain embodiments, the compounds described herein, e.g., EGCG, are naturally-occurring and may, e.g., be isolated from nature. Accordingly, in certain embodiments, a compound is used in an isolated or purified form, i.e., it is not in a form in which it is naturally occurring. For example, an isolated compound may contain less than about 50%, 30%, 10%, 1%, 0.1% or 0.01% of a molecule that is associated with the compound in nature. A purified preparation of a compound may comprise at least about 50%, 70%, 80%, 90%, 95%, 97%, 98% or 99% of the compound, by molecule number or by weight. Compositions may comprise, consist essentially of consist of one or more compounds described herein. Some compounds that are naturally occurring may also be synthesized in a laboratory and may be referred to as "synthetic." Yet other compounds described herein are non-naturally occurring.

In certain embodiments, the chemotherapeutic drug is in a preparation from a natural source, e.g., a preparation from green tea.

Pharmaceutical compositions comprising 1, 2, 3, 4, 5 or more chemotherapeutic drugs or pharmaceutically acceptable salts thereof are also provided herein. A pharmaceutical composition may comprise a pharmaceutically acceptable carrier. A composition, e.g., a pharmaceutical composition, may also comprise a vaccine, e.g., a DNA vaccine, and optionally 1, 2, 3, 4, 5 or more vectors, e.g., other DNA vaccines or other constructs, e.g., described herein.

Compounds may be provided with a pharmaceutically acceptable salt. The term "pharmaceutically acceptable salts" is art-recognized, and includes relatively non-toxic, inorganic and organic acid addition salts of compositions, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.,* 66:1-19 (1977).

Also provided herein are compositions and kits comprising one or more DNA vaccines and one or more chemotherapeutic drugs, and optionally one or more other constructs described herein.

Therapeutic Compositions and their Administration

The methods of the present invention can be practiced by administering annexin chimeric fusion proteins described herein alone or in a pharmaceutically acceptable carrier in a biologically-effective and/or a therapeutically-effective amount. The annexin chimeric fusion protein may comprise Annexin V fused to an immunogenic peptide such as ovalbumin (OVA), HPV16 E6, HPV16 E7, modified colon carcinoma antigen AH5, and influenza antigen M1. The annexin chimeric fusion protein may be used in combination with chemotherapy, wherein a chemotherapeutic agent, such as cisplatin, is administered.

Certain conditions as described herein are disclosed in the Examples. The composition may be given alone or in combination with another protein or peptide such as an immunostimulatory molecule. Treatment may include administration of an adjuvant, used in its broadest sense to include any nonspecific immune stimulating compound such as an interferon. Adjuvants contemplated herein include resorcinols, non-ionic surfactants such as polyoxyethylene oleyl ether and n-hexadecyl polyethylene ether.

A therapeutically effective amount is a dosage that, when given for an effective period of time, achieves the desired immunological or clinical effect.

A therapeutically active amount of an annexin chimeric fusion protein may vary according to factors such as the disease state, age, sex, and weight of the individual, and the ability of the fusion protein to elicit a desired response in the individual. Dosage regimes may be adjusted to provide the optimum therapeutic response. For example, several divided doses may be administered daily or the dose may be proportionally reduced as indicated by the exigencies of the therapeutic situation. A therapeutically effective amount of the protein, in cell associated form may be stated in terms of the protein or cell equivalents.

Thus an effective amount of an annexin chimeric fusion protein may be between about 1 nanogram and about 1 gram per kilogram of body weight of the recipient, between about 0.1 µg/kg and about 10 mg/kg, between about 1 µg/kg and about 1 mg/kg. Dosage forms suitable for internal administration may contain (for the latter dose range) from about 0.1 µg to 100 µg of active ingredient per unit. The active ingredient may vary from 0.5 to 95% by weight based on the total weight of the composition. Those skilled in the art of immunotherapy will be able to adjust these doses without undue experimentation.

The annexin chimeric fusion protein may be packaged into retrovirus vectors using packaging cell lines that produce replication-defective retroviruses, as is well-known in the art (e.g., Cone, R. D. et al., *Proc Natl Acad Sci USA* 81:6349-53, 1984; Mann, R F et al., *Cell* 33:153-9, 1983; Miller, A D et al., *Molec Cell Biol* 5:431-7, 1985; Sorge, J, et al., *Molec Cell Biol* 4:1730-7, 1984; Hock, R A et al., *Nature* 320:257, 1986; Miller, A D et al., *Molec Cell Biol* 6:2895-2902 (1986). Newer packaging cell lines which are efficient an safe for gene transfer have also been described (Bank et al., U.S. Pat. No. 5,278,056, incorporated by reference).

The above approach can be utilized in a site specific manner to deliver the retroviral vector to the tissue or organ of choice. Thus, for example, a catheter delivery system can be used (Nabel, E G et al., *Science* 244:1342 (1989)). Such methods, using either a retroviral vector or a liposome vector, are particularly useful to deliver the annexin chimeric fusion protein to a blood vessel wall, or into the blood circulation of a tumor.

Other pharmaceutically acceptable carriers for the annexin chimeric fusion protein according to the present invention are liposomes, pharmaceutical compositions in which the active protein is contained either dispersed or variously present in corpuscles consisting of aqueous concentric layers adherent to lipidic layers. The active protein may be present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Those skilled in the art will appreciate other suitable embodiments of the present liposomal formulations.

Embodiments disclosed herein also relate to methods of administering an annexin chimeric fusion protein described herein to a subject in order to contact in vivo cells with such compositions. The routes of administration can vary with the location and nature of the cells to be contacted, and include, e.g., intravascular, intradermal, transdermal, parenteral, intravenous, intramuscular, intranasal, subcutaneous, regional, percutaneous, intratracheal, intraperitoneal, intraarterial, intravesical, intratumoral, inhalation, perfusion, lavage, direct injection, and oral administration and formulation. In other embodiments, the routes of administration of the fusion protein may include (a) intratumoral, peritumoral, and/or intradermal delivery, (b) intramuscularly (i.m.) injection using a conventional syringe needle; and (c) use of a needle-free biojector such as the Biojector 2000 (Bioject Inc., Portland, Oreg.) which is an injection device consisting of an injector and a disposable syringe. The orifice size controls the depth of penetration.

The term "systemic administration" refers to administration of an annexin chimeric fusion protein or chemotherapeutic agent as described herein, in a manner that results in the introduction of the composition into the subject's circulatory system or otherwise permits its spread throughout the body. "Regional" administration refers to administration into a specific, and somewhat more limited, anatomical space, such as intraperitoneal, intrathecal, subdural, or to a specific organ. "Local administration" refers to administration of a composition or drug into a limited, or circumscribed, anatomic space, such as intratumoral injection into a tumor mass, subcutaneous injections, intradermal or intramuscular injections. Those of skill in the art will understand that local administration or regional administration may also result in entry of a composition into the circulatory system i.e., rendering it systemic to one degree or another. For example, the term "intravascular" is understood to refer to delivery into the vasculature of a patient, meaning into, within, or in a vessel or vessels of the patient, whether for systemic, regional, and/or local administration. In certain embodiments, the administration can be into a vessel considered to be a vein (intravenous), while in others administration can be into a vessel considered to be an artery. Veins include, but are not limited to, the internal jugular vein, a peripheral vein, a coronary vein, a hepatic vein, the portal vein, great saphenous vein, the pulmonary vein, superior vena cava, inferior vena cava, a gastric vein, a splenic vein, inferior mesenteric vein, superior mesenteric vein, cephalic vein, and/or femoral vein. Arteries include, but are not limited to, coronary artery, pulmonary artery, brachial artery, internal carotid artery, aortic arch, femoral artery, peripheral artery, and/or ciliary artery. It is contemplated that delivery may be through or to an arteriole or capillary.

Injection into the tumor vasculature is specifically contemplated for discrete, solid, accessible tumors. Local, regional or systemic administration also may be appropriate. For tumors of greater than about 4 cm, the volume to be administered can be about 4-10 ml (preferably 10 ml), while for tumors of less than about 4 cm, a volume of about 1-3 ml can be used (preferably 3 ml). Multiple injections delivered as single dose comprise about 0.1 to about 0.5 ml volumes. The annexin chimeric fusion protein may advantageously be contacted by administering multiple injections to the tumor, spaced at approximately 1 cm intervals.

Continuous administration also may be applied where appropriate. Such continuous administration, such as intravenous injection, may take place for a period of 9 days with periodic injections every 3 days. Generally, the dose of the therapeutic composition via continuous administration will be equivalent to that given by a single or multiple injections, adjusted over a period of time during which the treatment occurs. Other routes of administration include oral, intranasal or rectal or any other route known in the art.

Depending on the route of administration, the annexin chimeric fusion protein may be coated in a material to protect the compound from the action of enzymes, acids and other natural conditions which may inactivate the compound. Thus it may be necessary to coat the composition with, or co-administer the composition with, a material to prevent its inactivation. For example, an enzyme inhibitors of nucleases or proteases (e.g., pancreatic trypsin inhibitor, diisopropylfluorophosphate and trasylol) or in an appropriate carrier such as liposomes (including water-in-oil-in-water emulsions as well as conventional liposomes (Strejan et al., *J. Neuroimmunol* 7:27, 1984).

A chemotherapeutic drug may be administered in doses that are similar to the doses that the chemotherapeutic drug is used to be administered for cancer therapy. Alternatively, it may be possible to use lower doses, e.g., doses that are lower by 10%, 30%, 50%, or 2, 5, or 10 fold lower. Generally, the dose of chemotherapeutic agent is a dose that is effective to increase the effectiveness of the annexin chimeric fusion protein, but less than a dose that results in significant immunosuppression or immunosuppression that essentially cancels out the effect of the annexin chimeric fusion protein.

The route of administration of chemotherapeutic drugs may depend on the drug. For use in the methods described herein, a chemotherapeutic drug may be used as it is commonly used in known methods. Generally, the drugs will be administered orally or they may be injected. The regimen of administration of the drugs may be the same as it is commonly used in known methods. For example, certain drugs are administered one time, other drugs are administered every third day for a set period of time, yet other drugs are administered every other day or every third, fourth, fifth, sixth day or weekly. The Examples provide exemplary regimens for administrating the drugs, as well as an annexin chimeric fusion protein. In certain embodiments, the chemotherapeutic drug/agent is cisplatin. The cisplatin is administered via intraperitoneal injection two times at a three day interval. The intraperitoneal injection of the cisplatin may be spread out over a period of 1 week, 2 weeks, 3 weeks, 4 weeks or longer. Likewise, the cisplatin can be repeated administered over a 1 day, 2 day, 3 day, 4 day, or more interval.

The compositions of the present invention, may be administered simultaneously or subsequently. When administered simultaneously, the different components may be administered as one composition. Accordingly, also provided herein are compositions, e.g., pharmaceutical compositions comprising one or more agents.

In one embodiment, a subject first receives one or more doses of chemotherapeutic drug and then one or more doses of the annexin chimeric fusion protein. One may administer 1, 2, 3, 4, 5 or more doses of chemotherapeutic agent and 1, 2, 3, 4, 5 or more doses of annexin chimeric fusion protein.

A method may further comprise subjecting a subject to another cancer treatment, e.g., radiotherapy, an anti-angiogenesis agent and/or a hydrogel-based system.

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

Pharmaceutically acceptable diluents include saline and aqueous buffer solutions. Pharmaceutical compositions suitable for injection include sterile aqueous solutions (where water soluble) or dispersions and sterile powders for the extemporaneous preparation of sterile injectable solutions or dispersion. Isotonic agents, for example, sugars, polyalcohols such as mannitol, sorbitol, sodium chloride may be included in the pharmaceutical composition. In all cases, the composition should be sterile and should be fluid. It should be stable under the conditions of manufacture and storage and must include preservatives that prevent contamination with microorganisms such as bacteria and fungi. Dispersions can also be prepared in glycerol, liquid polyethylene glycols, and mixtures thereof and in oils. Under ordinary conditions of storage and use, these preparations may contain a preservative to prevent the growth of microorganisms.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms in the pharmaceutical composition can be achieved by various antibacterial and antifungal agents, for example, parabens, chlorobutanol, phenol, ascorbic acid, thimerosal, and the like.

Compositions may be formulated in dosage unit form for ease of administration and uniformity of dosage. Dosage unit form refers to physically discrete units suited as unitary dosages for a mammalian subject; each unit contains a predetermined quantity of active material (e.g., annexin chimeric fusion protein) calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, individual subjects.

For lung instillation, aerosolized solutions are used. In a sprayable aerosol preparations, the active protein may be in combination with a solid or liquid inert carrier material. This may also be packaged in a squeeze bottle or in admixture with a pressurized volatile, normally gaseous propellant. The aerosol preparations can contain solvents, buffers, surfactants, and antioxidants in addition to the protein of the invention.

Diseases that may be treated as described herein include hyper proliferative diseases, e.g., cancer, whether localized or having metastasized. Exemplary cancers include head and neck cancers and cervical cancer. Any cancer can be treated provided that there is a tumor associated antigen that is associated with the particular cancer. Other cancers include skin cancer, lung cancer, colon cancer, kidney cancer, breast cancer, prostate cancer, pancreatic cancer, bone cancer, ovarian cancer, brain cancer, as well as blood cancers, e.g., myeloma, leukemia and lymphoma. Generally, any cell growth can be treated provided that there is an antigen associated with the cell growth, which antigen or homolog thereof can be fused to annexin V.

Treating a subject includes curing a subject or improving at least one symptom of the disease or preventing or reducing the likelihood of the disease to return. For example, treating a subject having cancer could be reducing the tumor mass of a subject, e.g., by about 10%, 30%, 50%, 75%, 90% or more, eliminating the tumor, preventing or reducing the likelihood of the tumor to return, or partial or complete remission.

All references cited herein are all incorporated by reference herein, in their entirety, whether specifically incorporated or not. All publications, patents, patent applications, GenBank sequences and ATCC deposits, cited herein are hereby expressly incorporated by reference for all purposes. In particular, all nucleotide sequences, amino acid sequences, nucleic constructs, DNA vaccines, methods of administration, particular orders of administration of DNA vaccines and agents that are described in the patents, patent applications and other publications referred to herein or authored by one or more of the inventors of this application are specifically incorporated by reference herein. In case of conflict, the definitions within the instant application govern.

Having now fully described this invention, it will be appreciated by those skilled in the art that the same can be performed within a wide range of equivalent parameters, concentrations, and conditions without departing from the spirit and scope of the invention and without undue experimentation.

The present description is further illustrated by the following examples, which should not be construed as limiting in any way.

EXAMPLES

Example 1: Material and Methods for Examples 2-7

A. Mice

Six- to eight-week-old female C57BL/6 and BALB/c mice were purchased from the National Cancer Institute (Frederick, Md.). All animal procedures were performed according to approved protocols and in accordance with recommendations for the proper use and care of laboratory animals.

B. Cells

TC-1 cells, which are an E7-expressing murine tumor model, were obtained by co-transformation of primary C57BL/6 mouse lung epithelial cells with HPV-16 E6 and E7 and an activated ras oncogene as previously described. CT 26 murine colon carcinoma cells, PancO2 murine pancreatic cancer cells and OVCAR3 human ovarian cancer cells were purchased from ATCC. The HLA-A2-restricted influenza M1 peptide-specific CD8+ T cell line was generated using splenocytes from HLA-A2 (AAD) transgenic mice vaccinated with DNA encoding single chain trimer (SCT) encoding HLA-A2 linked to influenza M1 peptide using methods similar to what was described previously (11). E7 (aa49-57)-specific T cell line (12), OVA-specific T cell line (13) have also been previously described. These cell lines were cultured in vitro in PRMI10 (RPMI 1640 supplemented with 10% fetal bovine serum, 50 units/ml of penicillin/streptomycin, 2 mM L-glutamine, 1 mM sodium pyruvate, and 2 mM non-essential amino acids) and grown at 37° C. with 5% $CO_2$. Luciferase expressing TC-1 and OVCAR3 cells were generated by same methods above described.

C. Plasmid DNA Constructs and Preparation pET28 (pET28-annV, annV-E7 and other constructs) plasmids, which were identified by sequencing, were transformed into the *Escherichia coli* BL21(DE3) strain. The selected colony was cultured in 5 mL Luria-Bertani (LB) liquid medium containing kanamycin (25 μg/mL) and grown overnight at 37° C. on a shaking incubator, then transferred to 200 mL of fresh medium (with the antibiotic) and incubated for another 2 hours until the optical density of the cultured cells reached around 0.6 (OD 600). Expression of the fusion protein was induced with 1 mM isopropyl-b-D-thiogalactopyranoside (IPTG) at 37° C. for 5 h. The cultured cells were harvested by centrifugation at 6,000 rpm for 10 min at 4° C. The pellet was washed with phosphate buffered saline (PBS) 2 times and then suspended in bacteria lysis buffer (SoluLyse Reagent for Bacteria, Genlantis) containing lysozyme (100 μg/ml) (Gibco BRL) and deoxynuclease (Dnase) I (100 U/ml) (Invitrogen). The suspension was incubated for 2 hours at room temperature with stirring. The suspension was centrifuged at 12,000 rpm for 15 min. The clear supernatant (soluble fraction) was collected and recombinant protein was purified by $Ni^+$ affinity chromatography (Ni-NTA agarose, Qiagen) according to the manufacturer's protocol. In briefly, cell supernatant was loaded in 2 ml of $Ni^+$ affinity chromatography that is equilibrated with washing buffer (50 mM $NaH_2PO_4$, 300 mM NaCl, and 20 mM imidazole, pH 8.0) and then washed with 20 ml washing buffer. For the elution of binding protein, 10 ml of elution buffer (50 mM $NaH_2PO_4$, 300 mM NaCl, and 250 mM imidazole, pH 8.0) was used. The eluted protein was collected and analyzed using 10-15% gradient SDS-PAGE and Coomassie brilliant blue staining. The purity of proteins was characterized by limulus amoebocyte lysate (LAL) (Lonza) and Picogreen assays (Invitrogen). The endotoxin level of each protein was less than 25.0 EU/mg, and the bacterial DNA level was 8.6 ng/mg of protein in independent preparations.

D. In Vivo Tumor Treatment Experiments

For in vivo tumor treatment experiment using only protein, $1 \times 10^5$ TC-1 cells were injected subcutaneously into C57BL/6 mice (10 per group). After 3 days, 100 µg of each protein was injected intravenously three times with 3 day intervals. Mice were monitored for tumor growth by palpation and inspection twice a week. For in vivo combined tumor treatment experiments, $1 \times 10^5$ TC-1 cells or $5 \times 10^5$ CT 26 cells were subcutaneously injected into C57BL/6 mice (10 per group) or BALB/c mice. After 5 days, cisplatin (5 mg/kg) or saline (control) was intraperitoneally injected two times at a 3 day interval. 6 days after tumor challenge, mice received 100 µg of protein each, intravenously injected three times with 3 day intervals. Mice were monitored for tumor growth by palpation and inspection twice a week. $5 \times 10^6$ PancO2 cells were injected into C57BL/6 mice (10 per group) and after 25 days, cisplatin and protein treatment was initiated using the same methods mentioned above.

E. Tetramer Staining, Intracellular Cytokine Staining and Flow Cytometry Analysis Each mouse was treated as mentioned above In vivo tumor treatment experiments section. For tetramer staining, peripheral blood mononuclear cells (PBMCs) and tumor tissues were harvested 1 week after the last protein injection. PBMCs were prepared as described previously and tumor tissues were obtained from mice and cut into fragments in PBS, washed twice, and then digested with 500 U/ml of Dispase (Godo Shusei, Co., Ltd. Tokyo) at 37° C. for 20 min. The supernatants of the first digestion were discarded. The remaining fragments were suspended in 5 ml of PBS and then extensively pipetted with a Pasteur pipet to obtain free cell suspensions. The cell suspensions were passed through a stainless wire sieve and washed twice with 20 ml of PBS by centrifugation for 5 min at 150×g. Sedimented cells were resuspended in the PBS and used for staining. Phycoerythrin (PE)-labeled $H-2D^b$ HPV16 E7 (RAHYNIVTF) and $H-2K^b$ OVA (SIINFEKL) tetramer reagents were purchased from Beckman Coulter (Hialeah, Fla.) and were used for the fluorescence-activated cell sorter analysis of peptide-specific cytotoxic T lymphocyte immunity. Tetramer-positive and CD8+ cells from the blood and tumor tissues were quantified using flow cytometry (14). For intracellular cytokine staining, splenocytes from each vaccination group were harvested 1 week after the last protein injection. Before intracellular cytokine staining, $5 \times 10^6$ pooled splenocytes from each vaccination group were incubated with 1 µg/ml HPV16 E7 49-57 peptide (RAHYNIVTF), OVA 257-264 peptide (SIINFEKL) or AH1 423-431 peptide (SPSYVYHQF) and 1 µl/ml GolgiPlug (BD Cytofix/Cytoperm Kit) for 16 hours. Cells were then harvested and stained for CD8 and IFN-γ using a previously described standard protocol (15). Samples were analyzed on a FACSCalibur flow cytometer, using CellQuest software (Becton Dickinson, San Jose, Calif.). All of the analyses shown were carried out with gated lymphocyte populations.

F. In Vivo CD8 Antibody Depletion Experiment

In vivo CD8 antibody depletion was performed as described previously. Briefly, C57BL/6 mice (five per group) were injected with $1 \times 10^5$ TC-1 cells and were treated with three-time 100 µg of annV-E7 protein similar to what has been described previously (16). Depletion was started 1 day before injection of protein. mAb 2.43 was used for CD8 depletion and control IgG was used as control. Depletion was terminated on day 20 after tumor challenge.

F. In Vitro Cytotoxicity Assay

For in vitro cytotoxicity experiments, $1 \times 10^5$ of luciferase-expressing tumor cells (TC-1/luc or OVCAR3/luc) were treated with 5 µg/ml each of one of the various proteins on a 24-well plate for 18 hours. $2 \times 10^5$ OVA-specific or M1-specific cytotoxic T cells were then added to the wells. The degree of CTL-mediated killing of the tumor cells was measured by the IVIS Spectrum Imaging System Series 2000.

G. Luciferase-Based Bioluminescence Imaging

Gaussia luciferase (GLuc) (17) and the substrate coelenterazine (Sigma) were used to test for GLuc activity in vivo. For the in vivo luciferase attraction experiment, mice were injected with $1 \times 10^5$ TC-1 cells. After 10 days, cisplatin was intraperitoneally injected. 2 days after cisplatin treatment, 200 µg of Gluc or annV-Gluc protein was injected intravenously and 1 day later, luciferin substrate was injected intraperitoneally. The bioluminescence of the cells was detected via the IVIS Spectrum Imaging System Series 2000. The region of interest from displayed images was designated and quantified as total photon counts using Living Image 2.50 software (Xenogen).

H. Statistical Analysis

The data presented in this study are from one representative experiment of the two or three experiments performed, and are expressed as means±standard deviation (S.D.). The number of samples in each group for any given experiment was >3. Results for intracellular cytokine staining with flow cytometry analysis and tumor treatment experiments were evaluated by analysis of variance (one-way ANOVA) and the Tukey-Kramer multiple comparison test. Comparisons between individual data points were performed using Student's t-test. The event time distributions for different mice were compared using the Kaplan-Meier method and the log-rank statistic. All p values <0.05 were considered significant.

Example 2: Treatment with Annexin V-HPV16 E7 Fusion Protein Generates Potent Antitumor Responses in Tumor-Bearing Mice To examined whether treatment with a fusion protein consisting of annexin V (annV) and HPV16 E7 antigen (annV-E7) could control E7-expressing TC-1 tumors in mice, C57BL/6 mice were inoculated with TC-1 cells subcutaneously and then three days later, were injected intravenously with either PBS control, annV alone, E7 alone, annV plus E7, or annV-E7 fusion protein for a total of three times as outlined in FIG. 1A. As shown in FIG. 1B, mice treated with the annV-E7 fusion protein had substantially reduced tumor volume compared to all other treatment groups. Furthermore, mice treated with annV-E7 had improved survival compared to all other treatment groups (FIG. 1C). Next, splenocytes were isolated from tumor-bearing mice to assess the antigen-specific CD8+ T cell immune responses following protein injection. Flow cytometry analysis indicated that treatment with annV-E7 fusion protein generated a significantly greater number of IFN-γ-secreting E7-specific CD8+ T cells compared to treatment with annV plus E7 proteins or E7 protein only (FIG. 1D). In order to determine the importance of CD8+ T cells on the antitumor effects generated by annV-E7 fusion protein treatment, anti-CD8 antibody to was employed to deplete CD8+ cells in TC-1 tumor-bearing mice. As shown in FIG. 1E, mice treated with annV-E7 fusion protein and depleted of CD8+ cells were unable to control tumor growth. Finally, PBMCs of annV-E7-treated mice were tested for the presence of E7-specific CD8+ T cells. FIG. 1F shows that mice treated with annV-E7 generated significantly more E7-specific CD8+ T cells among PBMCs compared to mice treated with GFP-E7 fusion protein. Taken together, these data indicate that mice treated with annV-E7 fusion protein generate enhanced antitumor immune responses, particularly antigen-specific cell-mediated immune responses.

Example 3: Treatment with AnnexinV-E7 Fusion Protein and Cisplatin Generates Synergistic Antitumor Effects In order to demonstrate that the annV protein selectively accumulates in tumor cells, a fusion protein consisting of annV and gaussia luciferase (GLuc) was employed. C57BL/6 mice were injected with TC-1 cells subcutaneously and then treated with or without cisplatin 10 days later to enhance apoptosis of tumor cells. After an additional 2 days, mice were injected with PBS, annV only, or annV-Gluc proteins intravenously. The following day, bioluminescence imaging demonstrated that mice treated with cisplatin and annV-GLuc had significant accumulation of the annV fusion protein in tumor loci (FIG. 2A). To further characterize the effects of cisplatin on annV-E7 treatment, TC-1 tumor-bearing mice were treated with or without cisplatin combined with PBS, E7 peptide only, annV only, or annV-E7 protein. Mice treated with cisplatin combined with annV-E7 had a significantly greater percentage of E7-specific CD8+ T cells among all T cells compared to mice treated with annV-E7 only (FIG. 2B). Furthermore, treatment with cisplatin and annV-E7 generated decreased tumor volume and improved survival of mice compared to all other treatment groups (FIGS. 2C and D). These data suggest that annV delivers the fusion proteins to tumor loci and that annV-E7 treatment combined with cisplatin synergistically enhance antitumor effects.

Example 4: AnnexinV Fusion to Different Tumor Antigen is Capable of Generating Antitumor Effects To demonstrate that the concept of annV fusion to a tumor antigen to elicit antitumor effects could be applied to a different mouse system and tumor model, BALB/c mice were subcutaneously injected with AH1-expressing CT-26 tumor cells and then treated with or without cisplatin combined with annV, a modified AH1 peptide termed AH5, or annV-AH5 fusion protein as outlined in FIG. 3A. Splenocytes were isolated from each group of mice, stained for CD8 and IFN-γ, and analyzed by flow cytometry. Flow cytometry analysis indicated that mice treated with annV-AH5 combined with cisplatin generated the most activated IFN-γ-secreting AH1-specific CD8+ T-cells compared to all other treatment groups (FIG. 3A). Furthermore, mice treated with annV-AH5 combined with cisplatin had lower tumor volumes and prolonged survival compared to all other treatment groups. Taken together, these data indicate that the treatment strategy consisting of annV fusion to a tumor antigen combined with cisplatin to enhance tumor cell apoptosis can be applied to multiple tumor systems.

Example 4: AnnexinV Fused to OVA Peptide Generates Potent Antitumor Effects Against TC-1 Tumors when Combined with Cisplatin To further test the treatment methodology using a foreign non-tumor-specific antigen against TC-1 tumors, AnnV conjugated with OVA peptide fusion proteins were created with or without a furin cleavage site (annV-O and annV-RO, respectively) and annV expression was confirmed by gel electrophoresis as shown in FIGS. 4A and B. FIG. 4B also demonstrates that when TC-1 cells were treated with cisplatin and varying amounts of annV-RO and then stimulated with OVA peptide, the TC-1 cells were capable of loading the OVA peptide on MHC class I molecules at increased frequencies with increased amounts of annV-RO. As shown in FIG. 4C, TC-1 cells treated with annV-RO and cisplatin were more susceptible to antigen-specific killing by OT-1 T cells compared to TC-1 T cells treated with annV-O combined with cisplatin, as evidenced by decreased bioluminescence. This suggests that the presence of the furin cleavage is important for the cytotoxic effects because it may allow the foreign peptide to coat the tumor cells so that they can be recognized for killing by the CD8+ T cells. Next, the effects of annV-RO plus cisplatin treatment in vivo were examined. TC-1 tumor-bearing mice were treated as outlined in the top panel of FIG. 4D. Splenocytes were collected and then stained for CD8 and IFN-γ. The flow cytometry analysis presented in FIG. 4D shows that mice treated with annV-RO or annV-O plus cisplatin generated significantly greater numbers of activated IFN-γ secreting CD8+ T cells among splenocytes compared to those treated with annV-RO only. Additionally, as shown in FIG. 4E, treatment with annV-RO plus cisplatin elicited a significantly greater percentage of OVA-specific CD8+ T cells among all CD8+ T cells compared to annV-O plus cisplatin treatment. Mice treated with annV-RO plus cisplatin also had decreased tumor volume and improved survival compared to mice receiving any other treatment (FIGS. 4F and G). Taken together, these data suggest that treatment with annV protein conjugated to a foreign non-tumor antigen combined with cisplatin can elicit potent antitumor effects.

Example 5: AnnexinV Fused to OVA Peptide Combined with Cisplatin Generates Potent Antitumor Effects Against PancO2 Tumors The strategy using annV-RO fusion protein plus cisplatin to treat PancO2 tumors was applied. C57BL/6 mice were injected subcutaneously with PancO2 cells and, 25 days later, were treated with cisplatin and either annV-RO or GFP-RO fusion protein as indicated in FIG. 5A. PancO2 tumor-bearing mice treated with annV-RO and cisplatin experienced decreased tumor volume and prolonged survival compared to GFP-RO plus cisplatin treated mice (FIGS. 5A and B). These data indicate that annV-RO protein plus cisplatin treatment is effective not only against TC-1 tumors, but another tumor model as well.

Example 6: AnnexinV Fused to Influenza M1 Peptide Combined with Cisplatin Generates Potent Antitumor Effects Against OVCAR3 Tumors To modify the treatment strategy so that it would be applicable to tumor control in humans, annV was conjugated to a foreign non-tumor antigen highly relevant to human immunity, influenza virus M1 peptide, with or without a furin cleavage site (annV-RM1 and annV-M1 respectively) as depicted in FIG. 6A. To test the cytotoxic effects, luciferase-expressing OVCAR3 tumor cells were treated with cisplatin and either PBS, annV, annV-M1 or annV-RM1 and then incubated with M1-specific T cells. As shown in FIGS. 6B and C, OVCAR3 cells treated with annV-RM1 combined with cisplatin were killed significantly more effectively by M1-specific T cells than those treated with annV-M1 and cisplatin. These data suggest that the treatment methodology can be used with a foreign non-tumor antigen that is common to humans in order to be applicable to tumor control in humans.

Example 7: Characterization of Tumor Growth in Tumor-Bearing Mice Treated with Different Regimens Materials and Method
Plasmid DNA Constructs and Preparation pFuse-Fc (pFuse-mIgG2a-Fc2) was obtained from Invivogen (San Diego, USA). To generate pFuse-Hannv-Fc, human annexin v was PCR amplified by primers (AAAGAATTCGATGGCACAGGTTCTCAGAGG and TTTAGATCTGTCATCTTCTCCACAGAGCA) with Human annexin v cDNA as the template DNA (Addgene, Cambridge, Mass.), and then cloned into EcoRI and Bgl II sites of pFuse-IgG2a (Invivogen).

Transfection and Protein Purification

For the production of the recombinant protein pFuse-Hannv-Fc and control proteins IgG2a Fc (hereinafter "Con-Fc"), $1 \times 10^7$ BHK-21 cells were transfected with 50 μg of each plasmid in T-150 flasks using Lipofectamin 2000 (Invitrogen Corp., Carlsbad, Calif., USA) (PMID: 22509395). After 3 days, the cell-cultured media was accumulated, filtered with a 0.22 μm syringe filter (Millipore, Billerica Mass., USA) and concentrated with Amicon Ultra-15 50 kDa cut-off centrifugal filter units (Millipore, Billerica Mass., USA). The concentrated recombinant proteins were loaded onto a HiTrap Protein G HP column (GE Healthcare) and immobilized via Fc-protein G binding. The column was washed with 20 mM sodium phosphate buffer (pH 7.0) and the recombinant protein was eluted using 0.1M glycine-Cl buffer (pH 2.8). Protein concentrations were determined with the Coomassie Plus protein assay (Pierce, Rockford, USA) and purity was estimated by SDS polyacrylamide gel electrophoresis.

In Vivo Experiment $1 \times 10^5$ TC-1 tumor cells were inoculated subcutaneously into C57BL/6. Five days later, tumor-bearing mice were treated with intraperitoneal cisplatin (5 mg/kg body weight) or saline control. Six days later, mice were treated with intraperitoneal AnnexinV-FC or mouse IgG (100 ug/mouse) control. Tumor-bearing mice were treated continually weekly.

Result

Figure 2:
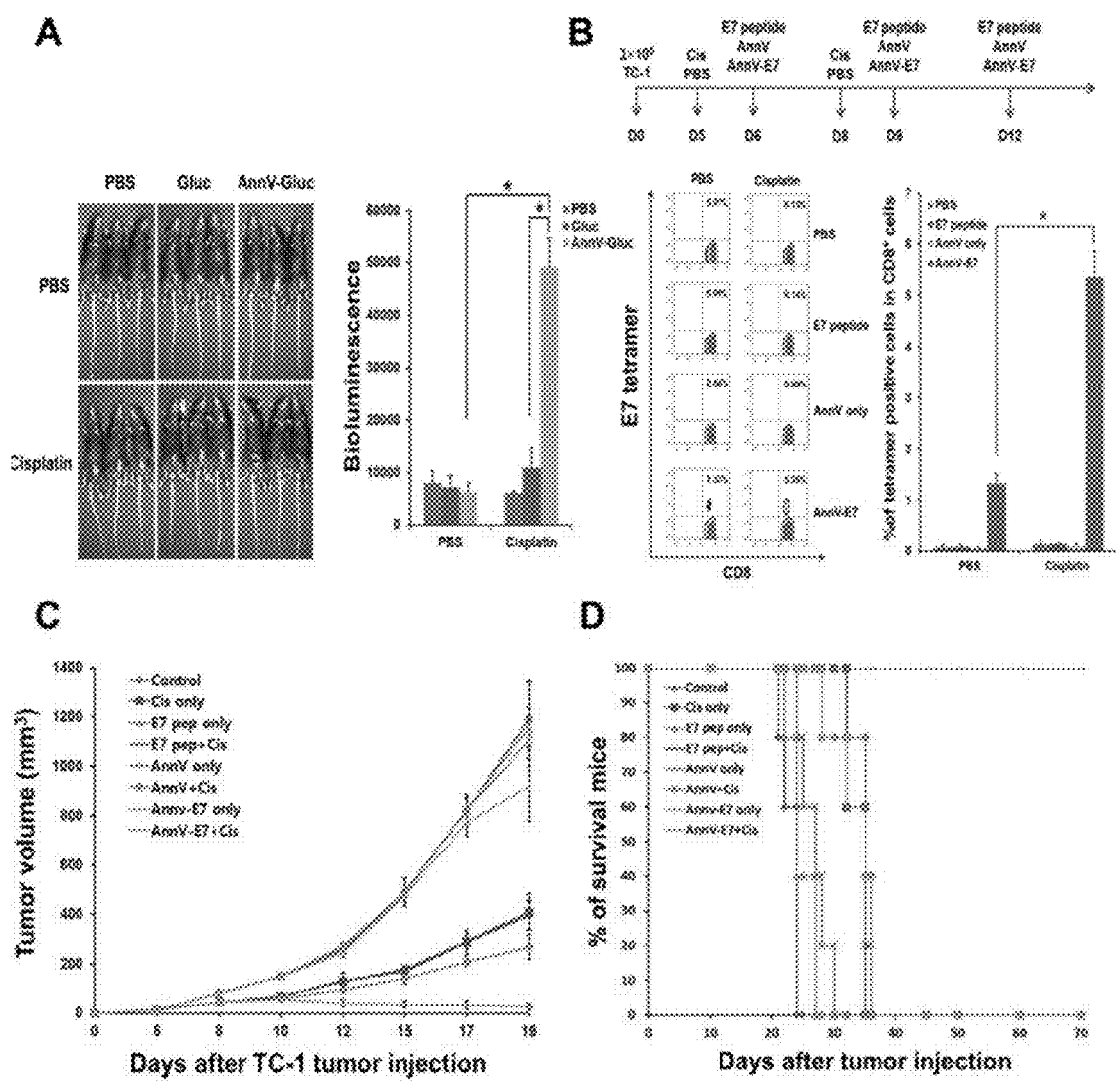
FIG. 2 includes four panels, 2A-2D.
Figure 3:
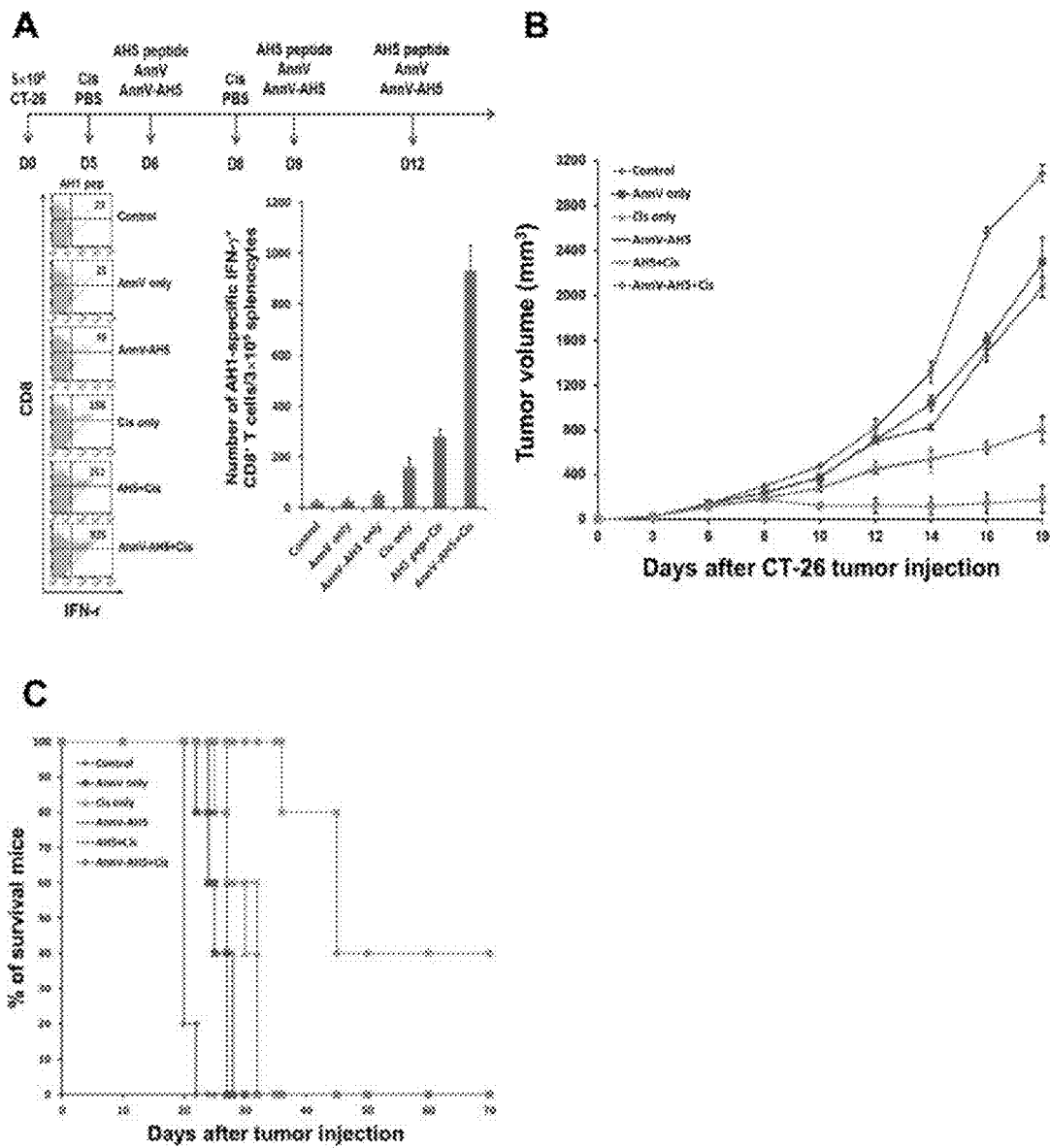
FIG. 3 includes three panels, 3A-3C.
Figure 4:
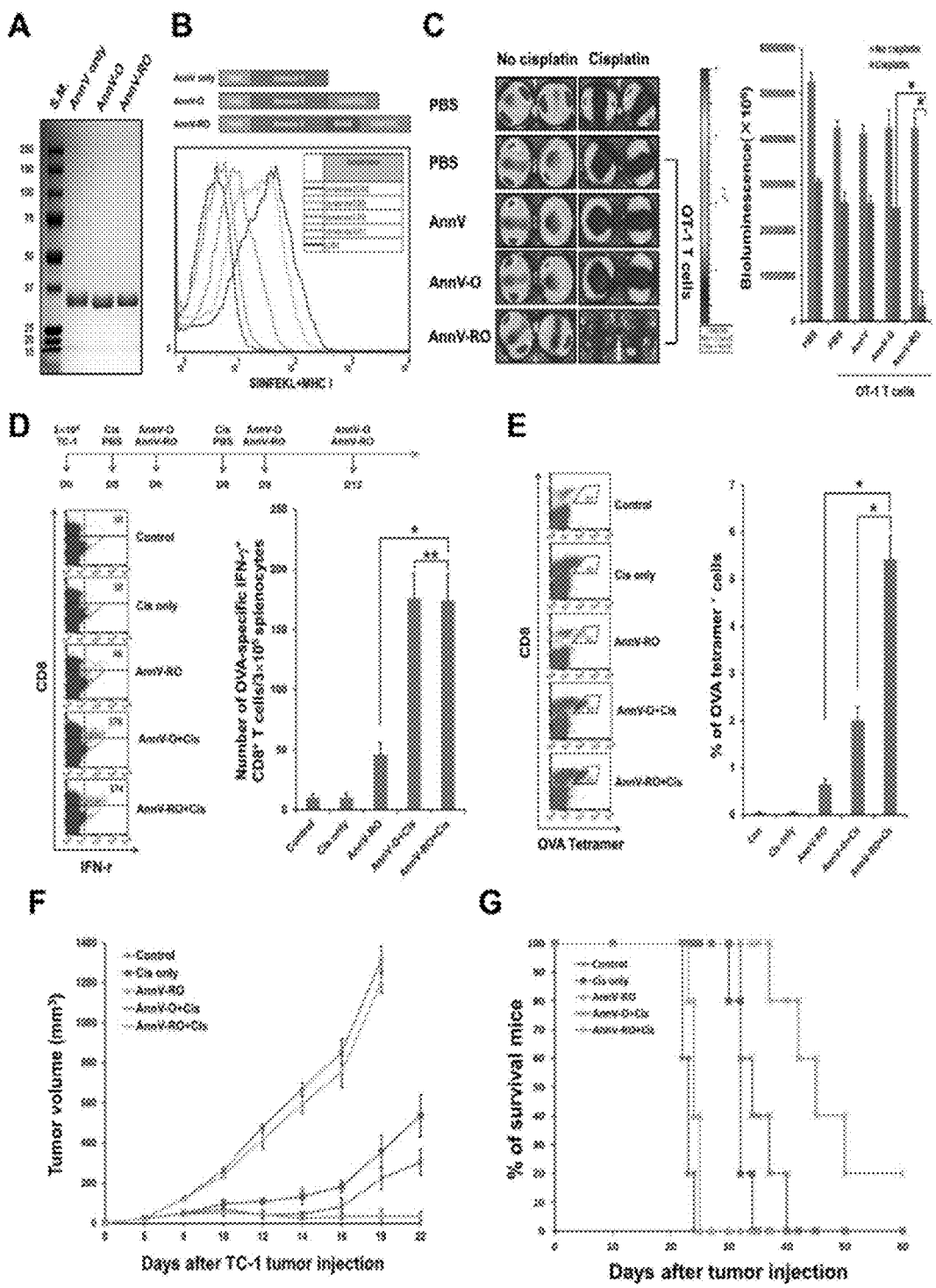
FIG. 4 has seven panels, 4A-4G.
Figure 5:
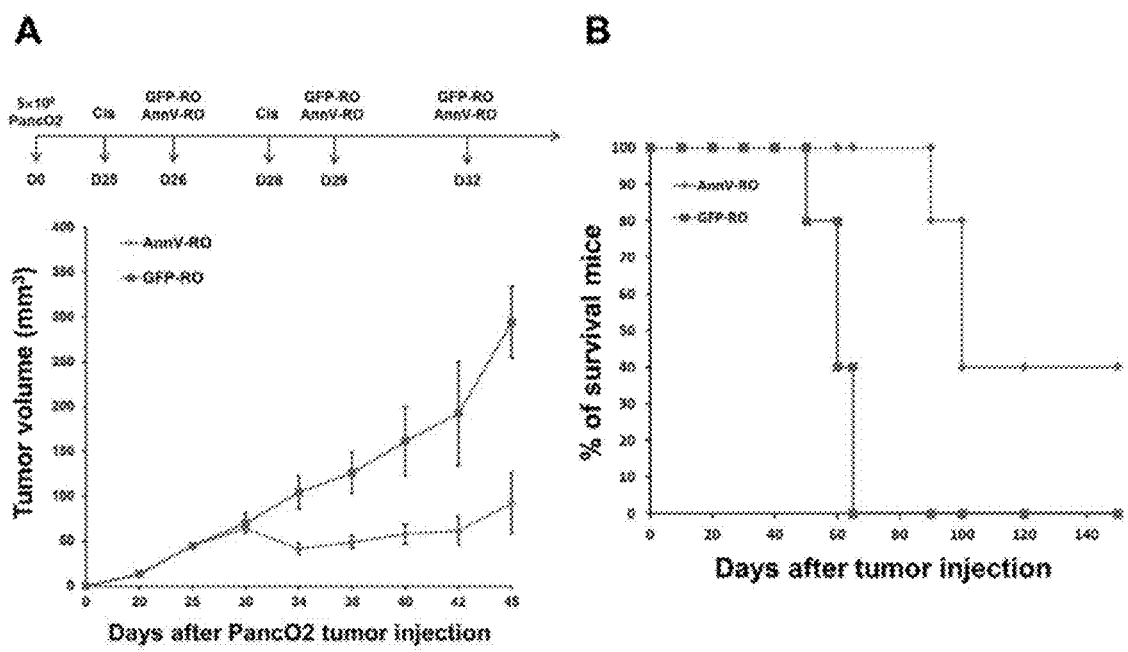
FIG. 5 includes 2 panels, 5A-5B.
Figure 6:
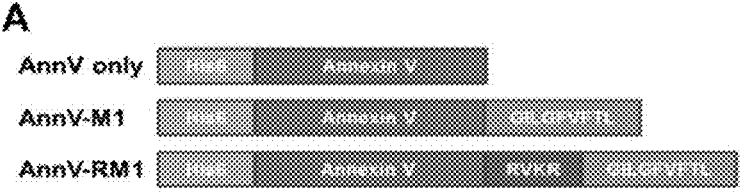
FIG. 6 includes three panels, 6A-6C.
Figure 6:
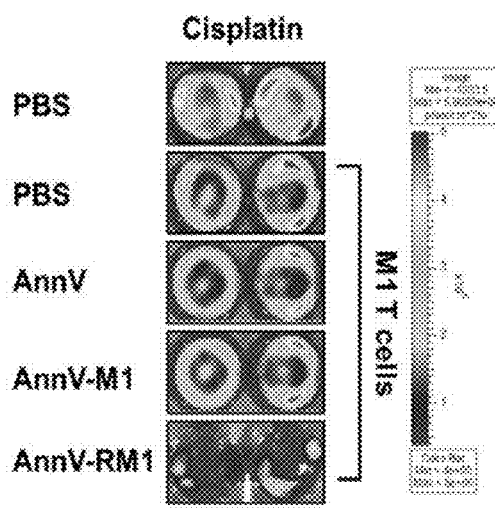
Figure 6:
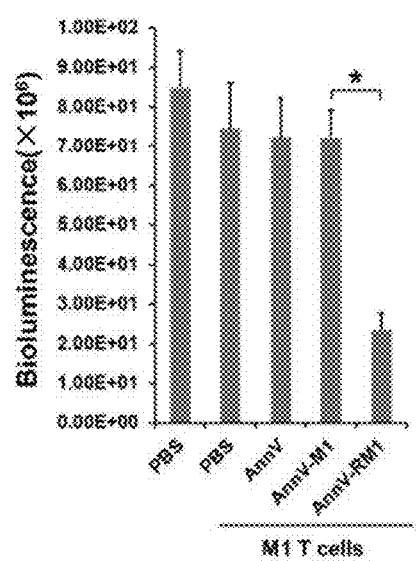
Figure 7:
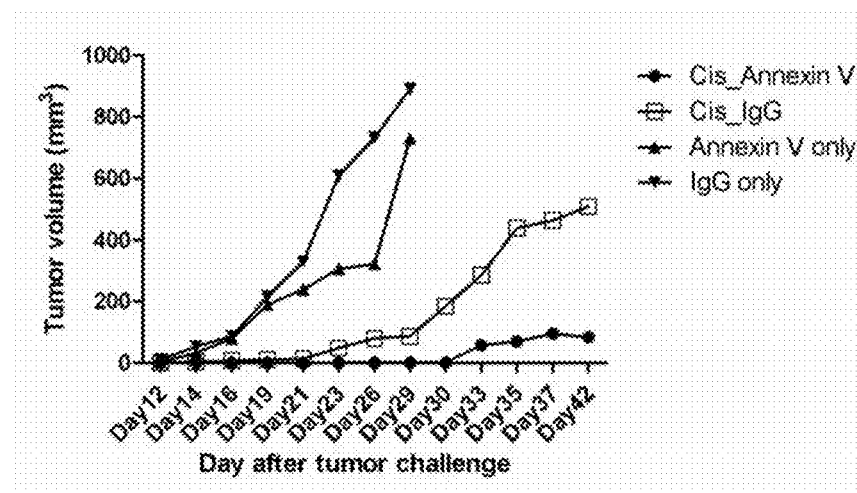
FIG. 7 includes two panels, 7A-7B.
Figure 7:
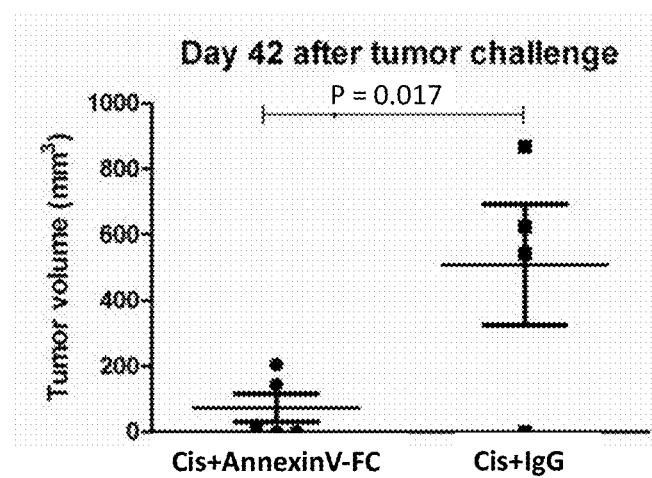

As demonstrated in FIG. 2, the combinatorial treatment of cisplatin and AnnexinV did not generate a significantly better therapeutic anti-tumor effect in TC-1 tumor bearing mice as compared to cisplatin alone. However, the combinatorial treatment of cisplatin and AnnexinV-E7 fusion protein generated a synergistic anti-tumor effect leading to impressive tumor control. Our results demonstrated that AnnexinV is capable of directing antigenic peptides to tumor location for the activation of antigen-specific immune responses in the tumor loci. It has been reported that antibody can elicit antibody-dependent cellular cytotoxicity (ADCC) against the tumor. Since AnnexinV can be used to target molecules to tumor location, we reason that AnnexinV can also be used to target FC portion of antibody to tumor location to elicit ADCC against tumor, resulting better therapeutic antitumor effects. To determine this, we linked the Fc portion of IgG2a to AnnexinV in the form of chimeric protein (AnnexinV-FC). We injected $1 \times 10^5$ TC-1 tumor cells/mice subcutaneously into C57BL/6 mice (five per group). Five days later, tumor-bearing mice were treated with intraperitoneal cisplatin (5 mg/kg body weight) or saline control. Six days later, mice were treated with intraperitoneal AnnexinV-FC or mouse IgG (100 ug/mouse) control. Tumor-bearing mice continue to receive the same protein treatment regimen at a weekly interval. As shown in FIG. 7A-B, mice treated with cisplatin and AnnexinV-FC generated most potent anti-tumor effect compared to other treatment group, leading to the control of TC-1 tumor. Our data indicate that AnnexinV-FC potentially can be used in conjunction with other therapeutic agents (such as cisplatin) to generate better therapeutic antitumor effects.

REFERENCES

1. Sznol M, Holmlund J. Antigen-specific agents in development. Semin Oncol. 1997; 24:173-86.
2. Kang T H, Ma B, Wang C, Wu T C, Hung C F. Targeted coating with antigenic peptide renders tumor cells susceptible to CD8(+) T cell-mediated killing. Molecular therapy: the journal of the American Society of Gene Therapy. 2013; 21:542-53.
3. Scholler N, Fu N, Yang Y, Ye Z, Goodman G E, Hellstrom K E, et al. Soluble member(s) of the mesothelin/megakaryocyte potentiating factor family are detectable in sera from patients with ovarian carcinoma. Proceedings of the National Academy of Sciences of the United States of America. 1999; 96:11531-6.
4. Hassan R, Bera T, Pastan I. Mesothelin: a new target for immunotherapy. Clinical cancer research: an official journal of the American Association for Cancer Research. 2004; 10:3937-42.
5. D'Amico A V, McKenna W G. Apoptosis and a re-investigation of the biologic basis for cancer therapy. Radiotherapy and oncology: journal of the European Society for Therapeutic Radiology and Oncology. 1994; 33:3-10.
6. Sen S, D'Incalci M. Apoptosis. Biochemical events and relevance to cancer chemotherapy. FEBS letters. 1992; 307:122-7.
7. Dive C, Evans C A, Whetton A D. Induction of apoptosis—new targets for cancer chemotherapy. Seminars in cancer biology. 1992; 3:417-27.
8. Schmitt C A, Lowe S W. Apoptosis and therapy. The Journal of pathology. 1999; 187:127-37.
9. Dewey W C, Ling C C, Meyn R E. Radiation-induced apoptosis: relevance to radiotherapy. International journal of radiation oncology, biology, physics. 1995; 33:781-96.
10. Ernst J D, Yang L, Rosales J L, Broaddus V C. Preparation and characterization of an endogenously fluorescent annexin for detection of apoptotic cells. Analytical biochemistry. 1998; 260:18-23.
11. Hung C F, Calizo R, Tsai Y C, He L, Wu T C. A DNA vaccine encoding a single-chain trimer of HLA-A2 linked to human mesothelin peptide generates antitumor effects against human mesothelin-expressing tumors. Vaccine. 2007; 25:127-35.
12. Wang T L, Ling M, Shih I M, Pham T, Pai S I, Lu Z, et al. Intramuscular administration of E7-transfected dendritic cells generates the most potent E7-specific anti-tumor immunity. Gene therapy. 2000; 7:726-33.
13. Peng S, Monie A, Kang T H, Hung C F, Roden R, Wu T C. Efficient delivery of DNA vaccines using human papillomavirus pseudovirions. Gene therapy. 2010; 17:1453-64.
14. Clay T M, Hobeika A C, Mosca P J, Lyerly H K, Morse M A. Assays for monitoring cellular immune responses to active immunotherapy of cancer. Clinical cancer research: an official journal of the American Association for Cancer Research. 2001; 7:1127-35.
15. Cheng W F, Hung C F, Lin K Y, Ling M, Juang J, He L, et al. CD8+ T cells, NK cells and IFN-gamma are important for control of tumor with downregulated MHC class I expression by DNA vaccination. Gene therapy. 2003; 10:1311-20.
16. Lin K Y, Guarnieri F G, Staveley-O'Carroll K F, Levitsky H I, August J T, Pardoll D M, et al. Treatment of established tumors with a novel vaccine that enhances major histocompatibility class II presentation of tumor antigen. Cancer research. 1996; 56:21-6.
17. Tannous B A, Kim D E, Fernandez J L, Weissleder R, Breakefield X O. Codon-optimized Gaussia luciferase cDNA for mammalian gene expression in culture and in vivo. Molecular therapy: the journal of the American Society of Gene Therapy. 2005; 11:435-43.
18. Kersemaekers A M, Fleuren G J, Kenter G G, Van den Broek L J, Uljee S M, Hermans J, et al. Oncogene alterations in carcinomas of the uterine cervix: overexpression of the epidermal growth factor receptor is associated with poor prognosis. Clinical cancer research: an official journal of the American Association for Cancer Research. 1999; 5:577-86.
19. Maurizi M, Almadori G, Ferrandina G, Distefano M, Romanini M E, Cadoni G, et al. Prognostic significance of epidermal growth factor receptor in laryngeal squamous cell carcinoma. Br J Cancer. 1996; 74:1253-7.
20. Inada S, Koto T, Futami K, Arima S, Iwashita A. Evaluation of malignancy and the prognosis of esophageal cancer based on an immunohistochemical study (p53, E-cadherin, epidermal growth factor receptor). Surg Today. 1999; 29:493-503.
21. Fischer-Colbrie J, Witt A, Heinzl H, Speiser P, Czerwenka K, Sevelda P, et al. EGFR and steroid receptors in ovarian carcinoma: comparison with prognostic parameters and outcome of patients. Anticancer Res. 1997; 17:613-9.
22. Mellon K, Wright C, Kelly P, Horne C H, Neal D E. Long-term outcome related to epidermal growth factor receptor status in bladder cancer. J Urol. 1995; 153: 919-25.
23. Normanno N, De Luca A, Bianco C, Strizzi L, Mancino M, Maiello M R, et al. Epidermal growth factor receptor (EGFR) signaling in cancer. Gene. 2006; 366:2-16.
24. Nicholson R I, Gee J M, Harper M E. EGFR and cancer prognosis. Eur J Cancer. 2001; 37 Suppl 4:S9-15.
25. Lu J, Higashimoto Y, Appella E, Celis E. Multiepitope Trojan antigen peptide vaccines for the induction of antitumor CTL and Th immune responses. J Immunol. 2004; 172:4575-82.
26. Currier J R, Kuta E G, Turk E, Earhart L B, Loomis-Price L, Janetzki S, et al. A panel of MHC class I restricted viral peptides for use as a quality control for vaccine trial ELISPOT assays. Journal of immunological methods. 2002; 260:157-72.

EQUIVALENTS

Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention may become apparent to those skilled in the art upon review of this specification. The full scope of the invention should be determined by reference to the claims, along with their full scope of equivalents, and the specification, along with such variations. Such equivalents are intended to be encompassed by the following claims.

LISTING OF ADDITIONAL SEQUENCES

SEQ ID NO: 1

```
atg cat gga gat aca cct aca ttg cat gaa tat atg tta gat ttg caa cca gag aca act      60
Met His Gly Asp Thr Pro Thr Leu His Glu Tyr Met Leu Asp Leu Gln Pro Glu Thr Thr       20 gat ctc tac tgt tat gag caa tta aat gac agc tca gag gag gag gat gaa ata gat ggt     120
Asp Leu Tyr Cys Tyr Glu Gln Leu Asn Asp Ser Ser Glu Glu Glu Asp Glu Ile Asp Gly       40 cca gct gga caa gca gaa ccg gac aga gcc cat tac aat att gta acc ttt tgt tgc aag     180
Pro Ala Gly Gln Ala Glu Pro Asp Arg Ala His Tyr Asn Ile Val Thr Phe Cys Cys Lys       60 tgt gac tct acg ctt cgg ttg tgc gta caa agc aca cac gta gac att cgt act ttg gaa     240
Cys Asp Ser Thr Leu Arg Leu Cys Val Gln Ser Thr His Val Asp Ile Arg Thr Leu Glu       80 gac ctg tta atg ggc aca cta gga att gtg tgc ccc atc tgt tct cag gat aag ctt         297
Asp Leu Leu Met Gly Thr Leu Gly Ile Val Cys Pro Ile Cys Ser Gln Asp Lys Leu           99
```

-continued

LISTING OF ADDITIONAL SEQUENCES

SEQ ID NO: 2
MHGDTPTLHE YMLDLQPETT DLYCYEQLND SSEEEDEIDG PAGQAEPDRA HYNIVTFCCK CDSTLRLCVQ
STHVDIRTLE DLLMGTLGIV CPICSQDKL
99

SEQ ID NO: 3
MHGDTPTLHE YMLDLQPETT DLYGYEGLND SSEEEDEIDG PAGQAEPDRA HYNIVTFCCK CDSTLRLCVQ
STHVDIRTLE DLLMGTLGIV CPICSQKP
97

SEQ ID NO: 4

| | | | | | | | | | | | | | | | | | | | | |
|---|---|---|---|---|---|---|---|---|---|---|---|---|---|---|---|---|---|---|---|---|
| atg | cac | caa | aag | aga | act | gca | atg | ttt | cag | gac | cca | cag | gag | cga | ccc | aga | aag | tta | cca | 60 |
| Met | His | Gln | Lys | Arg | Thr | Ala | Met | Phe | Gln | Asp | Pro | Gln | Glu | Arg | Pro | Arg | Lys | Leu | Pro | 20 |
| cag | tta | tgc | aca | gag | ctg | caa | aca | act | ata | cat | gat | ata | ata | tta | gaa | tgt | gtg | tac | tgc | 120 |
| Gln | Leu | Cys | Thr | Glu | Leu | Gln | Thr | Thr | Ile | His | Asp | Ile | Ile | Leu | Glu | Cys | Val | Tyr | Cys | 40 |
| aag | caa | cag | tta | ctg | cga | cgt | gag | gta | tat | gac | ttt | gct | ttt | cgg | gat | tta | tgc | ata | gta | 180 |
| Lys | Gln | Gln | Leu | Leu | Arg | Arg | Glu | Val | Tyr | Asp | Phe | Ala | Phe | Arg | Asp | Leu | Cys | Ile | Val | 60 |
| tat | aga | gat | ggg | aat | cca | tat | gct | gta | tgt | gat | aaa | tgt | tta | aag | ttt | tat | tct | aaa | att | 240 |
| Tyr | Arg | Asp | Gly | Asn | Pro | Tyr | Ala | Val | Cys | Asp | Lys | Cys | Leu | Lys | Phe | Tyr | Ser | Lys | Ile | 80 |
| agt | gag | tat | aga | cat | tat | tgt | tat | agt | ttg | tat | gga | aca | aca | tta | gaa | cag | caa | tac | aac | 300 |
| Ser | Glu | Tyr | Arg | His | Tyr | Cys | Tyr | Ser | Leu | Tyr | Gly | Thr | Thr | Leu | Glu | Gln | Gln | Tyr | Asn | 100 |
| aaa | ccg | ttg | tgt | gat | ttg | tta | att | agg | tgt | att | aac | tgt | caa | aag | cca | ctg | tgt | cct | gaa | 360 |
| Lys | Pro | Leu | Cys | Asp | Leu | Leu | Ile | Arg | Cys | Ile | Asn | Cys | Gln | Lys | Pro | Leu | Cys | Pro | Glu | 120 |
| gaa | aag | caa | aga | cat | ctg | gac | aaa | aag | caa | aga | ttc | cat | aat | ata | agg | ggt | cgg | tgg | acc | 420 |
| Glu | Lys | Gln | Arg | His | Leu | Asp | Lys | Lys | Gln | Arg | Phe | His | Asn | Ile | Arg | Gly | Arg | Trp | Thr | 140 |
| ggt | cga | tgt | atg | tct | tgt | tgc | aga | tca | tca | aga | aca | cgt | aga | gaa | acc | cag | ctg | taa | | 474 |
| Gly | Arg | Cys | Met | Ser | Cys | Cys | Arg | Ser | Ser | Arg | Thr | Arg | Arg | Glu | Thr | Gln | Leu | stop | | 158 |

SEQ ID NO: 5
MHQKRTAMFQ DPQERPRKLP QLCTELQTTI HDIILECVYC KQQLLRREVY DFAFRDLCIV YRDGNPYAVC DKCLKFYSKI
SEYRHYCYSL YGTTLEQQYN KPLCDLLIRC INCQKPLCPE EKQRHLDKKQ RFHNIRGRWT GRCMSCCRSS RTRRETQL
158

SEQ ID NO: 6
MFQDPQERPR KLPQLCTELQ TTIHDIILEC VYCKQQLLRR EVYDFAFRDL CIVYRDGNPY AVCDKCLKFY SKISEYRHYC
YSLYGTTLEQ QYNKPLCDLL IRCINCQKPL CPEEKQRHLD KKQRFHNIRG RWTGRCMSCC RSSRTRRETQ L

SEQ ID NO: 7
atgaaggcaaacctactggtcctgttaagtgcacttgcagctgcagatgcagacacaatatgtataggctaccatgcgaacaattcaaccga
cactgttgacacagtactcgagaagaatgtgacagtgacacactctgttaacctgctcgaagacagccacaacggaaaactatgtagattaa
aaggaatagccccactacaattggggaaatgtaacatcgccggatggctcttgggaaacccagaatgcgaccactgcttccagtgagatca
tggtcctacattgtagaaacaccaaactctgagaatggaatatgttatccaggagatttcatcgactatgaggagctgagggagcaattgag
ctcagtgtcatcattcgaaagattcgaaatatttcccaaagaaagctcatggcccaaccacaacacaaacggagtaacgcagcatgctccc
atgagggaaagcagttttttacagaaatttgctatggctgacggagaaggagcgtcatacccaaagctgaaaaattcttatgtgaacaaa
aaagggaaagaagtccttgtactgtggggtattcatcacccgcctaacagtaaggaacaacagaatatctatcagaatgaaaatgcttatgt
ctctgtagtgacttcaaattataacaggagatttaccccggaaatagcagaaagacccaaagtaagagatcaagctggggaggatgaactatt
actggaccttgctaaaaccaggagacacaataatatttgaggcaaatggaaatctaatagcaccaatgtatgctttcgcactgagtagaggc
tttgggtccggcatcatcacctcaaacgcatcaatgcatgagtgtaacacgaagtgtcaaacaccccctgggagctataaacagcagtctccc
ttaccagaatatacacccagtcacaataggagagtgcccaaaatacgtcaggagtgccaaattgaggatggtacaggactaaggaacactc
cgtccattcaatccagaggtctatttggagccattgccggttttattgaaggggatggactggaatgatagatggatggtatggttatcat
catcagaatgaacagggatcaggctatgcagcggatcaaaaaagcacacaaaatgccattaacgggattacaaacaaggtgaacactgttat
cgagaaaatgaacattcaattcacagctgtgggtaaagaattcaacaaattagaaaaaaggatggaaaatttaaataaaaaagttgatgatg
gatttctggacatttggacatataatgcagaattgttagttctactggaaaatgaaaggactctgagtttccatgactcaaatgtgaagaat
ctgtatgagaaagtaaaagccaattaaagaataatgccaaagaaatcggaaatggatgttttgagttctaccacaagtgtgacaatgaatg
catggaaagtgtaagaaatgggacttatgattatcccaaatattcagaagagtcaaagttgaacagggaaaaggtagatggagtgaaattgg
aatcaatggggatctatcagattctggcgatctactcaactgtcgccagttcactggtgcttttggtctccctgggggcaatcagtttctgg
atgtgttctaatggatctttgcagtgcagaatatgcatctga SEQ ID NO: 8
MKANLLVLLS ALAAADADTI CIGYHANNST DTVDTVLEKN VTVTHSVNLL EDSHNGKLCR LKGIAPLQLG KCNIAGWLLG
NPECDPLLPV RSWSYIVETP NSENGICYPG DFIDYEELRE QLSSVSSFER FEIFPKESSW PNHNTNGVTA ACSHEGKSSF
YRNLLWLTEK EGSYPKLKNS YVNKKGKEVL VLWGIHHPPN SKEQQNIYQN ENAYVSVVTS NYNRRFTPEI AERPKVRDQA
GRMNYYWTLL KPGDTIIFEA NGNLIAPMYA FALSRGFGSG IITSNASMHE CNTKCQTPLG AINSSLPYQN IHPVTIGECP -continued

LISTING OF ADDITIONAL SEQUENCES

KYVRSAKLRM VTGLRNTPSI QSRGLFGAIA GFIEGGWTGM IDGWYGYHHQ NEQGSGYAAD QKSTQNAING ITNKVNTVIE
KMNIQFTAVG KEFNKLEKRM ENLNKKVDDG FLDIWTYNAE LLVLLENERT LDFHDSNVKN LYEKVKSQLK NNAKEIGNGC
FEFYHKCDNE CMESVRNGTY DYPKYSEESK LNREKVDGVK LESMGIYQIL AIYSTVASSL VLLVSLGAIS FWMCSNGSLQ
CRICI

SEQ ID NO: 9
MGSIGAASMEFCFDVFKELKVHHANENIFYCPIAIMSALAMVYLGAKDSTRTQINKVVRFDKLPGFGDSIEAQCGTSVNV
HSSLRDILNQITKPNDVYSFSLASRLYAEERYPILPEYLQCVKELYRGGLEPINFQTAADQARELINSWVESQTNGIIRN
VLQPSSVDSQTAMVLVNAIVFKGLWEKTFKDEDTQAMPFRVTEQESKPVQMMYQIGLFRVASMASEKMKILELPFASGTM
SMLVLLPDEVSGLEQLESIINFEKLTEWTSSNVMEERKIKVYLPRMKMEEKYNLTSVLMAMGITDVFSSSANLSGISSAE
SLKISQAVHAAHAEINEAGREVVGSAEAGVDAASVSEEFRADHPFLFCIKHIATNAVLFFGRCVSP

SEQ ID NO: 10
ATGGCGGCCCCCGGCGCCCGGCGGCCGCTGCTCCTGCTGCTGCTGGCAGGCCTTGCACATGGCGCCTCAGCACTCTTTGAGGATCTAATCAT
GCATGGAGATACACCTACATTGCATGAATATATGTTAGATTTGCAACCAGAGACAACTGATCTCTACTGTTATGAGCAATTAAATGACAGCT
CAGAGGAGGAGGATGAAATAGATGGTCCAGCTGGACAAGCAGAACCGGACAGAGCCCATTACAATATTGTTACCTTTTGTTGCAAGTGTGAC
TCTACGCTTCGGTTGTGCGTACAAAGCACACACGTAGACATTCGTACTTTGGAAGACCTGTTAATGGGCACACTAGGAATTGTGTGCCCCAT
CTGTTCTCAGGATCTTAACAACATGTTGATCCCCATTGCTGTGGGCGGTGCCCTGGCAGGGCTGGTCCTCATCGTCCTCATTGCCTACCTCA
TTGGCAGGAAGAGGAGTCACGCCGGCTATCAGACCATCTAG

SEQ ID NO: 11
MAAPGARRPL LLLLLAGLAH GASALFEDLI MHGDTPTLHE YMLDLQPETT DLYCYEQLND SSEEEDEIDG PAGQAEPDRA
HYNIVTFCCK CDSTLRLCVQ STHVDIRTLE DLLMGTLGIV CPICSQDLNN MLIPIAVGGA LAGLVLIVLI AYLIGRKRSH
AGYQTI

SEQ ID NO: 12
GACGGATCGGGAGATCTCCCGATCCCCTATGGTCGACTCTCAGTACAATCTGCTCTGATGCCGCATAGTTAAGCCAGTATCTGCTCCCTGCT
TGTGTGTTGGAGGTCGCTGAGTAGTGCGCGAGCAAAATTTAAGCTACAACAAGGCAAGGCTTGACCGACAATTGCATGAAGAATCTGCTTAG
GGTTAGGCGTTTTGCGCTGCTTCGCGATGTACGGGCCAGATATACGCGTTGACATTGATTATTGACTAGTTATTAATAGTAATCAATTACGG
GGTCATTAGTTCATAGCCCATATATGGAGTTCCGCGTTACATAACTTACGGTAAATGGCCCGCCTGGCTGACGCCCAACGACCCCCGCCCA
TTGACGTCAATAATGACGTATGTTCCCATAGTAACGCCAATAGGGACTTTCCATTGACGTCAATGGGTGGACTATTTACGGTAAACTGCCCA
CTTGGCAGTACATCAAGTGTATCATATGCCAAGTACGCCCCCTATTGACGTCAATGGGCGTGGATAGCGGTTTGACTCACGGGGATTTCCAAGTCTCCACCCATTGACGTCAATGGGAGTTTGTTTTGGCACCAAAATCAACGGGACTTT
TCCAAAATGTCGTAACAACTCCGCCCCATTGACGCAAATGGGCGGTAGGCGTGTACGGTGGGAGGTCTATATAAGCAGAGCTCTCTGGCTAA
CTAGAGAACCCACTGCTTACTGGCTTATCGAAATTAATACGACTCACTATAGGGAGACCCAAGCTGGCTAGCGTTTAAACGGGCCCTCTAGA
CTCGAGCGGCCGCCACTGTGCTGGATATCTGCAGAATTCatggcggccccccggcgcccggcggccgctgctcctgctgctgctggcaggcct
tgcacatggcgcctcagcactctttgaggatctaatcatgcatggagatacacctacattgcatgaatatatgttagatttgcaaccagaga
caactgatctctactgttatgagcaattaaatgacagctcagaggaggaggatgaaatagatggtccagctggacaagcagaaccggacaga
gcccattacaatattgttaccttttgttgcaagtgtgactctacgcttcggttgtgcgtacaaagcacacacgtagacattcgtactttgga
agacctgttaatgggcacactaggaattgtgtgccccatctgttctcaggatcttaacaacatgttgatccccattgctgtgggcggtgccc
tggcagggctggtcctcatcgtcctcattgcctacctcattggcaggaagaggagtcacgccggctatcagaccatctagGGATCCGAGCTC
GGTACCAAGCTTAAGTTTAAACCGCTGATCAGCCTCGACTGTGCCTTCTAGTTGCCAGCCATCTGTTGTTTGCCCCTCCCCCGTGCCTTCCT
TGACCCTGGAAGGTGCCACTCCCACTGTCCTTTCCTAATAAAATGAGGAAATTGCATCGCATTGTCTGAGTAGGTGTCATTCTATTCTGGGG
GGTGGGGTGGGGCAGGACAGCAAGGGGGAGGATTGGGAAGACAATAGCAGGCATGCTGGGGATGCGGTGGGCTCTATGGCTTCTGAGGCGGA
AAGAACCAGCTGGGGCTCTAGGGGGTATCCCCACGCGCCCTGTAGCGGCGCATTAAGCGCGGCGGGTGTGGTGGTTACGCGCAGCGTGACCG
CTACACTTGCCAGCGCCCTAGCGCCCGCTCCTTTCGCTTTCTTCCCTTCCTTTCTCGCCACGTTCGCCGGCTTTCCCCGTCAAGCTCTAAAT
CGGGGCATCCCTTTAGGGTTCCGATTTAGTGCTTTACGGCACCTCGACCCCAAAAAACTTGATTAGGGTGATGGTTCACGTAGTGGGCCATC
GCCCTGATAGACGGTTTTTCGCCCTTTGACGTTGGAGTCCACGTTCTTTAATAGTGGACTCTTGTTCCAAACTGGAACAACACTCAACCCTA
TCTCGGTCTATTCTTTTGATTTATAAGGGATTTTGGGGATTTCGGCCTATTGGTTAAAAAATGAGCTGATTTAACAAAAATTTAACGCGAAT
TAATTCTGTGGAATGTGTGTCAGTTAGGGTGTGGAAAGTCCCCAGGCTCCCCAGCAGGCAGAAGTATGCAAAGCATGCATCTCAATTAGTC
AGCAACCAGGTGTGGAAAGTCCCCAGGCTCCCCAGCAGGCAGAAGTATGCAAAGCATGCATCTCAATTAGTCAGCAACCATAGTCCCGCCCC
TAACTCCGCCCATCCCGCCCCTAACTCCGCCCAGTTCCGCCCATTCTCCGCCCCATGGCTGACTAATTTTTTTTATTTATGCAGAGGCCGAG
GCCGCCTCTGCCTCTGAGCTATTCCAGAAGTAGTGAGGAGGCTTTTTTGGAGGCCTAGGCTTTTGCAAAAAGCTCCCGGAGCTTGTATATC
CATTTTCGGATCTGATCAAGAGACAGGATGAGGATCGTTTCGCATGATTGAACAAGATGGATTGCACGCAGGTTCTCCGGCCGCTTGGGTGG
AGAGGCTATTCGGCTATGACTGGGCACAACAGACAATCGGCTGCTCTGATGCCGCCGTGTTCCGGCTGTCAGCGCAGGGGCGCCCGGTTCTT
TTTGTCAAGACCGACCTGTCCGGTGCCCTGAATGAACTGCAGGACGAGGCAGCGCGGCTATCGTGGCTGGCCACGACGGGCGTTCCTTGCGC
AGCTGTGCTCGACGTTGTCACTGAAGCGGGAAGGGACTGGCTGCTATTGGGCGAAGTGCCGGGGCAGGATCTCCTGTCATCTCACCTTGCTC
CTGCCGAGAAAGTATCCATCATGGCTGATGCAATGCGGCGGCTGCATACGCTTGATCCGGCTACCTGCCCATTCGACCACCAAGCGAAACAT
CGCATCGAGCGAGCACGTACTCGGATGGAAGCCGGTCTTGTCGATCAGGATGATCTGGACGAAGAGCATCAGGGGCTCGCGCCAGCCGAACT
GTTCGCCAGGCTCAAGGCGCGCATGCCCGACGGCGAGGATCTCGTCGTGACCCATGGCGATGCCTGCTTGCCGAATATCATGGTGGAAAATG
GCCGCTTTTCTGGATTCATCGACTGTGGCCGGCTGGGTGTGGCGGACCGCTATCAGGACATAGCGTTGGCTACCCGTGATATTGCTGAAGAG
CTTGGCGGCGAATGGGCTGACCGCTTCCTCGTGCTTTACGGTATCGCCGCTCCCGATTCGCAGCGCATCGCCTTCTATCGCCTTCTTGACGA
GTTCTTCTGAGCGGGACTCTGGGGTTCGAAATGACCGACCAAGCGACGCCCAACCTGCCATCACGAGATTTCGATTCCACCGCCGCCTTCTA
TGAAAGGTTGGGCTTCGGAATCGTTTTCCGGGACGCCGGCTGGATGATCCTCCAGCGCGGGGATCTCATGCTGGAGTTCTTCGCCCACCCCA
ACTTGTTTATTGCAGCTTATAATGGTTACAAATAAAGCAATAGCATCACAAATTTCACAAATAAAGCATTTTTTTCACTGCATTCTAGTTGT
GGTTTGTCCAAACTCATCAATGTATCTTATCATGTCTGTATACCGTCGACCTCTAGCTAGAGCTTGGCGTAATCATGGTCATAGCTGTTTCC
TGTGTGAAATTGTTATCCGCTCACAATTCCACACAACATACGAGCCGGAAGCATAAAGTGTAAAGCCTGGGGTGCCTAATGAGTGAGCTAAC
TCACATTAATTGCGTTGCGCTCACTGCCCGCTTTCCAGTCGGGAAACCTGTCGTGCCAGCTGCATTAATGAATCGGCCAACGCGCGGGGAGA
GGCGGTTTGCGTATTGGGCGCTCTTCCGCTTCCTCGCTCACTGACTCGCTGCGCTCGGTCGTTCGGCTGCGGCGAGCGGTATCAGCTCACTC
AAAGGCGGTAATACGGTTATCCACAGAATCAGGGGATAACGCAGGAAAGAACATGTGAGCAAAAGGCCAGCAAAAGGCCAGGAACCGTAAAA
AGGCCGCGTTGCTGGCGTTTTTCCATAGGCTCCGCCCCCCTGACGAGCATCACAAAAATCGACGCTCAAGTCAGAGGTGGCGAAACCCGACA
GGACTATAAAGATACCAGGCGTTTCCCCCTGGAAGCTCCCTCGTGCGCTCTCCTGTTCCGACCCTGCCGCTTACCGGATACCTGTCCGCCTT
TCTCCCTTCGGGAAGCGTGGCGCTTTCTCAATGCTCACGCTGTAGGTATCTCAGTTCGGTGTAGGTCGTTCGCTCCAAGCTGGGCTGTGTGC
ACGAACCCCCCGTTCAGCCCGACCGCTGCGCCTTATCCGGTAACTATCGTCTTGAGTCCAACCCGGTAAGACACGACTTATCGCCACTGGCA
GCAGCCACTGGTAACAGGATTAGCAGAGCGAGGTATGTAGGCGGTGCTACAGAGTTCTTGAAGTGGTGGCCTAACTACGGCTACACTAGAAG
GACAGTATTTGGTATCTGCGCTCTGCTGAAGCCAGTTACCTTCGGAAAAAGAGTTGGTAGCTCTTGATCCGGCAAACAAACCACCGCTGGTA

LISTING OF ADDITIONAL SEQUENCES

```
GCGGTGGTTTTTTTGTTTGCAAGCAGCAGATTACGCGCAGAAAAAAGGATCTCAAGAAGATCCTTTGATCTTTTCTACGGGGTCTGACGCT
CAGTGGAACGAAAACTCACGTTAAGGGATTTTGGTCATGAGATTATCAAAAGGATCTTCACCTAGATCCTTTTAAATTAAAAATGAAGTTT
TAAATCAATCTAAAGTATATATGAGTAAACTTGGTCTGACAGTTACCAATGCTTAATCAGTGAGGCACCTATCTCAGCGATCTGTCTATTTC
GTTCATCCATAGTTGCCTGACTCCCCGTCGTGTAGATAACTACGATACGGGAGGGCTTACCATCTGGCCCCAGTGCTGCAATGATACCGCGA
GACCCACGCTCACCGGCTCCAGATTTATCAGCAATAAACCAGCCAGCCGGAAGGGCCGAGCGCAGAAGTGGTCCTGCAACTTTATCCGCCTC
CATCCAGTCTATTAATTGTTGCCGGGAAGCTAGAGTAAGTAGTTCGCCAGTTAATAGTTTGCGCAACGTTGTTGCCATTGCTACAGGCATCG
TGGTGTCACGCTCGTCGTTTGGTATGGCTTCATTCAGCTCCGGTTCCCAACGATCAAGGCGAGTTACATGATCCCCCATGTTGTGCAAAAAA
GCGGTTAGCTCCTTCGGTCCTCCGATCGTTGTCAGAAGTAAGTTGGCCGCAGTGTTATCACTCATGGTTATGGCAGCACTGCATAATTCTCT
TACTGTCATGCCATCCGTAAGATGCTTTTCTGTGACTGGTGAGTACTCAACCAAGTCATTCTGAGAATAGTGTATGCGGCGACCGAGTTGCT
CTTGCCCGGCGTCAATACGGGATAATACCGCGCCACATAGCAGAACTTTAAAAGTGCTCATCATTGGAAAACGTTCTTCGGGGCGAAAACTC
TCAAGGATCTTACCGCTGTTGAGATCCAGTTCGATGTAACCCACTCGTGCACCCAACTGATCTTCAGCATCTTTTACTTTCACCAGCGTTTC
TGGGTGAGCAAAAACAGGAAGGCAAAATGCCGCAAAAAAGGGAATAAGGGCGACACGGAAATGTTGAATACTCATACTCTTCCTTTTTCAAT
ATTATTGAAGCATTTATCAGGGTTATTGTCTCATGAGCGGATACATATTTGAATGTATTTAGAAAAATAAACAATAGGGGTTCCGCGCACA
TTTCCCCGAAAAGTGCCACCTGACGTC
```

SEQ ID NO: 13
```
atggctcg tgcggtcggg atcgacctcg ggaccaccaa ctccgtcgtc tcggttctgg aaggtggcga cccggtcgtc
gtcgccaact ccgagggctc caggaccacc ccgtcaattg tcgcgttcgc ccgcaacggt gaggtgctgg tcggccagcc
cgccaagaac caggcagtga ccaacgtcga tcgcaccgtg cgctcggtca agcgacacat gggcagcgac tggtccatag
agattgacgg caagaaatac accgcgccgg agatcagccg cattctg atgaagctga agcgcgacgc cgaggcctac
ctcggtgagg acattaccgc cgcggttatc acgacgcccg cctacttcaa tgaccgccaa cgtcaggcca caaggacgc
cggccagatc gccggcctca acgtgctgcg gatcgtcaac gagccgaccg cggccgcgct ggcctacggc ctcgacaagg
gcgagaagga gcagcgaatc ctggtcttcg acttgggtgg tggcactttc gacgtttccc tgctggagat cggcgagggt
gtggttgagg tccgtgccac ttccggtgac aaccacctcg gcgacgacg gcggtcgtcg attgctggt
ggacaagttc aagggcacca gcggcatcga tctgaccaag gacaagatgg cgatgcagcg gctgcgggaa gccgccgaga
aggcaaagat cgagctgagt tcgagtcagt ccacctcgat caacctgccc tacatcaccg tcgacgccga caagaacccg
ttgttcttag acgagcagct gacccgcgcg gagttccaac ggatcactca ggacctgctg gaccgcactc gcaagccgtt
ccagtcggtg atcgctgaca ccggcatttc ggtgtcggaa atcgatcacg ttgtgctcgt gggtggttcg acccggatgc
ccgcggtgac cgatctggtc aaggaactca ccggcggcaa ggaacccaac aagggcgtca accccgatga ggttgtcgcg
gtgggagccg ctctgcaggc cggcgtcctc aagggcgagg tgaaagacgt tctgctgctt gatgttaccc cgctgagcct
gggtatcgag accaagggcg gggtgatgac caggctcatc gagcgcaaca ccacgatccc caccaagcgg tcggagactt
tcaccaccgc cgacgacaac caaccgtcgg tgcagatcca ggtctatcag ggggagcgtg agatcgccgc gcacaacaag
ttgctcgggt ccttcgaact gaccggcatc ccgccgccgc cgcggggat tccgcagatc gaggtcactt tcgacatcga
cgccaacgtc attgtgcacg tcaccgccaa ggacaagggc accggcaagg agaacacgat ccgaatccag gaaggctcgg
gcctgtccaa ggaagacatt gaccgcatga tcaaggacgc cgaagcgcac gccgaggagg atcgcaagcg tcgcgaggag
gccgatgttc gtaatcaagc cgagacattg gtctaccaga cggagaagtt cgtcaaagaa cagcgtgagg ccgagggtgg
ttcgaaggta cctgaagaca cgctgaacaa ggttgatgcc gcggtggcgg aagcgaaggc ggcacttggc ggatcggata
tttcggccat caagtcggcg atggagaagc tgggccagga gtcgcaggct ctggggcaag cgatcctacga agcagctcag
gctgcgtcac aggccactgg cgctgcccac cccgcggcg agccgggcgg tgcccacccc ggctcggctg atgacgttgt
ggacgcggag gtggtcgacg acggccggga ggccaagtga
```

SEQ ID NO: 14
```
MARAVGIDLG TTNSVVSVLE GGDPVVVANS EGSRTTPSIV AFARNGEVLV GQPAKNQAVT NVDRTVRSVK RHMGSDWSIE
IDGKKYTAPE ISARILMKLK RDAEAYLGED ITDAVITTPA YFNDAQRQAT KDAGQIAGLN VLRIVNEPTA AALAYGLDKG
EKEQRILVFD LGGGTFDVSL LEIGEGVVEV RATSGDNHLG GDDWDQRVVD WLVDKFKGTS GIDLTKDKMA MQRLREAAEK
AKIELSSSQS TSINLPYITV DADKNPLFLD EQLTRAEFQR ITQDLLDRTR KPFQSVIADT GISVSEIDHV VLVGGSTRMP
AVTDLVKELT GGKEPNKGVN PDEVVAVGAA LQAGVLKGEV KDVLLLDVTP LSLGIETKGG VMTRLIERNT TIPTKRSETF
TTADDNQPSV QIQVYQGERE IAAHNKLLGS FELTGIPPAP RGIPQIEVTF DIDANGIVHV TAKDKGTGKE NTIRIQEGSG
LSKEDIDRMI KDAEAHAEED RKRREEADVR NQAETLVYQT EKFVKEQREA EGGSKVPEDT LNKVDAAVAE AKAALGGSDI
SAIKSAMEKL GQESQALGQA IYEAAQAASQ ATGAAHPGGE PGGAHPGSAD DVVDAEVVDD GREAK
```

SEQ ID NO: 15
```
1/1                            31/11
ATG CAT GGA GAT ACA CCT ACA TTG CAT GAA TAT ATG TTA GAT TTG CAA CCA GAG ACA ACT

61/21                          91/31
GAT CTC TAC TGT TAT GAG CAA TTA AAT GAC AGC TCA GAG GAG GAG GAT GAA ATA GAT GGT

121/41                         151/51
CCA GCT GGA CAA GCA GAA CCG GAC AGA GCC CAT TAC AAT ATT GTA ACC TTT TGT TGC AAG

181/61                         211/71
TGT GAC TCT ACG CTT CGG TTG TGC GTA CAA AGC ACA CAC GTA GAC ATT CGT ACT TTG GAA

241/81                         271/91
GAC CTG TTA ATG GGC ACA CTA GGA ATT GTG TGC CCC ATC TGT TCT CAA GGA TCC atg gct 301/101                        331/111
cgt gcg gtc ggg atc gac ctc ggg acc acc aac tcc gtc gtc tcg gtt ctg gaa ggt ggc 361/121                        391/131
gac ccg gtc gtc gtc gcc aac tcc gag ggc tcc agg acc acc ccg tca att gtc gcg ttc 421/141                        451/151
gcc cgc aac ggt gag gtg ctg gtc ggc cag ccc gcc aag aac cag gca gtg acc aac gtc
```

-continued

LISTING OF ADDITIONAL SEQUENCES

481/161                              511/171
gat cgc acc gtg cgc tcg gtc aag cga cac atg ggc agc gac tgg tcc ata gag att gac 541/181                              571/191
ggc aag aaa tac acc gcg ccg gag atc agc gcc cgc att ctg atg aag ctg aag cgc gac 601/201                              631/211
gcc gag gcc tac ctc ggt gag gac att acc gac gcg gtt atc acg acg ccc gcc tac ttc 661/221                              691/231
aat gac gcc cag cgt cag gcc acc aag gac gcc ggc cag atc gcc ggc ctc aac gtg ctg 721/241                              751/251
cgg atc gtc aac gag ccg acc gcg gcc gcg ctg gcc tac ggc ctc gac aag ggc gag aag 781/261                              811/271
gag cag cga atc ctg gtc ttc gac ttg ggt ggt ggc act ttc gac gtt ccc ctg ctg gag 841/281                              871/291
atc ggc gag ggt gtg gtt gag gtc cgt gcc act tcg ggt gac aac cac ctc ggc ggc gac 901/301                              931/311
gac tgg gac cag cgg gtc gtc gat tgg ctg gtg gac aag ttc aag ggc acc agc ggc atc 961/321                              991/331
gat ctg acc aag gac aag atg gcg atg cag cgg ctg cgg gaa gcc gcc gag aag gca aag 1021/341                             1051/351
atc gag ctg agt tcg agt cag tcc acc tcg atc aac ctg ccc tac atc acc gtc gac gcc 1081/361                             1111/371
gac aag aac ccg ttg ttc tta gac gag cag ctg acc cgc gcg gag ttc caa cgg atc act 1141/381                             1171/391
cag gac ctg ctg gac cgc act cgc aag ccg ttc cag tcg gtg atc gct gac acc ggc att 1201/401                             1231/411
tcg gtg tcg gag atc gat cac gtt gtg ctc gtg ggt ggt tcg acc cgg atg ccc gcg gtg 1261/421                             1291/431
acc gat ctg gtc aag gaa ctc acc ggc ggc aag gaa ccc aac aag ggc gtc aac ccc gat 1321/441                             1351/451
gag gtt gtc gcg gtg gga gcc gct ctg cag gcc ggc gtc ctc aag ggc gag gtg aaa gac 1381/461                             1411/471
gtt ctg ctg ctt gat gtt acc ccg ctg agc ctg ggt atc gag acc aag ggc ggg gtg atg 1441/481                             1471/491
acc agg ctc atc gag cgc aac acc acg atc ccc acc aag cgg tcg gag act ttc acc acc 1501/501                             1531/511
gcc gac gac aac caa ccg tcg gtg cag atc cag gtc tat cag ggg gag cgt gag atc gcc 1561/521                             1591/531
gcg cac aac aag ttg ctc ggg tcc ttc gag ctg acc ggc atc ccg ccg gcg ccg cgg ggg 1621/541                             1651/551
att ccg cag atc gag gtc act ttc gac atc gac gcc aac ggc att gtg cac gtc acc gcc 1681/561                             1711/571
aag gac aag ggc acc ggc aag gag aac acg atc cga atc cag gaa ggc tcg ggc ctg tcc 1741/581                             1771/591
aag gaa gac att gac cgc atg atc aag gac gcc gaa gcg cac gcc gag gag gat cgc aag 1801/601                             1831/611
cgt cgc gag gag gcc gat gtt cgt aat caa gcc gag aca ttg tcc tac cag acg gag aag 1861/621                             1891/631
ttc gtc aaa gaa cag cgt gag gcc gag ggt ggt tcg aag gta cct gaa gac acg ctg aac 1921/641                             1951/651
aag gtt gat gcc gcg gtg gcg gaa gcg aag gcg gca ctt ggc gga tcg gat att tcg gcc -continued

LISTING OF ADDITIONAL SEQUENCES

1981/661
atc aag tcg gcg atg gag aag ctg ggc cag

2011/671
gag tcg cag gct ctg ggg caa gcg atc tac

2041/681
gaa gca gct cag gct gcg tca cag gcc act

2071/691
ggc gct gcc cac ccc ggc tcg gct gat gaA

2101/701
AGC a

SEQ ID NO: 16
1/1
Met His Gly Asp Thr Pro Thr Leu His Glu

31/11
Tyr Met Leu Asp Leu Gln Pro Glu Thr Thr

61/21
Asp Leu Tyr Cys Tyr Glu Gln Leu Asn Asp

91/31
Ser Ser Glu Glu Glu Asp Glu Ile Asp Gly

121/41
Pro Ala Gly Gln Ala Glu Pro Asp Arg Ala

151/51
His Tyr Asn Ile Val Thr Phe Cys Cys Lys

181/61
Cys Asp Ser Thr Leu Arg Leu Cys Val Gln

211/71
Ser Thr His Val Asp Ile Arg Thr Leu Glu

241/81
Asp Leu Leu Met Gly Thr Leu Gly Ile Val

271/91
Cys Pro Ile Cys Ser Gln Gly Ser Met ala

301/101
Arg Ala Val Gly Ile Asp Leu Gly Thr Thr

331/111
Asn Ser Val Val Ser Val Leu Glu Gly Gly

361/121
Asp Pro Val Val Val Ala Asn Ser Glu Gly

391/131
Ser Arg Thr Thr Pro Ser Ile Val Ala Phe

421/141
Ala Arg Asn Gly Glu Val Leu Val Gly Gln

451/151
Pro Ala Lys Asn Gln Ala Val Thr Asn Val

481/161
Asp Arg Thr Val Arg Ser Val Lys Arg His

511/171
Met Gly Ser Asp Trp Ser Ile Glu Ile Asp

541/181
Gly Lys Lys Tyr Thr Ala Pro Glu Ile Ser

571/191
Ala Arg Ile Leu Met Lys Leu Lys Arg Asp

601/201
Ala Glu Ala Tyr Leu Gly Glu Asp Ile Thr

631/211
Asp Ala Val Ile Thr Thr Pro Ala Tyr Phe

661/221
Asn Asp Ala Gln Arg Gln Ala Thr Lys Asp

691/231
Ala Gly Gln Ile Ala Gly Leu Asn Val Leu

721/241
Arg Ile Val Asn Glu Pro Thr Ala Ala Ala

751/251
Leu Ala Tyr Gly Leu Asp Lys Gly Glu Lys

781/261
Glu Gln Arg Ile Leu Val Phe Asp Leu Gly

811/271
Gly Gly Thr Phe Asp Val Ser Leu Leu Glu

841/281
Ile Gly Glu Gly Val Val Glu Val Arg Ala

871/291
Thr Ser Gly Asp Asn His Leu Gly Gly Asp

901/301
Asp Trp Asp Gln Arg Val Val Asp Trp Leu

931/311
Val Asp Lys Phe Lys Gly Thr Ser Gly Ile

961/321
Asp Leu Thr Lys Asp Lys Met ala Met Gln

991/331
Arg Leu Arg Glu Ala Ala Glu Lys Ala Lys

1021/341
Ile Glu Leu Ser Ser Ser Gln Ser Thr Ser

1051/351
Ile Asn Leu Pro Tyr Ile Thr Val Asp Ala

1081/361
Asp Lys Asn Pro Leu Phe Leu Asp Glu Gln

1111/371
Leu Thr Arg Ala Glu Phe Gln Arg Ile Thr

1141/381
Gln Asp Leu Leu Asp Arg Thr Arg Lys Pro

1171/391
Phe Gln Ser Val Ile Ala Asp Thr Gly Ile

1201/401
Ser Val Ser Glu Ile Asp His Val Val Leu

1231/411
Val Gly Gly Ser Thr Arg Met Pro Ala Val

1261/421
Thr Asp Leu Val Lys Glu Leu Thr Gly Gly

1291/431
Lys Glu Pro Asn Lys Gly Val Asn Pro Asp

-continued

| LISTING OF ADDITIONAL SEQUENCES |
|---|

1321/441                           1351/451
Glu Val Val Ala Val Gly Ala Ala Leu Gln Ala Gly Val Leu Lys Gly Glu Val Lys Asp

1381/461                           1411/471
Val Leu Leu Leu Asp Val Thr Pro Leu Ser Leu Gly Ile Glu Thr Lys Gly Gly Val Met

1441/481                           1471/491
Thr Arg Leu Ile Glu Arg Asn Thr Thr Ile Pro Thr Lys Arg Ser Glu Thr Phe Thr Thr

1501/501                           1531/511
Ala Asp Asp Asn Gln Pro Ser Val Gln Ile Gln Val Tyr Gln Gly Glu Arg Glu Ile Ala

1561/521                           1591/531
Ala His Asn Lys Leu Leu Gly Ser Phe Glu Leu Thr Gly Ile Pro Pro Ala Pro Arg Gly

1621/541                           1651/551
Ile Pro Gln Ile Glu Val Thr Phe Asp Ile Asp Ala Asn Gly Ile Val His Val Thr Ala

1681/561                           1711/571
Lys Asp Lys Gly Thr Gly Lys Glu Asn Thr Ile Arg Ile Gln Glu Gly Ser Gly Leu Ser

1741/581                           1771/591
Lys Glu Asp Ile Asp Arg Met Ile Lys Asp Ala Glu Ala His Ala Glu Asp Arg Lys

1801/601                           1831/611
Arg Arg Glu Glu Ala Asp Val Arg Asn Gln Ala Glu Thr Leu Val Tyr Gln Thr Glu Lys

1861/621                           1891/631
Phe Val Lys Glu Gln Arg Glu Ala Glu Gly Gly Ser Lys Val Pro Glu Asp Thr Leu Asn

1921/641                           1951/651
Lys Val Asp Ala Ala Val Ala Glu Ala Lys Ala Ala Leu Gly Gly Ser Asp Ile Ser Ala

1981/661                           2011/671
Ile Lys Ser Ala Met Glu Lys Leu Gly Gln Glu Ser Gln Ala Leu Gly Gln Ala Ile Tyr

2041/681                           2071/691
GLU ALA ALA GLN ALA ALA SER GLN ALA THR GLY ALA ALA HIS PRO GLY SER ALA ASP GLU

2101/701
Ser

SEQ ID NO: 17
ctgcagctgg tcaggccgtt tccgcaacgc ttgaagtcct ggccgatata ccggcagggc cagccatcgt tcgacgaata
aagccacctc agccatgatg cccttttcat ccccagcgga accccgacat ggacgccaaa gccctgctcc tcggcagcct
ctgcctggcc gccccattcg ccgacgcggc gacgctcgac aatgctctct ccgcctgcct cgccgcccgg ctcggtgcac
cgcacacggc ggagggccag ttgcacctgc cactcaccct tgaggcccgg cgctccaccg gcgaatgcgg ctgtacctcg
gcgctggtgc gatatcggct gctggccagg ggcgccagcg ccgacagcct cgtgcttcaa gagggctgct cgatagtcgc
caggacacgc cgccgcacgct gaccctggcg gcggacgccg gcttggcgag cggccgcgaa ctggtcgtca ccctgggttg
tcaggcgcct gactgacagg ccgggctgcc accaccagge cgagatggac gccctgcatg tatcctccga tcggcaagcc
tcccgttcgc acattcacca ctctgcaatc cagttcataa atcccataaa agccctcttc cgctccccgc cagcctcccc
gcatcccgca ccctagacgc cccgccgctc tccgccggct cgcccgacaa gaaaaaccaa ccgctcgatc agcctcatcc
ttcacccatc acaggagcca tcgcgatgca cctgataccc cattggatcc ccctggtcgc cagcctcggc ctgctcgccg
gcggctcgtc cgcgtccgcc gccgaggaag ccttcgacct ctggaacgaa tgcgccaaag cctgcgtgct cgacctcaag
gacggcgtgc gttccagccg catgagcgtc gacccggcca tcgccgacac caacggccag ggcgtgctgc actactccat
ggtcctggag ggcggcaacg acgcgctcaa gctggccatc gacaacgccc tcagcatcac cagcgacggc ctgaccatcc
gcctcgaagg cggcgtcgag ccgaacaagc cggtgcgcta cagctacacg cgccaggcgc cggcagttg gtcgctgaac
tggctggtac cgatcggcca cgagaagccc tcgaacatca aggtgttcat ccacgaactg aacgccggca ccagctcag
ccacatgtcg ccgatctaca ccatcgagat gggcgacgag ttgctggcga agctggcgcg cgatgccacc ttcttcgtca
gggcgcacga gagcaacgag atgcagccga cgctcgccat cagccatgcc ggggtcagcg tggtcatgcc ccagacccag
ccgcgccggg aaaagcgctg gagcgaatgg gccagcggca aggtgttgtg cctgctcgac ccgctggacg gggtctacaa
ctacctcgcc cagcaacgct gcaacctcga cgataccctgg gaaggcaaga tctaccgggt gctcgccggc aacccggcga
agcatgacct ggacatcaaa cccacggtca tcagtcatcg cctgcacttt ccgagggcg gcagcctggc cgcgctgacc
gcgcaccagg cttgccacct gccgctggag actttcaccc gtcatcgcca gccgcgcggc tgggaacaac tggagcagtg
cggctatccg gtgcagcggc tggtcgccct ctacctggcg gcgcggctgt cgtggaacca ggtcgaccag gtgatccgca
acgccctggc cagccccggc agcggcggcg acctgggcga agcgatccgc gagcagccga agcaggcccg tctgccctg
accctggccg ccgccgagag cgagcgcttc gtccggcagg gcaccggcaa cgacgaggcc ggcgcggcca acgccgacgt
ggtgagcctg acctgcccgg tcgccgccgg tgaatgcgcg ggcccggcgg acagcggcga cgccctgctg gagcgcaact
atcccactgg cgcggagttc ctcggcgacg gcggcgacgt cagcttcagc acccgcggca cgcagaactg gacggtggag
cggctgctcc aggcgcaccg caactggaag gagcgcggct atgtgttcgt cggctaccac ggcaccttcc tcgaagcgca
gcaaagcatc gtcttcggcg gggtgcgcgc gcgcagccag gacctcgacg cgatctggcc cggtttctat atcgccggcg
atccggcgct ggcctacggc tacgcccagg accaggaacc cgacgcacgc ggccggatcc gcaacggtgc cctgctgcgc
gtctatgtgc cgcgctcgag cctgccgggc ttctaccgca ccagcctgac cctgccgcg ccggaggcgg cgggcgaggt
cgaacgctg atcggccatc cgctgccgct ggcctggac gccatcaccg gcccgagga ggaaggcggg cgcctggaga
ccattctcgg ctgccgctg gccgagcgca ccgtggtgat tccctcggcg atccccaccg acccgcgcaa cgtcggcggc -continued

LISTING OF ADDITIONAL SEQUENCES

```
gacctcgacc cgtccagcat ccccgacaag gaacaggcga tcagcgccct gccggactac gccagccagc ccggcaaacc
gccgcgcgag gacctgaagt aactgccgcg accggccggc tcccttcgca ggagccggcc ttctcggggc ctggccatac
atcaggtttt cctgatgcca gcccaatcga atatgaattc 2760
```

SEQ ID NO: 18
*NHLIPHWIPL VASLGLLAGG SSASA*AEEAF DLWNECAKAC VLDLKDGVRS SRMSVDPAIA DTNGQGVLHY SMVLEGGNDA
LKLAIDNALS ITSDGLTIRL EGGVEPNKPV RYSYTRQARG SWSLNWLVPI GHEKPSNIKV FIHELNAGNQ LSHMSPIYTI
EMGDELLAKL ARDATFFVRA HESNEMQPTL AISHAGVSVV MAQTQPRREK RWSEWASGKV LCLLDPLDGV YNYLAQQRCN
LDDTWEGKIY RVLAGNPAKH DLDIKPTVIS HRLHFPEGGS LAALTAHQAC HLPLETFTRH RQPRGWEQLE QCGYPVQRLV
ALYLAARLSW NQVDQVIRNA LASPGSGGDL GEAIREQPEQ ARLALTLAAA ESERFVRQGT GNDEAGAANA DVVSLTCPVA
AGECAGPADS GDALLERNYP TGAEFLGDGG DVSFSTRGTQ NWTVERLLQA HRQLEERGYV FVGYHGTFLE AAQSIVFGGV
RARSQDLDAI WRGFYIAGDP ALAYGYAQDQ EPDARGRIRN GALLRVYVPR SSLPGFYRTS LTLAAPEAAG EVERLIGHPL
PLRLDAITGP EEEGGRLETI LGWPLAERTV VIPSAIPTDP RNVGGDLDPS SIPDKEQAIS ALPDYASQPG KPPREDLK
     638

SEQ ID NO: 19
RLHFPEGGSL AALTAHQACH LPLETFTRHR QPRGWEQLEQ CGYPVQRLVA LYLAARLSWN QVDQVIRNAL ASPGSGGDLG
EAIREQPEQA RLALTLAAAE SERFVRQGTG NDEAGAANAD VVSLTCPVAA GECAGPADSG DALLERNYPT GAEFLGDGGD
VSFSTRGTQN W    171

SEQ ID NO: 20
```
1/1                          31/11
atg cgc ctg cac ttt ccc gag ggc ggc agc ctg gcc gcg ctg acc gcg cac cag gct tgc 61/21                        91/31
cac ctg ccg ctg gag act ttc acc cgt cat cgc cag ccg cgc ggc tgg gaa caa ctg gag 121/41                       151/51
cag tgc ggc tat ccg gtg cag cgg ctg gtc gcc ctc tac ctg gcg gcg cgg ctg tcg tgg 181/61                       211/71
aac cag gtc gac cag gtg atc cgc aac gcc ctg gcc agc ccc ggc agc ggc ggc gac ctg 241/81                       271/91
ggc gaa gcg atc cgc gag cag ccg gag cag gcc cgt ctg gcc ctg acc ctg gcc gcc gcc 301/101                      331/111
gag agc gag cgc ttc gtc cgg cag ggc acc ggc aac gac gag gcc ggc gcg gcc aac gcc 361/121                      391/131
gac gtg gtg agc ctg acc tgc ccg gtc gcc gcc ggt gaa tgc gcg ggc ccg gcg gac agc 421/141                      451/151
ggc gac gcc ctg ctg gag cgc aac tat ccc act ggc gcg gag ttc ctc ggc gac ggc ggc 481/161                      511/171
gac gtc agc ttc agc acc cgc ggc acg cag aac gaa ttc atg cat gga gat aca cct aca 541/181                      571/191
ttg cat gaa tat atg tta gat ttg caa cca gag aca act gat ctc tac tgt tat gag caa 601/201                      631/211
tta aat gac agc tca gag gag gag gat gaa ata gat ggt cca gct gga caa gca gaa ccg 661/221                      691/231
gac aga gcc cat tac aat att gta acc ttt tgt tgc aag tgt gac tct acg ctt cgg ttg 721/241                      751/251
tgc gta caa agc aca cac gta gac att cgt act ttg gaa gac ctg tta atg ggc aca cta 781/261                      811/271
gga att gtg tgc ccc atc tgt tct caa gga tcc gag ctc ggt acc aag ctt aag ttt aaa 841/281
ccg ctg atc agc ctc gac tgt gcc ttc tag
```

SEQ ID NO: 21
```
1/1                          31/11
Met arg leu his phe pro glu gly gly ser leu ala ala leu thr ala his gln ala cys 61/21                        91/31
His Leu Pro Leu Glu Thr Phe Thr Arg His Arg Gln Pro Arg Gly Trp Glu Gln Leu Glu 121/41                       151/51
Gln Cys Gly Tyr Pro Val Gln Arg Leu Val Ala Leu Tyr Leu Ala Ala Arg Leu Ser Trp

181/61                       211/71
```

```
                    LISTING OF ADDITIONAL SEQUENCES
Asn Gln Val Asp Gln Val Ile Arg Asn Ala Leu Ala Ser Pro Gly Ser Gly Gly Asp Leu

241/81                                271/91
Gly Glu Ala Ile Arg Glu Gln Pro Glu Gln Ala Arg Leu Ala Leu Thr Leu Ala Ala Ala

301/101                               331/111
Glu Ser Glu Arg Phe Val Arg Gln Gly Thr Gly Asn Asp Glu Ala Gly Ala Ala Asn Ala

361/121                               391/131
Asp Val Val Ser Leu Thr Cys Pro Val Ala Ala Gly Glu Cys Ala Gly Pro Ala Asp Ser

421/141                               451/151
Gly Asp Ala Leu Leu Glu Arg Asn Tyr Pro Thr Gly Ala Glu Phe Leu Gly Asp Gly Gly

481/161                               511/171
Asp Val Ser Phe Ser Thr Arg Gly Thr Gln Asn Glu Phe Met His Gly Asp Thr Pro Thr

541/181                               571/191
Leu His Glu Tyr Met Leu Asp Leu Gln Pro Glu Thr Thr Asp Leu Tyr Cys Tyr Glu Gln

601/201                               631/211
Leu Asn Asp Ser Ser Glu Glu Glu Asp Glu Ile Asp Gly Pro Ala Gly Gln Ala Glu Pro

661/221                               691/231
Asp Arg Ala His Tyr Asn Ile Val Thr Phe Cys Cys Lys Cys Asp Ser Thr Leu Arg Leu

721/241                               751/251
Cys Val Gln Ser Thr His Val Asp Ile Arg Thr Leu Glu Asp Leu Leu Met Gly Thr Leu

781/261                               811/271
Gly Ile Val Cys Pro Ile Cys Ser Gln *Gly Ser Glu Leu Gly Thr Lys Leu Lys Phe Lys*

841/281
ccg ctg atc agc ctc gac tgt gcc ttc tag
```

SEQ ID NO: 22

```
atg acc tct cgc cgc tcc gtg aag tcg ggt ccg cgg gag gtt ccg cgc    48
Met Thr Ser Arg Arg Ser Val Lys Ser Gly Pro Arg Glu Val Pro Arg
1               5                   10                  15 gat gag tac gag gat ctg tac tac acc ccg tct tca ggt atg gcg agt    96
Asp Glu Tyr Glu Asp Leu Tyr Tyr Thr Pro Ser Ser Gly Met Ala Ser
                20                  25                  30 ccc gat agt ccg cct gac acc tcc cgc cgt ggc gcc cta cag aca cgc   144
Pro Asp Ser Pro Pro Asp Thr Ser Arg Arg Gly Ala Leu Gln Thr Arg
        35                  40                  45 tcg cgc cag agg ggc gag gtc cgt ttc gtc cag tac gac gag tcg gat   192
Ser Arg Gln Arg Gly Glu Val Arg Phe Val Gln Tyr Asp Glu Ser Asp
    50                  55                  60 tat gcc ctc tac ggg ggc tcg tct tcc gaa gac gac gaa cac ccg gag   240
Tyr Ala Leu Tyr Gly Gly Ser Ser Ser Glu Asp Asp Glu His Pro Glu
65              70                  75                  80 gtc ccc cgg acg cgg cgt ccc gtt tcc ggg gcg gtt ttg tcc ggc ccg   288
Val Pro Arg Thr Arg Arg Pro Val Ser Gly Ala Val Leu Ser Gly Pro
                85                  90                  95 ggg cct gcg cgg gcg cct ccg cca ccc gct ggg tcc gga ggg gcc gga   336
Gly Pro Ala Arg Ala Pro Pro Pro Pro Ala Gly Ser Gly Gly Ala Gly
        100                 105                 110 cgc aca ccc acc acc gcc ccc cgg gcc ccc cga acc cag cgg gtg gcg   384
Arg Thr Pro Thr Thr Ala Pro Arg Ala Pro Arg Thr Gln Arg Val Ala
    115                 120                 125 tct aag gcc ccc gcg gcc ccg gcg gcg gag acc acc cgc ggc agg aaa   432
Ser Lys Ala Pro Ala Ala Pro Ala Ala Glu Thr Thr Arg Gly Arg Lys
130                 135                 140 tcg gcc cag cca gaa tcc gcc gca ctc cca gac gcc ccc gcg tcg acg   480
Ser Ala Gln Pro Glu Ser Ala Ala Leu Pro Asp Ala Pro Ala Ser Thr
145                 150                 155                 160 gcg cca acc cga tcc aag aca ccc gcg cag ggg ctg gcc aga aag ctg   528
```

| | |
|---|---|
| Ala Pro Thr Arg Ser Lys Thr Pro Ala Gln Gly Leu Ala Arg Lys Leu<br>              165                       170                     175 | |
| cac ttt agc acc gcc ccc cca aac ccc gac gcg cca tgg acc ccc cgg<br>His Phe Ser Thr Ala Pro Pro Asn Pro Asp Ala Pro Trp Thr Pro Arg<br>              180                       185                     190 | 576 |
| gtg gcc ggc ttt aac aag cgc gtc ttc tgc gcc gcg gtc ggg cgc ctg<br>Val Ala Gly Phe Asn Lys Arg Val Phe Cys Ala Ala Val Gly Arg Leu<br>              195                       200                     205 | 624 |
| gcg gcc atg cat gcc cgg atg gcg gct gtc cag ctc tgg gac atg tcg<br>Ala Ala Met His Ala Arg Met Ala Ala Val Gln Leu Trp Asp Met Ser<br>210                     215                       220 | 672 |
| cgt ccg cgc aca gac gaa gac ctc aac gaa ctc ctt ggc atc acc acc<br>Arg Pro Arg Thr Asp Glu Asp Leu Asn Glu Leu Leu Gly Ile Thr Thr<br>225                   230                     235                   240 | 720 |
| atc cgc gtg acg gtc tgc gag ggc aaa aac ctg ctt cag cgc gcc aac<br>Ile Arg Val Thr Val Cys Glu Gly Lys Asn Leu Leu Gln Arg Ala Asn<br>              245                       250                     255 | 768 |
| gag ttg gtg aat cca gac gtg gtg cag gac gtc gac gcg gcc acg gcg<br>Glu Leu Val Asn Pro Asp Val Val Gln Asp Val Asp Ala Ala Thr Ala<br>                    260                     265                     270 | 816 |
| act cga ggg cgt tct gcg gcg tcg cgc ccc acc gag cga cct cga gcc<br>Thr Arg Gly Arg Ser Ala Ala Ser Arg Pro Thr Glu Arg Pro Arg Ala<br>              275                       280                     285 | 864 |
| cca gcc cgc tcc gct tct cgc ccc aga cgg ccc gtc gag ggt acc gag<br>Pro Ala Arg Ser Ala Ser Arg Pro Arg Arg Pro Val Glu Gly Thr Glu<br>              290                       295                     300 | 912 |
| ctc gga tcc atg cat gga gat aca cct aca ttg cat gaa tat atg tta<br>Leu Gly Ser Met His Gly Asp Thr Pro Thr Leu His Glu Tyr Met Leu<br>305                     310                     315                   320 | 960 |
| gat ttg caa cca gag aca act gat ctc tac tgt tat gag caa tta aat<br>Asp Leu Gln Pro Glu Thr Thr Asp Leu Tyr Cys Tyr Glu Gln Leu Asn<br>              325                       330                     335 | 1008 |
| gac agc tca gag gag gag gat gaa ata gat ggt cca gct gga caa gca<br>Asp Ser Ser Glu Glu Glu Asp Glu Ile Asp Gly Pro Ala Gly Gln Ala<br>                    340                     345                     350 | 1056 |
| gaa ccg gac aga gcc cat tac aat att gta acc ttt tgt tgc aag tgt<br>Glu Pro Asp Arg Ala His Tyr Asn Ile Val Thr Phe Cys Cys Lys Cys<br>              355                       360                     365 | 1104 |
| gac tct acg ctt cgg ttg tgc gta caa agc aca cac gta gac att cgt<br>Asp Ser Thr Leu Arg Leu Cys Val Gln Ser Thr His Val Asp Ile Arg<br>              370                       375                     380 | 1152 |
| act ttg gaa gac ctg tta atg ggc aca cta gga att gtg tgc ccc atc<br>Thr Leu Glu Asp Leu Leu Met Gly Thr Leu Gly Ile Val Cys Pro Ile<br>385                     390                     395                   400 | 1200 |
| tgt tct cag gat aag ctt aag ttt aaa ccg ctg atc agc ctc gac tgt<br>Cys Ser Gln Asp Lys Leu Lys Phe Lys Pro Leu Ile Ser Leu Asp Cys<br>              405                       410                     415 | 1248 |
| gcc ttc tag<br>Ala Phe | 1257 |

SEQ ID NO: 23

```
  1         atgctgctat ccgtgccgct gctgctcggc ctcctcggcc tggccgtcgc cgagcccgcc 61         gtctacttca aggagcagtt tctggacgga gacgggtgga cttcccgctg gatcgaatcc 121         aaacacaagt cagattttgg caaattcgtt ctcagttccg gcaagttcta cggtgacgag 181         gagaaagata aggtttgcag acaagccag gatgcacgct tttatgctct gtcggccagt 241         ttcgagcctt tcagcaacaa aggccagacg ctggtggtgc agttcacggt gaaacatgag
```

| | |
|---|---|
| 301 | cagaacatcg actgtggggg cggctatgtg aagctgtttc ctaatagttt ggaccagaca |
| 361 | gacatgcacg gagactcaga atacaacatc atgtttggtc ccgacatctg tggccctggc |
| 421 | accaagaagg ttcatgtcat cttcaactac aagggcaaga acgtgctgat caacaaggac |
| 481 | atccgttgca aggatgatga gtttacacac ctgtacacac tgattgtgcg gccagacaac |
| 541 | acctatgagg tgaagattga caacagccag gtggagtccg gctccttgga agacgattgg |
| 601 | gacttcctgc cacccaagaa gataaaggat cctgatgctt caaaaccgga agactgggat |
| 661 | gagcgggcca agatcgatga tcccacagac tccaagcctg aggactggga caagcccgag |
| 721 | catatccctg accctgatgc taagaagccc gaggactggg atgaagagat ggacggagag |
| 781 | tgggaacccc cagtgattca gaaccctgag tacaagggtg agtggaagcc ccggcagatc |
| 841 | gacaacccag attacaaggg cacttggatc cacccagaaa ttgacaaccc cgagtattct |
| 901 | cccgatccca gtatctatgc ctatgataac tttggcgtgc tgggcctgga cctctggcag |
| 961 | gtcaagtctg gcaccatctt tgacaacttc ctcatcacca acgatgaggc atacgctgag |
| 1021 | gagtttggca cgagacgtg gggcgtaaca aaggcagcag agaaacaaat gaaggacaaa |
| 1081 | caggacgagg agcagaggct aaggaggag gaagaagaca agaaacgcaa agaggaggag |
| 1141 | gaggcagagg acaaggagga tgatgaggac aaagatgagg atgaggagga tgaggaggac |
| 1201 | aaggaggaag atgaggagga agatgtcccc ggccaggcca aggacgagct gtag | 1251 |

SEQ ID NO: 24
1     MLLSVPLLLG LLGLAVAEPA VYFKEQFLDG DGWTSRWIES KHKSDFGKFV LSSGKFYGDE
61    EKDKGLQTSQ DARFYALSAS FEPFSNKGQT LVVQFTVKHE QNIDCGGGYV KLFPNSLDQT
121   DMHGDSEYNI MFGPDICGPG TKKVHVIFNY KGKNVLINKD IRCKDDEFTH LYTLIVRPDN
181   TYEVKIDNSQ VESGSLEDDW DFLPPKKIKD PDASKPEDWD ERAKIDDPTD SKPEDWDKPE
241   HIPDPDAKKP EDWDEEMDGE WEPPVIQNPE YKGEWKPRQI DNPDYKGTWI HPEIDNPEYS
301   PDPSIYAYDN FGVLGLDLWQ VKSGTIFDNF LITNDEAYAE EFGNETWGVT KAAEKQMKDK
361   QDEEQRLKEE EEDKKRKEEE EAEDKEDDED KDEDEEDEED KEEDEEEDVP GQAKDEL     417

SEQ ID NO: 25
1     MLLSVPLLLG LLGLAVAEPA VYFKEQFLDG DGWTSRWIES KHKSDFGKFV LSSGKFYGDE
61    EKDKGLQTSQ DARFYALSAS FEPFSNKGQT LVVQFTVKHE QNIDCGGGYV KLFPNSLDQT
121   DMHGDSEYNI MFGPDICGPG TKKVHVIFNY KGKNVLINKD IRCKDDEFTH              170

SEQ ID NO: 26
1     LYTLIVRPDN TYEVKIDNSQ VESGSLEDDW DFLPPKKIKD PDASKPEDWD ERAKIDDPTD
61    SKPEDWDKPE HIPDPDAKKP EDWDEEMDGE WEPPVIQNPE YKGEWKPRQ               109

SEQ ID NO: 27
1     IDNPDYKGTW IHPEIDNPEY SPDPSIYAYD NFGVLGLDLW QVKSGTIFDN FLITNDEAYA
61    EEFGNETWGV TKAAEKQMKD KQDEEQRLKE EEEDKKRKEE EFAEDKEDDE DKDEDEEDEE
121   DKEEDEEEDV PGQAKDEL                                                138

SEQ ID NO: 28
1     ATGCTGCTAT CCGTGCCGCT GCTGCTCGGC CTCCTCGGCC TGGCCGTCGC CGAGCCCGCC
61    GTCTACTTCA AGGAGCAGTT TCTGGACGGA GACGGGTGGA CTTCCCGCTG GATCGAATCC
121   AAACACAAGT CAGATTTTGG CAAATTCGTT CTCAGTTCCG GCAAGTTCTA CGGTGACGAG
181   GAGAAAGATA AAGGTTTGCA GACAAGCCAG GATGCACGCT TTTATGCTCT GTCGGCCAGT
241   TTCGAGCCTT TCAGCAACAA AGGCCAGACG CTGGTGGTGC AGTTCACGGT GAAACATGAG

| | |
|---|---|
| 301 | CAGAACATCG ACTGTGGGGG CGGCTATGTG AAGCTGTTTC CTAATAGTTT GGACCAGACA |
| 361 | GACATGCACG GAGACTCAGA ATACAACATC ATGTTTGGTC CCGACATCTG TGGCCCTGGC |
| 421 | ACCAAGAAGG TTCATGTCAT CTTCAACTAC AAGGGCAAGA ACGTGCTGAT CAACAAGGAC |
| 481 | ATCCGTTGCA AGGATGATGA GTTTACACAC CTGTACACAC TGATTGTGCG GCCAGACAAC |
| 541 | *acctatgagg tgaagattga caacagccag gtggagtccg gctccttgga agacgattgg* |
| 601 | *gacttcctgc cacccaagaa gataaaggat cctgatgctt caaaaccgga agactgggat* |
| 661 | *gagcgggcca agatcgatga tcccacagac tccaagcctg aggactggga caagcccgag* |
| 721 | *catatccctg accctgatgc taagaagccc gaggactggg atgaagagat ggacggagag* |
| 781 | *tgggaacccc cagtgattca gaaccct*gag tacaagggtg agtggaagcc ccggcagatc |
| 841 | gacaacccag attacaaggg cacttggatc cacccagaaa ttgacaaccc cgagtattct |
| 901 | cccgatccca gtatctatgc ctatgataac tttggcgtgc tgggcctgga cctctggcag |
| 961 | gtcaagtctg gcaccatctt tgacaacttc ctcatcacca cgatgaggc atacgctgag |
| 1021 | gagtttggca cgagacgtg gggcgtaaca aaggcagcag agaaacaaat gaaggacaaa |
| 1081 | caggacgagg agcagaggct taaggaggag gaagaagaca agaaacgcaa agaggaggag |
| 1141 | gaggcagagg acaaggagga tgatgaggac aaagatgagg atgaggagga tgaggaggac |
| 1201 | aaggaggaag atgaggagga agatgtcccc ggccaggcca aggacgagct <u>gtag</u> 1251 |

SEQ ID NO: 29

| | |
|---|---|
| 1 | ATGCTGCTAT CCGTGCCGCT GCTGCTCGGC CTCCTCGGCC TGGCCGTCGC CGAGCCCGCC |
| 61 | GTCTACTTCA AGGAGCAGTT TCTGGAC<u>GGA</u> GACGGGTGGA CTTCCCGCTG GATCGAATCC |
| 121 | AAACACAAGT CAGATTTTGG CAAATTCGTT CTCAGTTCCG GCAAGTTCTA CGGTGACGAG |
| 181 | GAGAAAGATA AAGGTTTGCA GACAAGCCAG GATGCACGCT TTTATGCTCT GTCGGCCAGT |
| 241 | TTCGAGCCTT TCAGCAACAA AGGCCAGACG CTGGTGGTGC AGTTCACGGT GAAACATGAG |
| 301 | CAGAACATCG ACTGTGGGGG CGGCTATGTG AAGCTGTTTC CTAATAGTTT GGACCAGACA |
| 361 | GACATGCACG GAGACTCAGA ATACAACATC ATGTTTGGTC CCGACATCTG TGGCCCTGGC |
| 421 | ACCAAGAAGG TTCATGTCAT CTTCAACTAC AAGGGCAAGA ACGTGCTGAT CAACAAGGAC |
| 481 | ATCCGTTGCA AGGATGATGA GTTTACACAC CTGTACACAC TGATTGTGCG GCCAGACAAC |

SEQ ID NO: 30

| | |
|---|---|
| 1 | acctatgagg tgaagattga caacagccag gtggagtccg gctccttgga agacgattgg |
| 61 | gacttcctgc cacccaagaa gataaaggat cctgatgctt caaaaccgga agactgggat |
| 121 | gagcgggcca agatcgatga tcccacagac tccaagcctg aggactggga caagcccgag |
| 181 | catatccctg accctgatgc taagaagccc gaggactggg atgaagagat ggacggagag |
| 241 | tgggaacccc cagtgattca gaaccct 267 |

SEQ ID NO: 31

| | |
|---|---|
| 1 | gagtacaagg gtgagtggaa gccccggcag atcgacaacc cagattacaa gggcacttgg |
| 61 | atccacccag aaattgacaa ccccgagtat tctcccgatc ccagtatcta tgcctatgat |
| 121 | aactttggcg tgctgggcct ggacctctgg caggtcaagt ctggcaccat ctttgacaac |
| 181 | ttcctcatca ccacgatga ggcatacgct gaggagtttg gcaacgagac gtggggcgta |
| 241 | acaaaggcag cagagaaaca aatgaaggac aaacaggacg aggagcagag gcttaaggag |
| 301 | gaggaagaag acaagaaacg caaagaggag gaggaggcag aggacaagga ggatgatgag |

| LISTING OF ADDITIONAL SEQUENCES |
| --- |

```
 361        gacaaagatg aggatgagga ggatgaggag gacaaggagg aagatgagga ggaagatgtc
 421        cccggccagg ccaaggacga gctg             444
SEQ ID NO: 32
   1        gctccgcccc cctgacgagc atcacaaaaa tcgacgctca agtcagaggt ggcgaaaccc
  61        gacaggacta taaagatacc aggcgtttcc ccctggaagc tccctcgtgc gctctcctgt
 121        tccgaccctg ccgcttaccg gatacctgtc cgcctttctc ccttcgggaa gcgtggcgct
 181        ttctcatagc tcacgctgta ggtatctcag ttcggtgtag gtcgttcgct ccaagctggg
 241        ctgtgtgcac gaacccccg ttcagcccga ccgctgcgcc ttatccggta actatcgtct
 301        tgagtccaac ccggtaagac acgacttatc gccactggca gcagccactg gtaacaggat
 361        tagcagagcg aggtatgtag gcggtgctac agagttcttg aagtggtggc ctaactacgg
 421        ctacactaga gaacagtat ttggtatctg cgctctgctg aagccagtta ccttcggaaa
 481        aagagttggt agctcttgat ccggcaaaca aaccaccgct ggtagcggtg gtttttttgt
 541        ttgcaagcag cagattacgc gcagaaaaaa aggatctcaa gaagatcctt tgatcttttc
 601        tacggggtct gacgctcagt ggaacgaaaa ctcacgttaa gggattttgg tcatgagatt
 661        atcaaaaagg atcttcacct agatcctttt aaattaaaaa tgaagtttta aatcaatcta
 721        aagtatatat gagtaaactt ggtctgacag ttaccaatgc ttaatcagtg aggcacctat
 781        ctcagcgatc tgtctatttc gttcatccat agttgcctga ctcgggggg ggggcgctg
 841        aggtctgcct cgtgaagaag gtgttgctga ctcataccag gcaacgttg ttgccattgc
 901        tacaggcatc gtggtgtcac gctcgtcgtt tggtatggct tcattcagct ccggttccca
 961        acgatcaagg cgagttacat gatcccccat gttgtgcaaa aaagcggtta gctccttcgg
1021        tcctccgatc gttgtcagaa gtaagttggc cgcagtgtta tcactcatgg ttatggcagc
1081        actgcataat tctcttactg tcatgccatc cgtaagatgc ttttctgtga ctggtgagta
1141        ctcaaccaag tcattctgag aatagtgtat gcggcgaccg agttgctctt gcccggcgtc
1201        aatacgggat aataccgcgc cacatagcag aactttaaaa gtgctcatca ttggaaaacg
1261        ttcttcgggg cgaaaactct caaggatctt accgctgttg agatccagtt cgatgtaacc
1321        cactcgtgca cctgaatcgc cccatcatcc agccagaaag tgagggagcc acggttgatg
1381        agagctttgt tgtaggtgga ccagttggtg attttgaact tttgctttgc cacggaacgg
1441        tctgcgttgt cgggaagatg cgtgatctga tccttcaact cagcaaaagt tcgatttatt
1501        caacaaagcc gccgtcccgt caagtcagcg taatgctctg ccagtgttac aaccaattaa
1561        ccaattctga ttagaaaaac tcatcgagca tcaaatgaaa ctgcaattta ttcatatcag
1621        gattatcaat accatatttt tgaaaagcc gtttctgtaa tgaaggagaa aactcaccga
1681        ggcagttcca taggatggca agatcctggt atcggtctgc gattccgact cgtccaacat
1741        caatacaacc tattaatttc ccctcgtcaa aaataaggtt atcaagtgag aaatcaccat
1801        gagtgacgac tgaatccggt gagaatggca aaagcttatg catttctttc cagacttgtt
1861        caacaggcca gccattacgc tcgtcatcaa atcactcgc atcaaccaaa ccgttattca
1921        ttcgtgattg cgcctgagcg agacgaaata cgcgatcgct gttaaaagga caattacaaa
1981        caggaatcga atgcaaccgg cgcaggaaca ctgccagcgc atcaacaata ttttcacctg
2041        aatcaggata ttcttctaat acctggaatg ctgttttccc ggggatcgca gtggtgagta
2101        accatgcatc atcaggagta cggataaaat gcttgatggt cggaagaggc ataaattccg
```

-continued

| | LISTING OF ADDITIONAL SEQUENCES |
|---|---|
| 2161 | tcagccagtt tagtctgacc atctcatctg taacatcatt ggcaacgcta cctttgccat |
| 2221 | gtttcagaaa caactctggc gcatcgggct tcccatacaa tcgatagatt gtcgcacctg |
| 2281 | attgcccgac attatcgcga gcccatttat acccatataa atcagcatcc atgttggaat |
| 2341 | ttaatcgcgg cctcgagcaa gacgtttccc gttgaatatg gctcataaca ccccttgtat |
| 2401 | tactgtttat gtaagcagac agttttattg ttcatgatga tatatttta tcttgtgcaa |
| 2461 | tgtaacatca gagattttga dacacaacgt ggctttcccc cccccccat tattgaagca |
| 2521 | tttatcaggg ttattgtctc atgagcggat acatatttga atgtatttag aaaaataaac |
| 2581 | aaataggggt tccgcgcaca tttccccgaa aagtgccacc tgacgtctaa gaaaccatta |
| 2641 | ttatcatgac attaacctat aaaaataggc gtatcacgag gcccttttcgt ctcgcgcgtt |
| 2701 | tcggtgatga cggtgaaaac ctctgacaca tgcagctccc ggagacggtc acagcttgtc |
| 2761 | tgtaagcgga tgccgggagc agacaagccc gtcagggcgc gtcagcgggt gttggcgggt |
| 2821 | gtcggggctg gcttaactat gcggcatcag agcagattgt actgagagtg caccatatgc |
| 2881 | ggtgtgaaat accgcacaga tgcgtaagga gaaaataccg catcagattg gctattggcc |
| 2941 | attgcatacg ttgtatccat atcataatat gtacatttat attggctcat gtccaacatt |
| 3001 | accgccatgt tgacattgat tattgactag ttattaatag taatcaatta cggggtcatt |
| 3061 | agttcatagc ccatatatgg agttccgcgt tacataactt acggtaaatg gcccgcctgg |
| 3121 | ctgaccgccc aacgaccccc gcccattgac gtcaataatg acgtatgttc ccatagtaac |
| 3181 | gccaataggg actttccatt gacgtcaatg ggtggagtat ttacggtaaa ctgcccactt |
| 3241 | ggcagtacat caagtgtatc atatgccaag tacgccccct attgacgtca atgacggtaa |
| 3301 | atggcccgcc tggcattatg cccagtacat gaccttatgg gactttccta cttggcagta |
| 3361 | catctacgta ttagtcatcg ctattaccat ggtgatgcgg ttttggcagt acatcaatgg |
| 3421 | gcgtggatag cggtttgact cacggggatt tccaagtctc cacccattg acgtcaatgg |
| 3481 | gagtttgttt tggcaccaaa atcaacggga ctttccaaaa tgtcgtaaca actccgcccc |
| 3541 | attgacgcaa atgggcggta ggcgtgtacg gtgggaggtc tatataagca gagctcgttt |
| 3601 | agtgaaccgt cagatcgcct ggagacgcca tccacgctgt tttgacctcc atagaagaca |
| 3661 | ccgggaccga tccagcctcc gcggccggga acgtgcatt ggaacgcgga ttccccgtgc |
| 3721 | caagagtgac gtaagtaccg cctatagact ctataggcac accccttt gg ctcttatgca |
| 3781 | tgctatactg ttttt ggctt ggggcctata caccccgct tccttatgct ataggtgatg |
| 3841 | gtatagctta gcctataggt gtgggttatt gaccattatt gaccactcca acggtggagg |
| 3901 | gcagtgtagt ctgagcagta ctcgttgctg ccgcgcgcgc caccagacat aatagctgac |
| 3961 | agactaacag actgttcctt tccatgggtc ttttctgcag tcaccgtcgt cgacATGCTG |
| 4021 | CTATCCGTGC CGCTGCTGCT CGGCCTCCTC GGCCTGGCCG TCGCCGAGCC TGCCGTCTAC |
| 4081 | TTCAAGGAGC AGTTTCTGGA CGGGGACGGG TGGACTTCCC GCTGGATCGA ATCCAAACAC |
| 4141 | AAGTCAGATT TTGGCAAATT CGTTCTCAGT TCCGGCAAGT TCTACGGTGA CGAGGAGAAA |
| 4201 | GATAAAGGTT TGCAGACAAG CCAGGATGCA CGCTTTTATG CTCTGTCGGC CAGTTTCGAG |
| 4261 | CCTTTCAGCA ACAAAGGCCA GACGCTGGTG GTGCAGTTCA CGGTGAAACA TGAGCAGAAC |
| 4321 | ATCGACTGTG GGGGCGGCTA TGTGAAGCTG TTTCCTAATA GTTTGGACCA GACAGACATG |
| 4381 | CACGGAGACT CAGAATACAA CATCATGTTT GGTCCCGACA TCTGTGGCCC TGGCACCAAG |

LISTING OF ADDITIONAL SEQUENCES

```
4441      AAGGTTCATG TCATCTTCAA CTACAAGGGC AAGAACGTGC TGATCAACAA GGACATCCGT

4501      TGCAAGGATG ATGAGTTTAC ACACCTGTAC ACACTGATTG TGCGGCCAGA CAACACCTAT

4561      GAGGTGAAGA TTGACAACAG CCAGGTGGAG TCCGGCTCCT TGGAAGACGA TTGGGACTTC

4621      CTGCCACCCA GAAGATAAAG GATCCTGAT GCTTCAAAAC CGGAAGACTG GGATGAGCGG

4681      GCCAAGATCG ATGATCCCAC AGACTCCAAG CCTGAGGACT GGGACAAGCC CGAGCATATC

4741      CCTGACCCTG ATGCTAAGAA GCCCGAGGAC TGGGATGAAG AGATGGACGG AGAGTGGGAA

4801      CCCCCAGTGA TTCAGAACCC TGAGTACAAG GGTGAGTGGA AGCCCCGGCA GATCGACAAC

4861      CCAGATTACA AGGGCACTTG GATCCACCCA GAAATTGACA ACCCCGAGTA TTCTCCCGAT

4921      CCCAGTATCT ATGCCTATGA TAACTTTGGC GTGCTGGGCC TGGACCTCTG GCAGGTCAAG

4981      TCTGGCACCA TCTTTGACAA CTTCCTCATC ACCAACGATG AGGCATACGC TGAGGAGTTT

5041      GGCAACGAGA CGTGGGGCGT AACAAAGGCA GCAGAGAAAC AAATGAAGGA CAAACAGGAC

5101      GAGGAGCAGA GGCTTAAGGA GGAGGAAGAA GACAAGAAAC GCAAAGAGGA GGAGGAGGCA

5161      GAGGACAAGG AGGATGATGA GGACAAAGAT GAGGATGAGG AGGATGAGGA GGACAAGGAG

5221      GAAGATGAGG AGGAAGATGT CCCCGGCCAG GCCAAGGACG AGCTGgaatt CATGCATGGA

5281      GATACACCTA CATTGCATGA ATATATGTTA GATTTGCAAC CAGAGACAAC TGATCTCTAC

5341      GGTTATGGGC AATTAAATGA CAGCTCAGAG GAGGAGGATG AAATAGATGG TCCAGCTGGA

5401      CAAGCAGAAC CGGACAGAGC CCATTACAAT ATTGTAACCT TTTGTTGCAA GTGTGACTCT

5461      ACGCTTCGGT TGTGCGTACA AAGCACACAC GTAGACATTC GTACTTTGGA AGACCTGTTA

5521      ATGGGCACAC TAGGAATTGT GTGCCCATC TGTTCTCAGA AACCATAAgg atccagatct 5581      ttttccctct gccaaaaatt atggggacat catgaagccc cttgagcatc tgacttctgg 5641      ctaataaagg aaatttattt tcattgcaat agtgtgttgg aatttttgt gtctctcact 5701      cggaaggaca tatgggaggg caaatcattt aaaacatcag aatgagtatt tggtttagag 5761      tttggcaaca tatgcccatt cttccgcttc ctcgctcact gactcgctgc gctcggtcgt 5821      tcggctgcgg cgagcggtat cagctcactc aaaggcggta atacggttat ccacagaatc 5881      agggggataac gcaggaaaga acatgtgagc aaaaggccag caaaaggcca ggaaccgtaa 5941      aaaggccgcg ttgctggcgt ttttccatag      5970
```

SEQ ID NO: 33

```
atg acc tct cgc cgc tcc gtg aag tcg ggt ccg cgg gag gtt ccg cgc        48
Met Thr Ser Arg Arg Ser Val Lys Ser Gly Pro Arg Glu Val Pro Arg
1               5                   10                  15 gat gag tac gag gat ctg tac tac acc ccg tct tca ggt atg gcg agt        96
Asp Glu Tyr Glu Asp Leu Tyr Tyr Thr Pro Ser Ser Gly Met Ala Ser
            20                  25                  30 ccc gat agt ccg cct gac acc tcc cgc cgt ggc gcc cta cag aca cgc       144
Pro Asp Ser Pro Pro Asp Thr Ser Arg Arg Gly Ala Leu Gln Thr Arg
        35                  40                  45 tcg cgc cag agg ggc gag gtc cgt ttc gtc cag tac gac gag tcg gat       192
Ser Arg Gln Arg Gly Glu Val Arg Phe Val Gln Tyr Asp Glu Ser Asp
    50                  55                  60 tat gcc ctc tac ggg ggc tcg tct tcc gaa gac gac gaa cac ccg gag       240
Tyr Ala Leu Tyr Gly Gly Ser Ser Ser Glu Asp Asp Glu His Pro Glu
65                  70                  75                  80 gtc ccc cgg acg cgg cgt ccc gtt tcc ggg gcg gtt ttg tcc ggc ccg       288
Val Pro Arg Thr Arg Arg Pro Val Ser Gly Ala Val Leu Ser Gly Pro
                85                  90                  95
```

-continued

| LISTING OF ADDITIONAL SEQUENCES | |
|---|---|
| ggg cct gcg cgg gcg cct ccg cca ccc gct ggg tcc gga ggg gcc gga<br>Gly Pro Ala Arg Ala Pro Pro Pro Ala Gly Ser Gly Gly Ala Gly<br>100                    105                  110 | 336 |
| cgc aca ccc acc acc gcc ccc cgg gcc ccc cga acc cag cgg gtg gcg<br>Arg Thr Pro Thr Thr Ala Pro Arg Ala Pro Arg Thr Gln Arg Val Ala<br>115                  120                  125 | 384 |
| tct aag gcc ccc gcg gcc ccg gcg gcg gag acc acc cgc ggc agg aaa<br>Ser Lys Ala Pro Ala Ala Pro Ala Ala Glu Thr Thr Arg Gly Arg Lys<br>130                  135                  140 | 432 |
| tcg gcc cag cca gaa tcc gcc gca ctc cca gac gcc ccc gcg tcg acg<br>Ser Ala Gln Pro Glu Ser Ala Ala Leu Pro Asp Ala Pro Ala Ser Thr<br>145                  150                  155                  160 | 480 |
| gcg cca acc cga tcc aag aca ccc gcg cag ggg ctg gcc aga aag ctg<br>Ala Pro Thr Arg Ser Lys Thr Pro Ala Gln Gly Leu Ala Arg Lys Leu<br>                  165                  170                  175 | 528 |
| cac ttt agc acc gcc ccc cca aac ccc gac gcg cca tgg acc ccc cgg<br>His Phe Ser Thr Ala Pro Pro Asn Pro Asp Ala Pro Trp Thr Pro Arg<br>                180                  185                  190 | 576 |
| gtg gcc ggc ttt aac aag cgc gtc ttc tgc gcc gcg gtc ggg cgc ctg<br>Val Ala Gly Phe Asn Lys Arg Val Phe Cys Ala Ala Val Gly Arg Leu<br>        195                  200                  205 | 624 |
| gcg gcc atg cat gcc cgg atg gcg gct gtc cag ctc tgg gac atg tcg<br>Ala Ala Met His Ala Arg Met Ala Ala Val Gln Leu Trp Asp Met Ser<br>210                  215                  220 | 672 |
| cgt ccg cgc aca gac gaa gac ctc aac gaa ctc ctt ggc atc acc acc<br>Arg Pro Arg Thr Asp Glu Asp Leu Asn Glu Leu Leu Gly Ile Thr Thr<br>225                  230                  235                  240 | 720 |
| atc cgc gtg acg gtc tgc gag ggc aaa aac ctg ctt cag cgc gcc aac<br>Ile Arg Val Thr Val Cys Glu Gly Lys Asn Leu Leu Gln Arg Ala Asn<br>                245                  250                  255 | 768 |
| gag ttg gtg aat cca gac gtg gtg cag gac gtc gac gcg gcc acg gcg<br>Glu Leu Val Asn Pro Asp Val Val Gln Asp Val Asp Ala Ala Thr Ala<br>                260                  265                  270 | 816 |
| act cga ggg cgt tct gcg gcg tcg cgc ccc acc gag cga cct cga gcc<br>Thr Arg Gly Arg Ser Ala Ala Ser Arg Pro Thr Glu Arg Pro Arg Ala<br>        275                  280                  285 | 864 |
| cca gcc cgc tcc gct tct cgc ccc aga cgg ccc gtc gag<br>Pro Ala Arg Ser Ala Ser Arg Pro Arg Arg Pro Val Glu<br>290                  295                  300 | 903 |
| SEQ ID NO: 34<br>atg acc tct cgc cgc tcc gtg aag tcg ggt ccg cgg gag gtt ccg cgc<br>Met Thr Ser Arg Arg Ser Val Lys Ser Gly Pro Arg Glu Val Pro Arg<br>1                  5                  10                  15 | 48 |
| gat gag tac gag gat ctg tac tac acc ccg tct tca ggt atg gcg agt<br>Asp Glu Tyr Glu Asp Leu Tyr Tyr Thr Pro Ser Ser Gly Met Ala Ser<br>                20                  25                  30 | 96 |
| ccc gat agt ccg cct gac acc tcc cgc cgt ggc gcc cta cag aca cgc<br>Pro Asp Ser Pro Pro Asp Thr Ser Arg Arg Gly Ala Leu Gln Thr Arg<br>                35                  40                  45 | 144 |
| tcg cgc cag agg ggc gag gtc cgt ttc gtc cag tac gac gag tcg gat<br>Ser Arg Gln Arg Gly Glu Val Arg Phe Val Gln Tyr Asp Glu Ser Asp<br>      50                  55                  60 | 192 |
| tat gcc ctc tac ggg ggc tcg tct tcc gaa gac gac gaa cac ccg gag<br>Tyr Ala Leu Tyr Gly Gly Ser Ser Ser Glu Asp Asp Glu His Pro Glu<br>65                  70                  75                  80 | 240 |
| gtc ccc cgg acg cgg cgt ccc gtt tcc ggg gcg gtt ttg tcc ggc ccg<br>Val Pro Arg Thr Arg Arg Pro Val Ser Gly Ala Val Leu Ser Gly Pro<br>                85                  90                  95 | 288 |

| | |
|---|---|
| ggg cct gcg cgg gcg cct ccg cca ccc gct ggg tcc gga ggg gcc gga<br>Gly Pro Ala Arg Ala Pro Pro Pro Ala Gly Ser Gly Gly Ala Gly<br>             100                  105                110 | 336 |
| cgc aca ccc acc acc gcc ccc cgg gcc ccc cga acc cag cgg gtg gcg<br>Arg Thr Pro Thr Thr Ala Pro Arg Ala Pro Arg Thr Gln Arg Val Ala<br>             115                  120                125 | 384 |
| tct aag gcc ccc gcg gcc ccg gcg gcg gag acc acc cgc ggc agg aaa<br>Ser Lys Ala Pro Ala Ala Pro Ala Ala Glu Thr Thr Arg Gly Arg Lys<br>       130                  135                140 | 432 |
| tcg gcc cag cca gaa tcc gcc gca ctc cca gac gcc ccc gcg tcg acg<br>Ser Ala Gln Pro Glu Ser Ala Ala Leu Pro Asp Ala Pro Ala Ser Thr<br>145                 150                155              160 | 480 |
| gcg cca acc cga tcc aag aca ccc gcg cag ggg ctg gcc aga aag ctg<br>Ala Pro Thr Arg Ser Lys Thr Pro Ala Gln Gly Leu Ala Arg Lys Leu<br>                   165                170              175 | 528 |
| cac ttt agc acc gcc ccc cca aac ccc gac gcg cca tgg acc ccc cgg<br>His Phe Ser Thr Ala Pro Pro Asn Pro Asp Ala Pro Trp Thr Pro Arg<br>            180                  185              190 | 576 |
| gtg gcc ggc ttt aac aag cgc gtc ttc tgc gcc gcg gtc ggg cgc ctg<br>Val Ala Gly Phe Asn Lys Arg Val Phe Cys Ala Ala Val Gly Arg Leu<br>             195                  200              205 | 624 |
| gcg gcc atg cat gcc cgg atg gcg gct gtc cag ctc tgg gac atg tcg<br>Ala Ala Met His Ala Arg Met Ala Ala Val Gln Leu Trp Asp Met Ser<br>210                 215                220 | 672 |
| cgt ccg cgc aca gac gaa gac ctc aac gaa ctc ctt ggc atc acc acc<br>Arg Pro Arg Thr Asp Glu Asp Leu Asn Glu Leu Leu Gly Ile Thr Thr<br>225                 230                235              240 | 720 |
| atc cgc gtg acg gtc tgc gag ggc aaa aac ctg ctt cag cgc gcc aac<br>Ile Arg Val Thr Val Cys Glu Gly Lys Asn Leu Leu Gln Arg Ala Asn<br>                   245                250              255 | 768 |
| gag ttg gtg aat cca gac gtg gtg cag gac gtc gac gcg gcc acg gcg<br>Glu Leu Val Asn Pro Asp Val Val Gln Asp Val Asp Ala Ala Thr Ala<br>            260                  265              270 | 816 |
| act cga ggg cgt tct gcg gcg tcg cgc ccc acc gag cga cct cga gcc<br>Thr Arg Gly Arg Ser Ala Ala Ser Arg Pro Thr Glu Arg Pro Arg Ala<br>               275                280              285 | 864 |
| cca gcc cgc tcc gct tct cgc ccc aga cgg ccc gtc gag ggt acc gag<br>Pro Ala Arg Ser Ala Ser Arg Pro Arg Arg Pro Val Glu Gly Thr Glu<br>290                 295                300 | 912 |
| ctc gga tcc atg cat gga gat aca cct aca ttg cat gaa tat atg tta<br>Leu Gly Ser Met His Gly Asp Thr Pro Thr Leu His Glu Tyr Met Leu<br>305                 310                315              320 | 960 |
| gat ttg caa cca gag aca act gat ctc tac tgt tat gag caa tta aat<br>Asp Leu Gln Pro Glu Thr Thr Asp Leu Tyr Cys Tyr Glu Gln Leu Asn<br>               325                330              335 | 1008 |
| gac agc tca gag gag gag gat gaa ata gat ggt cca gct gga caa gca<br>Asp Ser Ser Glu Glu Glu Asp Glu Ile Asp Gly Pro Ala Gly Gln Ala<br>            340                  345              350 | 1056 |
| gaa ccg gac aga gcc cat tac aat att gta acc ttt tgt tgc aag tgt<br>Glu Pro Asp Arg Ala His Tyr Asn Ile Val Thr Phe Cys Cys Lys Cys<br>               355                360              365 | 1104 |
| gac tct acg ctt cgg ttg tgc gta caa agc aca cac gta gac att cgt<br>Asp Ser Thr Leu Arg Leu Cys Val Gln Ser Thr His Val Asp Ile Arg<br>            370                  375              380 | 1152 |
| act ttg gaa gac ctg tta atg ggc aca cta gga att gtg tgc ccc atc<br>Thr Leu Glu Asp Leu Leu Met Gly Thr Leu Gly Ile Val Cys Pro Ile<br>385                 390                395              400 | 1200 |

```
                    tgt tct cag gat aag ctt aag ttt aaa ccg ctg atc agc ctc gac tgt    1248
                    Cys Ser Gln Asp Lys Leu Lys Phe Lys Pro Leu Ile Ser Leu Asp Cys
                    405                 410                 415 gcc ttc tag                                                         1257
                    Ala Phe
```

SEQ ID NO: 35
```
  1       atg ggg gat tct gaa agg cgg aaa tcg gaa cgg cgt cgt tcc ctt gga
 48       tat ccc tct gca tat gat gac gtc tcg att cct gct cgc aga cca tca
 96       aca cgt act cag cga aat tta aac cag gat gat ttg tca aaa cat gga
144       cca ttt acc gac cat cca aca caa aaa cat aaa tcg gcg aaa gcc gta
192       tcg gaa gac gtt tcg tct acc acc cgg ggt ggc ttt aca aac aaa ccc
240       cgt acc aag ccc ggg gtc aga gct gta caa agt aat aaa ttc gct ttc
288       agt acg gct cct tca tca gca tct agc act tgg aga tca aat aca gtg
336       gca ttt aat cag cgt atg ttt tgc gga gcg gtt gca act gtg gct caa
384       tat cac gca tac caa ggc gcg ctc gcc ctt tgg cgt caa gat cct ccg
432       cga aca aat gaa gaa tta gat gca ttt ctt ccc aga gct gtc att aaa
480       att acc att caa gag ggt cca aat ttg atg ggg gaa gcc gaa acc tgt
528       gcc cgc aaa cta ttg gaa gag tct gga tta tcc cag ggg aac gag aac
576       gta aag tcc aaa tct gaa cgt aca acc aaa tct gaa cgt aca aga cgc
624       ggc ggt gaa att gaa atc aaa tcg cca gat ccg gga tct cat cgt aca
672       cat aac cct cgc act ccc gca act tcg cgt cgc cat cat tca tcc gcc
720       cgc gga tat cgt agc agt gat agc gaa taa  747
```

SEQ ID NO: 36
```
Met Thr Ser Arg Arg Ser Val Lys Ser Gly Pro Arg Glu Val Pro Arg
1               5                   10                  15

Asp Glu Tyr Glu Asp Leu Tyr Tyr Thr Pro Ser Ser Gly Met Ala Ser
                20                  25                  30

Pro Asp Ser Pro Pro Asp Thr Ser Arg Arg Gly Ala Leu Gln Thr Arg
            35                  40                  45

Ser Arg Gln Arg Gly Glu Val Arg Phe Val Gln Tyr Asp Glu Ser Asp
        50                  55                  60

Tyr Ala Leu Tyr Gly Gly Ser Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Ala Gly Ser Gly Gly Ala Gly
            100                 105                 110

Arg Thr Pro Thr Thr Ala Pro Arg Ala Pro Arg Thr Gln Arg Val Ala
            115                 120                 125

Ser Lys Ala Pro Ala Ala Pro Ala Glu Thr Thr Arg Gly Arg Lys
    130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175

His Phe Ser Thr Ala Pro Pro Asn Pro Asp Ala Pro Trp Thr Pro Arg
                180                 185                 190
```

Val Ala Gly Phe Asn Lys Arg Val Phe Cys Ala Ala Val Gly Arg Leu
    195                 200                 205

Ala Ala Met His Ala Arg Met Ala Ala Val Gln Leu Trp Asp Met Ser
    210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Val Val Gln Asp Val Asp Ala Ala Thr Ala
            260                 265                 270

Thr Arg Gly Arg Ser Ala Ala Ser Arg Pro Thr Glu Arg Pro Arg Ala
    275                 280                 285

Pro Ala Arg Ser Ala Ser Arg Pro Arg Pro Val Glu
    290                 295                 300

SEQ ID NO: 37
Met Thr Ser Arg Arg Ser Val Lys Ser Gly Pro Arg Glu Val Pro Arg
1               5                   10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
    50                  55                  60

Tyr Ala Leu Tyr Gly Ser Ser Ser Glu Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Ala Gly Ser Gly Gly Ala Gly
            100                 105                 110

Arg Thr Pro Thr Thr Ala Pro Arg Ala Pro Arg Thr Gln Arg Val Ala
            115                 120                 125

Ser Lys Ala Pro Ala Ala Pro Ala Ala Glu Thr Thr Arg Gly Arg Lys
    130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175

His Phe Ser Thr Ala Pro Pro Asn Pro Asp Ala Pro Trp Thr Pro Arg
            180                 185                 190

Val Ala Gly Phe Asn Lys Arg Val Phe Cys Ala Ala Val Gly Arg Leu
    195                 200                 205

Ala Ala Met His Ala Arg Met Ala Ala Val Gln Leu Trp Asp Met Ser
    210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Val Val Gln Asp Val Asp Ala Ala Thr Ala
            260                 265                 270

Thr Arg Gly Arg Ser Ala Ala Ser Arg Pro Thr Glu Arg Pro Arg Ala
    275                 280                 285

| LISTING OF ADDITIONAL SEQUENCES |
|---|
| Pro Ala Arg Ser Ala Ser Arg Pro Arg Pro Val Glu Gly Thr Glu<br>    290                        295                      300 |
| Leu Gly Ser Met His Gly Asp Thr Pro Thr Leu His Glu Tyr Met Leu<br>305                    310                      315                  320 |
| Asp Leu Gln Pro Glu Thr Thr Asp Leu Tyr Cys Tyr Glu Gln Leu Asn<br>                325                      330                  335 |
| Asp Ser Ser Glu Glu Glu Asp Glu Ile Asp Gly Pro Ala Gly Gln Ala<br>          340                      345                  350 |
| Glu Pro Asp Arg Ala His Tyr Asn Ile Val Thr Phe Cys Cys Lys Cys<br>          355                      360                  365 |
| Asp Ser Thr Leu Arg Leu Cys Val Gln Ser Thr His Val Asp Ile Arg<br>    370                        375                      380 |
| Thr Leu Glu Asp Leu Leu Met Gly Thr Leu Gly Ile Val Cys Pro Ile<br>385                    390                      395                  400 |
| Cys Ser Gln Asp Lys Leu Lys Phe Lys Pro Leu Ile Ser Leu Asp Cys<br>                405                      410                  415 |
| Ala Phe |
| SEQ ID NO: 38 |
| 2     Met Gly Asp Ser Glu Arg Arg Lys Ser Glu Arg Arg Arg Ser Leu Gly |
| 16    Tyr Pro Ser Ala Tyr Asp Asp Val Ser Ile Pro Ala Arg Arg Pro Ser |
| 32    Thr Arg Thr Gln Arg Asn Leu Asn Gln Asp Asp Leu Ser Lys His Gly |
| 48    Pro Phe Thr Asp His Pro Thr Gln Lys His Lys Ser Ala Lys Ala Val |
| 64    Ser Glu Asp Val Ser Ser Thr Thr Arg Gly Gly Phe Thr Asn Lys Pro |
| 80    Arg Thr Lys Pro Gly Val Arg Ala Val Gln Ser Asn Lys Phe Ala Phe |
| 96    Ser Thr Ala Pro Ser Ser Ala Ser Ser Thr Trp Arg Ser Asn Thr Val |
| 112   Ala Phe Asn Gln Arg Met Phe Cys Gly Ala Val Ala Thr Val Ala Gln |
| 128   Tyr His Ala Tyr Gln Gly Ala Leu Ala Leu Trp Arg Gln Asp Pro Pro |
| 144   Arg Thr Asn Glu Glu Leu Asp Ala Phe Leu Ser Arg Ala Val Ile Lys |
| 160   Ile Thr Ile Gln Glu Gly Pro Asn Leu Met Gly Glu Ala Glu Thr Cys |
| 176   Ala Arg Lys Leu Leu Glu Glu Ser Gly Leu Ser Gln Gly Asn Glu Asn |
| 192   Val Lys Ser Lys Ser Glu Arg Thr Thr Lys Ser Glu Arg Thr Arg Arg |
| 208   Gly Gly Glu Ile Glu Ile Lys Ser Pro Asp Pro Gly Ser His Arg Thr |
| 224   His Asn Pro Arg Thr Pro Ala Thr Ser Arg Arg His His Ser Ser Ala |
| 240   Arg Gly Tyr Arg Ser Ser Asp Ser Glu -- 249 |
| SEQ ID NO: 39<br>Met His Gly Asp Thr Pro Thr Leu His Glu Tyr Met Leu Asp Leu Gln<br>1               5                    10                  15 |
| Pro Glu Thr Thr Asp Leu Tyr Cys Tyr Glu Gln Leu Asn Asp Ser Ser<br>          20                      25                      30 |
| Glu Glu Glu Asp Glu Ile Asp Gly Pro Ala Gly Gln Ala Glu Pro Asp<br>            35                      40                  45 |
| Arg Ala His Tyr Asn Ile Val Thr Phe Cys Cys Lys Cys Asp Ser Thr<br>  50                        55                      60 |
| Leu Arg Leu Cys Val Gln Ser Thr His Val Asp Ile Arg Thr Leu Glu<br>65                   70                      75                  80 |
| Asp Leu Leu Met Gly Thr Leu Gly Ile Val Cys Pro Ile Cys Ser Gln<br>            85                      90                  95 |

-continued

LISTING OF ADDITIONAL SEQUENCES

SEQ ID NO: 40
```
gacggatcgg gagatctccc gatcccctat ggtcgactct cagtacaatc tgctctgatg        60
ccgcatagtt aagccagtat ctgctccctg cttgtgtgtt ggaggtcgct gagtagtgcg       120
cgagcaaaat ttaagctaca acaaggcaag gcttgaccga caattgcatg aagaatctgc       180
ttagggttag gcgttttgcg ctgcttcgcg atgtacgggc cagatatacg cgttgacatt       240
gattattgac tagttattaa tagtaatcaa ttacggggtc attagttcat agcccatata       300
tggagttccg cgttacataa cttacggtaa atggcccgcc tggctgaccg cccaacgacc       360
cccgcccatt gacgtcaata atgacgtatg ttcccatagt aacgccaata gggactttcc       420
attgacgtca atgggtggac tatttacggt aaactgccca cttggcagta catcaagtgt       480
atcatatgcc aagtacgccc cctattgacg tcaatgacgg taaatggccc gcctggcatt       540
atgcccagta catgacctta tgggactttc ctacttggca gtacatctac gtattagtca       600
tcgctattac catggtgatg cggttttggc agtacatcaa tgggcgtgga tagcggtttg       660
actcacgggg atttccaagt ctccacccca ttgacgtcaa tgggagtttg ttttggcacc       720
aaaatcaacg ggactttcca aaatgtcgta acaactccgc cccattgacg caaatgggcg       780
gtaggcgtgt acggtgggag gtctatataa gcagagctct ctggctaact agagaaccca       840
ctgcttactg gcttatcgaa attaatacga ctcactatag ggagacccaa gctggctagc       900
gtttaaacgg gccctctaga ctcgagcggc cgccactgtg ctggatatct gcagaattcc       960
accacactgg actagtggat ccgagctcgg taccaagctt aagtttaaac cgctgatcag      1020
cctcgactgt gccttctagt tgccagccat ctgttgtttg cccctccccc gtgccttcct      1080
tgaccctgga aggtgccact cccactgtcc tttcctaata aaatgaggaa attgcatcgc      1140
attgtctgag taggtgtcat tctattctgg ggggtggggt ggggcaggac agcaaggggg      1200
aggattggga agacaatagc aggcatgctg gggatgcggt gggctctatg gcttctgagg      1260
cggaaagaac cagctggggc tctaggggggt atccccacgc gccctgtagc ggcgcattaa      1320
gcgcggcggg tgtggtggtt acgcgcagcg tgaccgctac acttgccagc gccctagcgc      1380
ccgctccttt cgctttcttc ccttcctttc tcgccacgtt cgccggcttt ccccgtcaag      1440
ctctaaatcg gggcatccct ttagggttcc gatttagtgc tttacggcac ctcgacccca      1500
aaaaacttga ttagggtgat ggttcacgta gtgggccatc gccctgatag acggtttttc      1560
gccctttgac gttggagtcc acgttcttta atagtggact cttgttccaa actggaacaa      1620
cactcaaccc tatctcggtc tattcttttg atttataagg gattttgggg atttcggcct      1680
attggttaaa aaatgagctg atttaacaaa aatttaacgc gaattaattc tgtggaatgt      1740
gtgtcagtta gggtgtggaa agtccccagg ctccccaggc aggcagaagt atgcaaagca      1800
tgcatctcaa ttagtcagca accaggtgtg gaaagtcccc aggctcccca gcaggcagaa      1860
gtatgcaaag catgcatctc aattagtcag caaccatagt cccgccccta actccgccca      1920
tcccgcccct aactccgccc agttccgccc attctccgcc ccatggctga ctaattttttt      1980
ttatttatgc agaggccgag gccgcctctg cctctgagct attccagaag tagtgaggag      2040
gcttttttgg aggcctaggc ttttgcaaaa agctcccggg agcttgtata tccatttttcg      2100
gatctgatca agagacagga tgaggatcgt ttcgcatgat tgaacaagat ggattgcacg      2160
caggttctcc ggccgcttgg gtggagaggc tattcggcta tgactgggca caacagacaa      2220
tcggctgctc tgatgccgcc gtgttccggc tgtcagcgca ggggcgcccg gttcttttttg      2280
```

-continued

| LISTING OF ADDITIONAL SEQUENCES | |
|---|---|
| tcaagaccga cctgtccggt gccctgaatg aactgcagga cgaggcagcg cggctatcgt | 2340 |
| ggctggccac gacgggcgtt ccttgcgcag ctgtgctcga cgttgtcact gaagcgggaa | 2400 |
| gggactggct gctattgggc gaagtgccgg ggcaggatct cctgtcatct caccttgctc | 2460 |
| ctgccgagaa agtatccatc atggctgatg caatgcggcg gctgcatacg cttgatccgg | 2520 |
| ctacctgccc attcgaccac caagcgaaac atcgcatcga gcgagcacgt actcggatgg | 2580 |
| aagccggtct tgtcgatcag gatgatctgg acgaagagca tcaggggctc gcgccagccg | 2640 |
| aactgttcgc caggctcaag gcgcgcatgc ccgacgcgca ggatctcgtc gtgacccatg | 2700 |
| gcgatgcctg cttgccgaat atcatggtgg aaaatggccg cttttctgga ttcatcgact | 2760 |
| gtggccggct gggtgtggcg gaccgctatc aggacatagc gttggctacc cgtgatattg | 2820 |
| ctgaagagct tggcggcgaa tgggctgacc gcttcctcgt gctttacggt atcgccgctc | 2880 |
| ccgattcgca gcgcatcgcc ttctatcgcc ttcttgacga gttcttctga gcgggactct | 2940 |
| ggggttcgaa atgaccgacc aagcgacgcc caacctgcca tcacgagatt tcgattccac | 3000 |
| cgccgccttc tatgaaaggt tgggcttcgg aatcgttttc cgggacgccg gctggatgat | 3060 |
| cctccagcgc ggggatctca tgctggagtt cttcgcccac cccaacttgt ttattgcagc | 3120 |
| ttataatggt tacaaataaa gcaatagcat cacaaatttc acaaataaag cattttttc | 3180 |
| actgcattct agttgtggtt tgtccaaact catcaatgta tcttatcatg tctgtatacc | 3240 |
| gtcgacctct agctagagct tggcgtaatc atggtcatag ctgtttcctg tgtgaaattg | 3300 |
| ttatccgctc acaattccac acaacatacg agccggaagc ataaagtgta aagcctgggg | 3360 |
| tgcctaatga gtgagctaac tcacattaat tgcgttgcgc tcactgcccg ctttccagtc | 3420 |
| gggaaacctg tcgtgccagc tgcattaatg aatcggccaa cgcgcgggga gaggcggttt | 3480 |
| gcgtattggg cgctcttccg cttcctcgct cactgactcg ctgcgctcgg tcgttcggct | 3540 |
| gcggcgagcg gtatcagctc actcaaaggc ggtaatacgg ttatccacag aatcagggga | 3600 |
| taacgcagga aagaacatgt gagcaaaagg ccagcaaaag gccaggaacc gtaaaaaggc | 3660 |
| cgcgttgctg gcgtttttcc ataggctccg ccccctgac gagcatcaca aaaatcgacg | 3720 |
| ctcaagtcag aggtggcgaa acccgacagg actataaaga taccaggcgt ttccccctgg | 3780 |
| aagctccctc gtgcgctctc ctgttccgac cctgccgctt accggatacc tgtccgcctt | 3840 |
| tctcccttcg ggaagcgtgg cgctttctca atgctcacgc tgtaggtatc tcagttcggt | 3900 |
| gtaggtcgtt cgctccaagc tgggctgtgt gcacgaaccc cccgttcagc ccgaccgctg | 3960 |
| cgccttatcc ggtaactatc gtcttgagtc caacccggta agacacgact tatcgccact | 4020 |
| ggcagcagcc actggtaaca ggattagcag agcgaggtat gtaggcggtg ctacagagtt | 4080 |
| cttgaagtgg tggcctaact acggctacac tagaaggaca gtatttggta tctgcgctct | 4140 |
| gctgaagcca gttaccttcg gaaaaagagt tggtagctct tgatccggca acaaaccac | 4200 |
| cgctggtagc ggtggttttt tgtttgcaa gcagcagatt acgcgcagaa aaaaaggatc | 4260 |
| tcaagaagat cctttgatct tttctacggg gtctgacgct cagtggaacg aaaactcacg | 4320 |
| ttaagggatt ttggtcatga gattatcaaa aaggatcttc acctagatcc ttttaaatta | 4380 |
| aaaatgaagt tttaaatcaa tctaaagtat atatgagtaa acttggtctg acagttacca | 4440 |
| atgcttaatc agtgaggcac ctatctcagc gatctgtcta tttcgttcat ccatagttgc | 4500 |
| ctgactcccc gtcgtgtaga taactacgat acgggagggc ttaccatctg gccccagtgc | 4560 |

| LISTING OF ADDITIONAL SEQUENCES | |
|---|---|
| tgcaatgata ccgcgagacc cacgctcacc ggctccagat ttatcagcaa taaaccagcc | 4620 |
| agccggaagg gccgagcgca gaagtggtcc Igcaacttta tccgcctcca tccagtctat | 4680 |
| taattgttgc cggaaagcta gagtaagtag ttcgccagtt aatagtttgc gcaacgttgt | 4740 |
| tgccattgct acaggcatcg tggtgtcacg ctcgtcgttt ggtatggctt cattcagctc | 4800 |
| cggttcccaa cgatcaaggc gagttacatg atcccccatg ttgtgcaaaa aagcggttag | 4860 |
| ctccttcggt cctccgatcg ttgtcagaag taagttggcc gcagtgttat cactcatggt | 4920 |
| tatggcagca ctgcataatt ctcttactgt catgccatcc gtaagatgct tttctgtgac | 4980 |
| tggtgagtac tcaaccaagt cattctgaga atagtgtatg cggcgaccga gttgctcttg | 5040 |
| cccggcgtca atacgggata ataccgcgcc acatagcaga actttaaaag tgctcatcat | 5100 |
| tggaaaacgt tcttcggggc gaaaactctc aaggatctta ccgctgttga gatccagttc | 5160 |
| gatgtaaccc actcgtgcac ccaactgatc ttcagcatct tttactttca ccagcgtttc | 5220 |
| tgggtgagca aaaacaggaa ggcaaaatgc cgcaaaaaag gaataagggg cgacacggaa | 5280 |
| atgttgaata ctcatactct tcctttttca atattattga agcatttatc agggttattg | 5340 |
| tctcatgagc ggatacatat ttgaatgtat ttagaaaaat aaacaaatag gggttccgcg | 5400 |
| cacatttccc cgaaaagtgc cacctgacgt c | 5431 |
| SEQ ID NO: 41 | |
| tggccattgc atacgttgta tccatatcat aatatgtaca tttatattgg ctcatgtcca | 60 |
| acattaccgc catgttgaca ttgattattg actagttatt aatagtaatc aattacgggg | 120 |
| tcattagttc atagcccata tatggagttc cgcgttacat aacttacggt aaatggcccg | 180 |
| cctggctgac cgcccaacga cccccgccca ttgacgtcaa taatgacgta tgttcccata | 240 |
| gtaacgccaa tagggacttt ccattgacgt caatgggtgg agtatttacg gtaaactgcc | 300 |
| cacttggcag tacatcaagt gtatcatatg ccaagtacgc ccctattga cgtcaatgac | 360 |
| ggtaaatggc ccgcctggca ttatgcccag tacatgacct tatgggactt tcctacttgg | 420 |
| cagtacatct acgtattagt catcgctatt accatggtga tgcggttttg gcagtacatc | 480 |
| aatgggcgtg gatagcggtt tgactcacgg ggatttccaa gtctccaccc cattgacgtc | 540 |
| aatgggagtt tgttttggca ccaaaatcaa cgggactttc caaaatgtcg taacaactcc | 600 |
| gccccattga cgcaaatggg cggtaggcgt gtacggtggg aggtctatat aagcagagct | 660 |
| cgtttagtga accgtcagat cgcctggaga cgccatccac gctgttttga cctccataga | 720 |
| agacaccggg accgatccag cctccgcggc cgggaacggt gcattggaac gcggattccc | 780 |
| cgtgccaaga gtgacgtaag taccgcctat agagtctata ggcccacccc cttggcttct | 840 |
| tatgcatgct atactgtttt tggcttgggg tctatacacc cccgcttcct catgttatag | 900 |
| gtgatggtat agcttagcct ataggtgtgg gttattgacc attattgacc actccaacgg | 960 |
| tggagggcag tgtagtctga gcagtactcg ttgctgccgc gcgcgccacc agacataata | 1020 |
| gctgacagac taacagactg ttcctttcca tgggtctttt ctgcagtcac cgtcgtcgac | 1080 |
| ggtatcgata agcttgatat cgaattcacg tgggcccggt accgtatact ctagagcggc | 1140 |
| cgcggatcca gatctttttc cctcgccaaa aattatgggg acatcatgaa gccccttgag | 1200 |
| catctgactt ctggctaata aaggaaattt atttcattgc aatagtgtgt tggaattttt | 1260 |
| tgtgtctctc actcggaagg acatatggga gggcaaatca tttaaaacat cagaatcagt | 1320 |
| atttggttta gagtttggca acatatgcca ttcttccgct tcctcgctca ctgactcgct | 1380 |

-continued

| LISTING OF ADDITIONAL SEQUENCES | |
|---|---|
| gcgctcggtc gttcggctgc ggcgagcggt atcagctcac tcaaaggcgg taatacggtt | 1440 |
| atccacagaa tcagggata acgcaggaaa gaacatgtga gcaaaaggcc agcaaaaggc | 1500 |
| caggaaccgt aaaaaggccg cgttgctggc gtttttccat aggctccgcc cccctgacga | 1560 |
| gcatcacaaa aatcgacgct caagtcagag gtggcgaaac ccgacaggac tataaagata | 1620 |
| ccaggcgttt ccccctggaa gctccctcgt gcgctctcct gttccgaccc tgccgcttac | 1680 |
| cggatacctg tccgcctttc tcccttcggg aagcgtggcg ctttctcaat gctcacgctg | 1740 |
| taggtatctc agttcggtgt aggtcgttcg ctccaagctg ggctgtgtgc acgaaccccc | 1800 |
| cgttcagccc gaccgctgcg ccttatccgg taactatcgt cttgagtcca acccggtaag | 1860 |
| acacgactta tcgccactgg cagcagccac tggtaacagg attagcagag cgaggtatgt | 1920 |
| aggcggtgct acagagttct tgaagtggtg gcctaactac ggctacacta aaggacagt | 1980 |
| atttggtatc tgcgctctgc tgaagccagt taccttcgga aaaagagttg gtagctcttg | 2040 |
| atccggcaaa caaaccaccg ctggtagcgg tggttttttt gtttgcaagc agcagattac | 2100 |
| gcgcagaaaa aaaggatctc aagaagatcc tttgatcttt tctacggggt ctgacgctca | 2160 |
| gtggaacgaa aactcacgtt aagggatttt ggtcatgaga ttatcaaaaa ggatcttcac | 2220 |
| ctagatcctt ttaaattaaa aatgaagttt taaatcaatc taaagtatat atgagtaaac | 2280 |
| ttggtctgac agttaccaat gcttaatcag tgaggcacct atctcagcga tctgtctatt | 2340 |
| tcgttcatcc atagttgcct gactccgggg ggggggggcg ctgaggtctg cctcgtgaag | 2400 |
| aaggtgttgc tgactcatac cagggcaacg ttgttgccat tgctacaggc atcgtggtgt | 2460 |
| cacgctcgtc gtttggtatg gcttcattca gctccggttc ccaacgatca aggcgagtta | 2520 |
| catgatcccc catgttgtgc aaaaaagcgg ttagctcctt cggtcctccg atcgttgtca | 2580 |
| gaagtaagtt ggccgcagtg ttatcactca tggttatggc agcactgcat aattctctta | 2640 |
| ctgtcatgcc atccgtaaga tgcttttctg tgactggtga gtactcaacc aagtcattct | 2700 |
| gagaatagtg tatgcggcga ccgagttgct cttgcccggc gtcaatacgg gataataccg | 2760 |
| cgccacatag cagaacttta aaagtgctca tcattggaaa acgttcttcg gggcgaaaac | 2820 |
| tctcaaggat cttaccgctg ttgagatcca gttcgatgta acccactcgt gcacctgaat | 2880 |
| cgccccatca tccagccaga aagtgaggga gccacggttg atgagagctt tgttgtaggt | 2940 |
| ggaccagttg gtgattttga acttttgctt tgccacggaa cggtctgcgt tgtcgggaag | 3000 |
| atgcgtgatc tgatccttca actcagcaaa agttcgattt attcaacaaa gccgccgtcc | 3060 |
| cgtcaagtca gcgtaatgct ctgccagtgt tacaaccaat taaccaattc tgattagaaa | 3120 |
| aactcatcga gcatcaaatg aaactgcaat ttattcatat caggattatc aataccatat | 3180 |
| ttttgaaaaa gccgtttctg taatgaagga gaaaactcac cgaggcagtt ccataggatg | 3240 |
| gcaagatcct ggtatcggtc tgcgattccg actcgtccaa catcaataca acctattaat | 3300 |
| ttcccctcgt caaaaataag gttatcaagt gagaaatcac catgagtgac gactgaatcc | 3360 |
| ggtgagaatg gcaaaagctt atgcatttct ttccagactt gttcaacagg ccagccatta | 3420 |
| cgctcgtcat caaaatcact cgcatcaacc aaaccgttat tcattcgtga ttgcgcctga | 3480 |
| gcgagacgaa atacgcgatc gctgttaaaa ggacaattac aaacaggaat cgaatgcaac | 3540 |
| cggcgcagga acactgccag cgcatcaaca atattttcac ctgaatcagg atattcttct | 3600 |
| aatacctgga atgctgtttt cccggggatc gcagtggtga gtaaccatgc atcatcagga | 3660 |
| gtacggataa aatgcttgat ggtcggaaga ggcataaatt ccgtcagcca gtttagtctg | 3720 |

| | | | |
|---|---|---|---|
| accatctcat | ctgtaacatc attggcaacg ctacctttgc | catgtttcag aaacaactct | 3780 |
| ggcgcatcgg | gcttcccata caatcgatag attgtcgcac | ctgattgccc gacattatcg | 3840 |
| cgagcccatt | tatacccata taaatcagca tccatgttgg | aatttaatcg cggcctcgag | 3900 |
| caagacgttt | cccgttgaat atggctcata caccccttg | tattactgtt tatgtaagca | 3960 |
| gacagtttta | ttgttcatga tgatatattt ttatcttgtg | caatgtaaca tcagagattt | 4020 |
| tgagacacaa | cgtggctttc cccccccccc cattattgaa | gcatttatca gggttattgt | 4080 |
| ctcatgagcg | gatacatatt tgaatgtatt tagaaaaata | aacaaatagg ggttccgcgc | 4140 |
| acatttcccc | gaaaagtgcc acctgacgtc taagaaacca | ttattatcat gacattaacc | 4200 |
| tataaaaata | ggcgtatcac gaggcccttt cgtcctcgcg | cgtttcggtg atgacggtga | 4260 |
| aaacctctga | cacatgcagc tcccggagac ggtcacagct | tgtctgtaag cggatgccgg | 4320 |
| gagcagacaa | gcccgtcagg gcgcgtcagc gggtgttggc | gggtgtcggg gctggcttaa | 4380 |
| ctatgcggca | tcagagcaga ttgtactgag agtgcaccat | atgcggtgtg aaataccgca | 4440 |
| cagatgcgta | aggagaaaat accgcatcag attggctat | | 4479 |

SEQ ID NO: 42
UGCCUACGAACUCUUCACCdTdT

SEQ ID NO: 43
GGUGAAGAGUUCGUAGGCAdTdT

SEQ ID NO: 44
atggcatctggacaaggaccaggtcccccgaaggtgggctgcgatgagtccccgtccccttctgaacagcaggttgcccaggacacagagga
ggtctttcgaagctacgttttttacctccaccagcaggaacaggagacccaggggcggccgcctgccaaccccgagatggacaacttgcccc
tggaacccaacagcatcttcaggtgggtcggcagcttgctctcatcggagatgatattaaccggcgctacgacacagagttccagaat
ttactagaacagcttcagcccacagccgggaaTGCCTACGAACTCTTCACCaagatcgcctccagcctatttaagagtggcatcagctgggg
ccgcgtggtggctctctgggctttggctaccgtctggccctgtacgtctaccagcgtggtttgaccggcttcctgggccaggtgacctgct
ttttggctgatatcatactgcatcattacatcgccagatggatcgcacagagaggcggttgggtggcagccctgaatttgcgtagagacccc
atcctgaccgtaatggtgattttggtgtggttctgttgggccaattcgtggtacacagattcttcagatcatga 637

SEQ ID NO: 45
TGCCTACGAACTCTTCACC

SEQ ID NO: 46
UAUGGAGCUGCAGAGGAUGdTdT

SEQ ID NO: 47
CAUCCUCUGCAGCUCCAUAdTdT

SEQ ID NO: 48
atggacgggtccggggagcagcttgggagcggcgggcccaccagctctgaacagatcatgaagacaggggccttttgctacagggtttcat
ccaggatcgagcagggaggatggctggggagacacctgagctgaccttggagcagccgcccaggatgcgtccaccaagaagctgagcgagt
gtctccggcgaattggagatgaactggatagcaaTATGGAGCTGCAGAGGATGattgctgacgtggacacggactcccccgagaggtcttc
ttccgggtggcagctgacatgtttgctgatggcaacttcaactgggccgcgtggttgccctcttctactttgctagcaaactggtgctcaa
ggccctgtgcactaaagtgcccgagctgatcagaaccatcatgggctggacactggacttcctcgtgagcggctgcttgtctggatccaag
accagggtggctgggaaggcctcctctcctacttcgggaccccacatggcagacagtgaccatcttgtggctggagtcctcaccgcctcg
ctcaccatctggaagaagatgggctga   589

SEQ ID NO: 49
TATGGAGCTGCAGAGGATG

SEQ ID NO: 50
atg gac ttc agc aga aat ctt tat gat att ggg gaa caa ctg gac agt gaa gat ctg gcc tcc ctc aag
ttc ctg agc ctg gac tac att ccg caa agg aag caa gaa ccc atc aag gat gcc ttg atg tta ttc cag
aga ctc cag gaa aag aga atg ttg aag aga agc aat ctg tcc ttc gag gag cgt ctc ttc gaa att
aat aga ctg gat ttg ctg att acc tac cta aac act aga aag gag gag atg gaa agg gaa ctt cag aca
cca ggc agg gct caa att tct gcc tac agg ttc cac ttc tgc cgc atg agc tgg gct gaa gca aac agc
cag tgc cag aca cag tct gta cct ttc tgg cgg agg gtc gat cat cta tta ata agg gtc atg ctc tat
cag att tca gaa gaa gtg agc aga tca gaa ttg agg tct ttt aag ttt ctt ttg caa gag gaa atc tcc
aaa tgc aaa ctg gat gat gac atg gac atg ctg gat att ttc ata gag atg gag agg gtc atc ctg
gga gaa gga aag ttg gac atc ctg aaa aga gtc tgt gcc caa atc aac aag agc ctg ctg aag ata atc
aac gac tat gaa gaa ttc agc aaa ggg gag gag ttg tgt ggg gta atg aca atc tcg gac tct cca aga
gaa cag gat agt gaa tca cag act ttg gac aaa gtt tac caa atg aaa agc <u>aaa cct cgg gga tac tgt
ctg a</u>tc atc aac aat cac aat ttt gca aaa gca cgg gag aaa gtg ccc aaa ctt cac agc att agg gac
agg aat gga aca cac ttg gat gca ggg gct ttg acc acg acc ttt gaa gag ctt cat ttt gag atc aag

LISTING OF ADDITIONAL SEQUENCES ccc cac gat gac tgc aca gta gag caa atc tat gag att ttg aaa atc tac caa ctc atg gac cac agt
aac atg gac tgc ttc atc tgc tgt atc ctc tcc cat gga gac aag ggc atc atc tat ggc act gat gga
cag gag gcc ccc atc tat gag ctg aca tct cag ttc act ggt ttg aag tgc cct tcc ctt gct gga aaa
ccc aaa gtg ttt ttt att cag gct tgt cag ggg gat aac tac cag aaa ggt ata cct gtt gag act gat
tca gag gag caa ccc tat tta gaa atg gat tta tca tca cct caa acg aga tat atc ccg gat gag gct
gac ttt ctg ctg ggg atg gcc act gtg aat aac tgt gtt tcc tac cga aac cct gca gag gga acc tgg
tac atc cag tca ctt tgc cag agc ctg aga gag cga tgt cct cga ggc gat gat att ctc acc atc ctg
act gaa gtg aac tat gaa gta agc aac aag gat gac aag aaa aac atg ggg aaa cag atg cct cag cct
act ttc aca cta aga aaa aaa ctt gtc ttc cct tct gat tga 1491

SEQ ID NO: 51
AACCUCGGGGAUACUGUCUGAdTdT

SEQ ID NO: 52
UCAGACAGUAUCCCCGAGGUUdTdT

SEQ ID NO: 53
atg gac gaa gcg gat cgg cgg ctc ctg cgg cgg tgc cgg ctg cgg ctg gtg aaa gag ctg cag gtg gac
cag ctc tgg gac gcc ctg ctg agc cgc gag ctg ttc agg ccc cat atg atc gag gac atc cag cgg gca
ggc tct gga tct cgg cgg gat cag gcc agg cag ctg atc ata gat ctg gag act cga ggg agt cag gct
ctt cct ttg ttc atc tcc tgc tta gag gac aca ggc cag gac atg ctg gct tcg ttt ctg cga act aac
agg gca gca aag ttg tcg aag cca acc cta aga aac ctt acc cca gtg gtg ctc aga cca gga att
cgc aaa cca gag gtt ctc aga ccg gaa aca ccc aga cca gtg gac att ggt tct gga gga ttt ggt gat
gtc ggt gct ctt gag agt ttg agg gga aat gca gat ttg gct tac atc ctg agc atg gag ccc tgt ggc
cac tgc ctc att atc aac aat gtg aac ttc tgc cgt gag tcc ggg ctc cgc acc cgc act ggc tcc aac
atc gac tgt gag aag ttg cgg cgt cgc ttc tcc tcg ctg cat ttc atg gtg gag gtg aag ggc gac ctg
act gcc aag aaa atg gtg ctg gct ttg ctg gag ctg gcg cag cag ggt gct ctg gac tgc tgc
gtg gtg gtc att ctc tct cac ggc tgt cag gcc agc cac ctg cag ttc cca ggg cct gtc tac ggc aca
gat gga tgc cct gtg tcg gtc gag aag att gtg aac atc ttc aat ggg acc agc tgc ccc agc ctg gga
ggg aag ccc aag ctc ttt atc cag gcc tgt ggt ggg gag cag aaa gac cat ggg ttt gag gtg gcc
tcc act tcc cct gaa gac gag tcc cct ggc agt aac ccc gag cca gat gcc acc ccg ttc agg aag gt
ttg agg acc ttc aca cag cgg gac gcc ata tct ttg ttg cca gct gac atc ttt gtg tcc tac
tct act ttc cca ggt ttt gtt tcc tgg agg gac ccc aag agt ggc tcc tgg tac tgt gag acc ctg gac
gac atc ttt gag cag tgg gct cac tct gaa gac ctg cag tcc ctc ctg ctt agg gtc gct aat gct gtt
tcg gtg aaa ggg att tat aaa cag atg cct ggt tgc ttt aat ttc ctc cgg aaa aaa ctt ttc ttt aaa
aca tca taa 1191

SEQ ID NO: 54
atg gag aac act gaa aac tca gtg gat tca aaa tcc att aaa aat ttg gaa cca aag atc ata cat gga
agc gaa tca atg gac tct gga ata tcc tgg aca acc agt tat aaa atg gat tat cct gag atg ggt tta
tgt ata ata att aat aat aag aat ttt cat aaa agc act gga atg aca tct cgg tct ggt aca gat gtc
gat gca gca aac ctc agg gaa aca ttc aga aac ttg aaa tat gaa gtc agg aat aaa aat gat ctt aca
cgt gga gaa att gtg gaa ttg atg cgt gat gtt tct aaa gaa gat cac gac aaa agg agc agt gtt
tgt gtg ctt ctg agc cat ggt gaa gaa gga ata att ttt gga aca aat gga cct gtt gac ctg aaa aaa
ata aca aac ttt ttc aga ggg gat cgt gtt aga agt cta act gga aaa ccc aaa ctt ttc att att cag
gcc tgc cgt ggt aca gaa ctg gac tgt ggc att gag aca gac agt ggt gtt gat gat gac atg gcg tgt
cat aaa ata cca gtg gag gcc gac ttc ttg tat gca tac tcc aca gca cct ggt tat tat tct tgg cga
aat tca aag gat ggc tcc tgg ttc atc cag tcg ctt tgt gcc atg ctg aaa cag tat gcc gac aag ctt
gaa ttt atg cac att ctt acc cgg gtt aac cga aag gtg gca aca gaa ttt gag tcc ttt tcc ttt gac
gct act ttt cat gca aag aaa cag att cca tgt att gtt tcc atg ctc aca aaa gaa ctc tat ttt tat
cac taa 834

SEQ ID NO: 55
atggcgtacc catacgatgt tccagattac gctagcttga gatctaccat gtctcagagc           60
aaccgggagc tggtggttga ctttctctcc tacaagcttt cccagaaagg atacagctgg          120
agtcagttta gtgatgtgga agagaacagg actgaggccc agaagggac tgaatcggag           180 atggagaccc ccagtgccat caatggcaac ccatcctggc acctggcaga cagccccgcg          240
gtgaatggag ccactgcgca cagcagcagt ttggatgccc gggaggtgat ccccatggca          300
gcagtaaagc aagcgctgag ggaggcaggc gacgagtttg aactgcggta ccggcgggca          360
ttcagtgacc tgcatcccca gctccacatc accccaggga cagcatatca gagctttgaa          420
caggtagtga atgaactctt ccgggatggg gtaaactggg gtcgcattgt ggccttttc           480 tccttcggcg gggcactgtg cgtggaaagc gtagacaagg agatgcaggt attggtgagt          540
cggatcgcag cttggatggc cacttacctg aatgaccacc tagagcctg gatccaggag          600 aacggcggct gggatacttt tgtggaactc tatgggaaca atgcagcagc cgagagccga          660

| | |
|---|---|
| aagggccagg aacgcttcaa ccgctggttc ctgacgggca tgactgtggc cggcgtggtt | 720 |
| ctgctgggct cactcttcag tcggaaatga | 750 |

SEQ ID NO: 56

```
Met Ala Tyr Pro Tyr Asp Val Pro Asp Tyr Ala Ser Leu Arg Ser Thr
1               5                   10                  15
Met Ser Gln Ser Asn Arg Glu Leu Val Val Asp Phe Leu Ser Tyr Lys
                20                  25                  30
Leu Ser Gln Lys Gly Tyr Ser Trp Ser Gln Phe Ser Asp Val Glu Glu
                35                  40                  45
Asn Arg Thr Glu Ala Pro Glu Gly Thr Glu Ser Glu Met Glu Thr Pro
            50                  55                  60
Ser Ala Ile Asn Gly Asn Pro Ser Trp His Leu Ala Asp Ser Pro Ala
65                  70                  75                  80
Val Asn Gly Ala Thr Ala His Ser Ser Leu Asp Ala Arg Glu Val
                85                  90                  95
Ile Pro Met Ala Ala Val Lys Gln Ala Leu Arg Glu Ala Gly Asp Glu
                100                 105                 110
Phe Glu Leu Arg Tyr Arg Arg Ala Phe Ser Asp Leu Thr Ser Gln Leu
                115                 120                 125
His Ile Thr Pro Gly Thr Ala Tyr Gln Ser Phe Glu Gln Val Val Asn
            130                 135                 140
Glu Leu Phe Arg Asp Gly Val Asn Trp Gly Arg Ile Val Ala Phe Phe
145                 150                 155                 160
Ser Phe Gly Gly Ala Leu Cys Val Glu Ser Val Asp Lys Glu Met Gln
                165                 170                 175
Val Leu Val Ser Arg Ile Ala Ala Trp Met Ala Thr Tyr Leu Asn Asp
                180                 185                 190
His Leu Glu Pro Trp Ile Gln Glu Asn Gly Gly Trp Asp Thr Phe Val
                195                 200                 205
Glu Leu Tyr Gly Asn Asn Ala Ala Ala Glu Ser Arg Lys Gly Gln Glu
                210                 215                 220
Arg Phe Asn Arg Trp Phe Leu Thr Gly Met Thr Val Ala Gly Val Val
225                 230                 235                 240
Leu Leu Gly Ser Leu Phe Ser Arg Lys
                245
```

SEQ ID NO: 57

| | |
|---|---|
| gacggatcgg gagatctccc gatccctat ggtcgactct cagtcaaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag cttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta caaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaacgg gccctctaga ctcgagcggc cgccactgtg ctggatatct gcagaattcc | 960 |
| accacactgg actagtggat ctatggcgta cccatacgat gttccagatt acgctagctt | 1020 |
| gagatctacc atgtctcaga gcaaccggga gctggtggtt gactttctct cctacaagct | 1080 |
| ttcccagaaa ggatacagct ggagtcagtt tagtgatgtg gaagagaaca ggactgaggc | 1140 |

| LISTING OF ADDITIONAL SEQUENCES | |
|---|---|
| cccagaaggg actgaatcgg agatggagac ccccagtgcc atcaatggca acccatcctg | 1200 |
| gcacctggca gacagccccg cggtgaatgg agccactgcg cacagcagca gtttggatgc | 1260 |
| ccgggaggtg atccccatgg cagcagtaaa gcaagcgctg agggaggcag gcgacgagtt | 1320 |
| tgaactgcgg taccggcggg cattcagtga cctgacatcc cagctccaca tcaccccagg | 1380 |
| gacagcatat cagagctttg aacaggtagt gaatgaactc ttccgggatg gggtaaactg | 1440 |
| gggtcgcatt gtggccttt tctccttcgg cggggcactg tgcgtggaaa gcgtagacaa | 1500 |
| ggagatgcag gtattggtga gtcggatcgc agcttggatg gccacttacc tgaatgacca | 1560 |
| cctagagcct tggatccagg agaacggcgg ctgggatact tttgtggaac tctatgggaa | 1620 |
| caatgcagca gccgagagcc gaaagggcca ggaacgcttc aaccgctggt tcctgacggg | 1680 |
| catgactgtg gccggcgtgg ttctgctggg ctcactcttc agtcggaaat gaagatccga | 1740 |
| gctcggtacc aagcttaagt ttaaaccgct gatcagcctc gactgtgcct tctagttgcc | 1800 |
| agccatctgt tgtttgcccc tcccccgtgc cttccttgac cctggaaggt gccactccca | 1860 |
| ctgtcctttc ctaataaaat gaggaaaatg catcgcattg tctgagtagg tgtcattcta | 1920 |
| ttctgggggg tggggtgggg caggacagca agggggagga ttgggaagac aatagcaggc | 1980 |
| atgctgggga tgcggtgggc tctatggctt ctgaggcgga agaaccagc tggggctcta | 2040 |
| gggggtatcc ccacgcgccc tgtagcgcg cattaagcgc ggcgggtgtg gtggttacgc | 2100 |
| gcagcgtgac cgctacactt gccagcgccc tagcgcccgc tcctttcgct ttcttccctt | 2160 |
| cctttctcgc cacgttcgcc ggctttcccc gtcaagctct aaatcggggc atccctttag | 2220 |
| ggttccgatt tagtgcttta cggcacctcg accccaaaaa acttgattag ggtgatggtt | 2280 |
| cacgtagtgg gccatcgccc tgatagacgg ttttttcgcc tttgacgttg gagtccacgt | 2340 |
| tctttaatag tggactcttg ttccaaactg gaacaacact caaccctatc tcggtctatt | 2400 |
| cttttgattt ataagggatt ttgggaattt cggcctattg gttaaaaaat gagctgatttt | 2460 |
| aacaaaaatt taacgcgaat taattctgtg gaatgtgtgt cagttagggt gtggaaagtc | 2520 |
| cccaggctcc ccaggcaggc agaagtatgc aaagcatgca tctcaattag tcagcaacca | 2580 |
| ggtgtggaaa gtccccaggc tccccagcag gcagaagtat gcaaagcatg catctcaatt | 2640 |
| agtcagcaac catagtcccg cccctaactc cgcccatccc gcccctaact ccgcccagtt | 2700 |
| ccgcccattc tccgccccat ggctgactaa ttttttttat ttatgcagag gccgaggccg | 2760 |
| cctctgcctc tgagctattc cagaagtagt gaggaggctt ttttggaggc ctaggctttt | 2820 |
| gcaaaaagct cccgggagct tgtatatcca ttttcggatc tgatcaagag acaggatgag | 2880 |
| gatcgtttcg catgattgaa caagatggat tgcacgcagg ttctccggcc gcttgggtgg | 2940 |
| agaggctatt cggctatgac tgggcacaac agacaatcgg ctgctctgat gccgccgtgt | 3000 |
| tccggctgtc agcgcagggg cgcccggttc ttttgtcaa gaccgacctg tccggtgccc | 3060 |
| tgaatgaact gcaggacgag gcagcgcggc tatcgtggct ggccacgacg ggcgttcctt | 3120 |
| gcgcagctgt gctcgacgtt gtcactgaag cgggaaggga ctggctgcta ttgggcgaag | 3180 |
| tgccggggca ggatctcctg tcatctcacc ttgctcctgc cgagaaagta tccatcatgg | 3240 |
| ctgatgcaat gcggcggctg catacgcttg atccggctac ctgcccattc gaccaccaag | 3300 |
| cgaaacatcg catcgagcga gcacgtactc ggatggaagc cggtcttgtc gatcaggatg | 3360 |
| atctggacga agagcatcag gggctcgcgc cagccgaact gttcgccagg ctcaaggcgc | 3420 |
| gcatgcccga cggcgaggat ctcgtcgtga cccatggcga tgcctgcttg ccgaatatca | 3480 |

LISTING OF ADDITIONAL SEQUENCES

```
tggtggaaaa tggccgcttt tctggattca tcgactgtgg ccggctgggt gtggcggacc    3540
gctatcagga catagcgttg gctacccgtg atattgctga agagcttggc ggcgaatggg    3600
ctgaccgctt cctcgtgctt tacggtatcg ccgctcccga ttcgcagcgc atcgccttct    3660
atcgccttct tgacgagttc ttctgagcgg gactctgggg ttcgaaatga ccgaccaagc    3720
gacgcccaac ctgccatcac gagatttcga ttccaccgcc gccttctatg aaaggttggg    3780
cttcggaatc gttttccggg acgccggctg gatgatcctc cagcgcgggg atctcatgct    3840
ggagttcttc gcccacccca acttgtttat tgcagcttat aatggttaca aataaagcaa    3900
tagcatcaca aatttcacaa ataaagcatt tttttcactg cattctagtt gtggtttgtc    3960
caaactcatc aatgtatctt atcatgtctg tataccgtcg acctctagct agagcttggc    4020
gtaatcatgg tcatagctgt ttcctgtgtg aaattgttat ccgctcacaa ttccacacaa    4080
catacgagcc ggaagcataa agtgtaaagc ctggggtgcc taatgagtga gctaactcac    4140
attaattgcg ttgcgctcac tgcccgcttt ccagtcggga aacctgtcgt gccagctgca    4200
ttaatgaatc ggccaacgcg cggggagagg cggtttgcgt attgggcgct cttccgcttc    4260
ctcgctcact gactcgctgc gctcggtcgt tcggctgcgg cgagcggtat cagctcactc    4320
aaaggcggta atacggttat ccacagaatc aggggataac gcaggaaaga acatgtgagc    4380
aaaaggccag caaaaggcca ggaaccgtaa aaaggccgcg ttgctggcgt ttttccatag    4440
gctccgcccc cctgacgagc atcacaaaaa tcgacgctca agtcagaggt ggcgaaaccc    4500
gacaggacta taaagatacc aggcgtttcc ccctggaagc tccctcgtgc gctctcctgt    4560
tccgaccctg ccgcltaccg gatacctgtc cgcctttctc ccttcgggaa gcgtggcgct    4620
ttctcaatgc tcacgctgta ggtatctcag ttcggtgtag tcgttcgctc caagctggg    4680
ctgtgtgcac gaacccccg ttcagcccga ccgctgcgcc ttatccggta actatcgtct    4740
tgagtccaac ccggtaagac acgacttatc gccactggca gcagccactg gtaacaggat    4800
tagcagagcg aggtatgtag gcggtgctac agagttcttg aagtggtggc ctaactacgg    4860
ctacactaga aggacagtat ttggtatctg cgctctgctg aagccagtta ccttcggaaa    4920
aagagttggt agctcttgat ccggcaaaca accaccgct ggtagcggtg ttttttttgt    4980
ttgcaagcag cagattacgc gcagaaaaaa aggatctcaa gaagatcctt tgatcttttc    5040
tacggggtct gacgctcagt ggaacgaaaa ctcacgttaa gggattttgg tcatgagatt    5100
atcaaaaagg atcttcacct agatcctttt aaattaaaaa tgaagtttta atcaatcta    5160
aagtatatat gagtaaactt ggtctgacag ttaccaatgc ttaatcagtg aggcacctat    5220
ctcagcgatc tgtctatttc gttcatccat agttgcctga ctccccgtcg tgtagataac    5280
tacgatacgg gagggcttac catctggccc cagtgctgca atgataccgc gagacccacg    5340
ctcaccggct ccagatttat cagcaataaa ccagccagcc ggaagggccg agcgcagaag    5400
tggtcctgca actttatccg cctccatcca gtctattaat tgttgccggg aagctagagt    5460
aagtagttcg ccagttaata gtttgcgcaa cgttgttgcc attgctacag gcatcgtggt    5520
gtcacgctcg tcgtttggta tggcttcatt cagctccggt tcccaacgat caaggcgagt    5580
tacatgatcc cccatgttgt gcaaaaaagc ggttagctcc ttcggtcctc cgatcgttgt    5640
cagaagtaag ttggccgcag tgttatcact catggttatg gcagcactgc ataattctct    5700
tactgtcatg ccatccgtaa gatgcttttc tgtgactggt gagtactcaa ccaagtcatt    5760
```

| | |
|---|---:|
| ctgagaatag tgtatgcggc gaccgagttg ctcttgcccg gcgtcaatac gggataatac | 5820 |
| cgcgccacat agcagaactt taaaagtgct catcattgga aaacgttctt cggggcgaaa | 5880 |
| actctcaagg atcttaccgc tgttgagatc cagttcgatg taacccactc gtgcacccaa | 5940 |
| ctgatcttca gcatctttta ctttcaccag cgtttctggg tgagcaaaaa caggaaggca | 6000 |
| aaatgccgca aaaagggaa taagggcgac acggaaatgt tgaatactca tactcttcct | 6060 |
| ttttcaatat tattgaagca tttatcaggg ttattgtctc atgagcggat acatatttga | 6120 |
| atgtatttag aaaaataaac aaatagggt tccgcgcaca tttccccgaa aagtgccacc | 6180 |
| tgacgtc | 6187 |
| SEQ ID NO: 58 | |
| gacggatcgg gagatctccc gatccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta caactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaacgg gccctctaga ctcgagcggc cgccactgtg ctggatatct gcagaattca | 960 |
| tgcatggaga tacacctaca ttgcatgaat atatgttaga tttgcaacca gagacaactg | 1020 |
| atctctactg ttatgagcaa ttaaatgaca gctcagagga ggaggatgaa atagatggtc | 1080 |
| cagctggaca agcagaaccg gacagagccc attacaatat tgtaacctt tgttgcaagt | 1140 |
| gtgactctac gcttcggttg tgcgtacaaa gcacacacgt agacattcgt actttggaag | 1200 |
| acctgttaat gggcacacta ggaattgtgt gccccatctg ttctcagaaa ccaggatcta | 1260 |
| tggcgtaccc atacgatgtt ccagattacg ctagcttgag atctaccatg tctcagagca | 1320 |
| accgggagct ggtggttgac tttctctcct acaagctttc ccagaaagga tacagctgga | 1380 |
| gtcagtttag tgatgtggaa gagaacagga ctgaggcccc agaagggact gaatcggaga | 1440 |
| tggagacccc cagtgccatc aatggcaacc catcctggca cctggcagac agccccgcgg | 1500 |
| tgaatggagc cactgcgcac agcagcagtt tggatgcccg ggaggtgatc cccatggcag | 1560 |
| cagtaaagca agcgctgagg gaggcaggcg acgagtttga actgcggtac cggcgggcat | 1620 |
| tcagtgacct gacatcccag ctccacatca ccccagggac agcatatcag agctttgaac | 1680 |
| aggtagtgaa tgaactcttc cgggatgggg taaactgggg tcgcattgtg gcctttttct | 1740 |
| ccttcggcgg ggcactgtgc gtggaaagcg tagacaagga gatgcaggta ttggtgagtc | 1800 |

-continued

| LISTING OF ADDITIONAL SEQUENCES | |
|---|---|
| ggatcgcagc ttggatggcc acttacctga atgaccacct agagccttgg atccaggaga | 1860 |
| acggcggctg ggatactttt gtggaactct atgggaacaa tgcagcagcc gagagccgaa | 1920 |
| agggccagga acgcttcaac cgctggttcc tgacgggcat gactgtggcc ggcgtggttc | 1980 |
| tactgggctc actcttcagt cggaaatgaa gatccaagct taagtttaaa ccgctgatca | 2040 |
| gcctcgactg tgccttctag ttgccagcca tctgttgttt gcccctcccc cgtgccttcc | 2100 |
| ttgaccctgg aaggtgccac tcccactgtc ctttcctaat aaaatgagga aattgcatcg | 2160 |
| cattgtctga gtaggtgtca ttctattctg ggggtgggg tggggcagga cagcaagggg | 2220 |
| gaggattggg aagacaatag caggcatgct ggggatgcgg tgggctctat ggcttctgag | 2280 |
| gcggaaagaa ccagctgggg ctctagggg tatcccacg cgccctgtag cggcgcatta | 2340 |
| agcgcggcgg gtgtggtggt tacgcgcagc gtgaccgcta cacttgccag cgccctagcg | 2400 |
| cccgctcctt tcgctttctt cccttccttt ctcgccacgt tcgccggctt tccccgtcaa | 2460 |
| gctctaaatc ggggcatccc tttagggttc cgatttagtg ctttacggca cctcgacccc | 2520 |
| aaaaaacttg attagggtga tggttcacgt agtgggccat cgccctgata dacggttttt | 2580 |
| cgccctttga cgttggagtc cacgttcttt aatagtggac tcttgttcca aactggaaca | 2640 |
| acactcaacc ctatctcggt ctattctttt gatttataag gattttggg gatttcggcc | 2700 |
| tattggttaa aaaatgagct gatttaacaa aaatttaacg cgaattaatt ctgtggaatg | 2760 |
| tgtgtcagtt agggtgtgga aagtccccag gctccccagg caggcagaag tatgcaaagc | 2820 |
| atgcatctca attagtcagc aaccaggtgt ggaaagtccc caggctcccc agcaggcaga | 2880 |
| agtatgcaaa gcatgcatct caattagtca gcaaccatag tcccgcccct aactccgccc | 2940 |
| atcccgcccc taactccgcc cagttccgcc cattctccgc cccatggctg actaattttt | 3000 |
| tttatttatg cagaggccga ggccgcctct gcctctgagc tattccagaa gtagtgagga | 3060 |
| ggcttttttg gaggcctagg cttttgcaaa aagctcccgg gagcttgtat atccattttc | 3120 |
| ggatctgatc aagagacagg atgaggatcg tttcgcatga ttgaacaaga tggattgcac | 3180 |
| gcaggttctc cggccgcttg ggtggagagg ctattcggct atgactgggc acaacagaca | 3240 |
| atcggctgct ctgatgccgc cgtgttccgg ctgtcagcgc aggggcgccc ggttcttttt | 3300 |
| gtcaagaccg acctgtccgg tgccctgaat gaactgcagg acgaggcagc gcggctatcg | 3360 |
| tggctggcca cgacgggcgt tccttgcgca gctgtgctcg acgttgtcac tgaagcggga | 3420 |
| agggactggc tgctattggg cgaagtgccg gggcaggatc tcctgtcatc tcaccttgct | 3480 |
| cctgccgaga aagtatccat catggctgat gcaatgcggc ggctgcatac gcttgatccg | 3540 |
| gctacctgcc cattcgacca ccaagcgaaa catcgcatcg agcgagcacg tactcggatg | 3600 |
| gaagccggtc ttgtcgatca ggatgatctg gacgaagagc atcaggggct cgcgccagcc | 3660 |
| gaactgttcg ccaggctcaa ggcgcgcatg cccgacggcg aggatctcgt cgtgacccat | 3720 |
| ggcgatgcct gcttgccgaa tatcatggtg gaaaatggcc gcttttctgg attcatcgac | 3780 |
| tgtggccggc tgggtgtggc ggaccgctat caggacatag cgttggctac ccgtgatatt | 3840 |
| gctgaagagc ttggcggcga atgggctgac cgcttcctcg tgctttacgg tatcgccgct | 3900 |
| cccgattcgc agcgcatcgc cttctatcgc cttcttgacg agttcttctg agcgggactc | 3960 |
| tggggttcga aatgaccgac caagcgacgc ccaacctgcc atcacgagat ttcgattcca | 4020 |
| ccgccgcctt ctatgaaagg ttgggcttcg gaatcgtttt ccgggacgcc ggctggatga | 4080 |
| tcctccagcg cggggatctc atgctggagt tcttcgccca ccccaacttg tttattgcag | 4140 |

| LISTING OF ADDITIONAL SEQUENCES |

```
cttataatgg ttacaaataa agcaatagca tcacaaattt cacaaataaa gcattttttt      4200
cactgcattc tagttgtggt ttgtccaaac tcatcaatgt atcttatcat gtctgtatac      4260
cgtcgacctc tagctagagc ttggcgtaat catggtcata gctgtttcct gtgtgaaatt      4320
gttatccgct cacaattcca cacaacatac gagccggaag cataaagtgt aaagcctggg      4380
gtgcctaatg agtgagctaa ctcacattaa ttgcgttgcg ctcactgccc gctttccagt      4440
cgggaaacct gtcgtgccag ctgcattaat gaatcggcca acgcgcgggg agaggcggtt      4500
tgcgtattgg gcgctcttcc gcttcctcgc tcactgactc gctgcgctcg tcgttcggc       4560 tgcggcgagc ggtatcagct cactcaaagg cggtaatacg ttatccaca gaatcagggg       4620 ataacgcagg aaagaacatg tgagcaaaag gccagcaaaa ggccaggaac cgtaaaaagg      4680
ccgcgttgct ggcgtttttc cataggctcc gcccccctga cgagcatcac aaaaatcgac      4740
gctcaagtca gaggtggcga aacccgacag gactataaag ataccaggcg tttccccctg      4800
gaagctccct cgtgcgctct cctgttccga ccctgccgct taccggatac ctgtccgcct      4860
ttctcccttc gggaagcgtg cgctttctc aatgctcacg ctgtaggtat ctcagttcgg       4920
tgtaggtcgt tcgctccaag ctgggctgtg tgcacgaacc ccccgttcag cccgaccgct      4980
gcgccttatc cggtaactat cgtcttgagt ccaacccggt aagacacgac ttatcgccac      5040
tggcagcagc cactggtaac aggattagca gagcgaggta tgtaggcggt gctacagagt      5100
tcttgaagtg gtggcctaac tacggctaca ctagaaggac agtatttggt atctgcgctc      5160
tgctgaagcc agttaccttc ggaaaaagag ttggtagctc ttgatccggc aaacaaacca      5220
ccgctggtag cggtggtttt tttgtttgca agcagcagat tacgcgcaga aaaaaggat      5280 ctcaagaaga tcctttgatc ttttctacgg ggtctgacgc tcagtggaac gaaaactcac      5340
gttaagggat tttggtcatg agattatcaa aaaggatctt cacctagatc cttttaaatt      5400
aaaaatgaag ttttaaatca atctaaagta tatatgagta aacttggtct gacagttacc      5460
aatgcttaat cagtgaggca cctatctcag cgatctgtct atttcgttca tccatagttg      5520
cctgactccc cgtcgtgtag ataactacga tacgggaggg cttaccatct ggccccagtg      5580
ctgcaatgat accgcgagac ccacgctcac cggctccaga tttatcagca ataaaccagc      5640
cagccggaag ggccgagcgc agaagtggtc ctgcaacttt atccgcctcc atccagtcta      5700
ttaattgttg ccgggaagct agagtaagta gttcgccagt taatagtttg cgcaacgttg      5760
ttgccattgc tacaggcatc gtggtgtcac gctcgtcgtt tggtatggct tcattcagct      5820
ccggttccca acgatcaagg cgagttacat gatccccat gttgtgcaaa aaagcggtta      5880
gctccttcgg tcctccgatc gttgtcagaa gtaagttggc cgcagtgtta tcactcatgg      5940
ttatggcagc actgcataat tctcttactg tcatgccatc cgtaagatgc ttttctgtga      6000
ctggtgagta ctcaaccaag tcattctgag aatagtgtat gcggcgaccg agttgctctt      6060
gcccggcgtc aatacgggat aataccgcgc cacatagcag aactttaaaa gtgctcatca      6120
ttggaaaacg ttcttcgggg cgaaaactct caaggatctt accgctgttg agatccagtt      6180
cgatgtaacc cactcgtgca cccaactgat cttcagcatc ttttactttc accagcgttt      6240
ctgggtgagc aaaaacagga aggcaaaatg ccgcaaaaaa gggaataagg gcgacacgga      6300
aatgttgaat actcatactc ttcctttttc aatattattg aagcatttat cagggttatt      6360
```

```
gtctcatgag cggatacata tttgaatgta tttagaaaaa taaacaaata ggggttccgc        6420
gcacatttcc ccgaaaagtg ccacctgacg tc                                      6452
```

SEQ ID NO: 59

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Gly Ser Met Ala Tyr Pro Tyr Asp Val Pro Asp Tyr Ala Ser
            100                 105                 110

Leu Arg Ser Thr Met Ser Gln Ser Asn Arg Glu Leu Val Val Asp Phe
        115                 120                 125

Leu Ser Tyr Lys Leu Ser Gln Lys Gly Tyr Ser Trp Ser Gln Phe Ser
130                 135                 140

Asp Val Glu Glu Asn Arg Thr Glu Ala Pro Glu Gly Thr Glu Ser Glu
145                 150                 155                 160

Met Glu Thr Pro Ser Ala Ile Asn Gly Asn Pro Ser Trp His Leu Ala
                165                 170                 175

Asp Ser Pro Ala Val Asn Gly Ala Thr Ala His Ser Ser Ser Leu Asp
            180                 185                 190

Ala Arg Glu Val Ile Pro Met Ala Ala Val Lys Gln Ala Leu Arg Glu
        195                 200                 205

Ala Gly Asp Glu Phe Glu Leu Arg Tyr Arg Arg Ala Phe Ser Asp Leu
210                 215                 220

Thr Ser Gln Leu His Ile Thr Pro Gly Thr Ala Tyr Gln Ser Phe Glu
225                 230                 235                 240

Gln Val Val Asn Glu Leu Phe Arg Asp Gly Val Asn Trp Gly Arg Ile
                245                 250                 255

Val Ala Phe Phe Ser Phe Gly Gly Ala Leu Cys Val Glu Ser Val Asp
            260                 265                 270

Lys Glu Met Gln Val Leu Val Ser Arg Ile Ala Ala Trp Met Ala Thr
        275                 280                 285

Tyr Leu Asn Asp His Leu Glu Pro Trp Ile Gln Glu Asn Gly Gly Trp
290                 295                 300

Asp Thr Phe Val Glu Leu Tyr Gly Asn Asn Ala Ala Glu Ser Arg
305                 310                 315                 320

Lys Gly Gln Glu Arg Phe Asn Arg Trp Phe Leu Thr Gly Met Thr Val
                325                 330                 335

Ala Gly Val Val Leu Leu Gly Ser Leu Phe Ser Arg Lys
            340                 345
```

SEQ ID NO: 60
```
atggcgtacc catacgatgt tccagattac gctagcttga gatctaccat gtctcagagc        60
aaccgggagc tggtggttga ctttctctcc tacaagcttt cccagaaagg atacagctgg       120
```

-continued

LISTING OF ADDITIONAL SEQUENCES

```
agtcagttta gtgatgtgga agagaacagg actgaggccc cagaagggac tgaatcggag      180
atggagaccc ccagtgccat caatggcaac ccatcctggc acctggcaga cagccccgcg      240
gtgaatggag ccactgcgca cagcagcagt ttggatgccc gggaggtgat ccccatggca      300
gcagtaaagc aagcgctgag ggaggcaggc gacgagtttg aactgcggta ccggcgggca      360
ttcagtgacc tgacatccca gctccacatc accccaggga cagcatatca gagctttgaa      420
caggtagtga atgaactctt ccgggatggg gtagccattc ttcgcattgt ggcctttttc      480
tccttcggcg gggcactgtg cgtggaaagc gtagacaagg agatgcaggt attggtgagt      540
cggatcgcag cttggatggc cacttacctg aatgaccacc tagagccttg gatccaggag      600
aacggcggct gggatacttt tgtggaactc tatgggaaca atgcagcagc cgagagccga      660
aagggccagg aacgcttcaa ccgctggttc ctgacgggca tgactgtggc cggcgtggtt      720
ctgctgggct cactcttcag tcggaaatga                                      750
```

SEQ ID NO: 61

```
Met Ala Tyr Pro Tyr Asp Val Pro Asp Tyr Ala Ser Leu Arg Ser Thr
1               5                   10                  15

Met Ser Gln Ser Asn Arg Glu Leu Val Val Asp Phe Leu Ser Tyr Lys
            20                  25                  30

Leu Ser Gln Lys Gly Tyr Ser Trp Ser Gln Phe Ser Asp Val Glu Glu
        35                  40                  45

Asn Arg Thr Glu Ala Pro Glu Gly Thr Glu Ser Glu Met Glu Thr Pro
    50                  55                  60

Ser Ala Ile Asn Gly Asn Pro Ser Trp His Leu Ala Asp Ser Pro Ala
65                  70                  75                  80

Val Asn Gly Ala Thr Ala His Ser Ser Ser Leu Asp Ala Arg Glu Val
                85                  90                  95

Ile Pro Met Ala Ala Val Lys Gln Ala Leu Arg Glu Ala Gly Asp Glu
            100                 105                 110

Phe Glu Leu Arg Tyr Arg Arg Ala Phe Ser Asp Leu Thr Ser Gln Leu
        115                 120                 125

His Ile Thr Pro Gly Thr Ala Tyr Gln Ser Phe Glu Gln Val Val Asn
    130                 135                 140

Glu Leu Phe Arg Asp Gly Val Ala Ile Leu Arg Ile Val Ala Phe Phe
145                 150                 155                 160

Ser Phe Gly Gly Ala Leu Cys Val Glu Ser Val Asp Lys Glu Met Gln
                165                 170                 175

Val Leu Val Ser Arg Ile Ala Ala Trp Met Ala Thr Tyr Leu Asn Asp
            180                 185                 190

His Leu Glu Pro Trp Ile Gln Glu Asn Gly Gly Trp Asp Thr Phe Val
        195                 200                 205

Glu Leu Tyr Gly Asn Asn Ala Ala Ala Glu Ser Arg Lys Gly Gln Glu
    210                 215                 220

Arg Phe Asn Arg Trp Phe Leu Thr Gly Met Thr Val Ala Gly Val Val
225                 230                 235                 240

Leu Leu Gly Ser Leu Phe Ser Arg Lys
                245
```

SEQ ID NO: 62

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30
```

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro Gly Ser Met Ala Tyr Pro Tyr Asp Val Pro Asp Tyr Ala Ser
                100                 105                 110

Leu Arg Ser Thr Met Ser Gln Ser Asn Arg Glu Leu Val Val Asp Phe
        115                 120                 125

Leu Ser Tyr Lys Leu Ser Gln Lys Gly Tyr Ser Trp Ser Gln Phe Ser
        130                 135                 140

Asp Val Glu Glu Asn Arg Thr Glu Ala Pro Glu Gly Thr Glu Ser Glu
145                 150                 155                 160

Met Glu Thr Pro Ser Ala Ile Asn Gly Asn Pro Ser Trp His Leu Ala
                165                 170                 175

Asp Ser Pro Ala Val Asn Gly Ala Thr Ala His Ser Ser Ser Leu Asp
                180                 185                 190

Ala Arg Glu Val Ile Pro Met Ala Ala Val Lys Gln Ala Leu Arg Glu
        195                 200                 205

Ala Gly Asp Glu Phe Glu Leu Arg Tyr Arg Arg Ala Phe Ser Asp Leu
        210                 215                 220

Thr Ser Gln Leu His Ile Thr Pro Gly Thr Ala Tyr Gln Ser Phe Glu
225                 230                 235                 240

Gln Val Val Asn Glu Leu Phe Arg Asp Gly Val Ala Ile Leu Arg Ile
                245                 250                 255

Val Ala Phe Phe Ser Phe Gly Gly Ala Leu Cys Val Glu Ser Val Asp
                260                 265                 270

Lys Glu Met Gln Val Leu Val Ser Arg Ile Ala Ala Trp Met Ala Thr
        275                 280                 285

Tyr Leu Asn Asp His Leu Glu Pro Trp Ile Gln Glu Asn Gly Gly Trp
        290                 295                 300

Asp Thr Phe Val Glu Leu Tyr Gly Asn Asn Ala Ala Ala Glu Ser Arg
305                 310                 315                 320

Lys Gly Gln Glu Arg Phe Asn Arg Trp Phe Leu Thr Gly Met Thr Val
                325                 330                 335

Ala Gly Val Val Leu Leu Gly Ser Leu Phe Ser Arg Lys
                340                 345

SEQ ID NO: 63
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacgggtc attagttcat agcccatata      300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480

| LISTING OF ADDITIONAL SEQUENCES | |
|---|---|
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta caactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaacgg gccctctaga ctcgagcggc cgccactgtg ctggatatct gcagaattcc | 960 |
| accacactgg actagtggat ctatggcgta cccatacgat gttccagatt acgctagctt | 1020 |
| gagatctacc atgtctcaga gcaaccggga gctggtggtt gactttctct cctacaagct | 1080 |
| ttcccagaaa ggatacagct ggagtcagtt tagtgatgtg gaagagaaca ggactgaggc | 1140 |
| cccagaaggg actgaatcgg agatggagac ccccagtgcc atcaatggca acccatcctg | 1200 |
| gcacctggca gacagccccg cggtgaatgg agccactgcg cacagcagca gtttggatgc | 1260 |
| ccgggaggtg atccccatgg cagcagtaaa gcaagcgctg agggaggcag gcgacgagtt | 1320 |
| tgaactgcgg taccggcggg cattcagtga cctgacatcc cagctccaca tcaccccagg | 1380 |
| gacagcatat cagagctttg aacaggtagt gaatgaactc ttccgggatg gggtagccat | 1440 |
| tcttcgcatt gtggccttt tctccttcgg cggggcactg tgcgtggaaa gcgtagacaa | 1500 |
| ggagatgcag gtattggtga gtcggatcgc agcttggatg gccacttacc tgaatgacca | 1560 |
| cctagagcct tggatccagg agaacggcg ctgggatact tttgtggaac tctatgggaa | 1620 |
| caatgcagca gccgagagcc gaaagggcca ggaacgcttc aaccgctggt tcctgacggg | 1680 |
| catgactgtg gccggcgtgg ttctgctggg ctcactcttc agtcggaaat gaagatccga | 1740 |
| gctcggtacc aagcttaagt ttaaaccgct gatcagcctc gactgtgcct tctagttgcc | 1800 |
| agccatctgt tgtttgcccc tcccccgtgc cttccttgac cctggaaggt gccactccca | 1860 |
| ctgtcctttc ctaataaaat gaggaaaatg catcgcattg tctgagtagg tgtcattcta | 1920 |
| ttctgggggg tggggtgggg caggacagca aggggagga ttgggaagac aatagcaggc | 1980 |
| atgctgggga tgcggtgggc tctatggctt ctgaggcgga agaaccagc tggggctcta | 2040 |
| gggggtatcc ccacgcgccc tgtagcggcg cattaagcgc ggcgggtgtg gtggttacgc | 2100 |
| gcagcgtgac cgctacactt gccagcgccc tagcgcccgc tcctttcgct ttcttccctt | 2160 |
| cctttctcgc cacgttcgcc ggctttcccc gtcaagctct aaatcggggc atccctttag | 2220 |
| ggttccgatt tagtgcttta cggcacctcg accccaaaaa acttgattag ggtgatggtt | 2280 |
| cacgtagtgg gccatcgccc tgatagacgg ttttcgccc tttgacgttg gagtccacgt | 2340 |
| tctttaatag tggactcttg ttccaaactg gaacaacact caaccctatc tcggtctatt | 2400 |
| cttttgattt ataagggatt tgggggattt cggcctattg gttaaaaaat gagctgattt | 2460 |
| aacaaaaatt taacgcgaat taattctgtg gaatgtgtgt cagttagggt gtggaaagtc | 2520 |
| cccaggctcc ccaggcaggc agaagtatgc aaagcatgca tctcaattag tcagcaacca | 2580 |
| ggtgtggaaa gtccccaggc tccccagcag gcagaagtat gcaaagcatg catctcaatt | 2640 |
| agtcagcaac catagtcccg cccctaactc cgcccatccc gcccctaact ccgcccagtt | 2700 |
| ccgcccattc tccgccccat ggctgactaa ttttttttat ttatgcagag gccgaggccg | 2760 |

-continued

| LISTING OF ADDITIONAL SEQUENCES | |
|---|---|
| cctctgcctc tgagctattc cagaagtagt gaggaggctt ttttggaggc ctaggctttt | 2820 |
| gcaaaaagct cccgggagct tgtatatcca ttttcggatc tgatcaagag acaggatgag | 2880 |
| gatcgtttcg catgattgaa caagatggat tgcacgcagg ttctccggcc gcttgggtgg | 2940 |
| agaggctatt cggctatgac tgggcacaac agacaatcgg ctgctctgat gccgccgtgt | 3000 |
| tccggctgtc agcgcagggg cgcccggttc tttttgtcaa gaccgacctg tccggtgccc | 3060 |
| tgaatgaact gcaggacgag gcagcgcggc tatcgtggct ggccacgacg ggcgttcctt | 3120 |
| gcgcagctgt gctcgacgtt gtcactgaag cgggaaggga ctggctgcta ttgggcgaag | 3180 |
| tgccggggca ggatctcctg tcatctcacc ttgctcctgc cgagaaagta tccatcatgg | 3240 |
| ctgatgcaat gcggcggctg catacgcttg atccggctac ctgcccattc gaccaccaag | 3300 |
| cgaaacatcg catcgagcga gcacgtactc ggatggaagc cggtcttgtc gatcaggatg | 3360 |
| atctggacga agagcatcag gggctcgcgc cagccgaact gttcgccagg ctcaaggcgc | 3420 |
| gcatgcccga cggcgaggat ctcgtcgtga cccatggcga tgcctgcttg ccgaatatca | 3480 |
| tggtggaaaa tggccgcttt tctggattca tcgactgtgg ccggctgggt gtggcggacc | 3540 |
| gctatcagga catagcgttg gctacccgtg atattgctga agagcttggc ggcgaatggg | 3600 |
| ctgaccgctt cctcgtgctt tacggtatcg ccgctcccga ttcgcagcgc atcgccttct | 3660 |
| atcgccttct tgacgagttc ttctgagcgg gactctgggg ttcgaaatga ccgaccaagc | 3720 |
| gacgcccaac ctgccatcac gagatttcga ttccaccgcc gccttctatg aaaggttggg | 3780 |
| cttcggaatc gttttccggg acgccggctg atgatcctc cagcgcgggg atctcatgct | 3840 |
| ggagttcttc gcccacccca acttgtttat tgcagcttat aatggttaca ataaagcaa | 3900 |
| tagcatcaca aatttcacaa ataaagcatt ttttcactg cattctagtt gtggtttgtc | 3960 |
| caaactcatc aatgtatctt atcatgtctg tataccgtcg acctctagct agagcttggc | 4020 |
| gtaatcatgg tcatagctgt ttcctgtgtg aaattgttat ccgctcacaa ttccacacaa | 4080 |
| catacgagcc ggaagcataa agtgtaaagc ctggggtgcc taatgagtga gctaactcac | 4140 |
| attaattgcg ttgcgctcac tgcccgcttt ccagtcggga aacctgtcgt gccagctgca | 4200 |
| ttaatgaatc ggccaacgcg cggggagagg cggtttgcgt attgggcgct cttccgcttc | 4260 |
| ctcgctcact gactcgctgc gctcggtcgt tcggctgcgg cgagcggtat cagctcactc | 4320 |
| aaaggcggta atacggttat ccacagaatc aggggataac gcaggaaaga acatgtgagc | 4380 |
| aaaaggccag caaaaggcca ggaaccgtaa aaaggccgcg ttgctggcgt ttttccatag | 4440 |
| gctccgcccc cctgacgagc atcacaaaaa tcgacgctca agtcagaggt ggcgaaaccc | 4500 |
| gacaggacta taaagatacc aggcgtttcc ccctggaagc tccctcgtgc gctctcctgt | 4560 |
| tccgaccctg ccgcttaccg gatacctgtc cgcctttctc ccttcgggaa gcgtggcgct | 4620 |
| ttctcaatgc tcacgctgta ggtatctcag ttcggtgtag tcgttcgct ccaagctggg | 4680 |
| ctgtgtgcac gaaccccccg ttcagcccga ccgctgcgcc ttatccggta actatcgtct | 4740 |
| tgagtccaac ccggtaagac acgacttatc gccactggca gcagccactg gtaacaggat | 4800 |
| tagcagagcg aggtatgtag gcggtgctac agagttcttg aagtggtggc ctaactacgg | 4860 |
| ctacactaga aggacagtat ttggtatctg cgctctgctg aagccagtta ccttcggaaa | 4920 |
| aagagttggt agctcttgat ccggcaaaca accaccgct ggtagcggtg ttttttgt | 4980 |
| ttgcaagcag cagattacgc gcagaaaaaa aggatctcaa gaagatcctt tgatcttttc | 5040 |
| tacggggtct gacgctcagt ggaacgaaaa ctcacgttaa gggattttgg tcatgagatt | 5100 |

LISTING OF ADDITIONAL SEQUENCES

```
atcaaaaagg atcttcacct agatcctttt aaattaaaaa tgaagtttta aatcaatcta      5160
aagtatatat gagtaaactt ggtctgacag ttaccaatgc ttaatcagtg aggcacctat      5220
ctcagcgatc tgtctatttc gttcatccat agttgcctga ctccccgtcg tgtagataac     5280
tacgatacgg gagggcttac catctggccc cagtgctgca atgataccgc gagacccacg     5340
ctcaccggct ccagatttat cagcaataaa ccagccagcc ggaagggccg agcgcagaag     5400
tggtcctgca actttatccg cctccatcca gtctattaat tgttgccggg aagctagagt     5460
aagtagttcg ccagttaata gtttgcgcaa cgttgttgcc attgctacag gcatcgtggt     5520
gtcacgctcg tcgtttggta tggcttcatt cagctccggt tcccaacgat caaggcgagt     5580
tacatgatcc cccatgttgt gcaaaaaagc ggttagctcc ttcggtcctc cgatcgttgt     5640
cagaagtaag ttggccgcag tgttatcact catggttatg gcagcactgc ataattctct     5700
tactgtcatg ccatccgtaa gatgcttttc tgtgactggt gagtactcaa ccaagtcatt     5760
ctgagaatag tgtatgcggc gaccgagttg ctcttgcccg gcgtcaatac gggataatac     5820
cgcgccacat agcagaactt taaaagtgct catcattgga aaacgttctt cggggcgaaa     5880
actctcaagg atcttaccgc tgttgagatc cagttcgatg taacccactc gtgcacccaa     5940
ctgatcttca gcatctttta ctttcaccag cgtttctggg tgagcaaaaa caggaaggca     6000
aaatgccgca aaaaagggaa taagggcgac acggaaatgt tgaatactca tactcttcct     6060
ttttcaatat tattgaagca tttatcaggg ttattgtctc atgagcggat acatatttga     6120
atgtatttag aaaaataaac aatagggt tccgcgcaca tttccccgaa aagtgccacc      6180
tgacgtc                                                               6187
SEQ ID NO: 64
acggatcgg gagatctccc gatcccctat ggtcgactct cagtacaatc tgctctgatg       60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaacgg gccctctaga ctcgagcggc cgccactgtg ctggatatct gcagaattca     960
tgcatggaga tacacctaca ttgcatgaat atatgttaga tttgcaacca gagacaactg    1020
atctctactg ttatgagcaa ttaaatgaca gctcagagga ggaggatgaa atagatggtc    1080
cagctggaca agcagaaccg gacagagccc attacaatat tgtaacccttt tgttgcaagt    1140
```

| | |
|---|---|
| gtgactctac gcttcggttg tgcgtacaaa gcacacacgt agacattcgt actttggaag | 1200 |
| acctgttaat gggcacacta ggaattgtgt gccccatctg ttctcagaaa ccaggatcta | 1260 |
| tggcgtaccc atacgatgtt ccagattacg ctagcttgag atctaccatg tctcagagca | 1320 |
| accgggagct ggtggttgac tttctctcct acaagctttc ccagaaagga tacagctgga | 1380 |
| gtcagtttag tgatgtggaa gagaacagga ctgaggcccc agaagggact gaatcggaga | 1440 |
| tggagacccc cagtgccatc aatggcaacc catcctggca cctggcagac agccccgcgg | 1500 |
| tgaatggagc cactgcgcac agcagcagtt tggatgcccg ggaggtgatc cccatggcag | 1560 |
| cagtaaagca agcgctgagg gaggcaggcg acgagtttga actgcggtac cggcgggcat | 1620 |
| tcagtgacct gacatcccag ctccacatca ccccagggac agcatatcag agctttgaac | 1680 |
| aggtagtgaa tgaactcttc cgggatgggg tagccattct tcgcattgtg gccttttct | 1740 |
| ccttcggcgg ggcactgtgc gtggaaagcg tagacaagga gatgcaggta ttggtgagtc | 1800 |
| ggatcgcagc ttggatggcc acttacctga atgaccacct agagccttgg atccaggaga | 1860 |
| acggcggctg ggatacttt tgtggaactct atgggaacaa tgcagcagcc gagagccgaa | 1920 |
| agggccagga acgcttcaac cgctggttcc tgacgggcat gactgtggcc ggcgtggttc | 1980 |
| tgctgggctc actcttcagt cggaaatgaa gatccaagct taagtttaaa ccgctgatca | 2040 |
| gcctcgactg tgccttctag ttgccagcca tctgttgttt gcccctcccc cgtgccttcc | 2100 |
| ttgaccctgg aaggtgccac tcccactgtc ctttcctaat aaaatgagga aattgcatcg | 2160 |
| cattgtctga gtaggtgtca ttctattctg ggggtgggg tggggcagga cagcaagggg | 2220 |
| gaggattggg aagacaatag caggcatgct ggggatgcgg tgggctctat ggcttctgag | 2280 |
| gcggaaagaa ccagctgggg ctctaggggg tatccccacg cgccctgtag cggcgcatta | 2340 |
| agcgcggcgg gtgtggtggt tacgcgcagc gtgaccgcta cacttgccag cgccctagcg | 2400 |
| cccgctcctt tcgctttctt cccttcctt ctcgccacgt tcgccggctt tccccgtcaa | 2460 |
| gctctaaatc gggcatccc tttagggttc cgatttagtg ctttacgca cctcgacccc | 2520 |
| aaaaaacttg attagggtga tggttcacgt agtgggccat cgccctgata acggttttt | 2580 |
| cgcccttga cgttggagtc cacgttcttt aatagtggac tcttgttcca aactggaaca | 2640 |
| acactcaacc ctatctcggt ctattctttt gatttataag ggattttggg gatttcggcc | 2700 |
| tattggttaa aaatgagct gatttaacaa aaatttaacg cgaattaatt ctgtggaatg | 2760 |
| tgtgtcagtt agggtgtgga aagtccccag gctccccagg caggcagaag tatgcaaagc | 2820 |
| atgcatctca attagtcagc aaccaggtgt ggaaagtccc caggctcccc agcaggcaga | 2880 |
| agtatgcaaa gcatgcatct caattagtca gcaaccatag tcccgcccct aactccgccc | 2940 |
| atcccgcccc taactccgcc cagttccgcc cattctccgc cccatggctg actaatttt | 3000 |
| tttatttatg cagaggccga ggccgcctct gcctctgagc tattccagaa gtagtgagga | 3060 |
| ggcttttttg gaggcctagg cttttgcaaa aagctcccgg gagcttgtat atccatttc | 3120 |
| ggatctgatc aagagacagg atgaggatcg tttcgcatga ttgaacaaga tggattgcac | 3180 |
| gcaggttctc cggccgcttg ggtggagagg ctattcggct atgactgggc acaacagaca | 3240 |
| atcggctgct ctgatgccgc cgtgttccgg ctgtcagcgc agggggcgccc ggttcttttt | 3300 |
| gtcaagaccg acctgtccgg tgccctgaat gaactgcagg acgaggcagc gcggctatcg | 3360 |
| tggctggcca cgacgggcgt tccttgcgca gctgtgctcg acgttgtcac tgaagcggga | 3420 |

-continued

| LISTING OF ADDITIONAL SEQUENCES | |
|---|---|
| agggactggc tgctattggg cgaagtgccg gggcaggatc tcctgtcatc tcaccttgct | 3480 |
| cctgccgaga aagtatccat catggctgat gcaatgcggc ggctgcatac gcttgatccg | 3540 |
| gctacctgcc cattcgacca ccaagcgaaa catcgcatcg agcgagcacg tactcggatg | 3600 |
| gaagccggtc ttgtcgatca ggatgatctg gacgaagagc atcaggggct cgcgccagcc | 3660 |
| gaactgttcg ccaggctcaa ggcgcgcatg cccgacggcg aggatctcgt cgtgacccat | 3720 |
| ggcgatgcct gcttgccgaa tatcatggtg gaaaatggcc gcttttctgg attcatcgac | 3780 |
| tgtggccggc tgggtgtggc ggaccgctat caggacatag cgttggctac ccgtgatatt | 3840 |
| gctgaagagc ttggcggcga atgggctgac cgcttcctcg tgctttacgg tatcgccgct | 3900 |
| cccgattcgc agcgcatcgc cttctatcgc cttcttgacg agttcttctg agcgggactc | 3960 |
| tggggttcga aatgaccgac caagcgacgc ccaacctgcc atcacgagat ttcgattcca | 4020 |
| ccgccgcctt ctatgaaagg ttgggcttcg aatcgttttt ccgggacgcc ggctggatga | 4080 |
| tcctccagcg cggggatctc atgctggagt tcttcgccca ccccaacttg tttattgcag | 4140 |
| cttataatgg ttacaaataa agcaatagca tcacaaattt cacaaataaa gcatttttt | 4200 |
| cactgcattc tagttgtggt ttgtccaaac tcatcaatgt atcttatcat gtctgtatac | 4260 |
| cgtcgacctc tagctagagc ttggcgtaat catggtcata gctgtttcct gtgtgaaatt | 4320 |
| gttatccgct cacaattcca cacaacatac gagccggaag cataaagtgt aaagcctggg | 4380 |
| gtgcctaatg agtgagctaa ctcacattaa ttgcgttgcg ctcactgccc gctttccagt | 4440 |
| cgggaaacct gtcgtgccag ctgcattaat gaatcggcca acgcgcgggg agaggcggtt | 4500 |
| tgcgtattgg gcgctcttcc gcttcctcgc tcactgactc gctgcgctcg gtcgttcggc | 4560 |
| tgcggcgagc ggtatcagct cactcaaagg cggtaatacg gttatccaca gaatcagggg | 4620 |
| ataacgcagg aaagaacatg tgagcaaaag gccagcaaaa ggccaggaac cgtaaaaagg | 4680 |
| ccgcgttgct ggcgtttttc cataggctcc gcccccctga cgagcatcac aaaaatcgac | 4740 |
| gctcaagtca gaggtggcga aacccgacag gactataaag ataccaggcg tttccccctg | 4800 |
| gaagctccct cgtgcgctct cctgttccga ccctgccgct taccggatac ctgtccgcct | 4860 |
| ttctcccttc gggaagcgtg gcgctttctc aatgctcacg ctgtaggtat ctcagttcgg | 4920 |
| tgtaggtcgt tcgctccaag ctgggctgtg tgcacgaacc ccccgttcag cccgaccgct | 4980 |
| gcgccttatc cggtaactat cgtcttgagt ccaacccggt aagacacgac ttatcgccac | 5040 |
| tggcagcagc cactggtaac aggattagca gagcgaggta tgtaggcggt gctacagagt | 5100 |
| tcttgaagtg gtggcctaac tacggctaca ctagaaggac agtatttggt atctgcgctc | 5160 |
| tgctgaagcc agttaccttc ggaaaaagag ttggtagctc ttgatccggc aaacaaacca | 5220 |
| ccgctggtag cggtggtttt tttgtttgca agcagcagat tacgcgcaga aaaaaggat | 5280 |
| ctcaagaaga tcctttgatc ttttctacgg ggtctgacgc tcagtggaac gaaaactcac | 5340 |
| gttaagggat tttggtcatg agattatcaa aaaggatctt cacctagatc cttttaaatt | 5400 |
| aaaaatgaag ttttaaatca atctaaagta tatatgagta aacttggtct gacagttacc | 5460 |
| aatgcttaat cagtgaggca cctatctcag cgatctgtct atttcgttca tccatagttg | 5520 |
| cctgactccc cgtcgtgtag ataactacga tacgggaggg cttaccatct ggccccagtg | 5580 |
| ctgcaatgat accgcgagac ccacgctcac cggctccaga tttatcagca ataaaccagc | 5640 |
| cagccggaag ggccgagcgc agaagtggtc ctgcaacttt atccgcctcc atccagtcta | 5700 |
| ttaattgttg ccgggaagct agagtaagta gttcgccagt taatagtttg cgcaacgttg | 5760 |

| | |
|---|---|
| ttgccattgc tacaggcatc gtggtgtcac gctcgtcgtt tggtatggct tcattcagct | 5820 |
| ccggttccca acgatcaagg cgagttacat gatcccccat gttgtgcaaa aaagcggtta | 5880 |
| gctccttcgg tcctccgatc gttgtcagaa gtaagttggc cgcagtgtta tcactcatgg | 5940 |
| ttatggcagc actgcataat tctcttactg tcatgccatc cgtaagatgc ttttctgtga | 6000 |
| ctggtgagta ctcaaccaag tcattctgag aatagtgtat gcggcgaccg agttgctctt | 6060 |
| gcccggcgtc aatacgggat aataccgcgc cacatagcag aactttaaaa gtgctcatca | 6120 |
| ttggaaaacg ttcttcgggg cgaaaactct caaggatctt accgctgttg agatccagtt | 6180 |
| cgatgtaacc cactcgtgca cccaactgat cttcagcatc ttttactttc accagcgttt | 6240 |
| ctgggtgagc aaaaacagga aggcaaaatg ccgcaaaaaa gggaataagg gcgacacgga | 6300 |
| aatgttgaat actcatactc ttcctttttc aatattattg aagcatttat cagggttatt | 6360 |
| gtctcatgag cggatacata tttgaatgta tttagaaaaa taaacaaata ggggttccgc | 6420 |
| gcacatttcc ccgaaaagtg ccacctgacg tc | 6452 |

SEQ ID NO: 65

| | |
|---|---|
| atggcggatg tgtgacatac acgacgccaa aagattttgt tccagctcct gccacctccg | 60 |
| ctacgcgaga gattaaccac ccacgatggc cgccaaagtg catgttgata ttgaggctga | 120 |
| cagcccattc atcaagtctt tgcagaaggc atttccgtcg ttcgaggtgg agtcattgca | 180 |
| ggtcacacca aatgaccatg caaatgccag agcattttcg cacctggcta ccaaattgat | 240 |
| cgagcaggag actgacaaag acacactcat cttggatatc ggcagtgcgc cttccaggag | 300 |
| aatgatgtct acgcacaaat accactgcgt atgccctatg cgcagcgcag aagaccccga | 360 |
| aaggctcgat agctacgcaa agaaactggc agcggcctcc gggaaggtgc tggatagaga | 420 |
| gatcgcagga aaaatcaccg acctgcagac cgtcatggct acgccagacg ctgaatctcc | 480 |
| tacctttttgc ctgcatacag acgtcacgtg tcgtacggca gccgaagtgg ccgtatacca | 540 |
| ggacgtgtat gctgtacatg caccaacatc gctgtaccat caggcgatga aggtgtcag | 600 |
| aacggcgtat tggattgggt ttgacaccac cccgttttatg tttgacgcgc tagcaggcgc | 660 |
| gtatccaacc tacgccacaa actgggccga cgagcaggtg ttacaggcca ggaacatagg | 720 |
| actgtgtgca gcatccttga ctgagggaag actcggcaaa ctgtccattc tccgcaagaa | 780 |
| gcaattgaaa ccttgcgaca cagtcatgtt ctcggtagga tctacattgt acactgagag | 840 |
| cagaaagcta ctgaggagct ggcacttacc ctccgtattc cacctgaaag gtaaacaatc | 900 |
| ctttacctgt aggtgcgata ccatcgtatc atgtgaaggg tacgtagtta agaaaatcac | 960 |
| tatgtgcccc ggcctgtacg gtaaaacggt agggtacgcc gtgacgtatc acgcggaggg | 1020 |
| attcctagtg tgcaagacca cagacactgt caaaggagaa agagtctcat tccctgtatg | 1080 |
| cacctacgtc ccctcaacca tctgtgatca aatgactggc atactagcga ccgacgtcac | 1140 |
| accggaggac gcacagaagt tgttagtggg attgaatcag aggatagttg tgaacggaag | 1200 |
| aacacagcga aacactaaca cgatgaagaa ctatctgctt ccgattgtgg ccgtcgcatt | 1260 |
| tagcaagtgg gcgagggaat acaaggcaga ccttgatgat gaaaaacctc tgggtgtccg | 1320 |
| agagaggtca cttacttgct gctgcttgtg ggcatttaaa acgaggaaga tgcacaccat | 1380 |
| gtacaagaaa ccagacaccc agacaatagt gaaggtgcct tcagagttta actcgttcgt | 1440 |
| catcccgagc ctatggtcta caggcctcgc aatcccagtc agatcacgca ttaagatgct | 1500 |
| tttggccaag aagaccaagc gagagttaat acctgttctc gacgcgtcgt cagccaggga | 1560 |

-continued

| LISTING OF ADDITIONAL SEQUENCES | |
|---|---|
| tgctgaacaa gaggagaagg agaggttgga ggccgagctg actagagaag ccttaccacc | 1620 |
| cctcgtcccc atcgcgccgg cggagacggg agtcgtcgac gtcgacgttg aagaactaga | 1680 |
| gtatcacgca ggtgcagggg tcgtggaaac acctcgcagc gcgttgaaag tcaccgcaca | 1740 |
| gccgaacgac gtactactag gaaattacgt agttctgtcc ccgcagaccg tgctcaagag | 1800 |
| ctccaagttg gccccgtgc accctctagc agagcaggtg aaaataataa cacataacgg | 1860 |
| gagggccggc ggttaccagg tcgacggata tgacggcagg gtcctactac catgtggatc | 1920 |
| ggccattccg gtccctgagt ttcaagcttt gagcgagagc gccactatgg tgtacaacga | 1980 |
| aagggagttc gtcaacagga aactatacca tattgccgtt cacggaccgt cgctgaacac | 2040 |
| cgacgaggag aactacgaga aagtcagagc tgaaagaact gacgccgagt acgtgttcga | 2100 |
| cgtagataaa aaatgctgcg tcaagagaga ggaagcgtcg ggtttggtgt tggtgggaga | 2160 |
| gctaaccaac cccccgttcc atgaattcgc ctacgaaggg ctgaagatca ggccgtcggc | 2220 |
| accatataag actacagtag taggagtctt tggggttccg ggatcaggca agtctgctat | 2280 |
| tattaagagc ctcgtgacca aacacgatct ggtcaccagc ggcaagaagg agaactgcca | 2340 |
| ggaaatagtt aacgacgtga agaagcaccg cgggaagggg acaagtaggg aaaacagtga | 2400 |
| ctccatcctg ctaaacgggt gtcgtcgtgc cgtggacatc ctatatgtgg acgaggcttt | 2460 |
| cgctagccat tccggtactc tgctggccct aattgctctt gttaaacctc ggagcaaagt | 2520 |
| ggtgttatgc ggagaccca agcaatgcgg attcttcaat atgatgcagc ttaaggtgaa | 2580 |
| cttcaaccac aacatctgca ctgaagtatg tcataaaagt atatccagac gttgcacgcg | 2640 |
| tccagtcacg gccatcgtgt ctacgttgca ctacggaggc aagatgcgca cgaccaaccc | 2700 |
| gtgcaacaaa cccataatca tagacaccac aggacagacc aagcccaagc caggagacat | 2760 |
| cgtgttaaca tgcttccgag ctgggcaaa gcagctgcag ttggactacc gtggacacga | 2820 |
| agtcatgaca gcagcagcat ctcagggcct cacccgcaaa ggggtatacg ccgtaaggca | 2880 |
| gaaggtgaat gaaaatccct tgtatgcccc tgcgtcggag cacgtgaatg tactgctgac | 2940 |
| gcgcactgag gataggctgg tgtggaaaac gctggccggc gatccctgga ttaaggtcct | 3000 |
| atcaaacatt ccacagggta actttacggc cacattggaa gaatggcaag aagaacacga | 3060 |
| caaaataatg aaggtgattg aaggaccggc tgcgcctgtg gacgcgttcc agaacaaagc | 3120 |
| gaacgtgtgt tgggcgaaaa gcctggtgcc tgtcctggac actgccggaa tcagattgac | 3180 |
| agcagaggag tggagcacca taattacagc atttaaggag gacagagctt actctccagt | 3240 |
| ggtggccttg aatgaaattt gcaccaagta ctatggagtt gacctggaca gtggcctgtt | 3300 |
| ttctgccccg aaggtgtccc tgtattacga gaacaaccac tgggataaca gacctggtgg | 3360 |
| aaggatgtat ggattcaatg ccgcaacagc tgccaggctg gaagctagac ataccttcct | 3420 |
| gaaggggcag tggcatacgg gcaagcaggc agttatcgca gaaagaaaaa tccaaccgct | 3480 |
| ttctgtgctg acaatgtaa ttcctatcaa ccgcaggctg ccgcacgccc tggtggctga | 3540 |
| gtacaagacg gttaaaggca gtaggttga gtggctggtc aataaagtaa gagggtacca | 3600 |
| cgtcctgctg gtgagtgagt acaacctggc tttgcctcga cgcagggtca cttggttgtc | 3660 |
| accgctgaat gtcacaggcg ccgataggtg ctacgaccta agtttaggac tgccggctga | 3720 |
| cgccggcagg ttcgacttgg tctttgtgaa cattcacacg gaattcagaa tccaccacta | 3780 |
| ccagcagtgt gtcgaccacg ccatgaagct gcagatgctt gggggagatg cgctacgact | 3840 |

-continued

| LISTING OF ADDITIONAL SEQUENCES | |
|---|---|
| cgttgtttcc tccttaagca gaaagttctc gtctgcaaga gtgttgcgcc cggattgtgt | 3960 |
| caccagcaat acagaagtgt tcttgctgtt ctccaacttt gacaacggaa agagaccctc | 4020 |
| tacgctacac cagatgaata ccaagctgag tgccgtgtat gccggagaag ccatgcacac | 4080 |
| ggccgggtgt gcaccatcct acagagttaa gagagcagac atagccacgt gcacagaagc | 4140 |
| ggctgtggtt aacgcagcta acgcccgtgg aactgtaggg gatggcgtat gcagggccgt | 4200 |
| ggcgaagaaa tggccgtcag cctttaaggg agcagcaaca ccagtgggca caattaaaac | 4260 |
| agtcatgtgc ggctcgtacc ccgtcatcca cgctgtagcg cctaatttct ctgccacgac | 4320 |
| tgaagcggaa ggggaccgcg aattggccgc tgtctaccgg gcagtggccg ccgaagtaaa | 4380 |
| cagactgtca ctgagcagcg tagccatccc gctgctgtcc acaggagtgt tcagcggcgg | 4440 |
| aagagatagg ctgcagcaat ccctcaacca tctattcaca gcaatggacg ccacggacgc | 4500 |
| tgacgtgacc atctactgca gagacaaaag ttgggagaag aaaatccagg aagccattga | 4560 |
| catgaggacg gctgtggagt tgctcaatga tgacgtggag ctgaccacag acttggtgag | 4620 |
| agtgcacccg gacagcagcc tggtgggtcg taagggctac agtaccactg acgggtcgct | 4680 |
| gtactcgtac tttgaaggta cgaaattcaa ccaggctgct attgatatgg cagagatact | 4740 |
| gacgttgtgg cccagactgc aagaggcaaa cgaacagata tgcctatacg cgctgggcga | 4800 |
| aacaatggac aacatcagat ccaaatgtcc ggtgaacgat tccgattcat caacacctcc | 4860 |
| caggacagtg ccctgcctgt gccgctacgc aatgacagca gaacggatcg cccgccttag | 4920 |
| gtcacaccaa gttaaaagca tggtggtttg ctcatctttt cccctcccga ataccatgt | 4980 |
| agatggggtg cagaaggtaa agtgcgagaa ggttctcctg ttcgacccga cggtaccttc | 5040 |
| agtggttagt ccgcggaagt atgccgcatc tacgacggac cactcagatc ggtcgttacg | 5100 |
| agggtttgac ttggactgga ccaccgactc gtcttccact gccagcgata ccatgtcgct | 5160 |
| acccagtttg cagtcgtgtg acatcgactc gatctacgag ccaatggctc ccatagtagt | 5220 |
| gacggctgac gtacaccctg aacccgcagg catcgcggac ctggcggcag atgtgcaccc | 5280 |
| tgaacccgca gaccatgtgg acctcgagaa cccgattcct ccaccgcgcc cgaagagagc | 5340 |
| tgcataccct gcctcccgcg cggcggagcg accggtgccg gcgccgagaa agccgacgcc | 5400 |
| tgccccaagg actgcgttta ggaacaagct gcctttgacg ttcggcgact ttgacgagca | 5460 |
| cgaggtcgat gcgttggcct ccgggattac tttcggagac ttcgacgacg tcctgcgact | 5520 |
| aggccgcgcg ggtgcatata ttttctcctc ggacactggc agcggacatt tacaacaaaa | 5580 |
| atccgttagg cagcacaatc tccagtgcgc acaactggat gcggtccagg aggagaaaat | 5640 |
| gtacccgcca aaattggata ctgagaggga gaagctgttg ctgctgaaaa tgcagatgca | 5700 |
| cccatcggag gctaataaga gtcgatacca gtctcgcaaa gtggagaaca tgaaagccac | 5760 |
| ggtggtggac aggctcacat cgggggccag attgtacacg ggagcggacg taggccgcat | 5820 |
| accaacatac gcggttcggt accccgccc cgtgtactcc cctaccgtga tcgaaagatt | 5880 |
| ctcaagcccc gatgtagcaa tcgcagcgtg caacgaatac ctatccagaa attcccaac | 5940 |
| agtggcgtcg taccagataa cagatgaata cgacgcatac ttggacatgg ttgacgggtc | 6000 |
| ggatagttgc ttggacagag cgacattctg cccggcgaag ctccggtgct acccgaaaca | 6060 |
| tcatgcgtac caccagccga ctgtacgcag tgccgtcccg tcacccttc agaacacact | 6120 |
| acagaacgtg ctagccggcc gccaccaaga gaaactgcaac gtcacgcaaa tgcgagaact | 6180 |
| acccaccatg gactcggcag tgttcaacgt ggagtgcttc aagcgctatg cctgctccgg | 6240 |

| | |
|---|---|
| agaatattgg gaagaatatg ctaaacaacc tatccggata accactgaga acatcactac | 6300 |
| ctatgtgacc aaattgaaag gcccgaaagc tgctgccttg ttcgctaaga cccacaactt | 6360 |
| ggttccgctg caggaggttc ccatggacag attcacggtc gacatgaaac gagatgtcaa | 6420 |
| agtcactcca gggacgaaac acacagagga aagacccaaa gtccaggtaa ttcaagcagc | 6480 |
| ggagccattg gcgaccgctt acctgtgcgg catccacagg gaattagtaa ggagactaaa | 6540 |
| tgctgtgtta cgccctaacg tgcacacatt gtttgatatg tcggccgaag actttgacgc | 6600 |
| gatcatcgcc tctcacttcc acccaggaga cccggttcta gagacggaca ttgcatcatt | 6660 |
| cgacaaaagc caggacgact ccttggctct tacaggttta atgatcctcg aagatctagg | 6720 |
| ggtggatcag tacctgctgg acttgatcga ggcagccttt ggggaaatat ccagctgtca | 6780 |
| cctaccaact ggcacgcgct tcaagttcgg agctatgatg aaatcgggca tgtttctgac | 6840 |
| tttgtttatt aacactgttt tgaacatcac catagcaagc agggtactgg agcagagact | 6900 |
| cactgactcc gcctgtgcgg ccttcatcgg cgacgacaac atcgttcacg gagtgatctc | 6960 |
| cgacaagctg atggcggaga ggtgcgcgtc gtgggtcaac atggaggtga agatcattga | 7020 |
| cgctgtcatg ggcgaaaaac ccccatattt tgtgggggga ttcatagttt ttgacagcgt | 7080 |
| cacacagacc gcctgccgtg tttcagaccc acttaagcgc ctgttcaagt tgggtaagcc | 7140 |
| gctaacagct gaagacaagc aggacgaaga caggcgacga gcactgagtg acgaggttag | 7200 |
| caagtggttc cggacaggct tggggccgaa actggaggtg gcactaacat ctaggtatga | 7260 |
| ggtagagggc tgcaaaagta tcctcatagc catggccacc ttggcgaggg acattaaggc | 7320 |
| gtttaagaaa ttgagaggac ctgttataca cctctacggc ggtcctagat tggtgcgtta | 7380 |
| atacacagaa ttctgattgg atcccaaacg ggccctctag actcgagcgg ccgccactgt | 7440 |
| gctggatatc tgcagaattc caccacactg gactagtgga tctatggcgt acccatacga | 7500 |
| tgttccagat tacgctagct tgagatctac catgtctcag agcaaccggg agctggtggt | 7560 |
| tgactttctc tcctacaagc tttcccagaa aggatacagc tggagtcagt ttagtgatgt | 7620 |
| ggaagagaac aggactgagg ccccagaagg gactgaatcg gagatggaga cccccagtgc | 7680 |
| catcaatggc aacccatcct ggcacctggc agacagcccc gcggtgaatg gagccactgc | 7740 |
| gcacagcagc agtttggatg cccgggaggt gatccccatg gcagcagtaa agcaagcgct | 7800 |
| gagggaggca ggcgacgagt ttgaactgcg gtaccggcgg gcattcagtg acctgacatc | 7860 |
| ccagctccac atcaccccag ggacagcata tcagagcttt gaacaggtag tgaatgaact | 7920 |
| cttccgggat ggggtaaact ggggtcgcat tgtggccttt ttctccttcg gcggggcact | 7980 |
| gtgcgtggaa agcgtagaca aggagatgca ggtattggtg agtcggatcg cagcttggat | 8040 |
| ggccacttac ctgaatgacc acctagagcc ttggatccag gagaacggcg gctgggatac | 8100 |
| ttttgtggaa ctctatggga acaatgcagc agccgagagc cgaaagggcc aggaacgctt | 8160 |
| caaccgctgg ttcctgacgg gcatgactgt ggccggcatg gttctactgg gctcactctt | 8220 |
| cagtcggaaa tgaagatccg agctcggtac caagcttaag tttgggtaat taattgaatt | 8280 |
| acatccctac gcaaacgttt tacggccgcc ggtggcgccc gcgcccggcg gcccgtcctt | 8340 |
| ggccgttgca ggccactccg gtggctcccg tcgtcccga cttccaggcc cagcagatgc | 8400 |
| agcaactcat cagcgccgta aatgcgctga caatgagaca gaacgcaatt gctcctgcta | 8460 |
| ggcctcccaa accaaagaag aagaagacaa ccaaaccaaa gccgaaaacg cagcccaaga | 8520 |

-continued

| LISTING OF ADDITIONAL SEQUENCES | |
|---|---|
| agatcaacgg aaaaucgcag cagcaaaaga agaaagacaa gcaagccgac aagaagaaga | 8580 |
| agaaacccgg aaaaagagaa agautgtgca tgaagattga aaatgactgt atcttcgtat | 8640 |
| gcggctagcc acagtaacgt agtgtttcca gacatgtcgg gcaccgcact atcatgggtg | 8700 |
| cagaaaatct cgggtggtct gggggccttc gcaatcggcg ctatcctggt gctggttgtg | 8760 |
| gtcacttgca ttgggctccg cagataagtt agggtaggca atggcattga tatagcaaga | 8820 |
| aaattgaaaa cagaaaaagt tagggtaagc aatggcatat aaccataact gtataacttg | 8880 |
| taacaaagcg caacaagacc tgcgcaattg gccccgtggt ccgcctcacg gaaactcggg | 8940 |
| gcaactcata ttgacacatt aattggcaat aattggaagc ttacataagc ttaattcgac | 9000 |
| gaataattgg atttttattt tattttgcaa ttggttttta atatttccaa aaaaaaaaaa | 9060 |
| aaaaaaaaaa aaaaaaaaaa aaaaaaaaaa aaaaaaaaaa aaaaaaaaaa aaaaaaaact | 9120 |
| agtgatcata atcagccata ccacatttgt agaggtttta cttgctttaa aaacctccc | 9180 |
| acacctcccc ctgaacctga aacataaaat gaatgcaatt gttgttgtta acttgtttat | 9240 |
| tgcagcttat aatggttaca ataaagcaa tagcatcaca aatttcacaa ataaagcatt | 9300 |
| tttttcactg cattctagtt gtggtttgtc caaactcatc aatgtatctt atcatgtctg | 9360 |
| gatctagtct gcattaatga atcggccaac gcgcgggag aggcggtttg cgtattgggc | 9420 |
| gctcttccgc ttcctcgctc actgactcgc tgcgctcggt cgttcggctg cggcgagcgg | 9480 |
| tatcagctca ctcaaaggcg gtaatacggt tatccacaga atcaggggat aacgcaggaa | 9540 |
| agaacatgtg agcaaaaggc cagcaaaagg ccaggaaccg taaaaaggcc gcgttgctgg | 9600 |
| cgttttccca taggctccgc cccctgacg agcatcacaa aaatcgacgc tcaagtcaga | 9660 |
| ggtggcgaaa cccgacagga ctataaagat accaggcgtt tccccctgga agctccctcg | 9720 |
| tgcgctctcc tgttccgacc ctgccgctta ccggatacct gtccgccttt ctcccttcgg | 9780 |
| gaagcgtggc gctttctcaa tgctcgcgct gtaggtatct cagttcggtg taggtcgttc | 9840 |
| gctccaagct gggctgtgtg cacgaacccc ccgttcagcc cgaccgctgc gccttatccg | 9900 |
| gtaactatcg tcttgagtcc aacccggtaa gacacgactt atcgccactg gcagcagcca | 9960 |
| ctggtaacag gattagcaga gcgaggtatg taggcggtgc tacagagttc ttgaagtggt | 10020 |
| ggcctaacta cggctacact agaaggacag tatttggtat ctgcgctctg ctgaagccag | 10080 |
| ttaccttcgg aaaaagagtt ggtagctctt gatccggcaa acaaaccacc gctggtagcg | 10140 |
| gtggtttttt tgtttgcaag cagcagatta cgcgcagaaa aaaaggatct caagaagatc | 10200 |
| ctttgatctt ttctacgggg cattctgacg ctcagtggaa cgaaaactca cgttaaggga | 10260 |
| ttttggtcat gagattatca aaaaggatct tcacctagat ccttttaaat taaaaatgaa | 10320 |
| gttttaaatc aatctaaagt atatatgagt aaacttggtc tgacagttac caatgcttaa | 10380 |
| tcagtgaggc acctatctca gcgatctgtc tatttcgttc atccatagtt gcctgactcc | 10440 |
| ccgtcgtgta gataactacg atacgggagg gcttaccatc tggccccagt gctgcaatga | 10500 |
| taccgcgaga cccacgctca ccggctccag atttatcagc aataaaccag ccagccggaa | 10560 |
| gggccgagcg cagaagtggt cctgcaactt tatccgcctc catccagtct attaattgtt | 10620 |
| gccgggaagc tagagtaagt agttcgccag ttaatagttt gcgcaacgtt gttgccattg | 10680 |
| ctacaggcat cgtggtgtca cgctcgtcgt ttggtatggc ttcattcagc tccggttccc | 10740 |
| aacgatcaag gcgagttaca tgatccccca tgttgtgcaa aaaagcggtt agctccttcg | 10800 |
| gtcctccgat cgttgtcaga agtaagttgg ccgcagtgtt atcactcatg gttatggcag | 10860 |

|     |     |
| --- | --- |
| LISTING OF ADDITIONAL SEQUENCES | |
| cactgcataa ttctcttact gtcatgccat ccgtaagatg cttttctgtg actggtgagt | 10920 |
| actcaaccaa gtcattctga gaatagtgta tgcggcgacc gagttgctct tgcccggcgt | 10980 |
| caatacggga taataccgcg ccacatagca gaactttaaa agtgctcatc attggaaaac | 11040 |
| gttcttcggg gcgaaaactc tcaaggatct taccgctgtt gagatccagt tcgatgtaac | 11100 |
| ccactcgtgc acccaactga tcttcagcat ctttactttt caccagcgtt tctgggtgag | 11160 |
| caaaaacagg aaggcaaaat gccgcaaaaa agggaataag ggcgacacgg aaatgttgaa | 11220 |
| tactcatact cttcctttt caatattatt gaagcattta tcagggttat tgtctcatga | 11280 |
| gcggatacat atttgaatgt atttagaaaa ataaacaaat aggggttccg cgcacatttc | 11340 |
| cccgaaaagt gccacctgac gtctaagaaa ccattattat catgacatta acctataaaa | 11400 |
| ataggcgtat cacgaggccc tttcgtctcg cgcgtttcgg tgatgacggt gaaaacctct | 11460 |
| gacacatgca gctcccggag acggtcacag cttctgtcta gcggatgcc gggagcagac | 11520 |
| aagcccgtca gggcgcgtca gcgggtgttg gcgggtgtcg gggctggctt aactatgcgg | 11580 |
| catcagagca gattgtactg agagtgcacc atatcgacgc tctcccttat gcgactcctg | 11640 |
| cattaggaag cagcccagta ctaggttgag gccgttgagc accgccgccg caaggaatgg | 11700 |
| tgcatgcgta atcaattacg gggtcattag ttcatagccc atatatggag ttccgcgtta | 11760 |
| cataacttac ggtaaatggc ccgcctggct gaccgcccaa cgacccccgc ccattgacgt | 11820 |
| caataatgac gtatgttccc atagtaacgc caatagggac tttccattga cgtcaatggg | 11880 |
| tggagtattt acggtaaact gcccacttgg cagtacatca agtgtatcat atgccaagta | 11940 |
| cgccccctat tgacgtcaat gacggtaaat ggcccgcctg gcattatgcc cagtacatga | 12000 |
| ccttatggga ctttcctact tggcagtaca tctacgtatt agtcatcgct attaccatgg | 12060 |
| tgatgcggtt ttggcagtac atcaatgggc gtggatagcg gtttgactca cggggatttc | 12120 |
| caagtctcca ccccattgac gtcaatggga gtttgttttg gcaccaaaat caacgggact | 12180 |
| ttccaaaatg tcgtaacaac tccgccccat tgacgcaaat gggcggtagg cgtgtacggt | 12240 |
| gggaggtcta tataagcaga gctctctggc taactagaga acccactgct taactggctt | 12300 |
| atcgaaatta atacgactca ctatagggag accggaagct tgaattc | 12347 |
| SEQ ID NO: 66 | |
| atggcggatg tgtgacatac acgacgccaa aagattttgt tccagctcct gccacctccg | 60 |
| ctacgcgaga gattaaccac ccacgatggc cgccaaagtg catgttgata ttgaggctga | 120 |
| cagcccattc atcaagtctt tgcagaaggc atttccgtcg ttcgaggtgg agtcattgca | 180 |
| ggtcacacca aatgaccatg caaatgccag agcattttcg cacctggcta ccaaattgat | 240 |
| cgagcaggag actgacaaag acacactcat cttggatatc ggcagtgcgc cttccaggag | 300 |
| aatgatgtct acgcacaaat accactgcgt atgccctatg cgcagcgcag aagaccccga | 360 |
| aaggctcgat agctacgcaa agaaactggc agcggcctcc gggaaggtgc tggatagaga | 420 |
| gatcgcagga aaaatcaccg acctgcagac cgtcatggct acgccagacg ctgaatctcc | 480 |
| tacctttgc ctgcatacag acgtcacgtg tcgtacggca gccgaagtgg ccgtatacca | 540 |
| ggacgtgtat gctgtacatg caccaacatc gctgtaccat caggcgatga aggtgtcag | 600 |
| aacggcgtat tggattgggt ttgacaccac cccgtttatg tttgacgcgc tagcaggcgc | 660 |
| gtatccaacc tacgccacaa actgggccga cgagcaggtg ttacaggcca ggaacatagg | 720 |
| actgtgtgca gcatccttga ctgagggaag actcggcaaa ctgtccattc tccgcaagaa | 780 |

-continued

| LISTING OF ADDITIONAL SEQUENCES | |
|---|---|
| gcaattgaaa ccttgcgaca cagtcatgtt ctcggtagga tctacattgt acactgagag | 840 |
| cagaaagcta ctgaggagct ggcacttacc ctccgtattc cacctgaaag gtaaacaatc | 900 |
| ctttacctgt aggtgcgata ccatcgtatc atgtgaaggg tacgtagtta agaaaatcac | 960 |
| tatgtgcccc ggcctgtacg gtaaaacggt agggtacgcc gtgacgtatc acgcggaggg | 1020 |
| attcctagtg tgcaagacca cagacactgt caaaggagaa agagtctcat tccctgtatg | 1080 |
| cacctacgtc ccctcaacca tctgtgatca aatgactggc atactagcga ccgacgtcac | 1140 |
| accggaggac gcacagaagt tgttagtggg attgaatcag aggatagttg tgaacggaag | 1200 |
| aacacagcga aacactaaca cgatgaagaa ctatctgctt ccgattgtgg ccgtcgcatt | 1260 |
| tagcaagtgg gcgagggaat acaaggcaga ccttgatgat gaaaaacctc tgggtgtccg | 1320 |
| agagaggtca cttacttgct gctgcttgtg ggcatttaaa acgaggaaga tgcacaccat | 1380 |
| gtacaagaaa ccagacaccc agacaatagt gaaggtgcct tcagagttta actcgttcgt | 1440 |
| catcccgagc ctatggtcta caggcctcgc aatcccagtc agatcacgca ttaagatgct | 1500 |
| tttggccaag aagaccaagc gagagttaat acctgttctc gacgcgtcgt cagccaggga | 1560 |
| tgctgaacaa gaggagaagg agaggttgga ggccgagctg actagagaag ccttaccacc | 1620 |
| cctcgtcccc atcgcgccgg cggagacggg agtcgtcgac gtcgacgttg aagaactaga | 1680 |
| gtatcacgca ggtgcagggg tcgtggaaac acctcgcagc gcgttgaaag tcaccgcaca | 1740 |
| gccgaacgac gtactactag gaaattacgt agttctgtcc ccgcagaccg tgctcaagag | 1800 |
| ctccaagttg gcccccgtgc accctctagc agagcaggtg aaaataataa cacataacgg | 1860 |
| gagggccggc ggttaccagg tcgacggata tgacggcagg gtcctactac catgtggatc | 1920 |
| ggccattccg gtccctgagt ttcaagcttt gagcgagagc gccactatgg tgtacaacga | 1980 |
| aagggagttc gtcaacagga aactatacca tattgccgtt cacggaccgt cgctgaacac | 2040 |
| cgacgaggag aactacgaga agtcagagc tgaaagaact gacgccgagt acgtgttcga | 2100 |
| cgtagataaa aaatgctgcg tcaagagaga ggaagcgtcg ggtttggtgt tggtgggaga | 2160 |
| gctaaccaac cccccgttcc atgaattcgc ctacgaaggg ctgaagatca ggccgtcggc | 2220 |
| accatataag actacagtag taggagtctt tggggttccg ggatcaggca agtctgctat | 2280 |
| tattaagagc ctcgtgacca aacacgatct ggtcaccagc ggcaagaagg agaactgcca | 2340 |
| ggaaatagtt aacgacgtga agaagcaccg cgggaagggg acaagtaggg aaaacagtga | 2400 |
| ctccatcctg ctaaacgggt gtcgtcgtgc cgtggacatc ctatatgtgg acgaggcttt | 2460 |
| cgctagccat tccggtactc tgctggccct aattgctctt gttaaacctc ggagcaaagt | 2520 |
| ggtgttatgc ggagacccca agcaatgcgg attcttcaat atgatgcagc ttaaggtgaa | 2580 |
| cttcaaccac aacatctgca ctgaagtatg tcataaaagt atatccagac gttgcacgcg | 2640 |
| tccagtcacg gccatcgtgt ctacgttgca ctacggaggc aagatgcgca cgaccaaccc | 2700 |
| gtgcaacaaa cccataatca tagacaccac aggacagacc aagcccaagc caggagacat | 2760 |
| cgtgttaaca tgcttccgag ctgggcaaa gcagctgcag ttggactacc gtggacacga | 2820 |
| agtcatgaca gcagcagcat ctcagggcct cacccgcaaa ggggtatacg ccgtaaggca | 2880 |
| gaaggtgaat gaaaatcct tgtatgcccc tgcgtcggag cacgtgaatg tactgctgac | 2940 |
| gcgcactgag gataggctgg tgtggaaaac gctggccggc gatccctgga ttaaggtcct | 3000 |
| atcaaacatt ccacagggta actttacggc cacattggaa gaatggcaag aagaacacga | 3060 |

| LISTING OF ADDITIONAL SEQUENCES | |
|---|---|
| caaaataatg aaggtgattg aaggaccggc tgcgcctgtg gacgcgttcc agaacaaagc | 3120 |
| gaacgtgtgt tgggcgaaaa gcctggtgcc tgtcctggac actgccggaa tcagattgac | 3180 |
| agcagaggag tggagcacca taattacagc atttaaggag gacagagctt actctccagt | 3240 |
| ggtggccttg aatgaaattt gcaccaagta ctatggagtt gacctggaca gtggcctgtt | 3300 |
| ttctgccccg aaggtgtccc tgtattacga gaacaaccac tgggataaca gacctggtgg | 3360 |
| aaggatgtat ggattcaatg ccgcaacagc tgccaggctg gaagctagac ataccttcct | 3420 |
| gaaggggcag tggcatacgg gcaagcaggc agttatcgca gaaagaaaaa tccaaccgct | 3480 |
| ttctgtgctg gacaatgtaa ttcctatcaa ccgcaggctg ccgcacgccc tggtggctga | 3540 |
| gtacaagacg gttaaaggca gtaggggttga gtggctggtc aataaagtaa gagggtacca | 3600 |
| cgtcctgctg gtgagtgagt acaacctggc tttgcctcga cgcagggtca cttggttgtc | 3660 |
| accgctgaat gtcacaggcg ccgataggtg ctacgaccta agtttaggac tgccggctga | 3720 |
| cgccggcagg ttcgacttgg tctttgtgaa cattcacacg gaattcagaa tccaccacta | 3780 |
| ccagcagtgt gtcgaccacg ccatgaagct gcagatgctt gggggagatg cgctacgact | 3840 |
| gctaaaaccc ggcggcatct tgatgagagc ttacggatac gccgataaaa tcagcgaagc | 3900 |
| cgttgtttcc tccttaagca gaaagttctc gtctgcaaga gtgttgcgcc cggattgtgt | 3960 |
| caccagcaat acagaagtgt tcttgctgtt ctccaacttt gacaacggaa agagaccctc | 4020 |
| tacgctacac cagatgaata ccaagctgag tgccgtgtat gccggagaag ccatgcacac | 4080 |
| ggccgggtgt gcaccatcct acagagttaa gagagcagac atagccacgt gcacagaagc | 4140 |
| ggctgtggtt aacgcagcta acgcccgtgg aactgtaggg gatggcgtat gcagggccgt | 4200 |
| ggcgaagaaa tggccgtcag cctttaaggg agcagcaaca ccagtgggca caattaaaac | 4260 |
| agtcatgtgc ggctcgtacc ccgtcatcca cgctgtagcg cctaatttct ctgccacgac | 4320 |
| tgaagcggaa ggggaccgcg aattggccgc tgtctaccgg gcagtggccg ccgaagtaaa | 4380 |
| cagactgtca ctgagcagcg tagccatccc gctgctgtcc acaggagtgt tcagcggcgg | 4440 |
| aagagatagg ctgcagcaat ccctcaacca tctattcaca gcaatggacg ccacggacgc | 4500 |
| tgacgtgacc atctactgca gagacaaaag ttgggagaag aaaatccagg aagccattga | 4560 |
| catgaggacg gctgtggagt tgctcaatga tgacgtggag ctgaccacag acttggtgag | 4620 |
| agtgcacccg gacagcagcc tggtgggtcg taagggctac agtaccactg acgggtcgct | 4680 |
| gtactcgtac tttgaaggta cgaaattcaa ccaggctgct attgatatgg cagagatact | 4740 |
| gacgttgtgg cccagactgc aagaggcaaa cgaacagata tgcctatacg cgctgggcga | 4800 |
| aacaatggac aacatcagat ccaaatgtcc ggtgaacgat tccgattcat caacacctcc | 4860 |
| caggacagtg ccctgcctgt gccgctacgc aatgacagca gaacggatcg cccgccttag | 4920 |
| gtcacaccaa gttaaaagca tggtggtttg ctcatctttt cccctcccga aataccatgt | 4980 |
| agatgggggtg cagaaggtaa agtgcgagaa ggttctcctg ttcgacccga cggtaccttc | 5040 |
| agtggttagt ccgcggaagt atgccgcatc tacgacggac cactcagatc ggtcgttacg | 5100 |
| agggtttgac ttggactgga ccaccgactc gtcttccact gccagcgata ccatgtcgct | 5160 |
| acccagtttg cagtcgtgtg acatcgactc gatctacgag ccaatggctc ccatagtagt | 5220 |
| gacggctgac gtacaccctg aacccgcagg catcgcggac ctggcggcag atgtgcaccc | 5280 |
| tgaacccgca gaccatgtgg acctcgagaa cccgattcct ccaccgcgcc cgaagagagc | 5340 |
| tgcataccct tgcctcccgc ggcggagcg accggtgccg cgccgagaa agccgacgcc | 5400 |

-continued

| LISTING OF ADDITIONAL SEQUENCES | |
|---|---|
| tgccccaagg actgcgttta ggaacaagct gcctttgacg ttcggcgact ttgacgagca | 5460 |
| cgaggtcgat gcgttggcct ccgggattac tttcggagac ttcgacgacg tcctgcgact | 5520 |
| aggccgcgcg ggtgcatata ttttctcctc ggacactggc agcggacatt tacaacaaaa | 5580 |
| atccgttagg cagcacaatc tccagtgcgc acaactggat gcggtccagg aggagaaaat | 5640 |
| gtacccgcca aaattggata ctgagaggga gaagctgttg ctgctgaaaa tgcagatgca | 5700 |
| cccatcggag gclaataaga gtcgatacca gtctcgcaaa gtggagaaca tgaaagccac | 5760 |
| ggtggtggac aggctcacat cggggggccag attgtacacg ggagcggacg taggccgcat | 5820 |
| accaacatac gcggttcggt accccgccc cgtgtactcc cctaccgtga tcgaaagatt | 5880 |
| ctcaagcccc gatgtagcaa tcgcagcgtg caacgaatac ctatccagaa attacccaac | 5940 |
| agtggcgtcg taccagataa cagatgaata cgacgcatac ttggacatgg ttgacgggtc | 6000 |
| ggatagttgc ttggacagag cgacattctg cccggcgaag ctccggtgct acccgaaaca | 6060 |
| tcatgcgtac caccagccga ctgtacgcag tgccgtcccg tcacccttc agaacacact | 6120 |
| acagaacgtg ctagcggccg ccaccaagag aaactgcaac gtcacgcaaa tgcgagaact | 6180 |
| acccaccatg gactcggcag tgttcaacgt ggagtgcttc aagcgctatg cctgctccgg | 6240 |
| agaatattgg gaagaatatg ctaaacaacc tatccggata accactgaga acatcactac | 6300 |
| ctatgtgacc aaattgaaag gcccgaaagc tgctgccttg ttcgctaaga cccacaactt | 6360 |
| ggttccgctg caggaggttc ccatggacag attcacggtc gacatgaaac gagatgtcaa | 6420 |
| agtcactcca gggacgaaac acacagagga aagacccaaa gtccaggtaa ttcaagcagc | 6480 |
| ggagccattg gcgaccgctt acctgtgcgg catccacagg gaattagtaa ggagactaaa | 6540 |
| tgctgtgtta cgccctaacg tgcacacatt gtttgatatg tcggccgaag actttgacgc | 6600 |
| gatcatcgcc tctcacttcc acccaggaga cccggttcta gagacggaca ttgcatcatt | 6660 |
| cgacaaaagc caggacgact ccttggctct tacaggttta atgatcctcg aagatctagg | 6720 |
| ggtggatcag tacctgctgg acttgatcga ggcagccttt gggaaatat ccagctgtca | 6780 |
| cctaccaact ggcacgcgct tcaagttcgg agctatgatg aaatcgggca tgtttctgac | 6840 |
| tttgtttatt aacactgttt tgaacatcac catagcaagc agggtactgg agcagagact | 6900 |
| cactgactcc gcctgtgcgg ccttcatcgg cgacgacaac atcgttcacg gagtgatctc | 6960 |
| cgacaagctg atggcggaga ggtgcgcgtc gtgggtcaac atggaggtga agatcattga | 7020 |
| cgctgtcatg ggcgaaaaac ccccatattt tgtgggggga ttcatagttt ttgacagcgt | 7080 |
| cacacagacc gcctgccgtg tttcagaccc acttaagcgc ctgttcaagt tgggtaagcc | 7140 |
| gctaacagct gaagacaagc aggacgaaga caggcgacga gcactgagtg acgaggttag | 7200 |
| caagtggttc cggacaggct gggggccga actggaggtg gcactaacat ctaggtatga | 7260 |
| ggtagagggc tgcaaaagta tcctcatagc catggccacc ttggcgaggg acattaaggc | 7320 |
| gtttaagaaa ttgagaggac ctgttataca cctctacggc ggtcctagat tggtgcgtta | 7380 |
| atacacagaa ttctgattgg atcccaaacg ggccctctag actcgagcgg ccgccactgt | 7440 |
| gctggatatc tgcagaattc atgcatggag atacacctac attgcatgaa tatatgttag | 7500 |
| atttgcaacc agagacaact gatctctact gttatgagca attaaatgac agctcagagg | 7560 |
| aggaggatga aatagatggt ccagctggac aagcagaacc ggacagagcc cattacaata | 7620 |
| ttgtaacctt ttgttgcaag tgtgactcta cgcttcggtt gtgcgtacaa agcacacacg | 7680 |

-continued

| LISTING OF ADDITIONAL SEQUENCES | |
|---|---|
| tagacattcg tactttggaa gacctgttaa tgggcacact aggaattgtg tgccccatct | 7740 |
| gttctcagaa accaggatct atggcgtacc catacgatgt tccagattac gctagcttga | 7800 |
| gatctaccat gtctcagagc aaccgggagc tggtggttga ctttctctcc tacaagcttt | 7860 |
| cccagaaagg atacagctgg agtcagttta gtgatgtgga agagaacagg actgaggccc | 7920 |
| cagaagggac tgaatcggag atggagaccc ccagtgccat caatggcaac ccatcctggc | 7980 |
| acctggcaga cagccccgcg gtgaatggag ccactgcgca cagcagcagt ttggatgccc | 8040 |
| gggaggtgat ccccatggca gcagtaaagc aagcgctgag ggaggcaggc gacgagtttg | 8100 |
| aactgcggta ccggcgggca ttcagtgacc tgacatccca gctccacatc accccaggga | 8160 |
| cagcatatca gagctttgaa caggtagtga atgaactctt ccgggatggg gtaaactggg | 8220 |
| gtcgcattgt ggcctttttc tccttcggcg gggcactgtg cgtggaaagc gtagacaagg | 8280 |
| agatgcaggt attggtgagt cggatcgcag cttggatggc cacttacctg aatgaccacc | 8340 |
| tagagccttg gatccaggag aacggcggct ggatactttt tgtggaactc tatgggaaca | 8400 |
| atgcagcagc cgagagccga aagggccagg aacgcttcaa ccgctggttc ctgacgggca | 8460 |
| tgactgtggc cggcgtggtt ctgctgggct cactcttcag tcggaaatga agatccaagc | 8520 |
| ttaagtttgg gtaattaatt gaattacatc cctacgcaaa cgttttacgg ccgccggtgg | 8580 |
| cgcccgcgcc cggcggcccg tccttggccg ttgcaggcca ctccggtggc tcccgtcgtc | 8640 |
| cccgacttcc aggcccagca gatgcagcaa ctcatcagcg ccgtaaatgc gctgacaatg | 8700 |
| agacagaacg caattgctcc tgctaggcct cccaaaccaa agaagaagaa gacaaccaaa | 8760 |
| ccaaagccga aaacgcagcc caagaagatc aacggaaaaa cgcagcagca aaagaagaaa | 8820 |
| gacaagcaag ccgacaagaa gaagaagaaa cccggaaaaa gagaaagaat gtgcatgaag | 8880 |
| attgaaaatg actgtatctt cgtatgcggc tagccacagt aacgtagtgt ttccagacat | 8940 |
| gtcgggcacc gcactatcat gggtgcagaa aatctcgggt ggtctggggg ccttcgcaat | 9000 |
| cggcgctatc ctggtgctgg ttgtggtcac ttgcattggg ctccgcagat aagttagggt | 9060 |
| aggcaatggc attgatatag caagaaaatt gaaaacagaa aaagttaggg taagcaatgg | 9120 |
| catataacca taactgtata acttgtaaca aagcgcaaca agacctgcgc aattggcccc | 9180 |
| gtggtccgcc tcacgaaaac tcggggcaac tcatattgac acattaattg gcaataattg | 9240 |
| gaagcttaca taagcttaat tcgacgaata attggatttt tatttttattt tgcaattggt | 9300 |
| ttttaatatt tccaaaaaaa aaaaaaaaa aaaaaaaaa aaaaaaaaa aaaaaaaaa | 9360 |
| aaaaaaaaaa aaaaaaaaaa aaactagtga tcataatcag ccataccaca tttgtagagg | 9420 |
| ttttacttgc tttaaaaaac ctcccacacc tcccccctgaa cctgaaacat aaaatgaatg | 9480 |
| caattgttgt tgttaacttg tttattgcag cttataatgg ttacaaataa agcaatagca | 9540 |
| tcacaaattt cacaaataaa gcatttttt cactgcattc tagttgtggt ttgtccaaac | 9600 |
| tcatcaatgt atcttatcat gtctggatct agtctgcatt aatgaatcgg ccaacgcgcg | 9660 |
| gggagaggcg gtttgcgtat tgggcgctct tccgcttcct cgctcactga ctcgctgcgc | 9720 |
| tcggtcgttc ggctgcggcg agcggtatca gctcactcaa aggcggtaat acggttatcc | 9780 |
| acagaatcag gggataacgc aggaaagaac atgtgagcaa aaggccagca aaaggccagg | 9840 |
| aaccgtaaaa aggccgcgtt gctggcgttt ttccataggc tccgcccccc tgacgagcat | 9900 |
| cacaaaaatc gacgctcaag tcagaggtgg cgaaacccga caggactata agataccag | 9960 |
| gcgtttcccc ctggaagctc cctcgtgcgc tctcctgttc cgaccctgcc gcttaccgga | 10020 |

| | |
|---|---|
| tacctgtccg cctttctccc ttcgggaagc gtggcgcttt ctcaatgctc gcgctgtagg | 10080 |
| tatctcagtt cggtgtaggt cgttcgctcc aagctgggct gtgtgcacga accccccgtt | 10140 |
| cagcccgacc gctgcgcctt atccggtaac tatcgtcttg agtccaaccc ggtaagacac | 10200 |
| gacttatcgc cactggcagc agccactggt aacaggatta gcagagcgag gtatgtaggc | 10260 |
| ggtgctacag agttcttgaa gtggtggcct aactacggct acactagaag gacagtattt | 10320 |
| ggtatctgcg ctctgctgaa gccagttacc ttcggaaaaa gagttggtag ctcttgatcc | 10380 |
| ggcaaacaaa ccaccgctgg tagcggtggt ttttttgttt gcaagcagca gattacgcgc | 10440 |
| agaaaaaaag gatctcaaga agatcctttg atcttttcta cggggcattc tgacgctcag | 10500 |
| Lggaacgaaa actcacgtta agggattttg gtcatgagat tatcaaaaag gatcttcacc | 10560 |
| tagatccttt taaattaaaa atgaagtttt aaatcaatct aaagtatata tgagtaaact | 10620 |
| tggtctgaca gttaccaatg cttaatcagt gaggcaccta tctcagcgat ctgtctattt | 10680 |
| cgttcatcca tagttgcctg actccccgtc gtgtagataa ctacgatacg ggagggctta | 10740 |
| ccatctggcc ccagtgctgc aatgataccg cgagacccac gctcaccggc tccagattta | 10800 |
| tcagcaataa accagccagc cggaagggcc gagcgcagaa gtggtcctgc aactttatcc | 10860 |
| gcctccatcc agtctattaa ttgttgccgg gaagctagag taagtagttc gccagttaat | 10920 |
| agtttgcgca acgttgttgc cattgctaca ggcatcgtgg tgtcacgctc gtcgtttggt | 10980 |
| atggcttcat tcagctccgg ttcccaacga tcaaggcgag ttacatgatc ccccatgttg | 11040 |
| tgcaaaaaag cggttagctc cttcggtcct ccgatcgttg tcagaagtaa gttggccgca | 11100 |
| gtgttatcac tcatggttat ggcagcactg cataattctc ttactgtcat gccatccgta | 11160 |
| agatgctttt ctgtgactgg tgagtactca accaagtcat tctgagaata gtgtatgcgg | 11220 |
| cgaccgagtt gctcttgccc ggcgtcaata cgggataata ccgcgccaca tagcagaact | 11280 |
| ttaaaagtgc tcatcattgg aaaacgttct tcggggcgaa aactctcaag gatcttaccg | 11340 |
| ctgttgagat ccagttcgat gtaacccact cgtgcaccca actgatcttc agcatctttt | 11400 |
| actttcacca gcgtttctgg gtgagcaaaa acaggaaggc aaaatgccgc aaaaaaggga | 11460 |
| ataagggcga cacggaaatg ttgaatactc atactcttcc tttttcaata ttattgaagc | 11520 |
| atttatcagg gttattgtct catgagcgga tacatatttg aatgtattta gaaaaataaa | 11580 |
| caaatagggg ttccgcgcac atttccccga aaagtgccac ctgacgtcta agaaaccatt | 11640 |
| attatcatga cattaaccta taaaaatagg cgtatcacga ggccctttcg tctcgcgcgt | 11700 |
| ttcggtgatg acggtgaaaa cctctgacac atgcagctcc cggagacggt cacagcttct | 11760 |
| gtctaagcgg atgccgggag cagacaagcc cgtcagggcg cgtcagcggg tgttggcggg | 11820 |
| tgtcggggct ggcttaacta tgcggcatca gagcagattg tactgagagt gcaccatatc | 11880 |
| gacgctctcc cttatgcgac tcctgcatta ggaagcagcc cagtactagg ttgaggccgt | 11940 |
| tgagcaccgc cgccgcaagg aatggtgcat gcgtaatcaa ttacgggtc attagttcat | 12000 |
| agcccatata tggagttccg cgttacataa cttacggtaa atggcccgcc tggctgaccg | 12060 |
| cccaacgacc cccgcccatt gacgtcaata atgacgtatg ttcccatagt aacgccaata | 12120 |
| gggactttcc attgacgtca atgggtggag tatttacggt aaactgccca cttggcagta | 12180 |
| catcaagtgt atcatatgcc aagtacgccc cctattgacg tcaatgacgg taaatggccc | 12240 |
| gcctggcatt atgcccagta catgacctta tgggactttc ctacttggca gtacatctac | 12300 |

| LISTING OF ADDITIONAL SEQUENCES | |
|---|---|
| gtattagtca tcgctattac catggtgatg cggttttggc agtacatcaa tgggcgtgga | 12360 |
| tagcggtttg actcacgggg atttccaagt ctccacccca ttgacgtcaa tgggagtttg | 12420 |
| ttttggcacc aaaatcaacg ggactttcca aaatgtcgta acaactccgc cccattgacg | 12480 |
| caaatgggcg gtaggcgtgt acggtgggag gtctatataa gcagagctct ctggctaact | 12540 |
| agagaaccca ctgcttaact ggcttatcga aattaatacg actcactata gggagaccgg | 12600 |
| aagcttgaat tc | 12612 |
| SEQ ID NO: 67 | |
| atggcggatg tgtgacatac acgacgccaa aagatttttgt tccagctcct gccacctccg | 60 |
| ctacgcgaga gattaaccac ccacgatggc cgccaaagtg catgttgata ttgaggctga | 120 |
| cagcccattc atcaagtctt tgcagaaggc atttccgtcg ttcgaggtgg agtcattgca | 180 |
| ggtcacacca aatgaccatg caaatgccag agcattttcg cacctggcta ccaaattgat | 240 |
| cgagcaggag actgacaaag acacactcat cttggatatc ggcagtgcgc cttccaggag | 300 |
| aatgatgtct acgcacaaat accactgcgt atgccctatg cgcagcgcag aagacccccga | 360 |
| aaggctcgat agctacgcaa agaaactggc agcggcctcc gggaaggtgc tggatagaga | 420 |
| gatcgcagga aaaatcaccg acctgcagac cgtcatggct acgccagacg ctgaatctcc | 480 |
| tacctttttgc ctgcatacag acgtcacgtg tcgtacggca gccgaagtgg ccgtatacca | 540 |
| ggacgtgtat gctgtacatg caccaacatc gctgtaccat caggcgatga aggtgtcag | 600 |
| aacggcgtat tggattgggt ttgacaccac cccgtttatg tttgacgcgc tagcaggcgc | 660 |
| gtatccaacc tacgccacaa actgggccga cgagcaggtg ttacaggcca ggaacatagg | 720 |
| actgtgtgca gcatccttga ctgagggaag actcggcaaa ctgtccattc tccgcaagaa | 780 |
| gcaattgaaa ccttgcgaca cagtcatgtt ctcggtagga tctacattgt acactgagag | 840 |
| cagaaagcta ctgaggagct ggcacttacc ctccgtattc cacctgaaag gtaaacaatc | 900 |
| ctttacctgt aggtgcgata ccatcgtatc atgtgaaggg tacgtagtta agaaaatcac | 960 |
| tatgtgcccc ggcctgtacg gtaaaacggt agggtacgcc gtgacgtatc acgcggaggg | 1020 |
| attcctagtg tgcaagacca cagacactgt caaaggagaa agagtctcat tccctgtatg | 1080 |
| cacctacgtc ccctcaacca tctgtgatca aatgactggc ataactagcga ccgacgtcac | 1140 |
| accggaggac gcacagaagt tgttagtggg attgaatcag aggatagttg tgaacggaag | 1200 |
| aacacagcga aacactaaca cgatgaagaa ctatctgctt ccgattgtgg ccgtcgcatt | 1260 |
| tagcaagtgg gcgagggaat acaaggcaga ccttgatgat gaaaaacctc tgggtgtccg | 1320 |
| agagaggtca cttacttgct gctgcttgtg ggcatttaaa acgaggaaga tgcacaccat | 1380 |
| gtacaagaaa ccagacaccc agacaatagt gaaggtgcct tcagagttta actcgttcgt | 1440 |
| catcccgagc ctatggtcta caggcctcgc aatcccagtc agatcacgca ttaagatgct | 1500 |
| tttggccaag aagaccaagc gagagttaat acctgttctc gacgcgtcgt cagccaggga | 1560 |
| tgctgaacaa gaggagaagg agaggttgga ggccgagctg actagagaag ccttaccacc | 1620 |
| cctcgtcccc atcgcgccgg cggagacggg agtcgtcgac gtcgacgttg aagaactaga | 1680 |
| gtatcacgca ggtgcagggg tcgtggaaac acctcgcagc gcgttgaaag tcaccgcaca | 1740 |
| gccgaacgac gtactactag gaaattacgt agttctgtcc ccgcagaccg tgctcaagag | 1800 |
| ctccaagttg gcccccgtgc accctctagc agagcaggtg aaaataataa cacataacgg | 1860 |
| gagggccggc ggttaccagg tcgacggata tgacggcagg gtcctactac catgtggatc | 1920 |

| LISTING OF ADDITIONAL SEQUENCES | |
|---|---|
| ggccattccg gtccctgagt ttcaagcttt gagcgagagc gccactatgg tgtacaacga | 1980 |
| aagggagttc gtcaacagga aactatacca tattgccgtt cacggaccgt cgctgaacac | 2040 |
| cgacgaggag aactacgaga aagtcagagc tgaaagaact gacgccgagt acgtgttcga | 2100 |
| cgtagataaa aaatgctgcg tcaagagaga ggaagcgtcg ggtttggtgt tggtgggaga | 2160 |
| gctaaccaac cccccgttcc atgaattcgc ctacgaaggg ctgaagatca ggccgtcggc | 2220 |
| accatataag actacagtag taggagtctt tggggttccg ggatcaggca agtctgctat | 2280 |
| tattaagagc ctcgtgacca aacacgatct ggtcaccagc ggcaagaagg agaactgcca | 2340 |
| ggaaatagtt aacgacgtga agaagcaccg cgggaagggg acaagtaggg aaaacagtga | 2400 |
| ctccatcctg ctaaacgggt gtcgtcgtgc cgtggacatc ctatatgtgg acgaggcttt | 2460 |
| cgctagccat tccggtactc tgctggccct aattgctctt gttaaacctc ggagcaaagt | 2520 |
| ggtgttatgc ggagacccca agcaatgcgg attcttcaat atgatgcagc ttaaggtgaa | 2580 |
| cttcaaccac aacatctgca ctgaagtatg tcataaaagt atatccagac gttgcacgcg | 2640 |
| tccagtcacg gccatcgtgt ctacgttgca ctacggaggc aagatgcgca cgaccaaccc | 2700 |
| gtgcaacaaa cccataatca tagacaccac aggacagacc aagcccaagc caggagacat | 2760 |
| cgtgttaaca tgcttccgag gctgggcaaa gcagctgcag ttggactacc gtggacacga | 2820 |
| agtcatgaca gcagcagcat ctcagggcct cacccgcaaa ggggtatacg ccgtaaggca | 2880 |
| gaaggtgaat gaaaatccct gtatgccccc tgcgtcggag cacgtgaatg tactgctgac | 2940 |
| gcgcactgag gataggctgg tgtggaaaac gctggccggc gatccctgga ttaaggtcct | 3000 |
| atcaaacatt ccacagggta actttacggc cacattggaa gaatggcaag aagaacacga | 3060 |
| caaaataatg aaggtgattg aaggaccggc tgcgcctgtg gacgcgttcc agaacaaagc | 3120 |
| gaacgtgtgt tgggcgaaaa gcctggtgcc tgtcctggac actgccggaa tcagattgac | 3180 |
| agcagaggag tggagcacca taattacagc atttaaggag gacagagctt actctccagt | 3240 |
| ggtggccttg aatgaaattt gcaccaagta ctatggagtt gacctggaca gtggcctgtt | 3300 |
| ttctgccccg aaggtgtccc tgtattacga gaacaaccac tgggataaca gacctggtgg | 3360 |
| aaggatgtat ggattcaatg ccgcaacagc tgccaggctg gaagctagac ataccttcct | 3420 |
| gaaggggcag tggcatacgg gcaagcaggc agttatcgca gaaagaaaaa tccaaccgct | 3480 |
| ttctgtgctg gacaatgtaa ttcctatcaa ccgcaggctg ccgcacgccc tggtggctga | 3540 |
| gtacaagacg gttaaaggca gtaggggttga gtggctggtc aataaagtaa gagggtacca | 3600 |
| cgtcctgctg gtgagtgagt acaacctggc tttgcctcga cgcagggtca cttggttgtc | 3660 |
| accgctgaat gtcacaggcg ccgataggtg ctacgaccta agtttaggac tgccggctga | 3720 |
| cgccggcagg ttcgacttgg tctttgtgaa cattcacacg gaattcagaa tccaccacta | 3780 |
| ccagcagtgt gtcgaccacg ccatgaagct gcagatgctt gggggagatg cgctacgact | 3840 |
| gctaaaaccc ggcggcatct tgatgagagc ttacggatac gccgataaaa tcagcgaagc | 3900 |
| cgttgtttcc tccttaagca gaaagttctc gtctgcaaga gtgttgcgcc cggattgtgt | 3960 |
| caccagcaat acagaagtgt tcttgctgtt ctccaacttt gacaacggaa agagaccctc | 4020 |
| tacgctacac cagatgaata ccaagctgag tgccgtgtat gccggagaag ccatgcacac | 4080 |
| ggccgggtgt gcaccatcct acagagttaa gagagcagac atagccacgt gcacagaagc | 4140 |
| ggctgtggtt aacgcagcta acgcccgtgg aactgtaggg gatggcgtat gcagggccgt | 4200 |
| ggcgaagaaa tggccgtcag cctttaaggg agcagcaaca ccagtgggca caattaaaac | 4260 |

-continued

| LISTING OF ADDITIONAL SEQUENCES | |
|---|---|
| agtcatgtgc ggctcgtacc ccgtcatcca cgctgtagcg cctaatttct ctgccacgac | 4320 |
| tgaagcggaa ggggaccgcg aattggccgc tgtctaccgg gcagtggccg ccgaagtaaa | 4380 |
| cagactgtca ctgagcagcg tagccatccc gctgctgtcc acaggagtgt tcagcggcgg | 4440 |
| aagagatagg ctgcagcaat ccctcaacca tctattcaca gcaatggacg ccacggacgc | 4500 |
| tgacgtgacc atctactgca gagacaaaag ttgggagaag aaaatccagg aagccattga | 4560 |
| catgaggacg gctgtggagt tgctcaatga tgacgtggag ctgaccacag acttggtgag | 4620 |
| agtgcacccg gacagcagcc tggtgggtcg taagggctac agtaccactg acgggtcgct | 4680 |
| gtactcgtac tttgaaggta cgaaattcaa ccaggctgct attgatatgg cagagatact | 4740 |
| gacgttgtgg cccagactgc aagaggcaaa cgaacagata tgcctatacg cgctgggcga | 4800 |
| aacaatggac aacatcagat ccaaatgtcc ggtgaacgat tccgattcat caacacctcc | 4860 |
| caggacagtg ccctgcctgt gccgctacgc aatgacagca gaacggatcg cccgccttag | 4920 |
| gtcacaccaa gttaaaagca tggtggtttg ctcatctttt ccctcccga aataccatgt | 4980 |
| agatggggtg cagaaggtaa agtgcgagaa ggttctcctg ttcgacccga cggtaccttc | 5040 |
| agtggttagt ccgcggaagt atgccgcatc tacgacggac cactcagatc ggtcgttacg | 5100 |
| agggtttgac ttggactgga ccaccgactc gtcttccact gccagcgata ccatgtcgct | 5160 |
| acccagtttg cagtcgtgtg acatcgactc gatctacgag ccaatggctc ccatagtagt | 5220 |
| gacggctgac gtacaccctg aacccgcagg catcgcggac ctggcggcag atgtgcaccc | 5280 |
| tgaacccgca gaccatgtgg acctcgagaa cccgattcct ccaccgcgcc cgaagagagc | 5340 |
| tgcataccct gcctcccgcg cggcggagcg accggtgccg gcgccgagaa agccgacgcc | 5400 |
| tgccccaagg actgcgttta ggaacaagct gcctttgacg ttcggcgact ttgacgagca | 5460 |
| cgaggtcgat gcgttggcct ccgggattac tttcggagac ttcgacgacg tcctgcgact | 5520 |
| aggccgcgcg ggtgcatata ttttctcctc ggacactggc agcggacatt tacaacaaaa | 5580 |
| atccgttagg cagcacaatc tccagtgcgc acaactggat gcggtccagg aggagaaaat | 5640 |
| gtacccgcca aaattggata ctgagaggga gaagctgttg ctgctgaaaa tgcagatgca | 5700 |
| cccatcggag gctaataaga gtcgatacca gtctcgcaaa gtggagaaca tgaaagccac | 5760 |
| ggtggtggac aggctcacat cgggggccag attgtacacg ggagcggacg taggccgcat | 5820 |
| accaacatac gcggttcggt accccgccc cgtgtactcc cctaccgtga tcgaaagatt | 5880 |
| ctcaagcccc gatgtagcaa tcgcagcgtg caacgaatac ctatccagaa attacccaac | 5940 |
| agtggcgtcg taccagataa cagatgaata cgacgcatac ttggacatgg ttgacgggtc | 6000 |
| ggatagttgc ttggacagag cgacattctg cccggcgaag ctccggtgct acccgaaaca | 6060 |
| tcatgcgtac caccagccga ctgtacgcag tgccgtcccg tcacccttc agaacacact | 6120 |
| acagaacgtg ctagcggccg ccaccaagag aaactgcaac gtcacgcaaa tgcgagaact | 6180 |
| acccaccatg gactcggcag tgttcaacgt ggagtgcttc aagcgctatg cctgctccgg | 6240 |
| agaatattgg gaagaatatg ctaaacaacc tatccggata accactgaga acatcactac | 6300 |
| ctatgtgacc aaattgaaag gcccgaaagc tgctgccttg ttcgctaaga cccacaactt | 6360 |
| ggttccgctg caggaggttc ccatggacag attcacggtc gacatgaaac gagatgtcaa | 6420 |
| agtcactcca gggacgaaac acacagagga aagacccaaa gtccaggtaa ttcaagcagc | 6480 |
| ggagccattg gcgaccgctt acctgtgcgg catccacagg gaattagtaa ggagactaaa | 6540 |

-continued

| LISTING OF ADDITIONAL SEQUENCES | |
|---|---|
| tgctgtgtta cgccctaacg tgcacacatt gtttgatatg tcggccgaag actttgacgc | 6600 |
| gatcatcgcc tctcacttcc acccaggaga cccggttcta gagacggaca ttgcatcatt | 6660 |
| cgacaaaagc caggacgact ccttggctct tacaggttta atgatcctcg aagatctagg | 6720 |
| ggtggatcag tacctgctgg acttgatcga ggcagccttt ggggaaatat ccagctgtca | 6780 |
| cctaccaact ggcacgcgct tcaagttcgg agctatgatg aaatcgggca tgtttctgac | 6840 |
| tttgtttatt aacactgttt tgaacatcac catagcaagc agggtactgg agcagagact | 6900 |
| cactgactcc gcctgtgcgg ccttcatcgg cgacgacaac atcgttcacg gagtgatctc | 6960 |
| cgacaagctg atggcggaga ggtgcgcgtc gtgggtcaac atggaggtga agatcattga | 7020 |
| cgctgtcatg ggcgaaaaac ccccatattt ttgtggggga ttcatagttt ttgacagcgt | 7080 |
| cacacagacc gcctgccgtg tttcagaccc acttaagcgc ctgttcaagt tgggtaagcc | 7140 |
| gctaacagct gaagacaagc aggacgaaga caggcgacga gcactgagtg acgaggttag | 7200 |
| caagtggttc cggacaggct tgggggccga actggaggtg gcactaacat ctaggtatga | 7260 |
| ggtaqagqgc tgcaaaagta tcctcatagc catggccacc ttgqcgaggg acattaaggc | 7320 |
| gtttaagaaa ttgagaggac ctgttataca cctctacggc ggtcctagat tggtgcgtta | 7380 |
| atacacagaa ttctgattgg atcccaaacg ggccctctag actcgagcgg ccgccactgt | 7440 |
| gctggatatc tgcagaattc caccacactg gactagtgga tctatggcgt acccatacga | 7500 |
| tgttccagat tacgctagct tgagatctac catgtctcag agcaaccggg agctggtggt | 7560 |
| tgactttctc tcctacaagc tttcccagaa aggatacagc tggagtcagt ttagtgatgt | 7620 |
| ggaagagaac aggactgagg ccccagaagg gactgaatcg gagatggaga cccccagtgc | 7680 |
| catcaatggc aacccatcct ggacctggc agacagcccc gcggtgaatg gagccactgc | 7740 |
| gcacagcagc agtttggatg cccgggaggt gatccccatg gcagcagtaa agcaagcgct | 7800 |
| gagggaggca ggcgacgagt ttgaactgcg gtaccggcgg gcattcagtg acctgacatc | 7860 |
| ccagctccac atcaccccag ggacagcata tcagagcttt gaacaggtag tgaatgaact | 7920 |
| cttccgggat ggggtagcca ttcttcgcat tgtggccttt ttctccttcg gcggggcact | 7980 |
| gtgcgtggaa agcgtagaca aggagatgca ggtattggtg agtcggatcg cagcttggat | 8040 |
| ggccacttac ctgaatgacc acctagagcc ttggatccag gagaacggcg gctgggatac | 8100 |
| ttttgtggaa ctctatggga acaatgcagc agccgagagc cgaaagggcc aggaacgctt | 8160 |
| caaccgctgg ttcctgacgg gcatgactgt ggccggcgtg gttctgctgg gctcactctt | 8220 |
| cagtcggaaa tgaagatccg agctcggtac caagcttaag tttgggtaat taattgaatt | 8280 |
| acatccctac gcaaacgttt tacgccgcc ggtggcgccc gcgccggcg gcccgtcctt | 8340 |
| ggccgttgca ggccactccg gtggctcccg tcgtccccga cttccaggcc cagcagatgc | 8400 |
| agcaactcat cagcgccgta aatgcgctga caatgagaca gaacgcaatt gctcctgcta | 8460 |
| ggcctcccaa accaaagaag aagaagacaa ccaaaccaaa gccgaaaacg cagcccaaga | 8520 |
| agatcaacgg aaaaacgcag cagcaaaaga agaaagacaa gcaagccgac aagaagaaga | 8580 |
| agaaacccgg aaaaagagaa agaatgtgca tgaagattga aaatgactgt atcttcgtat | 8640 |
| gcggctagcc acagtaacgt agtgtttcca gacatgtcgg gcaccgcact atcatgggtg | 8700 |
| cagaaaatct cgggtggtct gggggccttc gcaatcggcg ctatcctggt gctggttgtg | 8760 |
| gtcacttgca ttgggctccg cagataagtt agggtaggca atggcattga tatagcaaga | 8820 |
| aaattgaaaa cagaaaaagt tagggtaagc aatggcatat aaccataact gtataacttg | 8880 |

-continued

| LISTING OF ADDITIONAL SEQUENCES | |
|---|---|
| taacaaagcg caacaagacc tgcgcaattg gccccgtggt ccgcctcacg gaaactcggg | 8940 |
| gcaactcata ttgacacatt aattggcaat aattggaagc ttacataagc ttaattcgac | 9000 |
| gaataattgg attttattt tattttgcaa ttggttttta atatttccaa aaaaaaaaa | 9060 |
| aaaaaaaaa aaaaaaaaa aaaaaaaaa aaaaaaaaa aaaaaaaaa aaaaaaaact | 9120 |
| agtgatcata atcagccata ccacatttgt agaggtttta cttgctttaa aaaacctccc | 9180 |
| acacctcccc ctgaacctga aacataaaat gaatgcaatt gttgttgtta acttgtttat | 9240 |
| tgcagcttat aatggttaca aataaagcaa tagcatcaca aatttcacaa ataaagcatt | 9300 |
| tttttcactg cattctagtt gtggtttgtc caaactcatc aatgtatctt atcatgtctg | 9360 |
| gatctagtct gcattaatga atcggccaac gcgcggggag aggcggtttg cgtattgggc | 9420 |
| gctcttccgc ttcctcgctc actgactcgc tgcgctcggt cgttcggctg cggcgagcgg | 9480 |
| tatcagctca ctcaaaggcg gtaatacggt tatccacaga atcaggggat aacgcaggaa | 9540 |
| agaacatgtg agcaaaaggc cagcaaaagg ccaggaaccg taaaaaggcc gcgttgctgg | 9600 |
| cgtttttcca taggctccgc ccccctgacg agcatcacaa aaatcgacgc tcaagtcaga | 9660 |
| ggtggcgaaa cccgacagga ctataaagat accaggcgtt tcccctgga agctccctcg | 9720 |
| tgcgctctcc tgttccgacc ctgccgctta ccggatacct gtccgccttt ctcccttcgg | 9780 |
| gaagcgtggc gctttctcaa tgctcgcgct gtaggtatct cagttcggtg taggtcgttc | 9840 |
| gctccaagct gggctgtgtg cacgaacccc ccgttcagcc cgaccgctgc gccttatccg | 9900 |
| gtaactatcg tcttgagtcc aacccggtaa gacacgactt atcgccactg gcagcagcca | 9960 |
| ctggtaacag gattagcaga gcgaggtatg taggcggtgc tacagagttc ttgaagtggt | 10020 |
| ggcctaacta cggctacact agaaggacag tatttggtat ctgcgctctg ctgaagccag | 10080 |
| ttaccttcgg aaaaagagtt ggtagctctt gatccggcaa acaaaccacc gctggtagcg | 10140 |
| gtggttttt tgtttgcaag cagcagatta cgcgcagaaa aaaaggatct caagaagatc | 10200 |
| ctttgatctt ttctacgggg cattctgacg ctcagtggaa cgaaaactca cgttaaggga | 10260 |
| ttttggtcat gagattatca aaaaggatct tcacctagat ccttttaaat taaaaatgaa | 10320 |
| gttttaaatc aatctaaagt atatatgagt aaacttggtc tgacagttac caatgcttaa | 10380 |
| tcagtgaggc acctatctca gcgatctgtc tatttcgttc atccatagtt gcctgactcc | 10440 |
| ccgtcgtgta gataactacg atacgggagg gcttaccatc tggccccagt gctgcaatga | 10500 |
| taccgcgaga cccacgctca ccggctccag atttatcagc aataaaccag ccagccggaa | 10560 |
| gggccgagcg cagaagtggt cctgcaactt tatccgcctc catccagtct attaattgtt | 10620 |
| gccgggaagc tagagtaagt agttcgccag ttaatagttt cgcaacgtt gttgccattg | 10680 |
| ctacaggcat cgtggtgtca cgctcgtcgt ttggtatggc ttcattcagc tccggttccc | 10740 |
| aacgatcaag gcgagttaca tgatccccca tgttgtgcaa aaaagcggtt agctccttcg | 10800 |
| gtcctccgat cgttgtcaga agtaagttgg ccgcagtgtt atcactcatg gttatggcag | 10860 |
| cactgcataa ttctcttact gtcatgccat ccgtaagatg cttttctgtg actggtgagt | 10920 |
| actcaaccaa gtcattctga gaatagtgta tgcggcgacc gagttgctct tgcccggcgt | 10980 |
| caatacggga taataccgcg ccacatagca gaactttaaa agtgctcatc attggaaaac | 11040 |
| gttcttcggg gcgaaaactc tcaaggatct taccgctgtt gagatccagt tcgatgtaac | 11100 |
| ccactcgtgc acccaactga tcttcagcat cttttacttt caccagcgtt tctgggtgag | 11160 |

| LISTING OF ADDITIONAL SEQUENCES | |
|---|---|
| caaaaacagg aaggcaaaat gccgcaaaaa agggaataag ggcgacacgg aaatgttgaa | 11220 |
| tactcatact cttccttttt caatattatt gaagcattta tcagggttat tgtctcatga | 11280 |
| gcggatacat atttgaatgt atttagaaaa ataaacaaat aggggttccg cgcacatttc | 11340 |
| cccgaaaagt gccacctgac gtctaagaaa ccattattat catgacatta acctataaaa | 11400 |
| ataggcgtat cacgaggccc tttcgtctcg cgcgtttcgg tgatgacggt gaaaacctct | 11460 |
| gacacatgca gctcccggag acggtcacag cttctgtcta agcggatgcc gggagcagac | 11520 |
| aagcccgtca gggcgcgtca gcgggtgttg gcgggtgtcg gggctggctt aactatgcgg | 11580 |
| catcagagca gattgtactg agagtgcacc atatcgacgc tctcccttat gcgactcctg | 11640 |
| cattaggaag cagcccagta ctaggttgag gccgttgagc accgccgccg caaggaatgg | 11700 |
| tgcatgcgta atcaattacg gggtcattag ttcatagccc atatatggag ttccgcgtta | 11760 |
| cataacttac ggtaaatggc ccgcctggct gaccgcccaa cgaccccgc ccattgacgt | 11820 |
| caataatgac gtatgttccc atagtaacgc caataggac tttccattga cgtcaatggg | 11880 |
| tggagtattt acggtaaact gcccacttgg cagtacatca agtgtatcat atgccaagta | 11940 |
| cgccccctat tgacgtcaat gacggtaaat ggcccgcctg gcattatgcc cagtacatga | 12000 |
| ccttatggga ctttcctact tggcagtaca tctacgtatt agtcatcgct attaccatgg | 12060 |
| tgatgcggtt ttggcagtac atcaatgggc gtggatagcg gtttgactca cggggatttc | 12120 |
| caagtctcca ccccattgac gtcaatggga gtttgttttg gcaccaaaat caacgggact | 12180 |
| ttccaaaatg tcgtaacaac tccgccccat tgacgcaaat gggcggtagg cgtgtacggt | 12240 |
| gggaggtcta taagcaga gctctctggc taactagaga acccactgct taactggctt | 12300 |
| atcgaaatta atacgactca ctatagggag accggaagct tgaattc | 12347 |
| SEQ ID NO: 68<br>atggcggatg tgtgacatac acgacgccaa aagattttgt tccagctcct gccacctccg | 60 |
| ctacgcgaga gattaaccac ccacgatggc cgccaaagtg catgttgata ttgaggctga | 120 |
| cagcccattc atcaagtctt tgcagaaggc atttccgtcg ttcgaggtgg agtcattgca | 180 |
| ggtcacacca aatgaccatg caaatgccag agcattttcg cacctggcta ccaaattgat | 240 |
| cgagcaggag actgacaaag acacactcat cttggatatc ggcagtgcgc cttccaggag | 300 |
| aatgatgtct acgcacaaat accactgcgt atgccctatg cgcagcgcag aagaccccga | 360 |
| aaggctcgat agctacgcaa agaaactggc agcggcctcc gggaaggtgc tggatagaga | 420 |
| gatcgcagga aaaatcaccg acctgcagac cgtcatggct acgccagacg ctgaatctcc | 480 |
| tacctttgc ctgcatacag acgtcacgtg tcgtacggca gccgaagtgg ccgtataccca | 540 |
| ggacgtgtat gctgtacatg caccaacatc gctgtaccat caggcgatga aaggtgtcag | 600 |
| aacggcgtat tggattgggt ttgacaccac cccgtttatg tttgacgcgc tagcaggcgc | 660 |
| gtatccaacc tacgccacaa actgggccga cgagcaggtg ttacaggcca ggaacatagg | 720 |
| actgtgtgca gcatccttga ctgagggaag actcggcaaa ctgtccattc tccgcaagaa | 780 |
| gcaattgaaa ccttgcgaca cagtcatgtt ctcggtagga tctacattgt acactgagag | 840 |
| cagaaagcta ctgaggagct ggcacttacc ctccgtattc cacctgaaag gtaaacaatc | 900 |
| ctttacctgt aggtgcgata ccatcgtatc atgtgaaggg tacgtagtta agaaaatcac | 960 |
| tatgtgcccc ggcctgtacg gtaaaacggt agggtacgcc gtgacgtatc acgcggaggg | 1020 |
| attcctagtg tgcaagacca cagacactgt caaaggagaa agagtctcat tccctgtatg | 1080 |

-continued

| LISTING OF ADDITIONAL SEQUENCES | |
|---|---|
| cacctacgtc ccctcaacca tctgtgatca aatgactggc atactagcga ccgacgtcac | 1140 |
| accggaggac gcacagaagt tgttagtggg attgaatcag aggatagttg tgaacggaag | 1200 |
| aacacagcga aacactaaca cgatgaagaa ctatctgctt ccgattgtgg ccgtcgcatt | 1260 |
| tagcaagtgg gcgagggaat acaaggcaga ccttgatgat gaaaaacctc tgggtgtccg | 1320 |
| agagaggtca cttacttgct gctgcttgtg ggcatttaaa acgaggaaga tgcacaccat | 1380 |
| gtacaagaaa ccagacaccc agacaatagt gaaggtgcct tcagagttta actcgttcgt | 1440 |
| catcccgagc ctatggtcta caggcctcgc aatcccagtc agatcacgca ttaagatgct | 1500 |
| tttggccaag aagaccaagc gagagttaat acctgttctc gacgcgtcgt cagccaggga | 1560 |
| tgctgaacaa gaggagaagg agaggttgga ggccgagctg actagagaag ccttaccacc | 1620 |
| cctcgtcccc atcgcgccgg cggagacggg agtcgtcgac gtcgacgttg aagaactaga | 1680 |
| gtatcacgca ggtgcagggg tcgtggaaac acctcgcagc gcgttgaaag tcaccgcaca | 1740 |
| gccgaacgac gtactactag gaaattacgt agttctgtcc ccgcagaccg tgctcaagag | 1800 |
| ctccaagttg gcccccgtgc accctctagc agagcaggtg aaaataataa cacataacgg | 1860 |
| gagggccggc ggttaccagg tcgacggata tgacggcagg gtcctactac catgtggatc | 1920 |
| ggccattccg gtccctgagt ttcaagcttt gagcgagagc gccactatgg tgtacaacga | 1980 |
| aagggagttc gtcaacagga aactatacca tattgccgtt cacggaccgt cgctgaacac | 2040 |
| cgacgaggag aactacgaga aagtcagagc tgaaagaact gacgccgagt acgtgttcga | 2100 |
| cgtagataaa aaatgctgcg tcaagagaga ggaagcgtcg ggtttggtgt tggtgggaga | 2160 |
| gctaaccaac ccccgttcc atgaattcgc ctacgaaggg ctgaagatca ggccgtcggc | 2220 |
| accatataag actacagtag taggagtctt tggggttccg ggatcaggca agtctgctat | 2280 |
| tattaagagc ctcgtgacca aacacgatct ggtcaccagc ggcaagaagg agaactgcca | 2340 |
| ggaaatagtt aacgacgtga agaagcaccg cgggaagggg acaagtaggg aaaacagtga | 2400 |
| ctccatcctg ctaaacgggt gtcgtcgtgc cgtggacatc ctatatgtgg acgaggcttt | 2460 |
| cgctagccat tccggtactc tgctggccct aattgctctt gttaaacctc ggagcaaagt | 2520 |
| ggtgttatgc ggagacccca agcaatgcgg attcttcaat atgatgcagc ttaaggtgaa | 2580 |
| cttcaaccac aacatctgca ctgaagtatg tcataaaagt atatccagac gttgcacgcg | 2640 |
| tccagtcacg gccatcgtgt ctacgttgca ctacggaggc aagatgcgca cgaccaaccc | 2700 |
| gtgcaacaaa cccataatca tagacaccac aggacagacc aagcccaagc caggagacat | 2760 |
| cgtgttaaca tgcttccgag gctgggcaaa gcagctgcag ttggactacc gtggacacga | 2820 |
| agtcatgaca gcagcagcat ctcagggcct caccccgcaaa ggggtatacg ccgtaaggca | 2880 |
| gaaggtgaat gaaaatccct tgtatgcccc tgcgtcggag cacgtgaatg tactgctgac | 2940 |
| gcgcactgag gataggctgg tgtggaaaac gctggccggc gatccctgga ttaaggtcct | 3000 |
| atcaaacatt ccacagggta actttacggc cacattggaa gaatggcaag aagaacacga | 3060 |
| caaaataatg aaggtgattg aaggaccggc tgcgcctgtg gacgcgttcc agaacaaagc | 3120 |
| gaacgtgtgt tgggcgaaaa gcctggtgcc tgtcctggac actgccggaa tcagattgac | 3180 |
| agcagaggag tggagcacca taattacagc atttaaggag gacagagctt actctccagt | 3240 |
| ggtggccttg aatgaaattt gcaccaagta ctatggagtt gacctggaca gtggcctgtt | 3300 |
| ttctgccccg aaggtgtccc tgtattacga gaacaaccac tgggataaca gacctggtgg | 3360 |
| aaggatgtat ggattcaatg ccgcaacagc tgccaggctg gaagctagac ataccttcct | 3420 |

-continued

| LISTING OF ADDITIONAL SEQUENCES | |
|---|---|
| gaaggggcag tggcatacgg gcaagcaggc agttatcgca gaaagaaaaa tccaaccgct | 3480 |
| ttctgtgctg gacaatgtaa ttcctatcaa ccgcaggctg ccgcacgccc tggtggctga | 3540 |
| gtacaagacg gttaaaggca gtagggttga gtggctggtc aataaagtaa gagggtacca | 3600 |
| cgtcctgctg gtgagtgagt acaacctggc tttgcctcga cgcagggtca cttggttgtc | 3660 |
| accgctgaat gtcacaggcg ccgataggtg ctacgaccta agtttaggac tgccggctga | 3720 |
| cgccggcagg ttcgacttgg tctttgtgaa cattcacacg gaattcagaa tccaccacta | 3780 |
| ccagcagtgt gtcgaccacg ccatgaagct gcagatgctt gggggagatg cgctacgact | 3840 |
| gctaaaaccc ggcggcatct tgatgagagc ttacggatac gccgataaaa tcagcgaagc | 3900 |
| cgttgtttcc tccttaagca gaaagttctc gtctgcaaga gtgttgcgcc cggattgtgt | 3960 |
| caccagcaat acagaagtgt tcttgctgtt ctccaacttt gacaacggaa agagaccctc | 4020 |
| tacgctacac cagatgaata ccaagctgag tgccgtgtat gccggagaag ccatgcacac | 4080 |
| ggccgggtgt gcaccatcct acagagttaa gagagcagac atagccacgt gcacagaagc | 4140 |
| ggctgtggtt aacgcagcta acgcccgtgg aactgtaggg gatggcgtat gcagggccgt | 4200 |
| ggcgaagaaa tggccgtcag cctttaaggg agcagcaaca ccagtgggca caattaaaac | 4260 |
| agtcatgtgc ggctcgtacc ccgtcatcca cgctgtagcg cctaatttct ctgccacgac | 4320 |
| tgaagcggaa ggggaccgcg aattggccgc tgtctaccgg gcagtggccg ccgaagtaaa | 4380 |
| cagactgtca ctgagcagcg tagccatccc gctgctgtcc acaggagtgt tcagcggcgg | 4440 |
| aagagatagg ctgcagcaat ccctcaacca tctattcaca gcaatggacg ccacggacgc | 4500 |
| tgacgtgacc atctactgca gagacaaaag ttgggagaag aaaatccagg aagccattga | 4560 |
| catgaggacg gctgtggagt tgctcaatga tgacgtggag ctgaccacag acttggtgag | 4620 |
| agtgcacccg gacagcagcc tggtgggtcg taagggctac agtaccactg acgggtcgct | 4680 |
| gtactcgtac tttgaaggta cgaaattcaa ccaggctgct attgatatgg cagagatact | 4740 |
| gacgttgtgg cccagactgc aagaggcaaa cgaacagata tgcctatacg cgctgggcga | 4800 |
| aacaatggac aacatcagat ccaaatgtcc ggtgaacgat tccgattcat caacacctcc | 4860 |
| caggacagtg ccctgcctgt gccgctacgc aatgacagca gaacggatcg cccgccttag | 4920 |
| gtcacaccaa gttaaaagca tggtggtttg ctcatctttt cccctcccga ataccatgt | 4980 |
| agatggggtg cagaaggtaa agtgcgagaa ggttctcctg ttcgacccga cggtaccttc | 5040 |
| agtggttagt ccgcggaagt atgccgcatc tacgacggac cactcagatc ggtcgttacg | 5100 |
| agggtttgac ttggactgga ccaccgactc gtcttccact gccagcgata ccatgtcgct | 5160 |
| acccagtttg cagtcgtgtg acatcgactc gatctacgag ccaatggctc ccatagtagt | 5220 |
| gacggctgac gtacaccctg aacccgcagg catcgcggac ctggcggcag atgtgcaccc | 5280 |
| tgaacccgca gaccatgtgg acctcgagaa cccgattcct ccaccgcgcc cgaagagagc | 5340 |
| tgcatacctt gcctcccgcg cggcggagcg accggtgccg gcgccgagaa agccgacgcc | 5400 |
| tgccccaagg actgcgttta ggaacaagct gcctttgacg ttcggcgact ttgacgagca | 5460 |
| cgaggtcgat gcgttggcct ccgggattac tttcggagac ttcgacgacg tcctgcgact | 5520 |
| aggccgcgcg ggtgcatata ttttctcctc ggacactggc agcggacatt tacaacaaaa | 5580 |
| atccgttagg cagcacaatc tccagtgcgc acaactggat gcggtccagg aggagaaaat | 5640 |
| gtacccgcca aaattggata ctgagaggga gaagctgttg ctgctgaaaa tgcagatgca | 5700 |

| LISTING OF ADDITIONAL SEQUENCES | |
|---|---|
| cccatcggag gctaataaga gtcgatacca gtctcgcaaa gtggagaaca tgaaagccac | 5760 |
| ggtggtggac aggctcacat cgggggccag attgtacacg ggagcggacg taggccgcat | 5820 |
| accaacatac gcggttcggt accccgccc cgtgtactcc cctaccgtga tcgaaagatt | 5880 |
| ctcaagcccc gatgtagcaa tcgcagcgtg caacgaatac ctatccagaa attacccaac | 5940 |
| agtggcgtcg taccagataa cagatgaata cgacgcatac ttggacatgg ttgacgggtc | 6000 |
| ggatagttgc ttggacagag cgacattctg cccggcgaag ctccggtgct acccgaaaca | 6060 |
| tcatgcgtac caccagccga ctgtacgcag tgccgtcccg tcacccttc agaacacact | 6120 |
| acagaacgtg ctagcggccg ccaccaagag aaactgcaac gtcacgcaaa tgcgagaact | 6180 |
| acccaccatg gactcggcag tgttcaacgt ggagtgcttc aagcgctatg cctgctccgg | 6240 |
| agaatattgg gaagaatatg ctaaacaacc tatccggata accactgaga acatcactac | 6300 |
| ctatgtgacc aaattgaaag gcccgaaagc tgctgccttg ttcgctaaga cccacaactt | 6360 |
| ggttccgctg caggaggttc ccatggacag attcacggtc gacatgaaac gagatgtcaa | 6420 |
| agtcactcca gggacgaaac acacagagga aagacccaaa gtccaggtaa ttcaagcagc | 6480 |
| ggagccattg gcgaccgctt acctgtgcgg catccacagg gaattagtaa ggagactaaa | 6540 |
| tgctgtgtta cgccctaacg tgcacacatt gtttgatatg tcggccgaag actttgacgc | 6600 |
| gatcatcgcc tctcacttcc acccaggaga cccggttcta gagacggaca ttgcatcatt | 6660 |
| cgacaaaagc caggacgact ccttggctct tacaggttta atgatcctcg aagatctagg | 6720 |
| ggtggatcag tacctgctgg acttgatcga ggcagccttt ggggaaatat ccagctgtca | 6780 |
| cctaccaact ggcacgcgct tcaagttcgg agctatgatg aaatcgggca tgtttctgac | 6840 |
| tttgtttatt aacactgttt tgaacatcac catagcaagc agggtactgg agcagagact | 6900 |
| cactgactcc gcctgtgcgg ccttcatcgg cgacgacaac atcgttcacg gagtgatctc | 6960 |
| cgacaagctg atggcggaga ggtgcgcgtc gtgggtcaac atggaggtga agatcattga | 7020 |
| cgctgtcatg ggcgaaaaac ccccatattt tgtgtgggga ttcatagttt ttgacagcgt | 7080 |
| cacacagacc gcctgccgtg tttcagaccc acttaagcgc ctgttcaagt tgggtaagcc | 7140 |
| gctaacagct gaagacaagc aggacgaaga caggcgacga gcactgagtg acgaggttag | 7200 |
| caagtggttc cggacaggct tgggggccga actggaggtg gcactaacat ctaggtatga | 7260 |
| ggtagagggc tgcaaaagta tcctcatagc catggccacc ttggcgaggg acattaaggc | 7320 |
| gtttaagaaa ttgagaggac ctgttataca cctctacggc ggtccagat tggtgcgtta | 7380 |
| atacacagaa ttctgattgg atcccaaacg ggccctctag actcgagcgg ccgccactgt | 7440 |
| gctggatatc tgcagaattc atgcatggag atacacctac attgcatgaa tatatgttag | 7500 |
| atttgcaacc agagacaact gatctctact gttatgagca attaaatgac agctcagagg | 7560 |
| aggaggatga aatagatggt ccagctggac aagcagaacc ggacagagcc cattacaata | 7620 |
| ttgtaacctt ttgttgcaag tgtgactcta cgcttcggtt gtgcgtacaa agcacacacg | 7680 |
| tagacattcg tactttggaa gacctgttaa tgggcacact aggaattgtg tgccccatct | 7740 |
| gttctcagaa accaggatct atggcgtacc catacgatgt tccagattac gctagcttga | 7800 |
| gatctaccat gtctcagagc aaccgggagc tggtggttga ctttctctcc tacaagcttt | 7860 |
| cccagaaagg atacagctgg agtcagttta gtgatgtgga agagaacagg actgaggccc | 7920 |
| cagagggac tgaatcggag atggagaccc ccagtgccat caatgcaac ccatcctggc | 7980 |
| acctggcaga cagccccgcg gtgaatggag ccactgcgca cagcagcagt ttggatgccc | 8040 |

| | |
|---|---|
| gggaggtgat ccccatggca gcagtaaagc aagcgctgag ggaggcaggc gacgagtttg | 8100 |
| aactgcggta ccggcgggca ttcagtgacc tgacatccca gctccacatc accccaggga | 8160 |
| cagcatatca gagctttgaa caggtagtga atgaactctt ccgggatggg gtagccattc | 8220 |
| ttcgcattgt ggccttttc tccttcggcg gggcactgtg cgtggaaagc gtagacaagg | 8280 |
| agatgcaggt attggtgagt cggatcgcag cttggatggc cacttacctg aatgaccacc | 8340 |
| tagagccttg gatccaggag aacggcggct gggatacttt tgtggaactc tatgggaaca | 8400 |
| atgcagcagc cgagagccga aagggccagg aacgcttcaa ccgctggttc ctgacgggca | 8460 |
| tgactgtggc cggcgtggtt ctgctgggct cactcttcag tcggaaatga agatccaagc | 8520 |
| ttaagtttgg gtaattaatt gaattacatc cctacgcaaa cgttttacgg ccgccggtgg | 8580 |
| cgcccgcgcc cggcggcccg tccttggccg ttgcaggcca ctccggtggc tcccgtcgtc | 8640 |
| cccgacttcc aggcccagca gatgcagcaa ctcatcagcg ccgtaaatgc gctgacaatg | 8700 |
| agacagaacg caattgctcc tgctaggcct cccaaaccaa agaagaagaa gacaaccaaa | 8760 |
| ccaaagccga aaacgcagcc caagaagatc aacggaaaaa cgcagcagca aaagaagaaa | 8820 |
| gacaagcaag ccgacaagaa gaagaagaaa cccggaaaaa gagaaagaat gtgcatgaag | 8880 |
| attgaaaatg actgtatctt cgtatgcggc tagccacagt aacgtagtgt ttccagacat | 8940 |
| gtcgggcacc gcactatcat gggtgcagaa atctcgggt ggtctggggg ccttcgcaat | 9000 |
| cggcgctatc ctggtgctgg ttgtggtcac ttgcattggg ctccgcagat aagttagggt | 9060 |
| aggcaatggc attgatatag caagaaaatt gaaaacagaa aaagttaggg taagcaatgg | 9120 |
| catataacca taactgtata acttgtaaca aagcgcaaca agacctgcgc aattggcccc | 9180 |
| gtggtccgcc tcacggaaac tcgggcaac tcatattgac acattaattg gcaataattg | 9240 |
| gaagcttaca taagcttaat tcgacgaata attggatttt tattttattt tgcaattggt | 9300 |
| ttttaatatt tccaaaaaaa aaaaaaaaaa aaaaaaaaaa aaaaaaaaaa aaaaaaaaaa | 9360 |
| aaaaaaaaaa aaaaaaaaaa aaactagtga tcataatcag ccataccaca tttgtagagg | 9420 |
| ttttacttgc tttaaaaaac ctcccacacc tcccctgaa cctgaaacat aaaatgaatg | 9480 |
| caattgttgt tgttaacttg tttattgcag cttataatgg ttacaaataa agcaatagca | 9540 |
| tcacaaattt cacaaataaa gcattttttt cactgcattc tagttgtggt ttgtccaaac | 9600 |
| tcatcaatgt atcttatcat gtctggatct agtctgcatt aatgaatcgg ccaacgcgcg | 9660 |
| gggagaggcg gtttgcgtat tgggcgctct tccgcttcct cgctcactga ctcgctgcgc | 9720 |
| tcggtcgttc ggctgcggcg agcggtatca gctcactcaa aggcggtaat acggttatcc | 9780 |
| acagaatcag gggataacgc aggaaagaac atgtgagcaa aaggccagca aaaggccagg | 9840 |
| aaccgtaaaa aggccgcgtt gctggcgttt ttccataggc tccgcccccc tgacgagcat | 9900 |
| cacaaaaatc gacgctcaag tcagaggtgg cgaaacccga caggactata agataccag | 9960 |
| gcgtttcccc ctggaagctc cctcgtgcgc tctcctgttc cgaccctgcc gcttaccgga | 10020 |
| tacctgtccg cctttctccc ttcgggaagc gtggcgcttt ctcaatgctc gcgctgtagg | 10080 |
| tatctcagtt cggtgtaggt cgttcgctcc aagctgggct gtgtgcacga accccccgtt | 10140 |
| cagcccgacc gctgcgcctt atccggtaac tatcgtcttg agtccaaccc ggtaagacac | 10200 |
| gacttatcgc cactggcagc agccactggt aacaggatta gcagagcgag gtatgtaggc | 10260 |
| ggtgctacag agttcttgaa gtggtggcct aactacggct acactagaag gacagtattt | 10320 |

| LISTING OF ADDITIONAL SEQUENCES | |
|---|---|
| ggtatctgcg ctctgctgaa gccagttacc ttcggaaaaa gagttggtag ctcttgatcc | 10380 |
| ggcaaacaaa ccaccgctgg tagcggtggt tttttgttt gcaagcagca gattacgcgc | 10440 |
| agaaaaaaag gatctcaaga agatcctttg atcttttcta cggggcattc tgacgctcag | 10500 |
| tggaacgaaa actcacgtta agggattttg gtcatgagat tatcaaaaag gatcttcacc | 10560 |
| tagatccttt taaattaaaa atgaagtttt aaatcaatct aaagtatata tgagtaaact | 10620 |
| tggtctgaca gttaccaatg cttaatcagt gaggcaccta tctcagcgat ctgtctattt | 10680 |
| cgttcatcca tagttgcctg actccccgtc gtgtagataa ctacgatacg ggagggctta | 10740 |
| ccatctggcc ccagtgctgc aatgataccg cgagacccac gctcaccggc tccagattta | 10800 |
| tcagcaataa accagccagc cggaagggcc gagcgcagaa gtggtcctgc aactttatcc | 10860 |
| gcctccatcc agtctattaa ttgttgccgg gaagctagag taagtagttc gccagttaat | 10920 |
| agtttgcgca acgttgttgc cattgctaca ggcatcgtgg tgtcacgctc gtcgtttggt | 10980 |
| atggcttcat tcagctccgg ttcccaacga tcaaggcgag ttacatgatc ccccatgttg | 11040 |
| tgcaaaaaag cggttagctc cttcggtcct ccgatcgttg tcagaagtaa gttggccgca | 11100 |
| gtgttatcac tcatggttat ggcagcactg cataattctc ttactgtcat gccatccgta | 11160 |
| agatgctttt ctgtgactgg tgagtactca accaagtcat tctgagaata gtgtatgcgg | 11220 |
| cgaccgagtt gctcttgccc ggcgtcaata cgggataata ccgcgccaca tagcagaact | 11280 |
| ttaaaagtgc tcatcattgg aaaacgttct cggggcgaaa actctcaag gatcttaccg | 11340 |
| ctgttgagat ccagttcgat gtaacccact cgtgcaccca actgatcttc agcatctttt | 11400 |
| actttcacca gcgtttctgg gtgagcaaaa acaggaaggc aaaatgccgc aaaaaaggga | 11460 |
| ataagggcga cacggaaatg ttgaatactc atactcttcc tttttcaata ttattgaagc | 11520 |
| atttatcagg gttattgtct catgagcgga tacatatttg aatgtattta gaaaaataaa | 11580 |
| caaatagggg ttccgcgcac atttccccga aaagtgccac ctgacgtcta agaaaccatt | 11640 |
| attatcatga cattaaccta taaaaatagg cgtatcacga ggccctttcg tctcgcgcgt | 11700 |
| ttcggtgatg acggtgaaaa cctctgacac atgcagctcc cggagacggt cacagcttct | 11760 |
| gtctaagcgg atgccgggag cagacaagcc cgtcagggcg cgtcagcggg tgttggcggg | 11820 |
| tgtcggggct ggcttaacta tgcggcatca gagcagattg tactgagagt gcaccatatc | 11880 |
| gacgctctcc cttatgcgac tcctgcatta ggaagcagcc cagtactagg ttgaggccgt | 11940 |
| tgagcaccgc cgccgcaagg aatggtgcat gcgtaatcaa ttacgggtc attagttcat | 12000 |
| agcccatata tggagttccg cgttacataa cttacggtaa atggcccgcc tggctgaccg | 12060 |
| cccaacgacc cccgcccatt gacgtcaata atgacgtatg ttcccatagt aacgccaata | 12120 |
| gggactttcc attgacgtca atgggtggag tatttacggt aaactgccca cttggcagta | 12180 |
| catcaagtgt atcatatgcc aagtacgccc cctattgacg tcaatgacgg taaatggccc | 12240 |
| gcctggcatt atgcccagta catgacctta tgggactttc ctacttggca gtacatctac | 12300 |
| gtattagtca tcgctattac catggtgatg cggttttggc agtacatcaa tgggcgtgga | 12360 |
| tagcggtttg actcacgggg atttccaagt ctccaccccca ttgacgtcaa tgggagtttg | 12420 |
| ttttggcacc aaaatcaacg ggactttcca aaatgtcgta acaactccgc cccattgacg | 12480 |
| caaatgggcg gtaggcgtgt acggtgggag gtctatataa gcagagctct ctggctaact | 12540 |
| agagaaccca ctgcttaact ggcttatcga aattaatacg actcactata gggagaccgg | 12600 |
| aagcttgaat tc | 12612 |

| LISTING OF ADDITIONAL SEQUENCES | |
|---|---|
| SEQ ID NO: 69 | |
| gtcgacttct gaggcggaaa gaaccagctg tggaatgtgt gtcagttagg gtgtggaaag | 60 |
| tccccaggct ccccagcagg cagaagtatg caaagcatgc atctcaatta gtcagcaacc | 120 |
| aggtgtggaa agtccccagg ctccccagca ggcagaagta tgcaaagcat gcatctcaat | 180 |
| tagtcagcaa ccatagtccc gcccctaact ccgcccatcc cgcccctaac tccgcccagt | 240 |
| tccgcccatt ctccgcccca tggctgacta attttttttta tttatgcaga ggccgaggcc | 300 |
| gcctcggcct ctgagctatt ccagaagtag tgaggaggct tttttggagg cctaggcttt | 360 |
| tgcaaaaagc tggatcgatc ctgagaactt cagggtgagt ttggggaccc ttgattgttc | 420 |
| tttcttttttc gctattgtaa aattcatgtt atatggaggg ggcaaagttt tcagggtgtt | 480 |
| gtttagaatg ggaagatgtc ccttgtatca ccatggaccc tcatgataat tttgtttctt | 540 |
| tcactttcta ctctgttgac aaccattgtc tcctcttatt ttcttttcat tttctgtaac | 600 |
| tttttcgtta aactttagct tgcatttgta acgaattttt aaattcactt ttgtttattt | 660 |
| gtcagattgt aagtactttc tctaatcact ttttttttcaa ggcaatcagg gtatattata | 720 |
| ttgtacttca gcacagtttt agagaacaat tgttataatt aaatgataag gtagaatatt | 780 |
| tctgcatata aattctggct ggcgtggaaa tattcttatt ggtagaaaca actacatcct | 840 |
| ggtcatcatc ctgcctttct ctttatggtt acaatgatat acactgtttg agatgaggat | 900 |
| aaaatactct gagtccaaac cgggcccctc tgctaaccat gttcatgcct tcttcttttt | 960 |
| cctacagctc ctgggcaacg tgctggttat tgtgctgtct catcattttg gcaaagaatt | 1020 |
| gtaatacgac tcactatagg gcgaattcgg atccagatct atggcgtacc catacgatgt | 1080 |
| tccagattac gctagcttga gatctaccat gtctcagagc aaccgggagc tggtggttga | 1140 |
| cttttctctcc tacaagcttt cccagaaagg atacagctgg agtcagttta gtgatgtgga | 1200 |
| agagaacagg actgaggccc cagaagggac tgaatcggag atggagaccc ccagtgccat | 1260 |
| caatggcaac ccatcctggc acctggcaga cagccccgcg gtgaatggag ccactgcgca | 1320 |
| cagcagcagt ttggatgccc gggaggtgat ccccatggca gcagtaaagc aagcgctgag | 1380 |
| ggaggcaggc gacgagtttg aactgcggta ccggcgggca ttcagtgacc tgacatccca | 1440 |
| gctccacatc accccaggga cagcatatca gagctttgaa caggtagtga atgaactctt | 1500 |
| ccgggatggg gtaaactggg gtcgcattgt ggccttttttc tccttcggcg gggcactgtg | 1660 |
| cgtggaaagc gtagacaagg agatgcaggt attggtgagt cggatcgcag cttggatggc | 1620 |
| cacttacctg aatgaccacc tagagccttg gatccaggag aacggcggct gggatacttt | 1680 |
| tgtggaactc tatgggaaca atgcagcagc cgagagccga aagggccagg aacgcttcaa | 1740 |
| ccgctggttc ctgacgggca tgactgtggc cggcgtggtt ctgctgggct cactcttcag | 1800 |
| tcggaaatga agatcttatt aaagcagaac ttgtttattg cagcttataa tggttacaaa | 1860 |
| taaagcaata gcatcacaaa tttcacaaat aaagcatttt tttcactgca ttctagttgt | 1920 |
| ggtttgtcca aactcatcaa tgtatcttat catgtctggt cgactctaga ctcttccgct | 1980 |
| tcctcgctca ctgactcgct gcgctcggtc gttcggctgc ggcgagcggt atcagctcac | 2040 |
| tcaaaggcgg taatacggtt atccacagaa tcagggggata acgcaggaaa gaacatgtga | 2100 |
| gcaaaggcca gcaaaaggcc aggaaccgta aaaaggccgc gttgctggcg ttttttccat | 2160 |
| aggctccgcc cccctgacga gcatcacaaa aatcgacgct caagtcagag gtggcgaaac | 2220 |
| ccgacaggac tataaagata ccaggcgttt ccccctggaa gctccctcgt gcgctctcct | 2280 |

| LISTING OF ADDITIONAL SEQUENCES | |
|---|---|
| gttccgaccc tgccgcttac cggatacctg tccgcctttc tcccttcggg aagcgtggcg | 2340 |
| ctttctcaat gctcacgctg taggtatctc agttcggtgt aggtcgttcg ctccaagctg | 2400 |
| ggctgtgtgc acgaaccccc cgttcagccc gaccgctgcg ccttatccgg taactatcgt | 2460 |
| cttgagtcca acccggtaag acacgactta tcgccactgg cagcagccac tggtaacagg | 2520 |
| attagcagag cgaggtatgt aggcggtgct acagagttct tgaagtggtg gcctaactac | 2580 |
| ggctacacta gaaggacagt atttggtatc tgcgctctgc tgaagccagt taccttcgga | 2640 |
| aaaagagttg gtagctcttg atccggcaaa caaaccaccg ctggtagcgg tggttttttt | 2700 |
| gtttgcaagc agcagattac gcgcagaaaa aaggatctc aagaagatcc tttgatcttt | 2760 |
| tctacggggt ctgacgctca gtggaacgaa aactcacgtt aagggatttt ggtcatgaga | 2820 |
| ttatcaaaaa ggatcttcac ctagatcctt ttaaattaaa aatgaagttt taaatcaatc | 2880 |
| taaagtatat atgagtaaac ttggtctgac agttaccaat gcttaatcag tgaggcacct | 2940 |
| atctcagcga tctgtctatt tcgttcatcc atagttgcct gactccccgt cgtgtagata | 3000 |
| actacgatac gggagggctt accatctggc cccagtgctg caatgatacc gcgagaccca | 3060 |
| cgctcaccgg ctccagattt atcagcaata aaccagccag ccggaagggc cgagcgcaga | 3120 |
| agtggtcctg caactttatc cgcctccatc cagtctatta attgttgccg ggaagctaga | 3180 |
| gtaagtagtt cgccagttaa tagtttgcgc aacgttgttg ccattgctac aggcatcgtg | 3240 |
| gtgtcacgct cgtcgtttgg tatggcttca ttcagctccg gttcccaacg atcaaggcga | 3300 |
| gttacatgat cccccatgtt gtgcaaaaaa gcggttagct ccttcggtcc tccgatcgtt | 3360 |
| gtcagaagta agttggccgc agtgttatca ctcatggtta tggcagcact gcataattct | 3420 |
| cttactgtca tgccatccgt aagatgcttt tctgtgactg gtgagtactc aaccaagtca | 3480 |
| ttctgagaat agtgtatgcg gcgaccgagt tgctcttgcc cggcgtcaat acgggataat | 3540 |
| accgcgccac atagcagaac tttaaaagtg ctcatcattg gaaaacgttc ttcggggcga | 3600 |
| aaactctcaa ggatcttacc gctgttgaga tccagttcga tgtaacccac tcgtgcaccc | 3660 |
| aactgatctt cagcatcttt tactttcacc agcgtttctg ggtgagcaaa aacaggaagg | 3720 |
| caaaatgccg caaaaaaggg aataagggcg acacggaaat gttgaatact catactcttc | 3780 |
| ctttttcaat attattgaag catttatcag ggttattgtc tcatgagcgg atacatattt | 3840 |
| gaatgtattt agaaaaataa acaaataggg gttccgcgca catttccccg aaaagtgcca | 3900 |
| cctgacgtct aagaaaccat tattatcatg acattaacct ataaaaatag gcgtatcacg | 3960 |
| aggccccttt cgtctcgcgc gtttcggtga tgacggtgaa aacctctgac acatgcagct | 4020 |
| cccggagacg tcacagcttg tctgtaagc ggatgccggg agcagacaag cccgtcaggg | 4080 |
| cgcgtcagcg ggtgttggcg ggtgtcgggg ctggcttaac tatgcggcat cagagcagat | 4140 |
| tgtactgaga gtgcaccata tgcggtgtga ataccgcac agatgcgtaa ggagaaaata | 4200 |
| ccgcatcagg aaattgtaaa cgttaatatt ttgttaaaat tcgcgttaaa tttttgttaa | 4260 |
| atcagctcat tttttaacca ataggccgaa atcggcaaaa tcccttataa atcaaaagaa | 4320 |
| tagaccgaga tagggttgag tgttgttcca gtttggaaca agagtccact attaaagaac | 4380 |
| gtggactcca acgtcaaagg gcgaaaaacc gtctatcagg gcgatggccc actacgtgaa | 4440 |
| ccatcaccct aatcaagttt tttggggtcg aggtgccgta agcactaaa tcggaaccct | 4500 |
| aaagggagcc cccgatttag agcttgacgg ggaaagccgg cgaacgtggc gagaaaggaa | 4560 |

| LISTING OF ADDITIONAL SEQUENCES | |
|---|---|
| gggaagaaag cgaaaggagc gggcgctagg gcgctggcaa gtgtagcggt cacgctgcgc | 4620 |
| gtaaccacca cacccgccgc gcttaatgcg ccgctacagg gcgcgtcgcg ccattcgcca | 4680 |
| ttcaggctac gcaactgttg ggaagggcga tcggtgcggg cctcttcgct attacgccag | 4740 |
| ctggcgaagg ggggatgtgc tgcaaggcga ttaagttggg taacgccagg gttttcccag | 4800 |
| tcacgacgtt gtaaaacgac ggccagtgaa tt | 4832 |
| SEQ ID NO: 70 | |
| gtcgacttct gaggcggaaa gaaccagctg tggaatgtgt gtcagttagg gtgtggaaag | 60 |
| tccccaggct ccccagcagg cagaagtatg caaagcatgc atctcaatta gtcagcaacc | 120 |
| aggtgtggaa agtccccagg ctccccagca ggcagaagta tgcaaagcat gcatctcaat | 180 |
| tagtcagcaa ccatagtccc gcccctaact ccgcccatcc cgcccctaac tccgcccagt | 240 |
| tccgcccatt ctccgcccca tggctgacta atttttttta tttatgcaga ggccgaggcc | 300 |
| gcctcggcct ctgagctatt ccagaagtag tgaggaggct tttttggagg cctaggcttt | 360 |
| tgcaaaaagc tggatcgatc ctgagaactt cagggtgagt ttggggaccc ttgattgttc | 420 |
| tttcttttc gctattgtaa aattcatgtt atatggaggg ggcaaagttt tcagggtgtt | 480 |
| gtttagaatg ggaagatgtc ccttgtatca ccatggaccc tcatgataat tttgtttctt | 540 |
| tcactttcta ctctgttgac aaccattgtc tcctcttatt ttcttttcat tttctgtaac | 600 |
| ttttttcgtta aactttagct tgcatttgta acgaattttt aaattcactt ttgtttattt | 660 |
| gtcagattgt aagtactttc tctaatcact ttttttttcaa ggcaatcagg gtatattata | 720 |
| ttgtacttca gcacagtttt agagaacaat tgttataatt aaatgataag gtagaatatt | 780 |
| tctgcatata aattctggct ggcgtggaaa tattcttatt ggtagaaaca actacatcct | 840 |
| ggtcatcatc ctgcctttct ctttatggtt acaatgatat acactgtttg agatgaggat | 900 |
| aaaatactct gagtccaaac cgggcccctc tgctaaccat gttcatgcct tcttcttttt | 960 |
| cctacagctc ctgggcaacg tgctggttat tgtgctgtct catcattttg gcaaagaatt | 1020 |
| gtaatacgac tcactatagg gcgaattcgg atccagatct atggcgtacc catacgatgt | 1080 |
| tccagattac gctagcttga gatctaccat gtctcagagc aaccgggagc tggtggttga | 1140 |
| cttttctctcc tacaagcttt cccagaaagg atacagctgg agtcagttta gtgatgtgga | 1200 |
| agagaacagg actgaggccc cagaagggac tgaatcggag atggagaccc ccagtgccat | 1260 |
| caatggcaac ccatcctggc acctggcaga cagccccgcg gtgaatggag ccactgcgca | 1320 |
| cagcagcagt ttggatgccc gggaggtgat ccccatggca gcagtaaagc aagcgctgag | 1380 |
| ggaggcaggc gacgagtttg aactgcggta ccggcgggca ttcagtgacc tgacatccca | 1440 |
| gctccacatc acccccaggga cagcatatca gagctttgaa caggtagtga atgaactctt | 1500 |
| ccgggatggg gtagccattc ttcgcattgt ggccttttct ccttcggcg gggcactgtg | 1560 |
| cgtggaaagc gtagacaagg agatgcaggt attggtgagt cggatcgcag cttggatggc | 1620 |
| cacttacctg aatgaccacc tagagccttg gatccaggag aacggcggct gggatacttt | 1680 |
| tgtggaactc tatgggaaca atgcagcagc cgagagccga aagggccagg aacgcttcaa | 1740 |
| ccgctggttc ctgacgggca tgactgtggc cggcgtggtt ctgctgggct cactcttcag | 1800 |
| tcggaaatga agatcttatt aaagcagaac ttgtttattg cagcttataa tggttacaaa | 1860 |
| taaagcaata gcatcacaaa tttcacaaat aaagcatttt tttcactgca ttctagttgt | 1920 |
| ggtttgtcca aactcatcaa tgtatcttat catgtctggt cgactctaga ctcttccgct | 1980 |

| LISTING OF ADDITIONAL SEQUENCES | |
|---|---|
| tcctcgctca ctgactcgct gcgctcggtc gttcggctgc ggcgagcggt atcagctcac | 2040 |
| tcaaaggcgg taatacggtt atccacagaa tcagggata acgcaggaaa gaacatgtga | 2100 |
| gcaaaggcca gcaaaaggcc aggaaccgta aaaaggccgc gttgctggcg ttttttccat | 2160 |
| aggctccgcc cccctgacga gcatcacaaa aatcgacgct caagtcagag gtggcgaaac | 2220 |
| ccgacaggac tataaagata ccaggcgttt ccccctggaa gctccctcgt gcgctctcct | 2280 |
| gttccgaccc tgccgcttac cggatacctg tccgcctttc tcccttcggg aagcgtggcg | 2340 |
| ctttctcaat gctcacgctg taggtatctc agttcggtgt aggtcgttcg ctccaagctg | 2400 |
| ggctgtgtgc acgaaccccc cgttcagccc gaccgctgcg ccttatccgg taactatcgt | 2460 |
| cttgagtcca acccggtaag acacgactta tcgccactgg cagcagccac tggtaacagg | 2520 |
| attagcagag cgaggtatgt aggcggtgct acagagttct tgaagtggtg gcctaactac | 2580 |
| ggctacacta aaggacagt atttggtatc tgcgctctgc tgaagccagt taccttcgga | 2640 |
| aaaagagttg gtagctcttg atccggcaaa caaaccaccg ctggtagcgg tggtttttttt | 2700 |
| gtttgcaagc agcagattac gcgcagaaaa aaggatctc aagaagatcc tttgatcttt | 2760 |
| tctacggggt ctgacgctca gtggaacgaa aactcacgtt aagggatttt ggtcatgaga | 2820 |
| ttatcaaaaa ggatcttcac ctagatcctt ttaaattaaa aatgaagttt taaatcaatc | 2880 |
| taaagtatat atgagtaaac ttggtctgac agttaccaat gcttaatcag tgaggcacct | 2940 |
| atctcagcga tctgtctatt tcgttcatcc atagttgcct gactccccgt cgtgtagata | 3000 |
| actacgatac gggagggctt accatctggc cccagtgctg caatgatacc gcgagaccca | 3060 |
| cgctcaccgg ctccagattt atcagcaata accagccag ccggaagggc cgagcgcaga | 3120 |
| agtggtcctg caactttatc cgcctccatc cagtctatta attgttgccg ggaagctaga | 3180 |
| gtaagtagtt cgccagttaa tagtttgcgc aacgttgttg ccattgctac aggcatcgtg | 3240 |
| gtgtcacgct cgtcgtttgg tatggcttca ttcagctccg gttcccaacg atcaaggcga | 3300 |
| gttacatgat cccccatgtt gtgcaaaaaa gcggttagct ccttcggtcc tccgatcgtt | 3360 |
| gtcagaagta agttggccgc agtgttatca ctcatggtta tggcagcact gcataattct | 3420 |
| cttactgtca tgccatccgt aagatgcttt tctgtgactg gtgagtactc aaccaagtca | 3480 |
| ttctgagaat agtgtatgcg gcgaccgagt tgctcttgcc cggcgtcaat acgggataat | 3540 |
| accgcgccac atagcagaac tttaaaagtg ctcatcattg gaaaacgttc ttcggggcga | 3600 |
| aaactctcaa ggatcttacc gctgttgaga tccagttcga tgtaacccac tcgtgcaccc | 3660 |
| aactgatctt cagcatcttt tactttcacc agcgtttctg ggtgagcaaa aacaggaagg | 3720 |
| caaaatgccg caaaaaaggg aataagggcg acacggaaat gttgaatact catactcttc | 3780 |
| ctttttcaat attattgaag catttatcag ggttattgtc tcatgagcgg atacatattt | 3840 |
| gaatgtattt agaaaaataa acaaataggg gttccgcgca catttccccg aaaagtgcca | 3900 |
| cctgacgtct aagaaaccat tattatcatg acattaacct ataaaaatag gcgtatcacg | 3960 |
| aggccccttt cgtctcgcgc gtttcggtga tgacggtgaa aacctctgac acatgcagct | 4020 |
| cccggagacg gtcacagctt gtctgtaagc ggatgccggg agcagacaag cccgtcaggg | 4080 |
| cgcgtcagcg ggtgttggcg ggtgtcgggg ctggcttaac tatgcggcat cagagcagat | 4140 |
| tgtactgaga gtgcaccata tgcggtgtga ataccgcac agatgcgtaa ggagaaaata | 4200 |
| ccgcatcagg aaattgtaaa cgttaatatt ttgttaaaat tcgcgttaaa ttttttgttaa | 4260 |
| atcagctcat tttttaacca ataggccgaa atcggcaaaa tcccttataa atcaaaagaa | 4320 |

| | |
|---|---|
| tagaccgaga tagggttgag tgttgttcca gtttggaaca agagtccact attaaagaac | 4380 |
| gtggactcca acgtcaaagg gcgaaaaacc gtctatcagg gcgatggccc actacgtgaa | 4440 |
| ccatcaccct aatcaagttt tttggggtcg aggtgccgta aagcactaaa tcggaaccct | 4500 |
| aaagggagcc cccgatttag agcttgacgg ggaaagccgg cgaacgtggc gagaaaggaa | 4560 |
| gggaagaaag cgaaaggagc gggcgctagg gcgctggcaa gtgtagcggt cacgctgcgc | 4620 |
| gtaaccacca cacccgccgc gcttaatgcg ccgctacagg gcgcgtcgcg ccattcgcca | 4680 |
| ttcaggctac gcaactgttg ggaagggcga tcggtgcggg cctcttcgct attacgccag | 4740 |
| ctggcgaagg ggggatgtgc tgcaaggcga ttaagttggg taacgccagg gttttcccag | 4800 |
| tcacgacgtt gtaaaacgac ggccagtgaa tt | 4832 |

SEQ ID NO: 71

| | |
|---|---|
| atgactttta acagttttga aggatctaaa acttgtgtac ctgcagacat caataaggaa | 60 |
| gaagaatttg tagaagagtt taatagatta aaaactttg ctaattttcc aagtggtagt | 120 |
| cctgtttcag catcaacact ggcacgagca gggtttcttt atactggtga aggagatacc | 180 |
| gtgcggtgct ttagttgtca tgcagctgta gatagatggc aatatggaga ctcagcagtt | 240 |
| ggaagacaca ggaaagtatc cccaaattgc agatttatca acggctttta tcttgaaaat | 300 |
| agtgccacgc agtctacaaa ttctggtatc cagaatggtc agtacaaagt tgaaaactat | 360 |
| ctgggaagca gagatcattt tgccttagac aggccatctg agacacatgc agactatctt | 420 |
| ttgagaactg gcaggttgt agatatatca gacaccatat acccgaggaa ccctgccatg | 480 |
| tattgtgaag aagctagatt aaagtccttt cagaactggc cagactatgc tcacctaacc | 540 |
| ccaagagagt tagcaagtgc tggactctac tacacaggta ttggtgacca agtgcagtgc | 600 |
| ttttgttgtg gtggaaaact gaaaaattgg gaaccttgtg atcgtgcctg gtcagaacac | 660 |
| aggcgacact tcctaattg cttctttgtt ttgggccgga atcttaatat tcgaagtgaa | 720 |
| tctgatgctg tgagttctga taggaatttc ccaaattcaa caaatcttcc aagaaatcca | 780 |
| tccatggcag attatgaagc acggatcttt acttttggga catggatata ctcagttaac | 840 |
| aaggagcagc ttgcaagagc tggatttat gctttaggtg aaggtgataa agtaaagtgc | 900 |
| tttcactgtg gaggagggct aactgattgg aagcccagtg aagacccttg gaacaacat | 960 |
| gctaaatggt atccagggtg caaatatctg ttagaacaga agggacaaga atatataaac | 1020 |
| aatattcatt taactcattc acttgaggag tgtctggtaa gaactactga gaaacacca | 1080 |
| tcactaacta gaagaattga tgataccatc ttccaaaatc ctatggtaca agaagctata | 1140 |
| cgaatggggt tcagtttcaa ggacattaag aaaataatgg aggaaaaaat tcagatatct | 1200 |
| gggagcaact ataaatcact tgaggttctg gttgcagatc tagtgaatgc tcagaaagac | 1260 |
| agtatgcaag atgagtcaag tcagacttca ttacagaaag agattagtac tgaagagcag | 1320 |
| ctaaggcgcc tgcaagagga gaagctttgc aaaatctgta tggatagaaa tattgctatc | 1380 |
| gttttttgttc cttgtggaca tctagtcact tgtaaacaat gtgctgaagc agttgacaag | 1440 |
| tgtcccatgt gctacacagt cattactttc aagcaaaaaa tttttatgtc ttaatctaa | 1499 |

SEQ ID NO: 72
Met Thr Phe Asn Ser Phe Glu Gly Ser Lys Thr Cys Val Pro Ala Asp
1               5                   10                  15

Ile Asn Lys Glu Glu Glu Phe Val Glu Glu Phe Asn Arg Leu Lys Thr
            20                  25                  30

-continued

| LISTING OF ADDITIONAL SEQUENCES |
|---|

```
Phe Ala Asn Phe Pro Ser Gly Ser Pro Val Ser Ala Ser Thr Leu Ala
            35                  40                  45

Arg Ala Gly Phe Leu Tyr Thr Gly Glu Gly Asp Thr Val Arg Cys Phe
 50                  55                  60

Ser Cys His Ala Ala Val Asp Arg Trp Gln Tyr Gly Asp Ser Ala Val
 65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
                100                 105                 110

Gly Gln Tyr Lys Val Glu Asn Tyr Leu Gly Ser Arg Asp His Phe Ala
                115                 120                 125

Leu Asp Arg Pro Ser Glu Thr His Ala Asp Tyr Leu Leu Arg Thr Gly
                130                 135                 140

Gln Val Val Asp Ile Ser Asp Thr Ile Tyr Pro Arg Asn Pro Ala Met
145                 150                 155                 160

Tyr Cys Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
                180                 185                 190

Gly Ile Gly Asp Gln Val Gln Cys Phe Cys Gly Gly Lys Leu Lys
                195                 200                 205

Asn Trp Glu Pro Cys Asp Arg Ala Trp Ser Glu His Arg Arg His Phe
                210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
                260                 265                 270

Gly Thr Trp Ile Tyr Ser Val Asn Lys Glu Gln Leu Ala Arg Ala Gly
                275                 280                 285

Phe Tyr Ala Leu Gly Glu Gly Asp Lys Val Lys Cys Phe His Cys Gly
                290                 295                 300

Gly Gly Leu Thr Asp Trp Lys Pro Ser Glu Asp Pro Trp Glu Gln His
305                 310                 315                 320

Ala Lys Trp Tyr Pro Gly Cys Lys Tyr Leu Leu Glu Gln Lys Gly Gln
                325                 330                 335

Glu Tyr Ile Asn Asn Ile His Leu Thr His Ser Leu Glu Glu Cys Leu
                340                 345                 350

Val Arg Thr Thr Glu Lys Thr Pro Ser Leu Thr Arg Arg Ile Asp Asp
                355                 360                 365

Thr Ile Phe Gln Asn Pro Met Val Gln Glu Ala Ile Arg Met Gly Phe
                370                 375                 380

Ser Phe Lys Asp Ile Lys Lys Ile Met Glu Glu Lys Ile Gln Ile Ser
385                 390                 395                 400

Gly Ser Asn Tyr Lys Ser Leu Glu Val Leu Val Ala Asp Leu Val Asn
                405                 410                 415

Ala Gln Lys Asp Ser Met Gln Asp Glu Ser Ser Gln Thr Ser Leu Gln
                420                 425                 430

Lys Glu Ile Ser Thr Glu Glu Gln Leu Arg Arg Leu Gln Glu Glu Lys
                435                 440                 445
```

Leu Cys Lys Ile Cys Met Asp Arg Asn Ile Ala Ile Val Phe Val Pro
    450                 455                 460

Cys Gly His Leu Val Thr Cys Lys Gln Cys Ala Glu Ala Val Asp Lys
465                 470                 475                 480

Cys Pro Met Cys Tyr Thr Val Ile Thr Phe Lys Gln Lys Ile Phe Met
                485                 490                 495

Ser

SEQ ID NO: 73

| | | | | | |
|---|---|---|---|---|---|
| gtcgacttct | gaggcggaaa | gaaccagctg | tggaatgtgt | gtcagttagg gtgtggaaag | 60 |
| tccccaggct | ccccagcagg | cagaagtatg | caaagcatgc | atctcaatta gtcagcaacc | 120 |
| aggtgtggaa | agtccccagg | ctccccagca | ggcagaagta | tgcaaagcat gcatctcaat | 180 |
| tagtcagcaa | ccatagtccc | gcccctaact | ccgcccatcc | cgcccctaac tccgcccagt | 240 |
| tccgcccatt | ctccgcccca | tggctgacta | atttttttta | tttatgcaga ggccgaggcc | 300 |
| gcctcggcct | ctgagctatt | ccagaagtag | tgaggaggct | tttttggagg cctaggcttt | 360 |
| tgcaaaaagc | tggatcgatc | ctgagaactt | cagggtgagt | tgggggaccc ttgattgttc | 420 |
| tttcttttc | gctattgtaa | aattcatgtt | atatggaggg | ggcaaagttt tcagggtgtt | 480 |
| gtttagaatg | ggaagatgtc | ccttgtatca | ccatggaccc | tcatgataat tttgtttctt | 540 |
| tcactttcta | ctctgttgac | aaccattgtc | tcctcttatt | ttcttttcat tttctgtaac | 600 |
| tttttcgtta | aactttagct | tgcatttgta | acgaatttt | aaattcactt ttgtttattt | 660 |
| gtcagattgt | aagtactttc | tctaatcact | ttttttttcaa | ggcaatcagg gtatattata | 720 |
| ttgtacttca | gcacagtttt | agagaacaat | tgttataatt | aaatgataag gtagaatatt | 780 |
| tctgcatata | aattctggct | ggcgtggaaa | taatcttatt | ggtagaaaca actacatcct | 840 |
| ggtcatcatc | ctgcctttct | ctttatggtt | acaatgatat | acactgtttg agatgaggat | 900 |
| aaaatactct | gagtccaaac | cgggcccctc | tgctaaccat | gttcatgcct tcttcttttt | 960 |
| cctacagctc | ctgggcaacg | tgctggttat | tgtgctgtct | catcattttg gcaaagaatt | 1020 |
| gtaatacgac | tcactatagg | gcgaattcgg | atccatgact | tttaacagtt ttgaaggatc | 1080 |
| taaaacttgt | gtacctgcag | acatcaataa | ggaagaagaa | tttgtagaag agtttaatag | 1140 |
| attaaaaact | tttgctaatt | ttccaagtgg | tagtcctgtt | tcagcatcaa cactggcacg | 1200 |
| agcagggttt | cttatactg | gtgaaggaga | taccgtgcgg | tgctttagtt gtcatgcagc | 1260 |
| tgtagataga | tggcaatatg | gagactcagc | agttggaaga | cacaggaaag tatccccaaa | 1320 |
| ttgcagattt | atcaacggct | tttatcttga | aaatagtgcc | acgcagtcta caaattctgg | 1380 |
| tatccagaat | ggtcagtaca | aagttgaaaa | ctatctggga | agcagagatc attttgcctt | 1440 |
| agacaggcca | tctgagacac | atgcagacta | tcttttgaga | actgggcagg ttgtagatat | 1500 |
| atcagacacc | atatacccga | ggaaccctgc | catgtattgt | gaagaagcta gattaaagtc | 1560 |
| cttttcagaac | tggccagact | atgctcacct | aaccccaaga | gagttagcaa gtgctggact | 1620 |
| ctactacaca | ggtattggtg | accaagtgca | gtgcttttgt | tgtggtggaa aactgaaaaa | 1680 |
| ttgggaacct | tgtgatcgtg | cctggtcaga | acacaggcga | cactttccta attgcttctt | 1740 |
| tgttttgggc | cggaatctta | atattcgaag | tgaatctgat | gctgtgagtt ctgataggaa | 1800 |
| tttcccaaat | tcaacaaatc | ttccaagaaa | tccatccatg | gcagattatg aagcacggat | 1860 |
| ctttacttttt | gggacatgga | tatactcagt | taacaaggag | cagcttgcaa gagctggatt | 1920 |

| LISTING OF ADDITIONAL SEQUENCES | |
|---|---|
| ttatgcttta ggtgaaggtg ataaagtaaa gtgctttcac tgtggaggag ggctaactga | 1980 |
| ttggaagccc agtgaagacc cttgggaaca acatgctaaa tggtatccag ggtgcaaata | 2040 |
| tctgttagaa cagaagggac aagaatatat aaacaatatt catttaactc attcacttga | 2100 |
| ggagtgtctg gtaagaacta ctgagaaaac accatcacta actagaagaa ttgatgatac | 2160 |
| catcttccaa aatcctatgg tacaagaagc tatacgaatg gggttcagtt tcaaggacat | 2220 |
| taagaaaata atggaggaaa aaattcagat atctgggagc aactataaat cacttgaggt | 2280 |
| tctggttgca gatctagtga atgctcagaa agacagtatg caagatgagt caagtcagac | 2340 |
| ttcattacag aaagagatta gtactgaaga gcagctaagg cgcctgcaag aggagaagct | 2400 |
| ttgcaaaatc tgtatggata gaaatattgc tatcgttttt gttccttgtg gacatctagt | 2460 |
| cacttgtaaa caatgtgctg aagcagttga caagtgtccc atgtgctaca cagtcattac | 2520 |
| tttcaagcaa aaaattttta tgtcttaatc taaagatctt attaaagcag aacttgttta | 2580 |
| ttgcagctta taatggttac aaataaagca atagcatcac aaatttcaca aataaagcat | 2640 |
| ttttttcact gcattctagt tgtggtttgt ccaaactcat caatgtatct tatcatgtct | 2700 |
| ggtcgactct agactcttcc gcttcctcgc tcactgactc gctgcgctcg gtcgttcggc | 2760 |
| tgcggcgagc ggtatcagct cactcaaagg cggtaatacg gttatccaca gaatcagggg | 2820 |
| ataacgcagg aaagaacatg tgagcaaaag gccagcaaaa ggccaggaac cgtaaaaagg | 2880 |
| ccgcgttgct ggcgtttttc cataggctcc gcccccctga cgagcatcac aaaaatcgac | 2940 |
| gctcaagtca gaggtggcga aacccgacag gactataaag ataccaggcg tttccccctg | 3000 |
| gaagctccct cgtgcgctct cctgttccga ccctgccgct taccggatac ctgtccgcct | 3060 |
| ttctcccttc gggaagcgtg gcgctttctc aatgctcacg ctgtaggtat ctcagttcgg | 3120 |
| tgtaggtcgt tcgctccaag ctgggctgtg tgcacgaacc ccccgttcag cccgaccgct | 3180 |
| gcgccttatc cggtaactat cgtcttgagt ccaacccggt aagacacgac ttatcgccac | 3240 |
| tggcagcagc cactggtaac aggattagca gagcgaggta tgtaggcggt gctacagagt | 3300 |
| tcttgaagtg gtggcctaac tacggctaca ctagaaggac agtatttggt atctgcgctc | 3360 |
| tgctgaagcc agttaccttc ggaaaaagag ttggtagctc ttgatccggc aaacaaacca | 3420 |
| ccgctggtag cggtggtttt tttgtttgca agcagcagat tacgcgcaga aaaaaaggat | 3480 |
| ctcaagaaga tcctttgatc ttttctacgg ggtctgacgc tcagtggaac gaaaactcac | 3540 |
| gttaagggat tttggtcatg agattatcaa aaaggatctt cacctagatc cttttaaatt | 3600 |
| aaaaatgaag ttttaaatca atctaaagta tatatgagta aacttggtct gacagttacc | 3660 |
| aatgcttaat cagtgaggca cctatctcag cgatctgtct atttcgttca tccatagttg | 3720 |
| cctgactccc cgtcgtgtag ataactacga tacgggaggg cttaccatct ggccccagtg | 3780 |
| ctgcaatgat accgcgagac ccacgctcac cggctccaga tttatcagca ataaccagc | 3840 |
| cagccggaag ggccgagcgc agaagtggtc ctgcaacttt atccgcctcc atccagtcta | 3900 |
| ttaattgttg ccgggaagct agagtaagta gttcgccagt taatagtttg cgcaacgttg | 3960 |
| ttgccattgc tacaggcatc gtggtgtcac gctcgtcgtt tggtatggct tcattcagct | 4020 |
| ccggttccca acgatcaagg cgagttacat gatcccccat gttgtgcaaa aaagcggtta | 4080 |
| gctccttcgg tcctccgatc gttgtcagaa gtaagttggc cgcagtgtta tcactcatgg | 4140 |
| ttatggcagc actgcataat tctcttactg tcatgccatc cgtaagatgc ttttctgtga | 4200 |
| ctggtgagta ctcaaccaag tcattctgag aatagtgtat gcggcgaccg agttgctctt | 4260 |

-continued

| LISTING OF ADDITIONAL SEQUENCES | |
|---|---|
| gcccggcgtc aatacgggat aataccgcgc cacatagcag aactttaaaa gtgctcatca | 4320 |
| ttggaaaacg ttcttcgggg cgaaaactct caaggatctt accgctgttg agatccagtt | 4380 |
| cgatgtaacc cactcgtgca cccaactgat cttcagcatc ttttactttc accagcgttt | 4440 |
| ctgggtgagc aaaaacagga aggcaaaatg ccgcaaaaaa gggaataagg gcgacacgga | 4500 |
| aatgttgaat actcatactc ttcttttttc aatattattg aagcatttat cagggttatt | 4560 |
| gtctcatgag cggatacata tttgaatgta tttagaaaaa taaacaaata ggggttccgc | 4620 |
| gcacatttcc ccgaaaagtg ccacctgacg tctaagaaac cattattatc atgacattaa | 4680 |
| cctataaaaa taggcgtatc acgaggcccc tttcgtctcg cgcgtttcgg tgatgacggt | 4740 |
| gaaaacctct gacacatgca gctcccggag acggtcacag cttgtctgta agcggatgcc | 4800 |
| gggagcagac aagcccgtca gggcgcgtca gcgggtgttg gcgggtgtcg ggctggctt | 4860 |
| aactatgcgg catcagagca gattgtactg agagtgcacc atatgcggtg tgaaataccg | 4920 |
| cacagatgcg taaggagaaa ataccgcatc aggaaattgt aaacgttaat attttgttaa | 4930 |
| aattcgcgtt aaattttgt taaatcagct cattttttaa ccataggcc gaaatcggca | 5040 |
| aaatccctta taaatcaaaa gaatagaccg agatagggtt gagtgttgtt ccagtttgga | 5100 |
| acaagagtcc actattaaag aacgtggact ccaacgtcaa agggcgaaaa accgtctatc | 5160 |
| agggcgatgg cccactacgt gaaccatcac cctaatcaag ttttttgggg tcgaggtgcc | 5220 |
| gtaaagcact aaatcggaac cctaaaggga gccccgatt tagagcttga cggggaaagc | 5280 |
| cggcgaacgt ggcgagaaag gaagggaaga aagcgaaagg agcgggcgct agggcgctgg | 5340 |
| caagtgtagc ggtcacgctg cgcgtaacca ccacacccgc cgcgcttaat gcgccgctac | 5400 |
| agggcgcgtc gcgccattcg ccattcaggc tacgcaactg ttgggaaggg cgatcggtgc | 5460 |
| gggcctcttc gctattacgc cagctggcga aggggggatg tgctgcaagg cgattaagtt | 5520 |
| gggtaacgcc agggttttcc cagtcacgac gttgtaaaac gacggccagt gaatt | 5575 |
| SEQ ID NO: 74 | |
| atggacttca gcagaaatct ttatgatatt ggggaacaac tggacagtga agatctggcc | 60 |
| tccctcaagt tcctgagcct ggactacatt ccgcaaagga agcaagaacc catcaaggat | 120 |
| gccttgatgt tattccagag actccaggaa aagagaatgt tggaggaaag caatctgtcc | 180 |
| ttcctgaagg agctgctctt ccgaattaat agactggatt tgctgattac ctacctaaac | 240 |
| actgaaaagg aggagatgga aagggaactt cagacaccag gcagggctca aatttctgcc | 300 |
| tacagggtca tgctctatca gatttcagaa gaagtgagca gatcagaatt gaggtctttt | 360 |
| aagtttcttt tgcaagagga aatctccaaa tgcaaactgg atgatgacat gaacctgctg | 420 |
| gatatttca tagagatgga aagagggtc atcctgggag aaggaaagtt ggacatcctg | 480 |
| aaaagagtct gtgcccaaat caacaagagc ctgctgaaga taatcaacga ctatgaagaa | 540 |
| ttcagcaaag gggaggagtt gtgtgggta atgcacaatct cggactctcc aagagaacag | 600 |
| gatagtgaat cacagacttt ggacaaagtt taccaaatga aaagcaaacc tcggggatac | 660 |
| tgtctgatca tcaacaatca caattttgca aaagcacggg agaaagtgcc caaacttcac | 720 |
| agcattaggg acaggaatgg aacacacttg gatgcagggg ctttgaccac gacctttgaa | 780 |
| gagcttcatt ttgagatcaa gccccacgat gactgcacag tagagcaaat ctatgagatt | 840 |
| ttgaaaatct accaactcat ggaccacagt aacatggact gcttcatctg ctgtatcctc | 900 |
| tcccatggag acaagggcat catctatggc actgatggac aggaggcccc catctatgag | 960 |

-continued

LISTING OF ADDITIONAL SEQUENCES

```
ctgacatctc agttcactgg tttgaagtgc ccttcccttg ctggaaaacc caaagtgttt    1020
tttattcagg cttgtcaggg ggataactac cagaaaggta tacctgttga gactgattca    1080
gaggagcaac cctatttaga aatggattta tcatcacctc aaacgagata tatcccggat    1140
gaggctgact ttctgctggg gatggccact gtgataact gtgtttccta ccgaaaccct    1200
gcagagggaa cctggtacat ccagtcactt tgccagagcc tgagagagcg atgtcctcga    1260
ggcgatgata ttctcaccat cctgactgaa gtgaactatg aagtaagcaa caaggatgac    1320
aagaaaaaca tggggaaaca gatgcctcag cctactttca cactaagaaa aaaacttgtc    1380
ttcccttctg attga                                                    1395
```

SEQ ID NO: 75

```
Met Asp Phe Ser Arg Asn Leu Tyr Asp Ile Gly Glu Gln Leu Asp Ser
1               5                  10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Gly Glu Glu Leu Cys Gly Val Met Thr
            180                 185                 190

Ile Ser Asp Ser Pro Arg Glu Gln Asp Ser Glu Ser Gln Thr Leu Asp
        195                 200                 205

Lys Val Tyr Gln Met Lys Ser Lys Pro Arg Gly Tyr Cys Leu Ile Ile
    210                 215                 220

Asn Asn His Asn Phe Lys Ala Arg Glu Lys Val Pro Lys Leu His
225                 230                 235                 240

Ser Ile Arg Asp Arg Asn Gly Thr His Leu Asp Ala Gly Ala Leu Thr
                245                 250                 255

Thr Thr Phe Glu Glu Leu His Phe Glu Ile Lys Pro His Asp Asp Cys
            260                 265                 270

Thr Val Glu Gln Ile Tyr Glu Ile Leu Lys Ile Tyr Gln Leu Met Asp
        275                 280                 285

His Ser Asn Met Asp Cys Phe Ile Cys Cys Ile Leu Ser His Gly Asp
    290                 295                 300

Lys Gly Ile Ile Tyr Gly Thr Asp Gly Gln Glu Ala Pro Ile Tyr Glu
305                 310                 315                 320
```

| LISTING OF ADDITIONAL SEQUENCES |
|---|

Leu Thr Ser Gln Phe Thr Gly Leu Lys Cys Pro Ser Leu Ala Gly Lys
            325                 330                 335

Pro Lys Val Phe Phe Ile Gln Ala Cys Gln Gly Asp Asn Tyr Gln Lys
            340                 345                 350

Gly Ile Pro Val Glu Thr Asp Ser Glu Glu Gln Pro Tyr Leu Glu Met
            355                 360                 365

Asp Leu Ser Ser Pro Gln Thr Arg Tyr Ile Pro Asp Glu Ala Asp Phe
        370                 375                 380

Leu Leu Gly Met Ala Thr Val Asn Asn Cys Val Ser Tyr Arg Asn Pro
385                 390                 395                 400

Ala Glu Gly Thr Trp Tyr Ile Gln Ser Leu Cys Gln Ser Leu Arg Glu
            405                 410                 415

Arg Cys Pro Arg Gly Asp Asp Ile Leu Thr Ile Leu Thr Glu Val Asn
            420                 425                 430

Tyr Glu Val Ser Asn Lys Asp Asp Lys Lys Asn Met Gly Lys Gln Met
            435                 440                 445

Pro Gln Pro Thr Phe Thr Leu Arg Lys Lys Leu Val Phe Pro Ser Asp
        450                 455                 460

SEQ ID NO: 76

| | |
|---|---:|
| gtcgacttct gaggcggaaa gaaccagctg tggaatgtgt gtcagttagg gtgtggaaag | 60 |
| tccccaggct ccccagcagg cagaagtatg caaagcatgc atctcaatta gtcagcaacc | 120 |
| aggtgtggaa agtccccagg ctccccagca ggcagaagta tgcaaagcat gcatctcaat | 180 |
| tagtcagcaa ccatagtccc gcccctaact ccgcccatcc cgcccctaac tccgcccagt | 240 |
| tccgcccatt ctccgcccca tggctgacta atttttttta tttatgcaga ggccgaggcc | 300 |
| gcctcggcct ctgagctatt ccagaagtag tgaggaggct ttttggagg cctaggcttt | 360 |
| tgcaaaaagc tggatcgatc ctgagaactt cagggtgagt ttggggaccc ttgattgttc | 420 |
| tttcttttc gctattgtaa aattcatgtt atatggaggg ggcaaagttt tcagggtgtt | 480 |
| gtttagaatg ggaagatgtc ccttgtatca ccatggaccc tcatgataat tttgtttctt | 540 |
| tcactttcta ctctgttgac aaccattgtc tcctcttatt ttcttttcat tttctgtaac | 600 |
| tttttcgtta aactttagct tgcatttgta acgaattttt aaattcactt ttgtttattt | 660 |
| gtcagattgt aagtactttc tctaatcact ttttttcaa ggcaatcagg gtatattata | 720 |
| ttgtacttca gcacagtttt agagaacaat tgttataatt aaatgataag gtagaatatt | 780 |
| tctgcatata aattctggct ggcgtggaaa tattcttatt ggtagaaaca actacatcct | 840 |
| ggtcatcatc ctgcctttct ctttatggtt acaatgatat acactgtttg agatgaggat | 900 |
| aaaatactct gagtccaaac cgggcccctc tgctaaccat gttcatgcct tcttcttttt | 960 |
| cctacagctc ctgggcaacg tgctggttat tgtgctgtct catcattttg gcaaagaatt | 1020 |
| gtaatacgac tcactatagg gcgaattcat ggacttcagc agaaatcttt atgatattgg | 1080 |
| ggaacaactg gacagtgaag atctggcctc cctcaagttc ctgagcctgg actacattcc | 1140 |
| gcaaaggaag caagaaccca tcaaggatgc cttgatgtta ttccagagac tccaggaaaa | 1200 |
| gagaatgttg gaggaaagca atctgtcctt cctgaaggag ctgctcttcc gaattaatag | 1260 |
| actggatttg ctgattacct acctaaacac tagaaaggag gagatggaaa gggaacttca | 1320 |
| gacaccaggc agggctcaaa tttctgccta cagggtcatg ctctatcaga tttcagaaga | 1380 |
| agtgagcaga tcagaattga ggtcttttaa gtttctttg caagaggaaa tctccaaatg | 1440 |

| LISTING OF ADDITIONAL SEQUENCES | |
|---|---|
| caaactggat gatgacatga acctgctgga tattttcata gagatggaga agagggtcat | 1500 |
| cctgggagaa ggaaagttgg acatcctgaa aagagtctgt gcccaaatca acaagagcct | 1560 |
| gctgaagata atcaacgact atgaagaatt cagcaaaggg gaggagttgt gtggggtaat | 1620 |
| gacaatctcg gactctccaa gagaacagga tagtgaatca cagactttgg acaaagttta | 1680 |
| ccaaatgaaa agcaaacctc gggatactgt ctgatcatca acaatcacaa ttttgcaaaa | 1740 |
| gcacgggaga aagtgcccca aacttcacag cattagggac aggaatggaa cacacttgga | 1800 |
| tgcaggggct ttgaccacga cctttgaaga gcttcatttt gagatcaagc cccacgatga | 1860 |
| ctgcacagta gagcaaatct atgagatttt gaaaatctac caactcatgg accacagtaa | 1920 |
| catggactgc ttcatctgct gtatcctctc ccatggagac aagggcatca tctatgcac | 1980 |
| tgatggacag gaggccccca tctatgagct gacatctcag ttcactggtt tgaagtgccc | 2040 |
| ttcccttgct ggaaaaccca aagtgttttt tattcaggct tgtcaggggg ataactacca | 2100 |
| gaaaggtata cctgttgaga ctgattcaga ggagcaaccc tatttagaaa tggatttatc | 2160 |
| atcacctcaa acgagatata tcccggatga ggctgacttt ctgctgggga tggccactgt | 2220 |
| gaataactgt gtttcctacc gaaaccctgc agagggaacc tggtacatcc agtcactttg | 2280 |
| ccagagcctg agagagcgat gtcctcgagg cgatgatatt ctcaccatcc tgactgaagt | 2340 |
| gaactatgaa gtaagcaaca aggatgacaa gaaaaacatg gggaaacaga tgcctcagcc | 2400 |
| tactttcaca ctaagaaaaa aacttgtctt cccttctgat tgaggatcca gatcttatta | 2460 |
| aagcagaact tgtttattgc agcttataat ggttacaaat aaagcaatag catcacaaat | 2520 |
| ttcacaaata aagcattttt ttcactgcat tctagttgtg gtttgtccaa actcatcaat | 2580 |
| gtatcttatc atgtctggtc gactctagac tcttccgctt cctcgctcac tgactcgctg | 2640 |
| cgctcggtcg ttcggctgcg gcgagcggta tcagctcact caaaggcggt aatacggtta | 2700 |
| tccacagaat caggggataa cgcaggaaag aacatgtgag caaaaggcca gcaaaaggcc | 2760 |
| aggaaccgta aaaaggccgc gttgctggcg tttttccata ggctccgccc cctgacgag | 2820 |
| catcacaaaa atcgacgctc aagtcagagg tggcgaaacc cgacaggact ataaagatac | 2880 |
| caggcgtttc cccctggaag ctccctcgtg cgctctcctg ttccgaccct gccgcttacc | 2940 |
| ggatacctgt ccgcctttct cccttcggga agcgtggcgc tttctcaatg ctcacgctgt | 3000 |
| aggtatctca gttcggtgta ggtcgttcgc tccaagctgg gctgtgtgca cgaaccccc | 3060 |
| gttcagcccg accgctgcgc cttatccggt aactatcgtc ttgagtccaa cccggtaaga | 3120 |
| cacgacttat cgccactggc agcagccact ggtaacagga ttagcagagc gaggtatgta | 3180 |
| ggcggtgcta cagagttctt gaagtggtgg cctaactacg gctacactag aaggacagta | 3240 |
| tttggtatct gcgctctgct gaagccagtt accttcggaa aaagagttgg tagctcttga | 3300 |
| tccggcaaac aaaccaccgc tggtagcggt ggtttttttg tttgcaagca gcagattacg | 3360 |
| cgcagaaaaa aaggatctca agaagatcct ttgatctttt ctacgggtc tgacgctcag | 3420 |
| tggaacgaaa actcacgtta agggattttg gtcatgagat tatcaaaaag gatcttcacc | 3480 |
| tagatccttt taaattaaaa atgaagtttt aaatcaatct aaagtatata tgagtaaact | 3540 |
| tggtctgaca gttaccaatg cttaatcagt gaggcaccta tctcagcgat ctgtctattt | 3600 |
| cgttcatcca tagttgcctg actccccgtc gtgtagataa ctacgatacg ggagggctta | 3660 |
| ccatctggcc ccagtgctgc aatgataccg cgagacccac gctcaccggc tccagattta | 3720 |
| tcagcaataa accagccagc cggaagggcc gagcgcagaa gtggtcctgc aactttatcc | 3780 |

| | |
|---|---:|
| gcctccatcc agtctattaa ttgttgccgg gaagctagag taagtagttc gccagttaat | 3840 |
| agtttgcgca acgttgttgc cattgctaca ggcatcgtgg tgtcacgctc gtcgtttggt | 3900 |
| atggcttcat tcagctccgg ttcccaacga tcaaggcgag ttacatgatc ccccatgttg | 3960 |
| tgcaaaaaag cggttagctc cttcggtcct ccgatcgttg tcagaagtaa gttggccgca | 4020 |
| gtgttatcac tcatggttat ggcagcactg cataattctc ttactgtcat gccatccgta | 4080 |
| agatgctttt ctgtgactgg tgagtactca accaagtcat tctgagaata gtgtatgcgg | 4140 |
| cgaccgagtt gctcttgccc ggcgtcaata cgggataata ccgcgccaca tagcagaact | 4200 |
| ttaaaagtgc tcatcattgg aaaacgttct cggggcgaa aactctcaag gatcttaccg | 4260 |
| ctgttgagat ccagttcgat gtaacccact cgtgcaccca actgatcttc agcatctttt | 4320 |
| actttcacca gcgtttctgg gtgagcaaaa acaggaaggc aaaatgccgc aaaaaaggga | 4380 |
| ataagggcga cacggaaatg ttgaatactc atactcttct ttttcaata ttattgaagc | 4440 |
| atttatcagg gttattgtct catgagcgga tacatatttg aatgtattta gaaaaataaa | 4500 |
| caaatagggg ttccgcgcac atttccccga aaagtgccac ctgacgtcta agaaaccatt | 4560 |
| attatcatga cattaaccta taaaaatagg cgtatcacga ggccccttc gtctcgcgcg | 4620 |
| tttcggtgat gacggtgaaa acctctgaca catgcagctc ccggagacgg tcacagcttg | 4680 |
| tctgtaagcg gatgccggga gcagacaagc ccgtcagggc gcgtcagcgg gtgttggcgg | 4740 |
| gtgtcgggc tggcttaact atgcggcatc agagcagatt gtactgagag tgcaccatat | 4800 |
| gcggtgtgaa ataccgcaca gatgcgtaag gagaaaatac cgcatcagga aattgtaaac | 4860 |
| gttaatattt tgttaaaatt cgcgttaaat ttttgttaaa tcagctcatt ttttaaccaa | 4920 |
| taggccgaaa tcggcaaaat cccttataaa tcaaaagaat agaccgagat agggttgagt | 4980 |
| gttgttccag tttggaacaa gagtccacta ttaaagaacg tggactccaa cgtcaaaggg | 5040 |
| cgaaaaaccg tctatcaggg cgatggccca ctacgtgaac catcacccta atcaagtttt | 5100 |
| ttggggtcga ggtgccgtaa agcactaaat cggaacccta agggagccc ccgatttaga | 5160 |
| gcttgacggg gaaagccggc gaacgtggcg agaaaggaag ggaagaaagc gaaggagcg | 5220 |
| ggcgctaggg cgctggcaag tgtagcggtc acgctgcgcg taaccaccac acccgccgcg | 5280 |
| cttaatgcgc cgctacaggg cgcgtcgcgc cattcgccat tcaggctacg caactgttgg | 5340 |
| gaagggcgat cggtgcgggc ctcttcgcta ttacgccagc tggcgaaggg gggatgtgct | 5400 |
| gcaaggcgat taagttgggt aacgccaggg ttttcccagt cacgacgttg taaaacgacg | 5460 |
| gccagtgaat t | 5471 |

SEQ ID NO: 77

| | |
|---|---:|
| atggcgcacg ctgggagaac agggtacgat aaccgggaga tagtgatgaa gtacatccat | 60 |
| tataagctgt cgcagagggg ctacgagtgg gatgcgggag atgtgggcgc cgcgcccccg | 120 |
| ggggccgccc ccgcaccggg catcttctcc tcccagcccg gcacacgcc ccatccagcc | 180 |
| gcatcccggg acccggtcgc caggacctcg ccgctgcaga cccggctgc ccccggcgcc | 240 |
| gccgcgggc ctgcgctcag cccggtgcca cctgtggtcc acctgaccct ccgccaggcc | 300 |
| ggcgacgact tctcccgccg ctaccgccgc gacttcgccg agatgtccag ccagctgcac | 360 |
| ctgacgccct tcaccgcgcg gggacgcttt gccacggtgg tggaggagct cttcagggac | 420 |
| ggggtgaact gggggaggat tgtggccttc tttgagttcg gtggggtcat gtgtgtggag | 480 |
| agcgtcaacc gggagatgtc gcccctggtg gacaacatcg ccctgtggat gactgagtac | 540 |

```
ctgaaccggc acctgcacac ctggatccag gataacggag gctgggtagg tgcacttggt      600
gatgtgagtc tgggctga                                                    618
```

SEQ ID NO: 78

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
                20                  25                  30

Gly Asp Val Gly Ala Ala Pro Pro Gly Ala Ala Pro Ala Pro Gly Ile
            35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
                100                 105                 110

Ala Glu Met Ser Ser Gln Leu His Leu Thr Pro Phe Thr Ala Arg Gly
            115                 120                 125

Arg Phe Ala Thr Val Val Glu Glu Leu Phe Arg Asp Gly Val Asn Trp
130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Val Gly Ala Leu Gly Asp Val Ser Leu Gly
            195                 200                 205
```

SEQ ID NO: 79

```
gtcgacttct gaggcggaaa gaaccagctg tggaatgtgt gtcagttagg gtgtggaaag       60
tccccaggct ccccagcagg cagaagtatg caaagcatgc atctcaatta gtcagcaacc      120
aggtgtggaa agtccccagg ctccccagca ggcagaagta tgcaaagcat gcatctcaat      180
tagtcagcaa ccatagtccc gcccctaact ccgcccatcc cgcccctaac tccgcccagt      240
tccgcccatt ctccgcccca tggctgacta atttttttta tttatgcaga ggccgaggcc      300
gcctcggcct ctgagctatt ccagaagtag tgaggaggct ttttggagg cctaggcttt       360 tgcaaaaagc tggatcgatc ctgagaactt cagggtgagt ttggggaccc ttgattgttc      420 tttcttttc gctattgtaa aattcatgtt atatggaggg ggcaaagttt tcagggtgtt       480
gtttagaatg ggaagatgtc ccttgtatca ccatggaccc tcatgataat tttgtttctt      540
tcactttcta ctctgttgac aaccattgtc tcctcttatt ttcttttcat tttctgtaac      600
tttttcgtta aactttagct tgcatttgta acgaattttt aaattcactt tgtttatttt      660
gtcagattgt aagtactttc tctaatcact ttttttttcaa ggcaatcagg gtatattata      720
ttgtacttca gcacagtttt agagaacaat tgttataatt aaatgataag gtagaatatt      780
tctgcatata aattctggct ggcgtggaaa tattcttatt ggtagaaaca actacatcct      840
ggtcatcatc ctgcctttct ctttatggtt acaatgatat acactgtttg agatgaggat      900
aaaatactct gagtccaaac cgggcccctc tgctaaccat gttcatgcct tcttcttttt      960
```

-continued

| LISTING OF ADDITIONAL SEQUENCES | |
|---|---|
| cctacagctc ctgggcaacg tgctggttat tgtgctgtct catcattttg gcaaagaatt | 1020 |
| gtaatacgac tcactatagg gcgaattcgg atccagatct atggcgcacg ctgggagaac | 1080 |
| agggtacgat aaccgggaga tagtgatgaa gtacatccat tataagctgt cgcagagggg | 1140 |
| ctacgagtgg gatgcgggag atgtgggcgc cgcgcccccg ggggccgccc ccgcaccggg | 1200 |
| catcttctcc tcccagcccg ggcacacgcc ccatccagcc gcatcccggg acccggtcgc | 1260 |
| caggacctcg ccgctgcaga ccccggctgc ccccggcgcc gccgcggggc ctgcgctcag | 1320 |
| cccggtgcca cctgtggtcc acctgaccct ccgccaggcc ggcgacgact tctcccgccg | 1380 |
| ctaccgccgc gacttcgccg agatgtccag ccagctgcac ctgacgccct tcaccgcgcg | 1440 |
| gggacgcttt gccacggtgg tggaggagct cttcagggac ggggtgaact gggggaggat | 1500 |
| tgtggccttc tttgagttcg gtggggtcat gtgtgtggag agcgtcaacc gggagatgtc | 1560 |
| gcccctggtg gacaacatcg ccctgtggat gactgagtac ctgaaccggc acctgcacac | 1620 |
| ctggatccag gataacggag gctgggtagg tgcacttggt gatgtgagtc tgggctgaag | 1680 |
| atcttattaa agcagaactt gtttattgca gcttataatg gttacaaata aagcaatagc | 1740 |
| atcacaaatt tcacaaataa agcattttt tcactgcatt ctagttgtgg tttgtccaaa | 1800 |
| ctcatcaatg tatcttatca tgtctggtcg actctagact cttccgcttc ctcgctcact | 1860 |
| gactcgctgc gctcggtcgt tcggctgcgg cgagcggtat cagctcactc aaaggcggta | 1920 |
| atacggttat ccacagaatc aggggataac gcaggaaaga acatgtgagc aaaaggccag | 1980 |
| caaaaggcca ggaaccgtaaa aaggccgcgt tgctggcgtt tttccatagg ctccgccccc | 2040 |
| ctgacgagca tcacaaaaat cgacgctcaa gtcagaggtg gcgaaacccg acaggactat | 2100 |
| aaagatacca ggcgtttccc cctggaagct ccctcgtgcg ctctcctgtt ccgaccctgc | 2160 |
| cgcttaccgg atacctgtcc gcctttctcc cttcgggaag cgtggcgctt tctcaatgct | 2220 |
| cacgctgtag gtatctcagt tcggtgtagg tcgttcgctc caagctgggc tgtgtgcacg | 2280 |
| aaccccccgt tcagcccgac cgctgcgcct tatccggtaa ctatcgtctt gagtccaacc | 2340 |
| cggtaagaca cgacttatcg ccactggcag cagccactgg taacaggatt agcagagcga | 2400 |
| ggtatgtagg cggtgctaca gagttcttga agtggtggcc taactacggc tacactagaa | 2460 |
| ggacagtatt tggtatctgc gctctgctga gccagttac cttcggaaaa agagttggta | 2520 |
| gctcttgatc cggcaaacaa accaccgctg gtagcggtgg tttttttgtt tgcaagcagc | 2580 |
| agattacgcg cagaaaaaaa ggatctcaag aagatccttt gatcttttct acggggtctg | 2640 |
| acgctcagtg gaacgaaaac tcacgttaag ggattttggt catgagatta tcaaaaagga | 2700 |
| tcttcaccta gatcctttta aattaaaaat gaagttttaa atcaatctaa agtatatatg | 2760 |
| agtaaacttg gtctgacagt taccaatgct taatcagtga ggcacctatc tcagcgatct | 2820 |
| gtctatttcg ttcatccata gttgcctgac tccccgtcgt gtagataact acgatacggg | 2880 |
| agggcttacc atctggcccc agtgctgcaa tgataccgcg agacccacgc tcaccggctc | 2940 |
| cagatttatc agcaataaac cagccagccg gaagggccga gcgcagaagt ggtcctgcaa | 3000 |
| ctttatccgc ctccatccag tctattaatt gttgccggga agctagagta agtagttcgc | 3060 |
| cagttaatag tttgcgcaac gttgttgcca ttgctacagg catcgtggtg tcacgctcgt | 3120 |
| cgtttggtat ggcttcattc agctccggtt cccaacgatc aaggcgagtt acatgatccc | 3180 |
| ccatgttgtg caaaaaagcg gttagctcct tcggtcctcc gatcgttgtc agaagtaagt | 3240 |

| LISTING OF ADDITIONAL SEQUENCES | |
|---|---|
| tggccgcagt gttatcactc atggttatgg cagcactgca taattctctt actgtcatgc | 3300 |
| catccgtaag atgcttttct gtgactggtg agtactcaac caagtcattc tgagaatagt | 3360 |
| gtatgcggcg accgagttgc tcttgcccgg cgtcaatacg ggataatacc gcgccacata | 3420 |
| gcagaacttt aaaagtgctc atcattggaa aacgttcttc ggggcgaaaa ctctcaagga | 3480 |
| tcttaccgct gttgagatcc agttcgatgt aacccactcg tgcacccaac tgatcttcag | 3540 |
| catcttttac tttcaccagc gtttctgggt gagcaaaaac aggaaggcaa aatgccgcaa | 3600 |
| aaaagggaat aagggcgaca cggaaatgtt gaatactcat actcttcttt tttcaatatt | 3660 |
| attgaagcat ttatcagggt tattgtctca tgagcggata catatttgaa tgtatttaga | 3720 |
| aaaataaaca aataggggtt ccgcgcacat ttccccgaaa agtgccacct gacgtctaag | 3780 |
| aaaccattat tatcatgaca ttaacctata aaaataggcg tatcacgagg ccctttcgt | 3840 |
| ctcgcgcgtt tcggtgatga cggtgaaaac ctctgacaca tgcagctccc ggagacggtc | 3900 |
| acagcttgtc tgtaagcgga tgccgggagc agacaagccc gtcagggcgc gtcagcgggt | 3960 |
| gttggcgggt gtcggggctg gcttaactat gcggcatcag agcagattgt actgagagtg | 4020 |
| caccatatgc ggtgtgaaat accgcacaga tgcgtaagga gaaaataccg catcaggaaa | 4080 |
| ttgtaaacgt taatattttg ttaaaattcg cgttaaattt tgttaaatc agctcatttt | 4140 |
| ttaaccaata ggccgaaatc ggcaaaatcc cttataaatc aaaagaatag accgagatag | 4200 |
| ggttgagtgt tgttccagtt tggaacaaga gtccactatt aaagaacgtg gactccaacg | 4260 |
| tcaaagggcg aaaaaccgtc tatcagggcg atggcccact acgtgaacca tcaccctaat | 4320 |
| caagtttttt ggggtcgagg tgccgtaaag cactaaatcg gaaccctaaa gggagccccc | 4380 |
| gatttagagc ttgacgggga agccggcga acgtggcgag aaaggaaggg aagaaagcga | 4440 |
| aaggagcggg cgctagggcg ctggcaagtg tagcggtcac gctgcgcgta accaccacac | 4500 |
| ccgccgcgct taatgcgccg ctacaggggcg cgtcgcgcca ttcgccattc aggctacgca | 4560 |
| actgttggga aggggcgatcg gtgcgggcct cttcgctatt acgccagctg gcgaaggggg | 4620 |
| gatgtgctgc aaggcgatta agttgggtaa cgccagggt tcccagtca cgacgttgta | 4680 |
| aaacgacggc cagtgaatt | 4699 |
| SEQ ID NO: 80 | |
| gtcgacttct gaggcggaaa gaaccagctg tggaatgtgt gtcagttagg gtgtggaaag | 60 |
| tccccaggct ccccagcagg cagaagtatg caaagcatgc atctcaatta gtcagcaacc | 120 |
| aggtgtggaa agtccccagg ctccccagca ggcagaagta tgcaaagcat gcatctcaat | 180 |
| tagtcagcaa ccatagtccc gcccctaact ccgcccatcc cgcccctaac tccgcccagt | 240 |
| tccgcccatt ctccgcccca tggctgacta atttttttta tttatgcaga ggccgaggcc | 300 |
| gcctcggcct ctgagctatt ccagaagtag tgaggaggct tttttggagg cctaggcttt | 360 |
| tgcaaaaagc tggatcgatc ctgagaactt caggtgagt ttggggaccc ttgattgttc | 420 |
| tttcttttc gctattgtaa aattcatgtt atatggaggg ggcaaagttt tcagggtgtt | 480 |
| gtttagaatg ggaagatgtc ccttgtatca ccatggaccc tcatgataat tttgtttctt | 540 |
| tcactttcta ctctgttgac aaccattgtc tcctcttatt ttcttttcat ttctgtaac | 600 |
| ttttttcgtta aactttagct tgcatttgta acgaattttt aaattcactt tgtttatttt | 660 |
| gtcagattgt aagtactttc tctaatcact ttttttcaa ggcaatcagg gtatattata | 720 |
| ttgtacttca gcacagtttt agagaacaat tgttataatt aaatgataag gtagaatatt | 780 |

| LISTING OF ADDITIONAL SEQUENCES | |
|---|---|
| tctgcatata aattctggct ggcgtggaaa tattcttatt ggtagaaaca actacatcct | 840 |
| ggtcatcatc ctgcctttct ctttatggtt acaatgatat acactgtttg agatgaggat | 900 |
| aaaatactct gagtccaaac cgggcccctc tgctaaccat gttcatgcct tcttctttt | 960 |
| cctacagctc ctgggcaacg tgctggttat tgtgctgtct catcattttg gcaaagaatt | 1020 |
| gtaatacgac tcactatagg gcgaattcgg atccatggac ttcagcagaa atctttatga | 1080 |
| tattggggaa caactggaca gtgaagatct ggcctccctc aagttcctga gcctggacta | 1140 |
| cattccgcaa aggaagcaag aacccatcaa ggatgccttg atgttattcc agagactcca | 1200 |
| ggaaaagaga atgttggagg aaagcaatct gtccttcctg aaggagctgc tcttccgaat | 1260 |
| taatagactg gatttgctga ttacctacct aaacactaga aaggaggaga tggaaaggga | 1320 |
| acttcagaca ccaggcaggg ctcaaatttc tgcctacagg gtcatgctct atcagatttc | 1380 |
| agaagaagtg agcagatcag aattgaggtc ttttaagttt cttttgcaag aggaaatctc | 1440 |
| caaatgcaaa ctggatgatg acatgaacct gctggatatt tcatagaga tggagaagag | 1500 |
| ggtcatcctg ggagaaggaa agttggacat cctgaaaaga gtctgtgccc aaatcaacaa | 1560 |
| gagcctgctg aagataatca acgactatga agaattcagc aaaggggagg agttgtgtgg | 1620 |
| ggtaatgaca atctcggact ctccaagaga acaggatagt gaatcacaga ctttggacaa | 1680 |
| agtttaccaa atgaaaagca aacctcgggg atactgtctg atcatcaaca atcacaattt | 1740 |
| tgcaaaagca cgggagaaag tgcccaaact tcacagcatt agggacagga atggaacaca | 1800 |
| cttggatgca ggggctttga ccacgacctt tgaagagctt cattttgaga tcaagcccca | 1860 |
| cgatgactgc acagtagagc aaatctatga gattttgaaa atctaccaac tcatggacca | 1920 |
| cagtaacatg gactgcttca tctgctgtat cctctcccat ggagacaagg gcatcatcta | 1980 |
| tggcactgat ggacaggagg cccccatcta tgagctgaca tctcagttca ctggtttgaa | 2040 |
| gtgcccttcc cttgctggaa aacccaaagt gttttttatt caggcttctc aggggataa | 2100 |
| ctaccagaaa ggtataccctg ttgagactga ttcagaggag caaccctatt tagaaatgga | 2160 |
| tttatcatca cctcaaacga gatatatccc ggatgaggct gactttctgc tggggatggc | 2220 |
| cactgtgaat aactgtgttt cctaccgaaa ccctgcagag ggaacctggt acatccagtc | 2280 |
| actttgccag agcctgagag agcgatgtcc tcgaggcgat gatattctca ccatcctgac | 2340 |
| tgaagtgaac tatgaagtaa gcaacaagga tgacaagaaa aacatgggga aacagatgcc | 2400 |
| tcagcctact ttcacactaa gaaaaaaact tgtcttccct tctgattgaa gatcttatta | 2460 |
| aagcagaact tgtttattgc agcttataat ggttacaaat aaagcaatag catcacaaat | 2520 |
| ttcacaaata aagcattttt ttcactgcat tctagttgtg gtttgtccaa actcatcaat | 2580 |
| gtatcttatc atgtctggtc gactctagac tcttccgctt cctcgctcac tgactcgctg | 2640 |
| cgctcggtcg ttcggctgcg gcgagcggta tcagctcact caaaggcggt aatacggtta | 2700 |
| tccacagaat caggggataa cgcaggaaag aacatgtgag caaaaggcca gcaaaaggcc | 2760 |
| aggaaccgta aaaaggccgc gttgctggcg tttttccata ggctccgccc cctgacgag | 2820 |
| catcacaaaa atcgacgctc aagtcagagg tggcgaaacc cgacaggact ataaagatac | 2880 |
| caggcgtttc cccctggaag ctccctcgtg cgctctcctg ttccgaccct gccgcttacc | 2940 |
| ggatacctgt ccgcctttct cccttcggga agcgtggcgc tttctcaatg ctcacgctgt | 3000 |
| aggtatctca gttcggtgta ggtcgttcgc tccaagctgg gctgtgtgca cgaaccccc | 3060 |
| gttcagcccg accgctgcgc cttatccggt aactatcgtc ttgagtccaa cccggtaaga | 3120 |

| LISTING OF ADDITIONAL SEQUENCES | |
|---|---|
| cacgacttat cgccactggc agcagccact ggtaacagga ttagcagagc gaggtatgta | 3180 |
| ggcggtgcta cagagttctt gaagtggtgg cctaactacg gctacactag aaggacagta | 3240 |
| tttggtatct gcgctctgct gaagccagtt accttcggaa aaagagttgg tagctcttga | 3300 |
| tccggcaaac aaaccaccgc tggtagcggt ggttttttg tttgcaagca gcagattacg | 3360 |
| cgcagaaaaa aaggatctca agaagatcct ttgatctttt ctacgggtc tgacgctcag | 3420 |
| tggaacgaaa actcacgtta agggattttg gtcatgagat tatcaaaaag gatcttcacc | 3480 |
| tagatccttt taaattaaaa atgaagtttt aaatcaatct aaagtatata tgagtaaact | 3540 |
| tggtctgaca gttaccaatg cttaatcagt gaggcaccta tctcagcgat ctgtctattt | 3600 |
| cgttcatcca tagttgcctg actccccgtc gtgtagataa ctacgatacg ggagggctta | 3660 |
| ccatctggcc ccagtgctgc aatgataccg cgagacccac gctcaccggc tccagattta | 3720 |
| tcagcaataa accagccagc cggaagggcc gagcgcagaa gtggtcctgc aactttatcc | 3780 |
| gcctccatcc agtctattaa ttgttgccgg gaagctagag taagtagttc gccagttaat | 3840 |
| agtttgcgca acgttgttgc cattgctaca ggcatcgtgg tgtcacgctc gtcgtttggt | 3900 |
| atggcttcat tcagctccgg ttcccaacga tcaaggcgag ttacatgatc ccccatgttg | 3960 |
| tgcaaaaaag cggttagctc cttcggtcct ccgatcgttg tcagaagtaa gttggccgca | 4020 |
| gtgttatcac tcatggttat ggcagcactg cataattctc ttactgtcat gccatccgta | 4080 |
| agatgctttt ctgtgactgg tgagtactca accaagtcat tctgagaata gtgtatgcgg | 4140 |
| cgaccgagtt gctcttgccc ggcgtcaata cgggataata ccgcgccaca tagcagaact | 4200 |
| ttaaaagtgc tcatcattgg aaaacgttct cggggcgaa aactctcaag gatcttaccg | 4260 |
| ctgttgagat ccagttcgat gtaacccact cgtgcaccca actgatcttc agcatctttt | 4320 |
| actttcacca gcgtttctgg gtgagcaaaa acaggaaggc aaaatgccgc aaaaaaggga | 4380 |
| ataagggcga cacggaaatg ttgaatactc atactcttct ttttttcaata ttattgaagc | 4440 |
| atttatcagg gttattgtct catgagcgga tacatatttg aatgtattta gaaaaataaa | 4500 |
| caaatagggg ttccgcgcac atttccccga aaagtgccac ctgacgtcta agaaaccatt | 4560 |
| attatcatga cattaaccta taaaaatagg cgtatcacga ggccccttc gtctcgcgcg | 4620 |
| tttcggtgat gacggtgaaa acctctgaca catgcagctc ccggagacgg tcacagcttg | 4680 |
| tctgtaagcg gatgccggga gcagacaagc ccgtcagggc gcgtcagcgg gtgttggcgg | 4740 |
| gtgtcggggc tggcttaact atgcggcatc agagcagatt gtactgagag tgcaccatat | 4800 |
| gcggtgtgaa ataccgcaca gatgcgtaag gagaaaatac cgcatcagga aattgtaaac | 4860 |
| gttaatattt tgttaaaatt cgcgttaaat ttttgttaaa tcagctcatt ttttaaccaa | 4920 |
| taggccgaaa tcggcaaaat cccttataaa tcaaagaat agaccgagat agggttgagt | 4980 |
| gttgttccag tttggaacaa gagtccacta ttaaagaacg tggactccaa cgtcaaaggg | 5040 |
| cgaaaaaccg tctatcaggg cgatggccca ctacgtgaac catcaccta atcaagtttt | 5100 |
| ttggggtcga ggtgccgtaa agcactaaat cggaaccta agggagccc ccgatttaga | 5160 |
| gcttgacggg gaaagccggc gaacgtggcg agaaaggaag ggaagaaagc gaaggagcg | 5220 |
| ggcgctaggg cgctggcaag tgtagcggtc acgctgcgcg taaccaccac acccgccgcg | 5280 |
| cttaatgcgc cgctacaggg cgcgtcgcgc cattcgccat tcaggctacg caactgttgg | 5340 |
| gaagggcgat cggtgcgggc ctcttcgcta ttacgccagc tggcgaaggg gggatgtgct | 5400 |

```
gcaaggcgat taagttgggt aacgccaggg ttttcccagt cacgacgttg taaaacgacg    5460
gccagtgaat t                                                         5471
```

SEQ ID NO: 81

| | | | | | | | | | | | | | | |
|---|---|---|---|---|---|---|---|---|---|---|---|---|---|---|
| Met | Asp | Phe | Ser | Arg | Asn | Leu | Tyr | Asp | Ile | Gly | Glu | Gln | Leu | Asp | Ser |
| 1 | | | | 5 | | | | | 10 | | | | | 15 | |
| Glu | Asp | Leu | Ala | Ser | Leu | Lys | Phe | Leu | Ser | Leu | Asp | Tyr | Ile | Pro | Gln |
| | | | 20 | | | | | 25 | | | | | 30 | | |
| Arg | Lys | Gln | Glu | Pro | Ile | Lys | Asp | Ala | Leu | Met | Leu | Phe | Gln | Arg | Leu |
| | | 35 | | | | | 40 | | | | | 45 | | | |
| Gln | Glu | Lys | Arg | Met | Leu | Glu | Glu | Ser | Asn | Leu | Ser | Phe | Leu | Lys | Glu |
| | 50 | | | | | 55 | | | | | 60 | | | | |
| Leu | Leu | Phe | Arg | Ile | Asn | Arg | Leu | Asp | Leu | Leu | Ile | Thr | Tyr | Leu | Asn |
| 65 | | | | | 70 | | | | | 75 | | | | | 80 |
| Thr | Arg | Lys | Glu | Glu | Met | Glu | Arg | Glu | Leu | Gln | Thr | Pro | Gly | Arg | Ala |
| | | | | 85 | | | | | 90 | | | | | 95 | |
| Gln | Ile | Ser | Ala | Tyr | Arg | Val | Met | Leu | Tyr | Gln | Ile | Ser | Glu | Glu | Val |
| | | | 100 | | | | | 105 | | | | | 110 | | |
| Ser | Arg | Ser | Glu | Leu | Arg | Ser | Phe | Lys | Phe | Leu | Leu | Gln | Glu | Glu | Ile |
| | | | 115 | | | | | 120 | | | | | 125 | | |
| Ser | Lys | Cys | Lys | Leu | Asp | Asp | Asp | Met | Asn | Leu | Leu | Asp | Ile | Phe | Ile |
| | | 130 | | | | | 135 | | | | | 140 | | | |
| Glu | Met | Glu | Lys | Arg | Val | Ile | Leu | Gly | Glu | Gly | Lys | Leu | Asp | Ile | Leu |
| 145 | | | | | 150 | | | | | 155 | | | | | 160 |
| Lys | Arg | Val | Cys | Ala | Gln | Ile | Asn | Lys | Ser | Leu | Leu | Lys | Ile | Ile | Asn |
| | | | | 165 | | | | | 170 | | | | | 175 | |
| Asp | Tyr | Glu | Glu | Phe | Ser | Lys | Gly | Glu | Glu | Leu | Cys | Gly | Val | Met | Thr |
| | | | 180 | | | | | 185 | | | | | 190 | | |
| Ile | Ser | Asp | Ser | Pro | Arg | Glu | Gln | Asp | Ser | Glu | Ser | Gln | Thr | Leu | Asp |
| | | 195 | | | | | 200 | | | | | 205 | | | |
| Lys | Val | Tyr | Gln | Met | Lys | Ser | Lys | Pro | Arg | Gly | Tyr | Cys | Leu | Ile | Ile |
| 210 | | | | | 215 | | | | | 220 | | | | | |
| Asn | Asn | His | Asn | Phe | Ala | Lys | Ala | Arg | Glu | Lys | Val | Pro | Lys | Leu | His |
| 225 | | | | | 230 | | | | | 235 | | | | | 240 |
| Ser | Ile | Arg | Asp | Arg | Asn | Gly | Thr | His | Leu | Asp | Ala | Gly | Ala | Leu | Thr |
| | | | | 245 | | | | | 250 | | | | | 255 | |
| Thr | Thr | Phe | Glu | Glu | Leu | His | Phe | Glu | Ile | Lys | Pro | His | Asp | Asp | Cys |
| | | | 260 | | | | | 265 | | | | | 270 | | |
| Thr | Val | Glu | Gln | Ile | Tyr | Glu | Ile | Leu | Lys | Ile | Tyr | Gln | Leu | Met | Asp |
| | | 275 | | | | | 280 | | | | | 285 | | | |
| His | Ser | Asn | Met | Asp | Cys | Phe | Ile | Cys | Cys | Ile | Leu | Ser | His | Gly | Asp |
| | 290 | | | | | 295 | | | | | 300 | | | | |
| Lys | Gly | Ile | Ile | Tyr | Gly | Thr | Asp | Gly | Gln | Glu | Ala | Pro | Ile | Tyr | Glu |
| 305 | | | | | 310 | | | | | 315 | | | | | 320 |
| Leu | Thr | Ser | Gln | Phe | Thr | Gly | Leu | Lys | Cys | Pro | Ser | Leu | Ala | Gly | Lys |
| | | | | 325 | | | | | 330 | | | | | 335 | |
| Pro | Lys | Val | Phe | Phe | Ile | Gln | Ala | Ser | Gln | Gly | Asp | Asn | Tyr | Gln | Lys |
| | | | 340 | | | | | 345 | | | | | 350 | | |
| Gly | Ile | Pro | Val | Glu | Thr | Asp | Ser | Glu | Glu | Gln | Pro | Tyr | Leu | Glu | Met |
| | | 355 | | | | | 360 | | | | | 365 | | | |
| Asp | Leu | Ser | Ser | Pro | Gln | Thr | Arg | Tyr | Ile | Pro | Asp | Glu | Ala | Asp | Phe |
| | 370 | | | | | 375 | | | | | 380 | | | | |

| LISTING OF ADDITIONAL SEQUENCES |
|---|
| Leu Leu Gly Met Ala Thr Val Asn Asn Cys Val Ser Tyr Arg Asn Pro<br>385                       390                       395                     400<br><br>Ala Glu Gly Thr Trp Tyr Ile Gln Ser Leu Cys Gln Ser Leu Arg Glu<br>                405                       410                       415<br><br>Arg Cys Pro Arg Gly Asp Asp Ile Leu Thr Ile Leu Thr Glu Val Asn<br>                    420                       425                     430<br><br>Tyr Glu Val Ser Asn Lys Asp Asp Lys Lys Asn Met Gly Lys Gln Met<br>            435                       440                       445<br><br>Pro Gln Pro Thr Phe Thr Leu Arg Lys Lys Leu Val Phe Pro Ser Asp<br>450                       455                       460 |

SEQ ID NO: 82

```
gtcgacttct gaggcggaaa gaaccagctg tggaatgtgt gtcagttagg gtgtggaaag      60
tccccaggct ccccagcagg cagaagtatg caaagcatgc atctcaatta gtcagcaacc     120
aggtgtggaa agtccccagg ctccccagca ggcagaagta tgcaaagcat gcatctcaat     180
tagtcagcaa ccatagtccc gcccctaact ccgcccatcc cgcccctaac tccgcccagt     240
tccgcccatt ctccgcccca tggctgacta atttttttta tttatgcaga ggccgaggcc     300
gcctcggcct ctgagctatt ccagaagtag tgaggaggct tttttggagg cctaggcttt     360
tgcaaaaagc tggatcgatc ctgagaactt cagggtgagt ttggggaccc ttgattgttc     420
tttcttttc gctattgtaa aattcatgtt atatggaggg ggcaaagttt tcagggtgtt     480
gtttagaatg ggaagatgtc ccttgtatca ccatggaccc tcatgataat tttgtttctt     540
tcactttcta ctctgttgac aaccattgtc tcctcttatt ttcttttcat tttctgtaac     600
ttttcgtta aactttagct tgcatttgta acgaattttt aaattcactt ttgtttattt     660
gtcagattgt aagtactttc tctaatcact ttttttcaa ggcaatcagg gtatattata     720
ttgtacttca gcacagtttt agagaacaat tgttataatt aaatgataag gtagaatatt     780
tctgcatata aattctggct ggcgtggaaa tattcttatt ggtagaaaca actacatcct     840
ggtcatcatc ctgcctttct ctttatggtt acaatgatat acactgtttg agatgaggat     900
aaaatactct gagtccaaac cgggcccctc tgctaaccat gttcatgcct tcttctttt     960
cctacagctc ctgggcaacg tgctggttat tgtgctgtct catcattttg gcaaagaatt    1020
gtaatacgac tcactatagg gcgaattcgg atccatggac gaagcggatc ggcggctcct    1080
gcggcggtgc cggctgcggc tggtggaaga gctgcaggtg gaccagctct gggacgccct    1140
gctgagccgc gagctgttca ggccccatat gatcgaggac atccagcggg caggtctctgg   1200
atctcggcgg gatcaggcca ggcagctgat catagatctg gagactcgag ggagtcaggc    1260
tcttcctttg ttcatctcct gcttagagga cacaggccag gacatgctgg cttcgttcct    1320
gcgaactaac aggcaagcag caaagttgtc gaagccaacc ctagaaaacc ttaccccagt    1380
ggtgctcaga ccagagattc gcaaaccaga ggttctcaga ccggaaacac ccagaccagt    1440
ggacattggt tctggaggat tggtgatgt cgtgctctt gagagtttga ggggaaatgc      1500
agatttggct tacatcctga gcatggagcc ctgtggccac tgcctcatta tcaacaatgt    1560
gaacttctgc cgtgagtccg ggctccgcac ccgcactggc tccaacatcg actgtgagaa    1620
gttgcggcgt cgcttctcct cgctgcattt catggtggag gtgaagggcg acctgactgc    1680
caagaaaatg gtgctggctt tgctggagct ggcgcagcag gaccacggtg tctctggactg   1740
ctgcgtggtg gtcattctct ctcacggctg tcaggccagc cacctgcagt cccaggggc     1800
tgtctacggc acagatggat gccctgtgtc ggtcgagaag attgtgaaca tcttcaatgg    1860
```

| | |
|---|---|
| gaccagctgc cccagcctgg gagggaagcc caagctcttt ttcatccagg cctctggtgg | 1920 |
| ggagcagaaa gaccatgggt ttgaggtggc ctccacttcc cctgaagacg agtcccctgg | 1980 |
| cagtaacccc gagccagatg ccaccccgtt ccaggaaggt tgaggacct tcgaccagct | 2040 |
| ggacgccata tctagtttgc ccacacccag tgacatcttt gtgtcctact ctactttccc | 2100 |
| aggttttgtt tcctggaggg accccaagag tggctcctgg tacgttgaga ccctggacga | 2160 |
| catctttgag cagtgggctc actctgaaga cctgcagtcc ctcctgctta gggtcgctaa | 2220 |
| tgctgtttcg gtgaaaggga tttataaaca gatgcctggt tgctttaatt tcctccggaa | 2280 |
| aaaactttc tttaaaacat cataaagatc ttattaaagc agaacttgtt tattgcagct | 2340 |
| tataatggtt acaaataaag caatagcatc acaaatttca caaataaagc attttttca | 2400 |
| ctgcattcta gttgtggttt gtccaaactc atcaatgtat cttatcatgt ctggtcgact | 2460 |
| ctagactctt ccgcttcctc gctcactgac tcgctgcgct cggtcgttcg gctgcggcga | 2520 |
| gcggtatcag ctcactcaaa ggcggtaata cggttatcca cagaatcagg ggataacgca | 2580 |
| ggaaagaaca tgtgagcaaa aggccagcaa aaggccagga accgtaaaaa ggccgcgttg | 2640 |
| ctggcgtttt tccataggct ccgcccccct gacgagcatc acaaaaatcg acgctcaagt | 2700 |
| cagaggtggc gaaacccgac aggactataa agataccagg cgtttccccc tggaagctcc | 2760 |
| ctcgtgcgct ctcctgttcc gaccctgccg cttaccggat acctgtccgc ctttctccct | 2820 |
| tcgggaagcg tggcgctttc tcaatgctca cgctgtaggt atctcagttc ggtgtaggtc | 2880 |
| gttcgctcca agctgggctg tgtgcacgaa ccccccgttc agcccgaccg ctgcgcctta | 2940 |
| tccggtaact atcgtcttga gtccaacccg gtaagacacg acttatcgcc actggcagca | 3000 |
| gccactggta acaggattag cagagcgagg tatgtaggcg gtgctacaga gttcttgaag | 3060 |
| tggtggccta actacggcta cactagaagg acagtatttg gtatctgcgc tctgctgaag | 3120 |
| ccagttacct tcggaaaaag agttggtagc tcttgatccg gcaaacaaac caccgctggt | 3180 |
| agcggtggtt tttttgtttg caagcagcag attacgcgca gaaaaaaagg atctcaagaa | 3240 |
| gatcctttga tcttttctac ggggtctgac gctcagtgga acgaaaactc acgttaaggg | 3300 |
| attttggtca tgagattatc aaaaaggatc ttcacctaga tccttttaaa ttaaaaatga | 3360 |
| agttttaaat caatctaaag tatatatgag taaacttggt ctgacagtta ccaatgctta | 3420 |
| atcagtgagg cacctatctc agcgatctgt ctatttcgtt catccatagt tgcctgactc | 3480 |
| cccgtcgtgt agataactac gatacgggag ggcttaccat ctggccccag tgctgcaatg | 3540 |
| ataccgcgag acccacgctc accggctcca gatttatcag caataaacca gccagccgga | 3600 |
| agggccgagc gcagaagtgg tcctgcaact ttatccgcct ccatccagtc tattaattgt | 3660 |
| tgccgggaag ctagagtaag tagttcgcca gttaatagtt tgcgcaacgt tgttgccatt | 3720 |
| gctacaggca tcgtggtgtc acgctcgtcg tttggtatgg cttcattcag ctccggttcc | 3780 |
| caacgatcaa ggcgagttac atgatccccc atgttgtgca aaaaagcggt tagctccttc | 3840 |
| ggtcctccga tcgttgtcag aagtaagttg gccgcagtgt tatcactcat ggttatggca | 3900 |
| gcactgcata attctcttac tgtcatgcca tccgtaagat gcttttctgt gactggtgag | 3960 |
| tactcaacca agtcattctg agaatagtgt atgcggcgac cgagttgctc ttgcccggcg | 4020 |
| tcaatacggg ataataccgc gccacatagc agaactttaa aagtgctcat cattggaaaa | 4080 |
| cgttcttcgg ggcgaaaact ctcaaggatc ttaccgctgt tgagatccag ttcgatgtaa | 4140 |

| | |
|---|---|
| cccactcgtg cacccaactg atcttcagca tcttttactt tcaccagcgt ttctgggtga | 4200 |
| gcaaaaacag gaaggcaaaa tgccgcaaaa aagggaataa gggcgacacg gaaatgttga | 4260 |
| atactcatac tcttcttttt tcaatattat tgaagcattt atcagggtta ttgtctcatg | 4320 |
| agcggataca tatttgaatg tatttagaaa aataaacaaa taggggttcc gcgcacattt | 4380 |
| ccccgaaaag tgccacctga cgtctaagaa accattatta tcatgacatt aacctataaa | 4440 |
| aataggcgta tcacgaggcc cctttcgtct cgcgcgtttc ggtgatgacg gtgaaaacct | 4500 |
| ctgacacatg cagctcccgg agacggtcac agcttgtctg taagcggatg ccggagcag | 4560 |
| acaagcccgt cagggcgcgt cagcgggtgt tggcgggtgt cggggctggc ttaactatgc | 4620 |
| ggcatcagag cagattgtac tgagagtgca ccatatgcgg tgtgaaatac cgcacagatg | 4680 |
| cgtaaggaga aaataccgca tcaggaaatt gtaaacgtta atattttgtt aaaattcgcg | 4740 |
| ttaaatttt gttaaatcag ctcatttttt aaccaatagg ccgaaatcgg caaaatccct | 4800 |
| tataaatcaa aagaatagac cgagataggg ttgagtgttg ttccagtttg gaacaagagt | 4860 |
| ccactattaa agaacgtgga ctccaacgtc aaagggcgaa aaaccgtcta tcagggcgat | 4920 |
| ggcccactac gtgaaccatc accctaatca agttttttgg ggtcgaggtg ccgtaaagca | 4980 |
| ctaaatcgga accctaaagg gagcccccga tttagagctt gacggggaaa gccggcgaac | 5040 |
| gtggcgagaa aggaagggaa gaaagcgaaa ggagcgggcg ctagggcgct ggcaagtgta | 5100 |
| gcggtcacgc tgcgcgtaac caccacaccc gccgcgctta atgcgccgct acagggcgcg | 5160 |
| tcgcgccatt cgccattcag gctacgcaac tgttgggaag ggcgatcggt gcgggcctct | 5220 |
| tcgctattac gccagctggc gaagggggga tgtgctgcaa ggcgattaag ttgggtaacg | 5280 |
| ccagggtttt cccagtcacg acgttgtaaa acgacggcca gtgaatt | 5327 |

SEQ ID NO: 83
```
Met Asp Glu Ala Asp Arg Arg Leu Leu Arg Arg Cys Arg Leu Arg Leu
1               5                   10                  15

Val Glu Glu Leu Gln Val Asp Gln Leu Trp Asp Ala Leu Leu Ser Arg
            20                  25                  30

Glu Leu Phe Arg Pro His Met Ile Glu Asp Ile Gln Arg Ala Gly Ser
        35                  40                  45

Gly Ser Arg Arg Asp Gln Ala Arg Gln Leu Ile Ile Asp Leu Glu Thr
    50                  55                  60

Arg Gly Ser Gln Ala Leu Pro Leu Phe Ile Ser Cys Leu Glu Asp Thr
65                  70                  75                  80

Gly Gln Asp Met Leu Ala Ser Phe Leu Arg Thr Asn Arg Gln Ala Ala
                85                  90                  95

Lys Leu Ser Lys Pro Thr Leu Glu Asn Leu Thr Pro Val Val Leu Arg
            100                 105                 110

Pro Glu Ile Arg Lys Pro Glu Val Leu Arg Pro Glu Thr Pro Arg Pro
        115                 120                 125

Val Asp Ile Gly Ser Gly Gly Phe Gly Asp Val Gly Ala Leu Glu Ser
    130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
            180                 185                 190
```

| LISTING OF ADDITIONAL SEQUENCES |
|---|

Arg Phe Ser Ser Leu His Phe Met Val Glu Val Lys Gly Asp Leu Thr
          195                   200                   205

Ala Lys Lys Met Val Leu Ala Leu Leu Glu Leu Ala Gln Gln Asp His
 210                   215                   220

Gly Ala Leu Asp Cys Cys Val Val Val Ile Leu Ser His Gly Cys Gln
225                  230                   235                   240

Ala Ser His Leu Gln Phe Pro Gly Ala Val Tyr Gly Thr Asp Gly Cys
          245                   250                   255

Pro Val Ser Val Glu Lys Ile Val Asn Ile Phe Asn Gly Thr Ser Cys
              260                   265                   270

Pro Ser Leu Gly Gly Lys Pro Lys Leu Phe Phe Ile Gln Ala Ser Gly
         275                   280                   285

Gly Glu Gln Lys Asp His Gly Phe Glu Val Ala Ser Thr Ser Pro Glu
          290                   295                   300

Asp Glu Ser Pro Gly Ser Asn Pro Glu Pro Asp Ala Thr Pro Phe Gln
305                  310                   315                   320

Glu Gly Leu Arg Thr Phe Asp Gln Leu Asp Ala Ile Ser Ser Leu Pro
              325                   330                   335

Thr Pro Ser Asp Ile Phe Val Ser Tyr Ser Thr Phe Pro Gly Phe Val
                340                   345                   350

Ser Trp Arg Asp Pro Lys Ser Gly Ser Trp Tyr Val Glu Thr Leu Asp
         355                   360                   365

Asp Ile Phe Glu Gln Trp Ala His Ser Glu Asp Leu Gln Ser Leu Leu
        370                   375                   380

Leu Arg Val Ala Asn Ala Val Ser Val Lys Gly Ile Tyr Lys Gln Met
385                  390                   395                   400

Pro Gly Cys Phe Asn Phe Leu Arg Lys Lys Leu Phe Phe Lys Thr Ser
              405                   410                   415

SEQ ID NO: 84
gaattccggg ctggattgag aagccgcaac tgtgactctg catcatgaat actctgtctg     60
aaggaaatgg caccttttgcc atccatcttt tgaagatgct atgtcaaagc aacccttcca   120
aaaatgtatg ttattctcct gcgagcatct cctctgctct agctatggtt ctcttgggtg   180
caaagggaca gacggcagtc cagatatctc aggcacttgg tttgaataaa gaggaaggca   240
tccatcaggg tttccagttg cttctcagga agctgaacaa gccagacaga aagtactctc   300
ttagagtggc caacaggctc tttgcagaca aaacttgtga agtcctccaa acctttaagg   360
agtcctctct tcacttctat gactcagaga tggagcagct ctcctttgct gaagaagcag   420
aggtgtccag gcaacacata aacacatggg tctccaaaca aactgaaggt aaaattccag   480
agttgttgtc aggtggctcc gtcgattcag aaaccaggct ggttctcatc aatgccttat   540
attttaaagg aaagtggcat caaccattta acaaagagta cacaatggac atgcccttta   600
aaataaacaa ggatgagaaa aggccagtgc agatgatgtg tcgtgaagac acatataacc   660
tcgcctatgt gaaggaggtg caggcgcaag tgctggtgat gccatatgaa ggaatggagc   720
tgagcttggt ggttctgctc ccagatgagg gtgtggacct cagcaaggtg gaaaacaatc   780
tcacttttga gaagttaaca gcctggatgg aagcagattt tatgaagagc actgatgttg   840
aggtttttcct tccaaaattt aaactccaag aggattatga catggagtct ctgtttcagc   900
gcttgggagt ggtggatgtc ttccaagagg acaaggctga cttatcagga atgtctccag   960
agagaaacct gtgtgtgtcc aagtttgttc accagagtgt agtggagatc aatgaggaag  1020

| | |
|---|---|
| gcacagaggc tgcagcagcc tctgccatca tagaattttg ctgtgcctct tctgtcccaa | 1080 |
| cattctgtgc tgaccacccc ttccttttct tcatcaggca caacaaagca aacagcatcc | 1140 |
| tgttctgtgg caggttctca tctccataaa gacacatata ctacacaggg agagttctct | 1200 |
| cttcagtatc cctaccactc ctacagctct gtcaagatgg gcaagtaggg ggaagtcatg | 1260 |
| ttctaagatg aagacacttt ccttctctgt cagcctgatc ttataatgcc tgcattcaac | 1320 |
| tctccctgtc ttgaatgcat ctatgccctt taccaggtta tgtctaatga tgccaaatac | 1380 |
| cttctgctat gctattgatt gatagcctag ccagtaattt atagccagtt agaactgact | 1440 |
| tgactgtgca agaatgctat aatggagcta gagagaaggc acaaacacta ggaaaggttg | 1500 |
| ctgttttgc agaggacaca gggacatttc ccaccactca catggctgct tacaacctct | 1560 |
| ggaaattcca gtttctgtcc atgacttgat tcctttcttt ggcttctact ggctccagca | 1620 |
| tcctgcacat acatgtatcg tcattcagtt acacacaaac aagtaaaatt ttaaaaataa | 1680 |
| ataaaattt aaagagagag tctaaaattt tagtaatggt tagataatag ctgctattgt | 1740 |
| gccttttca ggttttaatg tcattattct tgtgtataaa gtcaataatt tataggaaaa | 1800 |
| catcagtgcc ccggaattc | 1819 |

SEQ ID NO: 85

```
Met Asn Thr Leu Ser Glu Gly Asn Gly Thr Phe Ala Ile His Leu Leu
1               5                   10                  15

Lys Met Leu Cys Gln Ser Asn Pro Ser Lys Asn Val Cys Tyr Ser Pro
                20                  25                  30

Ala Ser Ile Ser Ser Ala Leu Ala Met Val Leu Leu Gly Ala Lys Gly
            35                  40                  45

Gln Thr Ala Val Gln Ile Ser Gln Ala Leu Gly Leu Asn Lys Glu Glu
        50                  55                  60

Gly Ile His Gln Gly Phe Gln Leu Leu Arg Lys Leu Asn Lys Pro
65                  70                  75                  80

Asp Arg Lys Tyr Ser Leu Arg Val Ala Asn Arg Leu Phe Ala Asp Lys
                85                  90                  95

Thr Cys Glu Val Leu Gln Thr Phe Lys Glu Ser Ser Leu His Phe Tyr
            100                 105                 110

Asp Ser Glu Met Glu Gln Leu Ser Phe Ala Glu Glu Ala Glu Val Ser
        115                 120                 125

Arg Gln His Ile Asn Thr Trp Val Ser Lys Gln Thr Glu Gly Lys Ile
    130                 135                 140

Pro Glu Leu Leu Ser Gly Gly Ser Val Asp Ser Glu Thr Arg Leu Val
145                 150                 155                 160

Leu Ile Asn Ala Leu Tyr Phe Lys Gly Lys Trp His Gln Pro Phe Met
                165                 170                 175

Lys Glu Tyr Thr Met Asp Met Pro Phe Lys Ile Asn Lys Asp Glu Lys
            180                 185                 190

Arg Pro Val Gln Met Met Cys Arg Glu Asp Thr Tyr Asn Leu Ala Tyr
        195                 200                 205

Val Lys Glu Val Gln Ala Gln Val Leu Val Met Pro Tyr Glu Gly Met
    210                 215                 220

Glu Leu Ser Leu Val Val Leu Pro Asp Glu Gly Val Asp Leu Ser
225                 230                 235                 240

Lys Val Glu Asn Asn Leu Thr Phe Glu Lys Leu Thr Ala Trp Met Glu
                245                 250                 255
```

| LISTING OF ADDITIONAL SEQUENCES |
|---|

Ala Asp Phe Met Lys Ser Thr Asp Val Glu Val Phe Leu Pro Lys Phe
            260                 265                 270

Lys Leu Gln Glu Asp Tyr Asp Met Glu Ser Leu Phe Gln Arg Leu Gly
        275                 280                 285

Val Val Asp Val Phe Gln Glu Asp Lys Ala Asp Leu Ser Gly Met Ser
    290                 295                 300

Pro Glu Arg Asn Leu Cys Val Ser Lys Phe Val His Gln Ser Val Val
305                 310                 315                 320

Glu Ile Asn Glu Glu Gly Thr Glu Ala Ala Ala Ser Ala Ile Ile
                325                 330                 335

Glu Phe Cys Cys Ala Ser Ser Val Pro Thr Phe Cys Ala Asp His Pro
            340                 345                 350

Phe Leu Phe Phe Ile Arg His Asn Lys Ala Asn Ser Ile Leu Phe Cys
        355                 360                 365

Gly Arg Phe Ser Ser Pro
    370

SEQ ID NO: 86
atgaatactc tgtctgaagg aaatggcacc tttgccatcc atcttttgaa gatgctatgt      60
caaagcaacc cttccaaaaa tgtatgttat tctcctgcga gcatctcctc tgctctagct     120
atggttctct gggtgcaaa gggacagacg gcagtccaga tatctcaggc acttggtttg     180
aataaagagg aaggcatcca tcagggtttc cagttgcttc tcaggaagct gaacaagcca     240
gacagaaagt actctcttag agtggccaac aggctctttg cagacaaaac ttgtgaagtc     300
ctccaaacct ttaaggagtc ctctcttcac ttctatgact cagagatgga gcagctctcc     360
tttgctgaag aagcagaggt gtccaggcaa cacataaaca catgggtctc caaacaaact     420
gaaggtaaaa ttccagagtt gttgtcaggt ggctccgtcg attcagaaac caggctggtt     480
ctcatcaatg ccttatattt taaaggaaag tggcatcaac catttaacaa agagtacaca     540
atggacatgc cctttaaaat aaacaaggat gagaaaaggc cagtgcagat gatgtgtcgt     600
gaagacacat ataacctcgc ctatgtgaag gaggtgcagg cgcaagtgct ggtgatgcca     660
tatgaaggaa tggagctgag cttggtggtt ctgctcccag atgagggtgt ggacctcagc     720
aaggtggaaa acaatctcac ttttgagaag ttaacagcct ggatggaagc agattttatg     780
aagagcactg atgttgaggt tttccttcca aatttaaac tccaagagga ttatgacatg     840
gagtctctgt ttcagcgctt gggagtggtg gatgtcttcc aagaggacaa ggctgactta     900
tcaggaatgt ctccagagag aaacctgtgt gtgtccaagt tgttcaccca gagtgtagtg     960
gagatcaatg aggaaggcag agaggctgca gcagcctctg ccatcataga attttgctgt    1020
gcctcttctg tcccaacatt ctgtgctgac caccccttcc tttttcttcat caggcacaac    1080
aaagcaaaca gcatcctgtt ctgtggcagg ttctcatctc cataa                     1125

SEQ ID NO: 87
Met Asn Thr Leu Ser Glu Gly Asn Gly Thr Phe Ala Ile His Leu Leu
1               5                   10                  15

Lys Met Leu Cys Gln Ser Asn Pro Ser Lys Asn Val Cys Tyr Ser Pro
            20                  25                  30

Ala Ser Ile Ser Ser Ala Leu Ala Met Val Leu Leu Gly Ala Lys Gly
        35                  40                  45

Gln Thr Ala Val Gln Ile Ser Gln Ala Leu Gly Leu Asn Lys Glu Glu
    50                  55                  60

Gly Ile His Gln Gly Phe Gln Leu Leu Leu Arg Lys Leu Asn Lys Pro

LISTING OF ADDITIONAL SEQUENCES

```
                65                  70                  75                  80
Asp Arg Lys Tyr Ser Leu Arg Val Ala Asn Arg Leu Phe Ala Asp Lys
                        85                  90                  95
Thr Cys Glu Val Leu Gln Thr Phe Lys Glu Ser Ser Leu His Phe Tyr
                100                 105                 110
Asp Ser Glu Met Glu Gln Leu Ser Phe Ala Glu Glu Ala Glu Val Ser
                115                 120                 125
Arg Gln His Ile Asn Thr Trp Val Ser Lys Gln Thr Glu Gly Lys Ile
                130                 135                 140
Pro Glu Leu Leu Ser Gly Gly Ser Val Asp Ser Glu Thr Arg Leu Val
145                 150                 155                 160
Leu Ile Asn Ala Leu Tyr Phe Lys Gly Lys Trp His Gln Pro Phe Asn
                165                 170                 175
Lys Glu Tyr Thr Met Asp Met Pro Phe Lys Ile Asn Lys Asp Glu Lys
                180                 185                 190
Arg Pro Val Gln Met Met Cys Arg Glu Asp Thr Tyr Asn Leu Ala Tyr
                195                 200                 205
Val Lys Glu Val Gln Ala Gln Val Leu Val Met Pro Tyr Glu Gly Met
210                 215                 220
Glu Leu Ser Leu Val Val Leu Leu Pro Asp Glu Gly Val Asp Leu Ser
225                 230                 235                 240
Lys Val Glu Asn Asn Leu Thr Phe Glu Lys Leu Thr Ala Trp Met Glu
                245                 250                 255
Ala Asp Phe Met Lys Ser Thr Asp Glu Val Phe Leu Pro Lys Phe
                260                 265                 270
Lys Leu Gln Glu Asp Tyr Asp Met Glu Ser Leu Phe Gln Arg Leu Gly
                275                 280                 285
Val Val Asp Val Phe Gln Glu Asp Lys Ala Asp Leu Ser Gly Met Ser
                290                 295                 300
Pro Glu Arg Asn Leu Cys Val Ser Lys Phe Val His Gln Ser Val Val
305                 310                 315                 320
Glu Ile Asn Glu Glu Gly Arg Glu Ala Ala Ala Ser Ala Ile Ile
                325                 330                 335
Glu Phe Cys Cys Ala Ser Ser Val Pro Thr Phe Cys Ala Asp His Pro
                340                 345                 350
Phe Leu Phe Phe Ile Arg His Asn Lys Ala Asn Ser Ile Leu Phe Cys
                355                 360                 365
Gly Arg Phe Ser Ser Pro
370
```

SEQ ID NO: 88

| | | | | | |
|---|---|---|---|---|---|
| gacggatcgg | gagatctccc | gatcccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggac | tatttacggt | aaactgccca | cttggcagta | catcaagtgt | 480 |
| atcatatgcc | aagtacgccc | cctattgacg | tcaatgacgg | taaatggccc | gcctggcatt | 540 |

-continued

LISTING OF ADDITIONAL SEQUENCES

```
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaacgg gccctctaga ctcgagcggc cgccactgtg ctggatatct gcagaattca      960
tgaatactct gtctgaagga atggcacctt tgccatcca tcttttgaag atgctatgtc      1020
aaagcaaccc ttccaaaaat gtatgttatt ctcctgcgag catctcctct gctctagcta     1080
tggttctctt gggtgcaaag gacagacgg cagtccagat atctcaggca cttggtttga      1140
ataaagagga aggcatccat cagggtttcc agttgcttct caggaagctg aacaagccag     1200
acagaaagta ctctcttaga gtggccaaca ggctctttgc agacaaaact tgtgaagtcc     1260
tccaaacctt taaggagtcc tctcttcact tctatgactc agagatggag cagctctcct    1320
ttgctgaaga agcagaggtg tccaggcaac acataaacac atgggtctcc aaacaaactg     1380
aaggtaaaat tccagagttg ttgtcaggtg gctccgtcga ttcagaaacc aggctggttc    1440
tcatcaatgc cttatatttt aaaggaaagt ggcatcaacc atttaacaaa gagtacacaa    1500
tggacatgcc ctttaaaata aacaaggatg agaaaaggcc agtgcagatg atgtgtcgtg    1560
aagacacata taacctcgcc tatgtgaagg aggtgcaggc gcaagtgctg gtgatgccat    1620
atgaaggaat ggagctgagc ttggtggttc tgctcccaga tgagggtgtg gacctcagca    1680
aggtggaaaa caatctcact tttgagaagt taacagcctg gatggaagca gatttttatga    1740
agagcactga tgttgaggtt ttccttccaa aatttaaact ccaagaggat tatgacatgg     1800
agtctctgtt tcagcgcttg ggagtggtgg atgtcttcca agaggacaag gctgacttat    1860
caggaatgtc tccagagaga aacctgtgtg tgtccaagtt tgttcaccag agtgtagtgg    1920
agatcaatga ggaaggcaca gaggctgcag cagcctctgc catcatagaa ttttgctgtg    1980
cctcttctgt cccaacattc tgtgctgacc accccttcct tttcttcatc aggcacaaca    2040
aagcaaacag catcctgttc tgtggcaggt tctcatctcc ataaggatcc gagctcggta    2100
ccaagcttaa gtttaaaccg ctgatcagcc tcgactgtgc cttctagttg ccagccatct    2160
gttgtttgcc cctcccccgt gccttccttg accctggaag gtgccactcc cactgtcctt    2220
tcctaataaa atgaggaaat tgcatcgcat tgtctgagta ggtgtcattc tattctgggg    2280
ggtggggtgg ggcaggacag caaggggag gattgggaag acaatagcag gcatgctggg    2340
gatgcggtgg gctctatggc ttctgaggcg gaaagaacca gctggggctc taggggggtat   2400
ccccacgcgc cctgtagcgg cgcattaagc gcggcgggtg tggtggttac gcgcagcgtg   2460
accgctacac ttgccagcgc cctagcgccc gctcctttcg ctttcttccc ttcctttctc    2520
gccacgttcg ccggctttcc ccgtcaagct ctaaatcggg gcatcccttt agggttccga   2580
tttagtgctt tacggcacct cgaccccaaa aaacttgatt agggtgatgg ttcacgtagt    2640
gggccatcgc cctgatagac ggttttttcgc cctttgacgt tggagtccac gttctttaat   2700
agtggactct gttccaaac tggaacaaca ctcaacccta tctcggtcta ttcttttgat    2760
ttataaggga ttttggggat ttcggcctat tggttaaaaa atgagctgat ttaacaaaaa    2820
```

| LISTING OF ADDITIONAL SEQUENCES | |
|---|---|
| tttaacgcga attaattctg tggaatgtgt gtcagttagg gtgtggaaag tccccaggct | 2880 |
| ccccaggcag gcagaagtat gcaaagcatg catctcaatt agtcagcaac caggtgtgga | 2940 |
| aagtccccag gctccccagc aggcagaagt atgcaaagca tgcatctcaa ttagtcagca | 3000 |
| accatagtcc cgcccctaac tccgcccatc ccgcccctaa ctccgcccag ttccgcccat | 3060 |
| tctccgcccc atggctgact aattttttt atttatgcag aggccgaggc cgcctctgcc | 3120 |
| tctgagctat tccagaagta gtgaggaggc ttttttggag gcctaggctt ttgcaaaaag | 3180 |
| ctcccgggag cttgtatatc cattttcgga tctgatcaag agacaggatg aggatcgttt | 3240 |
| cgcatgattg aacaagatgg attgcacgca ggttctccgg ccgcttgggt ggagaggcta | 3300 |
| ttcggctatg actgggcaca acagacaatc ggctgctctg atgccgccgt gttccggctg | 3360 |
| tcagcgcagg ggcgcccggt tctttttgtc aagaccgacc tgtccggtgc cctgaatgaa | 3420 |
| ctgcaggacg aggcagcgcg gctatcgtgg ctggccacga cgggcgttcc ttgcgcagct | 3480 |
| gtgctcgacg ttgtcactga agcgggaagg gactggctgc tattgggcga agtgccgggg | 3540 |
| caggatctcc tgtcatctca ccttgctcct gccgagaaag tatccatcat ggctgatgca | 3600 |
| atgcggcggc tgcatacgct tgatccggct acctgcccat tcgaccacca agcgaaacat | 3660 |
| cgcatcgagc gagcacgtac tcggatggaa gccggtcttg tcgatcagga tgatctggac | 3720 |
| gaagagcatc aggggctcgc gccagccgaa ctgttcgcca ggctcaaggc gcgcatgccc | 3780 |
| gacggcgagg atctcgtcgt gacccatggc gatgcctgct tgccgaatat catggtggaa | 3840 |
| aatggccgct tttctggatt catcgactgt ggccggctgg gtgtggcgga ccgctatcag | 3900 |
| gacatagcgt tggctacccg tgatattgct gaagagcttg gcggcgaatg ggctgaccgc | 3960 |
| ttcctcgtgc tttacggtat cgccgctccc gattcgcagc gcatcgcctt ctatcgcctt | 4020 |
| cttgacgagt tcttctgagc gggactctgg ggttcgaaat gaccgaccaa gcgacgccca | 4080 |
| acctgccatc acgagatttc gattccaccg ccgccttcta tgaaaggttg gcttcggaa | 4140 |
| tcgttttccg ggacgccggc tggatgatcc tccagcgcgg ggatctcatg ctggagttct | 4200 |
| tcgcccaccc caacttgttt attgcagctt ataatggtta caaataaagc aatagcatca | 4260 |
| caaatttcac aaataaagca tttttttcac tgcattctag ttgtggtttg tccaaactca | 4320 |
| tcaatgtatc ttatcatgtc tgtataccgt cgacctctag ctagagcttg gcgtaatcat | 4380 |
| ggtcatagct gtttcctgtg tgaaattgtt atccgctcac aattccacac aacatacgag | 4440 |
| ccggaagcat aaagtgtaaa gcctggggtg cctaatgagt gagctaactc acattaattg | 4500 |
| cgttgcgctc actgcccgct ttccagtcgg gaaacctgtc gtgccagctg cattaatgaa | 4560 |
| tcggccaacg cgcggggaga ggcggtttgc gtattgggcg ctcttccgct tcctcgctca | 4620 |
| ctgactcgct gcgctcggtc gttcggctgc ggcgagcggt atcagctcac tcaaaggcgg | 4680 |
| taatacggtt atccacagaa tcaggggata cgcaggaaa gaacatgtga gcaaaaggcc | 4740 |
| agcaaaaggc caggaaccgt aaaaaggccg cgttgctggc gtttttccat aggctccgcc | 4800 |
| cccctgacga gcatcacaaa aatcgacgct caagtcagag gtggcgaaac ccgacaggac | 4860 |
| tataaagata ccaggcgttt ccccctggaa gctccctcgt gcgctctcct gttccgaccc | 4920 |
| tgccgcttac cggatacctg tccgcctttc tcccttcggg aagcgtggcg ctttctcaat | 4980 |
| gctcacgctg taggtatctc agttcggtgt aggtcgttcg ctccaagctg ggctgtgtgc | 5040 |
| acgaaccccc cgttcagccc gaccgctgcg ccttatccgg taactatcgt cttgagtcca | 5100 |
| acccggtaag acacgactta tcgccactgg cagcagccac tggtaacagg attagcagag | 5160 |

LISTING OF ADDITIONAL SEQUENCES

```
cgaggtatgt aggcggtgct acagagttct tgaagtggtg gcctaactac ggctacacta    5220
gaaggacagt atttggtatc tgcgctctgc tgaagccagt taccttcgga aaaagagttg    5280
gtagctcttg atccggcaaa caaaccaccg ctggtagcgg tggttttttt gtttgcaagc    5340
agcagattac gcgcagaaaa aaaggatctc aagaagatcc tttgatcttt tctacggggt    5400
ctgacgctca gtggaacgaa aactcacgtt aagggatttt ggtcatgaga ttatcaaaaa    5460
ggatcttcac ctagatcctt ttaaattaaa aatgaagttt taaatcaatc taaagtatat    5520
atgagtaaac ttggtctgac agttaccaat gcttaatcag tgaggcacct atctcagcga    5580
tctgtctatt tcgttcatcc atagttgcct gactccccgt cgtgtagata actacgatac    5640
gggagggctt accatctggc cccagtgctg caatgatacc gcgagaccca cgctcaccgg    5700
ctccagattt atcagcaata aaccagccag ccggaagggc cgagcgcaga agtggtcctg    5760
caactttatc cgcctccatc cagtctatta attgttgccg ggaagctaga gtaagtagtt    5820
cgccagttaa tagtttgcgc aacgttgttg ccattgctac aggcatcgtg gtgtcacgct    5880
cgtcgtttgg tatggcttca ttcagctccg gttcccaacg atcaaggcga gttacatgat    5940
cccccatgtt gtgcaaaaaa gcggttagct ccttcggtcc tccgatcgtt gtcagaagta    6000
agttggccgc agtgttatca ctcatggtta tggcagcact gcataattct cttactgtca    6060
tgccatccgt aagatgcttt tctgtgactg gtgagtactc aaccaagtca ttctgagaat    6120
agtgtatgcg gcgaccgagt tgctcttgcc cggcgtcaat acgggataat accgcgccac    6180
atagcagaac tttaaaagtg ctcatcattg gaaaacgttc ttcggggcga aaactctcaa    6240
ggatcttacc gctgttgaga tccagttcga tgtaacccac tcgtgcaccc aactgatctt    6300
cagcatcttt tactttcacc agcgtttctg ggtgagcaaa aacaggaagg caaaatgccg    6360
caaaaaaggg aataagggcg acacggaaat gttgaatact catactcttc ctttttcaat    6420
attattgaag catttatcag ggttattgtc tcatgagcgg atacatattt gaatgtattt    6480
agaaaaataa acaaataggg gttccgcgca catttccccg aaaagtgcca cctgacgtc    6539
```

SEQ ID NO: 89
```
gacggatcgg gagatctccc gatccccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccaccccca ttgacgtcaa tgggagtttg ttttggcacc    720
aaaatcaacg ggactttcca aaatgtcgta caactccgcc ccattgacg caaatgggcg    780 gtaggcgtgt acggtgggag gtctatataa gcagagctct ctggctaact agagaaccca    840
ctgcttactg gcttatcgaa attaatacga ctcactatag ggagacccaa gctggctagc    900
```

-continued

| LISTING OF ADDITIONAL SEQUENCES | |
|---|---|
| gtttaaacgg gccctctaga ctcgagcggc cgccactgtg ctggatatct gcagaattca | 960 |
| tgaatactct gtctgaagga aatggcacct ttgccatcca tcttttgaag atgctatgtc | 1020 |
| aaagcaaccc ttccaaaaat gtatgttatt ctcctgcgag catctcctct gctctagcta | 1080 |
| tggttctctt gggtgcaaag ggacagacgg cagtccagat atctcaggca cttggtttga | 1140 |
| ataaagagga aggcatccat cagggtttcc agttgcttct caggaagctg aacaagccag | 1200 |
| acagaaagta ctctcttaga gtggccaaca ggctctttgc agacaaaact tgtgaagtcc | 1260 |
| tccaaacctt taaggagtcc tctcttcact tctatgactc agagatggag cagctctcct | 1320 |
| ttgctgaaga agcagaggtg tccaggcaac acataaacac atgggtctcc aaacaaactg | 1380 |
| aaggtaaaat tccagagttg ttgtcaggtg gctccgtcga ttcagaaacc aggctggttc | 1440 |
| tcatcaatgc cttatatttt aaaggaaagt ggcatcaacc atttaacaaa gagtacacaa | 1500 |
| tggacatgcc ctttaaaata aacaaggatg agaaaaggcc agtgcagatg atgtgtcgtg | 1560 |
| aagacacata taacctcgcc tatgtgaagg aggtgcaggc gcaagtgctg gtgatgccat | 1620 |
| atgaaggaat ggagctgagc ttggtggttc tgctcccaga tgagggtgtg gacctcagca | 1680 |
| aggtggaaaa caatctcact tttgagaagt taacagcctg gatggaagca gattttatga | 1740 |
| agagcactga tgttgaggtt ttccttccaa aatttaaact ccaagaggat tatgacatgg | 1800 |
| agtctctgtt tcagcgcttg ggagtggtgg atgtcttcca agaggacaag gctgacttat | 1860 |
| caggaatgtc tccagagaga aacctgtgtg tgtccaagtt tgttcaccag agtgtagtgg | 1920 |
| agatcaatga ggaaggcaga gaggctgcag cagcctctgc catcatagaa ttttgctgtg | 1980 |
| cctcttctgt cccaacattc tgtgctgacc accccttcct tttcttcatc aggcacaaca | 2040 |
| aagcaaacag catcctgttc tgtggcaggt tctcatctcc ataaggatcc gagctcggta | 2100 |
| ccaagcttaa gtttaaaccg ctgatcagcc tcgactgtgc cttctagttg ccagccatct | 2160 |
| gttgtttgcc cctcccccgt gccttccttg accctggaag gtgccactcc cactgtcctt | 2220 |
| tcctaataaa atgaggaaat tgcatcgcat tgtctgagta ggtgtcattc tattctgggg | 2280 |
| ggtggggtgg ggcaggacag caaggggag gattgggaag acaatagcag gcatgctggg | 2340 |
| gatgcggtgg gctctatggc ttctgaggcg gaaagaacca gctggggctc taggggtat | 2400 |
| ccccacgcgc cctgtagcgg cgcattaagc gcggcgggtg tggtggttac gcgcagcgtg | 2460 |
| accgctacac ttgccagcgc cctagcgccc gctcctttcg ctttcttccc ttcctttctc | 2520 |
| gccacgttcg ccggctttcc ccgtcaagct ctaaatcggg gcatcccttt agggttccga | 2580 |
| tttagtgctt tacggcacct cgaccccaaa aaacttgatt agggtgatgg ttcacgtagt | 2640 |
| gggccatcgc cctgatagac ggttttttcgc cctttgacgt tggagtccac gttctttaat | 2700 |
| agtggactct tgttccaaac tggaacaaca ctcaaccctta tctcggtcta ttcttttgat | 2760 |
| ttataaggga ttttggggat ttcggcctat tggttaaaaa atgagctgat ttaacaaaaa | 2820 |
| tttaacgcga attaattctg tggaatgtgt gtcagttagg gtgtggaaag tccccaggct | 2880 |
| ccccaggcag gcagaagtat gcaaagcatg catctcaatt agtcagcaac caggtgtgga | 2940 |
| aagtccccag gctccccagc aggcagaagt atgcaaagca tgcatctcaa ttagtcagca | 3000 |
| accatagtcc cgcccctaac tccgcccatc ccgcccctaa ctccgcccag ttccgcccat | 3060 |
| tctccgcccc atggctgact aatttttttt atttatgcag aggccgaggc cgcctctgcc | 3120 |
| tctgagctat tccagaagta gtgaggaggc ttttttggag gcctaggctt ttgcaaaaag | 3180 |

| LISTING OF ADDITIONAL SEQUENCES | |
|---|---|
| ctcccgggag cttgtatatc cattttcgga tctgatcaag agacaggatg aggatcgttt | 3240 |
| cgcatgattg aacaagatgg attgcacgca ggttctccgg ccgcttgggt ggagaggcta | 3300 |
| ttcggctatg actgggcaca acagacaatc ggctgctctg atgccgccgt gttccggctg | 3360 |
| tcagcgcagg ggcgcccggt tctttttgtc aagaccgacc tgtccggtgc cctgaatgaa | 3420 |
| ctgcaggacg aggcagcgcg gctatcgtgg ctggccacga cgggcgttcc ttgcgcagct | 3480 |
| gtgctcgacg ttgtcactga agcgggaagg gactggctgc tattgggcga agtgccgggg | 3540 |
| caggatctcc tgtcatctca ccttgctcct gccgagaaag tatccatcat ggctgatgca | 3600 |
| atgcggcggc tgcatacgct tgatccggct acctgcccat tcgaccacca agcgaaacat | 3660 |
| cgcatcgagc gagcacgtac tcggatggaa gccggtcttg tcgatcagga tgatctggac | 3720 |
| gaagagcatc aggggctcgc gccagccgaa ctgttcgcca ggctcaaggc gcgcatgccc | 3780 |
| gacggcgagg atctcgtcgt gacccatggc gatgcctgct tgccgaatat catggtggaa | 3840 |
| aatggccgct tttctggatt catcgactgt ggccggctgg gtgtggcgga ccgctatcag | 3900 |
| gacatagcgt tggctacccg tgatattgct gaagagcttg gcggcgaatg ggctgaccgc | 3960 |
| ttcctcgtgc tttacggtat cgccgctccc gattcgcagc gcatcgcctt ctatcgcctt | 4020 |
| cttgacgagt tcttctgagc gggactctgg ggttcgaaat gaccgaccaa gcgacgccca | 4080 |
| acctgccatc acgagatttc gattccaccg ccgccttcta tgaaaggttg gcttcggaa | 4140 |
| tcgtttccg ggacgccggc tggatgatcc tccagcgcgg ggatctcatg ctggagttct | 4200 |
| tcgcccaccc caacttgttt attgcagctt ataatggtta caaataaagc aatagcatca | 4260 |
| caaatttcac aaataaagca tttttttcac tgcattctag ttgtggtttg tccaaactca | 4320 |
| tcaatgtatc ttatcatgtc tgtataccgt cgacctctag ctagagcttg gcgtaatcat | 4380 |
| ggtcatagct gtttcctgtg tgaaattgtt atccgctcac aattccacac aacatacgag | 4440 |
| ccggaagcat aaagtgtaaa gcctggggtg cctaatgagt gagctaactc acattaattg | 4500 |
| cgttgcgctc actgcccgct ttccagtcgg gaaacctgtc gtgccagctg cattaatgaa | 4560 |
| tcggccaacg cgcggggaga ggcggtttgc gtattgggcg ctcttccgct tcctcgctca | 4620 |
| ctgactcgct gcgctcggtc gttcggctgc ggcgagcggt atcagctcac tcaaaggcgg | 4680 |
| taatacggtt atccacagaa tcaggggata acgcaggaaa gaacatgtga gcaaaaggcc | 4740 |
| agcaaaaggc caggaaccgt aaaaaggccg cgttgctggc gtttttccat aggctccgcc | 4800 |
| cccctgacga gcatcacaaa aatcgacgct caagtcagag gtggcgaaac ccgacaggac | 4860 |
| tataaagata ccaggcgttt ccccctggaa gctccctcgt gcgctctcct gttccgaccc | 4920 |
| tgccgcttac cggatacctg tccgcctttc tcccttcggg aagcgtggcg ctttctcaat | 4980 |
| gctcacgctg taggtatctc agttcggtgt aggtcgttcg ctccaagctg gctgtgtgc | 5040 |
| acgaaccccc cgttcagccc gaccgctgcg ccttatccgg taactatcgt cttgagtcca | 5100 |
| acccggtaag acacgactta tcgccactgg cagcagccac tggtaacagg attagcagag | 5160 |
| cgaggtatgt aggcggtgct acagagttct tgaagtggtg gcctaactac ggctacacta | 5220 |
| gaaggacagt atttggtatc tgcgctctgc tgaagccagt taccttcgga aaaagagttg | 5280 |
| gtagctcttg atccggcaaa caaaccaccg ctggtagcgg tggttttttt gtttgcaagc | 5340 |
| agcagattac gcgcagaaaa aaaggatctc aagaagatcc tttgatcttt tctacggggt | 5400 |
| ctgacgctca gtggaacgaa aactcacgtt aagggatttt ggtcatgaga ttatcaaaaa | 5460 |
| ggatcttcac ctagatcctt ttaaattaaa aatgaagttt taaatcaatc taaagtatat | 5520 |

| | |
|---|---|
| atgagtaaac ttggtctgac agttaccaat gcttaatcag tgaggcacct atctcagcga | 5580 |
| tctgtctatt tcgttcatcc atagttgcct gactccccgt cgtgtagata actacgatac | 5640 |
| gggagggctt accatctggc cccagtgctg caatgatacc gcgagaccca cgctcaccgg | 5700 |
| ctccagattt atcagcaata aaccagccag ccggaagggc cgagcgcaga agtggtcctg | 5760 |
| caactttatc cgcctccatc cagtctatta attgttgccg ggaagctaga gtaagtagtt | 5820 |
| cgccagttaa tagtttgcgc aacgttgttg ccattgctac aggcatcgtg gtgtcacgct | 5880 |
| cgtcgtttgg tatggcttca ttcagctccg gttcccaacg atcaaggcga gttacatgat | 5940 |
| cccccatgtt gtgcaaaaaa gcggttagct ccttcggtcc tccgatcgtt gtcagaagta | 6000 |
| agttggccgc agtgttatca ctcatggtta tggcagcact gcataattct cttactgtca | 6060 |
| tgccatccgt aagatgcttt tctgtgactg gtgagtactc aaccaagtca ttctgagaat | 6120 |
| agtgtatgcg gcgaccgagt tgctcttgcc cggcgtcaat acgggataat accgcgccac | 6180 |
| atagcagaac tttaaaagtg ctcatcattg gaaaacgttc ttcggggcga aaactctcaa | 6240 |
| ggatcttacc gctgttgaga tccagttcga tgtaacccac tcgtgcaccc aactgatctt | 6300 |
| cagcatcttt tactttcacc agcgtttctg ggtgagcaaa acaggaagg caaaatgccg | 6360 |
| caaaaaggg aataagggcg acacggaaat gttgaatact catactcttc ctttttcaat | 6420 |
| attattgaag catttatcag ggttattgtc tcatgagcgg atacatattt gaatgtattt | 6480 |
| agaaaaataa acaaataggg gttccgcgca catttccccg aaaagtgcca cctgacgtc | 6539 |

SEQ ID NO: 90

| | |
|---|---|
| atggatgacc agcgcgacct tatctccaac aatgagcaac tgcccatgct gggccggcgc | 60 |
| cctggggccc cggagagcaa gtgcagccgc ggagccctgt acacaggctt ttccatcctg | 120 |
| gtgactctgc tcctcgctgg ccaggccacc accgcctact tcctgtacca gcagcagggc | 180 |
| cggctggaca aactgacagt cacctcccag aacctgcagc tggagaacct gcgcatgaag | 240 |
| cttgccaagt tcgtggctgc ctggaccctg aaggctgccg ctgccctgcc caggggccc | 300 |
| atgcagaatg ccaccaagta tggcaacatg acagaggacc atgtgatgca cctgctccag | 360 |
| aatgctgacc ccctgaaggt gtacccgcca ctgaagggga gcttcccgga gaacctgaga | 420 |
| caccttaaga caccatggaa gaccatagac tggaaggtct ttgagagctg gatgcaccat | 480 |
| tggctcctgt ttgaaatgag caggcactcc ttggagcaaa agcccactga cgctccaccg | 540 |
| aaagtactga ccaagtgcca ggaagaggtc agccacatcc tgctgtccca cccgggttca | 600 |
| ttcaggccca gtgcgacga aacggcaac tatctgccac tccagtgcta tgggagcatc | 660 |
| ggctactgct ggtgtgtctt ccccaacggc acggaggtcc caacaccag aagccgcggg | 720 |
| caccataact gcagtgagtc actggaactg gaggacccgt cttctgggct gggtgtgacc | 780 |
| aagcaggatc tgggcccagt ccccatgtga | 810 |

SEQ ID NO: 91
Met Asp Asp Gln Arg Asp Leu Ile Ser Asn Asn Glu Gln Leu Pro Met
1               5                   10                  15

Leu Gly Arg Arg Pro Gly Ala Pro Glu Ser Lys Cys Ser Arg Gly Ala
            20                  25                  30

Leu Tyr Thr Gly Phe Ser Ile Leu Val Thr Leu Leu Leu Ala Gly Gln
        35                  40                  45

Ala Thr Thr Ala Tyr Phe Leu Tyr Gln Gln Gln Gly Arg Leu Asp Lys
    50                  55                  60

| LISTING OF ADDITIONAL SEQUENCES |
|---|
| Leu Thr Val Thr Ser Gln Asn Leu Gln Leu Glu Asn Leu Arg Met Lys<br>65                        70                       75                     80<br><br>Leu Ala Lys Phe Val Ala Ala Trp Thr Leu Lys Ala Ala Ala Ala Leu<br>                 85                     90                      95<br><br>Pro Gln Gly Pro Met Gln Asn Ala Thr Lys Tyr Gly Asn Met Thr Glu<br>               100                    105                   110<br><br>Asp His Val Met His Leu Leu Gln Asn Ala Asp Pro Leu Lys Val Tyr<br>       115                    120                   125<br><br>Pro Pro Leu Lys Gly Ser Phe Pro Glu Asn Leu Arg His Leu Lys Asn<br>             130                    135                   140<br><br>Thr Met Glu Thr Ile Asp Trp Lys Val Phe Glu Ser Trp Met His His<br>145                     150                    155                   160<br><br>Trp Leu Leu Phe Glu Met Ser Arg His Ser Leu Glu Gln Lys Pro Thr<br>               165                    170                   175<br><br>Asp Ala Pro Pro Lys Val Leu Thr Lys Cys Gln Glu Glu Val Ser His<br>             180                    185                   190<br><br>Ile Pro Ala Val His Pro Gly Ser Phe Arg Pro Lys Cys Asp Glu Asn<br>       195                    200                   205<br><br>Gly Asn Tyr Leu Pro Leu Gln Cys Tyr Gly Ser Ile Gly Tyr Cys Trp<br>     210                    215                   220<br><br>Cys Val Phe Pro Asn Gly Thr Glu Val Pro Asn Thr Arg Ser Arg Gly<br>225                     230                    235                   240<br><br>His His Asn Cys Ser Glu Ser Leu Glu Leu Glu Asp Pro Ser Ser Gly<br>             245                    250                   255<br><br>Leu Gly Val Thr Lys Gln Asp Leu Gly Pro Val Pro Met<br>         260                    265<br><br>SEQ ID NO: 92<br>Lys Pro Val Ser Gln Met Arg Met Ala Thr Pro Leu Leu Met Arg Pro<br>1               5                    10                   15<br>Met<br><br>SEQ ID NO: 93<br>Ala Lys Phe Val Ala Ala Trp Thr Leu Lys Ala Ala Ala<br>1               5                    10 |

SEQ ID NO: 94
```
atgcgttgcc tggctccacg ccctgctggg tcctacctgt cagagcccca aggcagctca      60
cagtgtgcca ccatggagtt gggggcccta aaggtggct  acctggagct tcttaacagc     120
gatgctgacc cctgtgcctc taccacttct atgaccagat ggacctggct ggagaagaag     180
agattgagct ctactcagaa cccgacacag acaccatcaa ctgcgaccag ttcagcaggc     240
tgttgtgtga catggaaggt gatgaagaga ccagggaggc ttatgccaat atcgcggaac     300
tggaccagta tgtcttccag gactcccagc tggagggcct gagcaaggac attttcaagc     360
acataggacc agatgaagtg atcggtgaga gtatggagat gccagcagaa gttgggcaga     420
aaagtcagaa aagaccccttc ccagaggagc ttccggcaga cctgaagcac tggaagccag     480
ctgagccccc cactgtggtg actggcagtc tcctagtggg accagtgagc gactgctcca     540
ccctgccctg cctgccactg cctgcgctgt tcaaccagga gccagcctcc ggccagatgc     600
gcctggagaa aaccgaccag attcccatgc ctttctccag ttcctcgttg agctgcctga     660
atctccctga gggacccatc cagtttgtcc ccaccatctc cactctgccc catgggctct     720
ggcaaatctc tgaggctgga acaggggtct ccagtatatt catctaccat ggtgaggtgc     780
cccaggccag ccaagtaccc cctcccagtg gattcactgt ccacggcctc ccaacatctc     840
```

| LISTING OF ADDITIONAL SEQUENCES | |
|---|---|
| cagaccggcc aggctccacc agcccctccg ctccatcagc cactgacctg cccagcatgc | 900 |
| ctgaacctgc cctgacctcc cgagcaaaca tgacagagca caagacgtcc cccacccaat | 960 |
| gcccggcagt ggagaggtc tccaacaagc ttccaaaatg gcctgagccg gtggagcagt | 1020 |
| tctaccgctc actgcaggac acgtatggtg ccgagcccgc aggcccggat ggcatcctag | 1080 |
| tggaggtgga tctggtgcag gccaggctgg agaggagcag cagcaagagc ctggagcggg | 1140 |
| aactggccac cccggactgg gcagaacggc agctggccca aggaggcctg gctgaggtgc | 1200 |
| tgttggctgc caaggagcac cggcggccgc gtgagacacg agtgattgct gtgctgggca | 1260 |
| aagctggtca gggcaagagc tattgggctg gggcagtgag ccgggcctgg gcttgtggcc | 1320 |
| ggcttcccca gtacgacttt gtcttctctg tccctgcca ttgcttgaac cgtccggggg | 1380 |
| atgcctatgg cctgcaggat ctgctcttct ccctgggccc acagccactc gtggcggccg | 1440 |
| atgaggtttt cagccacatc ttgaagagac ctgaccgcgt tctgctcatc ctagacggct | 1500 |
| tcgaggagct ggaagcgcaa gatggcttcc tgcacacac gtgcggaccg gcaccggcgg | 1560 |
| agccctgctc cctccggggg ctgctggccg gccttttcca gaagaagctg ctccgaggtt | 1620 |
| gcaccctcct cctcacagcc cggccccggg gccgcctggt ccagagcctg agcaaggccg | 1680 |
| acgccctatt tgagctgtcc ggcttctcca tggagcaggc ccaggcatac gtgatgcgct | 1740 |
| actttgagag ctcagggatg acagagcacc aagacagagc cctgacgctc ctccgggacc | 1800 |
| ggccacttct tctcagtcac agccacagcc ctactttgtg ccgggcagtg tgccagctct | 1860 |
| cagaggccct gctggagctt ggggaggacg ccaagctgcc ctccacgctc acgggactct | 1920 |
| atgtcggcct gctgggccgt gcagccctcg acagcccccc cggggccctg gcagagctgg | 1980 |
| ccaagctggc ctgggagctg ggccgcagac atcaaagtac cctacaggag gaccagttcc | 2040 |
| catccgcaga cgtgaggacc tgggcgatgg ccaaaggctt agtccaacac ccaccgcggg | 2100 |
| ccgcagagtc cgagctggcc ttccccagct tcctcctgca atgcttcctg ggggccctgt | 2160 |
| ggctggctct gagtggcgaa atcaaggaca aggagctccc gcagtaccta gcattgaccc | 2220 |
| caaggaagaa gaggccctat gacaactggc tggagggcgt gccacgcttt ctggctgggc | 2280 |
| tgatcttcca gcctcccgcc cgctgcctgg gagccatact cgggccatcg gcggctgcct | 2340 |
| cggtggacag gaagcagaag gtgcttgcga ggtacctgaa gcggctgcag ccggggacac | 2400 |
| tgcgggcgcg gcagctgctg gagctgctgc actgcgccca cgaggccgag gaggctggaa | 2460 |
| tttggcagca cgtggtacag gagctccccg gccgcctctc tttttctggc acccgcctca | 2520 |
| cgcctcctga tgcacatgta ctgggcaagg ccttggaggc ggcgggccaa gacttctccc | 2580 |
| tggacctccg cagcactggc atttgcccct ctggattggg gagcctcgtg ggactcagct | 2640 |
| gtgtcacccg tttcagggct gccttgagcg acacggtggc gctgtgggag tccctgcagc | 2700 |
| agcatgggga gaccaagcta cttcaggcag cagaggagaa gttcaccatc gagcctttca | 2760 |
| aagccaagtc cctgaaggat gtggaagacc tgggaaagct tgtgcagact cagaggacga | 2820 |
| gaagttcctc ggaagacaca gctggggagc tccctgctgt tcgggaccta agaaactgg | 2880 |
| agtttgcgct gggccctgtc tcaggccccc aggctttccc caaactggtg cggatcctca | 2940 |
| cggccttttc ctccctgcag catctggacc tggatgcgct gagtgagaac aagatcgggg | 3000 |
| acgagggtgt ctcgcagctc tcagccacct tcccccagct gaagtccttg gaaaccctca | 3060 |
| atctgtccca gaacaacatc actgacctgg gtgcctacaa actcgccgag gccctgcctt | 3120 |
| cgctcgctgc atccctgctc aggctaagct tgtacaataa ctgcatctgc gacgtgggag | 3180 |

| LISTING OF ADDITIONAL SEQUENCES | |
|---|---|
| ccgagagctt ggctcgtgtg cttccggaca tggtgtccct ccgggtgatg gacgtccagt | 3240 |
| acaacaagtt cacggctgcc ggggcccagc agctcgctgc cagccttcgg aggtgtcctc | 3300 |
| atgtggagac gctggcgatg tggacgccca ccatccccatt cagtgtccag gaacacctgc | 3360 |
| aacaacagga ttcacggatc agcctgagat ga | 3392 |

SEQ ID NO: 95

```
Met Arg Cys Leu Ala Pro Arg Pro Ala Gly Ser Tyr Leu Ser Glu Pro
1               5                   10                  15

Gln Gly Ser Ser Gln Cys Ala Thr Met Glu Leu Gly Pro Leu Glu Gly
            20                  25                  30

Gly Tyr Leu Glu Leu Leu Asn Ser Asp Ala Asp Pro Leu Cys Leu Tyr
            35                  40                  45

His Phe Tyr Asp Gln Met Asp Leu Ala Gly Glu Glu Glu Ile Glu Leu
        50                  55                  60

Tyr Ser Glu Pro Asp Thr Asp Thr Ile Asn Cys Asp Gln Phe Ser Arg
65                  70                  75                  80

Leu Leu Cys Asp Met Glu Gly Asp Glu Glu Thr Arg Glu Ala Tyr Ala
                85                  90                  95

Asn Ile Ala Glu Leu Asp Gln Tyr Val Phe Gln Asp Ser Gln Leu Glu
                100                 105                 110

Gly Leu Ser Lys Asp Ile Phe Lys His Ile Gly Pro Asp Glu Val Ile
            115                 120                 125

Gly Glu Ser Met Glu Met Pro Ala Glu Val Gly Gln Lys Ser Gln Lys
130                 135                 140

Arg Pro Phe Pro Glu Glu Leu Pro Ala Asp Leu Lys His Trp Lys Pro
145                 150                 155                 160

Ala Glu Pro Pro Thr Val Val Thr Gly Ser Leu Leu Val Gly Pro Val
                165                 170                 175

Ser Asp Cys Ser Thr Leu Pro Cys Leu Pro Leu Pro Ala Leu Phe Asn
                180                 185                 190

Gln Glu Pro Ala Ser Gly Gln Met Arg Leu Glu Lys Thr Asp Gln Ile
            195                 200                 205

Pro Met Pro Phe Ser Ser Ser Leu Ser Cys Leu Asn Leu Pro Glu
210                 215                 220

Gly Pro Ile Gln Phe Val Pro Thr Ile Ser Thr Leu Pro His Gly Leu
225                 230                 235                 240

Trp Gln Ile Ser Glu Ala Gly Thr Gly Val Ser Ser Ile Phe Ile Tyr
                245                 250                 255

His Gly Glu Val Pro Gln Ala Ser Gln Val Pro Pro Ser Gly Phe
            260                 265                 270

Thr Val His Gly Leu Pro Thr Ser Pro Asp Arg Pro Gly Ser Thr Ser
            275                 280                 285

Pro Phe Ala Pro Ser Ala Thr Asp Leu Pro Ser Met Pro Glu Pro Ala
            290                 295                 300

Leu Thr Ser Arg Ala Asn Met Thr Glu His Lys Thr Ser Pro Thr Gln
305                 310                 315                 320

Cys Pro Ala Ala Gly Glu Val Ser Asn Lys Leu Pro Lys Trp Pro Glu
                325                 330                 335

Pro Val Glu Gln Phe Tyr Arg Ser Leu Gln Asp Thr Tyr Gly Ala Glu
            340                 345                 350

Pro Ala Gly Pro Asp Gly Ile Leu Val Glu Val Asp Leu Val Gln Ala
```

355                 360                 365
Arg Leu Glu Arg Ser Ser Lys Ser Leu Glu Arg Glu Leu Ala Thr
    370                 375                 380
Pro Asp Trp Ala Glu Arg Gln Leu Ala Gln Gly Gly Leu Ala Glu Val
385                 390                 395                 400
Leu Leu Ala Ala Lys Glu His Arg Arg Pro Arg Glu Thr Arg Val Ile
                405                 410                 415
Ala Val Leu Gly Lys Ala Gly Gln Gly Lys Ser Tyr Trp Ala Gly Ala
                420                 425                 430
Val Ser Arg Ala Trp Ala Cys Gly Arg Leu Pro Gln Tyr Asp Phe Val
            435                 440                 445
Phe Ser Val Pro Cys His Cys Leu Asn Arg Pro Gly Asp Ala Tyr Gly
            450                 455                 460
Leu Gln Asp Leu Leu Phe Ser Leu Gly Pro Gln Pro Leu Val Ala Ala
465                 470                 475                 480
Asp Glu Val Phe Ser His Ile Leu Lys Arg Pro Asp Arg Val Leu Leu
                485                 490                 495
Ile Leu Asp Gly Phe Glu Glu Leu Glu Ala Gln Asp Gly Phe Leu His
                500                 505                 510
Ser Thr Cys Gly Pro Ala Pro Ala Glu Pro Cys Ser Leu Arg Gly Leu
            515                 520                 525
Leu Ala Gly Leu Phe Gln Lys Lys Leu Leu Arg Gly Cys Thr Leu Leu
        530                 535                 540
Leu Thr Ala Arg Pro Arg Gly Arg Leu Val Gln Ser Leu Ser Lys Ala
545                 550                 555                 560
Asp Ala Leu Phe Glu Leu Ser Gly Phe Ser Met Glu Gln Ala Gln Ala
                565                 570                 575
Tyr Val Met Arg Tyr Phe Glu Ser Ser Gly Met Thr Glu His Gln Asp
                580                 585                 590
Arg Ala Leu Thr Leu Leu Arg Asp Arg Pro Leu Leu Leu Ser His Ser
            595                 600                 605
His Ser Pro Thr Leu Cys Arg Ala Val Cys Gln Leu Ser Glu Ala Leu
        610                 615                 620
Leu Glu Leu Gly Glu Asp Ala Lys Leu Pro Ser Thr Leu Thr Gly Leu
625                 630                 635                 640
Tyr Val Gly Leu Leu Gly Arg Ala Ala Leu Asp Ser Pro Pro Gly Ala
                645                 650                 655
Leu Ala Glu Leu Ala Lys Leu Ala Trp Glu Leu Gly Arg Arg His Gln
                660                 665                 670
Ser Thr Leu Gln Glu Asp Gln Phe Pro Ser Ala Asp Val Arg Thr Trp
            675                 680                 685
Ala Met Ala Lys Gly Leu Val Gln His Pro Pro Arg Ala Ala Glu Ser
        690                 695                 700
Glu Leu Ala Phe Pro Ser Phe Leu Leu Gln Cys Phe Leu Gly Ala Leu
705                 710                 715                 720
Trp Leu Ala Leu Ser Gly Glu Ile Lys Asp Lys Glu Leu Pro Gln Tyr
                725                 730                 735
Leu Ala Leu Thr Pro Arg Lys Lys Arg Pro Tyr Asp Asn Trp Leu Glu
                740                 745                 750
Gly Val Pro Arg Phe Leu Ala Gly Leu Ile Phe Gln Pro Pro Ala Arg
            755                 760                 765

| LISTING OF ADDITIONAL SEQUENCES |
|---|
| Cys Leu Gly Ala Leu Leu Gly Pro Ser Ala Ala Ser Val Asp Arg
    770                    775                  780

Lys Gln Lys Val Leu Ala Arg Tyr Leu Lys Arg Leu Gln Pro Gly Thr
785                    790                    795                800

Leu Arg Ala Arg Gln Leu Leu Glu Leu His Cys Ala His Glu Ala
              805                    810                  815

Glu Glu Ala Gly Ile Trp Gln His Val Val Gln Glu Leu Pro Gly Arg
            820                    825                  830

Leu Ser Phe Leu Gly Thr Arg Leu Thr Pro Pro Asp Ala His Val Leu
        835                  840                    845

Gly Lys Ala Leu Glu Ala Ala Gly Gln Asp Phe Ser Leu Asp Leu Arg
    850                  855                  860

Ser Thr Gly Ile Cys Pro Ser Gly Leu Gly Ser Leu Val Gly Leu Ser
865                    870                    875                880

Cys Val Thr Arg Phe Arg Ala Ala Leu Ser Asp Thr Val Ala Leu Trp
              885                    890                  895

Glu Ser Leu Gln Gln His Gly Glu Thr Lys Leu Leu Gln Ala Ala Glu
        900                  905                    910

Glu Lys Phe Thr Ile Glu Pro Phe Lys Ala Lys Ser Leu Lys Asp Val
    915                  920                  925

Glu Asp Leu Gly Lys Leu Val Gln Thr Gln Arg Thr Arg Ser Ser Ser
930                    935                    940

Glu Asp Thr Ala Gly Glu Leu Pro Ala Val Arg Asp Leu Lys Lys Leu
945                    950                    955                960

Glu Phe Ala Leu Gly Pro Val Ser Gly Pro Gln Ala Phe Pro Lys Leu
            965                    970                  975

Val Arg Ile Leu Thr Ala Phe Ser Ser Leu Gln His Leu Asp Leu Asp
              980                    985                  990

Ala Leu Ser Glu Asn Lys Ile Gly Asp Glu Gly Val Ser Gln Leu Ser
        995                1000                  1005

Ala Thr Phe Pro Gln Leu Lys Ser Leu Glu Thr Leu Asn Leu Ser
    1010                  1015                  1020

Gln Asn Asn Ile Thr Asp Leu Gly Ala Tyr Lys Leu Ala Glu Ala
    1025                  1030                  1035

Leu Pro Ser Leu Ala Ala Ser Leu Leu Arg Leu Ser Leu Tyr Asn
    1040                  1045                  1050

Asn Cys Ile Cys Asp Val Gly Ala Glu Ser Leu Ala Arg Val Leu
    1055                  1060                  1065

Pro Asp Met Val Ser Leu Arg Val Met Asp Val Gln Tyr Asn Lys
    1070                  1075                  1080

Phe Thr Ala Ala Gly Ala Gln Gln Leu Ala Ala Ser Leu Arg Arg
    1085                  1090                  1095

Cys Pro His Val Glu Thr Leu Ala Met Trp Thr Pro Thr Ile Pro
    1100                  1105                  1110

Phe Ser Val Gln Glu His Leu Gln Gln Gln Asp Ser Arg Ile Ser
    1115                  1120                  1125

Leu Arg
    1130

SEQ ID NO: 96
1/1                                      31/11
ATG AGC CTG TGG CTG CCC AGC GAG GCC ACC GTG TAC CTG CCC CCC GTG CCC GTG AGC AAG

61/21                                91/31 |

| LISTING OF ADDITIONAL SEQUENCES |
|---|
| GTG GTG AGC ACC GAC GAG TAC GTG GCC AGG ACC AAC ATC TAC TAC CAC GCC GGC ACC AGC |
| 121/41                         151/51<br>AGG CTG CTG GCC GTG GGC CAC CCC TAC TTC CCC ATC AAG AAG CCC AAC AAC AAC AAG ATC |
| 181/61                         211/71<br>CTG GTG CCC AAG GTG AGC GGC CTG CAG TAC AGG GTG TTC AGG ATC CAC CTG CCC GAC CCC |
| 241/81                         271/91<br>AAC AAG TTC GGC TTC CCC GAC ACC AGC TTC TAC AAC CCC GAC ACC CAG AGG CTG GTG TGG |
| 301/101                        331/111<br>GCC TGC GTG GGC GTG GAG GTG GGC AGG GGC CAG CCC CTG GGC GTG GGC ATC AGC GGC CAC |
| 361/121                        391/131<br>CCC CTG CTG AAC AAG CTG GAC GAC ACC GAG AAC GCC AGC GCC TAC GCC GCC AAC GCC GGC |
| 421/141                        451/151<br>GTG GAC AAC AGG GAG TGC ATC AGC ATG GAC TAC AAG CAG ACC CAG CTG TGC CTG ATC GGC |
| 481/161                        511/171<br>TGC AAG CCC CCC ATC GGC GAG CAC TGG GGC AAG GGC AGC CCC TGC ACC AAC GTG GCC GTG |
| 541/181                        571/191<br>AAC CCC GGC GAC TGC CCC CCC CTG GAG CTG ATC AAC ACC GTG ATC CAG GAC GGC GAC ATG |
| 601/201                        631/211<br>GTG GAC ACC GGC TTC GGC GCC ATG GAC TTC ACC ACC CTG CAG GCC AAC AAG AGC GAG GTG |
| 661/221                        691/231<br>CCC CTG GAC ATC TGC ACC AGC ATC TGC AAG TAC CCC GAC TAC ATC AAG ATG GTG AGC GAG |
| 721/241                        751/251<br>CCC TAC GGC GAC AGC CTG TTC TTC TAC CTG AGG AGG GAG CAG ATG TTC GTG AGG CAC CTG |
| 781/261                        811/271<br>TTC AAC AGG GCC GGC GCC GTG GGC GAG AAC GTG CCC GAC GAC CTG TAC ATC AAG GGC AGC |
| 841/281                        871/291<br>GGC AGC ACC GCC AAC CTG GCC AGC AGC AAC TAC TTC CCC ACC CCC AGC GGC AGC ATG GTG |
| 901/301                        931/311<br>ACC AGC GAC GCC CAG ATC TTC AAC AAG CCC TAC TGG CTG CAG AGG GCC CAG GGC CAC AAC |
| 961/321                        991/331<br>AAC GGC ATC TGC TGG GGC AAC CAG CTG TTC GTG ACC GTG GTG GAC ACC ACC AGG AGC ACC |
| 1021/341                      1051/351<br>AAC ATG AGC CTG TGC GCC GCC ATC AGC ACC AGC GAG ACC ACC TAC AAG AAC ACC AAC TTC |
| 1081/361                      1111/371<br>AAG GAG TAC CTG AGG CAC GGC GAG GAG TAC GAC CTG CAG TTC ATC TTC CAG CTG TGC AAG |
| 1141/381                      1171/391<br>ATC ACC CTG ACC GCC GAC GTG ATG ACC TAC ATC CAC AGC ATG AAC AGC ACC ATC CTG GAG |
| 1201/401                      1231/411<br>GAC TGG AAC TTC GGC CTG CAG CCC CCC CCC GGC GGC ACC CTG GAG GAC ACC TAC AGG TTC |
| 1261/421                      1291/431<br>GTG ACC AGC CAG GCC ATC GCC TGC CAG AAG CAC ACC CCC CCC GCC CCC AAG GAG GAC CCC<br>ro |
| 1321/441                      1351/451<br>CTG AAG AAG TAC ACC TTC TGG GAG GTG AAC CTG AAG GAG AAG TTC AGC GCC GAC CTG GAC |
| 1381/461                      1411/471<br>CAG TTC CCC CTG GGC AGG AAG TTC CTG CTG CAG GCC GGC CTG AAG GCC AAG CCC AAG TTC |
| 1441/481                      1471/491<br>ACC CTG GGC AAG AGG AAG GCC ACC CCC ACC ACC AGC AGC ACC AGC ACC ACC GCC AAG AGG |
| 1501/501<br>AAG AAG AGG AAG CTG TGA |

SEQ ID NO: 97

LISTING OF ADDITIONAL SEQUENCES

```
1/1                              31/11
Met ser leu trp leu pro ser glu ala thr val tyr leu pro pro val pro val ser lys 61/21                            91/31
val val ser thr asp glu tyr val ala arg thr asn ile tyr tyr his ala gly thr ser 121/41                           151/51
arg leu leu ala val gly his pro tyr phe pro ile lys lys pro asn asn asn lys ile 181/61                           211/71
leu val pro lys val ser gly leu gln tyr arg val phe arg ile his leu pro asp pro 241/81                           271/91
asn lys phe gly phe pro asp thr ser phe tyr asn pro asp thr gln arg leu val trp 301/101                          331/111
ala cys val gly val glu val gly arg gly gln pro leu gly val gly ile ser gly his 361/121                          391/131
pro leu leu asn lys leu asp asp thr glu asn ala ser ala tyr ala ala asn ala gly 421/141                          451/151
val asp asn arg glu cys ile ser met asp tyr lys gln thr gln leu cys leu ile gly 481/161                          511/171
cys lys pro pro ile gly glu his trp gly lys gly ser pro cys thr asn val ala val 541/181                          571/191
asn pro gly asp cys pro pro leu glu leu ile asn thr val ile gln asp gly asp met 601/201                          631/211
val asp thr gly phe gly ala met asp phe thr thr leu gln ala asn lys ser glu val 661/221                          691/231
pro leu asp ile cys thr ser ile cys lys tyr pro asp tyr ile lys met val ser glu 721/241                          751/251
pro tyr gly asp ser leu phe phe tyr leu arg arg glu gln met phe val arg his leu 781/261                          811/271
phe asn arg ala gly ala val gly glu asn val pro asp asp leu tyr ile lys gly ser 841/281                          871/291
gly ser thr ala asn leu ala ser ser asn tyr phe pro thr pro ser gly ser met val 901/301                          931/311
thr ser asp ala gln ile phe asn lys pro tyr trp leu gln arg ala gln gly his asn 961/321                          991/331
asn gly ile cys trp gly asn gln leu phe val thr val val asp thr thr arg ser thr 1021/341                         1051/351
asn met ser leu cys ala ala ile ser thr ser glu thr thr tyr lys asn thr asn phe 1081/361                         1111/371
lys glu tyr leu arg his gly glu glu tyr asp leu gln phe ile phe gln leu cys lys 1141/381                         1171/391
ile thr leu thr ala asp val met thr tyr ile his ser met asn ser thr ile leu glu 1201/401                         1231/411
asp trp asn phe gly leu gln pro pro gly gly thr leu glu asp thr tyr arg phe 1261/421                         1291/431
val thr ser gln ala ile ala cys gln lys his thr pro pro ala pro lys glu asp pro 1321/441                         1351/451
leu lys lys tyr thr phe trp glu val asn leu lys glu lys phe ser ala asp leu asp 1381/461                         1411/471
gln phe pro leu gly arg lys phe leu leu gln ala gly leu lys ala lys pro lys phe 1441/481                         1471/491
thr leu gly lys arg lys ala thr pro thr thr ser ser thr ser thr thr ala lys arg 1501/501
lys lys arg lys leu OPA
```

LISTING OF ADDITIONAL SEQUENCES

SEQ ID NO: 98
```
   1    atgtgcctgt atacacgggt cctgatatta cattaccatc tactacctct gtatggccca
  61    ttgtatcacc cacggcccct gcctctacac agtatattgg tatacatggt acacattatt
 121    atttgtggcc attatattat tttattccta agaaacgtaa acgtgttccc tatttttttg
 181    cagatggctt tgtggcggcc tagtgacaat accgtatatc ttccacctcc ttctgtggca
 241    agagttgtaa ataccgatga ttatgtgact cccacaagca tatttatca tgctggcagc
 301    tctagattat taactgttgg taatccatat tttagggttc ctgcaggtgg tggcaataag
 361    caggatattc ctaaggtttc tgcataccaa tatagagtat ttagggtgca gttacctgac
 421    ccaaataaat ttggtttacc tgatactagt atttataatc ctgaaacaca acgtttagtg
 481    tgggcctgtg ctggagtgga aattggccgt ggtcagcctt taggtgttgg ccttagtggg
 541    catccatttt ataataaatt agatgacact gaaagttccc atgccgccac gtctaatgtt
 601    tctgaggacg ttagggacaa tgtgtctgta gattataagc agacacagtt atgtattttg
 661    ggctgtgccc ctgctattgg ggaacactgg gctaaaggca ctgcttgtaa atcgcgtcct
 721    ttatcacagg gcgattgccc cccttttagaa cttaaaaaca cagttttgga agatggtgat
 781    atggtagata ctggatatgg tgccatggac tttagtacat tgcaagatac taaatgtgag
 841    gtaccattgg atatttgtca gtctatttgt aaatatcctg attatttaca aatgtctgca
 901    gatccttatg gggattccat gttttttttgc ttacggcgtg agcagctttt tgctaggcat
 961    ttttggaata gagcaggtac tatgggtgac actgtgcctc aatccttata tattaaaggc
1021    acaggtatgc ctgcttcacc tggcagctgt gtgtattctc cctctccaag tggctctatt
1081    gttacctctg actcccagtt gtttaataaa ccatattggt tacataaggc acagggtcat
1141    aacaatggtg tttgctggca taatcaatta tttgttactg tggtagatac cactcccagt
1201    accaatttaa caatatgtgc ttctacacag tctcctgtac ctgggcaata tgatgctacc
1261    aaatttaagc agtatagcag acatgttgag gaatatgatt tgcagtttat ttttcagttg
1321    tgtactatta ctttaactgc agatgttatg tcctatattc atagtatgaa tagcagtatt
1381    ttagaggatt ggaactttgg tgttcccccc ccccaacta ctagtttggt ggatacatat
1441    cgttttgtac aatctgttgc tattacctgt caaaaggatg ctgcaccggc tgaaaataag
1501    gatccctatg ataagttaaa gttttggaat gtggatttaa aggaaaagtt ttctttagac
1561    ttagatcaat atcccttgg acgtaaattt ttggttcagg ctggattgcg tcgcaagccc
1621    accataggcc ctcgcaaacg ttctgctcca tctgccacta cgtcttctaa acctgccaag
1681    cgtgtgcgtg tacgtgccag gaagtaa
```

SEQ ID NO: 99
```
   1    mclytrvlil hyhllplygp lyhprplplh silvymvhii icghyiilfl rnvnvfpifl
  61    qmalwrpsdn tvylpppsva rvvntddyvt ptsifyhags srlltvgnpy frvpagggnk
 121    qdipkvsayq yrvfrvqlpd pnkfglpdts iynpetqrlv wacagveigr gqplgvglsg
 181    hpfynklddt esshaatsnv sedvrdnvsv dykqtqlcil gcapaigehw akgtacksrp
 241    lsqgdcpple lkntvledgd mvdtgygamd fstlqdtkce vpldicqsic kypdylqmsa
 301    dpygdsmffc lrreqlfarh fwnragtmgd tvpqslyikg tgmpaspgsc vyspspsgsi
 361    vtsdsqlfnk pywlhkaqgh nngvcwhnql fvtvvdttps tnlticastq spvpgqydat
 421    kfkqysrhve eydlqfifql ctitltadvm syihsmnssi ledwnfgvpp ppttslvdty
```

| | |
|---|---|
| 481 | rfvqsvaitc qkdaapaenk dpydklkfwn vdlkekfsld ldqyplgrkf lvqaglrrkp |
| 541 | tigprkrsap sattsskpak rvrvrark |
| SEQ ID NO: 100 | |
| 1 | atgtcttgtg gcctaaacga cgtaaacgtg tccactattt ctttgcagat ggctttgtgg |
| 61 | cggcctaatg aaagcaaggt atacctacct ccaacacctg tttcaaaggt gatcagtacg |
| 121 | gatgtctatg tcacgcggac taatgtgtat taccatggtg gcagttctag cttctcact |
| 181 | gtgggtcatc catattactc tataaagaag agtaataata aggtggctgt gcccaaggta |
| 241 | tctgggtacc aatatcgtgt atttcacgtg aagttgccag atccaaataa gtttggcctg |
| 301 | cccgatgctg atttgtatga tccagatacc cagagacttc tgtgggcgtg cgtgggagta |
| 361 | gaggtggggcc gtgggcagcc tttgggtgtg ggtgtgtctg gtcacccata ttacaataga |
| 421 | ctggatgaca ctgaaaatgc acacacacct gatacagctg atgatggcag ggaaaacatt |
| 481 | tctatggatt ataaacagac acagctgttc attctgggct gcaaaccccc tattggtgag |
| 541 | cactggtcta agggtaccac ctgtaatggg tcttctgctg ctggtgactg cccgcccctc |
| 601 | caatttacta cacaactat tgaggacggg gatatggttg aaacagggtt cggtgccttg |
| 661 | gattttgcca ctctgcagtc aaataagtca gatgttcctt ggatatttg taccaatacc |
| 721 | tgtaaatatc ctgattatct gaagatggct gcagagcctt atggtgattc tatgttcttc |
| 781 | tcgctgcgta gggaacaaat gttcactcgt catttttca atctgggtgg taagatgggt |
| 841 | gacaccatcc cggatgagtt atacattaaa agtacctcag ttccaactcc aggcagtcat |
| 901 | gtttatactt ccactcctag tggctctatg gtgtcctctg aacaacagtt gtttaataag |
| 961 | ccttactggc tacggagggc ccaagggcac aacaatggta tgtgctgggg caatagggtc |
| 1021 | tttctgactg tggtggacac cacacgtagc actaatgtat ctctgtgtgc cactgaggcg |
| 1081 | tctgatacta attataaggc taccaatttt aaggaatatc tcaggcatat ggaggaatat |
| 1141 | gatttgcagt tcatcttcca actgtgcaag ataacccta ctcctgaaat tatggcctat |
| 1201 | atacataata tggatcccca gttgttagag gattggaact tcggtgtacc ccctccgccg |
| 1261 | tctgccagtt tacaggatac ctatagatat ttgcagtccc aggctattac atgtcaaaaa |
| 1321 | cctacacctc ctaagacccc taccgatccc tatgcctccc tgacctttg ggatgtggat |
| 1381 | ctcagtgaaa gtttttccat ggatctggac caatttccct ggggtcgcaa gttttttgctg |
| 1441 | cagcgggggg ctatgcctac cgtgtctcgc aagcgcgccg ctgtttcggg gaccacgccg |
| 1501 | cccactagta aacgaaaacg ggtaaggcgt tag |
| SEQ ID NO: 101 | |
| 1 | mscglndvnv stislqmalw rpneskvylp ptpvskvist dvyvtrtnvy yhggssrllt |
| 61 | vghpyysikk snnkvavpkv sgyqyrvfhv klpdpnkfgl pdadlydpdt qrllwacvgv |
| 121 | evgrgqplgv gvsghpyynr lddtenahtp dtaddgreni smdykqtqlf ilgckppige |
| 181 | hwskgttcng ssaagdcppl qftnttiedg dmvetgfgal dfatlqsnks dvpldictnt |
| 241 | ckypdylkma aepygdsmff slrreqmftr hffnlggkmg dtipdelyik stsvptpgsh |
| 301 | vytstpsgsm vsseqqlfnk pywlrraqgh nngmcwgnry fltvvdttrs tnvslcatea |
| 361 | sdtnykatnf keylrhmeey dlqfifqlck itltpeimay ihnmdpqlle dwnfgvpppp |
| 421 | saslqdtyry lqsqaitcqk ptppktptdp yasltfwdvd lsesfsmdld qfplgrkfll |
| 481 | qrgamptvsr kraaysgttp ptskrkrvrr |

-continued

LISTING OF ADDITIONAL SEQUENCES

SEQ ID NO: 102
1/1                              31/11
ATG AGG CAC AAG AGG AGC GCC AAG AGG ACC AAG AGG GCC AGC GCC ACC CAG CTG TAC AAG

61/21                            91/31
ACC TGC AAG CAG GCC GGC ACC TGC CCC CCC GAC ATC ATC CCC AAG GTG GAG GGC AAG ACC

21/41                            151/51
ATC GCC GAC CAG ATC CTG CAG TAC GGC AGC ATG GGC GTG TTC TTC GGC GGC CTG GGC ATC

181/61                           211/71
GGC ACC GGC AGC GGC ACC GGC GGC AGG ACC GGC TAC ATC CCC CTG GGC ACC AGG CCC CCC

241/81                           271/91
ACC GCC ACC GAC ACC CTG GCC CCC GTG AGG CCC CCC CTG ACC GTG GAC CCC GTG GGC CCC

301/101                          331/111
AGC GAC CCC AGC ATC GTG AGC CTG GTG GAG GAG ACC AGC TTC ATC GAC GCC GGC GCC CCC

361/121                          391/131
ACC AGC GTG CCC AGC ATC CCC CCC GAC GTG AGC GGC TTC AGC ATC ACC ACC AGC ACC GAC

21/141                           451/151
ACC ACC CCC GCC ATC CTG GAC ATC AAC AAC ACC GTG ACC ACC GTG ACC ACC CAC AAC AAC

81/161                           511/171
CCC ACC TTC ACC GAC CCC AGC GTG CTG CAG CCC CCC ACC CCC GCC GAG ACC GGC GGC CAC

541/181                          571/191
TTC ACC CTG AGC AGC AGC ACC ATC AGC ACC CAC AAC TAC GAG GAG ATC CCC ATG GAC ACC

601/201                          631/211
TTC ATC GTG AGC ACC AAC CCC AAC ACC GTG ACC AGC AGC ACC CCC ATC CCC GGC AGC AGG

661/221                          691/231
CCC GTG GCC AGG CTG GGC CTG TAC AGC AGG ACC ACC CAG CAG GTG AAG GTG GTG GAC CCC

721/241                          751/251
GCC TTC GTG ACC ACC CCC ACC AAG CTG ATC ACC TAC GAC AAC CCC GCC TAC GAG GGC ATC

781/261                          811/271
GAC GTG GAC AAC ACC CTG TAC TTC AGC AGC AAC GAC AAC AGC ATC AAC ATC GCC CCC GAC

841/281                          871/291
CCC GAC TTC CTG GAC ATC GTG GCC CTG CAC AGG CCC GCC CTG ACC AGC AGG AGG ACC GGC

901/301                          931/311
ATC AGG TAC AGC AGG ATC GGC AAC AAG CAG ACC CTG AGG ACC AGG AGC GGC AAG AGC ATC

961/321                          991/331
GGC GCC AAG GTG CAC TAC TAC TAC GAC CTG AGC ACC ATC GAC CCC GCC GAG GAG ATC GAG

1021/341                         1051/351
CTG CAG ACC ATC ACC CCC AGC ACC TAC ACC ACC ACC AGC CAC GCC GCC AGC CCC ACC AGC

081/361                          1111/371
ATC AAC AAC GGC CTG TAC GAC ATC TAC GCC GAC GAC TTC ATC ACC GAC ACC AGC ACC ACC

1141/381                         1171/391
CCC GTG CCC AGC GTG CCC AGC ACC AGC CTG AGC GGC TAC ATC CCC GCC AAC ACC ACC ATC

1201/401                         1231/411
CCC TTC GGT GGC GCC TAC AAC ATC CCC CTG GTG AGC GGC CCC GAC ATC CCC ATC AAC ATC

1261/421                         1291/431
ACC GAC CAG GCC CCC AGC CTG ATC CCC ATC GTG CCC GGC AGC CCC CAG TAC ACC ATC ATC

1321/441                         1351/451
GCC GAC GCC GGC GAC TTC TAC CTG CAC CCC AGC TAC TAC ATG CTG AGG AAG AGG AGG AAG

1381/461                         1411/471
AGG CTG CCC TAC TTC TTC AGC GAC GTG AGC CTG GCC GCC TGA

SEQ ID NO: 103
1/1                              31/11
Met arg his lys arg ser ala lys arg thr lys arg ala ser ala thr gln leu tyr lys

```
                61/21                                91/31
                thr cys lys gln ala gly thr cys pro pro asp ile ile pro lys val glu gly lys thr 121/41                               151/51
                ile ala asp gln ile leu gln tyr gly ser met gly val phe phe gly gly leu gly ile 181/61                               211/71
                gly thr gly ser gly thr gly gly arg thr gly tyr ile pro leu gly thr arg pro pro 241/81                               271/91
                thr ala thr asp thr leu ala pro val arg pro pro leu thr val asp pro val gly pro 301/101                              331/111
                ser asp pro ser ile val ser leu val glu glu thr ser phe ile asp ala gly ala pro 361/121                              391/131
                thr ser val pro ser ile pro pro asp val ser gly phe ser ile thr thr ser thr asp 421/141                              451/151
                thr thr pro ala ile leu asp ile asn asn thr val thr thr val thr thr his asn asn 481/161                              511/171
                pro thr phe thr asp pro ser val leu gln pro pro thr pro ala glu thr gly gly his 541/181                              571/191
                phe thr leu ser ser ser thr ile ser thr his asn tyr glu glu ile pro met asp thr 601/201                              631/211
                phe ile val ser thr asn pro asn thr val thr ser ser thr pro ile pro gly ser arg 661/221                              691/231
                pro val ala arg leu gly leu tyr ser arg thr thr gln gln val lys val val asp pro 721/241                              751/251
                ala phe val thr thr pro thr lys leu ile thr tyr asp asn pro ala tyr glu gly ile 781/261                              811/271
                asp val asp asn thr leu tyr phe ser ser asn asp asn ser ile asn ile ala pro asp 841/281                              871/291
                pro asp phe leu asp ile val ala leu his arg pro ala leu thr ser arg arg thr gly 901/301                              931/311
                ile arg tyr ser arg ile gly asn lys gln thr leu arg thr arg ser gly lys ser ile 961/321                              991/331
                gly ala lys val his tyr tyr tyr asp leu ser thr ile asp pro ala glu glu ile glu 1021/341                             1051/351
                leu gln thr ile thr pro ser thr tyr thr thr thr ser his ala ala ser pro thr ser 1081/361                             1111/371
                ile asn asn gly leu tyr asp ile tyr ala asp asp phe ile thr asp thr ser thr thr 1141/381                             1171/391
                pro val pro ser val pro ser thr ser leu ser gly tyr ile pro ala asn thr thr ile 1201/401                             1231/411
                pro phe gly gly ala tyr asn ile pro leu val ser gly pro asp ile pro ile asn ile 1261/421                             1291/431
                thr asp gln ala pro ser leu ile pro ile val pro gly ser pro gln tyr thr ile ile 1321/441                             1351/451
                ala asp ala gly asp phe tyr leu his pro ser tyr tyr met leu arg lys arg arg lys 1381/461                             1411/471
                arg leu pro tyr phe phe ser asp val ser leu ala ala OPA SEQ ID NO: 104
    1       atggtatccc accgtgccgc acgacgcaaa cgggcttcgg taactgactt atataaaaca 61      tgtaaacaat ctggtacatg tccacctgat gttgttccta aggtggaggg caccacgtta 121     gcagataaaa tattgcaatg gtcaagcctt ggtatatttt tgggtggact tggcataggt
```

| | LISTING OF ADDITIONAL SEQUENCES |
|---|---|
| 181 | actggcagtg gtacaggggg tcgtacaggg tacattccat tgggtgggcg ttccaataca |
| 241 | gtggtggatg ttggtcctac acgtcccca gtggttattg aacctgtggg ccccacagac |
| 301 | ccatctattg ttacattaat agaggactcc agtgtggtta catcaggtgc acctaggcct |
| 361 | acgtttactg gcacgtctgg gtttgatata acatctgcgg gtacaactac acctgcggtt |
| 421 | ttggatatca caccttcgtc tacctctgtg tctatttcca caaccaattt taccaatcct |
| 481 | gcattttctg atccgtccat tattgaagtt ccacaaactg gggaggtggc aggtaatgta |
| 541 | tttgttggta cccctacatc tggaacacat gggtatgagg aaatacctt acaaacattt |
| 601 | gcttcttctg gtacggggga ggaacccatt agtagtaccc cattgcctac tgtgcggcgt |
| 661 | gtagcaggtc cccgccttta cagtagggcc taccaacaag tgtcagtggc taaccctgag |
| 721 | tttcttacac gtccatcctc tttaattaca tatgacaacc cggcctttga gcctgtggac |
| 781 | actacattaa catttgatcc tcgtagtgat gttcctgatt cagattttat ggatattatc |
| 841 | cgtctacata ggcctgcttt aacatccagg cgtgggactg ttcgctttag tagattaggt |
| 901 | caacgggcaa ctatgtttac ccgcagcggt acacaaatag gtgctagggt tcacttttat |
| 961 | catgatataa gtcctattgc accttcccca gaatatattg aactgcagcc tttagtatct |
| 1021 | gccacggagg acaatgactt gtttgatata tatgcagatg acatggaccc tgcagtgcct |
| 1081 | gtaccatcgc gttctactac ctcctttgca tttttttaaat attcgcccac tatatcttct |
| 1141 | gcctcttcct atagtaatgt aacggtccct ttaacctcct cttgggatgt gcctgtatac |
| 1201 | acgggtcctg atattacatt accatctact acctctgtat ggcccattgt atcacccacg |
| 1261 | gcccctgcct ctacacagta tattggtata catggtacac attattattt gtggccatta |
| 1321 | tattatttta ttcctaagaa acgtaaacgt gttccctatt ttttgcaga tggctttgtg |
| 1381 | gcggcctag |
| SEQ ID NO: 105 | |
| 1 | mvshraarrk rasvtdlykt ckqsgtcppd vvpkvegttl adkilqwssl giflgglgig |
| 61 | tgsgtggrtg yiplggrsnt vvdvgptrpp vviepvgptd psivtlieds svvtsgaprp |
| 121 | tftgtsgfdi tsagttpav lditpsstsv sisttnftnp afsdpsiiev pqtgevagnv |
| 181 | fvgtptsgth gyeeiplqtf assgtgeepi sstplptvrr vagprlysra yqqvsvanpe |
| 241 | fltrpsslit ydnpafepvd ttltfdprsd vpdsdfmdii rlhrpaltsr rgtvrfsrlg |
| 301 | qratmftrsg tqigarvhfy hdispiapsp eyielqplvs atedndlfdi yaddmdpavp |
| 361 | vpsrsttsfa ffkysptiss assysnvtvp ltsswdpvpy tgpditlpst tsvwpivspt |
| 421 | apastqyigi hgthyylwpl yyfipkkrkr vpyffadgfv aa |
| SEQ ID NO: 106 | |
| 1 | atgtctgttg gtgattctta tcctaatcgc cttttttattg ttgatgtttt atgtccgttt |
| 61 | gttaaaccac acctaacacc cccactttt tatattgttt tgatacattt tcattttgat |
| 121 | acatttgtgt ttttttgta tttgctgcgt tttaataaac gtgcaaccat gtctatacgt |
| 181 | gccaagcgtc gaaagcgcgc ctcccccaca gacctctatc gtacctgcaa gcaggcaggt |
| 241 | acctgccccc cagacattat cccaagagtg aacagaaca ctttagcaga taaaatcctt |
| 301 | aagtggggca gtttaggtgt gttttttggg ggtctaggta taggcaccgg cagcggcaca |
| 361 | gggggggcgta ctgggtacat tcctgtaggt tcgcgaccca ccactgtagt tgacattggt |
| 421 | ccaacgccca ggccgcctgt tatcattgaa cctgtggggg cctctgaacc ctctattgtc |
| 481 | actttggtgg aggactctag catcattaac gcaggagcgt cacatcccac ctttactggt |

-continued

LISTING OF ADDITIONAL SEQUENCES

```
 541      actggtggct tcgaagtgac aacctccacc gttacagacc ccgccgtctt ggatatcacc
 601      ccctcaggta ccagtgtgca ggtcagcagc agtagctttc ttaacccact atacactgag
 661      ccagctattg tggaggctcc ccaaacaggg aagtatctg gccatgtact tgttagtaca
 721      gccacctcag ggtctcatgg ctatgaggaa ataccaatgc agacgtttgc cacgtcgggg
 781      ggcagcggta cagagcctat cagtagcaca cccctccctg gcgtgcggag agttgccgga
 841      ccccgcctgt acagtagagc caatcagcaa gtgcaagtca gggatcctgc gtttcttgca
 901      aggcctgcta tctagtaac atttgacaat cctgtgtatg acccagagga actataata
 961      tttcagcatc cagacttgca tgagccaccg gatcctgatt ttttggacat agtggcgttg
1021      catcgtcccg ccctcacgtc cagaaggggg actgtccgtt ttagtaggtt gggacgcagg
1081      gctacactcc gcacccgtag tggtaaacaa attggggcac gggtgcactt ctatcatgat
1141      attagcccta taggtactga ggagttggag atggagccac tgttgccccc agcttctact
1201      gataacacag atatgttata tgatgtttat gctgattcgg atgtccttca gccattgctt
1261      gatgagttac ccgccgcccc tcgcggttca ctctctctgg ctgacactgc tgtgtctgcc
1321      acctccgcat ctacactacg ggggtccact actgtcccctt tatcaagtgg tattgatgtg
1381      cctgtgtaca ccggtcctga cattgaacca cccaatgttc ctggcatggg acctctgatt
1441      cctgtggctc catccttacc atcgtctgtg tacatatttg ggggagatta ttatttgatg
1501      ccaagttatg tcttgtggcc taaacgacgt aaacgtgtcc actatttctt tgcagatggc
1561      tttgtggcgg cctaa
```

SEQ ID NO: 107
```
   1      msvgdsypnr lfivdvlcpf vkphltpplf yivlihfhfd tfvfflyllr fnkratmsir
  61      akrrkraspt dlyrtckqag tcppdiipry eqntladkil kwgslgvffg glgigtgsgt
 121      ggrtgyipvg srpttvvdig ptprppviie pvgasepsiv tivedssiin agashptftg
 181      tggfevttst vtdpavldit psgtsvqvss ssflnplyte paiveapqtg evsghvlvst
 241      atsgshgyee ipmqtfatsg gsgtepisst plpgvrrvag prlysranqq vqvrdpafla
 301      rpadlvtfdn pvydpeetii fqhpdlhepp dpdfldival hrpaltsrrg tvrfsrlgrr
 361      atlrtrsgkq igarvhfyhd ispigteele meplippast dntdmlydvy adsdvlqpll
 421      delpaaprgs lsladtaysa tsastlrgst tvplssgidv pvytgpdiep pnvpgmgpli
 481      pvapslpssv yifggdyylm psyvlwpkrr krvhyffadg fvaa
```

SEQ ID NO: 108
```
   1      atggagctga ggccctggtt gctatgggtg gtagcagcaa caggaacctt ggtcctgcta
  61      gcagctgatg ctcagggcca gaaggtcttc accaacacgt gggctgtgcg catccctgga
 121      ggcccagcgg tggccaacag tgtggcacgg aagcatgggt tcctcaacct gggccagatc
 181      ttcgggact attaccactt ctggcatcga ggagtgacga gcggtccct gtcgcctcac
 241      cgcccgcggc acagccggct gcagagggag cctcaagtac agtggctgga acagcaggtg
 301      gcaaagcgac ggactaaacg ggacgtgtac caggagccca gaccccaa gtttcctcag
 361      cagtggtacc tgtctggtgt cactcagcgg gacctgaatg tgaaggcggc ctgggcgcag
 421      ggctacacag gcacggcat tgtggtctcc attctggacg atggcatcga agaaccac
 481      ccggacttgg caggcaatta tgatcctggg gccagttttg atgtcaatga ccaggaccct
 541      gacccccagc ctcggtacac acagatgaat gacaacaggg acggcacacg gtgtgcgggg
```

-continued

| | LISTING OF ADDITIONAL SEQUENCES |
|---|---|
| 601 | gaagtggctg cggtggccaa caacggtgtc tgtggtgtag gtgtggccta caacgcccgc |
| 661 | attggagggg tgcgcatgct ggatggcgag gtgacagatg cagtggaggc acgtcgctg |
| 721 | ggcctgaacc ccaaccacat ccacatctac agtgccagct ggggcccgga ggatgacggc |
| 781 | aagacagtgg atgggccagc ccgcctcgcc gaggaggcct tcttccgtgg ggttagccag |
| 841 | ggccgagggg ggctgggctc catctttgtc tgggcctcgg gaacggggg ccggaacat |
| 901 | gacagctgca actgcgacgg ctacaccaac agtatctaca cgctgtccat cagcagcgcc |
| 961 | acgcagtttg gcaacgtgcc cgtggtacagc gaggcctgct cgtccacact ggccacgacc |
| 1021 | tacagcagtg gcaaccagaa tgagaagcag atcgtgacga ctgacttgcg gcagaagtgc |
| 1081 | acggagtctc acacgggcac ctcagcctct gcccccttag cagccggcat cattgctctc |
| 1141 | accctggagg ccaataagaa cctcacatgg cgggacatgc aacacctggt ggtacagacc |
| 1201 | tcgaagccag cccacctcaa tgccaacgac tgggccacca atggtgtggg ccggaaagtg |
| 1261 | agccactcat atggctacgg gcttttggac gcaggcgcca tggtggccct ggcccagaat |
| 1321 | tggaccacag tggcccccca gcggaagtgc atcatcgaca tcctcaccga gcccaaagac |
| 1381 | atcgggaaac ggctcgaggt gcggaagacc gtgaccgcgt gcctgggcga gcccaaccac |
| 1441 | atcactcggc tggagcacgc tcaggcgcgg ctcaccctgt cctataatcg ccgtggcgac |
| 1501 | ctggccatcc acctggtcag ccccatgggc acccgctcca ccctgctggc agccaggcca |
| 1561 | catgactact ccgcagatgg gttaatgac tgggccttca tgacaactca ttcctgggat |
| 1621 | gaggatccct ctggcgagtg ggtcctagag attgaaaaca ccagcgaagc caacaactat |
| 1681 | gggacgctga ccaagttcac cctcgtactc tatggcaccg ccctgagggg gctgccgta |
| 1741 | cctccagaaa gcagtggctg caagacccatc acgtccagtc aggcctgtgt ggtgtgcgag |
| 1801 | gaaggcttct ccctgcacca aagagctgt gtccagcact gccctccagg gttcgccccc |
| 1861 | caagtcctcg atacgcacta tagcaccgag aatgacgtgg agaccatccg ggccagcgtc |
| 1921 | tgcgcccct gccacgcctc atgtgccaca tgccaggggc cggccctgac agactgcctc |
| 1981 | agctgcccca gccacgcctc cttggaccct gtggagcaga cttgctcccg gcaaagccag |
| 2041 | agcagccgag agtccccgcc acagcagcag ccacctcggc tgccccggga ggtggaggcg |
| 2101 | gggcaacggc tgcgggcagg gctgctgccc tcacacctgc ctgaggtggt ggccggcctc |
| 2161 | agctgcgcct tcatcgtgct ggtcttcgtc actgtcttcc tggtcctgca gctgcgctct |
| 2221 | ggctttagtt tcggggggt gaaggtgtac accatggacc gtggcctcat ctcctacaag |
| 2281 | gggctgcccc ctgaagcctg caggaggag tgcccgtctg actcagaaga ggacgagggc |
| 2341 | cggggcgaga ggaccgcctt tatcaaagac cagagcgccc tctga |

SEQ ID NO: 109

| 1 | melrpwllwv vaatgtlvll aadaqgqkvf tntwavripg gpavansvar khgflnlgqi |
|---|---|
| 61 | fgdyyhfwhr gvtkrslsph rprhsrlqre pqvqwleqqv akrrtkrdvy qeptdpkfpq |
| 121 | qwylsgvtqr dlnvkaawaq gytghgivvs ilddgieknh pdlagnydpg asfdvndqdp |
| 181 | dpqprytqmn dnrhgtrcag evaavannqv cgvgvaynar iggvrmldge vtdavearsl |
| 241 | glnpnhihiy saswgpeddg ktvdgparla eeaffrgvsq grgglgsifv wasgnggreh |
| 301 | dscncdgytn siytlsissa tqfgnvpwys eacsstlatt yssgnqnekq ivttdlrqkc |
| 361 | teshtgtsas aplaagiial tleanknitw rdmqhlvvqt skpahlnand watngvgrkv |
| 421 | shsygyglld agamvalaqn wttvapqrkc iidiltepkd igkrlevrkt vtaclgepnh |

| | | | | | | | | | | | | | | | |
|---|---|---|---|---|---|---|---|---|---|---|---|---|---|---|---|
|481| |itrlehaqar|ltlsynrrgd|laihlvspmg|trstllaarp|hdysadgfnd|wafmtthswd|
|541| |edpsgewvle|ientseanny|gtltkftivl|ygtapeglpv|ppessgcktl|tssqacvvce|
|601| |egfslhqksc|vqhcppgfap|qvldthyste|ndvetirasv|capchascat|cqgpaltdcl|
|661| |scpshasldp|veqtcsrqsq|ssresppqqq|pprlppevea|gqrlragllp|shlpevvagl|
|721| |scafivlvfv|tvflvlqlrs|gfsfrgvkvy|tmdrglisyk|glppeawqee|cpsdseedeg|
|781| |rgertafikd|qsal|

SEQ ID NO: 110
AATGGACCAGTTCTAATGT

SEQ ID NO: 111
GTCAGCCCTAAATTCTTC

SEQ ID NO: 112
TAATACGACTCACTATAGGG

SEQ ID NO: 113
TAGAAGGCACAGTCGAGG

SEQ ID NO: 114
ATGGTGAGCAAGGGCGAGGAG

SEQ ID NO: 115
CTTGTACAGCTCGTCCATGCC

SEQ ID NO: 116
CCGGATCCTGGGAAGCTTGTCATCAACGG

SEQ ID NO: 117
GGCTCGAGGCAGTGATGGCATGGACTG

---

What is claimed:

1. A method of inducing or enhancing an antigen-specific immune response in a mammal, comprising the steps of:
   (a) priming the mammal by administering to the mammal an effective amount of a chemotherapeutic agent; and
   (b) boosting the mammal by administering to the mammal an effective amount of an annexin chimeric fusion protein, wherein the annexin chimeric fusion protein comprises Annexin V (annV) fused to at least one immunogenic antigen selected from the group consisting of HPV16 E6, HPV16 E7, modified colon carcinoma antigen AH5, and influenza antigen M1;
   thereby inducing or enhancing the antigen-specific immune response.

2. The method of claim 1, wherein the annV chimeric fusion protein comprises a furin cleavage site.

3. The method of claim 2, wherein the annV chimeric fusion protein or chemotherapeutic agent is administered intradermally, intraperitoneally, or intravenously via injection.

4. The method of claim 1, wherein the chemotherapeutic agent is cisplatin.

5. The method of claim 1, wherein the mammal is a human, wherein the mammal is afflicted with cancer.

6. The method of claim 1, wherein step (a) is performed before step (b), step (a) and step (b) are performed at the same time, or step (a) is performed after step (b).

7. The method of claim 1, wherein step (a) and/or step (b) is repeated at least once.

8. The method of claim 1, wherein the dosage used in step (a) is 5 mg/kg, and/or the dosage used in step (b) is 100 ug.

9. The method of claim 1, wherein the antigen-specific immune response is greater in magnitude than an antigen-specific immune response induced by administration of the annexin chimeric fusion protein alone and/or wherein the antigen-specific immune response is greater in magnitude than an antigen-specific immune response induced by administration of the chemotherapeutic agent alone.

* * * * *